(12) United States Patent
Chai et al.

(10) Patent No.: US 11,667,644 B2
(45) Date of Patent: Jun. 6, 2023

(54) DISUBSTITUTED OCTAHYDROPYRROLO[3,4-C]PYRROLES AS OREXIN RECEPTOR MODULATORS

(71) Applicant: Janssen Pharmaceutica NV, Beerse (BE)

(72) Inventors: Wenying Chai, San Diego, CA (US); Michael A. Letavic, San Diego, CA (US); Kiev S. Ly, San Diego, CA (US); Daniel J. Pippel, Del Mar, CA (US); Dale A. Rudolph, San Diego, CA (US); Kathleen C. Sappey, San Diego, CA (US); Brad M. Savall, San Diego, CA (US); Chandravadan R. Shah, San Diego, CA (US); Brock T. Shireman, Poway, CA (US); Akinola Soyode Johnson, San Diego, CA (US); Emily M. Stocking, Encinitas, CA (US); Devin M. Swanson, La Jolla, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 17/372,168

(22) Filed: Jul. 9, 2021

(65) Prior Publication Data
US 2021/0347781 A1 Nov. 11, 2021

Related U.S. Application Data

(63) Continuation of application No. 16/601,832, filed on Oct. 15, 2019, now Pat. No. 11,059,828, which is a continuation of application No. 15/413,965, filed on Jan. 24, 2017, now abandoned, which is a continuation of application No. 14/734,225, filed on Jun. 9, 2015, now abandoned, which is a continuation of application No. 14/138,941, filed on Dec. 23, 2013, now Pat. No. 9,079,911, which is a continuation of application No. 13/503,231, filed as application No. PCT/US2010/053606 on Oct. 21, 2010, now Pat. No. 8,653,263.

(60) Provisional application No. 61/254,509, filed on Oct. 23, 2009.

(51) Int. Cl.
| | | |
|---|---|---|
| C07D 487/04 | (2006.01) |
| A61K 31/5377 | (2006.01) |
| A61K 31/506 | (2006.01) |
| A61K 31/428 | (2006.01) |
| A61K 31/498 | (2006.01) |
| A61K 31/4709 | (2006.01) |
| A61K 31/4439 | (2006.01) |
| A61K 31/53 | (2006.01) |

(52) U.S. Cl.
CPC .......... *C07D 487/04* (2013.01); *A61K 31/428* (2013.01); *A61K 31/4439* (2013.01); *A61K 31/4709* (2013.01); *A61K 31/498* (2013.01); *A61K 31/506* (2013.01); *A61K 31/53* (2013.01); *A61K 31/5377* (2013.01)

(58) Field of Classification Search
CPC .................................................... C07D 487/04
See application file for complete search history.

(56) References Cited

U.S. PATENT DOCUMENTS

| | | | |
|---|---|---|---|
| 4,085,225 A | 4/1978 | Welle et al. |
| 4,136,193 A | 1/1979 | Bogeso et al. |
| 6,838,465 B2 | 1/2005 | Yamada et al. |
| 7,279,578 B2 | 10/2007 | Aissaoui et al. |
| 7,396,958 B2 | 7/2008 | Courtemanche et al. |
| 7,435,815 B2 | 10/2008 | Aissaoui et al. |
| 7,538,109 B2 | 5/2009 | Aissaoui et al. |
| 7,553,836 B2 | 6/2009 | Zhao |
| 7,763,638 B2 | 7/2010 | Aissaoui et al. |
| 7,812,031 B2 | 10/2010 | Aranyi et al. |
| 7,834,028 B2 | 11/2010 | Aissaoui et al. |
| 7,851,622 B2 | 12/2010 | Washburn et al. |
| 7,923,470 B2 | 4/2011 | Knust et al. |
| 7,932,246 B2 | 4/2011 | Moffat et al. |
| 7,951,797 B2 | 5/2011 | Breslin et al. |
| 7,956,049 B2 | 6/2011 | Zhao |
| 7,968,534 B2 | 6/2011 | Despeyroux et al. |
| 7,973,159 B2 | 7/2011 | Washburn et al. |
| 7,994,336 B2 | 8/2011 | Aissaoui et al. |
| 8,012,984 B2 | 9/2011 | Stein et al. |
| 8,067,420 B2 | 11/2011 | Stein et al. |
| 8,093,255 B2 | 1/2012 | Alvaro et al. |
| 8,106,215 B2 | 1/2012 | Aissaoui et al. |
| 8,129,384 B2 | 3/2012 | Alvaro et al. |

(Continued)

FOREIGN PATENT DOCUMENTS

| | | |
|---|---|---|
| AU | 2010310595 B2 | 7/2015 |
| EP | 1288202 A1 | 3/2003 |

(Continued)

OTHER PUBLICATIONS

Donald, et al. Bioorganic & Medicinal Chemistry Letters 20 (2010) 6657-6660.*

(Continued)

*Primary Examiner* — Shawquia Jackson

(74) *Attorney, Agent, or Firm* — BakerHostetler

(57) ABSTRACT

Disubstituted octahydropyrrolo[3,4-c]pyrrole compounds are described, which are useful as orexin receptor modulators. Such compounds may be useful in pharmaceutical compositions and methods for the treatment of diseased states, disorders, and conditions mediated by orexin activity, such as insomnia.

31 Claims, 1 Drawing Sheet

(56) References Cited

U.S. PATENT DOCUMENTS

| | | |
|---|---|---|
| 8,133,908 B2 | 3/2012 | Alvaro et al. |
| 8,188,082 B2 | 5/2012 | Aissaoui et al. |
| 8,207,220 B2 | 6/2012 | Knust et al. |
| 8,236,964 B2 | 8/2012 | Aissaoui et al. |
| 8,288,411 B2 | 10/2012 | Aissaoui et al. |
| 8,288,429 B2 | 10/2012 | Aissaoui et al. |
| 8,357,700 B2 | 1/2013 | Cox et al. |
| 8,362,009 B2 | 1/2013 | Bergman et al. |
| 8,563,539 B2 | 10/2013 | Balding et al. |
| 8,598,119 B2 | 12/2013 | Mates et al. |
| 8,623,863 B2 | 1/2014 | Coleman et al. |
| 8,653,263 B2 | 2/2014 | Chai et al. |
| 8,680,275 B2 | 3/2014 | Branstetter et al. |
| 8,748,430 B2 | 6/2014 | Knust et al. |
| 8,877,773 B2 | 11/2014 | Shekhar et al. |
| 9,029,364 B2 | 5/2015 | Kuduk et al. |
| 9,079,911 B2 | 7/2015 | Chai et al. |
| 9,157,077 B2 | 10/2015 | Balding et al. |
| 9,168,258 B2 | 10/2015 | Mates et al. |
| 9,266,870 B2 | 2/2016 | Futamura et al. |
| 9,586,934 B2 | 3/2017 | Kuduk et al. |
| 9,586,962 B2 | 3/2017 | Letavic et al. |
| 9,624,197 B2 | 4/2017 | Kuduk et al. |
| 9,695,163 B2 | 7/2017 | Liverton et al. |
| 9,845,333 B2 | 12/2017 | Gelin et al. |
| 10,196,383 B2 | 2/2019 | Zhang et al. |
| 10,611,760 B2 | 4/2020 | Blaney et al. |
| 10,696,654 B2 | 6/2020 | Martin |
| 10,828,302 B2 | 11/2020 | De et al. |
| 2002/0019388 A1 | 2/2002 | Schrimpf et al. |
| 2004/0242641 A1 | 12/2004 | Buckley et al. |
| 2005/0065178 A1 | 3/2005 | Basha et al. |
| 2005/0101602 A1 | 5/2005 | Basha et al. |
| 2005/0176680 A1 | 8/2005 | Lalji et al. |
| 2006/0019985 A1 | 1/2006 | Ma et al. |
| 2006/0074121 A1 | 4/2006 | Chen et al. |
| 2006/0178515 A1 | 8/2006 | Aissaoui et al. |
| 2006/0241102 A1 | 10/2006 | Kase et al. |
| 2006/0258672 A1 | 11/2006 | Barbosa et al. |
| 2006/0258691 A1 | 11/2006 | Barbosa et al. |
| 2008/0009477 A1 | 1/2008 | Hutchison et al. |
| 2008/0132490 A1 | 6/2008 | Bergman et al. |
| 2008/0153811 A1 | 6/2008 | Barbosa et al. |
| 2008/0175795 A1 | 7/2008 | Neogi et al. |
| 2009/0011994 A1 | 1/2009 | Stein et al. |
| 2009/0022670 A1 | 1/2009 | Alvaro et al. |
| 2009/0036422 A1 | 2/2009 | Knust et al. |
| 2009/0054439 A1 | 2/2009 | Courtemanche et al. |
| 2009/0163485 A1 | 6/2009 | Knust et al. |
| 2009/0306100 A1 | 12/2009 | Barbosa et al. |
| 2010/0016401 A1 | 1/2010 | Aissaoui et al. |
| 2010/0029617 A1 | 2/2010 | Aissaoui et al. |
| 2010/0105614 A1 | 4/2010 | Jochelson |
| 2010/0144760 A1 | 6/2010 | Alvaro et al. |
| 2010/0160344 A1 | 6/2010 | Alvaro et al. |
| 2010/0160345 A1 | 6/2010 | Alvaro et al. |
| 2010/0168131 A1 | 7/2010 | Alvaro et al. |
| 2010/0184808 A1 | 7/2010 | Aissaoui et al. |
| 2010/0197733 A1 | 8/2010 | Aissaoui et al. |
| 2010/0210667 A1 | 8/2010 | Alvaro et al. |
| 2010/0256121 A1 | 10/2010 | Bergman et al. |
| 2010/0256182 A1 | 10/2010 | Aissaoui et al. |
| 2010/0267730 A1 | 10/2010 | Alvaro et al. |
| 2011/0009461 A1 | 1/2011 | Aissaoui et al. |
| 2011/0053979 A1 | 3/2011 | Alvaro et al. |
| 2011/0077200 A1 | 3/2011 | Jochelson et al. |
| 2011/0152235 A1 | 6/2011 | Baldino et al. |
| 2011/0207715 A1 | 8/2011 | Cox et al. |
| 2011/0257198 A1 | 10/2011 | Alvaro et al. |
| 2011/0263643 A1 | 10/2011 | Cox et al. |
| 2011/0288098 A1 | 11/2011 | Alvaro et al. |
| 2012/0040991 A1 | 2/2012 | Amantini et al. |
| 2012/0095034 A1 | 4/2012 | Alvaro et al. |
| 2012/0149711 A1 | 6/2012 | Di Fabio |
| 2012/0149723 A1 | 6/2012 | Di Fabio |
| 2012/0202783 A1 | 8/2012 | Branstetter et al. |
| 2012/0208812 A1 | 8/2012 | Chai et al. |
| 2013/0005655 A1 | 1/2013 | Jochelson et al. |
| 2013/0210911 A1 | 8/2013 | Lee et al. |
| 2013/0281465 A1 | 10/2013 | Nozawa et al. |
| 2014/0081025 A1 | 3/2014 | Suzuki et al. |
| 2014/0107084 A1 | 4/2014 | Jochelson et al. |
| 2014/0171430 A1 | 6/2014 | Letavic et al. |
| 2014/0179697 A1 | 6/2014 | Chai et al. |
| 2014/0228377 A1 | 8/2014 | Abe et al. |
| 2014/0275050 A1 | 9/2014 | Kuduk et al. |
| 2014/0364432 A1 | 12/2014 | Kamenecka et al. |
| 2014/0364433 A1 | 12/2014 | Kamenecka et al. |
| 2015/0011613 A1 | 1/2015 | Shekhar et al. |
| 2015/0018309 A1 | 1/2015 | Lindsley et al. |
| 2015/0166523 A1 | 6/2015 | Araki et al. |
| 2015/0183768 A1 | 7/2015 | Futamura et al. |
| 2015/0322039 A1 | 11/2015 | Kuduk et al. |
| 2015/0335651 A1 | 11/2015 | Chai et al. |
| 2016/0030425 A1 | 2/2016 | Mates et al. |
| 2016/0051533 A1 | 2/2016 | Ladd |
| 2016/0185768 A1 | 6/2016 | Liverton et al. |
| 2016/0368898 A1 | 12/2016 | Kuduk et al. |
| 2017/0015651 A1 | 1/2017 | Gelin et al. |
| 2017/0129901 A1 | 5/2017 | Chai et al. |
| 2018/0282309 A1 | 10/2018 | Fieldhouse et al. |

FOREIGN PATENT DOCUMENTS

| | | |
|---|---|---|
| EP | 2653469 A1 | 10/2013 |
| EP | 2708537 A1 | 3/2014 |
| EP | 2730573 A1 | 5/2014 |
| EP | 2862855 A1 | 4/2015 |
| EP | 2862860 A1 | 4/2015 |
| EP | 2491038 B1 | 4/2016 |
| JP | 2003-531210 A | 10/2003 |
| JP | 2009-506061 A | 2/2009 |
| JP | 2014-015452 A | 1/2014 |
| JP | 2014-111586 A | 6/2014 |
| JP | 2014-141480 A | 8/2014 |
| JP | 2015-131802 A | 7/2015 |
| JP | 2015-131803 A | 7/2015 |
| JP | 2016-028017 A | 2/2016 |
| WO | 96/39407 | 12/1996 |
| WO | 97/11945 | 4/1997 |
| WO | 00/55143 | 9/2000 |
| WO | 01/61347 A1 | 8/2001 |
| WO | 01/81347 A2 | 11/2001 |
| WO | 01/85693 A1 | 11/2001 |
| WO | 02/60902 | 8/2002 |
| WO | 02/70523 | 9/2002 |
| WO | 02/70527 | 9/2002 |
| WO | 03/02561 | 1/2003 |
| WO | 03/02581 | 1/2003 |
| WO | 03/51672 | 6/2003 |
| WO | 03/51872 | 6/2003 |
| WO | 2003/106450 | 12/2003 |
| WO | 2004/004733 A1 | 1/2004 |
| WO | 2004/033418 A2 | 4/2004 |
| WO | 2004/041791 A1 | 5/2004 |
| WO | 2004/085403 A1 | 10/2004 |
| WO | 2004/096780 A1 | 11/2004 |
| WO | 2005/005439 A1 | 1/2005 |
| WO | 2005/023231 A3 | 3/2005 |
| WO | 2005/084667 A1 | 9/2005 |
| WO | 2005/118548 A1 | 12/2005 |
| WO | 2006/012396 A1 | 2/2006 |
| WO | 2006/024779 A1 | 3/2006 |
| WO | 2006/052542 A2 | 5/2006 |
| WO | 2006/056848 A1 | 6/2006 |
| WO | 2006/067121 A1 | 6/2006 |
| WO | 2006/123121 A1 | 11/2006 |
| WO | 2006/124748 A2 | 11/2006 |
| WO | 2006/124897 A2 | 11/2006 |
| WO | 2007/007069 A1 | 1/2007 |
| WO | 2007/025069 A2 | 3/2007 |
| WO | 2007/085718 A1 | 8/2007 |
| WO | 2007/088276 A2 | 8/2007 |
| WO | 2007/092416 A2 | 8/2007 |

(56) References Cited

FOREIGN PATENT DOCUMENTS

| | | |
|---|---|---|
| WO | 2007/122591 A2 | 11/2007 |
| WO | 2007/126934 A2 | 11/2007 |
| WO | 2007/126935 A2 | 11/2007 |
| WO | 2007/146761 A2 | 12/2007 |
| WO | 2008/008517 A2 | 1/2008 |
| WO | 2008/008518 A1 | 1/2008 |
| WO | 2008/008551 A2 | 1/2008 |
| WO | 2008/020405 A2 | 2/2008 |
| WO | 2008/026149 A1 | 3/2008 |
| WO | 2008/034731 A1 | 3/2008 |
| WO | 2008/038251 A2 | 4/2008 |
| WO | 2008/052139 A2 | 5/2008 |
| WO | 2008/067121 A2 | 6/2008 |
| WO | 2008/069997 A1 | 6/2008 |
| WO | 2008/078291 A1 | 7/2008 |
| WO | 2008/117241 A2 | 10/2008 |
| WO | 2008/134480 A1 | 11/2008 |
| WO | 2008/143856 A1 | 11/2008 |
| WO | 2009/003993 A1 | 1/2009 |
| WO | 2009/003997 A1 | 1/2009 |
| WO | 2009/004584 A1 | 1/2009 |
| WO | 2009/009501 A1 | 1/2009 |
| WO | 2009/011775 A1 | 1/2009 |
| WO | 2009/016087 A1 | 2/2009 |
| WO | 2009/016286 A2 | 2/2009 |
| WO | 2009/016564 A2 | 2/2009 |
| WO | 2009/022311 A2 | 2/2009 |
| WO | 2009/037394 A2 | 3/2009 |
| WO | 2009/040730 A2 | 4/2009 |
| WO | 2009/058238 A1 | 5/2009 |
| WO | 2009/061197 A1 | 5/2009 |
| WO | 2009/081197 A1 | 7/2009 |
| WO | 2009/124956 A1 | 10/2009 |
| WO | 2009/145900 A1 | 12/2009 |
| WO | 2010/012620 A1 | 2/2010 |
| WO | 2010/017260 A1 | 2/2010 |
| WO | 2010/048010 A1 | 4/2010 |
| WO | 2010/048012 A1 | 4/2010 |
| WO | 2010/048013 A1 | 4/2010 |
| WO | 2010/048014 A1 | 4/2010 |
| WO | 2010/048016 A1 | 4/2010 |
| WO | 2010/048017 A1 | 4/2010 |
| WO | 2010/051236 A1 | 5/2010 |
| WO | 2010/051237 A1 | 5/2010 |
| WO | 2010/051238 A1 | 5/2010 |
| WO | 2010/060470 A1 | 6/2010 |
| WO | 2010/060471 A1 | 6/2010 |
| WO | 2010/060472 A1 | 6/2010 |
| WO | 2010/063662 A1 | 6/2010 |
| WO | 2010/063663 A1 | 6/2010 |
| WO | 2010/072722 A1 | 7/2010 |
| WO | 2010/098911 A2 | 9/2010 |
| WO | 2010/122151 A1 | 10/2010 |
| WO | 2011/023578 A1 | 3/2011 |
| WO | 2011/023585 A1 | 3/2011 |
| WO | 2011/050198 A1 | 4/2011 |
| WO | 2011/050200 A1 | 4/2011 |
| WO | 2011/050202 A1 | 4/2011 |
| WO | 2011/057471 A1 | 5/2011 |
| WO | 2012/081692 A1 | 6/2012 |
| WO | 2012/089606 A1 | 7/2012 |
| WO | 2012/089607 A1 | 7/2012 |
| WO | 2012/145581 A1 | 10/2012 |
| WO | 2012/153729 A1 | 11/2012 |
| WO | 2013/005755 A1 | 1/2013 |
| WO | 2013/059163 A1 | 4/2013 |
| WO | 2013/119639 A1 | 8/2013 |
| WO | 2013/187466 A1 | 12/2013 |
| WO | 2013/187467 A1 | 12/2013 |
| WO | 2014/085208 A1 | 6/2014 |
| WO | 2014/091876 A1 | 6/2014 |
| WO | 2015/020933 A1 | 2/2015 |
| WO | 2015/085004 A1 | 6/2015 |
| WO | 2015/088865 A1 | 6/2015 |
| WO | 2015/095108 A1 | 6/2015 |
| WO | 2015/123355 A1 | 8/2015 |
| WO | 2015/152367 A1 | 10/2015 |
| WO | 2015/152368 A1 | 10/2015 |
| WO | 2015/180060 A1 | 12/2015 |
| WO | 2016/025669 A1 | 2/2016 |
| WO | 2020/120994 A1 | 6/2020 |

OTHER PUBLICATIONS

Li et al., "Hypocretins, Neural Systems, Physiology, and Psychiatric Disorders", Current Psychiatry Reports, Jan. 1, 2016, 18, 1, 1-12.
Lin et al. "The sleep disorder canine narcolepsy is caused by a mutation in the hypocretin (orexin) receptor 2 gene", Cell 1999, 98, pp. 365-376.
Lovenberg et al., "Selective Orexin-2 Receptor Antagonism as Adjunctive Therapy for Insomnia in Depression", Neuropsychophamnacology, Dec. 2013, 38, S2, S543-S544.
Malherbe et al. "Biochemical and electrophysiological characterization of almorexant, a dual orexin 1 receptor (OX1)/orexin 2 receptor (OX2) antagonist comparison with selective OX1 and OX2 antagonists", Molecular Pharmacology 2009, 76(3) pp. 618-631.
Malherbe, P. et al., Biochemical and behavioural characterization of EMPA, a novel high-affinity, selective antagonist for the $OX_2$ Receptor, British Journal of Pharmacology 2009 156:1326-1341.
Mang et al., "The Dual Orexin Receptor Antagonist Almorexant Induces Sleep and Decreases Orexin-Induced Locomotion by Blocking Orexin 2 Receptors", Sleep, Dec. 2012, 35(12), 1625-1635.
Manka, et al., "Octahydropyrrolo [3, 4-c]pyrrole negative allosteric modulators of mGlu1", Bioorganic & Medicinal Chemistry Letters, Pergamon, Amsterdam, NL, Jul. 23, 2013, vol. 23, No. 18, pp. 5091-5096.
Marcus et al., "Differential Expression of Orexin Receptors 1 and 2 in the Rat Brain", Journal of Comparative Neurology, Jun. 2001, 435, 6-25.
McAtee et al., "Novel substituted 4-phenyl-[1,3]dioxanes: potent and selective orexin receptor 2 (OX2R) antagonists", Bioorganic & Medicinal Chemistry Letters, Aug. 2004, 14, 4225-4229.
McElhinny Jr. et al., "Hydrolytic instability of the important orexin 1 receptor antagonist SB-334867: Possible confounding effects on in vivo and in vitro studies", Bioorganic & Medicinal Chemistry Letters, Nov. 2012, 22, 6661-6664.
Mercer et al., "Discovery of 2,5-diarylnicotinamides as selective orexin-2 receptor antagonists (2-SORAs)", Bioorganic & Medicinal Chemistry Letters, Dec. 2013, 23, 6620-6624.
Micheli et al., "2-Methyl-3-furanyl-4H-1,2,4-triazol-3-ylthioamides: A new class of selective orexin 2 antagonists", Bioorganic & Medicinal Chemistry Letters, Nov. 2010, 20, 6405-6407.
Michelson et al., "Safety and efficacy of suvorexant during 1-year treatment of insomnia with subsequent abrupt treatment discontinuation: a phase 3 randomised, double-blind, placebo-controlled trial", The Lancet, May 2014, 13, 461-471.
Mignot et al. "Complex HLA-DR and -DQ interactions confer risk of narcolepsy-cataplexy in three ethnic groups", Am. J. Hum. Genet. 2001, 68 (3), pp. 686-699.
Mignot et al., "Narcolepsy and the HLA System", New England J. Med., Mar. 2001, 344 (9), 692.
Minerva Neurosciences Inc., Form 10-K, Mar. 14, 2016.
Minerva Neurosciences Inc., Form 10-K, Mar. 26, 2015.
Minerva Neurosciences Inc., Form 10-Q, Aug. 4, 2016.
Minerva Neurosciences Inc., Form 10-Q, Aug. 5, 2015.
Minerva Neurosciences Inc., Form 10-Q, Aug. 7, 2014.
Minerva Neurosciences Inc., Form 10-Q, May 3, 2016.
Minerva Neurosciences Inc., Form 10-Q, May 7, 2015.
Minerva Neurosciences Inc., Form 10-Q, Nov. 3, 2016.
Minerva Neurosciences Inc., Form 10-Q, Nov. 5, 2015.
Minerva Neurosciences Inc., Form 10-Q, Nov. 6, 2014.
Minerva Neurosciences Inc., Form 424B3, Jun. 16, 2015.
Minerva Neurosciences Inc., Form 424B4, Jul. 1, 2014.
Minerva Neurosciences Inc., Form 424B5, Jun. 14, 2016.
Minerva Neurosciences Inc., Form 424B5, Jun. 13, 2016.
Minerva Neurosciences Inc., Form 8-K, Aug. 7, 2014.
Minerva Neurosciences Inc., Form 8-K, Dec. 18, 2015.

(56) References Cited

OTHER PUBLICATIONS

Minerva Neurosciences Inc., Form 8-K, Dec. 29, 2015.
Minerva Neurosciences Inc., Form 8-K, Dec. 5, 2016.
Minerva Neurosciences Inc., Form 8-K, Dec. 9, 2015.
Minerva Neurosciences Inc., Form 8-K, Feb. 1, 2016.
Minerva Neurosciences Inc., Form 8-K, Feb. 22, 2016.
Minerva Neurosciences Inc., Form 8-K, Feb. 27, 2017.
Minerva Neurosciences Inc., Form 8-K, Jan. 11, 2016.
Minerva Neurosciences Inc., Form 8-K, Jan. 20, 2017.
Minerva Neurosciences Inc., Form 8-K, Jan. 21, 2015.
Minerva Neurosciences Inc., Form 8-K, Jan. 6, 2017.
Minerva Neurosciences Inc., Form 8-K, Jun. 13, 2016.
Minerva Neurosciences Inc., Form 8-K, Jun. 14, 2016.
Minerva Neurosciences Inc., Form 8-K, Jun. 16, 2015.
Minerva Neurosciences Inc., Form 8-K, Jun. 6, 2016.
Minerva Neurosciences Inc., Form 8-K, Mar. 11, 2016.
Minerva Neurosciences Inc., Form 8-K, Mar. 13, 2015.
Minerva Neurosciences Inc., Form 8-K, Mar. 26, 2015.
Minerva Neurosciences Inc., Form 8-K, Mar. 3, 2015.
Minerva Neurosciences Inc., Form 8-K, May 26, 2016.
Sifferlen et al., "Synthesis, structure-activity relationship studies, and identification of novel 5,6,7,8-tetrahydroimidazo[1,5-a]pyrazine derivatives as dual orexin receptor antagonists. Part 1", Bioorganic & Medicinal Chemistry Letters, Apr. 2013, 23, 2212-2216.
Smart et al., "Orexins and the treatment of obesity", European Journal of Pharmacology, Apr. 2002,440, 199-212.
Smart et al., "SB-334867-A: the first selective orexin-1 receptor antagonist", British Journal of Pharmacology, Mar. 2001, 132, 1179-1182.
Srinivasan et al., "Orexin Receptors Modulate Yohimbine-Induced Reinstatement of Ethanol Seeking and Gabaergic Transmission in the Central Amygdala", Alcoholism Clinical and Experimental Research, Jun. 2012, 36, S1, 116A.
Staner et al., "Comorbidity of insomnia and depression", Sleep Medicine Reviews, Feb. 2010, 14, 46-65.
Stasi et al., "Discovery, synthesis, selectivity modulation and DMPK characterization of 5-azaspiro[2.4]heptanes as potent orexin receptor antagonists", Bioorganic & Medicinal Chemistry Letters, May 2013, 23, 2653-2658.
Steiner et al. "Discovery and Characterization of ACT-335827, an Orally Available, Brain Penetrant Orexin Receptor Type 1 Selective Antagonist", Chem Med Chem, Jun. 2013, 8, 898-903.
Steiner et al., "Opportunities and perspectivesfor developing orexin receptor antagonists", Frontiers in Science, Jun. 2014, vol. 8, Article 158, 1-2.
Steiner et al., "The brain orexin system and almorexant in fear-conditioned startle reactions in the rat", Psychopharmacology, Oct. 2012, 223, 465-475.
Study NCT02067299; A Single Dose, 4-way Crossover, Placebo-controlled, Randomized Study to Investigate the Effect of JNJ-42847922 on Polysomnography (PSG) Measures in Subjects With Major Depressive Disorder With Insomnia Who Are Stably Treated With Antidepressants, submitted Feb. 19, 2014 (v1).
Sutcliffe et al., "The hypocretins: setting the arousal threshold", Nature Reviews Neuroscience, May 2002, 3, 339-349.
T.E. Scammell et al., 51 Annual Review of Pharmacology and Toxicology, 243-266 (2011).
Takahashi et al. "Stimulation of gastric acid secretion by centrally administered orexin-A in conscious rats", Biochem. Biophys. Res. Commun., 1999, 254 (3), pp. 623-627.
Takahashi, "Neuronal activity of orexin and non-orexin waking-active neurons during wake-sleep states in the mouse". Neuroscience, May 2008, 153, 860-870.
Trivedi et al., "Distribution of orexin receptor mRNA in the rat brain", FEBS Letters, Sep. 1998, 438, 71-75.
Uno, "P.1 k.037 Prescription survey of orexin receptor antagonist suvorexant", European Neuropsychopharmacology, Sep. 2015, vol. 25, Supplement 2, S373-S374.
Ursin et al., "Cognitive activation theory of stress (CATS)", Neuroscience and Biobehavioral Rev, May 2010, 34, 877-881.
Ursin et al., "The cognitive activation theory of stress", Psychoneuroendocrinology, Jun. 2004, 29, 567-592.
Van Den Pohl, "Hypothalamic hypocretin (orexin): Robust innervation of the spinal cord" J. Neurosci., 1999, 19(8), pp. 3171-3182.
Watson, "Rethinking the mood and anxiety disorders: a quantitative hierarchical model for DSM-V", J Abnorm Psychol, Nov. 1, 2005, 114(4), 522-536.
Whitman et al., "Discovery of a Potent, CNS-Penetrant Orexin Receptor Antagonist Based on an N,N-Disubstituted-1, 4-diazepane Scaffold that Promotes Sleep in Rats", Chem Med Chem, Jul. 2009, 4, 1069-1074.
Winrow et al., "Discovery and development of orexin receptor antagonists as therapeutics for insomnia", British Journal of Pharmacology, Jan. 2014, 171, 283-293.
Winrow, C. J., "Orexin receptor antagonism prevents transcriptional and behavioral plasticity resulting from stimulant exposure" Neuropharmacology 2010, 58(1):pp. 185-194.
Winsky-Sommerer et al., "Interaction between the corticotropin-releasing factor system and hypocretins (orexins): a novel circuit mediating stress response", J Neuroscience, Dec. 2004, 24(50), 11439-11448.
Yamanaka et al.", Orexins activate histaminergic neurons via the orexin 2 receptor", Biochem. Biophys. Res. Comm., Feb. 2002, 290 (4), 1237-1245.
Yeoh et al. "Orexin antagonists for neuropsychiatric disease: progress and potential pitfalls", Frontiers in Neuroscience, Feb. 25, 2014, 8, Article No. 36, 12 pages.
"A randomized, placebo-controlled, 2-way crossover, double-blind study to evaluate the efficacy, safety and tolerability of JNJ-42847922 in subjects with insomnia disorder without psychiatric comorbidity," Centrale Commissie Mensgebonden Onderzoek, dossier #54083.056.15, Jul. 28, 2015.
"A double-blind, randomized, controlled, 3-way crossover, pilot study to evaluate the duration of effects on simulated car driving and cognitive performance after a single dose of JNJ-42847922, zolpidem and placebo in healthy subjects," Centrale Commissie Mensgebonden Onderzoek, dossier #NL55279.056.15, Nov. 10, 2015.
"A single dose, 4-way crossover, double-blind, placebo-controlled, randomized study to investigate the effect ofJNJ-42847922 on polysomnography (PSG) measures in subjects with major depressive disorder with insomniawho are stably treated with antidepressants," Centrale Commissie Mensgebonden Onderzoek, dossier # NL47595.056.13, Jun. 18, 2014.
"An Exploratory Multicenter, Double-Blind, Diphenhydramine- and Placebo-Controlled Safety, Efficacy and Biomarker Study with JNJ-42847922 in Subjects with Major Depressive Disorder," Centrale Commissie Mensgebonden Onderzoek, dossier# NL53141.056.15, Aug. 17, 2015.
"An exploratory, multicenter, placebo-controlled, randomized, double-blind study to investigate the antidepressantmechanism-of-action of JNJ-42847922 in subjects with major depressive disorder," Centrale Commissie Mensgebonden Onderzoek, dossier# NL63487.056.17, Nov. 23, 2017.
Aissaoui et al., "N-Glycine-sulfonamides as potent dual orexin 1/orexin 2 receptor antagonists", Bioorganic & Medicinal Chemistry Letters, Nov. 2008, 18, 5729-5733.
Arendt et al., "Anxiolytic function of the orexin 2/hypocretin a receptor in the basolateral amygdala", Psychoneuroendocrinology, Feb. 2014, 40, 17-26.
Asnis et al., "Zolpidem for persistent insomnia in SSRI-treated depressed patients", J. Clin. Psychiatry, Oct. 1999, 60(10), 668-676.
Aston-Jones, G. et al., "Role of lateral hypothalamic orexin neurons in reward processing and addiction" Neuropharmacology 2009, 56 Supp.1 1:pp. 112-121.
Bagshawe, K., "Antibody-Directed Enzyme Prodrug Therapy: A Review" Drug Development Research 34:220-230, 1995.
Baxter et al., "The First Large-Scale Synthesis of MK-4305: A Dual Orexin Receptor Antagonist for the Treatment of Sleep Disorder", Organic Process Research & Development, Mar. 2011, 15, 367-375.
Berg, S. et al., "Pharmaceutical Salts" Journ. of Pharm. Sciences, 1977, 66:1-19, & Handbook of Pharmaceutical Salts, Properties, Selection & Use, Stahl and Wermuth, Eds., Wiley-VCH and VHCA, Zurich.

(56) References Cited

OTHER PUBLICATIONS

Bergman et al., "Proline bis-amides as potent dual orexin receptor antagonists", Bioorganic & Medicinal Chemistry Letters, Feb. 2008, 18, 1425-1430.
Bertolini, G., et al., "A New Rational Hypothesis for the Pharmacophore of the Active Metabolite of Leflunomide, a Potent Immunosuppressive Drug", J. Med. Chem 1997, 40, 2011-2016.
Betschart et al., "Identification of a Novel Series of Orexin Receptor Antagonists with a Distinct Effect on Sleep Architecture for the Treatment of Insomnia", Journal of Medicinal Chemistry, Oct. 2013, 56, 7590-7607.
Bettica et al., "Phase I studies on the safety, tolerability, pharmacokinetics and pharmacodynamics of SB-649868, a novel dual orexin receptor antagonist", Journal of Psychopharmacology, Aug. 2012, 26(8), 1058-1070.
Bettica et al., "The Orexin Antagonist Sb-649868 Promotes and Maintains Sleep in Men with Primary Insomnia", Sleep, Aug. 2012, 35(8), 1097-1104.
Bodor, N., "Novel Approaches to the Design of Safer Drugs: Soft Drugs and Site-Specific Chemical Delivery Systems", Advanced Drug Res., 1984 13, 224-231.
Boss et al. "Biomedical Application of Orexin/Hypocretin Receptor Ligands in Neuroscience", J. Med. Chem., 2009, 52(4), pp. 891-903.
Brisbare-Roch et al., "Promotion of sleep by targeting the orexin system in rats, dogs and humans", Nature Medicine, Feb. 2007, 13(2), 150-155.
Brosschot et al., "The perseverative cognition hypothesis: a review of worry, prolonged stress-related physiological activation, and health", J. Psychosomatic Res., Feb. 2006, 60, 113-124.
Brosschot, "Markers of chronic stress: prolonged physiological activation and (un)conscious perseverative cognition", neuroscience and Behavioral Rev., Sep. 2010, 35, 46-50.
Brucite, Van Nostrand's Encyclopedia of Chemistry, 5th ed., Considine, G.D., ed., 2005, 261.
Bundgaard, H. (Ed.), "Design of Prodrugs", Elsevier, 1985, 4 pages.
Chang et al., "Inhibitory effects of an orexin-2 receptor antagonist on orexin A- and stress-induced ACTH responses in conscious rats", Neuroscience Res., Mar. 2007, 57, 462-466.
Chemelli et al., "Narcolepsy in orexin knockout mice: Molecular genetics of sleep regulation", Cell, Aug. 1999, 98, 437-451.
Chen et al. "Pressor effects of orexins injected intracistemally and to rostral ventrolateral medulla of anesthetized rats", Am. J. Physiol., 2000, 278, pp. R692-R697.
Chen et al., "The Hypocretin/orexin system: An increasingly important role in neuropsychiatry", Medicinal Research reviews, Jan. 2015, 35(1), 152-197.
Chilean Application No. 1162-2010: Exam Report dated May 9, 2012, 6 pages.
Christopher, "Small-molecule antagonists of the orexin receptors", Pharmaceutical Patent Analyst, Pharm. Pat. Anal., Nov. 2014, 3(6), 625-638.
Clinical Trial NCT02476058 Report, ClinicalTrials.gov, Mar. 7, 2016.
Clinical Trial NCT02067299 Report, ClinicalTrials.gov, Feb. 3, 2016.
Clinical Trial NCT02230878 Report, ClinicalTrials.gov, Jan. 27, 2016.
Clinical Trial NCT02455856 Report, ClinicalTrials.gov, Jul. 24, 2015.
Clinical Trial NCT02464046 Report, ClinicalTrials.gov, Feb. 18, 2016.
Clinical Trial NCT02555124 Report, ClinicalTrials.gov, Feb. 22, 2016.
Clinical Trial NCT02578472 Report, ClinicalTrials.gov, Feb. 4, 2016.
Clinical Trial NCT02617810 Report, ClinicalTrials.gov, Feb. 19, 2016.
Clinical Trial NCT02661893 Report, ClinicalTrials.gov, Feb. 18, 2016.
Clinical Trial NCT03227224 Report, ClinicalTrials.gov, Jul. 21, 2017.
Clinical Trial NCT03375203 Report, ClinicalTrials.gov, Dec. 14, 2017.
Clinical Trial NCTNCT03321526 Report, ClinicalTrials.gov, Oct. 23, 2017.
Coleman et al "Discovery of 3,9-diazabicyclo[4.2.1]nonanes as potent dual orexin receptor antagonists with sleep-promoting activity in the rat" Bioorganic & Medicinal Chemistry Letters, 2010, 20 pp. 4201-4205.
Coleman et al. "Design and synthesis of conformationally constrained N, N-disubstituted 1,4-diazepanes as potent orexin receptor antagonists" Bioorganic & Medicinal Chemistry Letters, 2010, 20 pp. 2311-2315.
Coleman et al., "Discovery of [(2R,5R)-5-{[(5-Fluoropyridin-2-yl)oxy]methyl}-2-methylpiperidin-1-yl][5-methyl-2-(pyrimidin-2-yl)phenyl]methanone (MK-6096): A Dual Orexin Receptor Antagonist with Potent Sleep-Promoting Properties", Chem Med Chem, Mar. 2012, 7, 415-424.
Considine, G.D., ed., Van Nostrand's Encyclopedia of Chemistry, 5th ed. 2005 p. 261.
Covington et al., Handbook of Chemistry and Physics, 84th ed., 2003-2004 pp. 8-37 to 8-44.
Cox et al., "Conformational analysis of N,N-disubstituted-1,4-diazepane orexin receptor antagonists and implications for receptor binding", Bioorganic & Medicinal Chemistry Letters, Jun. 2009, 19, 2997-3001.
Cox et al., "Discovery of the dual orexin receptor antagonist [(7R)-4-(5-chloro-1,3-benzoxazol-2-yl)-7-methyl-1,4-diazepan-1-yl][(5-methyl-2-(2H-1,2,3-triazol-2-yl)phenyl] methanone (MK-4305) for the treatment of insomnia" Journal of Medicinal Chemistry 2010, 53(14):pp. 5320-5332.
Minerva Neurosciences Inc., Form 8-K, Nov. 6, 2014.
Minerva Neurosciences Inc., Form 8-K, Oct. 26, 2016.
Minerva Neurosciences Inc., Form 8-K, Sep. 24, 2015.
Minerva Neurosciences Inc., Form 8-K, Sep. 26, 2016.
Minerva Neurosciences Inc., Form DEF-14A, Apr. 29, 2016.
Minerva Neurosciences Inc., Form S-1, Apr. 9, 2014.
Minerva Neurosciences Inc., Form S-1, Jun. 10, 2014.
Minerva Neurosciences Inc., Form S-1A, Jun. 30, 2014.
Minerva Press Release, Feb. 1, 2016.
Minerva Press Release, Jan. 11, 2016.
Minerva Press Release, Jan. 21, 2015.
Minerva Press Release, Jun. 16, 2015.
Minerva Press Release, Mar. 11, 2016.
Minerva Press Release, Sep. 22, 2014.
Minerva Press Release, Sep. 24, 2015.
Moffitt et al., "Depression and generalized anxiety disorder. Cumulative and sequential comorbidity in a birth cohort followed prospectively to age 32 years", Arch Gen. Psychiatry, Jun. 2007, 64, 651-660.
Nakamura at al. "Orexin-induced hyperlocomotion end stereotypy are mediated by the dopaminergic system", Brain Res. 2000, 873 (1) pp. 181-187.
Nambu et al., "Distribution of orexin neurons in the adult rat brain", Brain Research, May 1999, 827, 243-260.
Nollet et al., "Activation of orexin neurons in dorsomedial/perifornical hypothalamus and antidepressant reversal in a rodent model of depression", Neuropharmacology, Jul.-Aug. 2011, 61(1-2), 336-346.
Nollet et al., "Neurogenesis-Independent Antidepressant-Like Effects on Behavior and Stress Axis Response of a Dual Orexin Receptor Antagonists in a Rodent Model of Depression", Neuropsychopharmacology, Sep. 2012, 37, 2210-2221.
Nollet et al., "Role of Orexin in the Pathophysiology of Depression: Potential for Pharmacological Intervention", CNS Drugs, Jun. 2013, 27(6), 411-422.
Nutt, D. et al., Sleep disorders as core symptoms of depression. Dialogues in Clinical Neuroscience, Sep. 30, 2008, vol. 10, No. 3, pp. 329-336 Whole document especially for table 1, pp. 329-330 section Incidence of sleep symptoms in depression.

(56) References Cited

OTHER PUBLICATIONS

Oi et al., "Synthesis and Evaluation of Novel Radioligands for Positron Emission Tomography Imaging of the Orexin-2 Receptor", Journal of Medicinal Chemistry, Jul. 2013, 56, 6371-6385.

P. Bonaventure et al., Characterization of JNJ-42847922, a Selective Orexin-2 Receptor Antagonist, as a Clinical Candidate for the Treatment of Insomnia. J. Pharmacol. Exp. Ther., Aug. 4, 2015, vol. 354, No. 3, pp. 471-482.

Panksepp et al., "Dynorphin and orexin interactions in the development and expression of depression-related anhedonia", Neuropsychopharmacology, Dec. 2011, 36, S1, S432-S433, Abstract 196.

Paulekuhn, "Trends in Active Pharmaceutical Ingredient Salt Selection based on Analysis of the Orange Book Database", J Med. Chem., Dec. 2007, 50, 6665-6672.

Perrey et al., "Diaryl urea analogues of SB-334867 as orexin-1 receptor antagonists", Bioorganic & Medicinal Chemistry Letters, May 2011, 21, 2980-2985.

Perrey et al., "Substituted Tetrahydroisoquinolines as Selective Antagonists for the Orexin 1 Receptor", Journal of Medicinal Chemistry, Sep. 2013, 56, 6901-6916.

Peyron et al, "Neurons Containing Hypocretin (Orexin) Project to Multiple Neuronal Systems", Journal of Neuroscience, Dec. 1998, 18(23), 9996-10015.

Peyron et al. "A mutation in a case of early onset narcolepsy and a generalized absence of hypocretin peptides in human narcoleptic brains", Nature Med. 2000, 6 (9), pp. 991-997.

Peyron et al. "Neurons containing hypocretin (Orexin) project to multiple neuronal systems" J. Neurosci., 1998, 18(23), pp. 9996-10015.

Piper et al. "The novel brain neuropeptide, orexin-A, modulates the sleep-wake cycle of rats", European Journal of Neuroscience, 2000, 12 (2), pp. 726-730.

Porter et al., "1,3-Biarylureas as Selective Non-peptide Antagonists of the Orexin-1 Receptor", Bioorganic & Medicinal Chemistry Letters, Jul. 2001, 11, 1907-1910.

Psychiatria et Neurologia Japonica, Choosing the Adequate Antidepressant Focusing on Efficacy, Tolerability and its Predictors, 2012, vol. 114, No. 5, p. 589-600.

Renzulli et al., "Disposition and Metabolism of [.sup.14C]SB-649868, an Orexin 1 and 2 Receptor Antagonist, in Humans", Drug Metabolism and Disposition, Feb. 2011, 39(2), 215-227.

Richards, J.K. et al., "Inhibition of orexin-1/hypocretin-1 receptors inhibits yohimbine-induced reinstatement of ethanol and sucrose seeking in Long-Evans rats" Psychophemacoloty 2008, 199(1):pp. 109-117.

Robinson, "Discovery of the Hemifumarate and (Alpha)-L-Alanyloxy)methyl Ether as Prodrugs of an Antirheumatic Oxindole: Prodrugs for the Enolic OH Group", J. Med. Chem., Jan. 1996, 39(1), 10-18.

Roecker et al., "Discovery of 5"-Chloro-N-[(5,6-dimethoxypyridin-2-yl)methyl]-2,2':5',3'-terpyridine-3'-carboxamide (MK-1064): A Selective Orexin 2 Receptor Antagonist (2-SORA) for the Treatment of Insomnia", Chem Med Chem, Feb. 2014, 9, 311-322.

Sakurai, T. "Orexins and orexin receptors: implication in feeding behavior" Regulatory Peptides 1999, 85(1): pp. 25-30.

Sakurai, T. et al., "Orexins and orexin receptors: a family of hypothalamic neuropeptides and G protein coupled receptors that regulate feeding behavior" Cell, Feb. 1998, 92(4), 573-585.

Sakurai, T., "The neural circuit of orexin (hypocretin): maintaining sleep and wakefulness", 2007, Nature Reviews Neuroscience, 8(3): pp. 171-181.

Samson et al. "Cardiovascular regulatory actions of the hypocretins in brain", Brain Res., 1999, 831: pp. 248-253.

Scammell et al., "Orexin Receptors: Pharmacology and Therapeutic Opportunities", Annual Review of Pharmacology and Toxicology, Feb. 2011, 51, 243-266.

Schneider, E. R., "Orexigenic peptides and alcohol intake: differential effects of orexin, gafanin, and ghrelin" Alcoholism: Clinical & Experimental Research 2007, 31(11):pp. 1858-1865.

Scott et al., "Hcrtr1 and 2 signaling differentially regulates depression-like behaviors", Behavioural Brain Research, Sep. 23, 2011, 222, 2, 289-294.

Shan, D. et al., "Prodrug Strategies Based on the Intramolecular Cyclization Reactions" J. Pharm. Sci., Jul. 1997, 86(7), 765-767.

Shirasaka et al."Sympathetic and cardiovascular actions of orexins in conscious rats", Am. J. Physio.., 1999, 277. pp. R1780-R1785.

Sifferlen et al., "Discovery of substituted lactams as novel dual orexin receptor antagonists. Synthesis, preliminary structure-activity relationship studies and efforts towards improved metabolic stability and pharmacokinetic properties. Part 1", Bioorganic & Medicinal Chemistry Letters, 24, Feb. 2014, 1201-1208.

Sifferlen et al., "Novel pyrazolo-tetrahydropyridines as potent orexin receptor antagonists", Bioorganic & Medicinal Chemistry Letters, Mar. 2010, 20, 1539-1542.

Sifferlen et al., "Structure-activity relationship studies and sleep-promoting activity of novel 1-chloro-5,6,7,8-tetrahydroimidazo[1,5-a]pyrazine derivatives as dual orexin receptor antagonists. Part 2", Bioorganic & Medicinal Chemistry Letters, Jul. 2013, 23, 3857-3863.

Shariq et al., Evaluating the role of orexins in the pathophysiology and treatment of depression: A comprehensive review, Progress in Neuro-Psychopharmacology and Biological Psychiatry, vol. 92, 2019, 1-7.

Stewart et al., "Insomnia Comorbidity and Impact and Hypnotic Use by Age Group in a National Survey Population Aged 16 to 74 Years," Sleep, vol. 29, Issue 11, 2006, pp. 1391-1397.

Summers et al., "Orexin/hypocretin receptor modulation of anxiolytic and antidepressive responses during social stress and decision-making: Potential for therapy," Brain Research, vol. 1731, 2020, 146085, pp. 1-15.

Surova et al., "Fatigue and brain arousal in patients with major depressive disorder," European Archives of Psychiatry and Clinical Neuroscience, vol. 271, 2021, pp. 527-536.

Thase et al., "Efficacy and safety of brexpiprazole as adjunctive treatment in major depressive disorder: overview of four short-term studies," Expert Opinion on Pharmacotherapy, vol. 20, Issue 15, 2019, pp. 1907-1916.

Ucok et al., "Side effects of atypical antipsychotics: a brief overview," World Psychiatry, vol. 7, Issue 1, 2008, pp. 58-62.

Wang et al., "Association between residual symptoms and social functioning in patients with depression," Comprehensive Psychiatry, vol. 98, 2020, 152164, pp. 1-5.

Wassing et al., "Slow dissolving of emotional distress contributes to hyperarousal," PNAS, vol. 113, Issue 9, 2016, pp. 2583-2543.

Yates et al., "Slow dissolving of emotional distress contributes to hyperarousal," J Clin Psychiatry, vol. 9, Issue 1, 2007, pp. 7-15.

Young et al., "Improvements in Neurocognitive Function and Mood Following Adjunctive Treatment with Mifepristone (RU-486) in Bipolar Disorder," Neuropsychopharmacology, vol. 29, 2004, pp. 1538-1545.

Yun et al., "Selective Inhibition of Orexin-2 Receptors Prevents Stress-Induced ACTH Release in Mice," Frontiers in Behavioral Neuroscience, vol. 11, 2017, pp. 1-7.

Zhang et al., "Switching of the Microglial Activation Phenotype Is a Possible Treatment for Depression Disorder," Frontiers in Cellular Neuroscience, vol. 12, 2018, pp. 1-13.

Agargun et al., "Sleep disturbances and suicidal behavior in patients with major depression," J Clin Psychiatry, vol. 58, Issue 6, 1997, pp. 249-251.

Albert, "Adult neuroplasticity: A new "cure" for major depression?," J Psychiatry Neuroscience, vol. 44, Issue 3, 2019, pp. 147-150.

Allen, "Economic Burden and Managed Care Considerations for the Treatment of Insomnia," vol. 26, Issue 4, 2020, pp. 1-11.

Arendt et al., "Depressive Behavior and Activation of the Orexin/Hypocretin System," Behavioral Neuroscience, vol. 127, Issue 1, 2013, pp. 86-94.

Bagherzadeh-Azbari et al., "Neuroimaging insights into the link between depression and Insomnia: A systematic review," Journal of Affective Disorders, vol. 258, 2019, pp. 133-143.

Basta et al., "Chronic Insomnia and Stress System," Sleep Med Clin., vol. 2, Issue 2, 2007, pp. 279-291.

(56) References Cited

OTHER PUBLICATIONS

Boland et al., "Preliminary support for the role of reward relevant effort and chronotype in the depression/insomnia comorbidity," J Affect Disord., vol. 242, 2019, pp. 220-223.

Brooks et al.,"The selective orexin-2 receptor antagonist seltorexant improves sleep: An exploratory double-blind, placebo controlled, crossover study in antidepressant-treated major depressive disorder patients with persistent insomnia," Journal of Psychopharmacology, vol. 33 Issue 2, 2019, pp. 202-209.

Carney et al., "A Comparison of Rates of Residual Insomnia Symptoms Following Pharmacotherapy or Cognitive-Behavioral Therapy for Major Depressive Disorder," The Journal of Clinical Psychiatry, 68(2), 2007, pp. 254-260 (Abstract).

Chieffi et al., "Orexin System: The Key for a Healthy Life," Frontiers in Physiology, 8:357, 2017, pp. 1-99.

Connor et al., "Phase II Proof-of-Concept Trial of the Orexin Receptor Antagonist Filorexant (MK-6096) in Patients with Major Depressive Disorder," International Journal of Neuropsychopharmacology, vol. 20, Issue 8, 2017, pp. 613-618.

Corponi et al., "Pharmacogenetics and Depression: A Critical Perspective," Korean Neuropsychiatric Association, vol. 16, Issue 9, 2019, pp. 645-653.

Dombrovski et al., "Residual symptoms and recurrence during maintenance treatment of late-life depression," J Affect Disord., vol. 103, Issue 1-3, 2007, pp. 77-82.

Fang et al., "Depression in sleep disturbance: A review on a bidirectional relationship, mechanisms and treatment," J Cell Mol Med., vol. 23, 2019, pp. 2324-2332.

Firouzabadi et al., "Orexin/Hypocretin Type 2 Receptor (HCRTR2) Gene as a Candidate Gene in Sertraline-Associated Insomnia in Depressed Patients," Neuropsychiatric Disease and Treatment, vol. 16, 2020, pp. 1121-1128.

Franzen et al., "Sleep disturbances and depression: risk relationships for subsequent depression and therapeutic implications," Dialogues in Clinical Neuroscience, vol. 10, Issue 4, 2008, pp. 473-481.

Germain et al., "Neurobiology of Non-REM Sleep in Depression: Further Evidence for Hypofrontality and Thalamic Dysregulation," Am J Psychiatry, vol. 161, 2004, pp. 1865-1863.

Gold et al., "Organization of the stress system and its dysregulation in melancholic and atypical depression: high vs low CRH/NE states," Molecular Psychiatry, vol. 7, 2002, pp. 254-275.

Grafe et al., "Orexins and stress," Front Neuroendocrinol, vol. 51, 2018, pp. 132-145.

Greden et al., "Impact of pharmacogenomics on clinical outcomes in major depressive disorder in the Guided trial: A large, patient- and rater-blinded, randomized, controlled study," Journal of Psychiatric Research, vol. 111, 2019, pp. 59-67.

Han et al., "Orexin Receptor Antagonists as Emerging Treatments for Psychiatric Disorders," Neurosci. Bull., vol. 36, 2020, pp. 432-448.

Hill et al., "The Therapeutic Potential of the Endocannabinoid System for the Development of a Novel Class of Antidepressants", Trends in Pharmacological Sciences, vol. 30, No. 9, 2009, 484-493.

Ho et al., "Brain Glucose Metabolism During Non-Rapid Eye Movement Sleep in Major Depression," Arch Gen Psychiatry, vol. 53, 1996, pp. 645-652.

Inutsuka et al., "The physiological role of orexin/hypocretin neurons in the regulation of sleep/wakefulness and neuroendocrine functions," Front. Endocrinol., vol. 4, 2013, pp. 1-10.

Jha, "Selective Orexin Receptor Antagonists as Novel Augmentation Treatments for Major Depressive Disorder: Evidence for Safety and Efficacy From a Phase 2B Study of Seltorexant," International Journal of Neuropsychopharmacology, vol. 25, Issue 1, 2022, pp. 85-88.

Jindal et al., Treatment of insomnia associated with clinical depression, Sleep Medicine Reviews, vol. 8, 2004, pp. 19-30.

Katz et al., "The Relationship Between Insomnia and Health-Related Quality of Life in Patients With Chronic Illness," The journal of family practice, vol. 51, Issue 3, 2002, pp. 229-235.

Katzman et al., "Neurobiology of the Orexin System and Its Potential Role in the Regulation of Hedonic Tone," Brain Sci., vol. 12(2): 150, 2022, pp. 1-15.

Leerssen et al., "Brain structural correlates of insomnia severity in 1053 individuals with major depressive disorder:results from the ENIGMA MDD Working Group," Translational Psychiatry, vol. 10:425, 2020, pp. 1-11.

Leggett et al., "The Association of Insomnia and Depressive Symptoms with All-Cause Mortality among Middle-Aged and Older Adults," Int J Geriatr Psychiatry, vol. 33, Issue 9, 2018, pp. 1265-1270.

Li et al., "Increased Hypocretin (Orexin) Plasma Level in Depression, Bipolar Disorder Patients," Frontiers in Psychiatry, vol. 12, 2021, pp. 1-7.

Li et al., "Insomnia and the risk of depression: a meta-analysis of prospective cohort studies," BMC Psychiatry, vol. 16, Article 375, 2016, pp. 1-16.

Li et al., "Major Depressive Disorder: Advances in Neuroscience Research and Translational Applications," Neurosci. Bull., vol. 37, Issue 6, 2021, pp. 863-880.

Liu et al., "Increased Salience Network Activity in Patients With Insomnia Complaints in Major Depressive Disorder," Frontiers in Psychiatry, vol. 9, Article 93, 2018, pp. 1-9.

Marek et al., "Orexin 2 Receptor Antagonists from Prefrontal Cortical Circuitry to Rodent Behavioral Screens," Chapter 5 in Antidepressants Preclinical, Clinical, and Translational Aspects, Ed. Olivier, IntechOpen, London, 2019, pp. 1-19.

Mason et al., "Focusing on Insomnia Symptoms to Better Understand Depression: a STAR*D Report," J Affect Disord, vol. 260, 2020, pp. 183-186.

Murphy et al., "Sleep Disturbances in Depression," Sleep Med Clin, vol. 10, Issue 1, 2015, pp. 17-23.

Nakamura et al., "Neuroendocrine, Autonomic, and Metabolic Responses to an Orexin Antagonist, Suvorexant, in Psychiatric Patients with Insomnia," Innov Clin Neurosci., vol. 14, Issue 3-4, 2017, pp. 30-37.

Ohayon et al., "Place of chronic insomnia in the course of depressive and anxiety disorders," Journal of Psychiatric Research, vol. 37, 2003, pp. 9-15.

Park et al., "Prevalence and Clinical Correlates of Insomnia in Depressive Disorders: The CRESCEND Study," Korean Neuropsychiatric Association, vol. 10, 2013, pp. 373-381.

Perlis et al., "Self-reported sleep disturbance as a prodromal symptom in recurrent depression," Journal of Affective Disorders, vol. 42, 1997, pp. 209-212.

Peterson et al., "Insomnia and psychiatric disorders," Psychiatric Annals, vol. 38, Issue 9, 2008, p. 1.

Pigeon et al., "Insomnia and Depression: Birds of a Feather?," Int J Sleep Disorders, vol. 1, Issue 3, 2007, pp. 82-91.

Pigeon et al., "Is Insomnia a Perpetuating Factor for Late-Life Depression in the IMPACT Cohort?," Sleep, vol. 31, Issue 4, 2008, pp. 481-488.

Radulescu et al., "Neuroplasticity and depression: Rewiring the brain's networks through pharmacological therapy (Review)," Experimental and Therapeutic Medicine, vol. 22(4), 2021, pp. 1-8.

Recourt et al., "The selective orexin-2 antagonist seltorexant (JNJ-42847922/MIN-202) shows antidepressant and sleep-promoting effects in patients with major depressive disorder," Translational Psychiatry, vol. 9, Issue 216, 2019, pp. 1-10.

Riemann et al., "Sleep, insomnia, and depression," Neuropsychopharmacology, vol. 45, 2020, pp. 74-89.

Salas et al., "Increased Use-Dependent Plasticity in Chronic Insomnia," Sleep, vol. 37, Issue 3, 2014, pp. 535-544.

Salomon et al., "Diurnal Variation of Cerebrospinal Fluid Hypocretin-1 (Orexin-A) Levels in Control and Depressed Subjects," Biol Psychiatry, vol. 54, 2003, pp. 96-104.

Savitz et al., "Efficacy and Safety of Seltorexant as Adjunctive Therapy in Major Depressive Disorder: A Phase 2b, Randomized, Placebo-Controlled, Adaptive Dose-Finding Study," International Journal of Neuropsychopharmacology, vol. 24, Issue 12, 2021, pp. 965-976.

(56) References Cited

OTHER PUBLICATIONS

Cruz et al., "Interaction study between almorexant, a dual orexin receptor antagonist, and desipramine in healthy male subjects", European Neuropsychopharmacology, Aug. 2010, Vo. 20, Suppl. 3, S253, Abstract No. P.1.c.032.

Cruz et al., "Interaction study between almorexant, a dual orexin receptor antagonist, and desipramine in healthy male subjects", European Neuropsychopharmacology, Aug. 2010, vol. 20, Suppl. 3, S253, Abstract No. P.1.C.032.

Dayas, C. V. et al., "Stimuli linked to ethanol availability activate hypothalamic CART and orexin neurons in a reinstatement model of relapse", Biological Psychiatry, Jan. 2008, 63(2),152-157.

De Lecea et al., "Optogenetic control of hypocretin/orexin neurons", Abstracts of Papers, 248th ACS National Meeting & Exposition, Aug. 2014, 1 page.

De Lecea et al., "The hypocretins: Hypothalamus-specific peptides with neuroexcitatory activity", Proc. Natl. Acad. Sci., Jan. 1998, 95, 322-327.

Difabio et al., "Discovery process and pharmacological characterization of a novel dual orexin 1 and orexin 2 receptor antagonist useful for treatment of sleep disorders", Bioorganic & Medicinal Chemistry Letters, Sep. 2011, 21, 5562-5567.

Dugovic et al., "Blockade of Orexin-1 Receptors Attenuates Orexin-2 Receptor Antagonism-Induced Sleep Promotion in the Rat", The Journal of Pharmacology and Experimental Therapeutics, Jul. 2009, 330(1), 142-151.

Dugovic et al., "Orexin-1 receptor blockade dysregulates REM sleep in the presence of orexin-2 receptor antagonism", Frontiers in Neuroscience, Feb. 2014, vol. 8, Article 29, 1-8.

European Patent Application. No. 10773477.4: Communication pursuant to Article 94(3) EPC dated Apr. 19, 2013, 3 pages.

Feng et al., "Brain orexins and wake regulation in rats exposed to maternal deprivation", Brain Research, Jun. 2007, 1154, 163-172.

Fitch et al., "LSN2424100: a novel, potent orexin-2 receptor antagonist with selectivity over orexin-1 receptors and activity in an animal model predictive of antidepressant-like efficacy", Frontiers in Neuroscience, Jan. 2014, 8, Article 5, 11 pages.

Fleisher, D. et al., "Improved Oral Drug Delivery: Solubility Limitations Overcome by the Use of Prodrugs", Advanced Drug Delivery Reviews, May 1996, 19, 115-130.

Frost, J., et al., "Synthesis and Structure-Activity Relationships of 3,8-Diazabicylclo [4.2.0] Octane Ligands, Potent Nicotinic Acetylcholine Receptor Agonists" J. Med. Chem. 2006, 49, 7843-7853.

Fujimoto et al., "Discovery of potent, selective, orally active benzoxazepine-based Orexin-2 receptor antagonists", Bioorganic & Medicinal Chemistry Letters, Nov. 2011, 21, 6414-6416.

Fujimoto et al., "Discovery of spiropiperidine-based potent and selective Orexin-2 receptor antagonists", Nov. 2011, 21, 6409-6413.

Gatfield et al., "Orexin Receptor Antagonists: A New Concept in CNS Disorders?", Chem Med Chem, Aug. 2010, 5, 1197-1214.

Georgescu, D. et al., "Involvement of the lateral hypothalamic peptide orexin in morphine dependence and withdrawal" Journal of Neuroscience 2003, 23(8), pp. 3106-3111.

Girardin et al., "Convergent Kilogram-Scale Synthesis of Dual Orexin Receptor Antagonist", Organic Process Research & Development, Jan. 2013, 17, 61-68.

Goldberg et al., "The importance of anxiety in both major depression and bipolar disorder", Depression and Anxiety, Jan. 2012, 29, 471-478.

Gotter et al., "International Union of Basic and Clinical Pharmacology. LXXXVI. Orexin Receptor Function, Nomenclature and Pharmacology", Pharmacological Reviews, Jul. 2012, 64(3), 389-420.

Gotter et al., "Orexin receptors as therapeutic drug targets", Progress in Brain Research, 2012, 198, 163-188.

Gozzi et al., "Functional Magnetic Resonance Imaging Reveals Different Neural Substrates for the Effects of Orexin-1 and Orexin-2 Receptor Antagonists", PLoS One, Jan. 2011, 6(1), e16406, 12 pages.

Gulbahar et al., "P-169, Plasma Orexin-A Levels Of Patients With Major Depression", Turkish Journal of Biochemistry, 22th National Biochemistry Congress, Oct. 27-30, 2010, vol. 35, Issue 1, 2 pages.

Hamlin, A. S. et al., "The neural correlates and role of D1 dopamine receptors in renewal of extinguished alcohol-seeking" Neuroscience 2007, 146(2) pp. 525-536.

Hara et al. "Genetic ablation of orexin neurons in mice results in narcolepsy, hypophagia, and obesity", Neuron, 2001, 30 (2), pp. 345-354.

Hassani et al., "Orexin Neurons Respond Differentially to Auditory Cues Associated with Appetitive versus Aversive Outcomes", J. Neuroscience, Feb. 2016, 36(5), 1747-1757.

Hirose et al., "N-Acyl 6,7-Dimethoxy-1,2,3,4-tetrahydroisoquinoline: The First Orexin-2 Receptor Selective Non peptidic Antagonist", Bioorganic & Medicinal Chemistry Letters, Dec. 2003, 13, 4497-4499.

International Patent Application No. PCT/US2010/053606: International Search Report dated Jan. 12, 2011, 3 pages.

International Patent Application No. PCT/US2010/053609: International Search Report dated Jan. 24, 2011, 3 pages.

International Patent Application No. PCT/US2010/053611: International Search Report dated Dec. 10, 2010, 4 pages.

International Search Report and Written Opinion dated Jun. 6, 2017 issued in International Patent Application No. PCT/US17/21565.

International Search Report dated Dec. 10, 2010, Int'l. App. No. PCT/US2010/053611, filing date Oct. 21, 2010.

J.H. Poupaert, Drug Design: Basic Principles and Applications, in 2 Encyclopedia of Pharmaceutical Technology 1362-1369 (James Swarbrick ed., 3rd ed., 2007).

Jiang et al., "Disubstituted piperidines as potent orexin (hypocretin) receptor antagonists", Bioorganic & Medicinal Chemistry Letters, Jun. 2012, 22, 3890-3894.

Johnson et al., "A key role for orexin in panic anxiety", Nature Medicine, Jan. 2010, vol. 16, No. 1, 111-115.

Johnson et al., "Orexin, stress, and anxiety/panic states", Progress in Brain Research, 2012, 198, 133-161.

Kane, J.K. et al., "Hypothalamic orexin-A binding sites are downregulated by chronic nicotine treatment in the rat" Neuroscience Letters 2001, 298(1):pp. 1-4.

Kane, J.K. et al., "Nicotine Up-Regulates Expression of Orexin and Its Receptors in Rat Brain" Endocrinology 2000 141(10). pp. 3623-3629.

Kang et al., "Amyloid-.beta. Dynamics Are Regulated by Orexin and the Sleep-Wake Cycle", Science Express, 2009 , pp. 1-10.

Kirchgessner and Liu "Orexin synthesis and response in the gut", Neuron, 1999, 24 (4), pp. 941-951.

Kuduk et al., "Orexin receptor antagonists in development for Insomnia and CNS disorders", Annual Reports in medicinal Chemistry, 2013, 48, 73-87.

Kuduk et al., "Synthesis and evaluation of carbon-linked analogs of dual orexin receptor antagonist filorexant", Bioorganic & Medicinal Chemistry Letters, Apr. 2014, 24, 1784-1789.

Kuehn et al., "Hormone may play role in triggering panic attacks", JAMA—Journal of the American Medical Association, Feb. 10, 2010, 303, 6, 498.

Langmead et al. "Characterisation of the binding of (3H)-SB-674042, a novel nonpeptide antagonist, to the human orexin 1 receptor", British Journal of Pharmacology 2004, 141 (2), pp. 340-346.

Larsen, "Design and Application of Prodrugs, Drug Design and Development", 1991, Krogsgaard-Larsen, et al., eds., Harwood Academic Publishers, 18 pages.

Lawrence, et al., "The orexin system regulates alcohol-seeking in rats" British Journal of Pharmacology 2006, 148(6) pp. 752-759.

Lebold et al., "Selective orexin receptor antagonists", Bioorganic & Medicinal Chemistry Letters, Sep. 2013, 23, 4761-4769.

Lee, "Discharge of Identified Orexin/Hypocretin Neurons across the Sleep-Walking Cycle", J. Neuroscience, Jul. 2005, 25(8), 6716-6720.

Leman et al., "Role of orexin in the unpredictable chronic mild stress model of depression in mice", European Neuropsychopharmacology, Oct. 2012, 22, S2, S146, Abstract S.27.04.

(56) References Cited

OTHER PUBLICATIONS

Letavic et al., "Novel Octahydropyrrolo [3,4-c ]pyrroles Are Selective Orexin-2 Antagonists: SAR Leading to Clinical Candidate", Journal of Medicinal Chemistry, Jul. 8, 2015, vol. 58, No. 14, pp. 5620-5636.

* cited by examiner

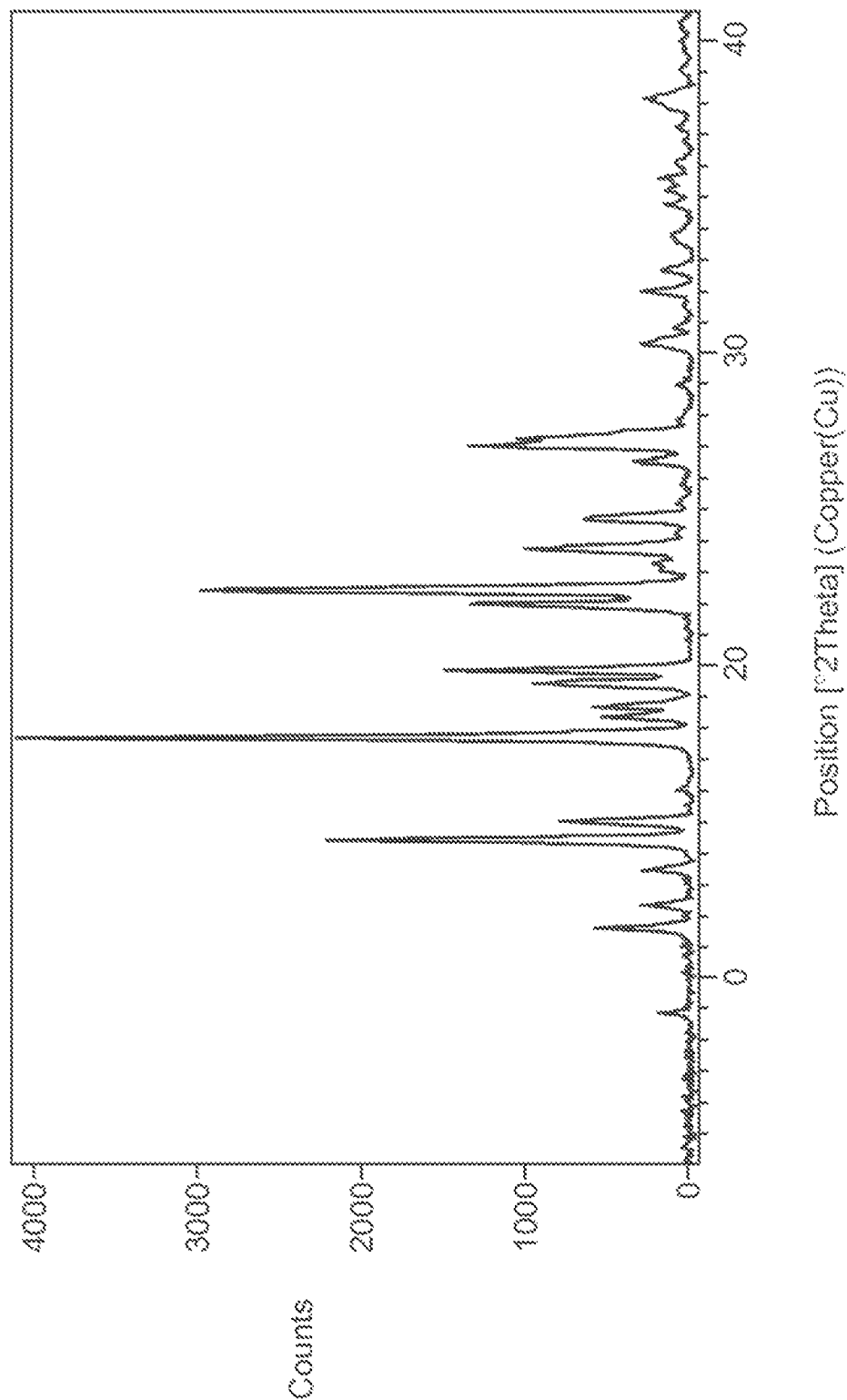

DISUBSTITUTED OCTAHYDROPYRROLO[3,4-C]PYRROLES AS OREXIN RECEPTOR MODULATORS

CROSS REFERENCE TO RELATED APPLICATIONS

This application is a continuation of U.S. patent application Ser. No. 16/601,832, filed Oct. 15, 2019, which is a continuation of U.S. patent application Ser. No. 15/413,965, filed Jan. 24, 2017, which is a continuation of U.S. patent application Ser. No. 14/734,225, filed Jun. 9, 2015, which is a continuation of U.S. patent application Ser. No. 14/138,941, filed Dec. 23, 2013, which is a continuation of U.S. patent application Ser. No. 13/503,231, filed Apr. 20, 2012, which is a national stage under 35 U.S.C. 371 of International Patent Application No. PCT/US2010/053606, filed Oct. 21, 2010, which claims benefit of priority under 35 U.S.C. § 119(e) of U.S. Provisional Patent Application No. 61/254,509 filed Oct. 23, 2009, the disclosures of which are hereby incorporated by reference in their entirety.

TECHNICAL FIELD

The present invention relates to certain disubstituted octahydropyrrolo[3,4-c]pyrrole compounds, pharmaceutical compositions containing them, methods of making them, and methods of using them for the modulation of the orexin receptor and for the treatment of disease states, disorders, and conditions mediated by orexin receptor activity.

BACKGROUND

Orexin (or hypocretin) signaling is mediated by two receptors and two peptide agonists. The two orexin peptides (orexin A and orexin B) herein after referred to as orexins, bind to two high affinity receptors, termed orexin-1 and orexin-2 receptors. The orexin-1 receptor is selective in favor of orexin A, while the orexin-2 receptor binds both orexins with similar affinities. The orexins are cleavage products of the same gene, prepro orexin. In the central nervous system neurons expressing prepro-orexin, the precursor from which orexin is produced, are found in the perifornical nucleus, the dorsal hypothalamus and the lateral hypothalamus (C. Peyron et al., *J. Neurosci.*, 1998, 18(23), 9996-10015). Orexinergic cells in these nuclei project to many areas of the brain, extending rostrally to the olfactory bulbs and caudally to the spinal cord (van den Pol, A. N. et al., *J. Neuroscience.*, 1999, 19(8), 3171-3182).

The broad CNS distribution of orexin projections and neurons expressing orexin receptors is suggestive of orexin involvement in a number of physiological functions including; feeding, drinking, arousal, stress, reward, metabolism and reproduction (T. Sakurai, *Nature Reviews Neuroscience*, 2007, 8(3), 171-181).

The targeted necrosis of cells expressing prepro-orexin suggests the most physiologically important roles of the orexins are likely to be effects on arousal, feeding and metabolism (J. Hara et al., *Neuron*, 2001, 30, 345-354). A prominent orexin neuronal projection via the vagus nerve probably mediates central orexin effects on cardiac parameters (W. K. Samson et al., *Brain Res.*, 1999, 831, 248-253; T. Shirasaka et al., *Am. J. Physiol.*, 1999, 277, R1780-R1785; C.-T. Chen et al., *Am. J. Physiol.*, 2000, 278, R692-R697), gastric acid secretion and gastric motility (A. L. Kirchgessner and M.-T. Liu, *Neuron*, 1999, 24, 941-951; N. Takahashi et al., *Biochem. Biophys. Res. Commun.*, 1999, 254, 623-627).

Several lines of evidence indicate that the orexin system is an important modulator of arousal. Rodents administered orexins intracerebroventricularly spend more time awake (Piper et al., *J. Neurosci.* 2000, 12, 726-730). Orexin-mediated effects on arousal have been linked to orexin neuronal projections to histaminergic neurons in the tubero-mammillary nucleus (TMN) (Yamanaka et al., *Biochem. Biophys. Res. Comm.* 2002, 290, 1237-1245). TMN neurons express the orexin-2 receptor primarily, and the orexin-1 receptor to a lesser extent. Rodents whose prepro orexin gene has been knocked out, or whose orexigenic neurons have been lesioned, display altered sleep/wake cycles similar to narcolepsy (Chemelli et al., *Cell* 1999, 98, 437-451; Hara et al., 2001, supra). Dog models of narcolepsy have been shown to have mutant or non-functional orexin-2 receptors (Lin et al., *Cell* 1999, 98, 365-376). Human narcolepsy appears to be linked to deficient orexin signaling, likely related to immune ablation of orexinergic neurons in the lateral hypothalamus (Mignot et al., *Am. J. Hum. Genet.* 2001, 68: 686-699; Minot & Thorsby, *New England J. Med.* 2001, 344, 692), or, in rare cases, to mutations in the orexin-2 gene (Peyron et al., *Nature Med.* 2000, 6, 991-997). The disclosure that rats, dogs and humans treated with the dual orexin-1/2 receptor antagonist, ACT-078573 (Brisbare-Roch et al., *Nature Medicine*, 2007, 13, 150-155) exhibited decreased alertness together with characteristic clinical and EEG (electroencephalographic) signs of sleep provides evidence to support a role for the orexin system in the regulation of arousal, sleep and wake states. EEG data indicates that orexin-2 may be more important than orexin-1 in the modulation of sleep/wake (P. Malherbe et al., *Molecular Pharmacology* (2009) 76(3):618-31; C. Dugovic et al., *J. Pharmacol. Exp. Ther.*, 2009, 330(1), 142-151). Disorders of the sleep-wake cycle are therefore likely targets for orexin-2 receptor antagonist therapy. Examples of such disorders include sleep-wake transition disorders, insomnia, restless legs syndrome, jet-lag, disturbed sleep, and sleep disorders secondary to neurological disorders (e.g., manias, depressions, manic depression, schizophrenia, and pain syndromes (e.g., fibromyalgia, neuropathic pain).

The orexin system also interacts with brain dopamine systems. Intracerebroventricular injections of orexins in mice increase locomotor activity, grooming and stereotypy; these behavioral effects are reversed by administration of $D_2$ dopamine receptor antagonists (Nakamura et al., *Brain Research*, 873(1), 181-7). Therefore, orexin-2 modulators may be useful to treat various neurological disorders; e.g., agonists or up-regulators to treat catatonia, antagonists or down-regulators to treat Parkinson's disease, Tourette's syndrome, anxiety, delirium and dementias.

Recent evidence indicates a role for orexin in the pathogenesis of Alzheimer's disease (Kang et al, *Science Express*, 2009, 1-10). Brain interstitial fluid levels of amyloid-beta were demonstrated to fluctuate diurnally in both humans and rodents with sleep deprivation in rodents leading to significant increases in brain interstitial fluid levels of amyloid-beta. Infusion of a dual orexin antagonist in rodents suppressed interstitial levels of amyloid-beta and abolished the natural diurnal variation of amyloid-beta. The reduction of interstitial fluid amyloid-beta levels is correlated with reduced amyloid plaque formation, a hallmark of Alzheimer's disease, and consequently the regulation of sleep time could potentially inhibit amyloid-beta aggregation and slow the progression of Alzheimer's disease.

Orexin neurons project to many regions of the brain associated with reward function (T. Sakurai, supra) and research, focusing on animal models of drug intake, reward, and reinstatement, has expanded the link between the orexin system and addiction. A comprehensive set of data suggest that drugs of abuse activate the orexin system, which in turn enhances drug reward or drug seeking (G. Aston-Jones et al., *Neuropharmacology*, 2009, 56 (Suppl 1) 112-121. Thus interactions between nicotine (J. K. Kane et al., *Endocrinology*, 2000, 141(10), 3623-3629; J. K. Kane et al., *Neurosci. Lett.*, 2001, 298(1), 1-4), morphine (D. Georgescu, et al., *J. Neurosci.*, 2003, 23(8), 3106-3111) and amphetamine (C. J. Winrow et al., *Neuropharmacology*, 2010, 58(1), 185-94) and the orexin system have been demonstrated. Additional studies from a number of laboratories have demonstrated an important relationship between the Orexin system and ethanol consumption. As examples, ethanol consumption in an alcohol-preferring strain of rat was shown to up regulate Orexin mRNA in the lateral hypothalamus and that an Orexin-1 receptor antagonist reduced operant responding for ethanol (Lawrence, et. al., *Br. J. Pharmacol.*, 2006, 148, 752-759). Treatment with an orexin-1 antagonist has also been shown to decrease operant responding for ethanol (Richards, et. al., *Psychopharmacology*, 2008, 199 (1), 109-117). Other studies have demonstrated increased Fos activation of orexin neurons following contextual reinstatement to ethanol seeking (Dayas, et. al., *Biol. Psychiatry*, 2008, 63 (2), 152-157 and Hamlin, et. al., *Neuroscience*, 2007, 146, 525-536). Studies have also shown increased ethanol consumption following Orexin infusion into the paraventricular nucleus of the hypothalamus or in the lateral hypothalamus (Schneider, et. al., *Alcohol. Clin. Exp. Res.*, 2007, 31(11), 1858-1865). These studies provide evidence that modulation of the Orexin system effects alcohol preference and therefore Orexin receptor antagonists are likely to be useful for the treatment of alcoholism.

Orexins and their receptors have been found in both the myenteric and submucosal plexus of the enteric nervous system, where orexins have been shown to increase motility in vitro (Kirchgessner & Liu, *Neuron* 1999, 24, 941-951) and to stimulate gastric acid secretion in vitro (Takahashi et al., *Biochem. Biophys. Res. Comm.* 1999, 254, 623-627). Orexin mediated effects on the gut may be driven by a projection via the vagus nerve (van den Pol, 1999, supra), as vagotomy or atropine prevent the effect of an intracerebroventricular injection of orexin on gastric acid secretion (Takahashi et al., 1999, supra). Orexin receptor antagonists or other down-regulators of orexin receptor-mediated systems are therefore potential treatments for ulcers, irritable bowel syndrome, diarrhea and gastroesophageal reflux.

Body weight may also be affected by orexin-mediated regulation of appetite and metabolism (T. Sakurai et al., *Cell*, 1998, 92(4), 573-585; T. Sakurai, *Reg. Pept.*, 1999, 85(1), 25-30). Some effects of orexin on metabolism and appetite may be mediated in the gut, where, as mentioned, orexins alter gastric motility and gastric acid secretion. Orexin receptor antagonists therefore are likely to be useful in treatment of overweight or obesity and conditions related to overweight or obesity, such as insulin resistance, type II diabetes, hyperlipidemia, gallstones, angina, hypertension, breathlessness, tachycardia, infertility, sleep apnea, back and joint pain, varicose veins and osteoarthritis. Conversely, orexin receptor agonists are likely to be useful in treatment of underweight and related conditions such as hypotension, bradycardia, amenorrhea and related infertility, and eating disorders such as anorexia and bulimia.

Intracerebroventricularly administered orexins have been shown to increase mean arterial pressure and heart rate in freely moving (awake) animals (Samson et al., *Brain Res.* 1999, 831, 248-253; Shirasaka et al., *Am. J. Physiol.* 1999, 277, R1780-R1785) and in urethane-anesthetized animals (Chen et al., *Am. J. Physiol.* 2000, 278, R692-R697), with similar results. Orexin receptor agonists may therefore be candidates for treatment of hypotension, bradycardia and heart failure related thereto, while orexin receptor antagonists may be useful for treatment of hypertension, tachycardia and other arrhythmias, angina pectoris and acute heart failure.

From the foregoing discussion, it can be seen that the identification of orexin receptor modulators, in one embodiment modulators of the orexin-2 receptor, will be of great advantage in the development of therapeutic agents for the treatment of a wide variety of disorders that are mediated through these receptor systems.

Citation of a reference herein shall not be construed as an admission that such reference is prior art to the present invention. All publications referred to herein are incorporated by reference in their entireties.

Various small-molecule orexin receptor modulators have been reported e.g., N-aroyl cyclic amine derivatives (International Publication No. WO2003002561, Jan. 9, 3003), ethylene diamine derivatives (International Publication No. WO2003051872, Jun. 26, 2003), sulfonylamino-acetic acid derivatives (International Publication No. WO2004033418, Apr. 22, 2004), N-aryl acetyl cyclic amine derivatives (International Publication No. WO2004041791, May 21, 2004), diazepan derivatives (International Publication No. WO2007126935, Nov. 8, 2007), amidoethylthioether derivatives (International Publication No. WO2007126934, Nov. 8, 2007), 2-substituted proline bis-amide derivatives (International Publication No. WO2008008551, Jan. 17, 2008), bridged diazepan derivatives (International Publication No. WO2008008517, Jan. 17, 2008), substituted diazepan derivatives (International Publication No. WO2008008518, Jan. 17, 2008; US20080132490, WO2009058238), oxo bridged diazepan derivatives (International Publication No. WO2008143856, Nov. 27, 2008), 1,2-diamido ethylene derivatives (International Publication No. WO2009022311, Feb. 19, 2009), heteroaryl derivatives (International Publication No. WO20090163485, Jun. 25, 2009), methyl substituted piperidinyl derivatives (International Publication No. WO2009124956, Oct. 15, 2009), N,N-disubstituted-1,4-diazepane derivatives (Cox et al, *Bioorganic & Medicinal Chemistry Letters*, 2009, 19(11), 2997-3001), Orexin/Hypocretin receptor ligands (Boss, et al., *Journal of Medicinal Chemistry*, 2009, 52(4), 891-903) 3,9-diazabicyclo[4.2.1]nonanes (Coleman et al, *Bioorganic & Medicinal Chemistry Letters*, 2010, 20(14), 4201-4205), the dual orexin receptor antagonist, [(7R)-4-(5-Chloro-1,3-benzoxazol-2-yl)-7-methyl-1,4-diazepan-1-yl][5-methyl-2-(2H-1,2,3-triazol-2-yl)phenyl]methanone, (Cox, et. al., *Journal of Medicinal Chemistry*, 2010 53(14) 5320-5332), pyridazine carboxamide derivatives (International Publication No. WO2010051238), 2,5-disubstituted benzamide derivatives (International Publication No WO2010051237, May 6, 2010), isonicotinamides (International Publication No WO2010051236), heterocyclylbenzoylpiperazines derivatives (International Publication No WO201048012), substituted diazepane derivatives (International Publication No WO2010048017), substituted pyrrolidine derivatives (International Publication No WO2010048014), triazolylbenzoylpiperidine derivatives (International Publication No WO2010048010), triazolylbenzoylmorpholine derivatives (WO2010048013), conformationally restrained N,N disubstituted 1,4-diazapane derivatives (Coleman et al, *Bioorganic & Medicinal Chemistry Letters*, 2010, 20(7), 2311-2315), tripyridyl carboxamide derivatives (International Publication No WO2010017260), imidazopyridylmethyl substituted piperidine derivatives (International Publication No WO2010072722), imidazopyrazine substituted piperidine derivatives (US2010160344, Jun. 24, 2010; US20100160345, Jun. 24, 2010; International Publication No WO2010060472, Jun. 3, 2010), N-{[(1R,4S,6R)-3-(2-pyridinylcarbonyl)-3-azabicyclo[4.1.0]hept-4-yl]methyl}-2-heteroarylamine derivatives (International Publication No WO2010063663), N-{[(1S,4S,6S)-3-(2-pyridinylcarbonyl)-3-azabicyclo[4.1.0]hept-4-yl]methyl}-2-heteroarylamine derivatives (International Publication No WO2010063662), imidazopyrimidine derivatives (International Publication No WO2010060471), and imidazopyrazine derivatives (International Publication No WO2010060470). There remains a need, however, for potent orexin receptor modulators with desirable pharmaceutical properties.

Substituted diaza-bicyclic compounds have been reported as active central nervous system agents (International Publication No. WO2001081347, Nov. 1, 2001; US2002/0019388, Feb. 14, 2002), α7 acetylcholine receptor modulators (US2005/101602, May 12, 2005; US2005/0065178, Mar. 24, 2005 and Frost et al, *Journal of Medicinal Chemistry*, 2006, 49(26), 7843-7853), proline transporter inhibitors for the treatment of cognitive impairment (WO2008067121, Jun. 5, 2008) and for improving cognition (WO 2006 124897, Nov. 23, 2006 and US20060258672, Nov. 16, 2006), as androgen receptor ligands for the treatment of androgen receptor associated conditions including cancer (WO2009081197, Jul. 2, 2009), and as histone deacetylase inhibitors for the treatment of cancers, neurodegenerative diseases and autoimmune diseases (WO20060123121, Nov. 23, 2006).

SUMMARY

Certain disubstituted octahydropyrrolo[3,4-c]pyrrole derivatives have been found to have orexin-modulating activity. Thus, the invention is directed to the general and preferred embodiments defined, respectively, by the independent and dependent claims appended hereto, which are incorporated by reference herein.

In one general aspect, the invention is directed to a chemical entity of Formula (I):

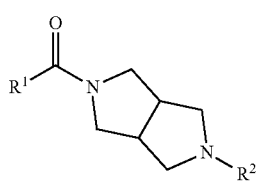

Formula (I)

wherein:
$R^1$ is a member selected from the group consisting of:
 A) phenyl substituted or unsubstituted with one or two $R^a$ members, and substituted in the ortho position with $R^b$;
  $R^a$ is independently selected from the group consisting of: —H, halo, —$C_{1-4}$alkyl, —$C_{1-4}$alkoxy, and —$NO_2$, wherein two adjacent $R^a$ members may come together to form a six membered aromatic ring;

$R^b$ is a member selected from the group consisting of:
 a) halo, —$C_{1-4}$alkoxy, —$C_{1-4}$alkyl, —$CF_3$, —$OCF_3$, or —CN;
 b) 5-membered heteroaryl ring containing one oxygen or one sulfur members;
 c) 5-6 membered heteroaryl ring containing one, two or three nitrogen members, optionally containing one oxygen member, substituted or unsubstituted with halo or —$C_{1-4}$alkyl; and
 d) phenyl substituted or unsubstituted with halo, —$CH_3$, or —$CF_3$;
B) pyridine substituted or unsubstituted with one or two $R^c$ members and substituted with $R^d$, wherein $R^d$ is positioned adjacent to the point of attachment by $R^1$;
 $R^c$ is $C_{1-4}$alkyl;
 $R^d$ is a member selected from the group consisting of:
  a) 5-6 membered heteroaryl ring selected from the group consisting of: 1H-1,2,3-triazol-1-yl, 2H-1,2,3-triazol-2-yl, 1H-pyrazol-5-yl, 3-methyl-1,2,4-oxadiazol-5-yl, pyridinyl, 3-methyl-pyridin-2-yl; 1-(tetrahydro-2H-pyran-2-yl)-1H-pyrazol-5-yl), phenyl, and pyrimidin-2-yl; and
  b) —$CF_3$, —Br, and —$C_{1-4}$alkoxy;
C) 5-membered heteroaryl ring selected from the group consisting of: 2-methyl-1,3-thiazol-yl, 1H-pyrazol-5-yl, oxazole, isoxazolyl, thiophen-2-yl, and furan-2-yl, each substituted with phenyl substituted or unsubstituted with —F; and
D) 5-13 membered aryl or heteroaryl ring selected from the group consisting of: 3-methylfuran-2-yl, 9H-fluorene, quinoline, cinnoline; 3-(1H-pyrrol-1-yl)thiophen-2-yl, 8-[1,2,3]-triazol-2-yl-naphthalen-1-yl, 2,3-dihydro-1,4-benzodioxin-5-yl, 1H-indol-7-yl, 4-fluoronaphthalen-1-yl, and naphthalen-1-yl;
$R^2$ is a member selected from the group consisting of:
A) 6-membered heteroaryl ring containing two nitrogen members substituted with one or more members independently selected from the group consisting of: halo, —$C_{1-4}$alkyl, —$CD_3$, -D, —$C_{1-4}$alkoxy, cyclopropyl, morpholin-2-yl, —$CO_2C_{1-4}$alkyl, —$CO_2H$, —$CH_2OH$, —$C(O)N(C_{1-4}alkyl)_2$, —$CF_3$, —CN, —OH, —$NO_2$, —$N(C_{1-4}alkyl)_2$, phenyl, furan-2-yl, thiophen-2-yl, 1H-pyrazol-4-yl, and pyrrolidin-1-yl;
B) pyridine substituted with one or two members independently selected from the group consisting of: halo, —$C_{1-4}$alkyl, —$C_{1-4}$alkoxy, and —$CF_3$;
C) 9-membered heteroaryl ring selected from the group consisting of: benzooxazol-2-yl, 6-fluoro-1,3-benzothiazole, 1,3-benzothiazole, 6-methoxy-1,3-benzothiazole, 6-methyl-1,3-benzothiazole, 6-chloro-benzothiazol-2-yl, and 4-methyl-6,7-dihydro-5H-cyclopenta[d]pyrimidine;
D) 10-membered heteroaryl ring selected from the group consisting of: quinoxalin-2-yl, 3-methylquinoxalin-2-yl, 6,7-difluoroquinoxalin-2-yl, 3-(trifluoromethyl)quinoxaline, quinoline, 4-methylquinoline, and 6-fluoroquinazolin-2-yl; and
E) 4-methyl-1,3,5-triazin-2-yl or 2-methylpyrimidin-4(3H)-one.

In another general aspect, the invention is directed to a chemical entity of Formula (II):

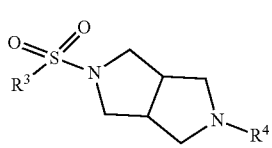

(II)

wherein
R³ is phenyl substituted or unsubstituted with a member independently selected from the group consisting of: —C₁₋₄alkoxy, and phenyl; and
R⁴ is a member selected from the group consisting of (5-trifluoromethyl)-pyridin-2-yl, (5-trifluoromethyl)-pyrimidin-2-yl, 4,6-dimethylpyrimidin-2-yl, and quinoxalin-2-yl.

Further embodiments are provided by pharmaceutically acceptable salts of compounds of Formula (I) or Formula (II), pharmaceutically acceptable prodrugs of compounds of Formula (I) or Formula (II), and pharmaceutically active metabolites of compounds of Formula (I) or Formula (II).

In certain embodiments, the compound of Formula (I) or Formula (II) is a compound selected from those species described or exemplified in the detailed description below.

In a further aspect, the invention relates to pharmaceutical compositions for treating a disease, disorder, or medical condition mediated by orexin receptor activity, comprising an effective amount of at least one chemical entity selected from compounds of Formula (I) or Formula (II), pharmaceutically acceptable salts of compounds of Formula (I) or Formula (II), pharmaceutically acceptable prodrugs of compounds of Formula (I) or Formula (II), and pharmaceutically active metabolites of Formula (I) or Formula (II).

Pharmaceutical compositions according to the invention may further comprise one or more pharmaceutically acceptable excipients.

In another aspect, the chemical embodiments of the present invention are useful as orexin receptor modulators. Thus, the invention is directed to a method for modulating orexin receptor activity, including when such receptor is in a subject, comprising exposing orexin receptor to an effective amount of at least one chemical entity selected from compounds of Formula (I) or Formula (II), pharmaceutically acceptable salts of compounds of Formula (I) or Formula (II), pharmaceutically acceptable prodrugs of compounds of Formula (I) or Formula (II), and pharmaceutically active metabolites of compounds of Formula (I) or Formula (II).

In another aspect, the invention is directed to a method of treating a subject suffering from or diagnosed with a disease, disorder, or medical condition mediated by orexin receptor activity, comprising administering to the subject in need of such treatment an effective amount of at least one chemical entity selected from compounds of Formula (I) or Formula (II), pharmaceutically acceptable salts of compounds of Formula (I) or Formula (II), pharmaceutically acceptable prodrugs of compounds of Formula (I) or Formula (II), and pharmaceutically active metabolites of compounds of Formula (I) or Formula (II). Additional embodiments of methods of treatment are set forth in the detailed description.

In another aspect, method of studying isotopically labeled compounds in metabolic studies (preferably with ¹⁴C), reaction kinetic studies (with, for example ²H or ³H), detection or imaging techniques [such as positron emission tomography (PET) or single-photon emission computed tomography (SPECT)] including drug or substrate tissue distribution assays, or in radioactive treatment of patients. For example, an ¹⁸F or ¹¹C labeled compound may be particularly preferred for PET or an I¹²³ for SPECT studies.

An object of the present invention is to overcome or ameliorate at least one of the disadvantages of the conventional methodologies and/or prior art, or to provide a useful alternative thereto. Additional embodiments, features, and advantages of the invention will be apparent from the following detailed description and through practice of the invention.

BRIEF DESCRIPTION OF THE DRAWINGS

FIG. 1 is a Powder X-Ray Diffraction of an exemplified compound X

DETAILED DESCRIPTION OF ILLUSTRATIVE EMBODIMENTS

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by the symbol, "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and SO₂.

The term "cyano" refers to the group —CN.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

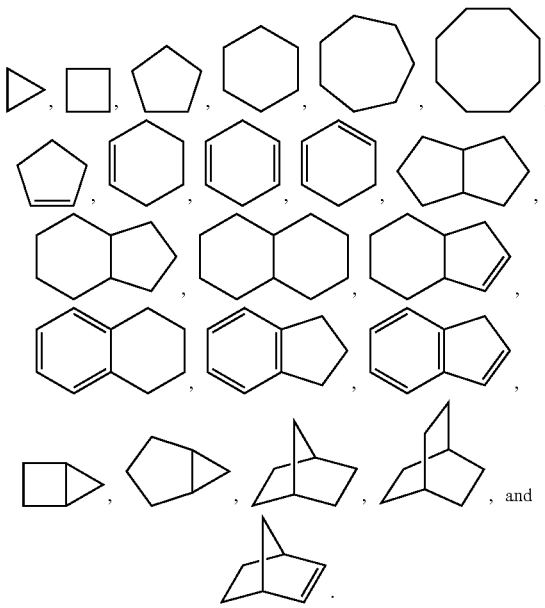

A "heterocycloalkyl" refers to a monocyclic ring structure that is saturated or partially saturated and has from 4 to 7 ring atoms per ring structure selected from carbon atoms and up to two heteroatoms selected from nitrogen, oxygen, and sulfur. The ring structure may optionally contain up to two oxo groups on sulfur ring members. Illustrative entities, in the form of properly bonded moieties, include:

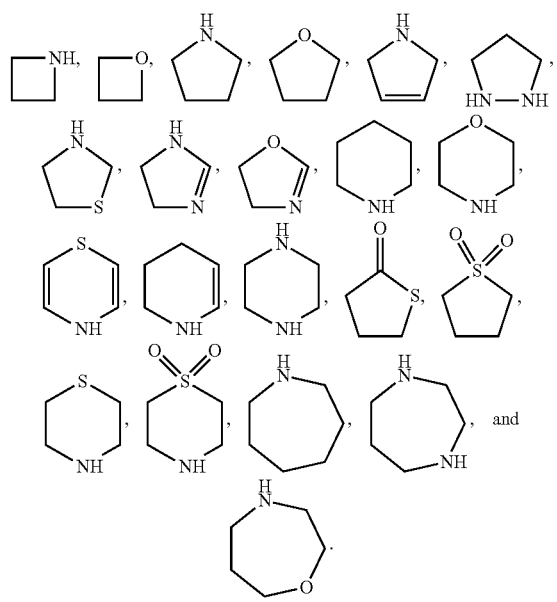

The term "aryl" refers to a monocyclic, or fused or spiro polycyclic, aromatic carbocycle (ring structure having ring atoms that are all carbon) having from 3 to 12 ring atoms per ring. (Carbon atoms in aryl groups are sp² hybridized.) Illustrative examples of aryl groups include the following moieties:

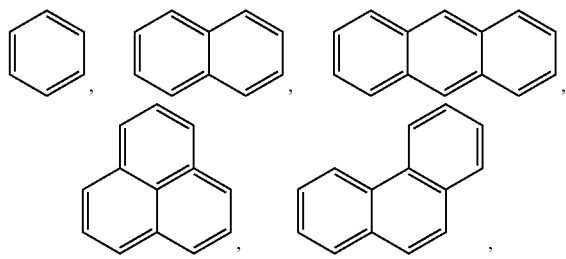

and the like.

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

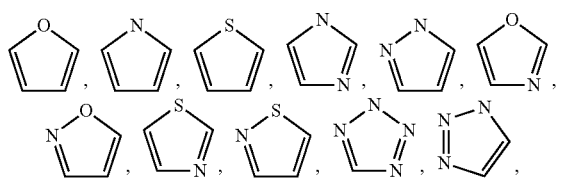

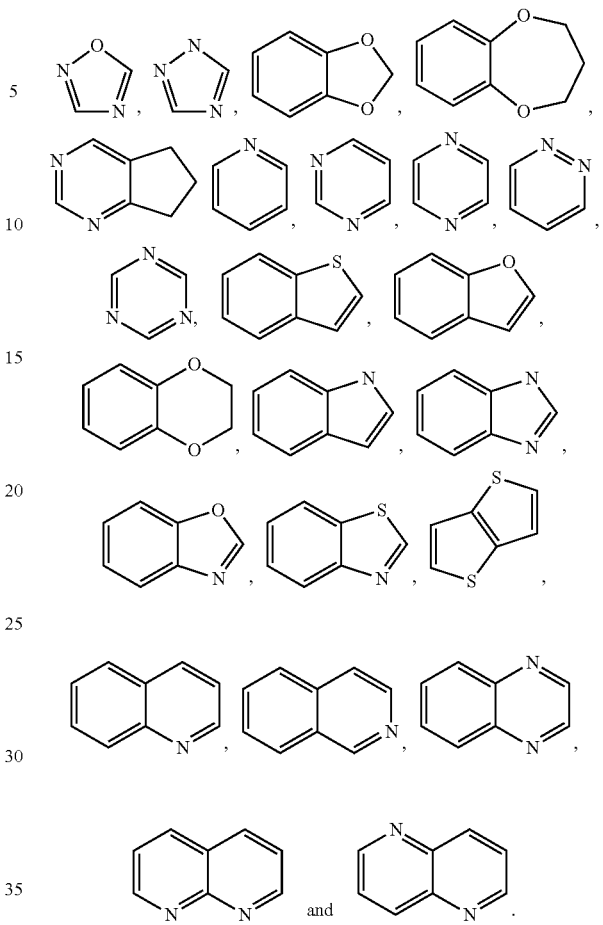

Those skilled in the art will recognize that the species of heteroaryl, cycloalkyl, aryl and heterocycloalkyl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment as illustrated below.

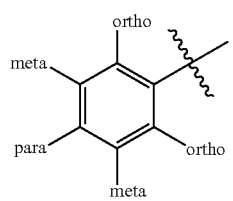

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., *Van Nostrand's Encyclopedia of Chemistry*, p. 261, 5$^{th}$ ed. (2005), describing, inter alia, buffer solutions and how the concentrations of the buffer constituents relate to the pH of the buffer. See also *Handbook of Chemistry and Physics*, 84$^{th}$ ed., pp. 8-37 to 8-44. For example, a buffered solution is obtained by adding $MgSO_4$ and $NaHCO_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

The symbols ▬▬▬ and ◄▬▬ are used as meaning the same spatial arrangement in chemical structures shown herein. Analogously, the symbols ⅢⅢⅢⅢⅢ and ·······ⅢⅢⅢ are used as meaning the same spatial arrangement in chemical structures shown herein.

Additionally, any formula given herein is intended to refer also to hydrates, solvates, and polymorphs of such compounds, and mixtures thereof, even if such forms are not listed explicitly. Certain compounds of Formula (I) or Formula (II) or pharmaceutically acceptable salts of compounds of Formula (I) or Formula (II) may be obtained as solvates. Solvates include those formed from the interaction or complexation of compounds of the invention with one or more solvents, either in solution or as a solid or crystalline form. In some embodiments, the solvent is water and then the solvates are hydrates. In addition, certain crystalline forms of compounds of Formula (I) or Formula (II) or pharmaceutically acceptable salts of compounds of Formula (I) or Formula (II) may be obtained as co-crystals. In certain embodiments of the invention, compounds of Formula (I) or Formula (II) were obtained in a crystalline form. In other embodiments, crystalline forms of compounds of Formula (I) or Formula (II) were cubic in nature. In other embodiments, pharmaceutically acceptable salts of compounds of Formula (I) or Formula (II) were obtained in a crystalline form. In still other embodiments, compounds of Formula (I) or Formula (II) were obtained in one of several polymorphic forms, as a mixture of crystalline forms, as a polymorphic form, or as an amorphous form. In other embodiments, compounds of Formula (I) or Formula (II) convert in solution between one or more crystalline forms and/or polymorphic forms.

Reference to a chemical entity herein stands for a reference to any one of: (a) the actually recited form of such chemical entity, and (b) any of the forms of such chemical entity in the medium in which the compound is being considered when named. For example, reference herein to a compound such as R—COOH, encompasses reference to any one of, for example, R—COOH$_{(s)}$, R—COOH$_{(sol)}$, and R—COO$^-$$_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-$$_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-$$_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, fluorine, and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively. Such isotopically labeled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an 18F or $^{11}C$ labeled compound may be particularly preferred for PET or an $I^{123}$ for SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, $R^3$, $R^4$, A, $R^a$, $R^b$, $R^c$, $R^d$, $R^e$, $R^f$, $R^g$, $R^h$, $R^i$, $R^j$, and $R^k$, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^2$, $R^3$, $R^4$, A, $R^a$, $R^b$, $R^c$, $R^d$, $R^e$, $R^f$, $R^g$, $R^h$, $R^i$, $R^j$, and $R^k$, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≤N≤m, with m>n. Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

Some embodiments are given by compounds of Formula (I) where $R^1$ is phenyl substituted with $R^a$, where $R^a$ is —F, —I, —Cl, —OCH$_3$, —OCH$_2$CH$_3$, —CH$_3$, —CH(CH$_3$)$_2$, —C(CH$_3$)$_3$ or —NO$_2$.

In some of these embodiments, $R^1$ is substituted phenyl wherein $R^b$ is a —Br, —F, —I, —C$_{1-4}$alkyl, —OCH$_3$, —OCH$_2$CH$_3$, —CN, —CF$_3$, or —OCF$_3$.

In some of these embodiments, $R^1$ is phenyl substituted with $R^a$, wherein $R^a$ is —H, —F, —Cl, —CH$_3$, —C(CH$_3$)$_3$, —OCH$_3$, or —OCH$_2$CH$_3$, and $R^b$ is —Br, —F, —I, —C$_{1-4}$alkyl, —OCH$_3$, —OCH$_2$CH$_3$, —CN, —CF$_3$, or —OCF$_3$.

In some of these embodiments, $R^1$ is substituted phenyl where $R^b$ is 2-thiophen-2-yl or 2-furan-2-yl.

In some of these embodiments, $R^1$ is substituted phenyl where $R^b$ is phenyl, 3-chlorophenyl, 4-fluorophenyl, 3-fluorophenyl, 4-methylphenyl, or 4-trifluoromethylphenyl.

In some of these embodiments, $R^1$ is substituted phenyl where $R^b$ is 1H-pyrrol-1-yl, 1H-pyrazol-1-yl, 1H-pyrazol-5-yl, 1H-imidazol-2-yl, 1-methyl-1H-imidazol-2-yl, 1H-1,2,3-triazol-1-yl, 2H-1,2,3-triazol-2-yl, 2H-1,2,3-triazol-1-yl, 1H-1,2,4-triazol-5-yl, 2H-1,2,4-triazol-1-yl, 2H-1,2,4-triazol-3-yl, 4H-1,2,4-triazol-3-yl, 4H-1,2,4-triazol-4-yl, 1-methyl-1H-1,2,4-triazol-3-yl, 1-methyl-1H-1,2,4-triazol-5-yl or 1-(tetrahydro-2H-pyran-2-yl)-1H-pyrazol-5-yl.

In some of these embodiments, $R^1$ is substituted phenyl, where $R^b$ is pyridin-2-yl, 3-chloropyridin-2-yl, 3-fluoropyridin-2-yl, 3-methylpyridin-2-yl, 4-methylpyridin-2-yl, 5-methylpyridin-2-yl, 6-methylpyridin-2-yl, 2-pyridin-3-yl, or 2-pyrimidin-2-yl.

In some of these embodiments, $R^1$ is substituted phenyl, where $R^b$ is 3-methyl-1,2,4-oxadiazol-5-yl or oxazol-2-yl.

In some of these embodiments, $R^1$ is phenyl substituted with $R^a$, where $R^a$ is halo, —C$_{1-4}$alkyl, or —C$_{1-4}$alkoxy, and $R^b$ is triazole or pyrimidine substituted or unsubstituted with halo or —C$_{1-4}$alkyl.

In some of these embodiments, $R^1$ is (1-methylethyl)-2-(2H-1,2,3-triazol-2-yl)phenyl, 2-(1H-1,2,3-triazol-1-yl)phenyl, 2-(2H-1,2,3-triazol-2-yl)phenyl, 2-fluoro-6-(2H-1,2,3-triazol-2-yl)phenyl, 2-methyl-6-(2H-1,2,3-triazol-2-yl)phenyl, 3-fluoro-2-(2H-1,2,3-triazol-2-yl)phenyl, 3-fluoro-2-(1H-1,2,3-triazol-1-yl)phenyl, 3-methoxy-2-(1H-1,2,3-triazol-1-yl)phenyl, 3-methoxy-2-(2H-1,2,3-triazol-2-yl)phenyl, 3-methyl-2-(2H-1,2,3-triazol-2-yl)phenyl, 3-methyl-2-(1H-1,2,3-triazol-1-yl)phenyl, 4-fluoro-2-(2H-1,2,3-triazol-2-yl)phenyl, 4-methoxy-2-(1H-1,2,3-triazol-2-yl)phenyl, 4-methoxy-2-(1H-1,2,3-triazol-2-yl)phenyl, 4,5-dimethoxy-2-[1,2,3]triazol-1-yl-phenyl, 4,5-dimethoxy-2-[1,2,3]triazol-2-yl-phenyl, 5-[1,2,3]triazol-2-yl-benzo[1,3]dioxol-4-yl, 5-chloro-2-(2H-1,2,3-triazol-2-yl)phenyl, 5-fluoro-2-(2H-1,2,3-triazol-2-yl)phenyl, 5-iodo-2-(2H-1,2,3-triazol-2-yl)phenyl, 5-methoxy-2-(2H-1,2,3-triazol-2-yl)phenyl, 5-methyl-2-(2H-1,2,3-triazol-2-yl)phenyl, 1-[1,2,3]triazol-2-yl-naphthalen-2-yl, 2-(1H-1,2,4-triazol-1-yl)phenyl, 2-(1H-1,2,4-triazol-5-yl)phenyl, 2-(1-methyl-1H-1,2,4-triazol-5-yl)phenyl, 2-(1-methyl-1H-1,2,4-triazol-3-yl)phenyl, 2-(4H-1,2,4-triazol-3-yl)phenyl, 2-(4H-1,2,4-triazol-4-yl)phenyl, 2-(3-methyl-1,2,4-oxadiazol-5-yl)phenyl, 3-fluoro-2-(3-methyl-1,2,4-oxadiazol-5-yl)phenyl, 2-fluoro-6-(3-methyl-1,2,4-oxadiazol-5-yl)phenyl, 4,5-difluoro-2-(4H-1,2,4-triazol-4-yl)phenyl), 2-fluoro-6-pyrimidin-2-ylphenyl, 2-(pyrimidin-2-yl)pyridin-3-yl, 3-fluoro-2-pyrimidin-2-ylphenyl, 4-fluoro-2-(pyrimidin-2-yl)phenyl, 4-methoxy-2-(pyrimidin-2-yl)phenyl, 5-fluoro-2-pyrimidin-2-ylphenyl, or 5-methyl-2-pyrimidin-2-ylphenyl.

Some embodiments are given by compounds of Formula (I) where $R^1$ is substituted pyridine, where $R^d$ is —CF$_3$, —Br, or —OCH$_2$CH$_2$CH$_3$.

In some of these embodiments, wherein $R^1$ is substituted pyridine, $R^d$ is 1H-pyrazol-5-yl, 2H-1,2,3-triazol-1-yl, 2H-1,2,3-triazol-2-yl, 4H-1,2,3-triazol-1-yl, 1-(tetrahydro-2H-pyran-2-yl)-1H-pyrazol-5-yl, 3-methylpyridin-2-yl, or 3-methyl-1,2,4-oxadiazol-5-yl.

In some of these embodiments, wherein $R^1$ is substituted pyridine, $R^d$ is 1H-pyrazol-5-yl, 2H-1,2,3-triazol-1-yl, or 2H-1,2,3-triazol-2-yl.

In some of these embodiments, wherein $R^1$ is 1-phenyl-1H-pyrazol-5-yl, 3-phenylthiophen-2-yl, 3-phenylfuran-2-yl, 5-phenyl-1,3-oxazol-4-yl, 5-phenylisoxazol-4-yl, 5-(2-fluorophenyl)-2-methyl-1,3-thiazol-4-yl, 2-methyl-5-phenyl-thiazol-4-yl, or 5-(4-fluorophenyl)-2-methyl-1,3-thiazol-4-yl.

Some embodiments are given by compounds of Formula (I), where $R^1$ is 3-methylfuran-2-yl, 9H-fluorene, quinoline, cinnoline, 3-(1H-pyrrol-1-yl)thiophen-2-yl, 8-[1,2,3]-triazol-2-yl-naphthalen-1-yl, 2,3-dihydro-1,4-benzodioxin-5-yl, 1H-indol-7-yl, 4-fluoronaphthalen-1-yl, and naphthalen-1-yl and $R^2$ is selected from the group consisting of 4,6-dimethylpyrimidin-2-yl, 4-phenyl-pyrimidin-2-yl, quinoxaline, or 4-methoxypyrimidin-2-yl.

Some embodiments are given by compounds of Formula (I), where $R^2$ is pyrimidine substituted with —F, —Cl, -D, —CD$_3$, —CH$_3$, ethyl, isopropyl, propyl, tert-butyl, —CF$_3$, —OCH$_3$, —N(CH$_3$)$_2$, —CN, —OH, —CH$_2$OH, —NO$_2$, —CO$_2$CH$_3$, —CO$_2$H, —C(O)N(CH$_3$)$_2$, phenyl, furan-2-yl, thiophen-2-yl, 1H-pyrazol-4-yl, cyclopropyl, pyrrolidin-1-yl, or morpholin-4-yl.

In some of these embodiments, $R^2$ is 4,6-dimethylpyrimidin-2-yl, 4,5-dimethylpyrimidin-2-yl, 4,6-dimethoxypyrimidin-2-yl, 4-phenyl-pyrimidin-2-yl, 4-furan-2-ylpyrimidin-2-yl, 4-methylpyrimidin-2-yl, 4-methoxypyrimidin-2-yl, 4-thiophen-2-ylpyrimidin-2-yl, N,N,6-trimethylpyrimidin-4-amine, 4-(trifluoromethyl)pyrimidin-2-yl, 4,5,6-trimethylpyrimidin-2-yl, 4-(trifluoromethyl)pyrimidine-5-carboxylate, 4-(trifluoromethyl)pyrimidine-5-carboxylic acid, 5-nitro-pyrimidin-2-yl, 6-methylpyrimidine-4-carboxylic acid, N,N-dimethyl-4-(trifluoromethyl)pyrimidine-5-carboxamide, N,N,6-trimethylpyrimidine-carboxamide, 6-methylpyrimidine-4-carbonitrile, 4,6-bis(trifluoromethyl)pyrimidin-2-yl, 6-methyl-pyrimidin-4-ol, 4-(furan-2-yl)-6-methylpyrimidin-2-yl, 5-fluoro-4-methylpyrimidin-2-yl, 5-fluoropyrimidin-2-yl, 4-methoxy-6-methylpyrimidin-2-yl, 4-ethyl-6-methylpyrimidin-2-yl, 4-isopropyl-6-methylpyrimidin-2-yl, 4-tertbutyl-6-methylpyrimidin-2-yl, 4-cyclopropyl-6-methylpyrimidin-2-yl, 4-methyl-6-morpholin-4-ylpyrimidin-2-yl, 5-chloro-4-methylpyrimidin-2-yl, 5-chloro-4,6-dimethylpyrimidin-2-yl, 5-fluoro-4,6-dimethylpyrimidin-2-yl, 5-trifluoromethylpyrimidin-2-yl, 4,6-bis[($^2$H3)methyl]($^2$H)pyrimidin-2-yl, or 5-ethyl-4,6-dimethylpyrimidin-2-yl.

In some of these embodiments, $R^2$ is pyrimidine substituted with one or more —Cl, —F, —CH$_3$, —CF$_3$, —N(CH$_3$)$_2$, -D, or —CD$_3$.

In some of these embodiments, $R^2$ is 4,6-dimethylpyrimidin-2-yl, 4,5-dimethylpyrimidin-2-yl, 4,6-dimethoxypyrimidin-2-yl, 4-methylpyrimidin-2-yl, 4-methoxypyrimidin-2-yl, N,N,6-trimethyl-pyrimidin-4-amine, 4-(trifluoromethyl)pyrimidin-2-yl, 4,5,6-trimethylpyrimidin-2-yl, 4,6-bis(trifluoromethyl)pyrimidin-2-yl, 6-methyl-pyrimidin-4-ol, 5-fluoro-4-methylpyrimidin-2-yl, 5-fluoropyrimidin-2-yl, 4-methoxy-6-methylpyrimidin-2-yl, 5-chloro-4-methylpyrimidin-2-yl, 5-chloro-4,6-dimethylpyrimidin-2-yl, 5-fluoro-4,6-dimethylpyrimidin-2-yl, 5-trifluoromethylpyrimidin-2-yl, or 4,6-bis[($^2$H3)methyl]($^2$H)pyrimidin-2-yl.

Some embodiments are given by compounds of Formula (I) where $R^2$ is pyrazine or triazine substituted with one or more —$CH_3$.

Some embodiments are given by compounds of Formula (I) where $R^2$ is pyridine substituted with one or more —F, —$OCH_3$, —$OCH_2CH_3$, —$CH_3$, or —$CF_3$.

In some of these embodiments, $R^2$ is benzooxazol-2-yl, 2-methylpyrimidin-4(3H)-one and 4-methyl-6,7-dihydro-5H-cyclopenta[d]pyrimidine and $R^1$ is phenyl, substituted in the ortho position with $R^b$, where $R^b$ is 2H-1,2,3-triazol-2-yl, 2H-1,2,3-triazol-1-yl, 3-methyl-1,2,4-oxadiazol-5-yl or 2-pyrimidin-2-yl.

Some embodiments are given by compounds of Formula (I) where $R^2$ is quinoxalin-2-yl, 3-methylquinoxalin-2-yl, 6,7-difluoroquinoxalin-2-yl, 3-(trifluoromethyl)quinoxaline, 4-methylquinoline, or 6-fluoroquinazolin-2-yl and $R^1$ is phenyl substituted in the ortho position with $R^b$, where $R^b$ is 2H-1,2,3-triazol-2-yl, 2H-1,2,3-triazol-1-yl, 3-methyl-1,2,4-oxadiazol-5-yl, or 2-pyrimidin-2-yl.

Some embodiments are given by compounds of Formula (II) where $R^3$ is biphenyl or 2-methoxyphenyl and $R^4$ is (5-trifluoromethyl)-pyridin-2-yl, (5-trifluoromethyl)-pyrimidin-2-yl, 4,6-dimethylpyrimidin-2-yl, or quinoxalin-2-yl.

Some embodiments are given by compounds of Formula (I) wherein $R^1$ is 2-(1H-1,2,3-triazol-1-yl)phenyl, 2-(2H-1,2,3-triazol-2-yl)phenyl, 2-fluoro-6-(2H-1,2,3-triazol-2-yl)phenyl, 2-methyl-6-(2H-1,2,3-triazol-2-yl)phenyl, 3-fluoro-2-(2H-1,2,3-triazol-2-yl)phenyl, 3-fluoro-2-(1H-1,2,3-triazol-1-yl)phenyl, 3-methoxy-2-(1H-1,2,3-triazol-1-yl)phenyl, 3-methoxy-2-(2H-1,2,3-triazol-2-yl)phenyl, 3-methyl-2-(2H-1,2,3-triazol-2-yl)phenyl, 3-methyl-2-(1H-1,2,3-triazol-1-yl)phenyl, 4-fluoro-2-(2H-1,2,3-triazol-2-yl)phenyl, 4-methoxy-2-(2H-1,2,3-triazol-2-yl)phenyl, 4-methoxy-2-(1H-1,2,3-triazol-2-yl)phenyl, 4,5-dimethoxy-2-[1,2,3]triazol-1-yl-phenyl, 4,5-dimethoxy-2-[1,2,3]triazol-2-yl-phenyl, 5-chloro-2-(2H-1,2,3-triazol-2-yl)phenyl, 5-fluoro-2-(2H-1,2,3-triazol-2-yl)phenyl, 5-methoxy-2-(2H-1,2,3-triazol-2-yl)phenyl, 5-methyl-2-(2H-1,2,3-triazol-2-yl)phenyl, 2-(1H-1,2,4-triazol-1-yl)phenyl, 2-(1H-1,2,4-triazol-5-yl)phenyl, 2-(1-methyl-1H-1,2,4-triazol-5-yl)phenyl, 2-(1-methyl-1H-1,2,4-triazol-3-yl)phenyl, 2-(4H-1,2,4-triazol-3-yl)phenyl, 2-(4H-1,2,4-triazol-4-yl)phenyl, 2-(3-methyl-1,2,4-oxadiazol-5-yl)phenyl, 3-fluoro-2-(3-methyl-1,2,4-oxadiazol-5-yl)phenyl, 2-fluoro-6-(3-methyl-1,2,4-oxadiazol-5-yl)phenyl, 4,5-difluoro-2-(4H-1,2,4-triazol-4-yl)phenyl), 2-fluoro-6-pyrimidin-2-ylphenyl, 2-(pyrimidin-2-yl)pyridin-3-yl, 3-fluoro-2-pyrimidin-2-ylphenyl, 4-fluoro-2-(pyrimidin-2-yl)phenyl, 4-methoxy-2-(pyrimidin-2-yl)phenyl, 5-fluoro-2-pyrimidin-2-ylphenyl, or 5-methyl-2-pyrimidin-2-ylphenyl and $R^2$ is 4,6-dimethylpyrimidin-2-yl, 4,5-dimethylpyrimidin-2-yl, 4,6-dimethoxypyrimidin-2-yl, 4-methylpyrimidin-2-yl, 4-methoxypyrimidin-2-yl, N,N,6-trimethyl-pyrimidin-4-amine, 4-(trifluoromethyl)pyrimidin-2-yl, 4,5,6-trimethylpyrimidin-2-yl, 4,6-bis(trifluoromethyl)pyrimidin-2-yl, 6-methylpyrimidin-4-ol, 5-fluoro-4-methylpyrimidin-2-yl, 5-fluoropyrimidin-2-yl, 4-methoxy-6-methylpyrimidin-2-yl, 5-chloro-4-methylpyrimidin-2-yl, 5-chloro-4,6-dimethylpyrimidin-2-yl, 5-fluoro-4,6-dimethylpyrimidin-2-yl, 5-trifluoromethylpyrimidin-2-yl, or 4,6-bis[($^2$H3)methyl]($^2$H)pyrimidin-2-yl.

Some embodiments are given by compounds of Formula (I) wherein $R^1$ is 3-fluoro-2-(3-methyl-1,2,4-oxadiazol-5-yl)phenyl, 6-fluoro-2-(2H-1,2,3-triazol-2-yl)phenyl, 4-methoxy-2-(2H-1,2,3-triazol-2-yl)phenyl, or 3-[1,2,3]triazol-2-yl-pyridin-2-yl and $R^2$ is 4,6-dimethylpyrimidin-2-yl, 5-fluoro-4,6-dimethylpyrimidin-2-yl, or 5-fluoro-4-methylpyrimidin-2-yl.

Compounds of Formula (I) and Formula (II) and pharmaceutically acceptable salts thereof are used, alone or in combination with one or more additional active ingredients, to formulate pharmaceutical compositions. A pharmaceutical composition therefore comprises an effective amount of at least one a compound of Formula (I) and Formula (II) or a pharmaceutically acceptable salt thereof.

The invention includes also pharmaceutically acceptable salts of the compounds of Formula (I) and Formula (II), preferably of those described above and of the specific compounds exemplified herein, and methods of treatment using such salts.

A "pharmaceutically acceptable salt" is intended to mean a salt of a free acid or base of a compound represented by Formula (I) and Formula (II), that is non-toxic, biologically tolerable, or otherwise biologically suitable for administration to the subject. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) and Formula (II) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compound of Formula (I) or Formula (II) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid/or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) or Formula (II) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I) and Formula (II), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I) or Formula (II)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I) or Formula (II). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) or Formula (II) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med Chem.* 1996, 39(1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I) or Formula (II), which may also be used in the methods of the invention. A "pharmaceutically active metabolite" means a pharmacologically active product of metabolism in the body of a compound of Formula (I) or Formula (II) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, Design of Prodrugs (Elsevier Press, 1985); and Larsen, *Design and Application of Prodrugs, Drug Design and Development* (Krogsgaard-Larsen, et al., eds., Harwood Academic Publishers, 1991).

The compounds of Formula (I) or Formula (II) and their pharmaceutically acceptable salts, pharmaceutically acceptable prodrugs, and pharmaceutically active metabolites of the present invention are useful as modulators of the orexin receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize or down-regulate orexin receptor expression or activity, and "activators" are compounds that increase, activate, facilitate, sensitize, or up-regulate orexin receptor expression or activity.

The term "treat" or "treating" as used herein is intended to refer to administration of an active agent or composition of the invention to a subject for the purpose of effecting a therapeutic benefit through modulation of orexin receptor activity. Treating includes reversing, ameliorating, alleviating, inhibiting the progress of, or lessening the severity of a disease, disorder, or condition, or one or more symptoms of such disease, disorder or condition mediated through modulation of orexin receptor activity. The term "subject" refers to a mammalian patient in need of such treatment, such as a human.

Accordingly, the invention relates to methods of using the compounds described herein to treat subjects diagnosed with or suffering from a disease, disorder, or condition mediated by orexin receptor activity, such as: disorders of the sleep-wake cycle, metabolic disorders, neurological disorders and other disorders (e.g., feeding, drinking, arousal, stress, addiction, metabolism and reproduction). Symptoms or disease states are intended to be included within the scope of "medical conditions, disorders, or diseases."

Sleep disorders include, but are not limited to, sleep-wake transition disorders, insomnia, restless legs syndrome, jet-lag, disturbed sleep, and sleep disorders secondary to neurological disorders (e.g., manias, depressions, manic depression, schizophrenia, and pain syndromes (e.g., fibromyalgia, neuropathic).

Metabolic disorders include, but are not limited to, overweight or obesity and conditions related to overweight or obesity, such as insulin resistance, type II diabetes, hyperlipidemia, gallstones, angina, hypertension, breathlessness, tachycardia, infertility, sleep apnea, back and joint pain, varicose veins and osteoarthritis.

Neurological disorders include, but are not limited to, Parkinson's disease, Alzheimer's disease, Tourette's Syndrome, catatonia, anxiety, delirium and dementias.

Other disorders include, but are not limited to, ulcers, irritable bowel syndrome, diarrhea and gastroesophageal reflux.

In treatment methods according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be coadministered separately with an active agent of compounds of Formulas (I) and (II) or included with such an agent in a pharmaceutical composition according to the invention. In an exemplary embodiment, additional active ingredients are those that are known or discovered to be effective in the treatment of conditions, disorders, or diseases mediated by orexin activity, such as another orexin modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The active agents of the invention are used, alone or in combination with one or more additional active ingredients, to formulate pharmaceutical compositions of the invention. A pharmaceutical composition of the invention comprises: (a) an effective amount of at least one active agent in accordance with the invention, and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations and acronyms used herein include the following:

| Term | Acronym |
| --- | --- |
| High-performance liquid chromatography | HPLC |
| Thin layer chromatography | TLC |
| Diisopropylethylamine | DIPEA |
| Tetrahydrofuran | THF |
| tert-Butylcarbamoyl | BOC |
| Carboxybenzyl | CBz |
| Dichloromethane | DCM |
| Trifluoroacetic acid | TFA |
| Acetic Acid | HOAc |
| N,N-Dimethylformamide | DMF |
| Methanol | MeOH |
| Isopropanol | IPA |
| Ethanol | EtOH |
| Acetonitrile | ACN |
| Ethyl Acetate | EtOAc, or EA |
| Triethylamine | TEA |
| 2-(1H-9-Azobenzotriazole-1-yl)-1,1,3,3-tetramethylaminium hexafluorophosphate | HATU |
| 1-Hydroxy-7-azabenzotriazole | HOAT |
| Methyl Tertiary Butyl Ether | MTBE |
| N-(3-Dimethylaminopropyl)-N-ethylcarbodiimide | EDCI |
| [1,1'-Bis(diphenylphosphino)ferrocene]palladium(II) Dichloride Dichloromethane Adduct | PdCl$_2$(dppf)-dcm adduct |

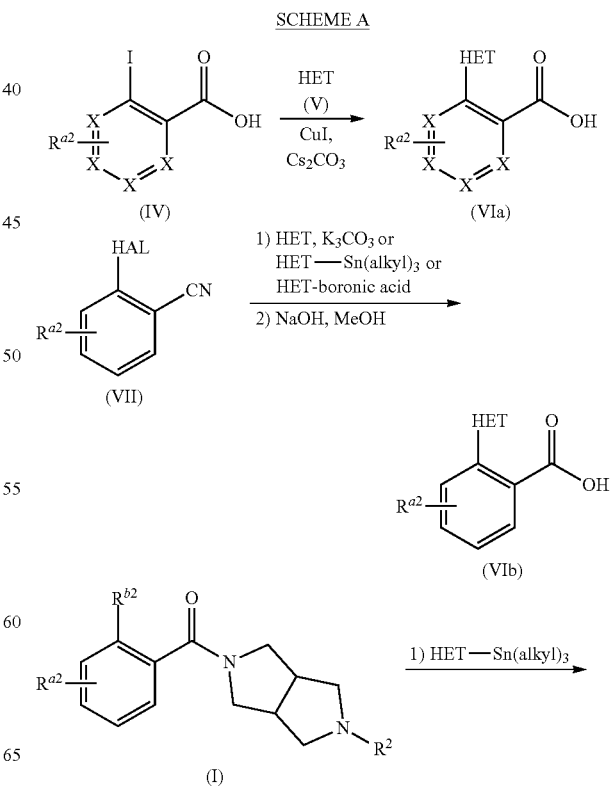

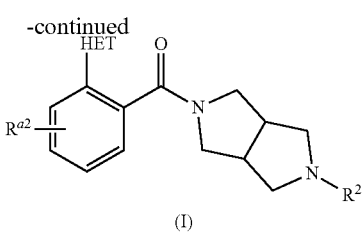

Intermediate compounds of formulae (VIa) and (VIb) are readily prepared as outlined in Scheme A from a commercially available or synthetically accessible compound of formula (IV). Compounds of formula (VIa) are obtained by reacting a compound of formula (IV), where $R^{a2}$ is —H, halo, —$C_{1-4}$alkyl, —$C_{1-4}$alkoxy, —$NO_2$, —$NHCOCH_3$, or two $R^{a2}$ members may come together to form a 6-membered aryl ring, where X is C or N (with the proviso that only one X member can be N), with commercially available HET compounds of formula (V), where HET is a 5-6 membered heteroaryl ring containing one to three nitrogen members, in the presence of copper(I)iodide, $Cs_2CO_3$ and N,N'-dimethylcyclohexane-1,2-diamine; in a solvent such as DMF or dioxane, at temperatures ranging from 60° C. to 100° C. (using conventional or microwave heating). One skilled in the art will recognize that 1,2,3-triazole can exist in two tautomeric forms defined as 2H-[1,2,3]triazole and 1H-[1,2,3]triazole thus accounting for the formation of two regioisomers.

Alternatively, compounds of formula (VIb) are prepared by the reaction of halobenzonitrile compounds of formula (VII) with HET, where HET is a 5-membered heteroaryl ring selected from the group consisting of triazole or pyrazole, in a solvent such as DMF and the like, in the presence of an inorganic base such as $K_2CO_3$ and the like, at temperatures ranging from 100° C. to 130° C. Subsequent hydrolysis of the nitrile using a base such as aqueous NaOH and the like, in a solvent such as methanol provides compounds of formula (VIb).

Compounds of formula (VIb) are also prepared by the reaction of halobenzonitrile compounds of formula (VII) with HET-Sn(alkyl)$_3$, where HET-Sn(alkyl)$_3$ is a commercially available or synthetically accessible trialkyltinheteroaryl compound, in a solvent such as DME, in the presence of a palladium catalyst such as Pd(PPh$_3$)$_4$, in the presence or absence of a catalytic amount of copper iodide, at temperatures ranging from 100° C. to 160° C., using conventional or microwave heating. Subsequent hydrolysis of the nitrile using a base such as aqueous NaOH and the like, in a solvent such as methanol provides compounds of formula (VIb).

Compounds of formula (VIb) are also prepared by the reaction of halobenzonitrile compounds of formula (VII) with HET-boronic acid, where HET-boronic acid is a commercially available or synthetically accessible heteroarylboronic acid, in a solvent such as DME, in the presence of a base such as NaHCO$_3$, a palladium catalyst such as Pd(PPh$_3$)$_4$, at temperatures ranging from 80° C. to the reflux temperature of the solvent. Subsequent hydrolysis using a base such as aqueous NaOH and the like, in a solvent such as methanol provides compounds of formula (VIb).

Compounds of formula (I), where $R^{b2}$ is —I, are further elaborated to compounds of formula (I), where $R^{b2}$ is HET, where HET is a 5-6 membered heteroaryl ring containing one to three nitrogen atoms optionally containing one oxygen member. Reaction of compounds of formula (I), where $R^{b2}$ is —I, with HET-Sn(alkyl)$_3$, where HET-Sn(alkyl)$_3$ is a commercially available or synthetically accessible trialkyltinheteroaryl compound, in a solvent such as DME, in the presence of a palladium catalyst such as Pd(PPh$_3$)$_4$, in the presence or absence of a catalytic amount of copper iodide, at temperatures ranging from 100° C. to 160° C., using conventional or microwave heating, provides compounds of formula (I).

SCHEME B

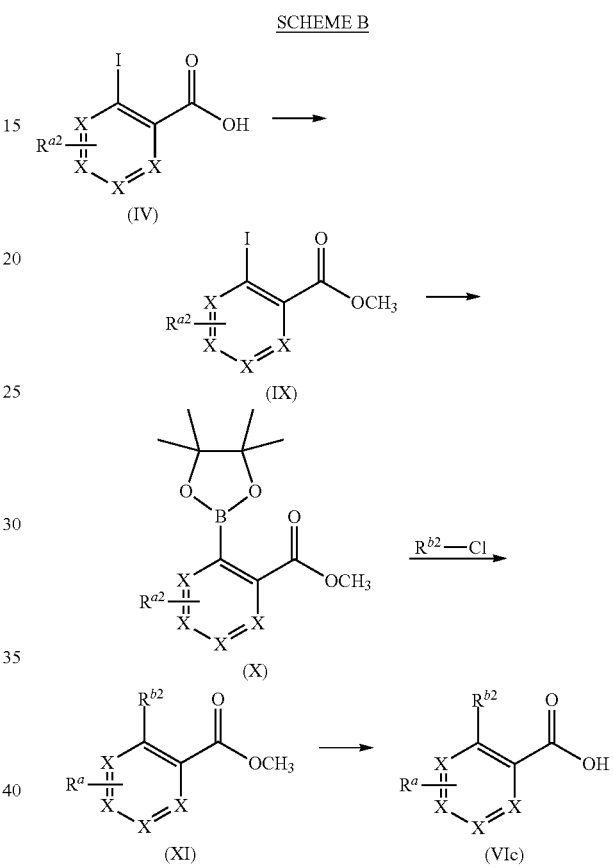

According to Scheme B, compounds of formula (VIc) are obtained from compounds of formula (IV), by first converting a commercially available or synthetically accessible compound of formula (IV), where $R^{a2}$ is —H, halo, —$C_{1-4}$alkyl, —$C_{1-4}$alkoxy, —$CF_3$, or —$NO_2$, and where X is C or N (with the proviso that only one X may be N) to one of formula (IX) under esterification conditions, for example by treating an alcohol solution of a compound of formula (IV) with an acid. In a preferred method the compound of formula (IV) is dissolved in a solvent such as MeOH and treated with $H_2SO_4$ to afford a compound of formula (IX). A compound of formula (X) is obtained by reacting a suitable compound of formula (IX) with pinacol borane in the presence of a phosphine and a palladium catalyst, in the presence of an amine base, in a solvent such as THF, at temperatures ranging from room temperature to 70° C. In a preferred method the phosphine is tri(o-tolyl)phosphine, the palladium catalyst is Pd(OAc)$_2$ and the amine base is triethylamine.

A compound of formula (VIc) is obtained by reacting a compound of formula (X) with a compound $R^{b2}$—Cl, where $R^{b2}$—Cl is a suitable commercially available or synthetically accessible 6-membered chloro-substituted heteroaryl compound, in the presence of a palladium catalyst, a base such as Na$_2$CO$_3$, and the like, in a solvent such as 2-methyl-tetrahydrofuran (2-methyl-THF), and the like, at temperatures ranging from room temperature to 80° C. In a preferred method the palladium catalyst is PdCl$_2$(dppf)-dcm adduct, the base is Na$_2$CO$_3$ and the solvent is 2-methyl-THF. A compound of formula (VIc) is obtained from a compound of formula (XI) via ester hydrolysis. In a preferred method of hydrolysis, a compound of formula (XI) in methyl-THF is treated with aqueous NaOH to afford a compound of formula (VIc).

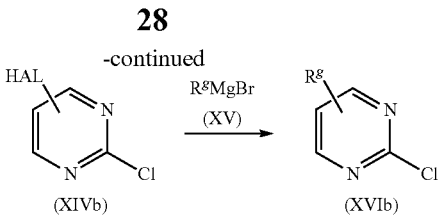

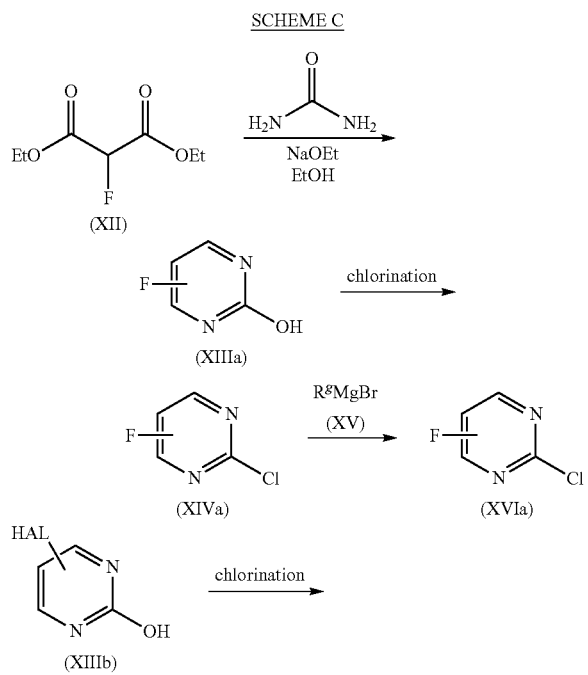

According to SCHEME C, substituted heteroaryl compounds R$^2$Cl of formula (XIVa) and (XVIb) are prepared from commercially available or synthetically accessible compounds of formula (XIIIa) or (XIIIb). Pyrimidols of formula (XIIIa) or formula (XIIIb) are commercially available or are prepared by reacting substituted alkyl malonates of formula (XII), where R$^e$ is halo, with urea in the presence of a base such as sodium ethoxide and the like; in a suitable solvent such as ethanol, at temperatures between room temperature and the reflux temperature of the solvent. Chlorination of commercially available pyrimidinols of formula (XIIIb) or synthetically accessible compounds of formula (XIIIa) using a chlorinating agent such as oxalyl chloride and the like; in a solvent such as CH$_2$Cl$_2$, in the presence of a base such as N,N-dimethylaniline and the like; at temperatures ranging between room temperature and the reflux temperature of the solvent provides chloropyrimidines of formula (XIVa) or (XIVb). Additionally, chloropyrimidines of formula (XIVa) or (XIVb) are further elaborated. Chloropyrimidines of formula (XIVa) or (XIVb) are reacted with Grignard reagents (R$^g$MgBr) of formula (XV); in the presence of a catalytic amount of Fe(acac)$_3$, in a solvent such as Et$_2$O at 0° C., provides alkyl chloropyrimidines of formula (XVIa) or (XVIb).

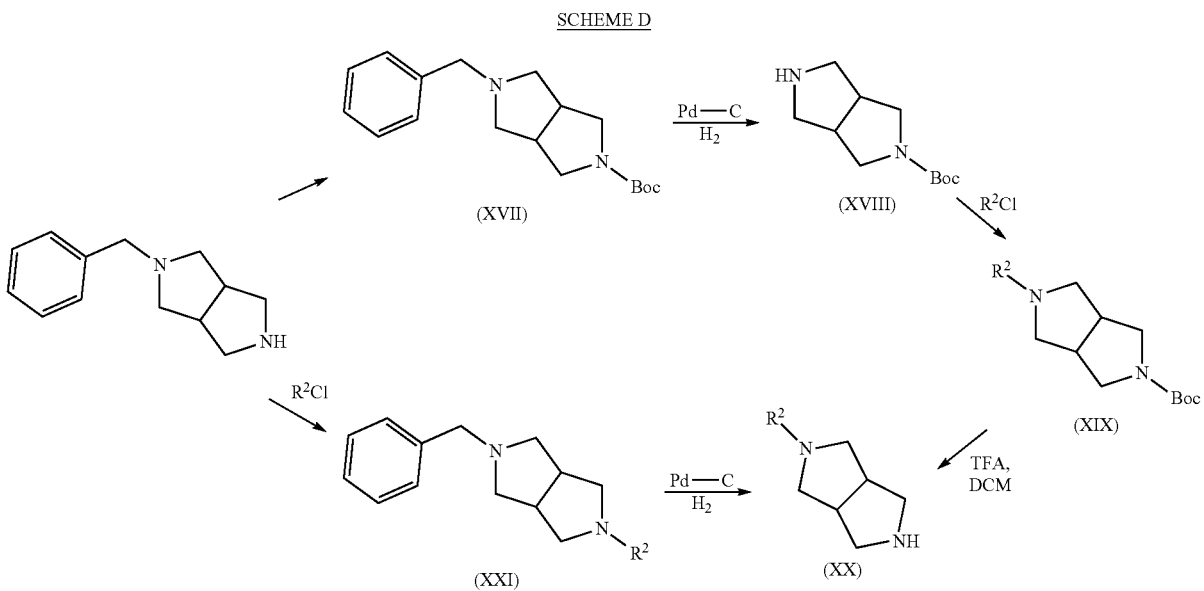

According to Scheme D, compounds of formula (XX) are obtained from synthetically accessible or commercially available 2-benzyl-octahydro-pyrrolo[3,4-c]pyrrole by first protecting the secondary nitrogen of 2-benzyl-octahydro-pyrrolo[3,4-c]pyrrole as a carbamate. In a preferred embodiment the carbamate is the tert-butylcarbamate (boc) which is introduced by treating 2-benzyl-octahydro-pyrrolo[3,4-c]pyrrole with di-tert-butyl-dicarbonate, in a solvent such as DCM, affording compound (XVII). Compound (XVIII) is obtained from treating compound (XVII) with hydrogen gas, in the presence of a catalyst. In a particularly preferred embodiment the catalyst is Pd on carbon, in a solvent such as MeOH in the presence of AcOH. A compound of formula (XIX) is obtained by treating compound (XVIII) with a compound of formula $R^2Cl$, where $R^2$ is as defined in formula (I). Commercially available or synthetically accessible appropriately heteroaryl compounds of formula $R^2Cl$ are reacted with compound (XVIII) in the presence of a suitably selected tertiary organic or inorganic base such as $Cs_2CO_3$, $Na_2CO_3$, TEA, and the like; in a solvent such as DMF, dichloromethane, THF, n-butanol, and the like; at a temperature between room temperature and the reflux temperature of the solvent, using conventional or microwave heating, to afford compounds of formula (XIX). In a preferred embodiment the base is $Cs_2CO_3$ and the solvent is DMF. Removal of the tert-butylcarbamate (boc) in compounds of formula (XIX) is accomplished by using methods known to one skilled in the art, such as, HCl, TFA, or p-toluenesulfonic acid, in a solvent such as $CH_3OH$, dioxane, or $CH_2Cl_2$. In a preferred embodiment, a compound of formula (XIX) is treated with TFA in DCM or HCl to afford a compound of formula (XX).

Compounds of formula (XX) are also obtained from 2-benzyl-octahydro-pyrrolo[3,4-c]pyrrole. Referring to Scheme D, 2-benzyl-octahydro-pyrrolo[3,4-c]pyrrole is treated with $R^2Cl$, where $R^2$ is as defined in a compound of formula (I). Commercially available or synthetically accessible suitably substituted heteroaryl compounds of formula $R^2Cl$ are reacted with compound 2-benzyl-octahydro-pyrrolo[3,4-c]pyrrole in the presence of a tertiary organic or inorganic base such as $Cs_2CO_3$, $Na_2CO_3$, TEA, and the like; in a solvent such as DMF, dichloromethane, THF, and the like; at a temperature between room temperature and the reflux temperature of the solvent to afford a compound of formula (XXI). In a preferred embodiment the base is $CS_2CO_3$ and the solvent is DMF. A compound of formula (XX) is obtained by treating a compound of formula (XXI) with hydrogen gas, in the presence of a catalyst, in a solvent such as AcOH. In a preferred embodiment the catalyst is Pd on carbon.

SCHEME E

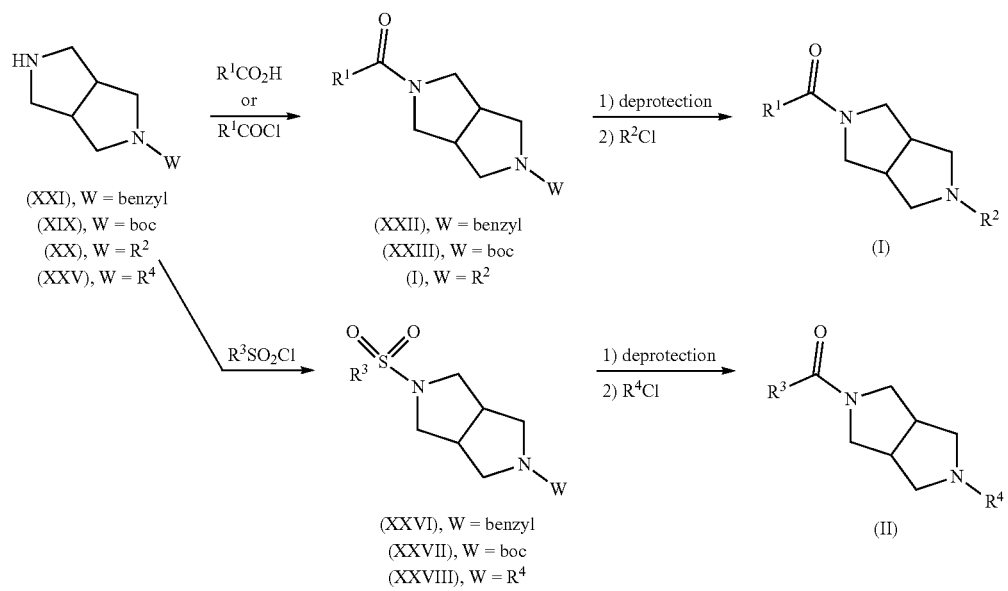

(XXI), W = benzyl
(XIX), W = boc
(XX), W = $R^2$
(XXV), W = $R^4$ (XXII), W = benzyl
(XXIII), W = boc
(I), W = $R^2$ (XXVI), W = benzyl
(XXVII), W = boc
(XXVIII), W = $R^4$ Referring to Scheme E, a compound of formula (I) is obtained from a compound of formula (XIX), (XX), or (XXI) by reacting a compound of formula (XIX), (XX), or (XXI) with a compound of formula $R^1CO_2H$ under amide formation conditions. Compounds of formula $R^1CO_2H$, where $R^1$ is as defined in formula (I), are commercially available, as described, or synthetically accessible appropriately substituted aryl or heteroaryl carboxylic acids. In a preferred embodiment a compound of formula (XIX), (XX), or (XXI), either as a free base or as an acid salt, is reacted with a compound of formula $R^1CO_2H$, in the presence of a dehydrating agent such as HOBt/EDAC, CDI, HATU, HOAT; a suitably selected base such as DIPEA, TEA, and the like; in an organic solvent or mixture thereof, such as toluene, acetonitrile, ethyl acetate, DMF, THF, methylene chloride, and the like; to afford a compound of formula (XXII), (XXIII) or (I). In a particularly preferred embodiment the dehydrating agent is HATU, and the base is DIPEA.

In an alternative embodiment, a compound of formula $R^1CO_2H$ (as described above) may be first converted to a compound of formula $R^1COCl$, or compound of formula $R^1COCl$ is a commercially available substituted aryl sulfonyl chloride. In a preferred embodiment, a compound of formula $R^1CO_2H$ is treated with thionyl chloride in a solvent such as toluene to afford a compound of formula $R^1COCl$. A compound of formula (I) is obtained by treating a compound of formula R¹COCl with a compound of formula (XIX), (XX), or (XXI), a suitably selected tertiary organic base such as TEA, and the like, in a solvent such as dichloromethane, THF, and the like, at a temperature between room temperature and the reflux temperature of the solvent. A compound of formula (II) is obtained by treating a compound of formula R¹SO₂Cl with a compound of formula (XIX), (XXI), or (XXV), where R⁴ is (5-trifluoromethyl)-pyridin-2-yl, (5-trifluoromethyl)-pyrimidin-2-yl, 4,6-dimethylpyrimidin-2-yl, or quinoxalin-2-yl; a suitably selected tertiary organic base such as TEA, and the like, in a solvent such as dichloromethane, THF, and the like, at a temperature between room temperature and the reflux temperature of the solvent.

Referring to Scheme E, one skilled in the art will recognize that the sequence of transformations shown in Schemes D and E may be reordered such that amide bond formation may be the initial reaction to give compounds of formulae (XXII) and (XXIII). Removal of the N-benzyl group from a compound of formulae (XXII) or removal of the carbamate from a compound of formula (XXIII) followed by the reaction with a compound R²Cl, where R²Cl is as described above gives a compound of formula (I).

and (XXIIb). Conversion of the acid to the acid chloride is accomplished under standard chlorination conditions. In a preferred method the acid is heated with oxalyl chloride in a solvent such as DCM. Subsequent reaction of the acid chloride with N-hydroxyacetamide in a solvent such as CH₂Cl₂ provides a mixture of esters (XXVIIIa) and (XXVIIIb). Finally, esters (XXVIIIa) and (XXVIIIb) are converted to a mixture of esters (XXIXa) and (XXIXb) and acids (XXXa) and (XXXb) by treatment with a base, preferably sodium acetate, in the presence of a solvent, preferably t-BuOH.

Alternately, acid (XXXa) is prepared by first converting 2-fluoro-6-iodobenzoic acid to the acid chloride by reaction with a chlorinating agent such as oxalyl chloride, in a solvent such as DCM, with a catalytic amount of DMF, at a temperature of 0° C. Subsequent reaction of the acid chloride with N-hydroxyacetamide in a solvent such as CH₂Cl₂ provides (Z)—N'-((2-fluoro-6-iodobenzoyl)oxy)acetimidamide. 5-(2-Fluoro-6-iodophenyl)-3-methyl-1,2,4-oxadiazole is prepared by reacting (Z)—N'-((2-fluoro-6-iodobenzoyl)oxy)acetimidamide with sodium acetate, in a solvent such as tert-butanol, at temperatures ranging from 100° C. to 110° C. 3-Fluoro-2-(3-methyl-1,2,4-oxadiazol-5-yl)benzoic

SCHEME F

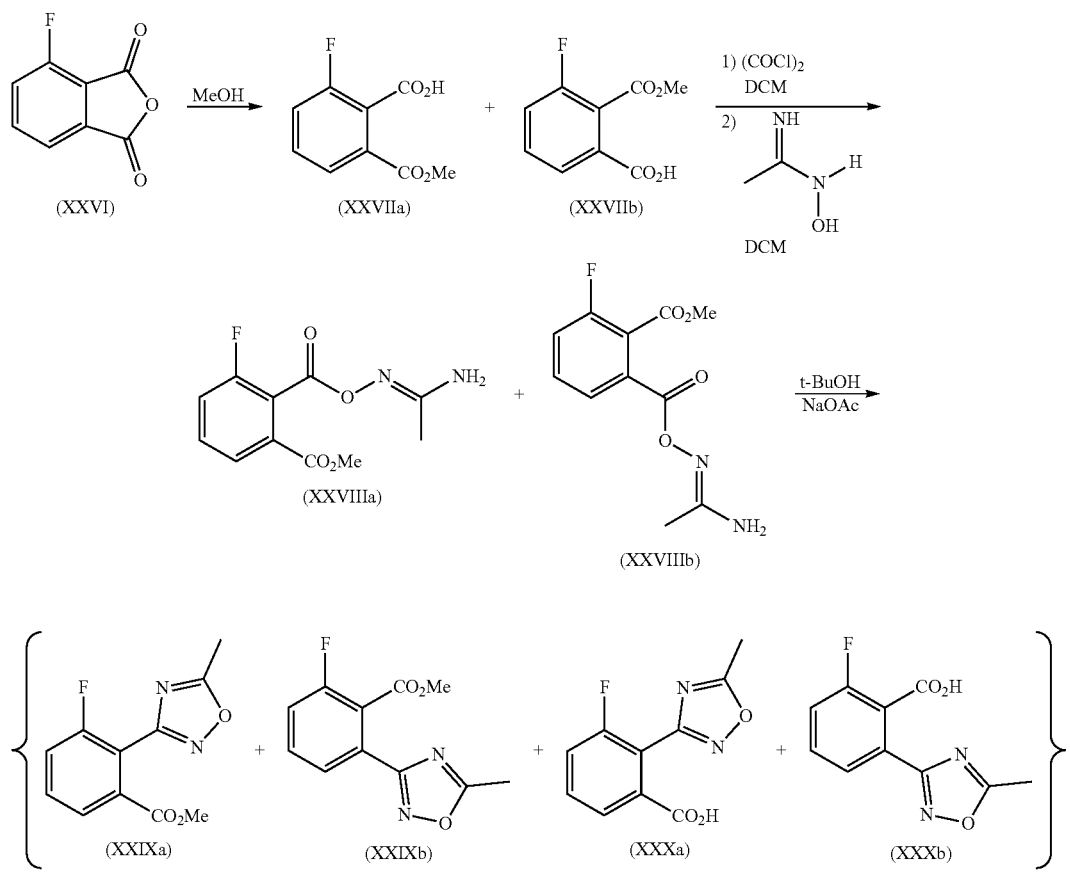

3-Fluoro-2-(3-methyl-1,2,4-oxadiazol-5-yl)benzoic acid and 2-fluoro-6-(3-methyl-1,2,4-oxadiazol-5-yl)benzoic acid are prepared according to SCHEME H. 3-Fluorophthalic anhydride was dissolved in a solvent such as MeOH, at temperatures ranging from room temperature to the reflux temperature of the solvent, to provide acid-esters (XXVIIa)

acid (XXXa) is prepared by reacting 5-(2-fluoro-6-iodophenyl)-3-methyl-1,2,4-oxadiazole with a grignard reagent such as i-PrMgCl, in a suitable solvent such as THF and the like, at a temperature of −78° C. Subsequent addition of CO₂ gas, at a temperature of −78° C. provides 3-fluoro-2-(3-methyl-1,2,4-oxadiazol-5-yl)benzoic acid (XXXa).

SCHEME H

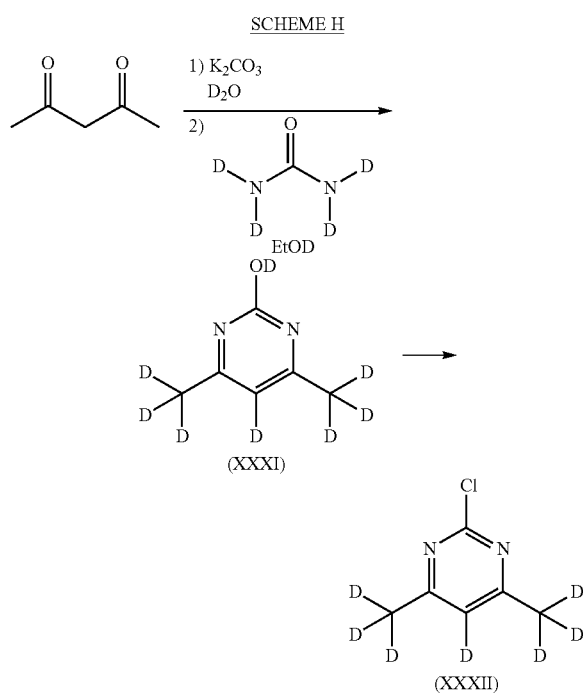

Deuterated pyrimidine compounds of formula (XXXII) are prepared according to Scheme H. Acetylacetone is reacted with an inorganic base such as K₂CO₃ in deuterated water, at temperatures ranging from 100° C. to 120° C. to provide 1,1,1,3,3,3,5,5-octadeuteriopentane-2,4-dione. 1,1,1,3,3,3,5,5-Octadeuteriopentane-2,4-dione is subsequently reacted with deuterated urea, in a solvent such as deuterated ethanol, 35% wt. DCl in D₂O, at temperatures ranging from 90° C. to 100° C. to provide deuterated pyrimidinols of formula (XXXI). Chlorination under standard chlorinating conditions provides chlorodeuteratedpyrimidine compounds of formula (XXXII).

Compounds of formula (I) may be converted to their corresponding salts using methods known to those skilled in the art. For example, amines of formula (I) may be treated with trifluoroacetic acid (TFA), HCl, maleic acid, or citric acid in a solvent such as diethyl ether (Et₂O), CH₂Cl₂, tetrahydrofuran (THF), or methanol (MeOH) to provide the corresponding salt forms. In a particularly preferred embodiment the acid is HCl and the solvent is isopropanol.

Compounds prepared according to the schemes described above may be obtained as single enantiomers, diastereomers, or regioisomers, by enantio-, diastero-, or regiospecific synthesis, or by resolution. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following examples are provided to further illustrate the invention and various preferred embodiments.

EXAMPLES

Chemistry:

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as Na₂SO₄ or MgSO₄. Where mixtures, solutions, and extracts were "concentrated", they were typically concentrated on a rotary evaporator under reduced pressure. Reactions under microwave irradiation conditions were carried out in a Biotage Initiator or CEM Discover instrument.

Normal-phase flash column chromatography (FCC) was performed on silica gel (SiO₂) using prepackaged cartridges, eluting with the indicated solvents. Preparative reverse-phase high performance liquid chromatography (HPLC) was performed on a Gilson HPLC with an Xterra Prep RP₁₈ or an XBridge C18 OBD (5 μm, 30×100 mm, or 50×150 mm) column, and a gradient of 10 to 99% acetonitrile/water (20 mM NH₄OH) over 12 to 18 min, and a flow rate of 30 mL/min. Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the ¹H NMR data below is: chemical shift in ppm downfield of the tetramethylsilane reference (multiplicity, coupling constant J in Hz, integration).

Chemical names were generated using ChemDraw Ultra 6.0.2 (CambridgeSoft Corp., Cambridge, Mass.) or ACD/Name Version 9 (Advanced Chemistry Development, Toronto, Ontario, Canada).

Intermediate 1:
5-Fluoro-2-[1,2,3]triazol-2-yl-benzoic Acid

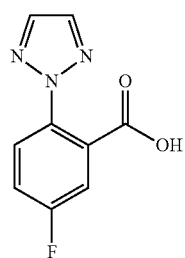 [SMILES: O=C(O)c1cc(F)ccc1-n1nccn1]

5-Fluoro-2-[1,2,3]triazol-2-yl-benzoic acid. To a solution of 5-fluoro-2-iodo-benzoic acid (3.86 g, 14.65 mmol), 2H-[1,2,3]triazole (2.5 g, 36.2 mmol), Cs₂CO₃ (8.62 g, 24.5 mmol), trans-N,N'-dimethyl-cyclohexane-1,2-diamine (0.4 mL), CuI (244 mg) and DMF (13 mL) were added to a microwave ready vessel and heated to 100° C. for 10 min. The mixture was cooled, diluted with water, and extracted with EtOAc. The aqueous layer was acidified and extracted with EtOAc. The organic layer was dried over Na₂SO₄ and concentrated. Chromatography (DCM to 10% MeOH/1% HOAc/DCM) gave the product as a white powder (2.14 g, 71%). ¹H NMR (400 MHz, CD₃OD): 7.91 (s, 2H), 7.76 (dd, J=8.9, 4.8 Hz, 1H), 7.59 (dd, J=8.5, 2.9 Hz, 1H), 7.49-7.42 (m, 1H).

Intermediates 2-12 were prepared in a manner analogous to Intermediate 1.

Intermediate 2: 2-[1,2,3]Triazol-2-yl-benzoic Acid

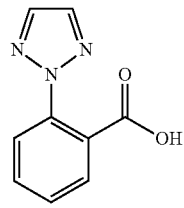 [SMILES: O=C(O)c1ccccc1-n1nccn1]

The title compound was prepared in a manner analogous to Intermediate 1, substituting 2-iodobenzoic acid for 5-fluoro-2-iodo-benzoic acid. Two products were formed in this reaction, 2-[1,2,3]triazol-2-yl-benzoic acid and 2-[1,2,3]triazol-1-yl-benzoic acid, as a result of the tautomeric forms of 1,2,3-triazole. ¹H NMR (400 MHz, CD₃OD): 7.91 (s, 2H), 7.85-7.82 (m, 1H), 7.75 (dd, J=8.1, 1.0 Hz, 1H), 7.69 (td, J=7.7, 1.5 Hz, 1H), 7.60-7.55 (m, 1H).

Intermediate 3: 2-[1,2,3]Triazol-1-yl-benzoic Acid

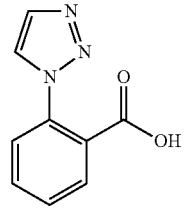

The title compound was isolated from the synthesis of Intermediate 2. ¹H NMR (400 MHz, CD₃OD): 6.70 (d, J=0.9 Hz, 1H), 6.50 (dd, J=7.7, 1.5 Hz, 1H), 6.30 (d, J=1.0 Hz, 1H), 6.24-6.18 (m, 1H), 6.17-6.11 (m, 1H), 6.01 (dd, J=7.8, 1.0 Hz, 1H).

Intermediate 4:
4-Fluoro-2-[1,2,3]triazol-2-yl-benzoic Acid

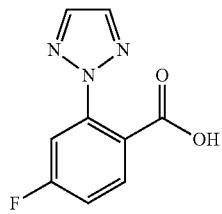 [SMILES: O=C(O)c1ccc(F)cc1-n1nccn1]

The title compound was prepared in a manner analogous to Intermediate 1, substituting for 4-fluoro-2-iodo-benzoic acid for 5-fluoro-2-iodo-benzoic acid in Step A. ¹H NMR (400 MHz, CD₃OD): 7.93 (s, 2H), 7.88 (dd, J=8.7, 5.9 Hz, 1H), 7.56 (dd, J=9.2, 2.5 Hz, 1H), 7.38-7.30 (m, 1H).

Intermediate 5:
3-Fluoro-2-[1,2,3]triazol-2-yl-benzoic Acid

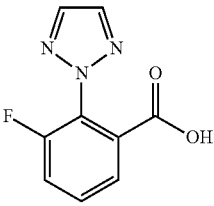

The title compound was prepared in a manner analogous to Intermediate 1, substituting for 3-fluoro-2-iodo-benzoic acid for 5-fluoro-2-iodo-benzoic acid in Step A. ¹H NMR (400 MHz, CD₃OD): 7.93 (s, 2H), 7.81 (d, J=8.3 Hz, 1H), 7.63-7.58 (m, 1H), 7.29 (td, J=8.9, 0.9 Hz, 1H).

Intermediate 6:
4-Chloro-2-[1,2,3]triazol-2-yl-benzoic Acid

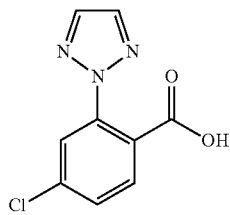 [SMILES: O=C(O)c1ccc(Cl)cc1-n1nccn1]

The title compound was prepared in a manner analogous to Intermediate 1, substituting 4-chloro-2-iodo-benzoic acid for 5-fluoro-2-iodo-benzoic acid in Step A. ¹H NMR (400 MHz, CD₃OD): 7.93 (s, 2H), 7.84-7.78 (m, 2H), 7.59 (dd, J=8.3, 2.1 Hz, 1H).

Intermediate 7: 5-Iodo-2-[1,2,3]triazol-2-yl-benzoic Acid

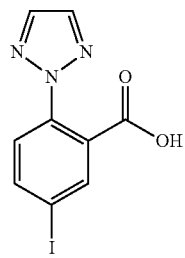

The title compound was prepared in a manner analogous to Intermediate 1, substituting 2-bromo-5-iodobenzoic acid for 5-fluoro-2-iodo-benzoic acid in Step A. ¹H NMR (400 MHz, CD₃OD): 8.09 (d, J=2.0, 1H), 8.03-7.97 (m, 1H), 7.95-7.86 (m, 3H), 7.53 (d, J=8.4, 1H).

Intermediate 8:
5-Methyl-2-[1,2,3]triazol-2-yl-benzoic Acid

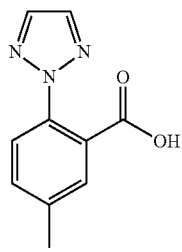

The title compound was prepared in a manner analogous to Intermediate 1, substituting for 2-iodo-5-methyl benzoic acid for 5-fluoro-2-iodo-benzoic acid in Step A. $^1$H NMR (400 MHz, CD$_3$OD): 7.87 (s 2H), 7.66 (d, J=1.3 Hz, 1H), 7.59 (d, J=8.2 Hz, 1H), 7.53-7.46 (m, 1H), 2.45 (s, 3H).

Intermediate 9:
5-Chloro-2-[1,2,3]triazol-2-yl-benzoic Acid

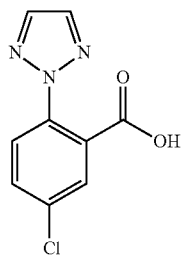

The title compound was prepared in a manner analogous to Intermediate 1, substituting 5-chloro-2-iodo-benzoic acid for 5-fluoro-2-iodo-benzoic acid in Step A. $^1$H NMR (400 MHz, CD$_3$OD): 7.91 (s, 2H), 7.82-7.74 (m, 2H), 7.71-7.66 (m, 1H).

Intermediate 10:
5-Methoxy-2-[1,2,3]triazol-2-yl-benzoic Acid

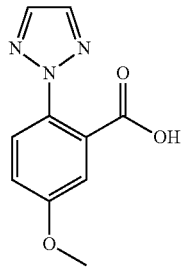 [SMILES: COc1ccc(-n2nccn2)c(C(=O)O)c1]

The title compound was prepared in a manner analogous to Intermediate 1, substituting for 2-iodo-5-methoxy benzoic acid for 5-fluoro-2-iodo-benzoic acid in Step A. $^1$H NMR (400 MHz, CD$_3$OD): 7.81 (s, J=6.4, 2H), 7.55 (d, J=8.8, 1H), 7.33 (d, J=2.9, 1H), 7.18 (dd, J=8.8, 2.9, 1H), 3.85 (s, 3H).

Intermediate 11:
2-Methyl-6-[1,2,3]triazol-2-yl-benzoic Acid

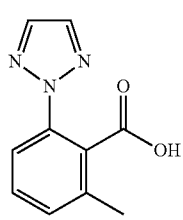

The title compound was prepared in a manner analogous to Intermediate 1, substituting for 2-iodo-6-methyl benzoic acid for 5-fluoro-2-iodo-benzoic acid in Step A. $^1$H NMR (400 MHz, CD$_3$OD): 7.89 (s, 2H), 7.72 (d, J=8.1 Hz, 1H), 7.48 (t, J=7.9 Hz, 1H), 7.36 (d, J=7.7 Hz, 1H), 2.46 (s, 3H).

Intermediate 12:
2-Fluoro-6-[1,2,3]triazol-2-yl-benzoic Acid

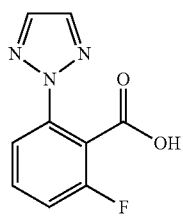 [SMILES: O=C(O)c1c(F)cccc1-n1nccn1]

Method A: The title compound was prepared in a manner analogous to Intermediate 1, substituting 2-fluoro-6-iodo-benzoic acid for 5-fluoro-2-iodo-benzoic acid. $^1$H NMR (400 MHz, CD$_3$OD): 7.96 (s, 2H), 7.87-7.82 (m, 1H), 7.70 (td, J=8.1, 5.1 Hz, 1H), 7.59 (ddd, J=9.7, 8.4, 1.4 Hz, 1H).

Method B: 2-Fluoro-6-[1,2,3]triazol-2-yl-benzoic acid. To a 2 L, 3-necked, round-bottomed flask equipped with an overhead mechanical stirrer, thermocouple probe, heating mantle, reflux condenser, and nitrogen inlet were added 2-fluoro-6-iodobenzoic acid (127.6 g, 480 mmol), copper iodide (4.57 g, 24 mmol), and Cs$_2$CO$_3$ (312.6 g, 959 mmol). To these solids were added dioxane (640 mL), then water (2.6 mL, 144 mmol), then 1H-1,2,3-triazole (55.6 mL, 959 mmol), and finally trans-1,2-dimethylcyclohexane-1,2-diamine (15.1 mL, 96 mmol). The mixture was then warmed to 60° C. for 30 min, then to 83° C. for 30 min, and then to 100° C. for 3 h. After the 3 h at 100° C., the mixture was cooled and then 1 L of MTBE and 1 L of water were added. After vigorous mixing, the layers were separated and the bottom aqueous layer was acidified to pH 1.72 with ~148 mL of concentrated hydrochloric acid. The aqueous was then extracted twice with EtOAc. The combined organic layers were dried over Na$_2$SO$_4$, filtered, and concentrated to provide a dark oil. The oil was stirred overnight in EtOAc (450 mL) and the resulting precipitate was removed by filtration. The mother-liquors were concentrated to a brown solid (106.21 g, 75 wt % by quantitative HPLC, 79.7 g, 80%). $^1$H NMR (400 MHz, DMSO-d$_6$): 8.22-8.13 (bs, 2H), 7.84-7.80 (m, 1H), 7.74-7.65 (m, 1H), 7.50-7.41 (m, 1H).

Intermediate 13: 5-Fluoro-2-pyrimidin-2-yl-benzoic Acid

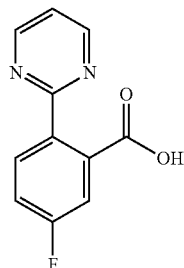

Step A: 5-Fluoro-2-iodo-benzoic acid methyl ester. To a 500 mL round-bottomed flask was added 5-fluoro-2-iodo-benzoic acid (23 g, 86.5 mmol) in methanol (230 mL). To the resulting solution was added conc. sulfuric acid (2.3 mL, 43.2 mmol). The reaction mixture was warmed to 65° C. and stirred for 15 h. The resulting mixture was concentrated under reduced pressure to give crude product which was then was partitioned between EtOAc (250 mL) and a half sat. $Na_2CO_{3(aq)}$ solution (250 mL). The layers were thoroughly mixed and then separated. The organic layer was dried over magnesium sulfate, filtered, and concentrated under reduced pressure to give a yellow oil (23 g, 95% yield). $^1$H NMR (400 MHz, $CDCl_3$): 7.94 (dd, J=8.7, 5.4 Hz, 1H), 7.54 (dd, J=9.0, 3.1 Hz, 1H), 6.93 (m, 1H), 3.94 (s, 3H).

Step B: 5-Fluoro-2-(4,4,5,5-tetramethyl-[1,3,2]dioxaborolan-2-yl)-benzoic acid methyl ester. To a 1 L round-bottomed flask equipped with a reflux condenser, temperature probe, and nitrogen line, was added 5-fluoro-2-iodo-benzoic acid methyl ester (23 g, 82 mmol) in anhydrous THF (250 mL). Anhydrous triethylamine (34 mL, 246.4 mmol) was added and the resulting mixture was degassed with a nitrogen sparge for 5 minutes. Pinacol borane (17.9 mL, 123.2 mmol) was added and the reaction mixture was degassed once more for 5 minutes. Lastly, tri(o-tolyl)phosphine (1.25 g, 4.1 mmol) and palladium acetate (461 mg, 2.053 mmol) were added. Again, the reaction mixture was degassed with a nitrogen sparge. The mixture was heated to 65° C. and stirred for 1 h. After cooling to room temperature, the reaction mixture was quenched with half sat. ammonium chloride solution (250 mL), and the resulting layers were separated. The aqueous layer was extracted with additional ethyl acetate (250 mL) and the combined organics were dried over magnesium sulfate. After filtration and concentration, the crude product was obtained as a yellow oil (23 g). The crude product was then slurried in 25% EtOAc/hexanes (250 mL). The resulting solids were not desired product and were removed by filtration. The resulting solution was then concentrated to a yellow oil (21 g, 75 wt % desired, 16.1 g actual product, 70% yield), which was used directly in the next step. By $^1$H-NMR, the crude product was also found to contain 14 wt % pinacol, 6.5 wt % ligand, and 4 wt % des-iodo starting material. $^1$H NMR (400 MHz, $CDCl_3$): 7.61 (dd, J=9.5, 2.5 Hz, 1H), 7.52-7.45 (m, 1H), 7.21 (td, J=8.3, 2.5 Hz, 1H), 3.91 (s, 3H), 1.41 (s, 12H).

Step C: 5-Fluoro-2-pyrimidin-2-yl-benzoic acid methyl ester. To a 250 mL round-bottomed flask, was added 5-fluoro-2-(4,4,5,5-tetramethyl-[1,3,2]dioxaborolan-2-yl)-benzoic acid methyl ester (5.9 g, 21.06 mmol) in 2-methyl-THF (50 mL). To the resulting solution was added 2-chloropyrimidine (2.9 g, 25.28 mmol), sodium carbonate (6.7 g, 63.19 mmol), and water (17 mL). The mixture was degassed for 30 minutes. $PdCl_2$(dppf)-dcm adduct (CAS #72287-26-4) (0.688 g, 0.843 mmol) was added and the reaction mixture was degassed once more for 30 minutes. The reaction mixture was warmed to 74° C. and stirred overnight. To the resulting solution was added diethyl ether (100 mL) and water (100 mL). The layers were thoroughly mixed then separated. The aqueous layer was extracted with additional diethyl ether (100 mL). The combined organics were dried over magnesium sulfate, filtered, and concentrated under reduced pressure to a brown crude material (5.85 g, 49% desired, 2.87 actual product). The crude product was further purified through recrystallization in 10% EtOAc/hexanes. The mixture was warmed to 70° C. and cooled slowly to room temperature. After filtration, the desired product was obtained as a brown solid (1.72 g actual product, 35% yield overall after recrystallization.) $^1$H NMR (400 MHz, $CDCl_3$): 8.78 (d, J=4.9 Hz, 2H), 8.09 (dd, J=8.7, 5.5 Hz, 1H), 7.39 (dd, J=8.6, 2.7 Hz, 1H), 7.30-7.20 (m, 2H), 3.77 (s, 3H).

Step D: 5-Fluoro-2-pyrimidin-2-yl-benzoic acid. To a solution of 5-fluoro-2-pyrimidin-2-ylbenzoic acid methyl ester (1.72 g, 7.407 mmol) in 2-methyl-THF (20 mL) was added sodium hydroxide (0.74 g, 18.517 mmol) and water (20 mL). The mixture was heated to 72° C. and stirred for 2 h. The layers were separated and the aqueous layer was extracted with additional MTBE. A 50% $HCl_{(aq)}$ solution was then dripped into the aqueous layer until a pH of 1 was reached. The resulting solid were filtered to provide the desired product as an off-white solid (1.34 g, 83% yield). $^1$H NMR (400 MHz, $CD_3OD$): 8.82 (d, J=5.0 Hz, 2H), 7.89 (dd, J=8.6, 5.4 Hz, 1H), 7.53 (dd, J=9.0, 2.7 Hz, 1H), 7.39 (m, 2H).

Intermediate 14: 2-Fluoro-6-pyrimidin-2-yl-benzoic Acid

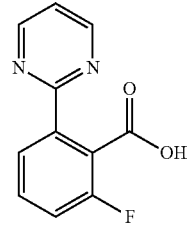 [SMILES: O=C(O)c1c(F)cccc1-c1ncccn1]

Step A: 2-Fluoro-6-iodo-benzoic acid methyl ester. To a 200 mL round-bottomed flask were added 2-fluoro-6-iodo-benzoic acid (7.5 g, 28.2 mmol), $LiOH \cdot H_2O$ (1.42 g, 33.8 mmol), and THF (100 mL). The resulting mixture was warmed to 50° C. and stirred for 2 h. Dimethyl sulfate (4.03 mL, 42.3 mmol) was then added and the mixture was warmed to 65° C. After 2 h, the mixture was cooled to room temperature and $NH_4Cl_{(aq)}$ (50 mL, 13 wt % solution) was added. The two resulting layers were thoroughly mixed and then separated. The organic layer was dried over $MgSO_4$, filtered, and concentrated under reduced pressure to a light brown oil (7.79 g, 99% yield). $^1$H NMR (400 MHz, $CDCl_3$): 7.68-7.60 (m, 1H), 7.15-7.06 (m, 2H), 3.98 (s, 3H).

Step B: 2-Fluoro-6-(4,4,5,5-tetramethyl-[1,3,2]dioxaborolan-2-yl)-benzoic acid methyl ester. To a 500 mL round-bottomed flask were added 2-fluoro-6-iodo-benzoic acid methyl ester (7.29, 26.0 mmol) and anhydrous THF (150 mL). This mixture was cooled to 0° C. and i-PrMgCl (13.7 mL, 2 M in THF, 27.3 mmol) was added dropwise. After 10 min, 2-isopropoxy-4,4,5,5-tetramethyl-1,3,2-dioxaborolane (5.58 mL, 27.3 mmol) was added. The mixture was allowed to warm to room temperature, and after 30 min NH₄Cl$_{(aq)}$ (150 mL, 13 wt % solution) was added. The layers were mixed and then separated, and the aqueous layer was extracted with 100 mL of MTBE. The combined organic layers were dried over Na₂SO₄, filtered, and concentrated to a final mass of 6.07 g (90% wt %, 75% yield). ¹H NMR (400 MHz, CDCl₃): 7.47-7.38 (m, 2H), 7.17-7.11 (m, 1H), 3.92 (s, 3H), 1.36 (s, 12H).

Step C: 2-Fluoro-6-pyrimidin-2-yl-benzoic acid methyl ester. To a 250 mL round-bottomed flask under nitrogen were added 2-fluoro-6-(4,4,5,5-tetramethyl-[1,3,2]dioxaborolan-2-yl)-benzoic acid methyl ester (5.46 g, 19.5 mmol) in 2-methyl-THF (50 mL), 2-chloropyrimidine (2.68 g, 23.4 mmol), and sodium carbonate (6.2 g, 58.5 mmol) in water (17 mL). PdCl₂(dppf)-dcm adduct (CAS #72287-26-4) (1.27 g, 1.56 mmol) was then added and the reaction mixture was warmed to 74° C. and stirred for 2.5 h. After cooling, the mixture was diluted with MTBE (50 mL) and water (80 mL). The layers were thoroughly mixed then separated. The aqueous layer was extracted with additional MTBE (100 mL). The combined organics were dried over magnesium sulfate, filtered, concentrated and then purified by flash chromatography (0-25% EA/hexanes) to provide the title compound (1.72 g, 72 wt %, 30% yield). ¹H NMR (400 MHz, CDCl₃): 8.79 (d, J=4.9 Hz, 2H), 8.15 (d, J=7.9 Hz, 1H), 7.51 (td, J=8.1, 5.6 Hz, 1H), 7.28-7.20 (m, 2H), 3.92 (s, 3H).

Step D: 2-Fluoro-6-pyrimidin-2-yl-benzoic acid. To a solution of 2-fluoro-6-pyrimidin-2-yl-benzoic acid methyl ester (1.36 g, 5.85 mmol) in 2-methyl-THF (20 mL) was added sodium hydroxide (2 M in water, 9.3 mL, 18.6 mmol). The mixture was heated to 72° C. and stirred for 9 h. The layers were separated and the aqueous layer acidified to pH 2 by dropwise addition of 50% HCl$_{(aq)}$ (3.1 mL). The resulting solids were stirred for 1 h, filtered, washed with water, MTBE, and heptanes, and then dried to provide the desired product as a white solid (1.12 g, 88% yield). ¹H NMR (400 MHz, CD₃OD): 8.83 (d, J=4.9 Hz, 2H), 8.03 (dd, J=7.9, 0.8 Hz, 1H), 7.59 (td, J=8.1, 5.6 Hz, 1H), 7.40 (t, J=4.9 Hz, 1H), 7.34 (ddd, J=9.4, 8.4, 1.0 Hz, 1H).

Intermediate 15: Hexahydro-pyrrolo[3,4-c]pyrrole-2-carboxylic Acid tert-butyl Ester

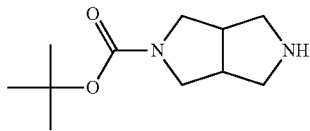

Step A. 5-Benzyl-hexahydro-pyrrolo[3,4-c]pyrrole-2-carboxylic acid tert-butyl ester. To a solution of 2-benzyl-octahydro-pyrrolo[3,4-c]pyrrole (5.62 g, 27.8 mmol) in DCM (100 mL) was added (Boc)₂O (6.16 g, 28.2 mmol). The reaction mixture was stirred for 24 hours at 23° C. The solvent was removed in vacuo and the resulting product was used in the next step without further purification. MS (ESI) mass calcd. for C₁₈H₂₆N₂O₂, 302.41. m/z found, 303.2 [M+H]⁺. ¹H NMR (400 MHz, CDCl₃): 7.36-7.20 (m, 5H), 3.61-3.46 (m, 4H), 3.24 (br s, 2H), 2.85-2.72 (m, 2H), 2.70-2.63 (m, 2H), 2.43-2.30 (m, 2H), 1.50-1.42 (s, 9H).

Step B: Hexahydro-pyrrolo[3,4-c]pyrrole-2-carboxylic acid tert-butyl ester. 5-Benzyl-hexahydro-pyrrolo[3,4-c]pyrrole-2-carboxylic acid tert-butyl ester (19.85 g, 65.6 mmol), MeOH (200 mL), HOAc (3 mL) and 10% Pd/C Degussa type (400 mg) were charged to a Parr shaker vial and shaken for 3 days at 70 psi hydrogen gas. The resulting material was filtered through Celite® and concentrated. The crude mixture was purified by flash column chromatography (FCC), DCM to 10% MeOH/DCM containing 1% NH₄OH, to afford the product. MS (ESI) mass calcd. for C₁₁H₂₀N₂O₂, 212.29. m/z found, 213.2 [M+H]⁺. ¹H NMR (400 MHz, CDCl₃): 3.60-3.55 (m, 2H), 3.38-3.25 (m, 4H), 2.95-2.86 (m, 4H), 1.47 (s, 9H).

Intermediate 16: (2-Fluoro-6-[1,2,3]triazol-2-yl-phenyl)-(hexahydro-pyrrolo[3,4-c]pyrrol-2-yl)-methanone

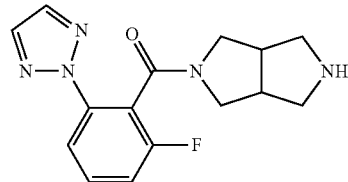 [SMILES: O=C(c1c(F)cccc1-n1nccn1)N1CC2CNCC2C1]

Method A:

Step A: 5-(2-Fluoro-6-[1,2,3]triazol-2-yl-benzoyl)-hexahydro-pyrrolo[3,4-c]pyrrole-2-carboxylic acid tert-butyl ester. In a 3-neck round bottom 100 mL flask was added toluene (8.5 mL), aqueous sodium carbonate (1.42 g in 10.7 mL water), and Intermediate 15 (0.905 mg, 4.26 mmol). The biphasic mixture was cooled to 0° C. After cooling to 0° C., 2-fluoro-6-[1,2,3]triazol-2-yl-benzoyl chloride was poured over the stirring biphasic mixture of amine and aqueous sodium carbonate. An exotherm was observed. The mixture was allowed to warm to room temperature. After 1 h, a sample of the organic layer was quenched into methanol and a small amount of acid chloride was determined to remain (observed as its methyl ester). Additional amine (~50 mg) was added and the mixture was stirred overnight at room temperature. At the end of this period, the layers were separated and 100 mL of methanol were added to the organic layer. The organic was concentrated and purified using flash column chromatography (FCC), gradient of 5-50% of a solution of 10% MeOH, 0.1% NH₄OH in DCM/DCM. The desired fractions were combined and concentrated to provide a white foamy solid (1.327 g, 76.8%). MS (ESI): mass calculated for C₂₀H₂₄FN₅O₃, 401.44, m/z found 346.2 [M+H-56]⁺. ¹H NMR (400 MHz, CDCl₃): 7.91-7.73 (m, 3H), 7.53-7.39 (m, 1H), 7.18-7.06 (m, 1H), 4.00-2.76 (m, 10H), 1.52-1.33 (m, 9H).

Step B: (2-Fluoro-6-[1,2,3]triazol-2-yl-phenyl)-(hexahydro-pyrrolo[3,4-c]pyrrol-2-yl)-methanone. 5-(2-Fluoro-6-[1,2,3]triazol-2-yl-benzoyl)-hexahydro-pyrrolo[3,4-c]pyrrole-2-carboxylic acid tert-butyl ester (1.3 g, 3.21 mmol) was taken up in DCM (6.0 mL) and TFA (3.0 mL) was added. The mixture was allowed to stir at rt for 1 hr. Solvent was removed and then taken back up in DCM and basified with 1 N aq. NaOH. The layers were separated. The aqueous was extracted 2 more time with DCM (and a small amount of MeOH). The organics were combined, dried (Na₂SO₄), filtered, and concentrated to provide the desired free base product, (2-fluoro-6-[1,2,3]triazol-2-yl-phenyl)-(hexahydro-pyrrolo[3,4-c]pyrrol-2-yl)-methanone, as a viscous/foamy residue that was found to be very hydroscopic (950.6 mg, 93.3%). MS (ESI): mass calculated for $C_{15}H_{16}FN_5O$, 301.32, m/z found 302.2 [M+H]$^+$. $^1$H NMR (400 MHz, CDCl$_3$): 7.90-7.73 (m, 3H), 7.54-7.42 (m, 1H), 7.19-7.10 (m, 1H), 3.85-2.65 (m, 10H).

Method B:

Step A: 2-Fluoro-6-[1,2,3]triazol-2-yl-benzoic acid (0.97 g, 4.71 mmol), hexahydro-pyrrolo[3,4-c]pyrrole-2-carboxylic acid tert-butyl ester (Intermediate 15, 1.0 g, 4.71 mmol), HATU (2.68 g, 7.06 mmol), in DMF (18.8 mL) was added DIEA (2.43 mL, 14.13 mmol). The mixture was stirred at rt for 1 hr. The mixture was diluted with EtOAc and washed with water. The aqueous layer was extracted with EtOAc, the organic layers were combined, dried (Na$_2$SO$_4$), filtered and concentrated to provide the crude product. Purification (FCC) (5-50% of a solution 10% MeOH, 0.1% NH$_4$OH in DCM/EtOAc over 25 minutes, and 50-100% from 25-35 minutes) provided 5-(2-fluoro-6-[1,2,3]triazol-2-yl-benzoyl)-hexahydro-pyrrolo[3,4-c]pyrrole-2-carboxylic acid tert-butyl ester (0.376 g, 19.5%).

Step B: (2-Fluoro-6-[1,2,3]triazol-2-yl-phenyl)-(hexahydro-pyrrolo[3,4-c]pyrrol-2-yl)-methanone. The title compound was prepared in a manner analogous to Intermediate 16, Method A, Step B.

Intermediate 17: Biphenyl-2-yl-(hexahydro-pyrrolo[3,4-c]pyrrol-2-yl)-methanone

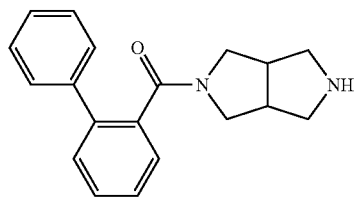 [SMILES: O=C(c1ccccc1-c1ccccc1)N1CC2CNCC2C1]

The title compound was prepared in a manner analogous to Intermediate 16, Method B, substituting biphenyl-2-carboxylic acid for 2-fluoro-6-[1,2,3]triazol-2-yl-benzoic acid in Step A.

Intermediate 18: [5-(2-Fluoro-phenyl)-2-methyl-thiazol-4-yl]-(hexahydro-pyrrolo[3,4-c]pyrrol-2-yl)-methanone

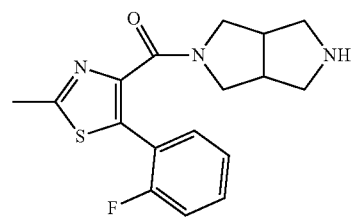 [SMILES: Cc1nc(C(=O)N2CC3CNCC3C2)c(-c2ccccc2F)s1]

The title compound was prepared in a manner analogous to Intermediate 16, Method B, substituting 5-(2-fluoro-phenyl)-2-methyl-thiazole-4-carboxylic acid for 2-fluoro-6-[1,2,3]triazol-2-yl-benzoic acid in Step A. MS (ESI): mass calculated for $C_{17}H_{18}FN_3OS$, 331.41, m/z found 332.1 [M+1]$^+$. $^1$H NMR (400 MHz, CDCl$_3$): 7.54-7.45 (m, 1H), 7.40-7.32 (m, 1H), 7.21-7.10 (m, 2H), 3.79-3.70 (m, 1H), 3.61-3.50 (m, 2H), 3.22-3.13 (m, 1H), 3.12-3.05 (m, 1H), 3.03-2.94 (m, 1H), 2.85-2.45 (m, 8H).

Intermediate 19: (Hexahydro-pyrrolo[3,4-c]pyrrol-2-yl)-(5-methyl-2-[1,2,3]triazol-2-yl-phenyl)-methanone

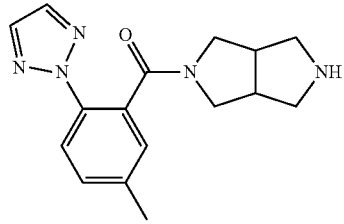 [SMILES: Cc1ccc(-n2nccn2)c(C(=O)N2CC3CNCC3C2)c1]

The title compound was prepared in a manner analogous to Intermediate 16, Method B, substituting 5-methyl-2-[1,2,3]triazol-2-yl-benzoic acid for 2-fluoro-6-[1,2,3]triazol-2-yl-benzoic acid in Step A. MS (ESI): mass calculated for $C_{17}H_{19}N_5O$, 297.36, m/z found 298.2 [M+1]$^+$. $^1$H NMR (400 MHz, CDCl$_3$): 7.88-7.76 (m, 3H), 7.36-7.29 (m, 1H), 7.22-7.18 (m, 1H), 3.81-2.59 (m, 10H), 2.42 (s, 3H).

Intermediate 20: 2(Hexahydro-pyrrolo[3,4-c]pyrrol-2-yl)-(2-[1,2,3]triazol-2-yl-phenyl)-methanone

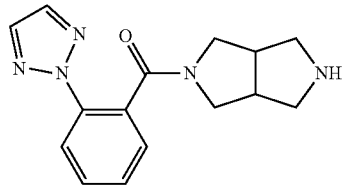 [SMILES: O=C(c1ccccc1-n1nccn1)N1CC2CNCC2C1]

The title compound was prepared in a manner analogous to Intermediate 16, Method B, substituting 2-[1,2,3]triazol-2-yl-benzoic acid for 2-fluoro-6-[1,2,3]triazol-2-yl-benzoic acid in Step A. MS (ESI): mass calculated for $C_{15}H_{17}N_5O$, 283.33, m/z found 284.1 [M+1]$^+$. $^1$H NMR (400 MHz, CDCl$_3$): 7.99 (d, J=8.2, 1H), 7.55-7.51 (m, 1H), 7.48-7.36 (m, 2H), 3.99-2.42 (m, 11H).

Intermediate 21: (5-Fluoro-2-[1,2,3]triazol-2-yl-phenyl)-(hexahydro-pyrrolo[3,4-c]pyrrol-2-yl)-methanone

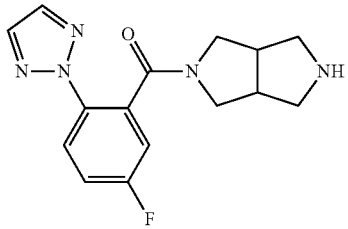 [SMILES: O=C(c1cc(F)ccc1-n1nccn1)N1CC2CNCC2C1]

The title compound was prepared in a manner analogous to Intermediate 16, Method B, substituting 5-fluoro-2-[1,2, 3]triazol-2-yl-benzoic acid (Intermediate 97) for 2-fluoro-6-[1,2,3]triazol-2-yl-benzoic acid in Step A. MS (ESI): mass calculated for $C_{15}H_{16}FN_5O$, 301.32, m/z found 302.0 [M+1]$^+$. $^1$H NMR (400 MHz, CDCl$_3$): 7.96 (dd, J=9.0, 4.8, 1H), 7.85-7.74 (m, 2H), 7.25-7.17 (m, 1H), 7.16-7.10 (m, 1H), 3.78-2.48 (m, 10H).

Intermediate 22: (4-Fluoro-2-[1,2,3]triazol-2-yl-phenyl)-(hexahydro-pyrrolo[3,4-c]pyrrol-2-yl)-methanone

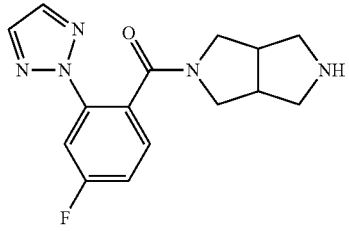 [SMILES: O=C(c1ccc(F)cc1-n1nccn1)N1CC2CNCC2C1]

The title compound was prepared in a manner analogous to Intermediate 16, Method B, substituting 4-fluoro-2-[1,2,3]triazol-2-yl-benzoic acid for 2-fluoro-6-[1,2,3]triazol-2-yl-benzoic acid in Step A. MS (ESI): mass calculated for $C_{15}H_{16}FN_5O$, 301.32. m/z found 302.0 [M+1]$^+$. $^1$H NMR (400 MHz, CDCl$_3$): 7.90-7.72 (m, 3H), 7.43-7.35 (m, 1H), 7.17-7.08 (m, 1H), 3.81-3.62 (m, 2H), 3.39-2.56 (m, 8H).

Intermediate 23: 2-(4,6-Dimethyl-pyrimidin-2-yl)-octahydro-pyrrolo[3,4-c]pyrrole

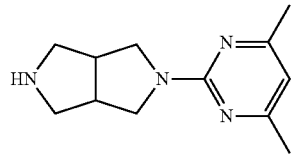 [SMILES: Cc1cc(C)nc(N2CC3CNCC3C2)n1]

Method A:
Step A: 5-(4,6-Dimethyl-pyrimidin-2-yl)-hexahydro-pyrrolo[3,4-c]pyrrole-2-carboxylic acid tert-butyl ester. Hexahydro-pyrrolo[3,4-c]pyrrole-2-carboxylic acid tert-butyl ester (1.20 g, 5.6 mmol), 2-chloro-4,6-dimethyl-pyrimidine (1.03 g, 7.2 mmol), Cs$_2$CO$_3$ (2.12 g, 6.5 mmol) and DMF (15 mL) were combined and heated to 100° C. for 24 hours. The reaction was then allowed to cool and water and EtOAc were added. The products were extracted into EtOAc, dried over Na$_2$SO$_4$, and concentrated. The resulting crude mixture was purified by flash column chromatography (EA/hex) to give the title compound (1.27 g, 71%). MS (ESI) mass calcd. for $C_{17}H_{26}N_4O_2$, 318.42. m/z found, 319.2 [M+H]$^+$. $^1$H NMR (400 MHz, CDCl$_3$): 6.25 (s, 1H), 3.85-3.75 (m, 2H), 3.69-3.46 (m, 4H), 3.38-3.20 (m, 2H), 2.94 (br s, 2H), 2.29 (s, 6H), 1.44 (s, 9H).

Step B: 2-(4,6-Dimethyl-pyrimidin-2-yl)-octahydro-pyrrolo[3,4-c]pyrrole. 5-(4,6-Dimethyl-pyrimidin-2-yl)-hexahydro-pyrrolo[3,4-c]pyrrole-2-carboxylic acid tert-butyl ester (0.92 g, 2.9 mmol), DCM (10 mL) and TFA (5 mL) were stirred at 23° C. for 2 h. The mixture was concentrated to remove the volatiles, diluted with EtOAc and 1 N aq. NaOH, and extracted with EtOAc (3×). The organic fractions were dried and concentrated to give the title compound (0.61 g, 96%) that contained a small amount of DCM and was used as is. MS (ESI) mass calcd. for $C_{12}H_{18}N_4$, 218.30. m/z found, 219.2 [M+H]$^+$. $^1$H NMR (400 MHz, CDCl$_3$): 6.27 (s, 1H), 3.81-3.70 (m, 2H), 3.55-3.48 (m, 2H), 3.16-3.07 (m, 2H), 2.94-2.78 (m, 4H), 2.29 (s, 6H).

Method B:
Step A: 2-Benzyl-5-(4,6-dimethyl-pyrimidin-2-yl)-octahydro-pyrrolo[3,4-c]pyrrole. To a 3 L, 3-necked, round-bottomed flask equipped with mechanical stirrer, reflux condenser, temperature probe, and nitrogen inlet, was added 2-benzyl-octahydro-pyrrolo[3,4-c]pyrrole (109 g, 538.8 mmol) in DMF (1.6 L). To the resulting solution were added 2-chloro-4,6-methylpyrimidine (76.8 g, 538.8 mmol) and Cs$_2$CO$_3$ (351.1 g, 1.08 mol). The heterogeneous mixture was heated to 100° C. and stirred for 15 h. After cooling to room temperature, the mixture was diluted with ethyl acetate (1.5 L) and water (1.5 L). The layers were thoroughly mixed and separated. The aqueous layer was extracted with additional ethyl acetate (1.5 L). The combined organics were dried over sodium sulfate, filtered, and concentrated under reduced pressure to a brown solid (160 g, 96% yield). MS (ESI) mass calcd. for $C_{19}H_{24}N_4$, 308.20. m/z found 309 [M+H]$^+$. $^1$H-NMR (500 MHz, CDCl$_3$): 7.32-7.26 (m, 4H), 7.25-7.20 (m, 1H), 6.27 (s, 1H), 3.81-3.73 (m, 2H), 3.58 (s, 2H), 3.54 (dd, J=11.4, 3.5 Hz, 2H), 2.95-2.86 (m, 2H), 2.80-2.68 (m, 2H), 2.47-2.40 (m, 2H), 2.35-2.24 (s, 6H).

Step B: 2-(4,6-Dimethyl-pyrimidin-2-yl)-octahydro-pyrrolo[3,4-c]pyrrole·HOAc. To a 4 L high pressure autoclave equipped with mechanical stirring, temperature probe, heating jacket, and gas inlet were added 5% Pd/C (66.9 g, Johnson Matthey 5R338, 56.8% H$_2$O, 3.45 mol %) and a solution of 2-benzyl-5-(4,6-dimethyl-pyrimidin-2-yl)-octahydro-pyrrolo[3,4-c]pyrrole (160 g, 519 mmol) and acetic acid (30 mL, 519 mmol) in ethanol (3.2 L). The mixture was stirred at 50° C. under 50 psi of H$_2$(g) for 4 h. The catalyst was removed and the resulting solution was then concentrated under reduced pressure to provide the desired product as a white solid (144 g, quantitative yield) as the HOAc salt. MS (ESI): mass calcd. for $C_{12}H_{18}N_4$, 218.15; m/z found 219 [M+H]$^+$. $^1$H-NMR (CDCl$_3$, 400 MHz): 6.30 (s, 1H), 3.79-3.59 (m, 4H), 3.39 (m, 2H), 3.09-2.88 (m, 4H), 2.29 (s, 6H), 1.93 (s, 3H).

Intermediate 24: [4-(Hexahydro-pyrrolo[3,4-c]pyrrol-2-yl)-6-methoxy-pyrimidin-2-yl]-dimethyl-amine

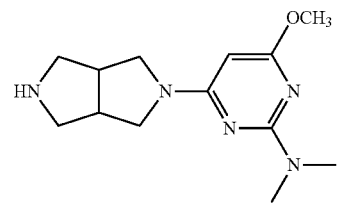 [SMILES: COc1cc(N2CC3CNCC3C2)nc(N(C)C)n1]

Step A: Intermediate 24 was prepared in a manner analogous to Intermediate 23, Method A, substituting (4-chloro-6-methoxy-pyrimidin-2-yl)-dimethyl-amine for 2-chloro-4,6-dimethyl-pyrimidine in Step A to afford 5-(2-dimethylamino-6-methoxy-pyrimidin-4-yl)-hexahydro-pyrrolo[3,4-c]pyrrole-2-carboxylic acid tert-butyl ester.

Step B: [4-(Hexahydro-pyrrolo[3,4-c]pyrrol-2-yl)-6-methoxy-pyrimidin-2-yl]-dimethyl-amine. A mixture of 5-(2-dimethylamino-6-methoxy-pyrimidin-4-yl)-hexahydro-pyrrolo[3,4-c]pyrrole-2-carboxylic acid tert-butyl ester (700 mg) and TFA (10 mL) was stirred in dioxane (30 mL) at room temperature for 18 h. Then the acid and solvents were removed to yield the crude trifluoro acetic acid salt of the title compound (1.3 g). The crude was purified by flash column chromatography (FCC) using 0-10% MeOH (2 M NH$_3$) and DCM (gradient) to yield pure title compound (155 mg, 30.4%). MS (ESI) mass calcd. for C$_{13}$H$_{21}$N$_5$O, 263.34. m/z found 264.1 [M+H]$^+$. The intermediate was used without further purification.

Intermediate 25: [6-(Hexahydro-pyrrolo[3,4-c]pyrrol-2-yl)-2-trifluoromethyl-pyrimidin-4-yl]-dimethyl-amine

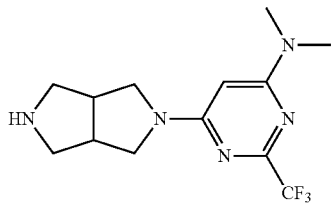

Step A: The title compound was prepared in a manner analogous to Intermediate 23, Method A, substituting (6-chloro-2-trifluoromethyl-pyrimidin-4-yl)-dimethyl-amine for 2-chloro-4,6-dimethyl-pyrimidine in Step A to afford 5-(6-dimethylamino-2-trifluoromethyl-pyrimidin-4-yl)-hexahydro-pyrrolo[3,4-c]pyrrole-2-carboxylic acid tert-butyl ester.
Step B: [6-(Hexahydro-pyrrolo[3,4-c]pyrrol-2-yl)-2-trifluoromethyl-pyrimidin-4-yl]-dimethyl-amine. A mixture of 5-(6-dimethylamino-2-trifluoromethyl-pyrimidin-4-yl)-hexahydro-pyrrolo[3,4-c]pyrrole-2-carboxylic acid tert-butyl ester (600 mg) and TFA (10.0 mL) was stirred in dioxane (30.0 mL) at room temperature for 18 h. Then the acid and solvents were removed to yield the crude trifluoro acetic acid salt of the title compound (800 mg, 165%). The crude was purified by flash column chromatography (FCC) using 0-10% MeOH (2M NH$_3$) and DCM (gradient) to yield pure title compound (260 mg, 53.5%). MS (ESI) mass calcd. for C$_{13}$H$_{18}$F$_3$N$_5$, 301.32; m/z found 302.2 [M+H]$^+$. The intermediate was used as such in the subsequent reactions.

Intermediate 26: 2-(4-Phenyl-pyrimidin-2-yl)-octahydro-pyrrolo[3,4-c]pyrrole

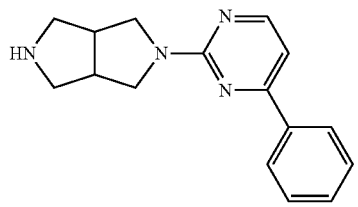 [SMILES: c1ccc(-c2ccnc(N3CC4CNCC4C3)n2)cc1]

The title compound was prepared in a manner analogous to Intermediate 23, Method A, substituting 2-chloro-4-phenyl-pyrimidine for 2-chloro-4,6-dimethyl-pyrimidine in Step A. MS (ESI) mass calcd. for C$_{29}$H$_{26}$N$_4$O, 266.35. m/z found, 267.2 [M+H]$^+$. $^1$H NMR (400 MHz, CD$_3$OD): 6.78-6.70 (m, 1H), 6.55-6.49 (m, 2H), 5.97-5.82 (m, 3H), 5.60-5.47 (m, 1H), 2.30-2.20 (m, 2H), 2.02 (dd, J=11.6, 2.6 Hz, 2H), 1.58 (br s, 2H), 1.42 (br s, 2H), 1.23 (br s, 2H).

Intermediate 27: 2-(4-Methyl-pyrimidin-2-yl)-octahydro-pyrrolo[3,4-c]pyrrole

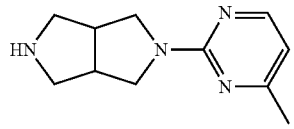

The title compound was prepared in a manner analogous to Intermediate 23, Method A, substituting 2-chloro-4-methyl-pyrimidine for 2-chloro-4,6-dimethyl-pyrimidine in Step A. MS (ESI) mass calcd. for C$_{11}$H$_{16}$N$_4$, 204.28. m/z found, 205.2 [M+H]$^+$. $^1$H NMR (400 MHz, CDCl$_3$): 8.20-8.12 (m, 1H), 8.16 (d, J=5.0 Hz, 1H), 6.43-6.33 (m, 1H), 6.38 (d, J=5.0 Hz, 1H), 3.81-3.69 (m, 2H), 3.52 (dd, J=11.6, 3.2 Hz, 2H), 3.16 (dd, J=11.1, 6.5 Hz, 2H), 2.97-2.77 (m, 5H), 2.33 (s, 3H).

Intermediate 28: 2-(Hexahydro-pyrrolo[3,4-c]pyrrol-2-yl)-benzooxazole

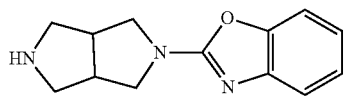 [SMILES: c1ccc2oc(N3CC4CNCC4C3)nc2c1]

The title compound was prepared in a manner analogous to Intermediate 23, Method A, substituting 2-chloro-benzooxazole for 2-chloro-4,6-dimethyl-pyrimidine in Step A. MS (ESI) mass calcd. for C$_{11}$H$_{16}$N$_4$, 229.28. m/z found, 230.15 [M+H]$^+$. $^1$H NMR (400 MHz, CDCl$_3$): 7.43-7.33 (m, 1H), 7.29-7.22 (m, 1H), 7.120-7.13 (m, 1H), 7.05-6.98 (m, 1H), 3.89-3.77 (m, 2H), 3.55 (dd, J=10.9, 3.2 Hz, 2H), 3.25-3.15 (m, 2H), 3.02-2.90 (m, 2H), 2.88-2.79 (m, 2H).

Intermediate 29: 2-(Hexahydro-pyrrolo[3,4-c]pyrrol-2-yl)-3-methyl-quinoxaline

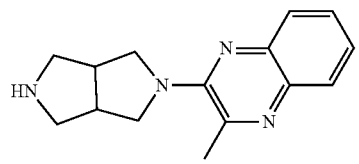 [SMILES: Cc1nc2ccccc2nc1N1CC2CNCC2C1]

The title compound was prepared in a manner analogous to Intermediate 23 substituting 2-chloro-3-methyl-quinoxaline for 2-chloro-4,6-dimethyl-pyrimidine in Step A. MS (ESI) mass calcd. for C$_{15}$H$_{18}$N$_4$, 254.34. m/z found, 255.2 [M+H]$^+$. $^1$H NMR (400 MHz, CD$_3$OD): 7.78 (dd, J=8.2, 1.1 Hz, 1H), 7.73 (dd, J=8.3, 0.9 Hz, 1H), 7.59-7.54 (m, 1H), 7.48-7.43 (m, 1H), 3.78-3.69 (m, 2H), 3.58 (dd, J=11.0, 3.1 Hz, 2H), 3.18-3.12 (m, 2H), 2.99-2.90 (m, 2H), 2.81 (dd, J=11.6, 4.0 Hz, 2H), 2.75 (s, 3H).

Intermediate 30: 2-(Hexahydro-pyrrolo[3,4-c]pyrrol-2-yl)-3-trifluoromethyl-quinoxaline

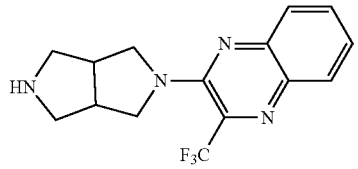

The title compound was prepared in a manner analogous to Intermediate 23 substituting 2-chloro-3-trifluoromethyl-quinoxaline for 2-chloro-4,6-dimethyl-pyrimidine in Step A. MS (ESI) mass calcd. for $C_{15}H_{15}F_3N_4$, 308.31. m/z found 309.2 [M+H]$^+$. $^1$H NMR (400 MHz, CD$_3$OD): 8.00-7.89 (m, 1H), 7.83-7.70 (m, 2H), 7.60-7.52 (m, 1H), 3.81-3.73 (m, 2H), 3.61 (dd, J=11.3, 3.0 Hz, 2H), 3.18-3.13 (m, 2H), 2.99-2.92 (m, 2H), 2.78 (dd, J=11.6, 4.1 Hz, 2H).

Intermediate 31: 2-(6-Methyl-2-trifluoromethyl-pyrimidin-4-yl)-octahydro-pyrrolo[3,4-c]pyrrole

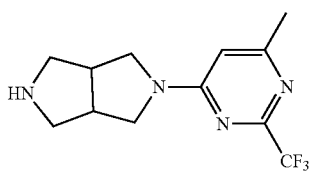 [SMILES: Cc1cc(N2CC3CNCC3C2)nc(C(F)(F)F)n1]

The title compound was prepared in a manner analogous to Intermediate 23 substituting 4-chloro-6-methyl-2-trifluoromethyl-pyrimidine for 2-chloro-4,6-dimethyl-pyrimidine in Step A. MS (ESI) mass calcd. for $C_{12}H_{15}F_3N_4$, 272.27; m/z found, 273.2 [M+H]$^+$. $^1$H NMR (400 MHz, CD$_3$OD): 6.48 (s, 1H), 3.90-3.24 (m, 4H), 3.20-3.10 (m, 2H), 3.00 (br s, 2H), 2.82-2.75 (m, 2H), 2.39 (s, 3H).

Intermediate 32: 2-(4-Methoxy-pyrimidin-2-yl)-octahydro-pyrrolo[3,4-c]pyrrole

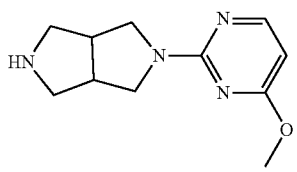 [SMILES: COc1ccnc(N2CC3CNCC3C2)n1]

The title compound was prepared in a manner analogous to Intermediate 23 substituting 2-chloro-4-methoxy-pyrimidine for 2-chloro-4,6-dimethyl-pyrimidine in Step A. MS (ESI) mass calculated for $C_{11}H_{16}N_4O$, 220.27, m/z found 221.2 [M+1]$^+$. $^1$H NMR (400 MHz, CD$_3$OD): 8.00 (d, J=6.0, 1H), 6.12 (d, J=6.0, 1H), 4.23 (s, 1H), 3.94 (s, 3H), 3.84-3.75 (m, 2H), 3.70-3.59 (m, 4H), 3.28-3.15 (m, 4H).

Intermediate 33: 2-(4-Trifluoromethyl-pyrimidin-2-yl)-octahydro-pyrrolo[3,4-c]pyrrole

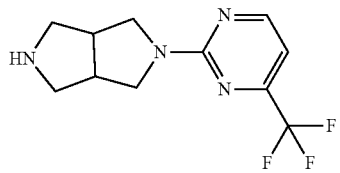 [SMILES: FC(F)(F)c1ccnc(N2CC3CNCC3C2)n1]

The title compound was prepared in a manner analogous to Intermediate 24, substituting 2-chloro-4-trifluoromethyl-pyrimidine for 2-chloro-4,6-dimethyl-pyrimidine in Step A. MS (ESI): mass calculated for $C_{11}H_{13}F_3N_4$, 258.25, m/z found 259.1 [M+1]$^+$. $^1$H NMR (400 MHz, CDCl$_3$): 8.52 (d, J=4.9, 1H), 6.88-6.83 (m, 1H), 3.94-3.54 (m, 6H), 3.29-3.11 (m, 4H).

Intermediate 34: 2-(3,6-Dimethyl-pyrazin-2-yl)-octahydro-pyrrolo[3,4-c]pyrrole

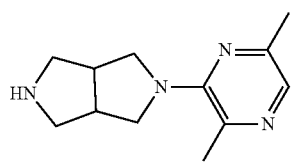

The title compound was prepared in a manner analogous to Intermediate 23 substituting 3-chloro-2,5-dimethyl-pyrazine for 2-chloro-4,6-dimethyl-pyrimidine in Step A. MS (ESI): mass calculated for $C_{12}H_{18}N_4$, 218.30, m/z found 219.2 [M+1]$^+$. $^1$H NMR (400 MHz, CDCl$_3$): 10.13-9.85 (m, 1H), 7.89 (s, 1H), 3.71-3.40 (m, 6H), 3.17 (s, 4H), 2.54 (s, 3H), 2.39 (s, 3H).

Intermediate 35: 2-(Hexahydro-pyrrolo[3,4-c]pyrrol-2-yl)-quinoxaline

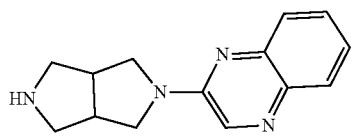 [SMILES: c1ccc2nc(N3CC4CNCC4C3)cnc2c1]

The title compound was prepared in a manner analogous to Intermediate 23 substituting 2-chloro-quinoxaline for 2-chloro-4,6-dimethyl-pyrimidine in Step A. MS (ESI): mass calculated for $C_{14}H_{16}N_4$, 240.31, m/z found 241.2 [M+1]$^+$. $^1$H NMR (400 MHz, CDCl$_3$): 8.39-8.34 (m, 1H), 7.91-7.84 (m, 1H), 7.72-7.66 (m, 1H), 7.60-7.53 (m, 1H), 7.40-7.32 (m, 1H), 3.95-3.80 (m, 2H), 3.65-3.52 (m, 2H), 3.27-3.11 (m, 2H), 3.08-2.94 (m, 2H), 2.92-2.82 (m, 2H).

Intermediate 36: [4-(Hexahydro-pyrrolo[3,4-c]pyrrol-2-yl)-6-trifluoromethyl-pyrimidin-2-yl]-dimethyl-amine

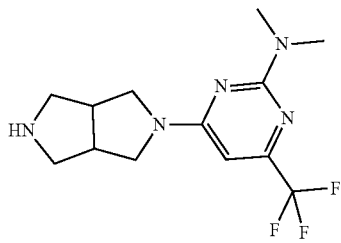 [SMILES: CN(C)c1nc(N2CC3CNCC3C2)cc(C(F)(F)F)n1]

The title compound was prepared in a manner analogous to Intermediate 23 substituting (4-chloro-6-trifluoromethyl-pyrimidin-2-yl)-dimethyl-amine for 2-chloro-4,6-dimethyl-pyrimidine in Step A. MS (ESI): mass calculated for $C_{34}H_{18}F_3N_5$, 301.32, m/z found 302.1 [M+1]$^+$. $^1$H NMR (400 MHz, CDCl$_3$): 5.92 (s, 1H), 3.91-3.54 (m, 2H), 3.50-3.24 (m, 2H), 3.21-3.05 (m, 9H), 2.99-2.75 (m, 4H).

Intermediate 37: (Hexahydro-pyrrolo[3,4-c]pyrrol-2-yl)-(2-thiophen-2-yl-phenyl)-methanone

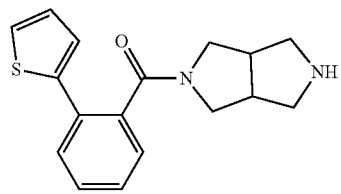 [SMILES: O=C(c1ccccc1-c1cccs1)N1CC2CNCC2C1]

The title compound was prepared in a manner analogous to Intermediate 16, Method B, substituting 2-thiophen-2-yl-benzoic acid for 2-fluoro-6-[1,2,3]triazol-2-yl-benzoic acid in Step A. MS (ESI): mass calculated for $C_{17}H_{18}N_2OS$, 298.41, m/z found 299.1 [M+1]$^+$. $^1$H NMR (400 MHz, CDCl$_3$): 7.55-7.50 (m, 1H), 7.48-7.31 (m, 4H), 7.22-7.11 (m, 1H), 7.08-7.03 (m, 1H), 4.06-1.63 (m, 10H).

Intermediate 38: (2,4-Dimethoxy-phenyl)-(hexahydro-pyrrolo[3,4-c]pyrrol-2-yl)-methanone

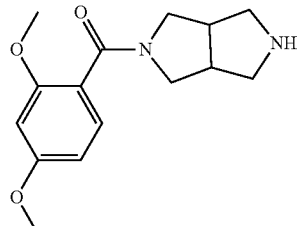

The title compound was prepared in a manner analogous to Intermediate 16, Method B, substituting 2,4-dimethoxy-benzoic acid for 2-fluoro-6-[1,2,3]triazol-2-yl-benzoic acid and substituting EDCl for HATU in Step A.

Intermediate 39: 2-(4,6-Dimethoxy-pyrimidin-2-yl)-octahydro-pyrrolo[3,4-c]pyrrole

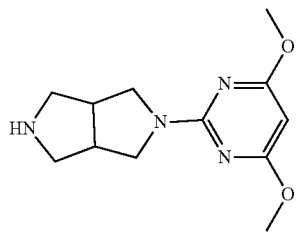

The title compound was prepared in a manner analogous to Intermediate 23 utilizing 2-chloro-4,6-dimethoxypyrimidine and hexahydro-pyrrolo[3,4-c]pyrrole-2-carboxylic acid tert-butyl ester as starting materials.

Intermediate 40: 6-Chloro-2-(hexahydro-pyrrolo[3,4-c]pyrrol-2-yl)-benzothiazole

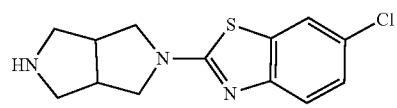 [SMILES: Clc1ccc2nc(N3CC4CNCC4C3)sc2c1]

The title compound was prepared in a manner analogous to Intermediate 23 utilizing 2,6-dichloro-benzothiazole and hexahydro-pyrrolo[3,4-c]pyrrole-2-carboxylic acid tert-butyl ester as starting materials.

Intermediate 41: (2,6-Dimethoxy-phenyl)-(hexahydro-pyrrolo[3,4-c]pyrrol-2-yl)-methanone

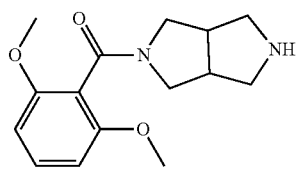 [SMILES: COc1cccc(OC)c1C(=O)N1CC2CNCC2C1]

The title compound was prepared in a manner analogous to Intermediate 16, Method B, substituting 2,6-dimethoxy-benzoic acid for 2-fluoro-6-[1,2,3]triazol-2-yl-benzoic acid in Step A.

Intermediate 42: 2-(4,5,6-trimethylpyrimidin-2-yl)octahydropyrrolo[3,4-c]pyrrole

The title compound was prepared in a manner analogous to Intermediate 23 substituting 2-chloro-4,5,6-trimethylpyrimidine (Intermediate 56) for 2-chloro-4,6-dimethylpyrimidine in Step A. MS (ESI): mass calculated for $C_{24}H_{25}FN_6O$, 232.17. m/z found 233.1 $[M+H]^+$.

Intermediate 43: 6-Fluoro-2-(hexahydropyrrolo[3,4-c]pyrrol-2(1H)-yl)quinazoline

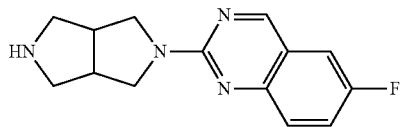 [SMILES: Fc1ccc2nc(N3CC4CNCC4C3)ncc2c1]

The title compound was prepared in a manner analogous to Intermediate 23 substituting 2-chloro-6-fluoroquinazoline for 2-chloro-4,6-dimethylpyrimidine in Step A. MS (ESI): mass calculated for $C_{24}H_{25}FN_6O$, 258.13; m/z found 259.1 $[M+H]^+$.

Intermediate 44: 6,7-Difluoro-2-(hexahydropyrrolo[3,4-c]pyrrol-2(1H)-yl)quinoxaline

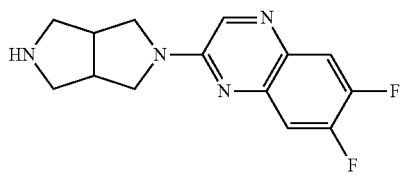 [SMILES: Fc1cc2ncc(N3CC4CNCC4C3)nc2cc1F]

The title compound was prepared in a manner analogous to Intermediate 23 substituting 2-chloro-6,7-difluoroquinoxaline for 2-chloro-4,6-dimethylpyrimidine in Step A. MS (ESI): mass calculated for $C_{24}H_{25}FN_6O$, 276.12; m/z found 277.1 $[M+H]^+$.

Intermediate 45: 2-(4,6-Dimethoxypyrimidin-2-yl)octahydropyrrolo[3,4-c]pyrrole

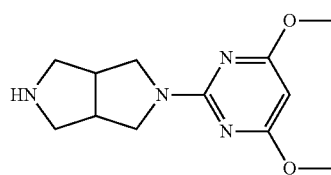 [SMILES: COc1cc(OC)nc(N2CC3CNCC3C2)n1]

The title compound was prepared in a manner analogous to Intermediate 23 substituting 2-chloro-4,6-dimethoxypyrimidine for 2-chloro-4,6-dimethylpyrimidine in Step A. MS (ESI): mass calculated for $C_{12}H_{18}N_4O_2$, 250.14; m/z found 251.2 $[M+H]^+$.

Intermediate 46: 2-(5-Nitropyrimidin-2-yl)octahydropyrrolo[3,4-c]pyrrole

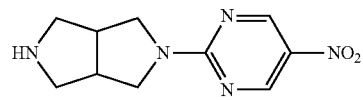 [SMILES: O=[N+]([O-])c1cnc(N2CC3CNCC3C2)nc1]

The title compound was prepared in a manner analogous to Intermediate 23 substituting 2-chloro-5-nitropyrimidine for 2-chloro-4,6-dimethylpyrimidine in Step A. MS (ESI): mass calculated for $C_{10}H_{13}NO_2$, 235.11; m/z found 236.2 $[M+H]^+$.

Intermediate 47: Methyl 2-(hexahydropyrrolo[3,4-c]pyrrol-2(1H)-yl)-4-(trifluoromethyl)pyrimidine-5-carboxylate

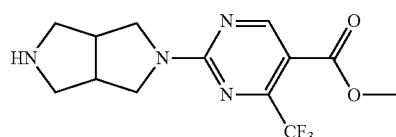

The title compound was prepared in a manner analogous to Intermediate 23 substituting methyl 2-chloro-4-(trifluoromethyl)pyrimidine-5-carboxylate for 2-chloro-4,6-dimethylpyrimidine in Step A. MS (ESI): mass calculated for $C_{13}H_{15}F_3N_4O_2$, 316.11. m/z found 317.2 $[M+H]^+$.

Intermediate 48: (5-(4-Fluorophenyl)-2-methylthiazol-4-yl)(hexahydropyrrolo[3,4-c]pyrrol-2(1H)-yl)methanone

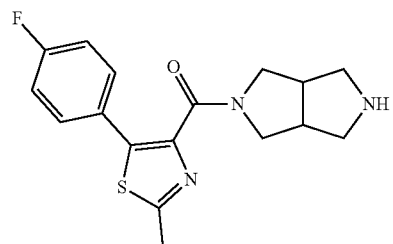

The title compound was prepared in a manner analogous to Intermediate 16, Method B, substituting 5-(4-fluorophenyl)-2-methylthiazole-4-carboxylic acid for 3-fluoro-2-[1,2,3]triazol-2-yl-benzoic acid in the last step. MS (ESI): mass calculated for $C_{12}H_{18}N_4$, 218.30, m/z found 219.2 $[M+1]^+$ Intermediate 49: 2-(Hexahydropyrrolo[3,4-c]pyrrol-2(1H)-yl)-6-methylpyrimidine-4-carbonitrile

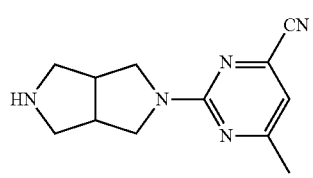 [SMILES: Cc1cc(C#N)nc(N2CC3CNCC3C2)n1]

The title compound was prepared in a manner analogous to Intermediate 23 substituting methyl 2-chloro-6-methylpyrimidine-4-carbonitrile for 2-chloro-4,6-dimethylpyrimidine in Step A. MS (ESI): mass calculated for $C_{12}H_{18}N_5$, 229.3. m/z found 230.2 $[M+H]^+$.

Intermediate 50: 3-Fluoro-2-(pyrimidin-2-yl)benzoic Acid

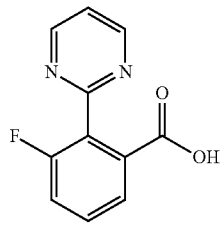 [SMILES: O=C(O)c1cccc(F)c1-c1ncccn1]

Step A: 3-Fluoro-2-(pyrimidin-2-yl)benzonitrile. 2-Iodo-3-fluorobenzonitrile (2.5 g, 10.3 mmol) and 2-tributylstannane pyrimidine (3.7 g, 10.0 mmol) were combined and dissolved in degassed DME (18 ml) then purged with bubbling $N_2$ for 5 minutes. The reaction was treated with Pd(PPh$_3$)$_4$ (577 mg, 0.5 mmol) and then purged with bubbling for 5 minutes in a sealed vessel and then heated in microwave at 160° C. for 90 min. The reaction was cooled and filtered through celite and concentrated to minimum volume and the ppt the formed was diluted with hexanes (40 ml) and cooled to 0° C. then filtered. The solid purified (FCC) (20-100% EA/hex) to give 3-fluoro-2-(pyrimidin-2-yl)benzonitrile. $^1$H NMR (400 MHz, CDCl$_3$): 8.93 (d, J=4.9 Hz, 2H), 8.14 (dd, J=9.6, 2.7 Hz, 1H), 7.86 (dd, J=8.6, 5.3 Hz, 1H), 7.36 (t, J=4.9 Hz, 1H), 7.32-7.24 (m, 1H).

Step B: 3-Fluoro-2-(pyrimidin-2-yl)benzoic acid. 3-Fluoro-2-(pyrimidin-2-yl)benzonitrile (98 mg, 0.5 mmol) was dissolved in MeOH (3 mL) and 2M NaOH (aq, 1 mL). The reaction was heated at reflux for 15 h, then cooled to 23° C., acidified with 1N aq. HCl to pH=1 and extracted with EtOAc (2×). The combined organics were washed with brine and dried over sodium sulfate to give the title compound. $^1$H NMR (400 MHz, DMSO-d$_6$): 8.89 (d, J=4.9 Hz, 1H), 7.74 (dd, J=7.6, 1.2 Hz, 1H), 7.63 (td, J=8.0, 5.5 Hz, 1H), 7.60-7.53 (m, 1H), 7.52 (t, J=4.9 Hz, 1H).

Intermediate 51: 5-Fluoro-2-(1H-pyrazol-5-yl)benzoic Acid

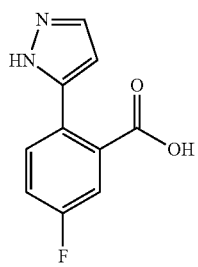 [SMILES: O=C(O)c1cc(F)ccc1-c1ccn[nH]1]

Step A: Methyl 2-bromo-5-fluorobenzoate (1.0 g, 4.2 mmol) and (1H-pyrazol-5-yl)boronic acid (485 mg, 4.6 mmol) were combined and dissolved in degassed DME (15 ml) then treated with NaHCO$_3$ (706 mg, 8.4 mmol) in water and the reaction purged with bubbling $N_2$ for 5 minutes. The reaction was treated with Pd(PPh$_3$)$_4$ (243 mg (0.2 mmol) and then purged with bubbling for 5 minutes in a sealed vessel and then heated to reflux for 2 h. The reaction mixture was cooled to 23° C., filtered, and solid rinsed with EtOAc. The organic layers were separated, dried and concentrated. Purification via FCC (ethyl acetate/hexanes, 0-30%) afforded methyl 5-fluoro-2-(1H-pyrazol-5-yl)benzoate (415 mg, 44%).

Step B: A solution of methyl 5-fluoro-2-(1H-pyrazol-5-yl)benzoate (415 mg, 1.9 mmol) in EtOH (10 ml) was treated with 4.0 eq of LiOH and stirred and monitored for two hours until the reaction was complete. The reaction mixture was then made to pH=5, and then the solution concentrated under reduced pressure, during which time a ppt formed. The solution was concentrated to minimum volume and cooled in ice, filtered and washed with ice water to give 5-fluoro-2-(1H-pyrazol-5-yl)benzoic acid (172 mg, 44%). $^1$H NMR (400 MHz, DMSO-d$_6$): 13.03 (s, 1H), 7.71 (d, J=2.0 Hz, 1H), 7.67 (dd, J=8.3, 5.6 Hz, 1H), 7.37 (td, J=8.6, 2.9 Hz, 2H), 6.44 (d, J=2.2 Hz, 1H).

Intermediate 52: 3-Fluoro-2-(2H-1,2,3-triazol-2-yl)benzoic Acid

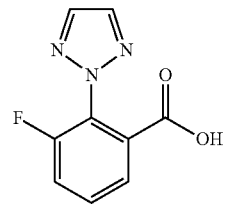

Step A: 3-Fluoro-2-(2H-1,2,3-triazol-2-yl)benzonitrile and 3-fluoro-2-(1H-1,2,3-triazol-1-yl)benzonitrile. A mixture of 2,3-difluorobenzonitrile (4.0 g, 28.8 mmol), 2H-1,2,3-triazole (1.9 g, 28.8 mmol) in DMF (85.0 mL) and K$_2$CO$_3$ (7.9 g, 57.5 mmol) were heated to 125° C. for 1.5 h. After cooling to rt, water was added and the mixture extracted with EtOAc (2×). The combined organics were washed with brine and dried (Na$_2$SO$_4$). Purification via FCC (10-100% EtOAc in hexanes) gave two products. 3-Fluoro-2-(2H-1,2,3-triazol-2-yl)benzonitrile (1.6 g, 29%), $^1$H NMR (CDCl$_3$): 7.99 (s, J=6.6 Hz, 2H), 7.67-7.63 (m, 1H), 7.61-7.53 (m, 2H), 7.26 (s, 6H) and 3-fluoro-2-(1H-1,2,3-triazol-1-yl)benzonitrile (2.0 g, 38%) $^1$H NMR (CDCl$_3$): 7.97 (dd, J=4.4, 2.8 Hz, 1H), 7.95 (d, J=1.2 Hz, 1H), 7.70 (tt, J=5.7, 2.8 Hz, 1H), 7.65 (td, J=8.1, 4.9 Hz, 1H), 7.62-7.57 (m, 1H).

Step B: 3-Fluoro-2-(2H-1,2,3-triazol-2-yl)benzoic acid. To 3-fluoro-2-(2H-1,2,3-triazol-2-yl)benzonitrile (1.5 g, 8.0 mmol) in MeOH (30 mL) was added 2M aq. NaOH (10 mL). The reaction was heated at reflux for 15 h, then cooled to rt, acidified with 1 N aq. HCl to pH=1 and extracted with DCM (2×). The combined organics were washed with brine and dried (Na$_2$SO$_4$). Purification via Agilent (Reverse-Phase HPLC, basic conditions) gave the title compound (290 mg, 18%). $^1$H NMR (CDCl$_3$): 7.90 (s, 2H), 7.89-7.85 (m, 1H), 7.63-7.56 (m, 1H), 7.50-7.44 (m, 1H) and 3-methoxy-2-(2H-1,2,3-triazol-2-yl)benzoic acid (Intermediate 53, 140 mg, 8%).

Intermediate 53: 3-Methoxy-2-(2H-1,2,3-triazol-2-yl)benzoic Acid

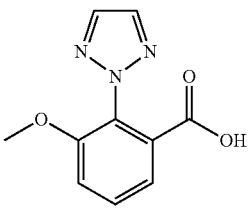 [SMILES: COc1cccc(C(=O)O)c1-n1nccn1]

The title compound was obtained during the synthesis of Intermediate 52, Step B. $^1$H NMR (CDCl$_3$): 7.92-7.83 (m, 2H), 7.66 (dd, J=7.9, 1.3 Hz, 1H), 7.61-7.54 (m, 1H), 7.27 (dd, J=8.4, 1.2 Hz, 1H), 3.82 (s, 3H).

Intermediate 54: 4-Methoxy-2-(2H-1,2,3-triazol-2-yl)benzoic Acid

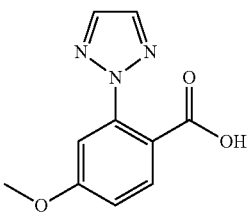 [SMILES: COc1ccc(C(=O)O)c(-n2nccn2)c1]

The title compound was prepared in a manner analogous to Intermediate 12, substituting 2-bromo-4-methoxybenzoic acid for 5-fluoro-2-iodo-benzoic acid in Step A. Upon purification, two fractions were obtained, one containing pure 4-methoxy-2-(2H-1,2,3-triazol-2-yl)benzoic acid ($^1$H NMR (CDCl$_3$): 7.99-7.90 (m, 1H), 7.83 (s, 2H), 7.20 (d, J=2.5 Hz, 1H), 7.03 (dd, J=8.8, 2.6 Hz, 1H), 3.89 (s, J=17.6 Hz, 3H), and the other containing a mixture of 4-methoxy-2-(2H-1,2,3-triazol-2-yl)benzoic acid and 4-methoxy-2-(1H-1,2,3-triazol-2-yl)benzoic acid.

Intermediate 55: 2-Chloro-5-fluoro-4-methylpyrimidine

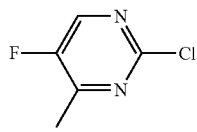

To a solution of 2,4-dichloro-5-fluoropyrimidine (1.02 g, 6.08 mmol) in THF/NMP (38 mL/3 mL) was added Fe(acac)$_3$ (215 mg, 0.61 mmol) and the mixture was cooled to 0° C. 3.0 M methylmagnesium bromide in Et$_2$O (3.04 mL, 9.12 mmol) was added dropwise. After 30 min at 0° C., the reaction was complete and quenched with saturated aqueous NH$_4$Cl solution. Et$_2$O was added and the layers were separated and the aqueous layer was further extracted with several portions of Et$_2$O. The combined organic extracts were dried over Na$_2$SO$_4$, filtered and concentrated in vacuo. Chromatography (Hexanes to 10% EtOAc/Hexanes) gave the desired product as a waxy white solid (430 mg, 48%). $^1$H NMR (400 MHz, CDCl$_3$): 8.35 (s, 1H), 2.55 (d, J=2.5 Hz, 3H).

Intermediate 56: 2-Chloro-4,5,6-trimethylpyrimidine

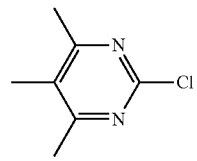

To 4,5,6-trimethylpyrimidin-2-ol (3.69 g, 26.7 mmol) was added POCl$_3$ (21.7 mL, 26.7 mmol) followed by Et$_2$NPh (2.17 mL, 13.6 mmol) dropwise. The mixture was heated at reflux for 48 h and then added to ice dropwise. The aqueous layer was extracted with EtOAc (2×). Extraction was difficult due to a large amount of precipitate. The aqueous layer pH was adjusted to pH 4-5 with 28% NH$_4$OH and was filtered through Celite®. The aqueous layer was then extracted with DCM and the combined organic extracts dried over Na$_2$SO$_4$, filtered and concentrated in vacuo to a yellow solid. Chromatography (FCC) (0 to 30% EtOAc/Hex) afforded 2-chloro-4,5,6-trimethylpyrimidine (4.26 g, 100%).

Intermediate 57: 2-Chloro-4,5-dimethylpyrimidine

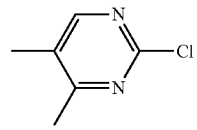

The title compound was prepared in a manner analogous to Intermediate 55, substituting 2,4-dichloro-5-methylpyrimidine for 2,4-dichloro-5-fluoropyrimidine. MS (ESI): mass calculated for C$_6$H$_7$ClN$_2$, 142.03, m/z found 143.1 [M+1]$^+$. $^1$H NMR (500 MHz, CDCl$_3$): 8.32-8.25 (m, 1H), 2.52-2.46 (m, 3H), 2.28-2.22 (m, 3H).

Intermediate 58: 2-(5-(2-Fluoro-6-(2H-1,2,3-triazol-2-yl)benzoyl)hexahydro-pyrrolo[3,4-c]pyrrol-2(1H)-yl)-6-methylpyrimidin-4-yl trifluoromethanesulfonate

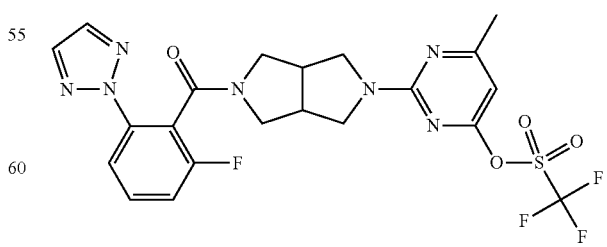

To a solution of 2-[5-{[2-fluoro-6-(2H-1,2,3-triazol-2-yl)phenyl]carbonyl}hexahydropyrrolo[3,4-c]pyrrol-2(1H)-yl]-6-methylpyrimidin-4-ol (1.02 g, 2.5 mmol) in THF (12 mL)

was added 1.0 M KOtBu in THF (5 mL, 5 mmol) followed by N-phenylbis(trifluoromethanesulfonimide) (0.893 g, 2.5 mmol). The mixture was stirred at room temperature overnight and then diluted with 2 M aq. $K_2CO_3$ solution and the layers separated. The aqueous layer was extracted with DCM and the combined organic layers were dried over $Na_2SO_4$, filtered and concentrated under reduced pressure. Chromatography (FCC, Hexanes to 100% EtOAc) afforded the desired product (1.07 g, 79%) plus a small amount of 2-{[2-fluoro-6-(2H-1,2,3-triazol-2-yl)phenyl]carbonyl}-5-(4-methoxy-6-methylpyrimidin-2-yl)octahydropyrrolo[3,4-c]pyrrole (55 mg, 5%) due to residual MeOH in the pyrimidine starting material. MS (ESI): mass calculated for $C_{21}H_{19}F_4N_7O_4S$, 541.12, m/z found 542.1 $[M+1]^+$.

Intermediate 59: tert-Butyl 5-{[2-(4H-1,2,4-triazol-3-yl)phenyl]carbonyl}hexahydropyrrolo[3,4-c]pyrrole-2(1H)-carboxylate

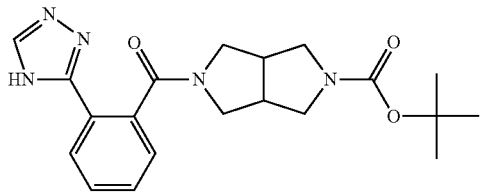 [SMILES: CC(C)(C)OC(=O)N1CC2CN(C(=O)c3ccccc3-c3nnc[nH]3)CC2C1]

To a solution of Intermediate 15 (1.0 g, 4.73 mmol) in DCM (24 mL) was added 2-(4H-[1,2,4]triazol-3-yl)-benzoic acid (895 mg, 4.73 mmol) followed by EDCI (1.36 g, 7.09 mmol), HOBt (959 mg, 7.09 mmol) and TEA (1.97 mL, 14.19 mmol). The mixture was stirred for 14 h at room temperature and then washed 2× with saturated aqueous $NH_4Cl$ solution. The organic layer was dried over $Na_2SO_4$, filtered and concentrated in vacuo. Chromatography (DCM to 8% 2M $NH_3$ in MeOH/DCM) afforded the desired product as a pale yellow foam (1.36 g, 75%). MS (ESI): mass calculated for $C_{20}H_{25}N_5O_3$, 383.45, m/z found 384.1 $[M+1]^+$. $^1$H NMR (500 MHz, $CDCl_3$): 12.62 (s, 1H), 8.19-8.03 (m, 2H), 7.56-7.44 (m, 2H), 7.39-7.32 (m, 1H), 3.96-2.72 (m, 10H), 1.53-1.35 (m, 9H).

Intermediate 60: tert-Butyl 5-{[2-(1-methyl-1H-1,2,4-triazol-5-yl)phenyl]carbonyl}hexahydropyrrolo[3,4-c]pyrrole-2(1H)-carboxylate

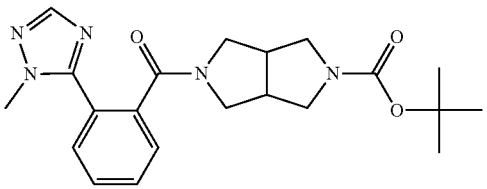 [SMILES: Cn1ncnc1-c1ccccc1C(=O)N1CC2CN(C(=O)OC(C)(C)C)CC2C1]

To a heterogeneous mixture of NaH (60% dispersion in mineral oil, 80 mg, 2 mmol) in DMF (4 mL) was added Intermediate 59 (641 mg, 1.67 mmol) in DMF (4 mL). 30 min after gas evolution had ceased methyliodide (0.115 mL, 1.84 mmol) was added dropwise. The mixture was diluted with $H_2O$ and extracted with EtOAc. The combined organic extracts were dried over $Na_2SO_4$, filtered and concentrated in vacuo. Chromatography (DCM to 8% 2 M $NH_3$ in MeOH/DCM) afforded two products, tert-butyl 5-{[2-(1-methyl-1H-1,2,4-triazol-5-yl)phenyl]carbonyl}hexahydropyrrolo[3,4-c]pyrrole-2(1H)-carboxylate (120 mg, 18%) and tert-butyl 5-{[2-(1-methyl-1H-1,2,4-triazol-3-yl)phenyl]carbonyl}hexahydropyrrolo[3,4-c]pyrrole-2(1H)-carboxylate (454 mg, 68%) due to the tautomeric nature of the 1,2,4-triazole moiety. MS (ESI): mass calculated for $C_{21}H_{27}N_5O_3$, 397.21, m/z found 398.2 $[M+1]^+$. $^1$H NMR (500 MHz, $CDCl_3$): 7.90 (s, 1H), 7.61-7.41 (m, 4H), 3.83 (s, 3H), 3.74-3.36 (m, 5H), 3.29-3.12 (m, 3H), 2.88-2.75 (m, 2H), 1.47 (s, 9H).

Intermediate 61: tert-Butyl 5-{[2-(1-methyl-1H-1,2,4-triazol-3-yl)phenyl]carbonyl}hexahydropyrrolo[3,4-c]pyrrole-2(1H)-carboxylate

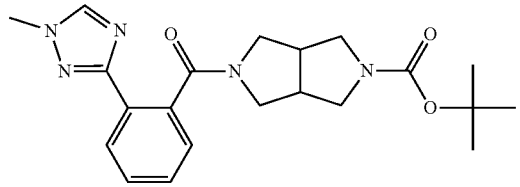 [SMILES: Cn1cnc(-c2ccccc2C(=O)N2CC3CN(C(=O)OC(C)(C)C)CC3C2)n1]

The title compound was isolated from the synthesis of Intermediate 60. MS (ESI): mass calculated for $C_{21}H_{27}N_5O_3$, 397.21, m/z found 398.2 $[M+1]^+$. $^1$H NMR (500 MHz, $CDCl_3$): 8.15-8.07 (m, 1H), 8.03 (s, 1H), 7.49-7.40 (m, 2H), 7.37-7.29 (m, 1H), 3.97-3.86 (m, 3H), 3.86-3.27 (m, 6H), 3.18-2.73 (m, 4H), 1.54-1.36 (m, 9H).

Intermediate 62: tert-Butyl 5-{[2-(3-methyl-1,2,4-oxadiazol-5-yl)phenyl]carbonyl}hexahydropyrrolo[3,4-c]pyrrole-2(1H)-carboxylate

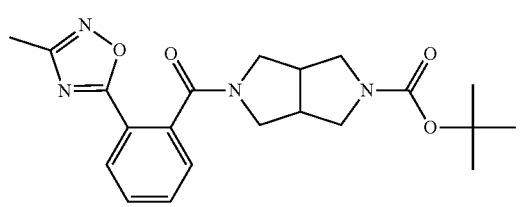 [SMILES: Cc1noc(-c2ccccc2C(=O)N2CC3CN(C(=O)OC(C)(C)C)CC3C2)n1]

The title compound was prepared in a manner analogous to Intermediate 59 substituting 2-(3-methyl-1,2,4-oxadiazol-5-yl)benzoic acid for 2-(4H-[1,2,4]triazol-3-yl)-benzoic acid. MS (ESI) mass calculated for $C_{21}H_{26}N_4O_4$, 398.20; m/z found, 399.2. $^1$H NMR (500 MHz, $CDCl_3$): 8.12 (d, J=7.8 Hz, 1H), 7.63 (td, J=7.6 Hz, 1.2 Hz, 1H), 7.55 (td, J=7.7 Hz, 1.3 Hz, 1H), 7.42 (d, J=7.5 Hz, 1H), 3.97-3.86 (m, 1H), 3.76-3.61 (m, 2H), 3.56-3.33 (m, 3H), 3.29-3.15 (m, 1H), 3.08-2.93 (m, 2H), 2.90-2.82 (m, 1H), 2.45 (s, 3H), 1.51-1.41 (m, 9H).

Intermediate 63: 3-Fluoro-2-(3-methyl-1,2,4-oxadiazol-5-yl)benzoic Acid

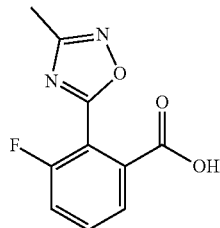

Method A:

Step A: 2-Fluoro-6-(methoxycarbonyl)benzoic acid. 3-Fluorophthalic anhydride (377 mg, 2.27 mmol) was dissolved in MeOH (6 mL) and heated to reflux for 15 h. The mixture was concentrated in vacuo and the two products (400 mg, 89%), 2-fluoro-6-(methoxycarbonyl)benzoic acid and 3-fluoro-2-(methoxycarbonyl)benzoic acid, were taken on to the next step without purification.

Step B: (Z)-Methyl 2-((((1-aminoethylidene)amino)oxy)carbonyl)-3-fluorobenzoate. To a heterogeneous mixture of the two acids from step A (400 mg, 2 mmol) at 0° C. in DCM (5 mL) was added oxalyl chloride (0.244 mL, 2.32 mmol) followed by DMF (0.05 mL). Gas evolution commenced immediately and after 5 min the ice bath was removed. When gas evolution had ceased and the mixture was homogeneous an aliquot was removed and quenched with MeOH. Formation of the methyl ester was confirmed by HPLC and the mixture was concentrated in vacuo. The viscous liquid was dissolved in fresh DCM (5 mL) and treated with solid N-hydroxyacetamidine (165 mg, 2.22 mmol) in several portions followed by TEA (0.351 mL, 2.52 mmol). After stirring for 14 h at ambient temperature the mixture was concentrated in vacuo. Chromatography (Hex to 100% EtOAc/Hex) afforded two products (477 mg, 94%), (Z)-methyl 2-((((1-aminoethylidene)amino)oxy)carbonyl)-3-fluorobenzoate and (Z)-methyl 2-((((1-aminoethylidene)amino)oxy)carbonyl)-6-fluorobenzoate, which were taken on to the next step as a mixture. MS (ESI) mass calculated for $C_{11}H_{11}FN_2O_4$, 254.07. m/z found, 255.0.

Step C: 3-Fluoro-2-(3-methyl-1,2,4-oxadiazol-5-yl)benzoic acid. To the mixture of products from Step B (477 mg, 1.88 mmol) in t-BuOH (9 mL) was added NaOAc (156 mg, 1.88 mmol). The mixture was heated at 90° C. for 50 h and then concentrated in vacuo. This resulted in four products. The residue was dissolved in 1 M aq. $K_2CO_3$ and extracted with DCM to isolate methyl 2-fluoro-6-(3-methyl-1,2,4-oxadiazol-5-yl)benzoate and methyl 3-fluoro-2-(3-methyl-1,2,4-oxadiazol-5-yl)benzoate along with unreacted (Z)-methyl 2-((((1-aminoethylidene)amino)oxy)carbonyl)-3-fluorobenzoate. The aqueous layer was then acidified with concentrated HCl and extracted with DCM. The combined organic layers from this extraction were dried over $Na_2SO_4$, filtered and concentrated in vacuo. The acid isomers were purified on a Prep Agilent system with a XBridge $C_{18}$ OBD 50×100 mm column eluting with 5 to 99% 0.05% $NH_4OH$ in $H_2O/ACN$ over 17 min to afford the desired product (63 mg, 15%) as a white solid after acidification with 1 M aq. HCl in $Et_2O$. MS (ESI) mass calculated for $C_{10}H_7FN_2O_3$, 222.04. m/z found, 223.0.

Method B:

Step A: (Z)—N'-((2-Fluoro-6-iodobenzoyl)oxy)acetimidamide. To a heterogeneous mixture of 2-fluoro-6-iodobenzoic acid (1.51 g, 5.66 mmol) at 0° C. in DCM (28 mL) was added oxalyl chloride (0.635 mL, 7.36 mmol) followed by DMF (0.15 mL). Gas evolution commenced immediately and after 5 min the ice bath was removed. When gas evolution had ceased and the mixture was homogeneous an aliquot was removed and quenched with MeOH. Formation of the methyl ester was confirmed by HPLC and the mixture was concentrated in vacuo. The viscous liquid was dissolved in fresh DCM (28 mL) and treated with solid N-hydroxyacetamidine (503 mg, 6.79 mmol) in several portions followed by TEA (1.2 mL, 8.49 mmol) at 0° C. After stirring for 14 h at ambient temperature the mixture was washed with saturated aqueous $NaHCO_3$ solution. The combined organic extracts were dried over $Na_2SO_4$, filtered and concentrated in vacuo. Chromatography (Hex to 100% EtOAc/Hex) afforded the desired product as a colorless oil (1.57 g, 86%). MS (ESI) mass calculated for $C_9H_8FIN_2O_2$, 321.96. m/z found, 323.0. 1H NMR (500 MHz, $CDCl_3$): 7.70-7.65 (m, 1H), 7.15-7.11 (m, 2H), 4.87 (br s, 2H), 2.06 (s, 3H).

Step B: 5-(2-Fluoro-6-iodophenyl)-3-methyl-1,2,4-oxadiazole. To a heterogeneous mixture of the product of Step A in t-BuOH (24 mL) was added NaOAc (603 mg, 7.27 mmol) in $H_2O$ (0.9 mL). The mixture was then heated to 110° C. for 12 days. The reaction was concentrated in vacuo and then dissolved in toluene. The toluene was then filtered to remove NaOAc and then concentrated in vacuo. Chromatography (Hex to 40% EtOAc/Hex) afforded the desired product as a colorless oil (1.21 g, 82%). MS (ESI) mass calculated for $C_9H_6FIN_2O$, 303.95. m/z found, 304.9. 1H NMR (500 MHz, $CDCl_3$): 7.82-7.77 (m, 1H), 7.29-7.20 (m, 2H), 2.55 (s, 3H).

Step C: 3-Fluoro-2-(3-methyl-1,2,4-oxadiazol-5-yl)benzoic acid. To THF (15 mL) was added 2 M i-PrMgCl in THF (2.2 mL, 4.47 mmol). This mixture was cooled to −78° C. and the product of Step B (1.09 g, 3.58 mmol) was added dropwise in THF (20 mL). The mixture was stirred for 30 min at −78° C. and then $CO_2$ from a lecture bottle was bubbled into the solution for 3 h while allowing the temperature to slowly rise. When the temperature reached −20° C. the dry ice bath was replaced with an ice bath, bubbling of $CO_2$ was ceased and the mixture was allowed to come to room temperature overnight. The mixture was quenched by the addition of $H_2O$ and a small amount of $Et_2O$. The organic layer was washed 2× with 2N aq. NaOH and the combined aqueous layers were then washed 3× with $Et_2O$. The aqueous layer was then acidified with concentrated HCl and extracted with DCM. The combined organic layers were dried over $Na_2SO_4$, filtered and concentrated in vacuo to afford the desired product as a white solid (661 mg, 83%). MS (ESI) mass calculated for $C_{10}H_7FN_2O_3$, 222.04. m/z found, 223.0. 1H NMR (500 MHz, $CDCl_3$): 7.96 (d, J=7.8, 1H), 7.72-7.64 (m, 1H), 7.50-7.44 (m, 1H), 2.56-2.48 (m, 3H).

Intermediate 64:
2-Fluoro-6-(3-methyl-1,2,4-oxadiazol-5-yl)benzoic Acid

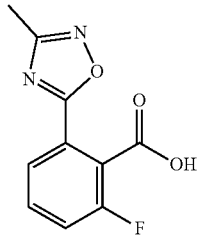 [SMILES: Cc1noc(-c2cccc(F)c2C(=O)O)n1]

The title compound was isolated from the synthesis of Intermediate 63, Method A. MS (ESI) mass calculated for $C_{10}H_7FN_2O_3$, 222.04. m/z found, 223.0. $^1$H NMR (500 MHz, CDCl$_3$): 7.89 (d, J=7.7, 1H), 7.65-7.59 (m, 1H), 7.44-7.38 (m, 1H), 2.50 (s, 3H).

Intermediate 65: 2,5-Dichloro-4-methylpyrimidine

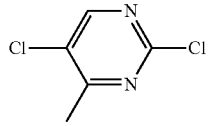

The title compound was prepared in a manner analogous to Intermediate 55, substituting 2,4,5-trichloropyrimidine for 2,4-dichloro-5-fluoropyrimidine. $^1$H NMR (500 MHz, CDCl$_3$): 8.47 (s, 1H), 2.61 (s, 3H).

Intermediate 66: 2,5-Dichloro-4,6-dimethylpyrimidine

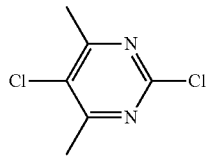

To 5-chloro-4,6-dimethylpyrimidin-2-ol (992 mg, 6.26 mmol) was added POCl$_3$ (2.22 mL, 23.77 mmol) followed by Et$_2$NPh (0.75 mL, 4.69 mmol) dropwise. The mixture was heated at 125° C. for 2 h. At approximately 2 h the reaction became homogeneous and was checked by HPLC and it showed all starting material had been consumed. The mixture was allowed to cool to room temperature and was then added dropwise to ice. After the ice had melted there was a white solid in a pink liquid. The aqueous layer was extracted with DCM and the combined organic layers were dried over Na$_2$SO$_4$, filtered and concentrated in vacuo. Chromatography (Hex to 10% EtOAc/Hex) afforded the desired product as a white solid (915 mg, 83%). $^1$H NMR (500 MHz, CDCl$_3$): 2.57 (s, 6H).

Intermediate 67: 2-Chloro-5-ethyl-4,6-dimethylpyrimidine

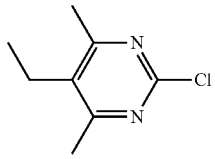

The title compound was prepared in a manner analogous to Intermediate 56, substituting 5-ethyl-4,6-dimethylpyrimidin-2-ol for 4,5,6-trimethylpyrimidin-2-ol. MS (ESI): mass calculated for $C_8H_{11}ClN_2$, 170.06, m/z found 171.1 [M+1]$^+$. $^1$H NMR (500 MHz, CDCl$_3$): 2.65 (q, J=7.6 Hz, 2H), 2.50 (s, 6H), 1.15 (t, J=7.6 Hz, 3H).

Intermediate 68: (3-(2H-1,2,3-Triazol-2-yl)pyridin-2-yl)(hexahydropyrrolo[3,4-c]pyrrol-2(1H)-yl)methanone

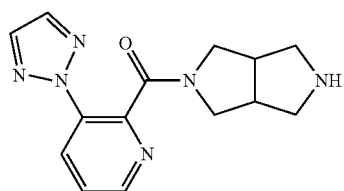 [SMILES: O=C(c1ncccc1-n1nccn1)N1CC2CNCC2C1]

Step A: tert-Butyl 5-(3-(2H-1,2,3-triazol-2-yl)picolinoyl)hexahydropyrrolo[3,4-c]pyrrole-2(1H)-carboxylate. tert-Butyl 5-(3-(2H-1,2,3-triazol-2-yl)picolinoyl)hexahydropyrrolo[3,4-c]pyrrole-2(1H)-carboxylate was prepared in a manner analogous to Intermediate 59 substituting 3-[1,2,3]triazol-2-yl-pyridine-2-carboxylic acid (Intermediate 72) for 2-(4H-[1,2,4]triazol-3-yl)-benzoic acid. MS (ESI) mass calculated for $C_{19}H_{24}N_6O_3$, 384.19. m/z found, 385.1.

Step B: (3-(2H-1,2,3-Triazol-2-yl)pyridin-2-yl)(hexahydropyrrolo[3,4-c]pyrrol-2(1H)-yl)methanone. tert-Butyl 5-(3-(2H-1,2,3-triazol-2-yl)picolinoyl)hexahydropyrrolo[3,4-c]pyrrole-2(1H)-carboxylate (491 mg, 1.28 mmol) in DCM (6 mL) was added TFA (3 mL). After stirring for 2 h at room temperature the reaction was complete and concentrated in vacuo. The TFA salt was purified on a Prep Agilent system with a XBridge C$_{18}$ OBD 50×100 mm column eluting with 5 to 99% 0.05% NH$_4$OH in H$_2$O/ACN over 17 min to afford (3-(2H-1,2,3-triazol-2-yl)pyridin-2-yl)(hexahydropyrrolo[3,4-c]pyrrol-2(1H)-yl)methanone as a white solid (306 mg, 84%). MS (ESI) mass calculated for $C_{14}H_{16}N_6O$, 284.14. m/z found, 285.0.

Intermediate 69: 2-Chloro-5-fluoro-4,6-dimethylpyrimidine

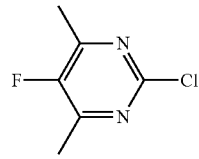

Step A: 5-Fluoropyrimidine-2,4,6-triol. To a heterogeneous mixture of urea (641 mg, 10.67 mmol) and diethylfluoromalonate (1.96 g, 10.67 mmol) in EtOH (11 mL) was added 2.68 M NaOEt in EtOH (7.96 mL, 21.34 mmol). The mixture was heated at reflux for 60 h and then allowed to cool to room temperature. The mixture was filtered and the cake was then dissolved in warm water and the resulting solution was acidified with concentrated HCl to pH 2. The mixture was allowed to cool to room temperature and then cooled in an ice bath before filtering. The cake was washed with water and dried to afford 5-fluoropyrimidine-2,4,6-triol as a slightly off white solid (1.45 g, 93%).

Step B: 2,4,6-Trichloro-5-fluoropyrimidine. To $POCl_3$ (4.49 mL, 48.15 mmol) was added 5-fluoropyrimidine-2,4,6-triol (1.41 g, 9.63 mmol) in several portions. There was a 2° C. increase in temperature. The N,N-dimethylaniline (1.23 mL, 9.73 mmol) was then added dropwise and the mixture heated at 110° C. for 24 h. The reaction mixture was allowed to cool only briefly and then was quenched by dropwise addition onto ice. When the ice was melted the aqueous layer was extracted several times with $Et_2O$. The combined organic extracts were dried over $Na_2SO_4$, filtered and concentrated in vacuo to a yellow solid after storing in the refrigerator overnight. This material was not purified further, but taken on to the next step without further purification.

Step C: 2-Chloro-5-fluoro-4,6-dimethylpyrimidine was prepared in a manner analogous to Intermediate 55, substituting 2,4,6-trichloro-5-fluoropyrimidine for 2,4-dichloro-5-fluoropyrimidine. $^1$H NMR (500 MHz, $CDCl_3$): 2.50 (d, J=2.7 Hz, 6H).

Intermediate 70:
6-Methyl-2-[1,2,3]triazol-2-yl-nicotinic Acid

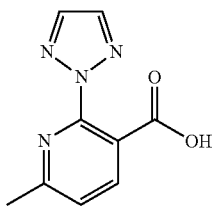

6-Methyl-2-[1,2,3]triazol-2-yl-nicotinic acid. To a 100 ml round bottom flask containing 2-chloro-6-methylnicotinic acid (3 g, 17.4 mmol), copper iodide (0.16 g, 0.5 mol %), and cesium carbonate (11.4 g, 35 mmol) was added a mixture of dioxane (20 mL) and $H_2O$ (0.1 ml, 5.25 mmol). Next triazole (2.03 mL, 35 mmol) and finally (R,R)—(–)—N,N'-dimethyl-1,2-cyclohexanediamine ligand (0.56 mL, 3.5 mmol) were added. The resulting clumpy yellow slurry was stirred until evenly dispersed. Upon heating to 100° C. the reaction mixture changed from a yellow slurry to pale green. As heating progressed the slurry became less thick and was stirred more easily. The light green slurry was stirred for 4 hr at 100° C. and left to stir at room temp overnight. At this point the reaction mixture appeared as a cobalt blue slurry which was then diluted with 20 mL ether and 20 mL $H_2O$. The resulting solution was thoroughly stirred and transferred to a separatory funnel then the RBF was subsequently rinsed with 20 mL ether and $H_2O$ each. The aqueous layer was separated from the organic layer and acidified to pH 1 with 6 mL conc. HCl. The now brown/lime green aqueous layer was extracted twice with EtOAc. The bright yellow organic layers were combined and dried with $Na_2SO_4$ and then conc. into a yellow powder under reduced pressure. To the yellow powder was added EtOAc to form a yellow slurry. The solids were filtered off and washed with EtOAc to give a very pale yellow powder, which was found by $^1$H NMR to be the Intermediate 71 (25% yield). The filtrate was conc. into a yellow solid and purified (FCC, 0-5% MeOH in DCM w/0.5% AcOH) to give the title product in a 20% yield. MS (ESI): mass calculated for $C_9H_8N_4O_2$, 204.18. m/z found 205.3 $[M+H]^+$. $^1$H NMR (400 MHz, $CD_3OD$): 8.21-8.18 (m, 1H), 7.98 (s, 2H), 7.51 (d, J=7.9 Hz, 1H), 2.64 (s, 3H).

Intermediate 71:
6-Methyl-2-[1,2,3]triazol-1-yl-nicotinic Acid

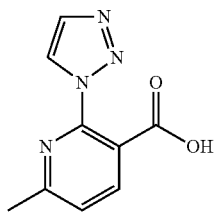

The title compound was isolated as a byproduct from the procedure used to prepare Intermediate 70 with a 25% yield. MS (ESI): mass calculated for $C_9H_8N_4O_2$, 204.18. m/z found 205.3 $[M+H]^+$. $^1$H NMR (400 MHz, $CD_3OD$): 8.48 (d, J=1.1 Hz, 1H), 8.25 (dd, J=7.9, 3.8 Hz, 1H), 7.88 (d, J=1.1 Hz, 1H), 7.54 (d, J=7.9 Hz, 1H), 2.64 (s, 3H).

Intermediate 72: 3-[1,2,3]Triazol-2-yl-pyridine-2-carboxylic Acid

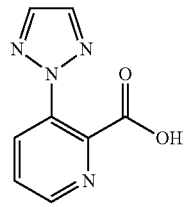 [SMILES: O=C(O)c1ncccc1-n1nccn1]

The title compound was prepared in a manner analogous to Intermediate 70 substituting 3-bromo-2-pyridinecarboxylic acid for 2-chloro-6-methylnicotinic acid. MS (ESI): mass calculated for $C_8H_6N_4O_2$, 190.10. m/z found 191.1 $[M+H]^+$. $^1$H NMR (400 MHz, $CDCl_3$): 8.77 (d, J=4.3 Hz, 1H), 8.26 (dt, J=6.5, 3.3 Hz, 1H), 7.88 (s, 2H), 7.65 (dd, J=8.2, 4.7 Hz, 1H).

Intermediate 73: 1-[1,2,3]Triazol-2-yl-naphthalene-2-carboxylic Acid

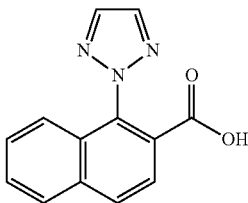 [SMILES: O=C(O)c1ccc2ccccc2c1-n1nccn1]

The title compound was prepared in a manner analogous to Intermediate 70 substituting 1-bromo-2-napthoic acid for 2-chloro-6-methylnicotinic acid. The title compound was obtained (484 mg, 50%). MS (ESI): mass calculated for $C_{13}H_9N_3O_2$, 239.23. m/z found 240.3 [M+H]$^+$. $^1$H NMR (400 MHz, CD$_3$OD): 8.19 (d, J=8.7 Hz, 1H), 8.09-8.03 (m, 4H), 7.70-7.66 (m, 1H), 7.58 (ddd, J=8.2, 6.9, 1.2 Hz, 1H), 7.25 (d, J=8.6 Hz, 1H).

Intermediate 74: 1-[1,2,3]Triazol-1-yl-naphthalene-2-carboxylic Acid

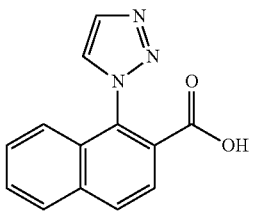 [SMILES: O=C(O)c1ccc2ccccc2c1-n1ccnn1]

The title compound was isolated as a byproduct from the preparation of Intermediate 73 (25% yield). MS (ESI): mass calculated for $C_{13}H_9N_3O_2$, 239.23; m/z found 240.3 [M+H]$^+$. $^1$H NMR (400 MHz, CD$_3$OD): 8.33 (d, J=0.9 Hz, 1H), 8.24 (d, J=8.6 Hz, 1H), 8.14-8.07 (m, 2H), 8.01 (d, J=0.9 Hz, 1H), 7.71 (t, J=7.6 Hz, 1H), 7.60 (t, J=7.7 Hz, 1H), 7.11 (d, J=8.5 Hz, 1H).

Intermediate 75: 8-[1,2,3]Triazol-2-yl-naphthalene-1-carboxylic Acid

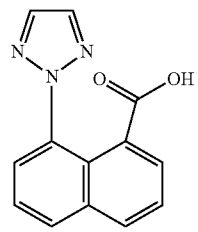 [SMILES: O=C(O)c1cccc2cccc(-n3nccn3)c12]

The title compound was prepared in a manner analogous to Intermediate 70 substituting 8-bromo-2-napthoic acid for 2-chloro-6-methylnicotinic acid. The desired 8-[1,2,3]triazol-2-yl-naphthalene-1-carboxylic acid was obtained (474 mg, 16%). MS (ESI): mass calculated for $C_1H_9N_3O_2$, 239.20. m/z found 240.3 [M+H]$^+$. $^1$H NMR (400 MHz, CD$_3$OD): 8.13 (t, J=9.0 Hz, 2H), 7.95-7.91 (m, 3H), 7.82 (dd, J=7.4, 1.0 Hz, 1H), 7.70 (dd, J=9.8, 5.8 Hz, 1H), 7.64-7.59 (m, 1H).

Intermediate 76: 5-[1,2,3]Triazol-2-yl-benzo[1,3]dioxole-4-carboxylic Acid

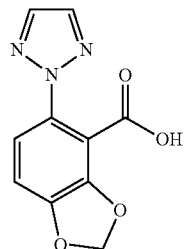 [SMILES: O=C(O)c1c(-n2nccn2)ccc2c1OCO2]

The title compound was prepared in a manner analogous to Intermediate 70 substituting 5-bromobenzo[1,3]dioxole-4-carboxylic acid for 2-chloro-6-methylnicotinic acid. MS (ESI): mass calculated for $C_{10}H_7N_3O_4$, 233.18. m/z found 234.3 [M+H]$^+$. $^1$H NMR (400 MHz, CD$_3$OD): 7.85 (s, 2H), 7.23 (d, J=8.4 Hz, 1H), 7.04 (d, J=8.4 Hz, 1H), 6.16 (s, 2H).

Intermediate 77: 2,3-Dimethoxy-6-[1,2,3]triazol-2-yl-benzoic Acid

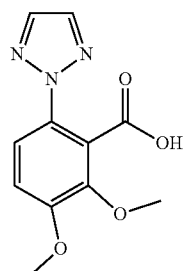

To a 20 ml microwave vial containing 2-bromo-4,5-dimethoxybenzoic acid (3 g, 11.5 mmol), copper iodide (0.04 g, 0.5 mol %), cesium carbonate (7.5 g, 23 mmol), triazole (1.33 mL, 23 mmol) and finally (R,R)—(−)—N,N'-dimethyl-1,2-cyclohexanediamine ligand (0.36 mL, 2.3 mmol) was added DMF (12 mL). The resulting clumpy yellow slurry was stirred until evenly dispersed then heated to 120° C. for 10-20 min using a microwave. At this point the reaction mixture appeared as a blue slurry which was then diluted with 20 mL ether and 20 mL H$_2$O. The resulting solution was thoroughly stirred and transferred to a separatory funnel then the RBF was subsequently rinsed with 20 mL ether and H$_2$O each. The aqueous layer was separated from the organic layer and acidified to pH 1 with 6 mL conc. HCl. The now brown/lime green aqueous layer was extracted twice with EtOAc. The bright yellow organic layers were combined and dried with Na$_2$SO$_4$ and then conc. into a yellow powder under reduced pressure which was purified by FCC (0-5% MeOH in DCM w/0.5% AcOH) to afford 2,3-dimethoxy-6-[1,2,3]triazol-2-yl-benzoic acid (60%) and 2,3-dimethoxy-6-[1,2,3]triazol-1-yl-benzoic acid (20%). Data for 2,3-dimethoxy-6-[1,2,3]triazol-2-yl-benzoic acid, MS (ESI): mass calculated for $C_{11}H_{11}N_3O_4$, 249.23. m/z found 250.3 [M+H]⁺. ¹H NMR (400 MHz, CD₃OD): 7.87 (s, 2H), 7.47 (s, 1H), 7.18 (s, 1H), 3.94 (s, 3H), 3.91 (s, 3H).

Intermediate 78: 2,3-Dimethoxy-6-[1,2,3]triazol-1-yl-benzoic Acid

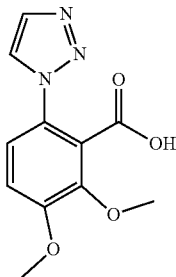 [SMILES: COc1ccc(-n2ccnn2)c(C(=O)O)c1OC]

The title compound was isolated from the procedure used to prepare Intermediate 77 with a 20% yield. MS (ESI): mass calculated for $C_{11}H_{11}N_3O_4$, 249.23; m/z found 250.3 [M+H]⁺. ¹H NMR (400 MHz, CD₃OD): 8.17 (d, J=1.0 Hz, 1H), 7.82 (d, J=1.0 Hz, 1H), 7.62 (s, 1H), 7.09 (s, 1H), 3.95 (s, 3H), 3.91 (s, 3H).

Intermediate 79: 5-Acetylamino-2-[1,2,3]triazol-2-yl-benzoic Acid

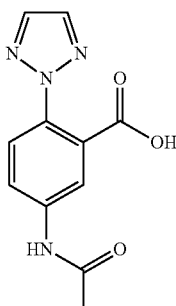

The title compound was prepared in a manner analogous to Intermediate 70 substituting 5-acetamido-2-bromobenzoic acid for 2-bromo-4,5-dimethoxybenzoic acid. MS (ESI): mass calculated for $C_{11}H_{10}N_4O_3$, 246.22. m/z found 247.3 [M+H]⁺. ¹H NMR (400 MHz, CD₃OD): 8.09 (t, J=2.8 Hz, 1H), 7.92-7.86 (m, 3H), 7.66 (dd, J=8.7, 3.3 Hz, 1H), 2.17 (dd, J=2.5, 1.3 Hz, 3H).

Intermediate 80: 4-(1H-1,2,3-Triazol-1-yl)nicotinic Acid

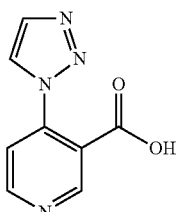

The title compound was prepared in a manner analogous to Intermediate 70 substituting 4-chloronicotinic acid for 2-chloro-6-methylnicotinic acid. MS (ESI): mass calculated for $C_{11}H_{10}N_4O_3$, 246.22. m/z found 247.3 [M+H]⁺. ¹H NMR (400 MHz, CD₃OD): 8.09 (t, J=2.8 Hz, 1H), 7.92-7.86 (m, 3H), 7.66 (dd, J=8.7, 3.3 Hz, 1H), 2.17 (dd, J=2.5, 1.3 Hz, 3H).

Intermediate 81: 3-Methyl-2-(2H-1,2,3-triazol-2-yl)benzonitrile

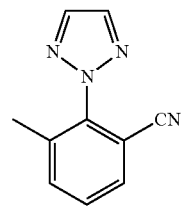

To a mixture of 2-fluoro-3-methylbenzonitrile (4.0 g, 29.6 mmol) and 2H-1,2,3-triazole (2.04 g, 29.6 mmol) in DMF (80 mL) was added potassium carbonate (8.26 g, 59.2 mmol). The resulting mixture was heated to 120° C. for 2 h. The mixture was cooled, diluted with water and extracted with EtOAc. The organic layers were combined, dried over Na₂SO₄, filtered and concentrated. The residue was purified by FCC (SiO₂, ethyl acetate/hexanes, gradient 0-50%) to yield the title compound (1.5 g, 26%). MS (ESI) mass calcd. for $C_{10}H_8N_4$, 184.2. m/z found, 185.1 [M+H]+. ¹H NMR (500 MHz, CDCl₃): 7.95 (s, 2H), 7.66 (d, J=7.7, 0.7 Hz, 1H), 7.59 (d, J=7.8, 0.6 Hz, 1H), 7.50 (dd, J=9.8, 5.7 Hz, 1H), 2.20 (s, 3H).

Intermediate 82: 3-Methyl-2-(2H-1,2,3-triazol-2-yl)benzoic Acid

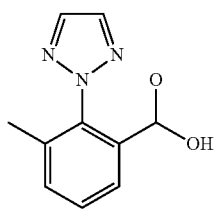

To a solution of 3-methyl-2-(2H-1,2,3-triazol-2-yl)benzonitrile (1.4 g, 7.82 mmol) in MeOH (15 mL) was added a 4N aqueous solution of NaOH (10 mL). The resulting mixture was heated to 90° C. After 15 h the reaction mixture was cooled to ambient temperature then diluted with water (50 mL). The aqueous layer was acidified to pH2 and extracted with EtOAc (50 mL) three times. The organic layers were combined, dried over Na₂SO₄, filtered and concentrated. The residue was purified by FCC (SiO₂, gradient DCM to 10% MeOH/1% HOAc/DCM) to yield the title compound (1.3 g, 78%). ¹H NMR (500 MHz, CDCl₃): 7.90 (d, J=7.7, Hz, 1H), 7.83 (s, 2H), 7.57-7.53 (m, 1H), 7.49 (dd, J=9.7, 5.8 Hz, 1H), 2.10 (s, 3H).

Intermediate 83: 3-Fluoro-2-(1H-pyrazol-5-yl)benzoic Acid

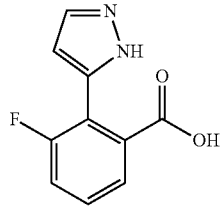 [SMILES: O=C(O)c1cccc(F)c1-c1ccn[nH]1]

Method A:

Step A: 2-Bromo-3-fluorobenzonitrile (1.0 g, 5.0 mmol) and (1H-pyrazol-5-yl)boronic acid (647 mg, 4.6 mmol) were combined and dissolved in degassed DME (15 mL) then treated with $NaHCO_3$ (1260 mg, 8.4 mmol) in water and the reaction purged with bubbling $N_2$ for 5 minutes. The reaction was treated with $Pd(PPh_3)_4$ (288 mg, 0.2 mmol) and then purged with bubbling for 5 minutes in a sealed vessel and then heated to reflux for 2 h. The reaction was then cooled to 23° C. filtered and the solids were rinsed with EtOAc and the layers separated. The organic layers were combined, dried and concentrated under reduced pressure. Chromatography (0-30% ethyl acetate/hexanes) afforded 3-fluoro-2-(1H-pyrazol-5-yl)benzonitrile (178 mg, 19%).

Step B: To 3-fluoro-2-(1H-pyrazol-5-yl)benzonitrile in MeOH (3 mL) was added 2M aq. NaOH (1 mL). The reaction was heated at reflux for 15 h, then cooled to rt, acidified with 1N aq. HCl to pH=1 and extracted with EtOAc to give (210 mg, 99%) of 3-fluoro-2-(1H-pyrazol-5-yl)benzoic acid which was used crude.

Method B:

The title compound was prepared in a manner analogous to Intermediate 51, substituting methyl 2-iodo-3-fluorobenzoate for methyl 2-bromo-5-fluorobenzoate in Step A. MS (ESI): mass calculated for $C_{10}H_7FN_2O_2$, 206.05; m/z found 207.0 $[M+1]^+$.

Intermediate 84: 2-(1H-1,2,3-Triazol-1-yl)-6-(trifluoromethyl)nicotinic Acid

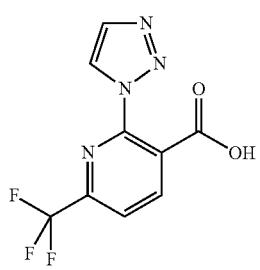 [SMILES: O=C(O)c1ccc(C(F)(F)F)nc1-n1ccnn1]

The title compound was prepared in a manner analogous to Intermediate 13, substituting 2-chloro-6-(trifluoromethyl)nicotinic acid for 5-fluoro-2-iodo-benzoic acid in step A, and substituting 1,4-dioxane for MeOH as the solvent, with 0.3 eq of water as an additive. $^1$H NMR (400 MHz, DMSO-$d_6$): 8.64 (s, 1H), 8.37 (d, J=7.6 Hz, 1H), 8.11 (d, J=7.8 Hz, 1H), 7.93 (s, 1H).

Intermediate 85: 5-Fluoro-2-(1H-pyrazol-5-yl)benzoic Acid

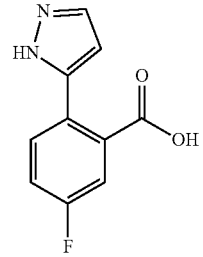 [SMILES: O=C(O)c1cc(F)ccc1-c1ccn[nH]1]

Step A: Methyl-2-fluoro-bromobenzoate (1.0 gram, 4.2 mmol) and (1H-pyrazol-5-yl)boronic acid (485 mg, 4.6 mmol) were combined and dissolved in degassed DME (15 mL) then treated with $NaHCO_3$ (706 mg, 8.4 mmol) in water and the reaction purged with bubbling $N_2$ for 5 minutes. The reaction was treated with $Pd(PPh_3)_4$ (243 mg (0.2 mmol) and then purged with bubbling for 5 minutes in a sealed vessel and then heated to reflux for 2 h. The reaction mixture was cooled to 23° C., filtered, and the solid was rinsed with EtOAc and the layers separated. The organic layers were combined, dried and concentrated. Chromatography (ethyl acetate/hexanes, 0-30%) gave methyl 5-fluoro-2-(1H-pyrazol-5-yl)benzoate (415 mg, 44%).

Step B: A solution of methyl 5-fluoro-2-(1H-pyrazol-5-yl)benzoate (415 mg, 1.9 mmol) in EtOH (10 mL) was treated with 4.0 eq of LiOH and stirred and monitored for two hours the reaction was complete. Reaction was made to pH=5, and then the solution concentrated under reduced pressure during which time a ppt formed. The reactions was then concentrated to minimum volume and cooled in ice, then filtered and washed with ice water to give 5-fluoro-2-(1H-pyrazol-5-yl)benzoic acid (172 mg, 44% yield). $^1$H NMR (400 MHz, DMSO-$d_6$): 13.03 (s, 1H), 7.71 (d, J=2.0 Hz, 1H), 7.67 (dd, J=8.3, 5.6 Hz, 1H), 7.37 (td, J=8.6, 2.9 Hz, 2H), 6.44 (d, J=2.2 Hz, 1H).

Intermediate 86: 3-Methyl-2-(1H-1,2,3-triazol-1-yl)benzoic Acid

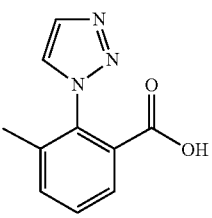

The title compound was prepared in a manner analogous to Intermediate 82, substituting 3-methyl-2-(1H-1,2,3-triazol-1-yl)benzonitrile for 3-methyl-2-(2H-1,2,3-triazol-2-yl)benzonitrile. $^1$H NMR (500 MHz, $CDCl_3$): 8.17 (s, 1H), 7.94 (s, 1H), 7.69 (d, J=6.8 Hz, 1H), 7.65 (d, J=7.7 Hz, 1H), 7.63-7.56 (m, 1H), 2.06 (s, 3H).

Intermediate 87: 4-Fluoro-2-(pyrimidin-2-yl)benzoic Acid

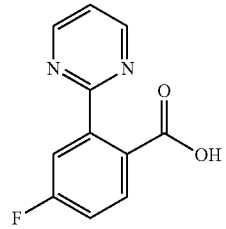 [SMILES: O=C(O)c1ccc(F)cc1-c1ncccn1]

Step A: 2-Iodo-4-fluorobenzonitrile (2.54 g, 10.3 mmol) and 2-tributylstannane pyrimidine (3.69 g, 10.0 mmol) were dissolved in dimethoxyethane (18 mL) and treated with tetrakistriphenylphosphine palladium (0) (578 mg, 0.5 mmol) and copper (1) iodide (95 mg, 0.5 mmol). The reaction was then heated to 160° C. for 90 minutes in the microwave. The reaction was cooled, concentrated under reduced pressure. Chromatography (20-100% EA in hexanes) gave the desired product. $^1$H NMR (400 MHz, CDCl$_3$): 8.93 (d, J=4.9 Hz, 2H), 8.14 (dd, J=9.6, 2.7 Hz, 1H), 7.86 (dd, J=8.6, 5.3 Hz, 1H), 7.36 (t, J=4.9 Hz, 1H), 7.32-7.23 (m, 1H).

Step: 4-Fluoro-2-(pyrimidin-2-yl)benzonitrile (85 mg, 0.4 mmol) was hydrolyzed to the acid in water (1 mL) by addition of 18 M H$_2$SO$_4$ (1 mL). The reaction was heated at 100° C. for 10 min, then cooled to 23° C., and extracted with EtOAc (3×5 mL). The combined organics were dried (Na$_2$SO$_4$) and concentrated under reduced pressure. This material was used crude in subsequent reactions.

Intermediate 88: 4-Methoxy-2-(pyrimidin-2-yl)benzoic Acid

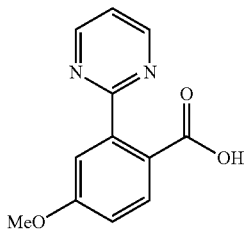 [SMILES: COc1ccc(C(=O)O)c(-c2ncccn2)c1]

Step A: 4-Methoxy-2-(pyrimidin-2-yl)benzonitrile was prepared in a manner analogous to Intermediate 87. $^1$H NMR (400 MHz, CDCl$_3$): 8.93 (d, J=4.9 Hz, 2H), 8.14 (dd, J=9.6, 2.7 Hz, 1H), 7.86 (dd, J=8.6, 5.3 Hz, 1H), 7.36 (t, J=4.9 Hz, 1H), 7.32-7.23 (m, 1H).

Step B: 4-Methoxy-2-(pyrimidin-2-yl)benzonitrile (85 mg, 0.4 mmol) was dissolved in MeOH (20 mL) was treated with 2M aq NaOH (15 mL). The reaction was heated at reflux overnight, the reaction was cooled to room temperature and filtered to remove the solids and washed with cold MeOH. The filtrate was concentrated to minimum volume and then acidified to pH=3 with 6 N aq. HCl and cooled to 0° C. then filtered and washed with cold water. This material was used crude in subsequent reactions.

Intermediate 89: 2-Chloro-4,4,4,5,6,6,6-septadeuteriopyrimidine

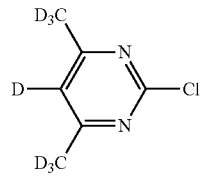

Step A: 1,1,1,3,3,3,5,5-Octadeuteriopentane-2,4-dione. To a solution of acetylacetone (10 mL, 95.1 mmol) in D$_2$O (90 mL) was added K$_2$CO$_3$ (1.0 g, 7.29 mmol). The mixture was heated at 120° C. overnight. The aqueous layer was extracted with DCM and the combined organic layers were dried over Na$_2$SO$_4$, filtered and concentrated in vacuo to an orange liquid (Frediani et. al., *Catalysis Comm.* 2, 2001, 125).

Step B: 2-Deuteriohydroxy-4,4,4,5,6,6,6-septadeuteriopyrimidine. To a solution of 1,1,1,3,3,3,5,5-Octadeuteriopentane-2,4-dione (product of Step A) (1.60 g, 14.82 mmol) in EtOD (7 mL) was added urea-d$_4$ (0.95 g, 14.82 mmol) followed by 35% wt. DCl in D$_2$O (2 mL, 23.71 mmol). The mixture was heated at 90° C. for 36 h, cooled to room temperature and then chilled in an ice bath before filtration and washing of the white solid with cold EtOD to afford the desired product as the DCl salt (1.53 g, 61%).

Step C: 2-Chloro-4,4,4,5,6,6,6-septadeuteriopyrimidine. To 2-deuteriohydroxy-4,4,4,5,6,6,6-septadeuteriopyrimidine (product of Step B) (1.53 g, 9.04 mmol) was added POCl$_3$ (7.9 mL, 9.04 mmol) and the mixture was heated at reflux for 16 h. The mixture was allowed to cool to room temperature and then added to ice drop wise. The aqueous mixture was neutralized to pH 6 in an ice bath with 5 N NaOH. The aqueous layer was extracted with DCM and the combined organic layers were dried over Na$_2$SO$_4$, filtered and concentrated in vacuo to afford the desired product as a yellow solid (1.3 g, 96%). (ESI): mass calculated for C$_6$D$_7$ClN$_2$, 149.07. m/z found, 150.1.

Intermediate 90: tert-Butyl 5-{4,6-bis[($^2$H$_3$)methyl]($^2$H)pyrimidin-2-yl}hexahydropyrrolo[3,4-c]pyrrole-2(1H)-carboxylate

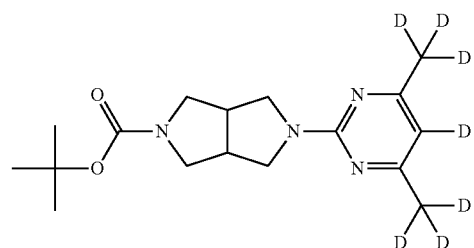 [SMILES: [2H]c1c(C([2H])([2H])[2H])nc(N2CC3CN(C(=O)OC(C)(C)C)CC3C2)nc1C([2H])([2H])[2H]]

A mixture of Intermediate 15 (294 mg, 1.38 mmol), Intermediate 89 (207 mg, 1.38 mmol) and DIPEA (0.48 mL, 2.77 mmol) in ACN (3.5 mL) was heated in the microwave at 150° C. for 2 h. The mixture was concentrated in vacuo. The crude mixture was purified by FCC (Hex to 50% EtOAc/Hex) to afford the title compound (344 mg, 76%). MS (ESI): mass calculated for C$_{17}$H$_{19}$D$_7$N$_4$O$_2$, 325.25. m/z found 326.2 [M+1]+. 1H NMR (500 MHz, CDCl3): 3.86-3.76 (m, 2H), 3.67-3.50 (m, 4H), 3.37-3.24 (m, 2H), 2.98-2.90 (m, 2H), 1.44 (s, 9H).

Intermediate 91: 5-{4,6-Bis[($^2$H$_3$)methyl]($^2$H)pyrimidin-2-yl}hexahydropyrrolo[3,4-c]pyrrole

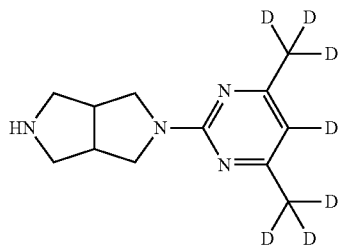 [SMILES: [2H]c1c(C([2H])([2H])[2H])nc(N2CC3CNCC3C2)nc1C([2H])([2H])[2H]]

Intermediate 90 (325 mg, 1 mmol), DCM (5 mL) and TFA (1 mL) were stirred at room temperature for 2 h. The mixture was concentrated in vacuo and was used as is. MS (ESI): mass calculated for C$_{12}$H$_{11}$D$_7$N$_4$, 225.25. m/z found 225.2 [M+1]+.

Intermediate 92: 2-(4,6-Dimethylpyrimidin-2-yl) octahydropyrrolo[3,4-c]pyrrole, bis-HCl Salt

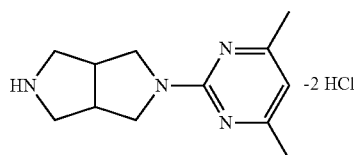

A 150 mL EasyMax reactor was fitted with a mechanical stirrer, a reflux condenser and a temperature probe and 2-chloro-4,6-dimethyl pyrimidine (7.10 g, 49.8 mmol), potassium carbonate (9.77 g, 70.7 mmol), N-boc-3,7diazabicylco[3.3.0]octane (10.03 g, 47.3 mmol) and 2-propanol (54.2 g) were added. The reaction was slurried at 20° C. for 5 minutes and then the temperature was raised to 80° C. over 30 minutes. The reaction was then stirred at 80° C. for 8 hours, cooled to 20° C. within 30 minutes and allowed to stand overnight. To the resulting mixture was added toluene (15.8 g) and the mixture was stirred at 30° C. for 30 minutes prior to removing all salts by suction filtration. The reactor and filter cake were then washed with toluene (20.2 g) and the resulting filtrates (~115 mL) were added to a 150 mL EasyMax reactor held at a temperature of 20° C. 5-6 N HCl in 2-propanol (25.90 g) was then added dropwise over a 30 minute period. The mixture was then heated to 60° C. over 20 minutes and stirred for 4 hours. After approximately 1.5 hours crystallization of the product started and the yellowish suspension was then cooled to 0-5° C. and was then stirred for another 1.5 hours. The product was then isolated via suction filtration and washed with 2-propanol (25.0 g) in two portions. The resulting wet product cake was dried in vacuo at 50° C. overnight then at 70° C. for 4 hours to obtain the title compound (11.52 g, 77%) as an off-white crystalline solid. Purity was assessed by HPLC (99.5%, 99.7%, and 99.5 area % (at 254, 235, and 280 nm, respectively). HCl content was determined to be 25.26%.

Intermediate 93:
3-Fluoro-2-(1H-pyrazol-1-yl)benzoic Acid

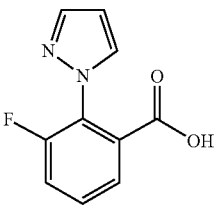

3-Fluoro-2-(1H-pyrazol-1-yl)benzoic acid. To a mixture of 3-fluoro-2-iodobenzoic acid (1.4 g, 5.26 mmol), 1H-pyrazole (0.72 g, 10.5 mmol), trans-N,N'-dimethyl-cyclohexane-1,2-diamine (0.17 mL, 1.05 mmol), CuI (50.1 mg, 0.26 mmol), dioxane (50 mL) and water (0.028 mL) was added Cs$_2$CO$_3$ (3.43 g, 10.5 mmol). The reaction mixture was heated to 100° C. for 1 h. The reaction mixture was cooled to ambient temperature then diluted with water. The aqueous layer was acidified to pH2 and extracted with EtOAc (30 mL) three times. The organic layers were combined, dried over Na$_2$SO$_4$, filtered and concentrated. Purification (FCC), (DCM to 10% MeOH/1% HOAC/DCM) afforded the title compound as a colorless oil (790 mg, 72%). 1H NMR (400 MHz, CDCl3): 7.85-7.73 (m, 1H), 7.54-7.44 (m, 1H), 7.44-7.34 (m, 1H), 6.55 (s, 1H).

Intermediate 94:
3-Methyl-2-(1H-pyrazol-1-yl)benzoic Acid

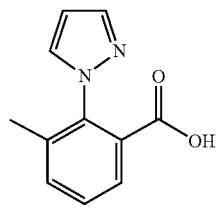

The title compound was prepared in a manner analogous to Intermediate 93 substituting 3-methyl-2-iodobenzoic acid for 3-fluoro-2-iodobenzoic acid. 1H NMR (500 MHz, CDCl3): 7.79 (d, J=7.4 Hz, 2H), 7.48 (d, J=7.5 Hz, 1H), 7.42 (t, J=7.6 Hz, 1H), 6.53 (s, 1H), 2.07 (s, 3H).

Intermediate 95: 2-Fluoro-6-(pyrimidin-2-yl)benzoic Acid

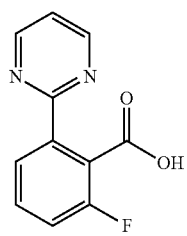 [SMILES: O=C(O)c1c(F)cccc1-c1ncccn1]

Step A: 2-Fluoro-6-iodo-benzoic acid methyl ester. To a 200 mL round-bottomed flask were added 2-fluoro-6-iodobenzoic acid (7.5 g, 28.2 mmol), LiOH·H$_2$O (1.42 g, 33.8 mmol), and THF (100 mL). The resulting mixture was warmed to 50° C. and stirred for 2 h. Dimethyl sulfate (4.03 mL, 42.3 mmol) was then added and the mixture was warmed to 65° C. After 2 h, the mixture was cooled to room temperature and NH$_4$Cl$_{(aq)}$ (50 mL, 13 wt % solution) was added. The two resulting layers were thoroughly mixed and then separated. The organic layer was dried over MgSO$_4$, filtered, and concentrated under reduced pressure to a light brown oil (7.79 g, 99% yield). $^1$H NMR (400 MHz, CDCl$_3$): 7.68-7.60 (m, 1H), 7.15-7.06 (m, 2H), 3.98 (s, 3H).

Step B: 2-Fluoro-6-(4,4,5,5-tetramethyl-[1,3,2]dioxaborolan-2-yl)-benzoic acid methyl ester. To a 500 mL round-bottomed flask were added 2-fluoro-6-iodo-benzoic acid methyl ester (7.29, 26.0 mmol) and anhydrous THF (150 mL). This mixture was cooled to 0° C. and i-PrMgCl (13.7 mL, 2 M in THF, 27.3 mmol) was added dropwise. After 10 min, 2-isopropoxy-4,4,5,5-tetramethyl-1,3,2-dioxaborolane (5.58 mL, 27.3 mmol) was added. The mixture was allowed to warm to room temperature, and after 30 min NH$_4$Cl$_{(aq)}$ (150 mL, 13 wt % solution) was added. The layers were mixed and then separated, and the aqueous layer was extracted with 100 mL of MTBE. The combined organic layers were dried over Na$_2$SO$_4$, filtered, and concentrated to a final mass of 6.07 g (90% wt %, 75% yield). $^1$H NMR (400 MHz, CDCl$_3$): 7.47-7.38 (m, 2H), 7.17-7.11 (m, 1H), 3.92 (s, 3H), 1.36 (s, 12H).

Step C: 2-Fluoro-6-pyrimidin-2-yl-benzoic acid methyl ester. To a 250 mL round-bottomed flask under nitrogen were added 2-fluoro-6-(4,4,5,5-tetramethyl-[1,3,2]dioxaborolan-2-yl)-benzoic acid methyl ester (5.46 g, 19.5 mmol) in 2-methyl-THF (50 mL), 2-chloropyrimidine (2.68 g, 23.4 mmol), and sodium carbonate (6.2 g, 58.5 mmol) in water (17 mL). PdCl$_2$(dppf)-dcm adduct (CAS #72287-26-4) (1.27 g, 1.56 mmol) was then added and the reaction mixture was warmed to 74° C. and stirred for 2.5 h. After cooling, the mixture was diluted with MTBE (50 mL) and water (80 mL). The layers were thoroughly mixed separated. The aqueous layer was extracted with additional MTBE (100 mL). The combined organics were dried over magnesium sulfate, filtered, concentrated and then purified by flash chromatography (0-25% EA/hexanes) to provide the title compound (1.72 g, 72 wt %, 30% yield). $^1$H NMR (400 MHz, CDCl$_3$): 8.79 (d, J=4.9 Hz, 2H), 8.15 (d, J=7.9 Hz, 1H), 7.51 (td, J=8.1, 5.6 Hz, 1H), 7.28-7.20 (m, 2H), 3.92 (s, 3H).

Step D: 2-Fluoro-6-pyrimidin-2-yl-benzoic acid. To a solution of 2-fluoro-6-pyrimidin-2-yl-benzoic acid methyl ester (1.36 g, 5.85 mmol) in 2-methyl-THF (20 mL) was added sodium hydroxide (2 M in water, 9.3 mL, 18.6 mmol). The mixture was heated to 72° C. and stirred for 9 h. The layers were separated and the aqueous layer acidified to pH 2 by dropwise addition of 50% HCl$_{(aq)}$ (3.1 mL). The resulting solids were stirred for 1 h, filtered, washed with water, MTBE, and heptanes, and then dried to provide the desired product as a white solid (1.12 g, 88% yield). $^1$H NMR (400 MHz, CD$_3$OD): 8.83 (d, J=4.9 Hz, 2H), 8.03 (dd, J=7.9, 0.8 Hz, 1H), 7.59 (td, J=8.1, 5.6 Hz, 1H), 7.40 (t, J=4.9 Hz, 1H), 7.34 (ddd, J=9.4, 8.4, 1.0 Hz, 1H).

Intermediate 96:
3-Methyl-2-(1H-1,2,3-triazol-1-yl)benzonitrile

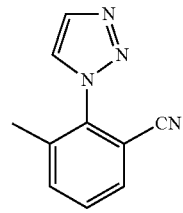

The title compound was a byproduct of the synthesis of Intermediate 81 (3.1 g, 56%). MS (ESI) mass calcd. for C$_{10}$H$_8$N$_4$, 184.2. m/z found, 185.1 [M+H]$^+$. $^1$H NMR (500 MHz, CDCl$_3$): 7.94 (d, J=2.1 Hz, 1H), 7.87 (d, J=1.1 Hz, 1H), 7.71-7.67 (m, 1H), 7.67-7.62 (m, 1H), 7.56 (dd, J=9.7, 5.8 Hz, 1H), 2.17 (s, 3H).

Intermediate 97:
5-Fluoro-2-[1,2,3]triazol-2-yl-benzoic Acid

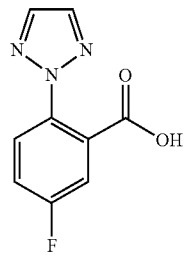 [SMILES: O=C(O)c1cc(F)ccc1-n1nccn1]

5-Fluoro-2-[1,2,3]triazol-2-yl-benzoic acid. To a solution of 5-fluoro-2-iodo-benzoic acid (3.86 g, 14.65 mmol), 2H-[1,2,3]triazole (2.5 g, 36.2 mmol), Cs$_2$CO$_3$ (8.62 g, 24.5 mmol), trans-N,N'-dimethyl-cyclohexane-1,2-diamine (0.4 mL), CuI (244 mg) and DMF (13 mL) were added to a microwave ready vessel and heated to 100° C. for 10 min. The mixture was cooled, diluted with water, and extracted with EtOAc. The aqueous layer was acidified and extracted with EtOAc. The organic layer was dried over Na$_2$SO$_4$ and concentrated. The residue was purified by FCC (SiO$_2$, gradient DCM to 10% MeOH/1% HOAc/DCM) gave the product as a white powder, (2.14 g, 71%). $^1$H NMR (400 MHz, CD$_3$OD): 7.91 (s, 2H), 7.76 (dd, J=8.9, 4.8 Hz, 1H), 7.59 (dd, J=8.5, 2.9 Hz, 1H), 7.49-7.42 (m, 1H).

Example 1: 4-[5-{[2-Fluoro-6-(2H-1,2,3-triazol-2-yl)phenyl]carbonyl}hexahydropyrrolo[3,4-c]pyrrol-2(1H)-yl]-6-methoxy-N,N-dimethylpyrimidin-2-amine

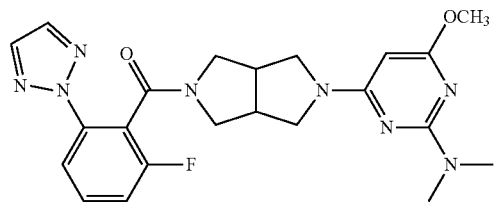 [SMILES: COc1cc(N2CC3CN(C(=O)c4c(F)cccc4-n4nccn4)CC3C2)nc(N(C)C)n1]

A mixture of [4-(Hexahydro-pyrrolo[3,4-c]pyrrol-2-yl)-6-methoxy-pyrimidin-2-yl]-dimethyl-amine (60.0 mg, 0.23 mmol), 2-fluoro-6-[1,2,3]triazol-2-yl-benzoic acid (52.0 mg, 0.25 mmol), HATU (130.0 mg, 0.34 mmol) and DIPEA (0.12 mL, 0.68 mmol) was stirred into DMF (4.0 mL) at room temperature for 30 minutes. The reaction mixture was diluted with ethyl acetate (60.0 mL) and washed with water (2×100 mL). The organic phase was dried (Na$_2$SO$_4$), filtered and concentrated to dryness to yield crude title compound (354.0 mg, 343%). The crude product was purified using Agilent HPLC (Basic system) to yield pure title compound (84.0 mg, 81.5%). MS (ESI) mass calcd. for C$_{22}$H$_{25}$FN$_8$O$_2$, 452.49. m/z found 453.3 [M+H]$^+$. $^1$H NMR (CDCl$_3$): 7.88-7.79 (m, 2H), 7.72 (d, J=6.7, 1H), 7.54-7.41 (m, 1H), 7.19-7.08 (m, 1H), 5.02-4.92 (m, 1H), 3.96-3.86 (m, 1H), 3.87-3.83 (m, 3H), 3.81-3.50 (m, 5H), 3.43-3.19 (m, 2H), 3.15-3.09 (m, 6H)), 3.09-2.91 (m, 2H).

Example 2: N,N-Dimethyl-6-[5-{[2-(2H-1,2,3-triazol-2-yl)phenyl]carbonyl}hexahydropyrrolo[3,4-c]pyrrol-2(1H)-yl]-2-(trifluoromethyl)pyrimidin-4-amine

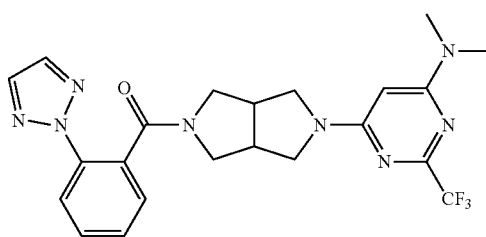

A mixture of [6-(hexahydro-pyrrolo[3,4-c]pyrrol-2-yl)-2-trifluoromethyl-pyrimidin-4-yl]-dimethyl-amine (50 mg, 0.17 mmol), 2-[1,2,3]triazol-2-yl-benzoic acid (34.5 mg, 0.18 mmol), HATU (94.6 mg, 0.25 mmol) and DIPEA (0.09 mL, 0.50 mmol) in DMF (4.0 mL) was stirred at room temperature for 30 minutes. The reaction mixture was diluted with ethyl acetate (60.0 mL) and washed with water (2×100 mL). The organic phase was dried (Na$_2$SO$_4$), filtered and concentrated to dryness. The crude product was purified using Agilent HPLC (Basic system) to yield pure title compound (34.0 mg, 43.4%). MS (ESI) mass calcd. for C$_{22}$H$_{23}$F$_3$N$_8$O, 472.47. m/z found 473.2 [M+H]$^+$. $^1$H NMR (CDCl$_3$): 7.98 (d, J=8.1, 1H), 7.70-7.69 (m, 2H), 7.56-7.49 (m, 1H), 7.45-7.37 (m, 2H), 5.20-5.10 (m, 1H), 3.90-3.66 (m, 4H), 3.60-3.28 (m, 4H), 3.08 (s, 6H), 3.02-2.89 (m, 2H).

Example 3: 6-[5-{[2-Fluoro-6-(2H-1,2,3-triazol-2-yl)phenyl]carbonyl}hexahydropyrrolo[3,4-c]pyrrol-2(1H)-yl]-N,N-dimethyl-2-(trifluoromethyl)pyrimidin-4-amine

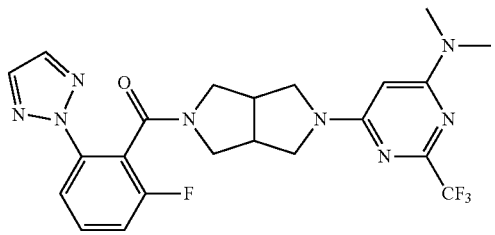 [SMILES: CN(C)c1cc(N2CC3CN(C(=O)c4c(F)cccc4-n4nccn4)CC3C2)nc(C(F)(F)F)n1]

A mixture of [6-(hexahydro-pyrrolo[3,4-c]pyrrol-2-yl)-2-trifluoromethyl-pyrimidin-4-yl]-dimethyl-amine (50 mg, 0.17 mmol), 2-fluoro-6-[1,2,3]triazol-2-yl-benzoic acid (37.8 mg, 0.18 mmol), HATU (94.6 mg, 0.25 mmol) and DIPEA (0.09 mL, 0.50 mmol) in DMF (4.0 mL) was stirred at room temperature for 30 minutes. The reaction mixture was diluted with ethyl acetate (60.0 mL) and washed with water (2×100 mL). The organic phase was dried (Na$_2$SO$_4$), filtered and concentrated to dryness. The crude product was purified using Agilent HPLC (Basic system) to yield pure title compound (19.0 mg, 23.4%). MS (ESI) mass calcd. for C$_{22}$H$_{22}$F$_4$N$_5$O, 490.46. m/z found [M+H]$^+$. $^1$H NMR (CDCl$_3$): 7.89-7.79 (m, 2H), 7.74 (s, 1H), 7.55-7.37 (m, 1H), 7.21-7.05 (m, 1H), 5.25-5.09 (m, 1H), 4.25-3.51 (m, 6H), 3.50-2.95 (m, 10H).

Example 4: 4-[5-{[5-Fluoro-2-(2H-1,2,3-triazol-2-yl)phenyl]carbonyl}hexahydropyrrolo[3,4-c]pyrrol-2(1H)-yl]-6-methoxy-N,N-dimethylpyrimidin-2-amine

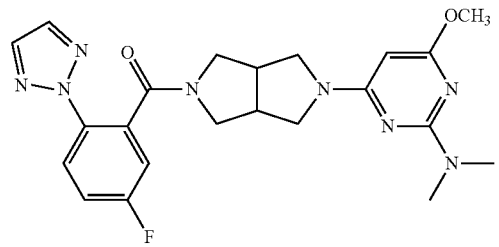 [SMILES: COc1cc(N2CC3CN(C(=O)c4cc(F)ccc4-n4nccn4)CC3C2)nc(N(C)C)n1]

A mixture of [4-(hexahydro-pyrrolo[3,4-c]pyrrol-2-yl)-6-methoxy-pyrimidin-2-yl]-dimethyl-amine (60.0 mg, 0.23 mmol), 5-fluoro-2-[1,2,3]triazol-2-yl-benzoic acid (52.0 mg, 0.25 mmol), HATU (130.0 mg, 0.34 mmol) and DIPEA (0.12 mL, 0.68 mmol) was stirred into DMF (4.0 mL) at room temperature for 30 minutes. The reaction mixture was diluted with ethyl acetate (60.0 mL) and washed with water (2×100 mL). The organic phase was dried (Na$_2$SO$_4$), filtered and concentrated to dryness. The crude product was purified using Agilent HPLC (Basic system) to yield pure title compound (160.0 mg, 54%). MS (ESI) mass calcd. for C$_{22}$H$_{25}$FN$_8$O$_2$, 452.49. m/z found 453.3 [M+H]$^+$. $^1$H NMR (CDCl$_3$): 7.95 (dd, J=9.0, 4.8, 1H), 7.73 (s, 2H), 7.25-7.17 (m, 1H), 7.16-7.10 (m, 1H), 5.00-4.90 (m, 1H), 3.92-3.78 (m, 4H), 3.76-3.25 (m, 6H), 3.18-3.07 (m, 6H), 3.05-2.86 (m, 3H).

Example 5: 4-Methoxy-N,N-dimethyl-6-[5-{[2-(2H-1,2,3-triazol-2-yl)phenyl]carbonyl}hexahydropyrrolo-[3,4-c]pyrrol-2(1H)-yl]pyrimidin-2-amine

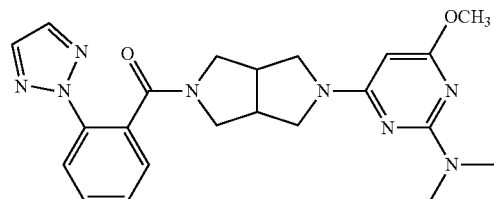

A mixture of [4-(hexahydro-pyrrolo[3,4-c]pyrrol-2-yl)-6-methoxy-pyrimidin-2-yl]-dimethyl-amine (60.0 mg, 0.23 mmol), 2-[1,2,3]triazol-2-yl-benzoic acid (47.4 mg, 0.25 mmol), HATU (130.0 mg, 0.34 mmol) and DIPEA (0.12 mL, 0.68 mmol) was stirred into DMF (4.0 mL) at room temperature for 30 minutes. The reaction mixture was diluted with ethyl acetate (60.0 mL) and washed with water (2×100 mL). The organic phase was dried ($Na_2SO_4$), filtered and concentrated to dryness. The crude product was purified using Agilent HPLC (Basic system) to yield pure title compound (47.0 mg, 47.5%). MS (ESI) mass calcd. for $C_{22}H_{26}NO_2$, 434.5. m/z found [M+H]⁺. ¹H NMR (CDCl₃): 7.98 (d, J=8.1, 1H), 7.73 (s, 2H), 7.75 (s, 2H), 7.55-7.47 (m, 1H), 7.45-7.37 (m, 2H), 5.00-4.90 (m, 1H), 3.91-3.80 (m, 5H), 3.70 (dd, J=12.5, 3.9, 2H), 3.60-3.29 (m, 4H), 3.19-3.04 (m, 8H).

Example 6: 6-[5-{[4-Fluoro-2-(2H-1,2,3-triazol-2-yl)phenyl]carbonyl}hexahydropyrrolo[3,4-c]pyrrol-2(1H)-yl]-N,N-dimethyl-2-(trifluoromethyl)pyrimidin-4-amine

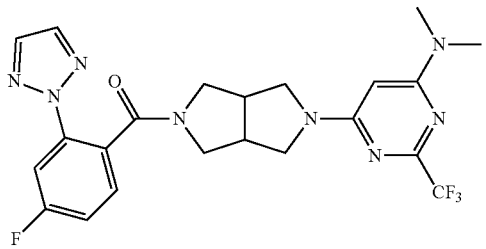 [SMILES: CN(C)c1cc(N2CC3CN(C(=O)c4ccc(F)cc4-n4nccn4)CC3C2)nc(C(F)(F)F)n1]

A mixture of [6-(hexahydro-pyrrolo[3,4-c]pyrrol-2-yl)-2-trifluoromethyl-pyrimidin-4-yl]-dimethyl-amine (50 mg, 0.17 mmol), 4-fluoro-6-[1,2,3]triazol-2-yl-benzoic acid (37.8 mg, 0.18 mmol), HATU (94.6 mg, 0.25 mmol) and DIPEA (0.09 mL, 0.50 mmol) in DMF (4.0 mL) was stirred at room temperature for 30 minutes. The reaction mixture was diluted with ethyl acetate (60.0 mL) and washed with water (2×100 mL). The organic phase was dried ($Na_2SO_4$), filtered and concentrated to dryness. The crude product was purified using Agilent HPLC (Basic system) to yield pure title compound (42.0 mg, 51.6%). MS (ESI) mass calcd. for $C_{22}H_{22}F_4N_8O$, 490.46; m/z found [M+H]⁺. ¹H NMR (CDCl₃): 7.90-7.65 (m, 3H), 7.57-7.35 (m, 1H), 7.18-7.02 (m, 1H), 5.23-5.05 (m, 1H), 4.02-3.20 (m, 7H), 3.16-2.84 (m, 9H).

Example 7: 4-[5-{[4-Fluoro-2-(2H-1,2,3-triazol-2-yl)phenyl]carbonyl}hexahydropyrrolo[3,4-c]pyrrol-2(1H)-yl]-6-methoxy-N,N-dimethylpyrimidin-2-amine

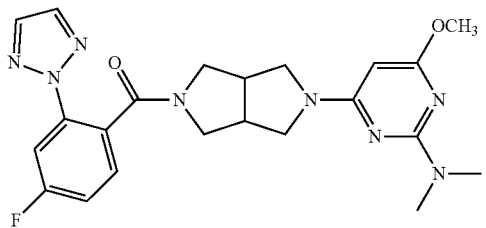 [SMILES: COc1cc(N2CC3CN(C(=O)c4ccc(F)cc4-n4nccn4)CC3C2)nc(N(C)C)n1]

A mixture of [4-(hexahydro-pyrrolo[3,4-c]pyrrol-2-yl)-6-methoxy-pyrimidin-2-yl]-dimethyl-amine (60.0 mg, 0.23 mmol), 4-fluoro-2-[1,2,3]triazol-2-yl-benzoic acid (52.0 mg, 0.25 mmol), HATU (130.0 mg, 0.34 mmol) and DIPEA (0.12 mL, 0.68 mmol) was stirred into DMF (4.0 mL) at room temperature for 30 minutes. The reaction mixture was diluted with ethyl acetate (60.0 mL) and washed with water (2×100 mL). The organic phase was dried ($Na_2SO_4$), filtered and concentrated to dryness. The crude product was purified using Agilent HPLC (Basic system) to yield pure title compound (52.0 mg, 50.5%). MS (ESI) mass calcd. for $C_{22}H_{25}FN_8O_2$, 452.49; m/z found [M+H]⁺. ¹H NMR (CDCl₃): 7.83-7.66 (m, 3H), 7.42-7.36 (m, 1H), 7.16-7.08 (m, 1H), 5.00-4.89 (m, 1H), 3.90-3.78 (m, 4H), 3.77-3.19 (m, 6H), 3.17-2.82 (m, 9H).

Example 8: 2-(4,6-Dimethylpyrimidin-2-yl)-5-{[3-(1H-pyrrol-1-yl)thiophen-2-yl]carbonyl}octahydropyrrolo[3,4-c]pyrrole

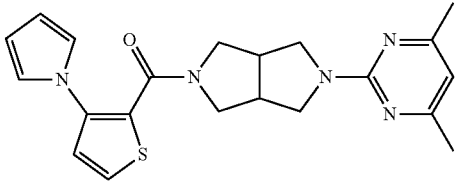 [SMILES: Cc1cc(C)nc(N2CC3CN(C(=O)c4sccc4-n4cccc4)CC3C2)n1]

A mixture of 2-(4,6-dimethyl-pyrimidin-2-yl)-octahydro-pyrrolo[3,4-c]pyrrole (60.0 mg, 0.28 mmol), 3-pyrrol-1-yl-thiophene-2-carboxylic acid (58.4 mg, 0.30 mmol), HATU (156.8 mg, 0.41 mmol) and DIPEA (106.6 mg, 0.83 mmol) was stirred into DMF (5.0 mL) at room temperature for 30 minutes. The reaction mixture was diluted with ethyl acetate (60.0 mL) and washed with water (2×100 mL). The organic phase was dried ($Na_2SO_4$), filtered and concentrated to dryness. The crude product was purified using Agilent HPLC (Basic system) to yield pure title compound (79.0 mg, 73%). MS (ESI) mass calcd. for $C_{21}H_{23}N_5OS$, 393.51. m/z found [M+H]⁺. ¹H NMR (CDCl₃): 7.42-7.39 (m, 1H), 7.04-7.01 (m, 1H), 6.85 (t, J=2.1, 2H), 6.29 (s, 1H), 6.14 (t, J=2.1, 2H), 3.88-3.73 (m, 2H), 3.66-3.52 (m, 2H), 3.50-3.41 (m, 1H), 3.32-3.20 (m, 1H), 3.00-2.86 (m, 2H), 2.80-2.66 (m, 1H), 2.60-2.47 (m, 1H), 2.34-2.25 (m, 6H).

Example 9: 6-[5-{[5-Fluoro-2-(2H-1,2,3-triazol-2-yl)phenyl]carbonyl}hexahydropyrrolo[3,4-c]pyrrol-2(1H)-yl]-N,N-dimethyl-2-(trifluoromethyl)pyrimidin-4-amine

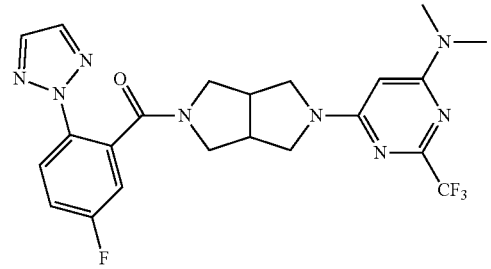 [SMILES: CN(C)c1cc(N2CC3CN(C(=O)c4cc(F)ccc4-n4nccn4)CC3C2)nc(C(F)(F)F)n1]

A mixture of [6-(hexahydro-pyrrolo[3,4-c]pyrrol-2-yl)-2-trifluoromethyl-pyrimidin-4-yl]-dimethyl-amine (50 mg, 0.17 mmol), 5-fluoro-2-[1,2,3]triazol-2-yl-benzoic acid (37.8 mg, 0.18 mmol), HATU (94.6 mg, 0.25 mmol) and DIPEA (0.09 mL, 0.50 mmol) in DMF (4.0 mL) was stirred at room temperature for 30 minutes. The reaction mixture was diluted with ethyl acetate (60.0 mL) and washed with water (2×100 mL). The organic phase was dried ($Na_2SO_4$), filtered and concentrated to dryness. The crude product was purified using Agilent HPLC (Basic system) to yield pure title compound (42.0 mg, 51.6%). MS (ESI) mass calcd. for $C_{22}H_{22}F_4N_8O$, 490.46. m/z found [M+H]$^+$. $^1$H NMR (CDCl$_3$): 7.96 (dd, J=9.0, 4.8, 1H), 7.80-7.66 (m, 2H), 7.25-7.18 (m, 1H), 7.16-7.10 (m, 1H), 5.22-5.11 (m, 1H), 3.90-3.30 (m, 8H), 3.13-3.06 (m, 7H), 3.00 (s, 6H).

Example 10: 2-(4,6-Dimethylpyrimidin-2-yl)-5-[(1-phenyl-1H-pyrazol-5-yl)carbonyl]octahydropyrrolo[3:4-c]pyrrole

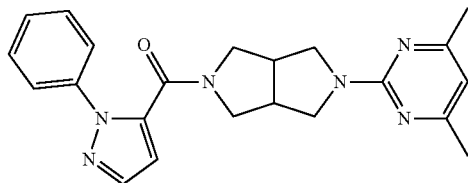

A mixture of 2-(4,6-dimethyl-pyrimidin-2-yl)-octahydro-pyrrolo[3,4-c]pyrrole (60.0 mg, 0.28 mmol), 2-phenyl-2H-pyrazole-3-carboxylic acid (56.9 mg, 0.30 mmol), HATU (156.8 mg, 0.41 mmol) and DIPEA (106.6 mg, 0.83 mmol) was stirred into DMF (5.0 mL) at room temperature for 30 minutes. The reaction mixture was diluted with ethyl acetate (60.0 mL) and washed with water (2×100 mL). The organic phase was dried ($Na_2SO_4$), filtered and concentrated to dryness. The crude product was purified using Agilent HPLC (Basic system) to yield pure title compound (79.0 mg, 74%). MS (ESI) mass calcd. for $C_{22}H_{24}N_6O$, 388.47. m/z found 389.2 [M+H]$^+$. $^1$H NMR (CDCl$_3$): 7.67 (d, J=1.7, 1H), 7.50 (d, J=7.4, 2H), 7.37 (t, J=7.8, 2H), 7.29-7.23 (m, 1H), 6.56 (d, J=1.7, 1H), 6.30 (s, 1H), 3.86-3.71 (m, 2H), 3.70-3.51 (m, 2H), 3.43-3.22 (m, 3H), 3.05-2.77 (m, 3H), 2.29 (s, 6H).

Example 11: 8-{[5-(4,6-Dimethylpyrimidin-2-yl)hexahydropyrrolo[3,4-c]pyrrol-2(1H)-yl]carbonyl}-quinoline

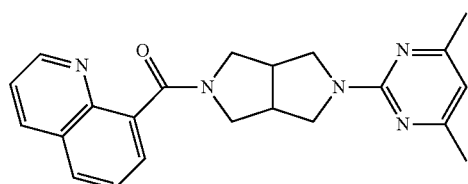

A mixture of 2-(4,6-dimethyl-pyrimidin-2-yl)-octahydro-pyrrolo[3,4-c]pyrrole (60.0 mg, 0.28 mmol), quinoline-8-carboxylic acid (52.4 mg, 0.30 mmol), HATU (156.8 mg, 0.41 mmol) and DIPEA (106.6 mg, 0.83 mmol) was stirred into DMF (5.0 mL) at room temperature for 30 minutes. The reaction mixture was diluted with ethyl acetate (60.0 mL) and washed with water (2×100 mL). The organic phase was dried ($Na_2SO_4$), filtered and concentrated to dryness. The crude product was purified using Agilent HPLC (Basic system) to yield pure title compound (68.0 mg, 66.2%). MS (ESI) mass calcd. for $C_{22}H_{23}N_5O$, 373.46. m/z found 374.2 [M+H]$^+$. $^1$H NMR (CDCl$_3$): 8.95 (s, 1H), 8.16 (d, J=7.9, 1H), 7.89-7.79 (m, 1H), 7.69 (d, J=6.8, 1H), 7.61-7.49 (m, 1H), 7.41 (s, 1H), 6.26 (d, J=19.1, 1H), 4.29-4.03 (m, 1H), 3.96-3.59 (m, 4H), 3.65-3.29 (m, 2H), 3.21-2.84 (m, 3H), 2.37-2.18 (m, 6H).

Example 12: 2-(4,6-Dimethylpyrimidin-2-yl)-5-[(3-phenylthiophen-2-yl)carbonyl]octahydropyrrolo[3,4-c]pyrrole

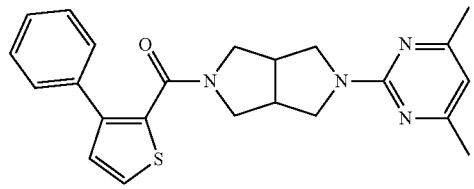 [SMILES: Cc1cc(C)nc(N2CC3CN(C(=O)c4sccc4-c4ccccc4)CC3C2)n1]

A mixture of 2-(4,6-dimethyl-pyrimidin-2-yl)-octahydro-pyrrolo[3,4-c]pyrrole (60.0 mg, 0.28 mmol), 3-phenyl-thiophene-2-carboxylic acid (61.8 mg, 0.30 mmol), HATU (156.8 mg, 0.41 mmol) and DIPEA (107.0 mg, 0.83 mmol) was stirred into DMF (5.0 mL) at room temperature for 30 minutes. The reaction mixture was diluted with ethyl acetate (60.0 mL) and washed with water (2×100 mL). The organic phase was dried ($Na_2SO_4$), filtered and concentrated to dryness. The crude product was purified using Agilent HPLC (Basic system) to yield pure title compound (30.0 mg, 27.0%). MS (ESI) mass calcd. for $C_{23}H_{24}N_4OS$, 404.54. m/z found 405.2 [M+H]$^+$. $^1$H NMR (CDCl$_3$): 7.45-7.41 (m, 2H), 7.39-(d, J=5.1, 1H), 7.34-7.27 (m, 2H), 7.18-7.14 (m, 1H), 7.13 (d, J=5.0, 1H), 6.28 (s, 1H), 3.88-3.66 (m, 2H), 3.61-3.49 (m, 2H), 3.30 (dd, J=11.5, 5.1, 1H), 3.19-3.04 (m, 2H), 2.92-2.78 (m, 1H), 2.75-2.61 (m, 2H), 2.37-2.22 (m, 6H).

Example 13: 2-(4,6-Dimethylpyrimidin-2-yl)-5-[(3-phenylfuran-2-yl)carbonyl]octahydropyrrolo[3,4-c]pyrrole

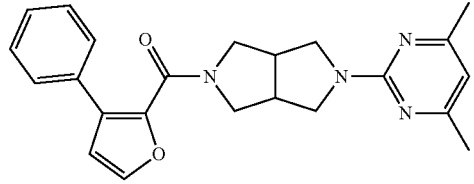

A mixture of 2-(4,6-dimethyl-pyrimidin-2-yl)-octahydro-pyrrolo[3,4-c]pyrrole (60.0 mg, 0.28 mmol), 3-phenyl-furan-2-carboxylic acid (61.8 mg, 0.30 mmol), HATU (156.8 mg, 0.41 mmol) and DIPEA (107.0 mg, 0.83 mmol) was stirred into DMF (5.0 mL) at room temperature for 30 minutes. The reaction mixture was diluted with ethyl acetate (60.0 mL) and washed with water (2×100 mL). The organic phase was dried ($Na_2SO_4$), filtered and concentrated to dryness. The crude product was purified using Dionex HPLC to yield pure title compound (30.0 mg, 28.0%). MS (ESI) mass calcd. for $C_{23}H_{24}N_4O_2$, 388.47. m/z found 389.2 $[M+H]^+$. $^1$H NMR ($CDCl_3$): 7.56-7.50 (m, 2H), 7.46 (d, J=1.8, 1H), 7.37-7.30 (m, 2H), 7.25-7.19 (m, 1H), 6.61 (d, J=1.8, 1H), 6.29 (s, 1H), 3.95-3.80 (m, 2H), 3.75-3.60 (m, 3H), 3.51 (dd, J=11.6, 5.01H), 3.42 (dd, J=11.6, 4.1, 1H), 3.33 (dd, J=11.6, 5.4, 1H), 3.02-2.81 (m, 2H), 2.35-2.22 (m, 6H).

Example 14: 2-(4,6-Dimethylpyrimidin-2-yl)-5-{[2-(1H-1,2,4-triazol-5-yl)phenyl]carbonyl} octahydropyrrolo[3,4-c]pyrrole

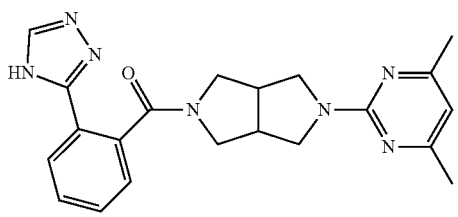 [SMILES: Cc1cc(C)nc(N2CC3CN(C(=O)c4ccccc4-c4nnc[nH]4)CC3C2)n1]

A mixture of 2-(4,6-dimethyl-pyrimidin-2-yl)-octahydropyrrolo[3,4-c]pyrrole (60.0 mg, 0.28 mmol), 2-(4H-[1,2,4] triazol-3-yl)-benzoic acid (57.2 mg, 0.30 mmol), HATU (156.8 mg, 0.41 mmol) and DIPEA (107.0 mg, 0.83 mmol) was stirred into DMF (5.0 mL) at room temperature for 30 minutes. The reaction mixture was diluted with ethyl acetate (60.0 mL) and washed with water (2×100 mL). The organic phase was dried ($Na_2SO_4$), filtered and concentrated to dryness. The crude product was purified using Agilent HPLC (basic system) to yield pure title compound (60.0 mg, 56%). MS (ESI) mass calcd. for $C_{21}H_{23}N_7O$, 389.46. m/z found 390.2 $[M+H]^+$. $^1$H NMR ($CDCl_3$): 8.12 (d, J=7.5, 1H), 8.05 (s, 1H), 7.53-7.39 (m, 2H), 7.37-7.31 (m, 1H), 6.28 (s, 1H), 3.95-3.77 (m, 2H), 3.76-3.55 (m, 3H), 3.48-3.33 (m, 2H), 3.19-3.03 (m, 1H), 3.02-2.95 (m, 1H), 2.91-2.82 (m, 1H), 2.36-2.19 (m, 6H).

Example 15: 2-(4,6-Dimethylpyrimidin-2-yl)-5-{[3-fluoro-2-(2H-1,2,3-triazol-2-yl)phenyl]carbonyl} octahydropyrrolo[3,4-c]pyrrole

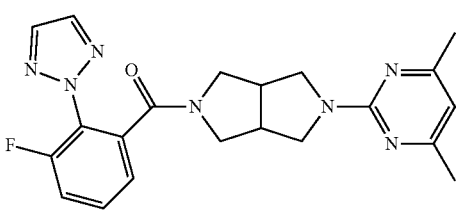 [SMILES: Cc1cc(C)nc(N2CC3CN(C(=O)c4cccc(F)c4-n4nccn4)CC3C2)n1]

A mixture of 2-(4,6-dimethyl-pyrimidin-2-yl)-octahydropyrrolo[3,4-c]pyrrole (437.3 mg, 2.0 mmol), 3-fluoro-2-[1, 2,3]triazol-2-yl-benzoic acid (415 mg, 2.0 mmol), HATU (1.14 g, 3.0 mmol) and DIPEA (777 mg, 6.0 mmol) was stirred into DMF (20 mL) at room temperature for 30 minutes. The reaction mixture was diluted with ethyl acetate (250 mL) and washed with water (2×500 mL). The organic phase was dried ($Na_2SO_4$), filtered and concentrated to dryness. The crude product was purified using Agilent HPLC (basic system) to yield pure title compound (458.0 mg, 56%). MS (ESI) mass calcd. for $C_{21}H_{22}FN_7O$, 407.45. m/z found 408.2 $[M+H]^+$. $^1$H NMR ($CDCl_3$): 7.79 (s, 2H), 7.52-7.45 (m, 1H), 7.36-7.28 (m, 1H), 7.25-7.22 (m, 1H), 6.30 (s, 1H), 3.82 (dd, J=11.6, 7.5, 1H), 3.75-3.66 (m, 2H), 3.58-3.41 (m, 4H), 3.13 (dd, J=10.9, 5.2, 1H), 3.02-2.87 (m, 2H), 2.36-2.24 (m, 6H).

Examples 16-106, 108-214 were prepared in a manner analogous to Example 15.

Example 16: 2-{5-[(2,4-Dimethoxyphenyl)carbonyl] hexahydropyrrolo[3,4-c]pyrrol-2(1H)-yl}-6-fluoro-1,3-benzothiazole

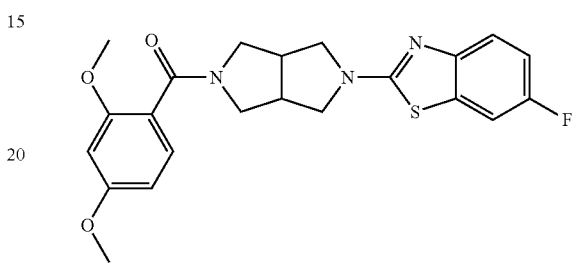

The title compound was prepared in a manner analogous to Example 15, utilizing Intermediate 38 and 2-chloro-6-fluoro-benzothiazole. MS (ESI) mass calcd. for $C_{22}H_{22}FN_3O_3S$, 427.5. m/z found, 428.2 $[M+H]^+$.

Example 17: 2-{5-[(2,4-Dimethoxyphenyl)carbonyl] hexahydropyrrolo[3,4-c]pyrrol-2(1H)-yl}-1,3-benzothiazole

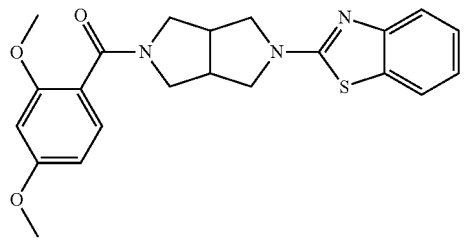 [SMILES: COc1ccc(C(=O)N2CC3CN(c4nc5ccccc5s4)CC3C2)c(OC)c1]

The title compound was prepared in a manner analogous to Example 15 utilizing Intermediate 38 and 2-chloro-benzothiazole. MS (ESI) mass calcd. for $C_{22}H_{23}N_3O_3S$, 409.51. m/z found, 410.2 $[M+H]^+$.

Example 18: 2-[5-{[2-(1H-Pyrazol-1-yl)phenyl] carbonyl}hexahydropyrrolo[3,4-c]pyrrol-2(1H)-yl] quinoxaline

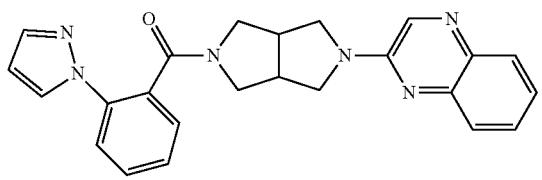 [SMILES: O=C(c1ccccc1-n1cccn1)N1CC2CN(c3cnc4ccccc4n3)CC2C1]

The title compound was prepared in a manner analogous to Example 15 utilizing Intermediate 35 and 2-pyrazol-1- yl-benzoic acid. MS (ESI) mass calcd. for $C_{24}H_{22}N_6O$, 410.48. m/z found, 411.2 $[M+H]^+$.

Example 19: 2-{5-[(2-Thiophen-2-ylphenyl)carbonyl]hexahydropyrrolo[34-c]pyrrol-2(1H)-yl}quinoxaline

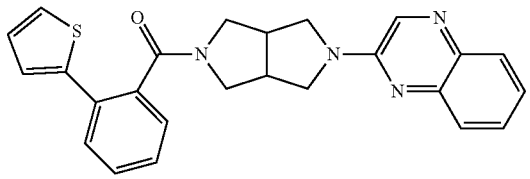 [SMILES: O=C(c1ccccc1-c1cccs1)N1CC2CN(c3cnc4ccccc4n3)CC2C1]

The title compound was prepared in a manner analogous to Example 15 utilizing Intermediate 35 and 2-thiophen-2-yl-benzoic acid. MS (ESI) mass calcd. for $C_{25}H_{22}N_4OS$, 426.54. m/z found, 427.2 $[M+H]^+$.

Example 20: 2-{5-[(2-Methylnaphthalen-1-yl)carbonyl]hexahydropyrrolo[3,4-c]pyrrol-2(1H)-yl}quinoxaline

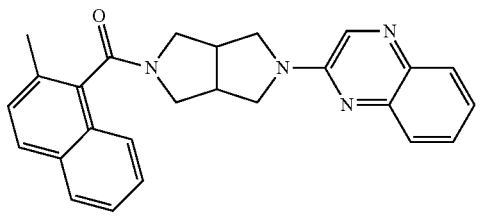 [SMILES: Cc1ccc2ccccc2c1C(=O)N1CC2CN(c3cnc4ccccc4n3)CC2C1]

The title compound was prepared in a manner analogous to Example 15 utilizing Intermediate 35 and 2-methylnaphthalene-1-carboxylic acid. MS (ESI) mass calcd. for $C_{25}H_{22}N_4OS$, 426.54. m/z found, 427.2 $[M+H]^+$.

Example 21: 2-(2,3-Dihydro-1,4-benzodioxin-5-ylcarbonyl)-5-(4-phenylpyrimidin-2-yl)octahydropyrrolo[3,4-c]pyrrole

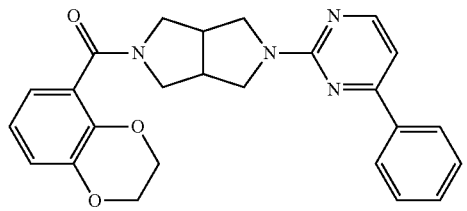 [SMILES: O=C(c1cccc2c1OCCO2)N1CC2CN(c3nccc(-c4ccccc4)n3)CC2C1]

The title compound was prepared in a manner analogous to Example 15 utilizing Intermediate 26 and 2,3-dihydrobenzo[1,4]dioxine-5-carboxylic acid. MS (ESI) mass calcd. for $C_{25}H_{24}N_4O_3$, 428.50. m/z found, 429.2 $[M+H]^+$.

Example 22: 2-(4-Phenylpyrimidin-2-yl)-5-[(2-thiophen-2-ylphenyl)carbonyl]octahydro-pyrrolo[3,4-c]pyrrole

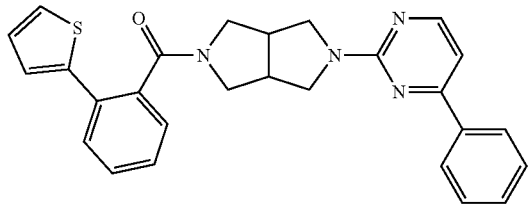 [SMILES: O=C(c1ccccc1-c1cccs1)N1CC2CN(c3nccc(-c4ccccc4)n3)CC2C1]

The title compound was prepared in a manner analogous to Example 15 utilizing Intermediate 26 and 2-thiophen-2-yl-benzoic acid. MS (ESI) mass calcd. for $C_{27}H_{24}N_4OS$, 452.58. m/z found, 453.2 $[M+H]^+$.

Example 23: 2-(4-Phenylpyrimidin-2-yl)-5-{[2-(1H-pyrazol-1-yl)phenyl]carbonyl}octahydro-pyrrolo[3,4-c]pyrrole

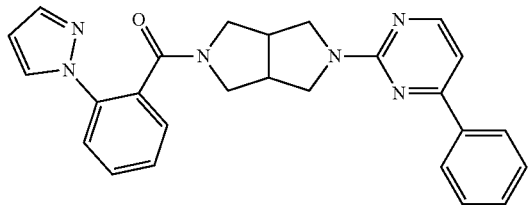 [SMILES: O=C(c1ccccc1-n1cccn1)N1CC2CN(c3nccc(-c4ccccc4)n3)CC2C1]

The title compound was prepared in a manner analogous to Example 15 utilizing Intermediate 26 and 2-pyrazol-1-yl-benzoic acid. MS (ESI) mass calcd. for $C_{26}H_{24}N_6$, 436.52. m/z found, 437.2 $[M+H]^+$.

Example 24: 2-(4-Phenylpyrimidin-2-yl)-5-{[2-(1H-pyrrol-1-yl)phenyl]carbonyl}octahydro-pyrrolo[3,4-c]pyrrole

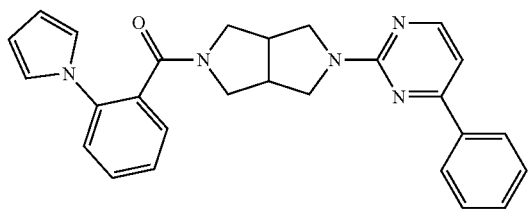 [SMILES: O=C(c1ccccc1-n1cccc1)N1CC2CN(c3nccc(-c4ccccc4)n3)CC2C1]

The title compound was prepared in a manner analogous to Example 15 utilizing Intermediate 26 and 2-pyrrol-1-yl-benzoic acid. MS (ESI) mass calcd. for $C_{27}H_{25}N_5O$, 435.53. m/z found, 436.3 $[M+H]^+$.

Example 25: 2-[(2-Methylnaphthalen-1-yl)carbonyl]-5-(4-phenylpyrimidin-2-yl)octahydropyrrolo[3,4-c]pyrrole

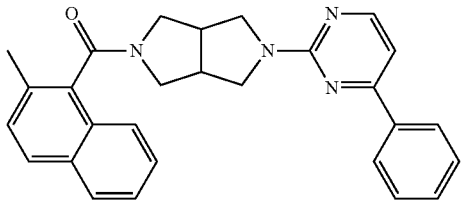 [SMILES: Cc1ccc2ccccc2c1C(=O)N1CC2CN(c3nccc(-c4ccccc4)n3)CC2C1]

The title compound was prepared in a manner analogous to Example 15 utilizing Intermediate 26 and 2-methylnaphthalene-1-carboxylic acid. MS (ESI) mass calcd. for $C_{28}H_{26}N_4O$, 434.51. m/z found, 435.3 [M+H]$^+$.

Example 26: 2-(5-Quinoxalin-2-yl-hexahydro-pyrrolo[3,4-c]pyrrole-2-carbonyl)-benzonitrile

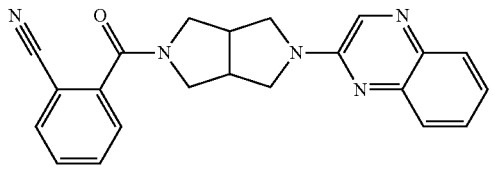 [SMILES: N#Cc1ccccc1C(=O)N1CC2CN(c3cnc4ccccc4n3)CC2C1]

The title compound was prepared in a manner analogous to Example 15 utilizing Intermediate 35 and 2-cyano-benzoic acid. MS (ESI): mass calculated for $C_{22}H_{19}N_5O$, 369.43. m/z found 370.3 [M+H]$^+$.

Example 27: 2-[5-{[2-(1H-Pyrrol-1-yl)phenyl]carbonyl}hexahydropyrrolo[3,4-c]pyrrol-2(1H)-yl]quinoxaline

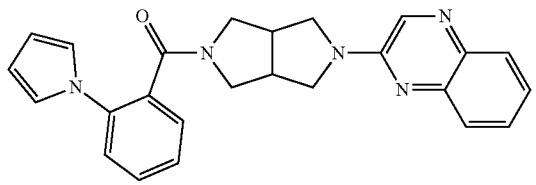 [SMILES: O=C(c1ccccc1-n1cccc1)N1CC2CN(c3cnc4ccccc4n3)CC2C1]

The title compound was prepared in a manner analogous to Example 15 utilizing Intermediate 35 and 2-pyrrol-1-yl-benzoic acid. MS (ESI) mass calcd. for $C_{25}H_{23}N_5O$, 409.49. m/z found, 410.2 [M+H]$^+$.

Example 28: 2-{5-[(4'-Fluorobiphenyl-2-yl)carbonyl]hexahydropyrrolo[3,4-c]pyrrol-2(1H)-yl}quinoxaline

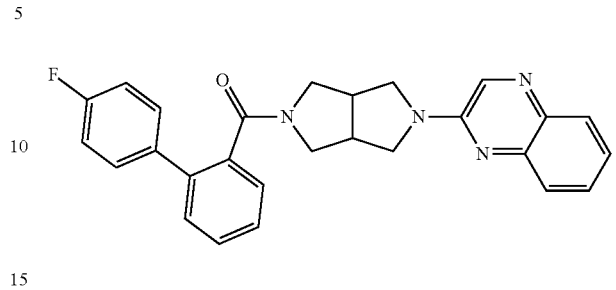

The title compound was prepared in a manner analogous to Example 15 utilizing Intermediate 35 and 4'-fluorobiphenyl-2-carboxylic acid. MS (ESI) mass calcd. for $C_{27}H_{23}FN_4O$, 438.51. m/z found, 439.2 [M+H]$^+$.

Example 29: 2-{5-[(3'-Fluorobiphenyl-2-yl)carbonyl]hexahydropyrrolo[3,4-c]pyrrol-2(1H)-yl}quinoxaline

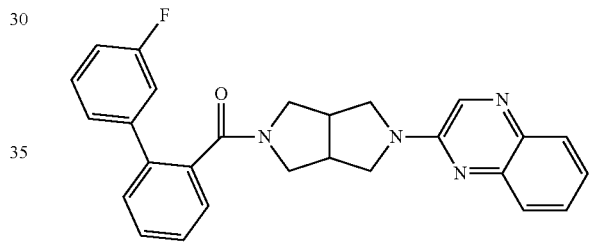

The title compound was prepared in a manner analogous to Example 15 utilizing Intermediate 35 and 3'-fluorobiphenyl-2-carboxylic acid. MS (ESI) mass calcd. for $C_{27}H_{23}FN_4O$, 438.51. m/z found, 439.2 [M+H]$^+$.

Example 30: 2-{5-[(2-Methylphenyl)carbonyl]hexahydropyrrolo[3,4-c]pyrrol-2(1H)-yl}quinoxaline

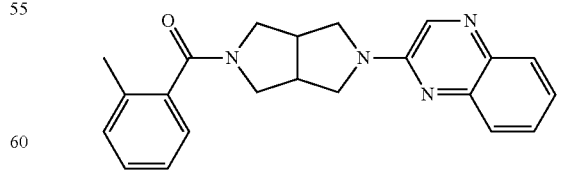

The title compound was prepared in a manner analogous to Example 15 utilizing Intermediate 35 and 2-methylbenzoic acid. MS (ESI) mass calcd. for $C_{22}H_{22}N_4O$, 358.45. m/z found, 359.2 [M+H]$^+$.

Example 31: 2-(Biphenyl-2-ylcarbonyl)-5-(4-furan-2-ylpyrimidin-2-yl)octahydropyrrolo[3,4-c]pyrrole

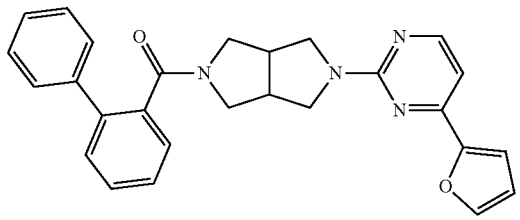 [SMILES: O=C(c1ccccc1-c1ccccc1)N1CC2CN(c3nccc(-c4ccco4)n3)CC2C1]

The title compound was prepared in a manner analogous to Example 15 utilizing Intermediate 17 and 2-chloro-4-furan-2-yl-pyrimidine. MS (ESI) mass calcd. for $C_{27}H_{24}N_4O_2$, 436.52. m/z found, 437.2 [M+H]$^+$.

Example 32: 2-(4-Methylpyrimidin-2-yl)-5-[(2-thiophen-2-ylphenyl)carbonyl]octahydro-pyrrolo[3,4-c]pyrrole

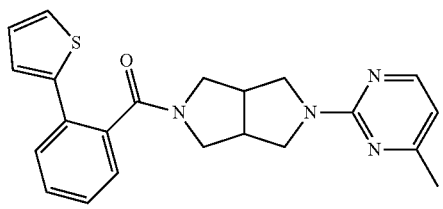 [SMILES: Cc1ccnc(N2CC3CN(C(=O)c4ccccc4-c4cccs4)CC3C2)n1]

The title compound was prepared in a manner analogous to Example 15 utilizing Intermediate 37 and 2-chloro-4-methyl-pyrimidine. MS (ESI) mass calcd. for $C_{22}H_{22}N_4OS$, 390.51. m/z found, 391.2 [M+H]$^+$.

Example 33: 2-{5-[(2-Thiophen-2-ylphenyl)carbonyl]hexahydropyrrolo[3,4-c]pyrrol-2(1H)-yl}quinoline

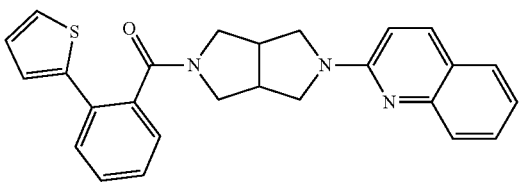 [SMILES: O=C(c1ccccc1-c1cccs1)N1CC2CN(c3ccc4ccccc4n3)CC2C1]

The title compound was prepared in a manner analogous to Example 15 utilizing Intermediate 37 and 2-chloro-quinoline. MS (ESI) mass calcd. for $C_{26}H_{23}N_3OS$, 425.56. m/z found, 426.2 [M+H]$^+$.

Example 34: 2-(4-Furan-2-ylpyrimidin-2-yl)-5-[(2-thiophen-2-ylphenyl)carbonyl]octahydro-pyrrolo[3,4-c]pyrrole

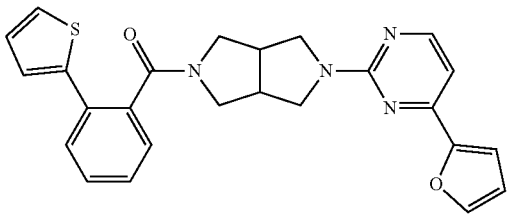 [SMILES: O=C(c1ccccc1-c1cccs1)N1CC2CN(c3nccc(-c4ccco4)n3)CC2C1]

The title compound was prepared in a manner analogous to Example 15 utilizing Intermediate 37 and 2-chloro-4-furan-2-yl-pyrimidine. MS (ESI) mass calcd. for $C_{25}H_{22}N_4O_2S$, 442.50. m/z found, 443.2 [M+H]$^+$.

Example 35: 2-{5-[(2-Ethylphenyl)carbonyl]hexahydropyrrolo[3,4-c]pyrrol-2(1H)-yl}quinoxaline

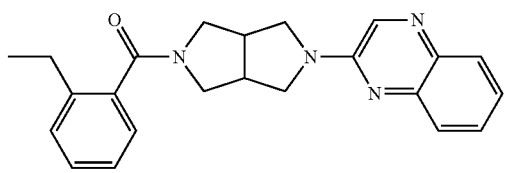 [SMILES: CCc1ccccc1C(=O)N1CC2CN(c3cnc4ccccc4n3)CC2C1]

The title compound was prepared in a manner analogous to Example 15 utilizing Intermediate 35 and 2-ethylbenzoic acid. MS (ESI) mass calcd. for $C_{23}H_{24}N_4O$, 372.46. m/z found, 373.2 [M+H]$^+$.

Example 36: 2-[5-(1H-Indol-7-ylcarbonyl)hexahydropyrrolo[3,4-c]pyrrol-2(1H)-yl]quinoxaline

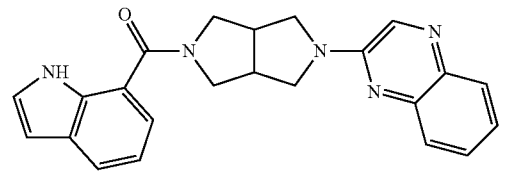 [SMILES: O=C(c1cccc2cc[nH]c12)N1CC2CN(c3cnc4ccccc4n3)CC2C1]

The title compound was prepared in a manner analogous to Example 15 utilizing Intermediate 35 and 1H-indole-7-carboxylic acid. MS (ESI) mass calcd. for $C_{23}H_{21}N_5O$, 383.45. m/z found, 384.2 [M+H]$^+$.

Example 37: 2-[(2-Thiophen-2-ylphenyl)carbonyl]-5-(4-thiophen-2-ylpyrimidin-2-yl)octahydro-pyrrolo[3,4-c]pyrrole

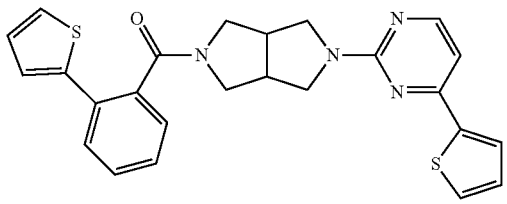 [SMILES: O=C(c1ccccc1-c1cccs1)N1CC2CN(c3nccc(-c4cccs4)n3)CC2C1]

The title compound was prepared in a manner analogous to Example 15 utilizing Intermediate 37 and 2-chloro-4-thiophen-2-yl-pyrimidine. MS (ESI) mass calcd. for $C_{25}H_{22}N_4OS_2$, 458.60. m/z found, 459.1 [M+H]$^+$.

Example 38: 2-(Biphenyl-2-ylcarbonyl)-5-(4-thiophen-2-ylpyrimidin-2-yl)octahydropyrrolo[3,4-c]pyrrole

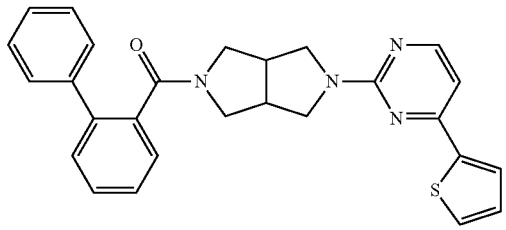 [SMILES: O=C(c1ccccc1-c1ccccc1)N1CC2CN(c3nccc(-c4cccs4)n3)CC2C1]

The title compound was prepared in a manner analogous to Example 15 utilizing Intermediate 17 and 2-chloro-4-thiophen-2-yl-pyrimidine. MS (ESI) mass calcd. for $C_{27}H_{24}N_4OS$, 452.57. m/z found, 453.1 [M+H]$^+$.

Example 39: [5-(4,6-Dimethyl-pyrimidin-2-yl)-hexahydro-pyrrolo[3,4-c]pyrrol-2-yl]-[2-(1-methyl-1H-imidazol-2-yl)-phenyl]-methanone

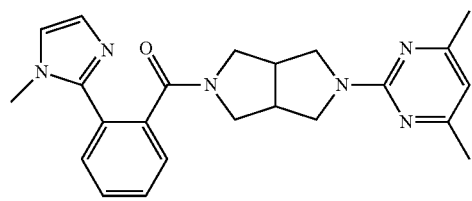

The title compound was prepared in a manner analogous to Example 15 utilizing Intermediate 23 and 2-(1-methyl-1H-imidazol-2-yl)-benzoic acid. MS (ESI) mass calcd. for $C_{23}H_{26}N_6O$, 402.50. m/z found, 403.2 [M+H]$^+$.

Example 40: 2-[(2-Bromophenyl)carbonyl]-5-(4-phenylpyrimidin-2-yl)octahydropyrrolo[3,4-c]pyrrole

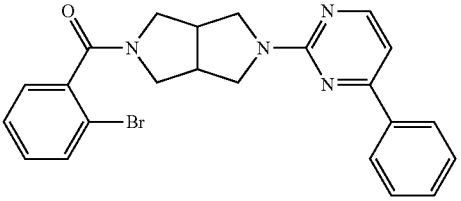 [SMILES: O=C(c1ccccc1Br)N1CC2CN(c3nccc(-c4ccccc4)n3)CC2C1]

The title compound was prepared in a manner analogous to Example 15 utilizing Intermediate 26 and 2-bromobenzoic acid. MS (ESI) mass calcd. for $C_{23}H_{21}BrN_4O$, 449.34. m/z found, 449.1, 451.1 [M+H]$^+$.

Example 41: 2-{5-[(3'-Chlorobiphenyl-2-yl)carbonyl]hexahydropyrrolo[3,4-c]pyrrol-2(1H)-yl}quinoxaline

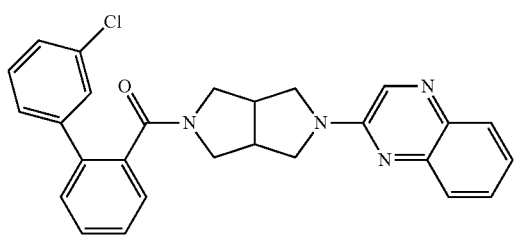 [SMILES: O=C(c1ccccc1-c1cccc(Cl)c1)N1CC2CN(c3cnc4ccccc4n3)CC2C1]

The title compound was prepared in a manner analogous to Example 15 utilizing Intermediate 35 and 3'-chlorobiphenyl-2-carboxylic acid. MS (ESI) mass calcd. for $C_{27}H_{23}ClN_4O$, 454.95. m/z found, 455.1 [M+H]$^+$.

Example 42: 2-{5-[(2-Bromophenyl)carbonyl]hexahydropyrrolo[3,4-c]pyrrol-2(1H)-yl}quinoxaline

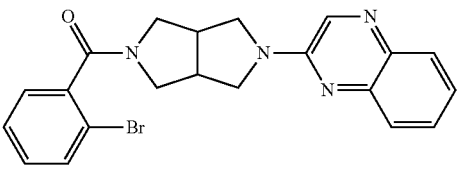 [SMILES: O=C(c1ccccc1Br)N1CC2CN(c3cnc4ccccc4n3)CC2C1]

The title compound was prepared in a manner analogous to Example 15 utilizing Intermediate 35 and 2-bromobenzoic acid. MS (ESI) mass calcd. for $C_{21}H_{19}BrN_4O$, 423.31. m/z found, 423.0, 425.0 [M+H]$^+$.

Example 43: 2-(4,6-Dimethylpyrimidin-2-yl)-5-[(2-thiophen-2-ylphenyl)carbonyl]octahydro-pyrrolo[3,4-c]pyrrole

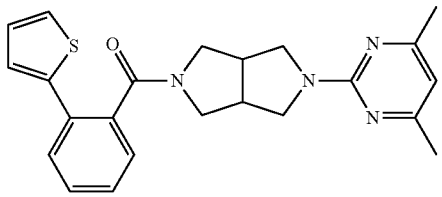 [SMILES: Cc1cc(C)nc(N2CC3CN(C(=O)c4ccccc4-c4cccs4)CC3C2)n1]

The title compound was prepared in a manner analogous to Example 15 utilizing Intermediate 37 and 2-chloro-4,6-dimethyl-pyrimidine. MS (ESI) mass calcd. for $C_{23}H_{24}N_4OS$, 404.53. m/z found, 405.1 $[M+H]^+$.

Example 44: 2-(Biphenyl-2-ylcarbonyl)-5-(4,6-dimethylpyrimidin-2-yl)octahydropyrrolo[3,4-c]pyrrole

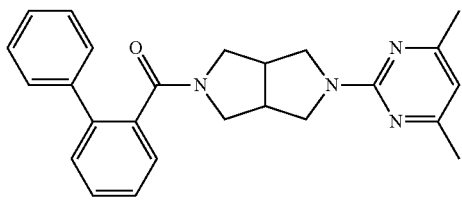 [SMILES: Cc1cc(C)nc(N2CC3CN(C(=O)c4ccccc4-c4ccccc4)CC3C2)n1]

The title compound was prepared in a manner analogous to Example 15 utilizing Intermediate 17 and 2-chloro-4,6-dimethyl-pyrimidine. MS (ESI) mass calcd. for $C_{25}H_{26}N_4O$, 398.5. m/z found, 399.2 $[M+H]^+$.

Example 45: 2-(4-Methoxypyrimidin-2-yl)-5-[(2-thiophen-2-ylphenyl)carbonyl]octahydro-pyrrolo[3,4-c]pyrrole

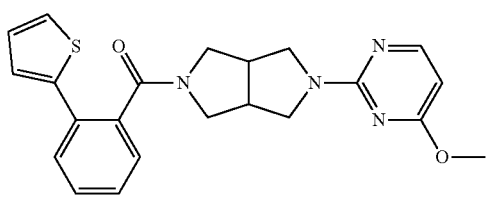 [SMILES: COc1ccnc(N2CC3CN(C(=O)c4ccccc4-c4cccs4)CC3C2)n1]

The title compound was prepared in a manner analogous to Example 15 utilizing Intermediate 37 and 2-chloro-4-methoxy-pyrimidine. MS (ESI) mass calcd. for $C_{22}H_{22}N_4O_2S$, 406.50. m/z found, 407.0 $[M+H]^+$.

Example 46: 6-Fluoro-2-{5-[(2-thiophen-2-ylphenyl)carbonyl]hexahydropyrrolo[3,4-c]pyrrol-2(1H)-yl}-1,3-benzothiazole

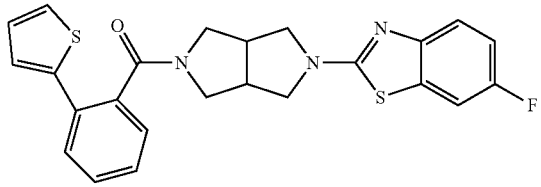 [SMILES: O=C(c1ccccc1-c1cccs1)N1CC2CN(c3nc4ccc(F)cc4s3)CC2C1]

The title compound was prepared in a manner analogous to Example 15 utilizing Intermediate 37 and 2-chloro-6-fluoro-benzothiazole. MS (ESI) mass calcd. for $C_{24}H_{20}FN_3OS_2$, 449.57. m/z found, 450.0 $[M+H]^+$.

Example 47: 2-(4,6-Dimethylpyrimidin-2-yl)-5-[(2-methylnaphthalen-1-yl)carbonyl]octahydro-pyrrolo[3,4-c]pyrrole

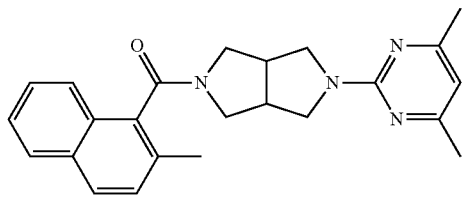 [SMILES: Cc1cc(C)nc(N2CC3CN(C(=O)c4c(C)ccc5ccccc45)CC3C2)n1]

The title compound was prepared in a manner analogous to for Example 15 utilizing Intermediate 23 and 2-methyl-naphthalene-1-carboxylic acid. MS (ESI) mass calcd. for $C_{24}H_{26}N_4O$, 386.5. m/z found, 387.3 $[M+H]^+$.

Example 48: 2-[(3'-Fluorobiphenyl-2-yl)carbonyl]-5-(4-methylpyrimidin-2-yl)octahydro-pyrrolo[3,4-c]pyrrole

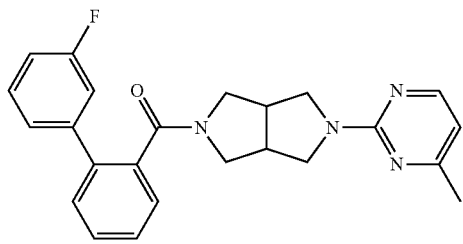 [SMILES: Cc1ccnc(N2CC3CN(C(=O)c4ccccc4-c4cccc(F)c4)CC3C2)n1]

The title compound was prepared in a manner analogous to Example 15 utilizing Intermediate 27 and 3'-fluoro-biphenyl-2-carboxylic acid. MS (ESI) mass calcd. for $C_{24}H_{23}FN_4O$, 402.46. m/z found, 403.1 $[M+H]^+$.

Example 49: 2-(4-Methoxypyrimidin-2-yl)-5-[(2-methylnaphthalen-1-yl)carbonyl]octahydro-pyrrolo[3,4-c]pyrrole

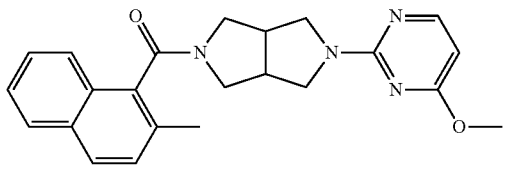 [SMILES: COc1ccnc(N2CC3CN(C(=O)c4c(C)ccc5ccccc45)CC3C2)n1]

The title compound was prepared in a manner analogous to Example 15 utilizing Intermediate 32 and 2-methyl-naphthalene-1-carboxylic acid. MS (ESI) mass calcd. for $C_{23}H_{24}N_4O_2$, 388.46. m/z found, 389.1 [M+H]$^+$.

Example 50: 2-[(2-Methylnaphthalen-1-yl)carbonyl]-5-(4-methylpyrimidin-2-yl)octahydro-pyrrolo[3,4-c]pyrrole

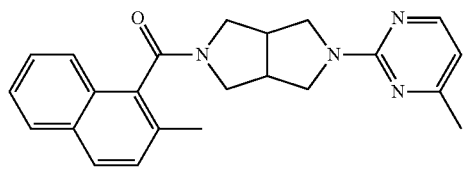 [SMILES: Cc1ccnc(N2CC3CN(C(=O)c4c(C)ccc5ccccc45)CC3C2)n1]

The title compound was prepared in a manner analogous to Example 15 utilizing and 2-methyl-naphthalene-1-carboxylic acid. MS (ESI) mass calcd. for $C_{23}H_{24}N_4O$, 372.46. m/z found, 373.1 [M+H]$^+$.

Example 51: 2-[(3'-Fluorobiphenyl-2-yl)carbonyl]-5-(4-methoxypyrimidin-2-yl)octahydro-pyrrolo[3,4-c]pyrrole

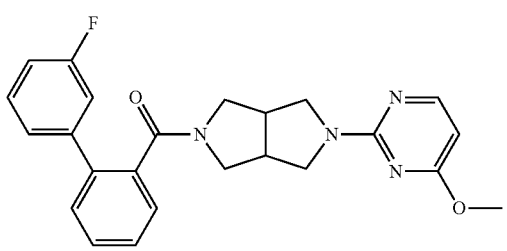 [SMILES: COc1ccnc(N2CC3CN(C(=O)c4ccccc4-c4cccc(Cl)c4)CC3C2)n1]

The title compound was prepared in a manner analogous to Example 15 utilizing Intermediate 32 and 3'-fluoro-biphenyl-2-carboxylic acid. MS (ESI) mass calcd. for $C_{24}H_{23}FN_4O_2$, 418.46. m/z found, 419.1 [M+H]$^+$.

Example 52: 2-(4,6-Dimethylpyrimidin-2-yl)-5-[(3'-fluorobiphenyl-2-yl)carbonyl]octahydro-pyrrolo[3,4-c]pyrrole

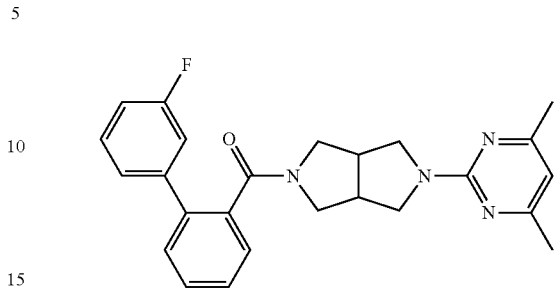

The title compound was prepared in a manner analogous to Example 15 utilizing Intermediate 23 and 3'-fluoro-biphenyl-2-carboxylic acid. MS (ESI) mass calcd. for $C_{25}H_{25}FN_4O$, 416.49. m/z found, 417.1 [M+H]$^+$.

Example 53: [5-(4,6-Dimethyl-pyrimidin-2-yl)-hexahydro-pyrrolo[3,4-c]pyrrol-2-yl]-(2-fluoro-phenyl)-methanone

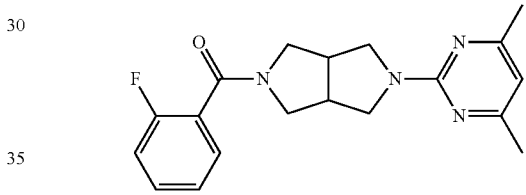

The title compound was prepared in a manner analogous to Example 15 utilizing Intermediate 23 and 2-fluorobenzoic acid. MS (ESI) mass calcd. for $C_{19}H_{21}FN_4O$, 340.4. m/z found, 341.2 [M+H]$^+$.

Example 54: 2-(4-Methoxypyrimidin-2-yl)-5-[(4'-methylbiphenyl-2-yl)carbonyl]octahydro-pyrrolo[3,4-c]pyrrole

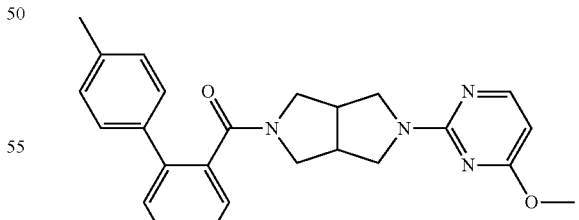

The title compound was prepared in a manner analogous to Example 15 utilizing Intermediate 32 and 4'-methyl-biphenyl-2-carboxylic acid. MS (ESI) mass calcd. for $C_{25}H_{26}N_4O_2$, 414.50. m/z found, 415.1 [M+H]$^+$. $^1$H NMR (CDCl$_3$): 8.06 (d, J=5.7 Hz, 1H), 7.54-7.34 (m, 6H), 7.17 (s, 2H), 6.01 (d, J=5.7 Hz, 1H), 3.90 (s, 3H), 3.82-3.66 (m, 2H), 3.65-3.35 (m, 2H), 3.25-2.55 (m, 6H), 2.33 (s, 3H).

Example 55: 2-[(3'-Chlorobiphenyl-2-yl)carbonyl]-5-(4-methoxypyrimidin-2-yl)octahydro-pyrrolo[3,4-c]pyrrole

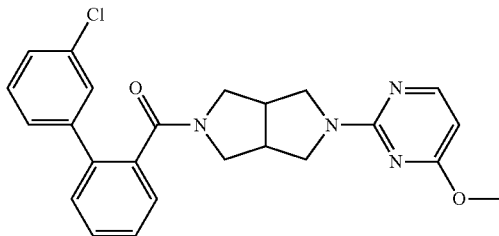

The title compound was prepared in a manner analogous to Example 15 utilizing Intermediate 32 and 3'-chlorobiphenyl-2-carboxylic acid. MS (ESI) mass calcd. for $C_{24}H_{23}ClN_4O_2$, 434.92. m/z found, 435.1 [M+H]$^+$. $^1$H NMR (CDCl$_3$): 8.06 (d, J=5.6 Hz, 1H), 7.55-7.33 (m, 6H), 7.32-7.14 (m, 2H), 6.03 (d, J=5.7 Hz, 1H), 3.92 (s, 3H), 3.81-3.64 (m, 2H), 3.61-3.45 (m 2H), 3.14 (br s, 3H), 2.91-2.55 (m, 3H).

Example 56: 2-[(2-Ethoxynaphthalen-1-yl)carbonyl]-5-(4-methoxypyrimidin-2-yl)octahydropyrrolo[3,4-c]pyrrole

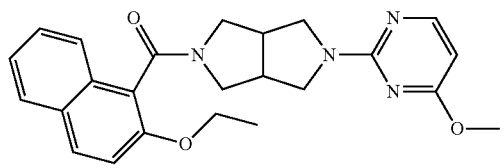 [SMILES: CCOc1ccc2ccccc2c1C(=O)N1CC2CN(c3nccc(OC)n3)CC2C1]

The title compound was prepared according to the procedure used for Example 15 utilizing Intermediate 32 and 2-ethoxy-naphthalene-1-carboxylic acid. MS (ESI) mass calcd. for $C_{24}H_{26}N_4O_3$, 418.49. m/z found, 419.3 [M+H]$^+$. $^1$H NMR (CDCl$_3$): rotamers observed, 8.07 (t, J=6.3 Hz, 1H), 7.89-7.76 (m, 2H), 7.74 (d, J=8.4 Hz, 0.6H), 7.66 (d, J=8.4 Hz, 0.4H), 7.50 (t, J=7.6 Hz, 0.6H), 7.46-7.32 (m, 1.5H), 7.31-7.22 (m, 1H), 6.05-6.00 (m, 1H), 4.32-3.81 (m, 7.7H), 3.80-3.52 (m, 3.0H), 3.43-3.31 (m, 1H), 3.27 (dd, J=11.1, 5.9 Hz, 0.6H), 3.19-3.07 (m, 1H), 3.05-2.92 (m 1.5H), 1.46 (t, J=7.0 Hz, 1.3H), 1.36 (t, J=6.9 Hz, 1.8H).

Example 57: 2-[(4-Fluoronaphthalen-1-yl)carbonyl]-5-(4-methoxypyrimidin-2-yl)octahydro-pyrrolo[3,4-c]pyrrole

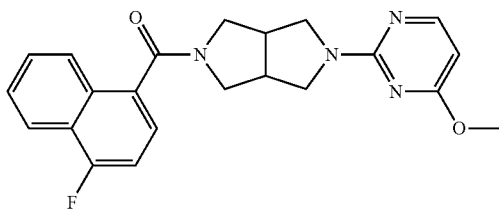 [SMILES: COc1ccnc(N2CC3CN(C(=O)c4ccc(F)c5ccccc45)CC3C2)n1]

The title compound was prepared in a manner analogous to Example 15 utilizing Intermediate 32 and 4-fluoro-naphthalene-1-carboxylic acid. MS (ESI) mass calcd. for $C_{22}H_{21}FN_4O_2$, 392.43. m/z found, 393.2 [M+H]$^+$. $^1$H NMR (CDCl$_3$): 8.22-8.13 (m, 1H), 8.08 (d, J=5.7 Hz, 1H), 7.89 (d, J=7.7 Hz, 1H), 7.66-7.53 (m, 2H), 7.43 (dd, J=7.8, 5.3 Hz, 1H), 7.17 (dd, J=10.1, 7.9 Hz, 1H), 6.04 (d, J=5.7 Hz, 1H), 4.11 (dd, J=12.8, 7.8 Hz, 1H), 4.00-3.80 (m, 5H), 3.80-3.63 (m, 2H), 3.57-3.39 m, 2H), 3.22-3.08 (m, 2H), 3.04-2.92 (m, 1H).

Example 58: 2-(4-Methoxypyrimidin-2-yl)-5-(naphthalen-1-ylcarbonyl)octahydropyrrolo[3,4-c]pyrrole

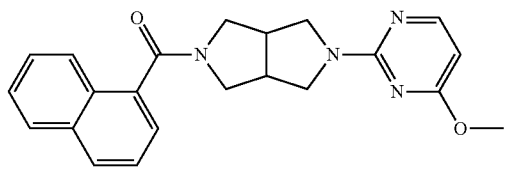 [SMILES: COc1ccnc(N2CC3CN(C(=O)c4cccc5ccccc45)CC3C2)n1]

The title compound was prepared in a manner analogous to Example 15 utilizing Intermediate 32 and naphthalene-1-carboxylic acid. MS (ESI) mass calcd. for $C_{22}H_{22}N_4O_2$, 374.44. m/z found, 375.2 [M+H]$^+$. $^1$H NMR (CDCl$_3$): 8.08 (d, J=5.7 Hz, 1H), 7.95-7.81 (m, 3H), 7.59-7.46 (m, 4H), 6.04 (d, J=5.7 Hz, 1H), 4.13 (dd, J=12.8, 7.9 Hz, 1H), 4.00-3.80 (m, 5H), 3.80-3.65 (m, 2H), 3.55-3.40 (m, 2H), 3.22-3.09 (m, 2H), 3.05-2.91 (m, 1H).

Example 59: 2-[(2-Ethoxyphenyl)carbonyl]-5-(4-methoxypyrimidin-2-yl)octahydropyrrolo[3,4-c]pyrrole

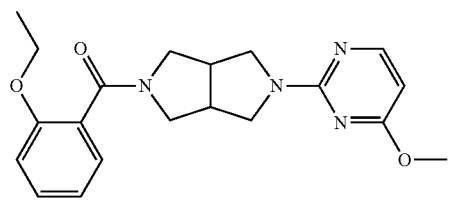 [SMILES: CCOc1ccccc1C(=O)N1CC2CN(c3nccc(OC)n3)CC2C1]

The title compound was prepared according to the procedure used for Example 15 utilizing 2-(4-methoxy-pyrimidin-2-yl)-octahydro-pyrrolo[3,4-c]pyrrole and 2-ethoxybenzoic acid. MS (ESI) mass calcd. for $C_{20}H_{24}N_4O_3$, 368.44. m/z found, 369.3 [M+H]$^+$. $^1$H NMR (CDCl$_3$): 8.07 (d, J=5.7 Hz, 1H), 7.37-7.28 (m, 2H), 6.99 (t, J=7.4 Hz, 1H), 6.91 (d, J=8.3 Hz, 1H), 6.02 (d, J=5.7 Hz, 1H), 4.07 (q, J=7.0 Hz, 2H), 4.01-3.85 (m, 5H), 3.84-3.70 (m, 2H), 3.65-3.45 (m, 3H), 3.34-3.22 (m, 1H), 3.16-2.92 (m, 2H), 1.35 (t, J=6.8 Hz, 3H).

Example 60: 2-[(2-Methoxynaphthalen-1-yl)carbonyl]-5-(4-methoxypyrimidin-2-yl)octahydropyrrolo[3,4-c]pyrrole

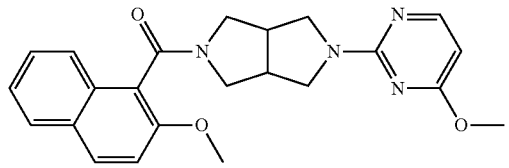 [SMILES: COc1ccnc(N2CC3CN(C(=O)c4c(OC)ccc5ccccc45)CC3C2)n1]

The title compound was prepared in a manner analogous to Example 15 utilizing Intermediate 32 and 2-methoxynaphthalene-1-carboxylic acid. MS (ESI) mass calcd. for $C_{23}H_{24}N_4O_3$, 404.46. m/z found, 405.2 [M+H]$^+$. $^1$H NMR (rotamers observed) 8.12-8.00 (m, 1H), 7.88 (d, J=9.1 Hz, 1H), 7.80 (t, J=7.8 Hz, 1H), 7.70 (d, J=8.4 Hz, 0.6H), 7.63 (d, J=8.4 Hz, 0.4H), 7.49 (t, J=7.6 Hz, 0.6H), 7.45-7.23 (m, 3.4H), 6.06-5.97 (m, 1H), 4.16-4.02 (m, 1H), 3.99-3.79 (m, 7H), 3.80-3.62 (m, 2H), 3.61-3.47 (m, 1H), 3.41-3.28 (m, 1H), 3.25-3.06 (m, 2H), 2.98 (d, J=8.2 Hz, 2H).

Example 61: 2-(Biphenyl-2-ylcarbonyl)-5-[4-(1H-pyrazol-4-yl)pyrimidin-2-yl]octahydro-pyrrolo[3,4-c]pyrrole

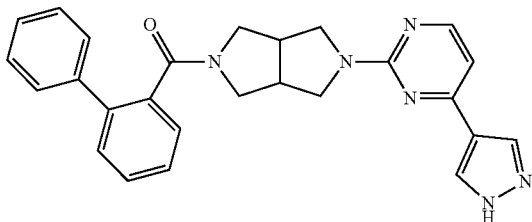 [SMILES: O=C(c1ccccc1-c1ccccc1)N1CC2CN(c3nccc(-c4cn[nH]c4)n3)CC2C1]

The title compound was prepared in a manner analogous to Example 15 utilizing Intermediate 17 and 2-chloro-4-(1H-pyrazol-3-yl)-pyrimidine. MS (ESI) mass calcd. for $C_{26}H_{24}N_6O$, 436.57. m/z found, 437.2 [M+H]$^+$.

Example 62: 2-[4-(1H-Pyrazol-4-yl)pyrimidin-2-yl]-5-[(2-thiophen-2-ylphenyl)carbonyl]octahydro-pyrrolo[3,4-c]pyrrole

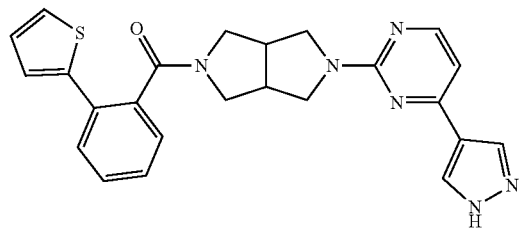 [SMILES: O=C(c1ccccc1-c1cccs1)N1CC2CN(c3nccc(-c4cn[nH]c4)n3)CC2C1]

The title compound was prepared in a manner analogous to Example 15 utilizing Intermediate 37 and 2-chloro-4-(1H-pyrazol-3-yl)-pyrimidine. MS (ESI) mass calcd. for $C_{24}H_{22}N_6OS$, 442.54. m/z found, 443.1 [M+H]$^+$.

Example 63: 2-(3,6-Dimethylpyrazin-2-yl)-5-[(2-thiophen-2-ylphenyl)carbonyl]octahydro-pyrrolo[3,4-c]pyrrole

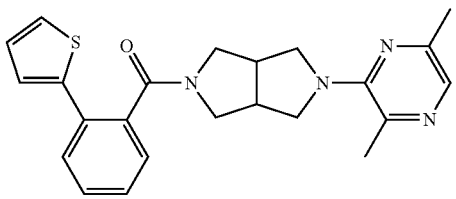 [SMILES: Cc1cnc(C)c(N2CC3CN(C(=O)c4ccccc4-c4cccs4)CC3C2)n1]

The title compound was prepared in a manner analogous to Example 15 utilizing Intermediate 37 and 3-chloro-2,5-dimethyl-pyrazine. MS (ESI) mass calcd. for $C_{23}H_{24}N_4OS$, 404.54. m/z found, 405.2 [M+H]$^+$.

Example 64: 2-(Biphenyl-2-ylcarbonyl)-5-(3,5-dimethylpyrazin-2-yl)octahydropyrrolo[3,4-c]pyrrole

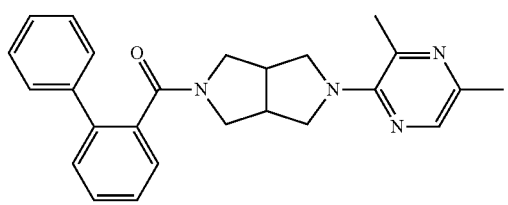 [SMILES: Cc1cnc(N2CC3CN(C(=O)c4ccccc4-c4ccccc4)CC3C2)c(C)n1]

The title compound was prepared in a manner analogous to Example 15 utilizing Intermediate 17 and 2-chloro-3,5-dimethyl-pyrazine. MS (ESI) mass calcd. for $C_{25}H_{26}N_4O$, 398.50. m/z found, 399.2 [M+H]$^+$.

Example 65: 2-Methyl-3-{5-[(2-thiophen-2-ylphenyl)carbonyl]hexahydropyrrolo[3,4-c]pyrrol-2(1H)-yl}quinoxaline

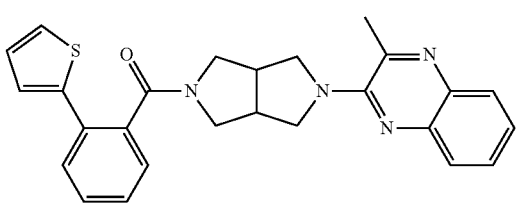 [SMILES: Cc1nc2ccccc2nc1N1CC2CN(C(=O)c3ccccc3-c3cccs3)CC2C1]

The title compound was prepared in a manner analogous to Example 15 utilizing Intermediate 37 and 2-chloro-3-methyl-quinoxaline. MS (ESI) mass calcd. for $C_{26}H_{24}N_4OS$, 440.56. m/z found, 441.1 [M+H]$^+$. $^1$H NMR (CDCl$_3$): rotamers observed 7.77 (d, J=7.9 Hz, 1H), 7.64 (d, J=7.9 Hz, 1H), 7.51-7.40 (m, 2H), 7.40-7.25 (m, 4H), 7.20-7.14 (m, 2H), 6.93 (br s, 1H), 3.86-3.74 (m, 2H), 3.70-3.60 (br m, 1.3H), 3.58-3.40 (br m, 1.6H), 3.26-3.10 (m, 1.7H), 2.95-2.82 (br m, 1.7H), 2.76 (br m, 1.5H), 2.62 (s, 3H).

Example 66: 2-[5-(Biphenyl-2-ylcarbonyl)hexahydropyrrolo[3,4-c]pyrrol-2(1H)-yl]-3-methylquinoxaline

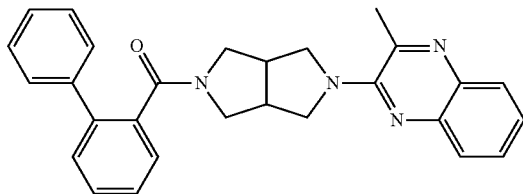 [SMILES: Cc1nc2ccccc2nc1N1CC2CN(C(=O)c3ccccc3-c3ccccc3)CC2C1]

The title compound was prepared in a manner analogous to Example 15 utilizing Intermediate 17 and 2-chloro-3-methyl-quinoxaline. MS (ESI) mass calcd. for $C_{28}H_{26}N_4O$, 434.53. m/z found, 435.1 $[M+H]^+$. $^1H$ NMR ($CDCl_3$): 7.85-7.72 (m, 1H), 7.65 (br s, 1H), 7.53-7.30 (m, 9H), 7.21 (d, J=10.5 Hz, 2H), 3.80-3.54 (br m, 3.5H), 3.44-3.28 (br m, 1.5H), 3.15-2.90 broad (m, 2.5H), 2.85-2.70 (br m, 1.5H), 2.65-2.50 (m, 4H).

Example 67: 2-(4,6-Dimethylpyrimidin-2-yl)-5-{[2-(1H-pyrazol-1-yl)phenyl]carbonyl}octahydro-pyrrolo[3,4-c]pyrrole

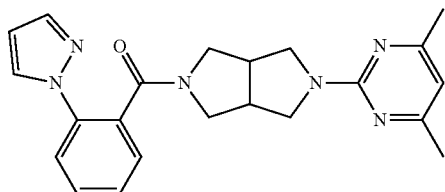

The title compound was prepared in a manner analogous to Example 15 utilizing Intermediate 23 and 2-pyrazol-1-yl-benzoic acid. MS (ESI) mass calcd. for $C_{24}H_{24}N_6O$, 388.47. m/z found, 389.1 $[M+H]^+$. $^1H$ NMR ($CDCl_3$): rotamers observed, 7.73 (broad d, J=1.9 Hz, 1H), 7.52 (broad d, J=7.9 Hz, 1.6H), 7.48-7.39 (m, 1.3H), 7.38-7.29 (m, 2H), 6.31 (br s, 1H), 6.22 (s, 1H), 3.75-3.64 (m, 2H), 3.46 (dd, J=12.7, 4.4 Hz, 1.4H), 3.38 broad (s, 7H), 3.27 (dd, J=11.7, 4.2 Hz, 1.3H), 3.10 (br s, 1H), 2.90-2.65 (m, 3.3H), 2.23 (s, 6H).

Example 68: 2-(4,6-Dimethoxypyrimidin-2-yl)-5-[(2-fluoro-6-pyrimidin-2-ylphenyl)carbonyl] octahydropyrrolo[3,4-c]pyrrole

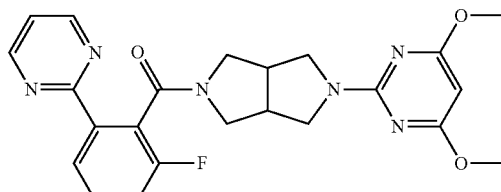

The title compound was prepared in a manner analogous to Example 15 utilizing Intermediate 14 and Intermediate 39. MS (ESI) mass calcd. for $C_{23}H_{23}FN_6O_3$, 450.47. m/z found, 451.1 $[M+H]^+$. $^1H$ NMR ($CDCl_3$): rotamers observed, 8.75-8.65 (m, 2H), 8.12-8.01 (m, 1H), 7.45-7.38 (m, 1H), 7.20-7.12 (m, 1H), 7.05 (t, J=4.9 Hz, 1H), 5.32 (s, 1H), 3.96-3.41 (m, 12.4H), 3.32-2.27 (m, 0.7H), 3.22-3.15 (m, 0.5H), 3.06-2.86 (m, 2.4H).

Example 69: 2-(4,6-Dimethylpyrimidin-2-yl)-5-[(2-pyridin-2-ylphenyl)carbonyl]octahydro-pyrrolo[3,4-c]pyrrole

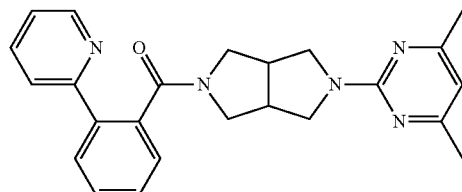

The title compound was prepared in a manner analogous to Example 15 utilizing Intermediate 23 and 2-pyridin-2-yl-benzoic acid. MS (ESI) mass calcd. for $C_{24}H_{25}N_5O$, 399.49. m/z found, 400.1 $[M+H]^+$.

Example 70: 2-(4,6-Dimethoxypyrimidin-2-yl)-5-[(2-pyridin-2-ylphenyl)carbonyl]octahydro-pyrrolo[3,4-c]pyrrole

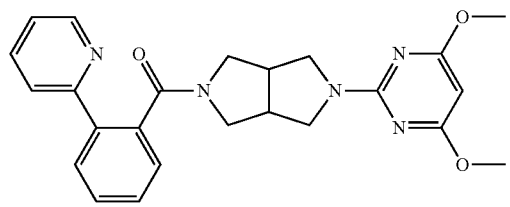 [SMILES: COc1cc(OC)nc(N2CC3CN(C(=O)c4ccccc4-c4ccccn4)CC3C2)n1]

The title compound was prepared in a manner analogous to Example 15 utilizing Intermediate 39 and 2-pyridin-2-yl-benzoic acid. MS (ESI) mass calcd. for $C_{24}H_{25}N_5O_3$, 431.49. m/z found, 432.2 $[M+H]^+$. $^1H$ NMR ($CDCl_3$): 8.49 (d, J=3.9 Hz, 1H), 7.69-7.49 (m, 3H), 7.48-7.29 (m, 3H), 7.15-7.04 (m, 1H), 5.32 (s, 1H), 3.92-3.61 (m, 8H), 3.60-3.40 (m, 2H), 3.35-3.15 (m, 3H), 2.98-2.65 (m, 3H).

Example 71: 2-(4,6-Dimethoxypyrimidin-2-yl)-5-[(5-fluoro-2-pyrimidin-2-ylphenyl)carbonyl] octahydropyrrolo[3,4-c]pyrrole

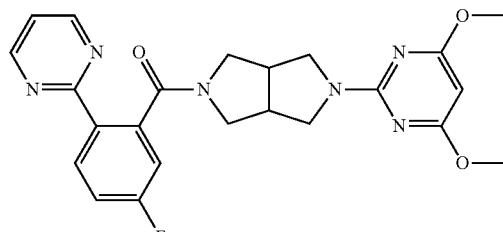

The title compound was prepared in a manner analogous to Example 15 utilizing Intermediate 39 and Intermediate 13. MS (ESI) mass calcd. for $C_{23}H_{23}FN_6O_3$, 450.18. m/z found, 451.1 [M+H]$^+$. $^1$H NMR (CDCl$_3$): 8.68 (d, J=4.9 Hz, 2H), 8.25 (dd, J=8.7, 5.5 Hz, 1H), 7.28-7.15 (m, 2H), 7.12 (dd, J=8.6, 2.5 Hz, 1H), 5.31 (s, 1H), 3.84-3.65 (m, 7H), 3.63-3.33 (m, 5H), 3.13-2.86 (m, 4H).

Example 72: 2-(4,6-Dimethoxypyrimidin-2-yl)-5-{[5-fluoro-2-(2H-1,2,3-triazol-2-yl)phenyl]carbonyl}octahydropyrrolo[3,4-c]pyrrole

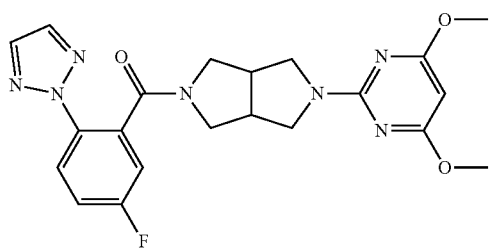

The title compound was prepared in a manner analogous to Example 15 utilizing Intermediate 39 and Intermediate 1. MS (ESI) mass calcd. for $C_{22}H_{22}FN_7O_3$, 439.18. m/z found, 440.1 [M+H]$^+$. $^1$H NMR (CDCl$_3$): 7.89 (dd, J=8.9, 4.7 Hz, 1H), 7.66 (s, 1H), 7.25-7.01 (m, 2H), 5.32 (s, 1H), 3.77 (m, 8H), 3.67-3.54 (m, 2H), 3.52-3.26 (m, 3H), 3.01-2.78 (m, 3H).

Example 73: 2-(4,6-Dimethylpyrimidin-2-yl)-5-[(2-fluoro-6-pyrimidin-2-ylphenyl)carbonyl]octahydropyrrolo[3,4-c]pyrrole

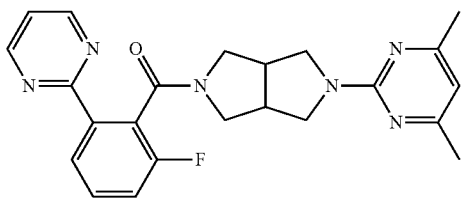 [SMILES: Cc1cc(C)nc(N2CC3CN(C(=O)c4c(F)cccc4-c4ncccn4)CC3C2)n1]

The title compound was prepared in a manner analogous to Example 15 utilizing Intermediate 23 and Intermediate 14. MS (ESI) mass calcd. for $C_{23}H_{23}FN_6O$, 418.47. m/z found, 419.1 [M+H]$^+$. $^1$H NMR (CDCl$_3$): 8.75-8.65 (m, 2H), 8.10-7.96 (m, 1.2H), 7.40 (dd, J=13.8, 8.0 Hz, 1.2H), 7.24-7.08 (m, 2.7H), 7.08-7.00 (m, 0.8H), 6.22 (s, 1H), 4.00-3.39 (m, 7H), 3.34-3.14 (m, 1H), 3.01 (d, J=6.8 Hz, 2H), 2.23 (s, 6H).

Example 74: 2-(4,6-Dimethylpyrimidin-2-yl)-5-[(5-fluoro-2-pyrimidin-2-ylphenyl)carbonyl]octahydropyrrolo[3,4-c]pyrrole

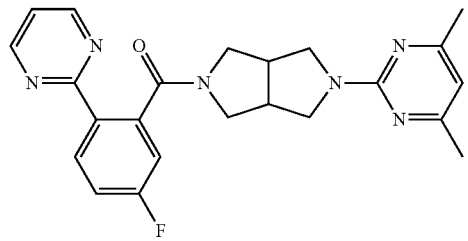 [SMILES: Cc1cc(C)nc(N2CC3CN(C(=O)c4cc(F)ccc4-c4ncccn4)CC3C2)n1]

The title compound was prepared in a manner analogous to Example 15 utilizing Intermediate 23 and Intermediate 13. MS (ESI) mass calcd. for $C_{23}H_{23}FN_6O$, 418.47. m/z found, 419.1 [M+H]$^+$. $^1$H NMR (CDCl$_3$): 8.81 (d, J=4.9 Hz, 2H), 8.36 (dd, J=8.8, 5.6 Hz, 1H), 7.44-7.14 (m, 3H), 6.44 (s, 1H), 6.44 (s, 1H), 3.98-3.75 (m, 2H), 3.76-3.48 (m, 5H), 3.24-2.97 (m, 3H), 2.32 (s, 6H).

Example 75: 2-(4,6-Dimethylpyrimidin-2-yl)-5-{[5-fluoro-2-(2H-1,2,3-triazol-2-yl)phenyl]carbonyl}octahydropyrrolo[3,4-c]pyrrole

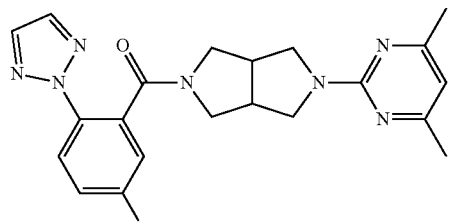

The title compound was prepared in a manner analogous to Example 15 utilizing Intermediate 23 and Intermediate 1. MS (ESI): mass calculated for $C_{21}H_{22}FN_7O$, 407.45, m/z found 408.2 [M+1]$^+$. $^1$H NMR (CDCl$_3$) 7.97-7.92 (m, 1H), 7.73 (s, 2H), 7.23-7.06 (m, 2H), 6.30 (s, 1H), 3.90-3.80 (m, Hz, 2H), 3.72-3.55 (m, 5.9 Hz, 4H), 3.53-3.46 (m, Hz, 1H), 3.39 (br s, 1H), 3.08-2.87 (m, 4H), 2.30 (s, 6H).

Example 76: 2-(4,6-Dimethylpyrimidin-2-yl)-5-[(2-ethylphenyl)carbonyl]octahydropyrrolo[3,4-c]pyrrole

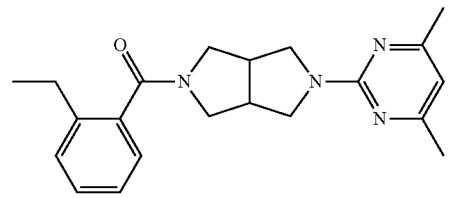 [SMILES: CCc1ccccc1C(=O)N1CC2CN(c3nc(C)cc(C)n3)CC2C1]

The title compound was prepared in a manner analogous to Example 15 utilizing Intermediate 23 and 2-ethylbenzoic acid. MS (ESI) mass calcd. for $C_{21}H_{26}N_4O$, 350.47. m/z found, 351.3 [M+H]+. 1H NMR (CDCl3): 7.34-7.14 (m, 4H), 6.30 (s, 1H), 3.93 (m, 2H), 3.77 (dd, J=11.6, 7.3 Hz, 1H), 3.64 (m, 2H), 3.51-3.41 (m, 2H), 3.16-3.02 (m, 2H), 3.01-2.90 (m, 1H), 2.69-2.57 (m, 2H), 2.29 (s, 6H), 1.20 (t, J=7.6 Hz, 3H).

Example 77: 2-(4,6-Dimethylpyrimidin-2-yl)-5-[(2-ethoxynaphthalen-1-yl)carbonyl]octahydro-pyrrolo[3,4-c]pyrrole

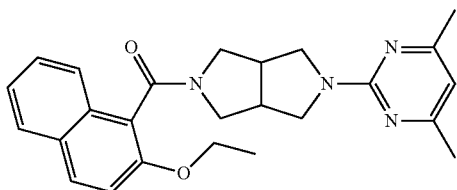

The title compound was prepared in a manner analogous to Example 15 utilizing Intermediate 23 and 2-ethoxy-naphthalene-1-carboxylic acid. MS (ESI) mass calcd. for $C_{25}H_{26}N_4O_2$, 416.53. m/z found, 417.2 [M+H]+.

Example 78: 2-(4,6-Dimethoxypyrimidin-2-yl)-5-{[2-(1H-pyrazol-1-yl)phenyl]carbonyl}octahydro-pyrrolo[3,4-c]pyrrole

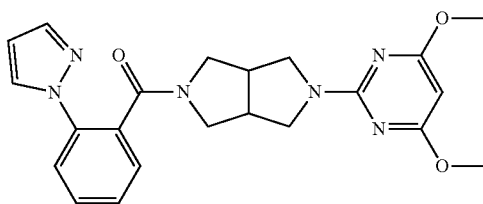 [SMILES: COc1cc(OC)nc(N2CC3CN(C(=O)c4ccccc4-n4cccn4)CC3C2)n1]

The title compound was prepared in a manner analogous to Example 15 utilizing Intermediate 39 and 2-pyrazol-1-yl-benzoic acid. MS (ESI) mass calcd. for $C_{22}H_{24}N_6O_3$, 420.46. m/z found, 421.1 [M+H]+. 1H NMR (CDCl3): 7.74 (d, J=2.0 Hz, 1H), 7.59-7.29 (m, 5H), 6.31 (br s, 1H), 5.32 (s, 1H), 3.90-3.64 (m, 7.8H), 3.61-3.41 (m, 2.2H), 3.40-3.05 (m, 3H), 2.95-2.65 (m, 3H).

Example 79: 2-(4,6-Dimethylpyrimidin-2-yl)-5-[(5-phenyl-1,3-oxazol-4-yl)carbonyl]octahydro-pyrrolo[3,4-c]pyrrole

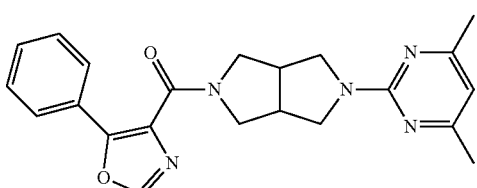

The title compound was prepared in a manner analogous to Example 15 utilizing Intermediate 23 and 5-phenyl-oxazole-4-carboxylic acid. MS (ESI) mass calcd. for $C_{22}H_{23}N_5O_2$, 389.46. m/z found, 390.2 [M+H]+. 1H NMR (CDCl3): 7.91 (m, 2H), 7.86 (s, 1H), 7.46-7.33 (m, 3H), 6.28 (s, 1H), 4.03-3.83 (m, 3H), 3.74 (m, 2H), 3.64-3.47 (m, 3H), 3.08-2.98 (m, 2H), 2.29 (m, 6H).

Example 80: 2-(4,6-Dimethylpyrimidin-2-yl)-5-[(5-phenylisoxazol-4-yl)carbonyl]octahydro-pyrrolo[3,4-c]pyrrole

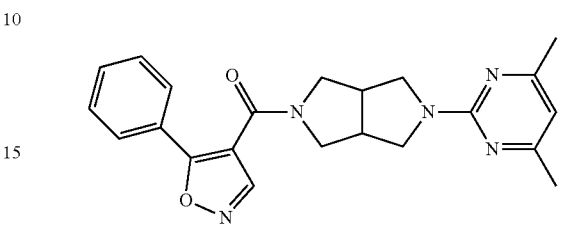

The title compound was prepared in a manner analogous to Example 15 utilizing Intermediate 23 and 5-phenyl-isoxazole-4-carboxylic acid. MS (ESI) mass calcd. for $C_{22}H_{23}N_5O_2$, 389.46. m/z found, 390.2 [M+H]+. 1H NMR (CDCl3): 8.37 (s, 1H), 7.84-7.75 (m, 2H), 7.49-7.36 (m, 3H), 6.30 (s, 1H), 4.00-3.80 (m, 2H), 3.73-3.62 (m, 2H), 3.59-3.42 (m, 2H), 3.36 (dd, J=11.7, 4.5 Hz, 1H), 3.16-2.85 (m, 3H), 2.37-2.22 (s, 6H).

Example 81: [5-(2-Isopropyl-6-methyl-pyrimidin-4-yl)-hexahydro-pyrrolo[3,4-c]pyrrol-2-yl]-(2-[1,2,3]triazol-2-yl-phenyl)-methanone

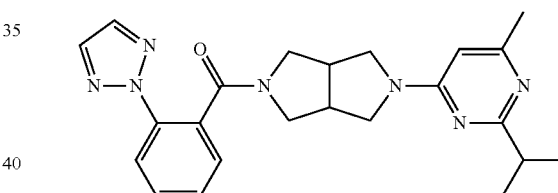

The title compound was prepared in a manner analogous to Example 15 utilizing Intermediate 20 and 4-chloro-2-isopropyl-6-methyl-pyrimidine. MS (ESI): mass calculated for $C_{23}H_{27}N_7O$, 417.51, m/z found 418.2 [M+H]+. 1H NMR (400 MHz, CDCl3): 7.99 (d, J=8.0 Hz, 1H), 7.73 (s, 2H), 7.59-7.38 (m, 3H), 5.92 (s, 1H), 3.97-2.85 (m, 10H), 2.35 (s, 3H), 1.33-1.21 (m, 6H).

Example 82: 2-[(2-Bromophenyl)carbonyl]-5-(4,6-dimethylpyrimidin-2-yl)octahydropyrrolo[3,4-c]pyrrole

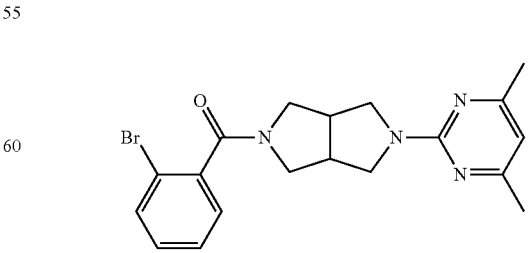

The title compound was prepared in a manner analogous to Example 15 utilizing Intermediate 23 and 2-bromobenzoic acid. MS (ESI) mass calcd. for $C_{19}H_{21}BrN_4O$, 401.31. m/z found, 401.1, 403.1 [M+H]$^+$.

Example 83: 2-(4,6-Dimethylpyrimidin-2-yl)-5-{[2-(2H-1,2,3-triazol-2-yl)phenyl]carbonyl}octahydropyrrolo[3,4-c]pyrrole

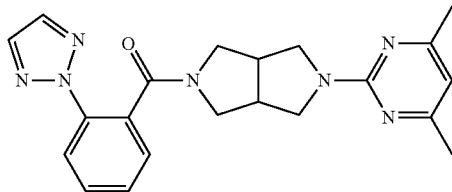 [SMILES: Cc1cc(C)nc(N2CC3CN(C(=O)c4ccccc4-n4nccn4)CC3C2)n1]

The title compound was prepared in a manner analogous to Example 15 utilizing Intermediate 23 and Intermediate 2. MS (ESI) mass calcd. for $C_{21}H_{23}N_7O$, 389.46. m/z found, 374.2 [M+H]$^+$. $^1$H NMR (CDCl$_3$): 7.98 (d, J=8.1 Hz, 1H), 7.74 (br s, 2H), 7.55-7.48 (m, 1H), 7.42 (d, J=4.1 Hz, 2H), 6.29 (s, 1H), 3.93-3.81 (m, 2H), 3.64 (m, 3H), 3.48 (dd, J=11.6, 4.2 Hz, 1H), 3.36 (br s, 1H), 3.08-2.86 (m, 3H), 2.30 (s, 6H).

Example 84: 2-(4,6-Dimethoxypyrimidin-2-yl)-5-{[2-(2H-1,2,3-triazol-2-yl)phenyl]carbonyl} octahydropyrrolo[3,4-c]pyrrole

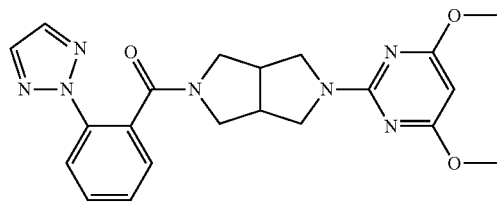 [SMILES: COc1cc(OC)nc(N2CC3CN(C(=O)c4ccccc4-n4nccn4)CC3C2)n1]

The title compound was prepared in a manner analogous to Example 15 utilizing Intermediate 20 and 2-chloro-4,6-dimethoxypyrimidine. MS (ESI) mass calcd. for $C_{21}H_{23}N_7O_3$, 421.46. m/z found, 422.2 [M+H]$^+$. $^1$H NMR (CDCl$_3$): 8.05-7.95 (m, 2H), 7.75 (br s, 1H), 7.57-7.48 (m, 1H), 7.46-7.41 (m, 2H), 5.39 (s, 1H), 3.93-3.79 (m, 5H), 3.76-3.62 (m, 2H), 3.56 (dd, J=11.8, 5.4 Hz, 1H), 3.49-3.33 (m, 2H), 2.96 (s, 3H), 2.89 (s, 3H).

Example 85: 2-[5-{[2-(4H-1,2,4-Triazol-3-yl)phenyl]carbonyl}hexahydropyrrolo[3,4-c]pyrrol-2(1H)-yl]quinoxaline

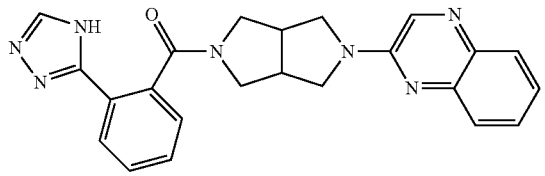 [SMILES: O=C(c1ccccc1-c1nnc[nH]1)N1CC2CN(c3cnc4ccccc4n3)CC2C1]

The title compound was prepared in a manner analogous to Example 15 utilizing Intermediate 35 and 2-(4H-[1,2,4] triazol-3-yl)-benzoic acid. MS (ESI) mass calcd. for $C_{23}H_{21}N_7O$, 411.47. m/z found, 412.2 [M+H]$^+$. $^1$H NMR (CDCl$_3$): 8.28 (s, 1H), 8.11 (d, J=8.1 Hz, 1H), 8.01 (br s, 1H), 7.89 (dd, J=8.2, 1.2 Hz, 1H), 7.69 (dd, J=8.4, 1.0 Hz, 1H), 7.59 (ddd, J=8.4, 7.0, 1.4 Hz, 1H), 7.55-7.43 (m, 2H), 7.42-7.33 (m, 2H), 3.89-4.00 (m, 2H), 3.82-3.72 (m, 2H), 3.71-3.64 (m, 1H), 3.55-3.42 (m, 2H), 3.20-2.98 (m, 3H).

Example 86: 2-[5-{[2-(4H-1,2,4-Triazol-3-yl)phenyl]carbonyl}hexahydropyrrolo[3,4-c]pyrrol-2(1H)-yl]-1,3-benzoxazole

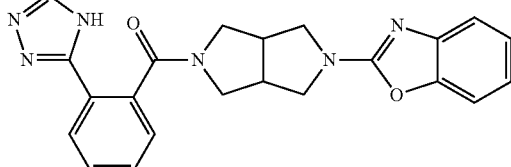

The title compound was prepared in a manner analogous to Example 15 utilizing Intermediate 28 and 2-(4H-[1,2,4]triazol-3-yl)-benzoic acid. MS (ESI) mass calcd. for $C_{22}H_{20}N_6O_2$, 400.43. m/z found, 401.2 [M+H]$^+$. $^1$H NMR (CDCl$_3$): 8.15-8.02 (m 2H), 7.56-7.40 (m, 2H), 7.347-7.30 (m, 2H), 7.29-7.23 (m, 1H), 7.17 (td, J=7.7, 1.1 Hz, 1H), 7.05-6.98 (m, 1H), 3.98-3.42 (m, 7H), 3.26-2.93 (m, 3H).

Example 87: 2-(4-Methylpyrimidin-2-yl)-5-{[2-(4H-1,2,4-triazol-3-yl)phenyl]carbonyl}octahydro-pyrrolo[3,4-c]pyrrole

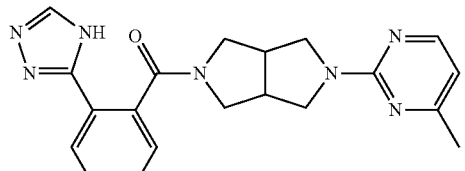

The title compound was prepared in a manner analogous to Example 15 utilizing Intermediate 27 and 2-(4H-[1,2,4] triazol-3-yl)-benzoic acid. MS (ESI) mass calcd. for $C_{20}H_{21}N_7O$, 375.55. m/z found, 376.2 [M+H]$^+$. $^1$H NMR (CDCl$_3$): 8.18-8.04 (m, 3H), 7.55-7.42 (m, 2H), 7.39-7.33 (m, 1H), 6.39 (d, J=5.0 Hz, 1H), 3.96-3.79 (m, 2H), 3.77-3.63 (m, 2H), 3.62-3.55 (m, 1H), 3.46-3.37 (m, 2H), 3.15-3.06 (m, 1H), 3.05-2.98 (m, 1H), 2.95-2.90 (m, 1H), 2.33 (s, 3H).

Example 88: 2-(4,6-Dimethylpyrimidin-2-yl)-5-[(2-ethoxyphenyl)carbonyl]octahydropyrrolo[3,4-c]pyrrole

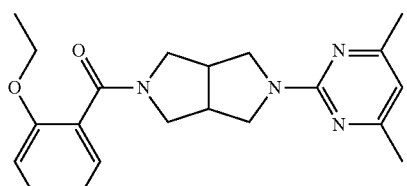

The title compound was prepared in a manner analogous to Example 15 utilizing Intermediate 23 and 2-ethoxybenzoic acid. MS (ESI) mass calcd. for $C_{21}H_{26}N_4O_2$, 366.46. m/z found, 367.2 $[M+H]^+$. $^1$H NMR (CDCl$_3$): 7.37-7.21 (m, 2H), 7.03-6.91 (m, 1H), 6.88 (d, J=8.3 Hz, 1H), 6.26 (d, J=20.0 Hz, 1H), 4.04 (q, J=7.0 Hz, 2H), 3.95-3.85 (m, 2H), 3.76 (dd, J=11.5, 7.3 Hz, 1H), 3.69-3.59 (m, 2H), 3.57-3.45 (m, 2H), 3.29-3.20 (m, 1H), 3.12-2.89 (m, 2H), 2.29 (s, 6H), 1.33 (t, J=7.0 Hz, 3H).

Example 89: 2-(4,6-Dimethylpyrimidin-2-yl)-5-{[4-fluoro-2-(trifluoromethyl)phenyl]carbonyl} octahydropyrrolo[3,4-c]pyrrole

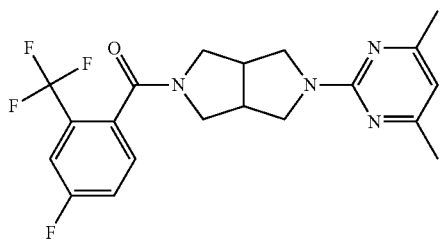 [SMILES: Cc1cc(C)nc(N2CC3CN(C(=O)c4ccc(F)cc4C(F)(F)F)CC3C2)n1]

The title compound was prepared in a manner analogous to Example 15 utilizing Intermediate 23 and 2-trifluoromethyl-4-fluorobenzoic acid. MS (ESI) mass calcd. for $C_{20}H_{20}F_4N_4O$, 408.4. m/z found, 409.2 $[M+H]^+$. $^1$H NMR (CDCl$_3$): 7.46-7.27 (m, 3H), 6.37-6.25 (m, 1H), 4.01-3.87 (m, 2H), 3.82-3.76 (m 1H), 3.67-3.57 (m, 2H), 3.53-3.38 (m, 2H), 3.14-3.04 (m, 2H), 3.04-2.96 m, 1H), 2.31 (s 6H).

Example 90: 2-(4,6-Dimethylpyrimidin-2-yl)-5-[(4-fluoronaphthalen-1-yl)carbonyl]octahydro-pyrrolo[3,4-c]pyrrole

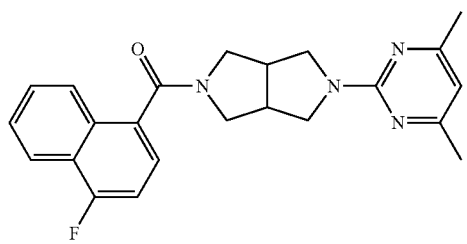 [SMILES: Cc1cc(C)nc(N2CC3CN(C(=O)c4ccc(F)c5ccccc45)CC3C2)n1]

The title compound was prepared in a manner analogous to Example 15 utilizing Intermediate 23 and 4-fluoro-naphthalene-1-carboxylic acid. MS (ESI) mass calcd. for $C_{23}H_{23}FN_4O$, 390.45. m/z found, 391.2 $[M+H]^+$. $^1$H NMR (CDCl$_3$): 8.16-8.10 (m 1H), 7.92-7.82 (m, 1H), 7.63-7.53 (m, 2H), 7.403-7.36 (m, 1H), 7.14 (dd, J=10.2, 7.8 Hz, 1H), 6.31 (s, 1H), 4.14-4.06 (m, 1H), 3.95-3.89 (m, 1H), 3.84-3.63 (m, 3H), 3.50-3.37 (m, 2H), 3.17-3.08 (m, 2H), 2.98-2.90 (m, 1H), 2.30 (s, 6H).

Example 91: 2-(4,6-Dimethylpyrimidin-2-yl)-5-{[2-(1-methylethyl)phenyl]carbonyl}octahydro-pyrrolo[3,4-c]pyrrole

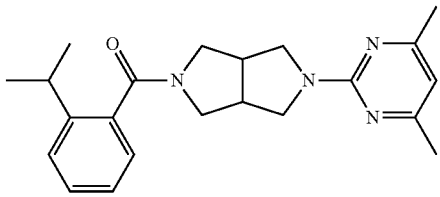 [SMILES: Cc1cc(C)nc(N2CC3CN(C(=O)c4ccccc4C(C)C)CC3C2)n1]

The title compound was prepared in a manner analogous to Example 15 utilizing Intermediate 23 and 2-isopropylbenzoic acid. MS (ESI) mass calcd. for $C_{22}H_{28}N_4O$, 364.48. m/z found, 365.3 $[M+H]^+$. $^1$H NMR (CDCl$_3$): 7.37-7.30 (m, 2H), 7.23-7.10 (m, 2H), 6.30 (s, 1H), 4.00-3.86 (m, 2H), 3.79-3.73 (m, 1H), 3.71-3.58 (m, 2H), 3.51-3.40 (m, 2H), 3.19-2.89 (m, 4H), 2.30 (s, 6H), 1.29-1.17 (m, 6H).

Example 92: 2-(4,6-Dimethylpyrimidin-2-yl)-5-[(3-methoxy-2-methylphenyl)carbonyl]octahydro-pyrrolo[3,4-c]pyrrole

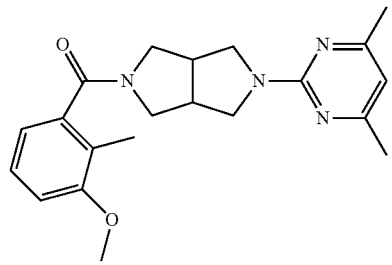 [SMILES: COc1cccc(C(=O)N2CC3CN(c4nc(C)cc(C)n4)CC3C2)c1C]

The title compound was prepared in a manner analogous to Example 15 utilizing Intermediate 23 and 3-methoxy-2-methyl-benzoic acid. MS (ESI) mass calcd. for $C_{21}H_{26}N_4O_2$, 366.47. m/z found, 367.2 $[M+H]^+$. $^1$H NMR (CDCl$_3$): 7.19 (dd, J=14.3, 6.5 Hz, 1H), 6.81 (dd, J=14.3, 7.8 Hz, 2H), 6.30 (s, 1H), 4.01-3.85 (m, 2H), 3.83 (s, 3H), 3.77 (dd, J=11.6, 7.3 Hz, 1H), 3.69-3.58 (m, 2H), 3.50-3.39 (m, 2H), 3.15-3.00 (m, 2H), 3.00-2.90 (m, 1H), 2.30 (s, 6H), 2.14 (s, 3H).

Example 93: 2-(4,6-Dimethylpyrimidin-2-yl)-5-(naphthalen-1-ylcarbonyl)octahydropyrrolo[3,4-c]pyrrole

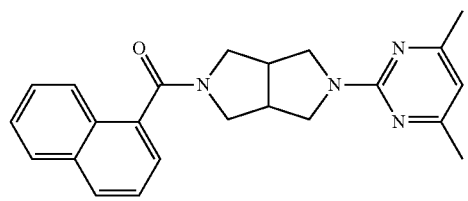 [SMILES: Cc1cc(C)nc(N2CC3CN(C(=O)c4cccc5ccccc45)CC3C2)n1]

The title compound was prepared in a manner analogous to Example 15 utilizing Intermediate 23 and naphthalene- 1-carboxylic acid. MS (ESI) mass calcd. for C₂₃H₂₄N₄O, 372.46. m/z found, 373.2 [M+H]⁺. ¹H NMR (CDCl₃): 7.91-7.79 (m, 3H), 7.54-7.40 (m, 4H), 6.30 (s, 1H), 4.11 (dd, J=12.8, 7.9 Hz, 1H), 3.92 (dd, J=11.6, 7.6 Hz, 1H), 3.80 (dd, J=12.8, 4.9 Hz, 1H), 3.75-3.64 (m, 2H), 3.49-3.36 (m, 2H), 3.17-3.06 (m, 2H), 2.97-2.87 (m, 1H), 2.31 (s, 6H).

Example 94: 2-[5-{[2-(4H-1,2,4-Triazol-3-yl)phenyl]carbonyl}hexahydropyrrolo[3,4-c]pyrrol-2(1H)-yl]-3-(trifluoromethyl)quinoxaline

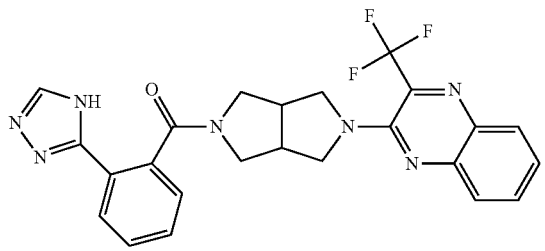 [SMILES: O=C(c1ccccc1-c1nnc[nH]1)N1CC2CN(c3nc4ccccc4nc3C(F)(F)F)CC2C1]

The title compound was prepared in a manner analogous to Example 15 utilizing Intermediate 30 and 2-(4H-[1,2,4]triazol-3-yl)-benzoic acid. MS (ESI) mass calcd. for C₂₄H₂₀F₄N₇O, 479.47. m/z found, 480.2 [M+H]⁺. ¹H NMR (CDCl₃): 8.12-7.93 (m, 3H), 7.77 (dd, J=8.5, 0.9 Hz, 1H), 7.69 (ddd, J=8.4, 6.8, 1.4 Hz, 1H), 7.52-7.41 (m, 3H), 7.38-7.34 (m, 1H), 4.01-3.79 (m, 3H), 3.78-3.66 (m, 2H), 3.49 (dd, J=23.0, 15.0 Hz, 2H), 3.16-2.88 (m, 3H).

Example 95: 2-Methyl-3-[5-{[2-(4H-1,2,4-triazol-3-yl)phenyl]carbonyl}hexahydropyrrolo[3,4-c]pyrrol-2(1H)-yl]quinoxaline

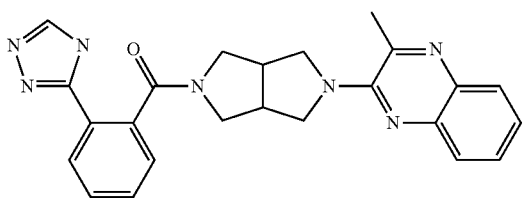 [SMILES: Cc1nc2ccccc2nc1N1CC2CN(C(=O)c3ccccc3-c3nnc[nH]3)CC2C1]

The title compound was prepared in a manner analogous to Example 15 utilizing Intermediate 29 and 2-(4H-[1,2,4]triazol-3-yl)-benzoic acid. MS (ESI) mass calcd. for C₂₄H₂₃N₇O, 425.49. m/z found, 426.3 [M+H]⁺. ¹H NMR (CDCl₃): 8.13 (d, J=7.3 Hz, 1H), 8.01 (s, 1H), 7.83 (dd, J=8.2, 1.1 Hz, 1H), 7.72 (dd, J=8.3, 1.0 Hz, 1H), 7.59-7.35 (m, 5H), 4.00-3.65 (m, 5H), 3.47 (s, 2H), 3.22-2.89 (m, 3H), 2.70 (s, 3H).

Example 96: 2-[6-Methyl-2-(trifluoromethyl)pyrimidin-4-yl]-5-{[2-(4H-1,2,4-triazol-3-yl)phenyl]carbonyl}octahydropyrrolo[3,4-c]pyrrole

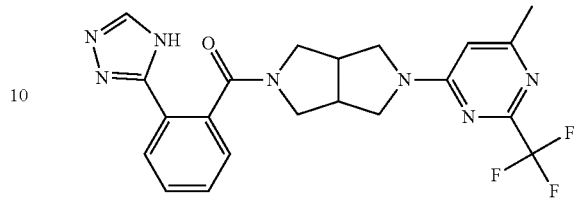

The title compound was prepared in a manner analogous to Example 15 utilizing Intermediate 31 and 2-(4H-[1,2,4]triazol-3-yl)-benzoic acid. MS (ESI) mass calcd. for C₂₁H₂₀F₃N₇O, 443.43. m/z found, 444.2 [M+H]⁺. ¹H NMR (CDCl₃): 8.11-7.99 (m, 2H), 7.55-7.42 (m, 2H), 7.37-7.29 (m, 1H), 6.17 (br s, 1H), 3.92-3.39 (m, 7H), 3.15-2.90 (m, 3H), 2.42 (s, 3H).

Example 97: 2-[6-Methyl-2-(trifluoromethyl)pyrimidin-4-yl]-5-{[2-(2H-1,2,3-triazol-2-yl)phenyl]carbonyl}octahydropyrrolo[3,4-c]pyrrole

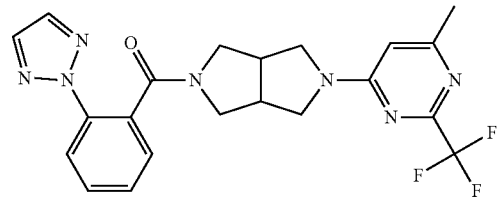 [SMILES: Cc1cc(N2CC3CN(C(=O)c4ccccc4-n4nccn4)CC3C2)nc(C(F)(F)F)n1]

The title compound was prepared in a manner analogous to Example 15 utilizing Intermediate 31 and Intermediate 2. MS (ESI) mass calcd. for C₂₁H₂₀F₃N₇O, 443.43. m/z found, 444.2 [M+H]⁺. ¹H NMR (CDCl₃): 7.99 (d, J=8.0 Hz, 1H), 7.74 (s, 2H), 7.58-7.49 (m, 1H), 7.48-7.38 (m, 2H), 6.22 (br s, 1H), 4.05-3.33 (m, 7H), 3.24-2.91 (m, 3H), 2.45 (s, 3H).

Example 98: 2-{[2-Fluoro-6-(2H-1,2,3-triazol-2-yl)phenyl]carbonyl}-5-[6-methyl-2-(trifluoromethyl)pyrimidin-4-yl]octahydropyrrolo[3,4-c]pyrrole

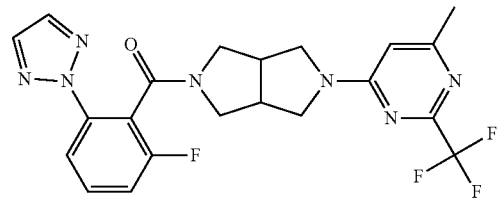 [SMILES: Cc1cc(N2CC3CN(C(=O)c4c(F)cccc4-n4nccn4)CC3C2)nc(C(F)(F)F)n1]

The title compound was prepared in a manner analogous to Example 15 utilizing Intermediate 31 and Intermediate 12. MS (ESI) mass calcd. for C₂₁H₁₉F₄N₇O, 461.42. m/z found, 462.1 [M+H]⁺. ¹H NMR (CDCl₃): 7.91-7.78 (m, 2H), 7.72 (s, 1H), 7.54-7.43 (m, 1H), 7.20-7.10 (m, 1H), 6.30-6.20 (br m, 1H), 4.07-3.52 (m, 6H), 3.42-3.02 (m, 4H), 2.47 (d, J=19.9 Hz, 3H).

Example 99: 2-{[4-Fluoro-2-(2H-1,2,3-triazol-2-yl)phenyl]carbonyl}-5-[6-methyl-2-(trifluoromethyl)pyrimidin-4-yl]octahydropyrrolo[3,4-c]pyrrole

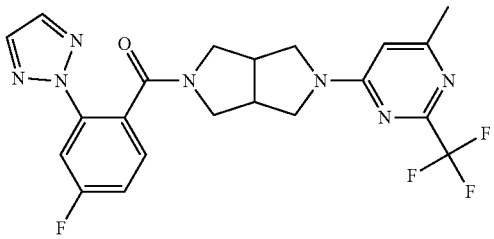 [SMILES: Cc1cc(N2CC3CN(C(=O)c4ccc(F)cc4-n4nccn4)CC3C2)nc(C(F)(F)F)n1]

The title compound was prepared in a manner analogous to Example 15 utilizing Intermediate 31 and Intermediate 4. MS (ESI) mass calcd. for $C_{21}H_{19}F_4N_7O$, 461.42. m/z found, 462.2 [M+H]$^+$. $^1$H NMR (CDCl$_3$): 7.76 (br s, 3H), 7.47-7.36 (m, 1H), 7.19-7.09 (m, 1H), 6.22 (br s, 1H), 4.05-3.32 (m, 7H), 2.98 (dd, J=40.7, 34.8 Hz, 3H), 2.44 (s, 3H).

Example 100: 2-(6-Methylpyrazin-2-yl)-5-{[5-methyl-2-(2H-1,2,3-triazol-2-yl)phenyl]carbonyl}octahydropyrrolo[3,4-c]pyrrole

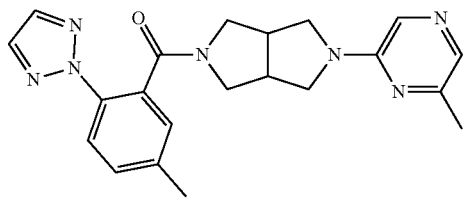 [SMILES: Cc1ccc(-n2nccn2)c(C(=O)N2CC3CN(c4cncc(C)n4)CC3C2)c1]

The title compound was prepared in a manner analogous to Example 15 utilizing Intermediate 8 and 2-chloro-6-methyl-pyrazine. MS (ESI): mass calculated for $C_{21}H_{23}N_7O$, 389.46. m/z found 390.2 [M+H]$^+$. $^1$H NMR (400 MHz, CDCl$_3$): 7.87-7.81 (m, 1H), 7.75-7.53 (m, 4H), 7.35-7.29 (m, 1H), 7.24-7.18 (m, 1H), 3.94-3.83 (m, 1H), 3.80-3.66 (m, 2H), 3.64-3.54 (m, 1H), 3.50-3.30 (m, 3H), 3.12-2.90 (m, 3H), 2.41 (s, 2H), 2.38 (s, 3H).

Example 101: 2-(3,6-Dimethylpyrazin-2-yl)-5-{[2-fluoro-6-(2H-1,2,3-triazol-2-yl)phenyl]carbonyl}octahydropyrrolo[3,4-c]pyrrole

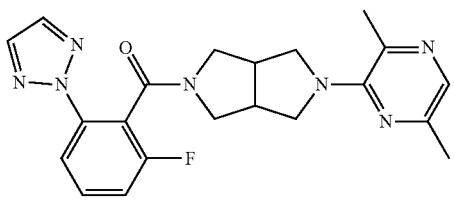 [SMILES: Cc1cnc(C)c(N2CC3CN(C(=O)c4c(F)cccc4-n4nccn4)CC3C2)n1]

The title compound was prepared in a manner analogous to Example 15 utilizing Intermediate 34 and Intermediate 12. MS (ESI): mass calculated for $C_{21}H_{22}FN_7O$, 407.45. m/z found 408.2 [M+H]$^+$. $^1$H NMR (400 MHz, CDCl$_3$): 7.90-7.80 (m, 2H), 7.78-7.71 (m, 2H), 7.54-7.44 (m, 1H), 7.20-7.12 (m, 1H), 3.97-3.90 (m, 1H), 3.86-3.40 (m, 6H), 3.32-3.22 (m, 1H), 3.13-2.91 (m, 2H), 2.55-2.49 (m, 3H), 2.39-2.33 (m, 3H).

Example 102: 2-(4,6-Dimethylpyrimidin-2-yl)-5-[(5-methyl-2-pyrimidin-2-ylphenyl)carbonyl] octahydropyrrolo[3,4-c]pyrrole

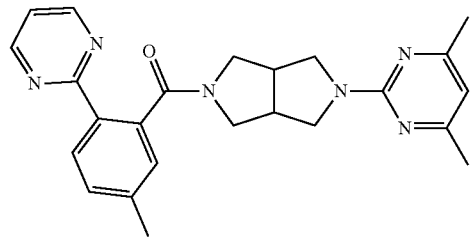 [SMILES: Cc1ccc(-c2ncccn2)c(C(=O)N2CC3CN(c4nc(C)cc(C)n4)CC3C2)c1]

The title compound was prepared in a manner analogous to Example 15 utilizing Intermediate 23 and 5-methyl-2-pyrimidin-2-yl-benzoic acid. MS (ESI): mass calculated for $C_{24}H_{26}N_6O$, 414.51. m/z found 415.2 [M+H]$^+$. $^1$H NMR (400 MHz, CDCl$_3$): 8.74 (d, J=4.9, 2H), 8.20 (d, J=8.1, 1H), 7.34-7.28 (m, 1H), 7.17-7.15 (m, 1H), 7.10-7.03 (m, 1H), 6.29 (s, 1H), 3.95-3.79 (m, 2H), 3.76-3.61 (m, 3H), 3.59-3.40 (m, 2H), 3.18-3.10 (m, 1H), 3.09-2.87 (m, 2H), 2.41 (s, 3H), 2.30 (s, 6H).

Example 103: 2-(3,6-Dimethylpyrazin-2-yl)-5-[(5-methyl-2-pyrimidin-2-ylphenyl)carbonyl] octahydropyrrolo[3,4-c]pyrrole

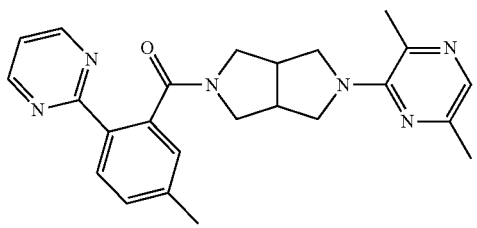 [SMILES: Cc1ccc(-c2ncccn2)c(C(=O)N2CC3CN(c4nc(C)cnc4C)CC3C2)c1]

The title compound was prepared in a manner analogous to Example 15 utilizing Intermediate 34 and 5-methyl-2-pyrimidin-2-yl-benzoic acid. MS (ESI): mass calculated for $C_{24}H_{26}N_6O$, 414.51. m/z found 415.2 [M+H]$^+$. $^1$H NMR (400 MHz, CDCl$_3$): 8.77 (d, J=4.9, 2H), 8.22 (d, J=8.1, 1H), 7.73 (s, 1H), 7.34-7.29 (m, 1H), 7.21-7.16 (m, 1H), 7.11 (t, J=4.8, 1H), 3.96-3.89 (m, 1H), 3.86-3.79 (m, 1H), 3.74-3.61 (m, 2H), 3.57-3.51 (m, 1H), 3.49-3.38 (m, 2H), 3.18-3.12 (m, 1H), 3.08-2.98 (m, 1H), 2.96-2.86 (m, 1H), 2.50 (s, 3H), 2.42 (s, 3H), 2.36 (s, 3H).

Example 104: 2-(3,6-Dimethylpyrazin-2-yl)-5-{[4-fluoro-2-(2H-1,2,3-triazol-2-yl)phenyl]carbonyl}octahydropyrrolo[3,4-c]pyrrole

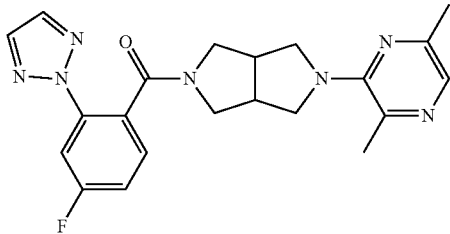 [SMILES: Cc1cnc(C)c(N2CC3CN(C(=O)c4ccc(F)cc4-n4nccn4)CC3C2)n1]

The title compound was prepared in a manner analogous to Example 15 utilizing Intermediate 34 and Intermediate 4. MS (ESI): mass calculated for $C_{21}H_{22}FN_7O$, 407.45. m/z found 408.2 [M+H]$^+$. $^1$H NMR (400 MHz, CDCl$_3$) 7.83-7.72 (m, 4H), 7.42 (dd, J=8.5, 5.8, 1H), 7.14 (ddd, J=8.5, 7.8, 2.5, 1H), 3.94-3.86 (m, 1H), 3.82-3.74 (m, 1H), 3.73-3.60 (m, 2H), 3.56-3.47 (m, 1H), 3.42-3.31 (m, 2H), 3.10-2.82 (m, 3H), 2.50 (s, 3H), 2.36 (s, 3H).

Example 105: 2-(4,6-Dimethylpyrimidin-2-yl)-5-{[5-iodo-2-(2H-1,2,3-triazol-2-yl)phenyl]carbonyl}octahydropyrrolo[3,4-c]pyrrole

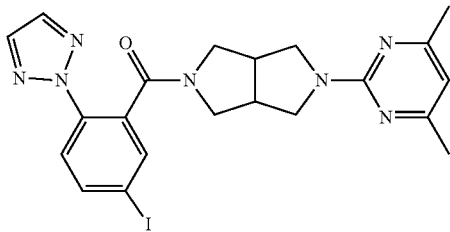 [SMILES: Cc1cc(C)nc(N2CC3CN(C(=O)c4cc(I)ccc4-n4nccn4)CC3C2)n1]

The title compound was prepared in a manner analogous to Example 15 utilizing Intermediate 23 and Intermediate 12. MS (ESI): mass calculated for $C_{21}H_{22}IN_7O$, 515.36. m/z found 516.1 [M+H]$^+$. $^1$H NMR (400 MHz, CDCl$_3$): 7.87-7.80 (m, 1H), 7.79-7.67 (m, 4H), 6.30 (s, 1H), 3.94-3.82 (m, 2H), 3.74-3.56 (m, 3H), 3.53-3.30 (m, 2H), 3.13-2.85 (m, 3H), 2.29 (s, 6H).

Example 106: 4-[5-{[2-Fluoro-6-(2H-1,2,3-triazol-2-yl)phenyl]carbonyl}hexahydropyrrolo[3,4-c]pyrrol-2(1H)-yl]-N,N-dimethyl-6-(trifluoromethyl)pyrimidin-2-amine

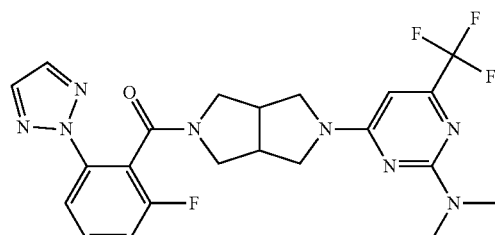

The title compound was prepared in a manner analogous to Example 15 utilizing Intermediate 36 and Intermediate 12. MS (ESI): mass calculated for $C_{22}H_{22}F_4N_8O$, 490.47. m/z found 491.0 [M+H]$^+$. $^1$H NMR (400 MHz, CDCl$_3$): 7.89-7.64 (m, 3H), 7.56-7.44 (m, 1H), 7.19-7.10 (m, 1H), 6.01-5.74 (m, 1H), 4.10-2.86 (m, 16H).

Example 107: [5-(4,6-Dimethyl-pyrimidin-2-yl)-hexahydro-pyrrolo[3,4-c]pyrrol-2-yl]-(2-fluoro-6-[1,2,3]triazol-2-yl-phenyl)-methanone

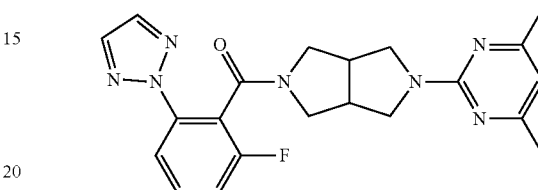

Method A:
[5-(4,6-Dimethyl-pyrimidin-2-yl)-hexahydro-pyrrolo[3,4-c]pyrrol-2-yl]-(2-fluoro-6-[1,2,3]triazol-2-yl-phenyl)-methanone. To a 3-necked, 3 L, round-bottomed flask equipped with a nitrogen line, temperature probe, heating mantle, reflux condenser, mechanical stirrer, and 1 N aq. NaOH scrubber were added 2-fluoro-6-[1,2,3]triazol-2-yl-benzoic acid (Intermediate 12, 120.98 g, 75 wt %, 90.74 g actual, 438 mmol) and toluene (1 L). The mixture was warmed to 50° C. for 1 h with stirring. The mixture was then cooled to 25° C. and thionyl chloride (47.9 mL, 657 mmol) was added. The mixture was warmed back to 50° C. and held for 1 h. During this time, in a separate 5 L jacketed reactor equipped with a mechanical stirrer and temperature probe were added toluene (600 mL), aqueous sodium carbonate (185.7 g, 1.75 mol in 1.6 L water), and 2-(4,6-dimethyl-pyrimidin-2-yl)-octahydro-pyrrolo[3,4-c]pyrrole·HOAc (Intermediate 23, 122 g, 438 mmol). This biphasic mixture was cooled to 0° C. After cooling to 0° C., the original slurry was poured through a filter and over the stirring biphasic mixture of amine and aqueous sodium carbonate. The mixture was allowed to warm to room temperature. After 2 h, additional 2-(4,6-dimethyl-pyrimidin-2-yl)-octahydro-pyrrolo[3,4-c]pyrrole·HOAc (4 g, 14 mmol) was added and the mixture was stirred for 30 additional minutes. At the end of this period, the layers were separated and 100 mL of methanol were added to the organic layer. The organic layer was dried over MgSO$_4$, filtered, and concentrated to a white solid. This solid was taken up in ethanol (1.4 L) and warmed to 77° C. The mixture was then cooled to 55° C. and seeded with previously crystallized material. (Note: The seeds were generated from slurrying the initial product in 2-propanol at room temperature [100 mg/mL]). The mixture was cooled to room temperature at a rate of 5° C. per hour. After stirring at room temperature for 14 h, the mixture was filtered and dried to provide the final product as a white crystalline solid (136.84 g, 74%). $^1$H NMR (400 MHz, CDCl$_3$): 7.88-7.78 (m, 1.78H), 7.75-7.69 (s, 1.22H), 7.51-7.43 (m, 1H), 7.17-7.11 (m, 1H), 6.30-6.28 (m, 1H), 4.03-3.48 (m, 7H), 3.29-3.21 (m, 1H), 3.15-2.92 (m, 2H), 2.30 (s, 6H). MS (ESI) mass calcd for $C_{21}H_{22}FN_7O$, 407.19. m/z found, 408 [M+H]$^+$. Anal. calcd. for $C_{21}H_{22}FN_7OC$, 61.90, H, 5.44, N, 24.06; found C, 61.83, H, 5.42, N, 24.08.

Method B:

Step A: A one-piece EasyMax reactor was equipped with a mechanical stirred, a temperature probe, a reflux condenser and an NaOH scrubber. To the reactor was added 2-fluoro-6-triazol-2-yl benzoic acid (15.01 g, 72.5 mmol) and toluene (150.0 g), N,N-dimethylformamide (0.06 g, 0.26 mmol) was then added, the reaction was held at 20° C. prior to the addition of thionyl chloride (11.31 g, 94.1 mmol) via syringe pump. The reaction mixture was then heated to 50° C. over 15 minutes and then was stirred at that temperature for 1.5 hours. The mixture was then heated to 55° C. and 20.4 g of solvent were distilled in vacuo to give 139.4 g of acid chloride solution which was used as is in Step C below.

Step B. In a 500 mL jacketed reactor equipped with a mechanical stirrer, thermometer and reflux condenser was charged with 2-(4,6-dimethylpyrimidin-2-yl)octahydropyrrolo[3,4-c]pyrrole, bis-HCl salt (21.01 g, 72.1 mmol) and toluene (60.1 g) and the slurry was stirred at 0° C. Sodium carbonate (30.6 g, 288.7 mmol) was then separately dissolved in water (151.5 g) and then added to the slurry over 15 minutes to give the crude amine solution which was used directly in Step C.

Step C. To the crude amine solution from Step B in a 500 mL reactor held at 0° C. was added the crude acid chloride solution from Step 1 and the reaction was held at 0° C. for another 15 minutes, then heated to 30° C. over 30 minutes. During this time the product started to precipitate and the aqueous layer formed a slurry. The reaction was then cooled to 20° C. over 30 minutes and stirred at this temperature overnight. The mixture was then heated to 75° C. over 40 minutes and stirred for 35 minutes. Stirring was then stopped and after 30 minutes the aqueous layer was removed. To the organic layer was then added water (90.0 g) and the mixture was stirred for 20 minutes at 75° C., then the stirrer was again stopped. After 10 minutes the aqueous layer was removed. To the remaining organic layer was added water (90.0 g) and the mixture was again stirred at 75° C. for 15 minutes, before the stirrer was again stopped, and after 10 minutes the aqueous layer was again removed. Distillation of the remaining toluene solution was then performed (at 75° C., 350 mbar) to remove 70 mL of solvent. The remaining solution was then cooled to 50° C., and stirred for 20 minutes prior to the addition of Example 107 (0.04 g, seed crystals to start the crystallization). The reaction was then stirred at 50° C. for 1.5 hour, then the thin suspension was cooled to 30° C. over 1 hour then cooled to 0° C. over 1 hour. After 90 minutes the product was isolated by suction filtration, the filter cake was washed with cyclohexane (75 g), then washed with water (85.0 g) and the wet product cake was dried in vacuo at 55° C. overnight to give the title compound (25.21 g, 83%), Purity was assessed by HPLC (99.3%, 99.6%, and 99.3 area % (at 254, 235, and 280 nm, respectively).

Step D: The product of Step C (20.0 g, 48.9 mmol) was added to a one-piece EasyMax reactor and activated charcoal (Norit CN1, 2.00 g), ethanol (120.0 g) and 2-propanol (20.0 g) were then added. The mixture was heated to 85° C. over 30 minutes, then stirred for 45 minutes, then cooled to 75° C. over 15 minutes. The mixture was then filtered via a glass fiber filter, the filter was washed with 2-propanol (20.0 g) that was previously heated to 70° C., The filtrates were then placed into a 500 mL jacketed reactor equipped with a mechanical stirrer, reflux condenser and thermometer and heated to 85° C., stirred for 5 minutes, cooled to 55° C. over 20 minutes and after 10 minutes at 55° C. a suspension of Example 107 (0.02 g) in 2-propanol (0.20 g) was added. The resulting thin suspension was stirred at 55° C. for 1 hour, then was cooled to 45 over 1 hour and stirred for 30 minutes before it was cooled to 0° C. over 3 hours and was stirred at that temperature overnight. After 13 hours, the product was isolated by suction filtration, the filter cake was washed via the reactor with 2-propanol (40.0 g, at 10° C.) to provide the wet product cake which was dried in vacuo at 60° C. overnight to give the title compound (18.18 g, 91.3%) as a white to off-white crystalline solid. Purity was assessed by HPLC (99.7%, 99.8%, and 99.6 area % (at 254, 235, and 280 nm, respectively). Assays for residual solvents showed the following: ethanol 1089 ppm, 2-propanol 348 ppm, toluene 202 ppm, cyclohexane<20 ppm.

Example 108: N,N-Dimethyl-4-{5-[(5-methyl-2-pyrimidin-2-ylphenyl)carbonyl]hexahydropyrrolo[3,4-c]pyrrol-2(1H)-yl}-6-(trifluoromethyl)pyrimidin-2-amine

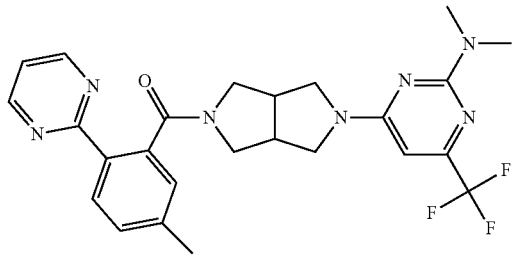 [SMILES: Cc1ccc(-c2ncccn2)c(C(=O)N2CC3CN(c4cc(C(F)(F)F)nc(N(C)C)n4)CC3C2)c1]

The title compound was prepared in a manner analogous to Example 15 utilizing Intermediate 36 and 5-methyl-2-pyrimidin-2-yl-benzoic acid. MS (ESI): mass calculated for $C_{25}H_{26}F_3N_7O$, 497.53. m/z found 498.0 [M+H]$^+$. $^1$H NMR (400 MHz, CDCl$_3$): 8.67 (dd, J=20.0, 4.9, 2H), 8.20 (d, J=10.1, 1H), 7.34-7.30 (m, 1H), 7.19-7.15 (m, 1H), 7.13-7.03 (m, 1H), 5.85 (br s, 1H), 3.98-2.83 (m, 16H), 2.42 (s, 3H).

Example 109: 4-{5-[(5-Fluoro-2-pyrimidin-2-ylphenyl)carbonyl]hexahydropyrrolo[3,4-c]pyrrol-2(1H)-yl}-N,N-dimethyl-6-(trifluoromethyl)pyrimidin-2-amine

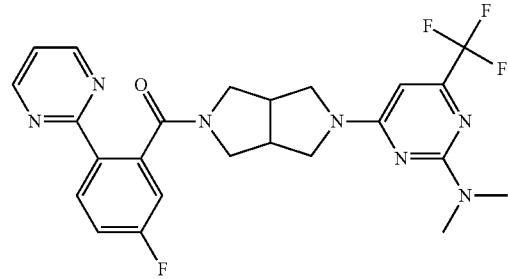 [SMILES: CN(C)c1nc(N2CC3CN(C(=O)c4cc(F)ccc4-c4ncccn4)CC3C2)cc(C(F)(F)F)n1]

The title compound was prepared in a manner analogous to Example 15 utilizing Intermediate 36 and Intermediate 13. MS (ESI): mass calculated for $C_{24}H_{23}F_4N_7O$, 501.49. m/z found 502.0 [M+H]$^+$. $^1$H NMR (400 MHz, CDCl$_3$): 8.70 (d, J=4.9, 2H), 8.38-8.31 (m, 1H), 7.24-7.17 (m, 1H), 7.14-7.02 (m, 2H), 5.86 (br s, 1H), 4.06-2.78 (m, 16H).

Example 110: 4-[5-{[5-Fluoro-2-(2H-1,2,3-triazol-2-yl)phenyl]carbonyl}hexahydropyrrolo[3,4-c]pyrrol-2(1H)-yl]-N,N-dimethyl-6-(trifluoromethyl)pyrimidin-2-amine

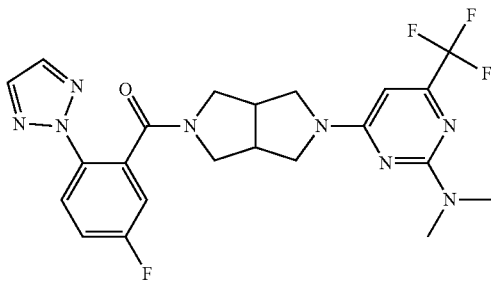 [SMILES: CN(C)c1nc(N2CC3CN(C(=O)c4cc(F)ccc4-n4nccn4)CC3C2)cc(C(F)(F)F)n1]

The title compound was prepared in a manner analogous to Example 15 utilizing Intermediate 36 and Intermediate 1. MS (ESI): mass calculated for C$_{22}$H$_{22}$F$_4$N$_5$O, 490.46. m/z found 490.9 [M+H]$^+$. $^1$H NMR (400 MHz, CDCl$_3$): 8.00-7.92 (m, 1H), 7.78-7.64 (m, 2H), 7.26-7.20 (m, 1H), 7.17-7.11 (m, 1H), 5.87 (br s, 1H), 3.96-2.87 (m, 16H).

Example 111: [5-(2-Dimethylamino-6-trifluoromethyl-pyrimidin-4-yl)-hexahydro-pyrrolo[3,4-c]pyrrol-2-yl]-(4-fluoro-2-[1,2,3]triazol-2-yl-phenyl)-methanone

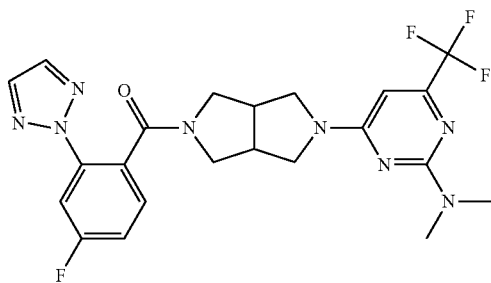 [SMILES: CN(C)c1nc(N2CC3CN(C(=O)c4ccc(F)cc4-n4nccn4)CC3C2)cc(C(F)(F)F)n1]

The title compound was prepared in a manner analogous to Example 15 utilizing Intermediate 36 and Intermediate 4. MS (ESI): mass calculated for C$_{22}$H$_{22}$F$_4$N$_5$O, 490.46. m/z found 490.9 [M+H]$^+$. $^1$H NMR (400 MHz, CDCl$_3$): 7.84-7.64 (m, 3H), 7.45-7.36 (m, 1H), 7.20-7.07 (m, 1H), 5.87 (br s, 1H), 4.04-2.79 (m, 16H).

Example 112: 2-[(5-Methyl-2-pyrimidin-2-ylphenyl)carbonyl]-5-[6-methyl-2-(trifluoromethyl) pyrimidin-4-yl]octahydropyrrolo[3,4-c]pyrrole

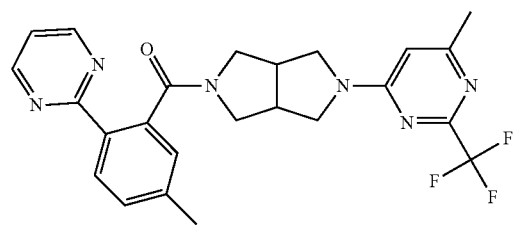 [SMILES: Cc1ccc(-c2ncccn2)c(C(=O)N2CC3CN(c4cc(C)nc(C(F)(F)F)n4)CC3C2)c1]

The title compound was prepared in a manner analogous to Example 15 utilizing Intermediate 31 and 5-methyl-2-pyrimidin-2-yl-benzoic acid. MS (ESI): mass calculated for C$_{24}$H$_{23}$F$_3$N$_6$O, 468.48. m/z found 469.2 [M+H]$^+$. $^1$H NMR (400 MHz, CDCl$_3$): 8.80-8.68 (m, 2H), 8.27-8.13 (m, 1H), 7.35-7.29 (m, 1H), 7.20-7.03 (m, 2H), 6.31-6.04 (m, 1H), 4.15-2.80 (m, 10H), 2.56-2.30 (m, 6H).

Example 113: 2-[(5-Fluoro-2-pyrimidin-2-ylphenyl)carbonyl]-5-(4-phenylpyrimidin-2-yl)octahydropyrrolo[3,4-c]pyrrole

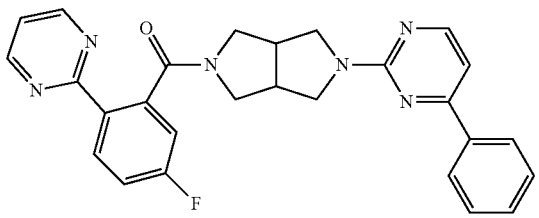 [SMILES: O=C(c1cc(F)ccc1-c1ncccn1)N1CC2CN(c3nccc(-c4ccccc4)n3)CC2C1]

The title compound was prepared in a manner analogous to Example 15 utilizing Intermediate 26 and Intermediate 13. MS (ESI): mass calculated for C$_{27}$H$_{23}$FN$_6$O, 466.52. m/z found 467.2 [M+H]$^+$. $^1$H NMR (400 MHz, CDCl$_3$): 8.72-8.66 (m, 2H), 8.44-8.29 (m, 2H), 8.16-8.02 (m, 2H), 7.53-7.45 (m, 3H), 7.21-7.14 (m, 1H), 7.10-7.06 (m, 1H), 7.01-6.98 (m, 1H), 6.87 (br s, 1H), 4.05-3.50 (m, 7H), 3.31-2.98 (m, 3H).

Example 114: 2-{[5-Fluoro-2-(2H-1,2,3-triazol-2-yl)phenyl]carbonyl}-5-[6-methyl-2-(trifluoromethyl)pyrimidin-4-yl]octahydropyrrolo[3,4-c]pyrrole

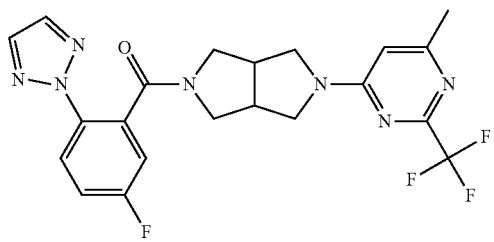 [SMILES: Cc1cc(N2CC3CN(C(=O)c4cc(F)ccc4-n4nccn4)CC3C2)nc(C(F)(F)F)n1]

The title compound was prepared in a manner analogous to Example 15 utilizing Intermediate 21 and 4-chloro-6-methyl-2-trifluoromethyl-pyrimidine. MS (ESI): mass calculated for C$_{21}$H$_{19}$F$_4$N$_7$O, 461.42. m/z found 462.2 [M+H]$^+$. $^1$H NMR (400 MHz, CDCl$_3$): 8.04-7.87 (m, 1H), 7.81-7.63 (m, 1H), 7.29-7.18 (m, 1H), 7.17-7.08 (m, 1H), 6.31-6.03 (m, 1H), 4.13-2.84 (m, 10H), 2.44 (s, 3H).

Example 115: [5-(2,6-Dimethyl-pyrimidin-4-yl)-hexahydro-pyrrolo[3,4-c]pyrrol-2-yl]-(5-fluoro-2-[1,2,3]triazol-2-yl-phenyl)-methanone

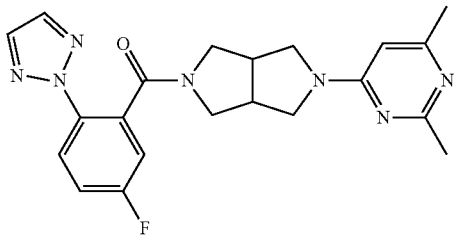 [SMILES: Cc1cc(N2CC3CN(C(=O)c4cc(F)ccc4-n4nccn4)CC3C2)nc(C)n1]

The title compound was prepared in a manner analogous to Example 15 utilizing Intermediate 21 and 4-chloro-2,6-dimethyl-pyrimidine. MS (ESI): mass calculated for $C_{21}H_{22}FN_7O$, 407.45, m/z found 408.2 [M+H]$^+$. $^1$H NMR (CDCl$_3$) 7.97 (dd, J=9.0, 4.8 Hz, 1H), 7.73 (s, 2H), 7.25-7.19 (m, 1H), 7.16-7.10 (m, 1H), 5.94 (s, 1H), 3.95-2.88 (m, 10H), 2.50 (s, 3H), 2.34 (s, 3H).

Example 116: 4-{5-[(2-Fluoro-6-pyrimidin-2-ylphenyl)carbonyl]hexahydropyrrolo[3,4-c]pyrrol-2(1H)-yl}-N,N-dimethyl-6-(trifluoromethyl)pyrimidin-2-amine

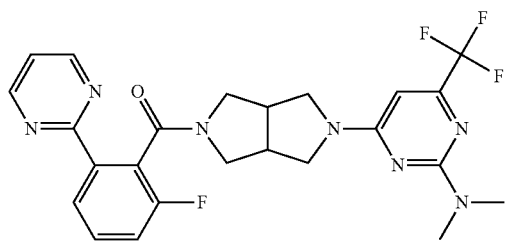 [SMILES: CN(C)c1nc(N2CC3CN(C(=O)c4c(F)cccc4-c4ncccn4)CC3C2)cc(C(F)(F)F)n1]

The title compound was prepared in a manner analogous to Example 15 utilizing Intermediate 36 and Intermediate 14. MS (ESI): mass calculated for $C_{24}H_{23}F_4N_7O$, 501.49. m/z found 502.0 [M+H]$^+$. $^1$H NMR (400 MHz, CDCl$_3$): 8.86-8.63 (m, 2H), 8.22-8.05 (m, 1H), 7.56-7.40 (m, 1H), 7.29-7.18 (m, 1H), 7.12 (br s, 1H), 6.03-5.73 (m, 1H), 4.19-2.90 (m, 16H).

Example 117: 2-[(2-Fluoro-6-pyrimidin-2-ylphenyl)carbonyl]-5-[6-methyl-2-(trifluoromethyl) pyrimidin-4-yl]octahydropyrrolo[3,4-c]pyrrole

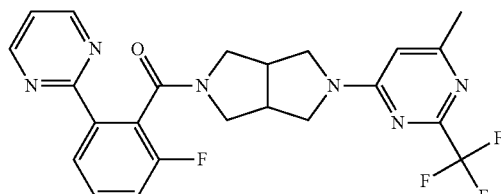

The title compound was prepared in a manner analogous to Example 15 utilizing Intermediate 31 and Intermediate 14. MS (ESI): mass calculated for $C_{23}H_{20}F_4N_6O$, 472.45. m/z found 473.2 [M+H]$^+$. $^1$H NMR (400 MHz, CDCl$_3$): 8.81-8.72 (m, 2H), 8.21-8.01 (m, 1H), 7.54-7.42 (m, 1H), 7.27-7.20 (m, 1H), 7.18-7.10 (m, 1H), 6.36-6.04 (m, 1H), 4.19-2.93 (m, 10H), 2.60-2.29 (m, 3H).

Example 118: 2-(4,6-Dimethylpyrimidin-2-yl)-5-{[4-fluoro-2-(2H-1,2,3-triazol-2-yl)phenyl]carbonyl}octahydropyrrolo[3,4-c]pyrrole

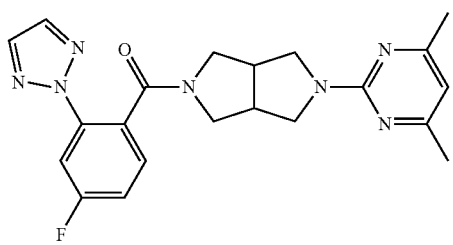 [SMILES: Cc1cc(C)nc(N2CC3CN(C(=O)c4ccc(F)cc4-n4nccn4)CC3C2)n1]

The title compound was prepared in a manner analogous to Example 15 utilizing Intermediate 23 and Intermediate 1. MS (ESI): mass calculated for $C_{21}H_{22}FN_7O$, 408.45. m/z found 408.2 [M+H]$^+$. $^1$H NMR (400 MHz, CDCl$_3$): 7.81-7.69 (m, 3H), 7.43-7.36 (m, 1H), 7.16-7.08 (m, 1H), 6.30 (s, 1H), 3.93-3.81 (m, 2H), 3.75-3.56 (m, 3H), 3.52-3.30 (m, 2H), 3.10-2.87 (m, 3H), 2.30 (s, 6H).

Example 119: N,N,6-Trimethyl-2-[5-{[2-(2H-1,2,3-triazol-2-yl)phenyl]carbonyl}hexahydro pyrrolo[3,4-c]pyrrol-2(1H)-yl]pyrimidin-4-amine

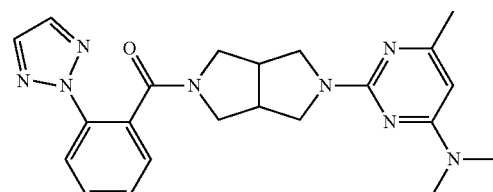

The title compound was prepared in a manner analogous to Example 15 utilizing Intermediate 20 and (2-chloro-6-methyl-pyrimidin-4-yl)-dimethyl-amine. MS (ESI): mass calculated for $C_{22}H_{26}N_8O$, 418.50. m/z found 419.2 [M+H]$^+$. $^1$H NMR (400 MHz, CDCl$_3$): 8.02-7.94 (m, 1H), 7.75 (s, 2H), 7.56-7.46 (m, 1H), 7.44-7.36 (m, 2H), 5.69 (s, 1H), 3.92-3.81 (m, 2H), 3.76-3.62 (m, 2H), 3.60-3.52 (m, 1H), 3.50-3.42 (m, 1H), 3.40-3.29 (m, 1H), 3.04 (s, 6H), 3.01-2.80 (m, 3H), 2.24 (s, 3H).

Example 120: N,N,4-Trimethyl-6-[5-{[2-(2H-1,2,3-triazol-2-yl)phenyl]carbonyl}hexahydro pyrrolo[3,4-c]pyrrol-2(1H)-yl]pyrimidin-2-amine

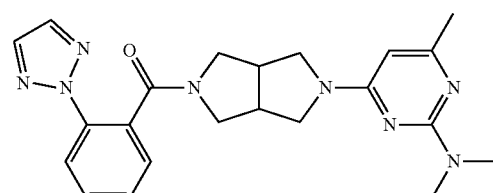

The title compound was prepared in a manner analogous to Example 15 utilizing Intermediate 20 and (4-chloro-6-methyl-pyrimidin-2-yl)-dimethyl-amine. MS (ESI): mass calculated for $C_{22}H_{26}N_5O$, 418.50. m/z found 419.2 [M+H]⁺. ¹H NMR (400 MHz, CDCl₃): 8.01-7.95 (m, 1H), 7.80-7.65 (m, 2H), 7.57-7.48 (m, 1H), 7.45-7.35 (m, 2H), 5.51-5.39 (m, 1H), 3.91-2.85 (m, 19H).

Example 121: N,N-Dimethyl-4-[5-{[2-(2H-1,2,3-triazol-2-yl)phenyl]carbonyl}hexahydropyrrolo[3,4-c]pyrrol-2(1H)-yl]-6-(trifluoromethyl)pyrimidin-2-amine

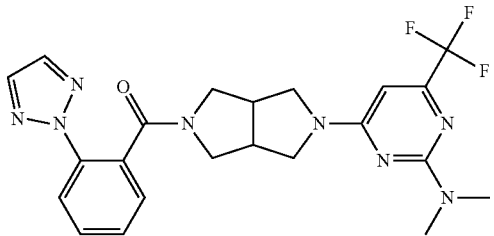 [SMILES: CN(C)c1nc(N2CC3CN(C(=O)c4ccccc4-n4nccn4)CC3C2)cc(C(F)(F)F)n1]

The title compound was prepared in a manner analogous to Example 15 utilizing Intermediate 20 and (4-chloro-6-trifluoromethyl-pyrimidin-2-yl)-dimethyl-amine. MS (ESI): mass calculated for $C_{22}H_{23}F_3N_5O$, 472.47. m/z found 473.2 [M+H]⁺. ¹H NMR (400 MHz, CDCl₃): 8.02-7.95 (m, 1H), 7.73 (s, 2H), 7.57-7.50 (m, 1H), 7.46-7.39 (m, 2H), 5.97-5.75 (m, 1H), 3.99-2.80 (m, 16H).

Example 122: 2-(2,6-Dimethylpyrimidin-4-yl)-5-{[2-(2H-1,2,3-triazol-2-yl)phenyl]carbonyl} octahydropyrrolo[3,4-c]pyrrole

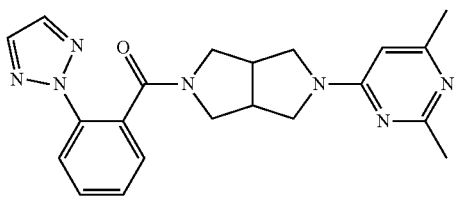 [SMILES: Cc1cc(N2CC3CN(C(=O)c4ccccc4-n4nccn4)CC3C2)nc(C)n1]

The title compound was prepared in a manner analogous to Example 15 utilizing Intermediate 20 and 4-chloro-2,6-dimethyl-pyrimidine. MS (ESI): mass calculated for $C_{21}H_{23}N_7O$, 408.45. m/z found 389.46 [M+H]⁺. m/z found 390.2 [M+H]⁺. ¹H NMR (400 MHz, CDCl₃): 8.01-7.95 (m, 1H), 7.74 (s, 2H), 7.56-7.37 (m, 3H), 6.01-5.85 (m, 1H), 3.99-2.86 (m, 10H), 2.50 (s, 3H), 2.34 (s, 3H).

Example 123: [5-(3,6-Dimethyl-pyrazin-2-yl)-hexahydro-pyrrolo[3,4-c]pyrrol-2-yl]-(5-methyl-2-[1,2,3]triazol-2-yl-phenyl)-methanone

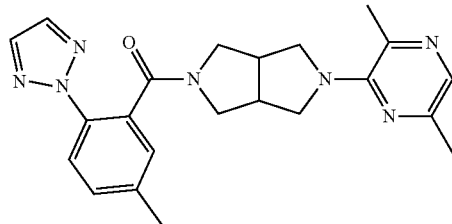 [SMILES: Cc1ccc(-n2nccn2)c(C(=O)N2CC3CN(c4nc(C)cnc4C)CC3C2)c1]

The title compound was prepared in a manner analogous to Example 15 utilizing Intermediate 19 and 3-chloro-2,5-dimethyl-pyrazine. MS (ESI): mass calculated for $C_{22}H_{25}N_7O$, 413.49, m/z found 404.2 [M+H]⁺. ¹H NMR (CDCl₃) 7.85 (d, J=8.3 Hz, 1H), 7.78-7.70 (m, 3H), 7.35-7.29 (m, 1H), 7.25-7.21 (m, 1H), 3.92-3.85 (m, 1H), 3.80-3.72 (m, 1H), 3.70-3.59 (m, 2H), 3.53-3.47 (m, 1H), 3.45-3.23 (m, 1H), 3.04-2.78 (m, 4H), 2.50 (s, 3H), 2.42 (s, 3H), 2.36 (s, 3H).

Example 124: 2-[5-{[5-Fluoro-2-(2H-1,2,3-triazol-2-yl)phenyl]carbonyl}hexahydropyrrolo[3,4-c]pyrrol-2(1H)-yl]-N,N,6-trimethylpyrimidin-4-amine

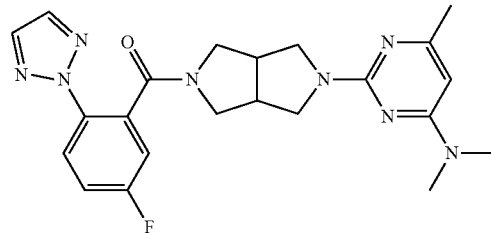 [SMILES: Cc1cc(N(C)C)nc(N2CC3CN(C(=O)c4cc(F)ccc4-n4nccn4)CC3C2)n1]

The title compound was prepared in a manner analogous to Example 15 utilizing Intermediate 21 and (2-chloro-6-methyl-pyrimidin-4-yl)-dimethyl-amine. MS (ESI): mass calculated for $C_{22}H_{25}FN_8O$, 435.49. m/z found 437.3 [M+H]⁺. ¹H NMR (400 MHz, CDCl₃): 7.99-7.93 (m, 1H), 7.73 (s, 2H), 7.23-7.18 (m, 1H), 7.15-7.12 (m, 1H), 5.69 (s, 1H), 3.88-3.80 (m, 2H), 3.71-3.62 (m, 2H), 3.59-3.52 (m, 1H), 3.49-3.32 (m, 2H), 3.15-2.83 (m, 9H), 2.24 (s, 3H).

Example 125: 2-(5-Methoxypyridin-2-yl)-5-[(2-thiophen-2-ylphenyl)carbonyl]octahydropyrrolo[3,4-c]pyrrole

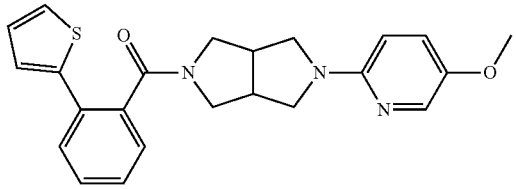 [SMILES: COc1ccc(N2CC3CN(C(=O)c4ccccc4-c4cccs4)CC3C2)nc1]

The title compound was prepared in a manner analogous to Example 15 utilizing Intermediate 37 and 2-chloro-5-methoxy-pyridine. MS (ESI): mass calculated for $C_{23}H_{23}N_3O_2S$, 405.52. m/z found 406.2 $[M+H]^+$. $^1H$ NMR (400 MHz, $CDCl_3$): 7.88 (d, J=2.7, 1H), 7.54-7.47 (m, 1H), 7.45-7.31 (m, 4H), 7.25-7.19 (m, 1H), 7.18-7.12 (m, 1H), 7.06-6.88 (m, 1H), 6.30-6.13 (m, 1H), 3.94-2.47 (m, 13H).

Example 126: 2-[(2-Ethoxynaphthalen-1-yl)carbonyl]-5-(4-phenylpyrimidin-2-yl)octahydro pyrrolo[3,4-c]pyrrole

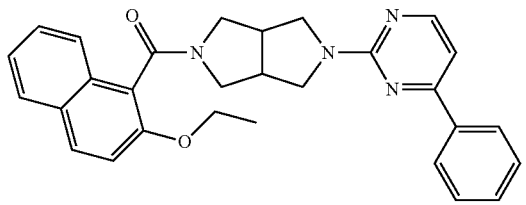 [SMILES: CCOc1ccc2ccccc2c1C(=O)N1CC2CN(c3nccc(-c4ccccc4)n3)CC2C1]

The title compound was prepared in a manner analogous to Example 15 utilizing Intermediate 26 and 2-ethoxy-naphthalene-1-carboxylic acid. MS (ESI): mass calculated for $C_{29}H_{26}N_4O_2$, 464.57. m/z found 465.2 $[M+H]^+$. $^1H$ NMR (400 MHz, $CDCl_3$): 8.42-8.33 (m, 1H), 8.14-7.98 (m, 2H), 7.89-7.61 (m, 3H), 7.53-7.43 (m, 3H), 7.41-7.18 (m, 3H), 7.01-6.95 (m, 1H), 4.31-2.91 (m, 12H), 1.49-1.23 (m, 3H).

Example 127: 2-{[5-Methyl-2-(2H-1,2,3-triazol-2-yl)phenyl]carbonyl}-5-(4-phenylpyrimidin-2-yl)octahydropyrrolo[3,4-c]pyrrole

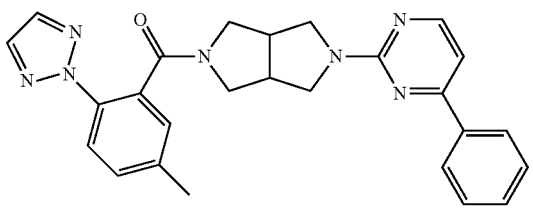 [SMILES: Cc1ccc(-n2nccn2)c(C(=O)N2CC3CN(c4nccc(-c5ccccc5)n4)CC3C2)c1]

The title compound was prepared in a manner analogous to Example 15 utilizing Intermediate 19 and 2-chloro-4-phenyl-pyrimidine. MS (ESI): mass calculated for $C_{26}H_{25}N_7O$, 451.53. m/z found 452.2 $[M+H]^+$. $^1H$ NMR (400 MHz, $CDCl_3$): 8.43-8.32 (m, 1H), 8.15-7.99 (m, 2H), 7.88-7.80 (m, 1H), 7.78-7.57 (m, 2H), 7.55-7.39 (m, 3H), 7.34-7.28 (m, 1H), 7.25-7.21 (m, 1H), 7.01-6.96 (m, 1H), 4.09-2.87 (m, 10H), 2.41 (s, 3H).

Example 128: (4-Chloro-2-[1,2,3]triazol-2-yl-phenyl)-[5-(4,6-dimethyl-pyrimidin-2-yl)-hexahydro-pyrrolo[3,4-c]pyrrol-2-yl]-methanone

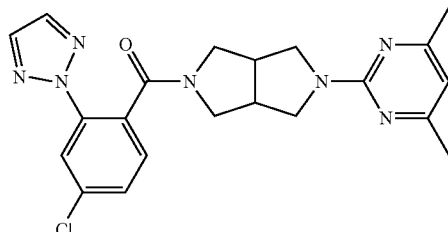

The title compound was prepared in a manner analogous to Example 15 utilizing Intermediate 6 and 2-chloro-4,6-dimethylpyrimidine. MS (ESI): mass calculated for $C_{21}H_{22}ClN_7O$, 423.91. m/z found 424.2 $[M+H]^+$. $^1H$ NMR (400 MHz, $CDCl_3$): 8.03 (t, J=10.1 Hz, 1H), 7.76 (s, 2H), 7.41-7.29 (m, 2H), 6.30 (s, 1H), 3.92-3.79 (m, 2H), 3.74-3.58 (m, 3H), 3.53-3.29 (m, 2H), 3.10-2.86 (m, 3H), 2.30 (s, 6H).

Example 129: 2-(4,6-Dimethoxypyrimidin-2-yl)-5-{[5-methyl-2-(2H-1,2,3-triazol-2-yl)phenyl]carbonyl}octahydropyrrolo[3,4-c]pyrrole

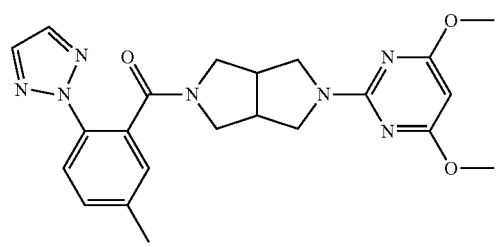 [SMILES: COc1cc(OC)nc(N2CC3CN(C(=O)c4cc(C)ccc4-n4nccn4)CC3C2)n1]

The title compound was prepared in a manner analogous to Example 15 utilizing Intermediate 19 and 2-chloro-4,6-dimethoxypyrimidine. MS (ESI): mass calculated for $C_{22}H_{25}N_7O_3$, 435.49. m/z found 436.2 $[M+H]^+$. $^1H$ NMR (400 MHz, $CDCl_3$): 7.85 (d, J=8.3, 1H), 7.72 (s, 2H), 7.34-7.29 (m, 1H), 7.24-7.21 (m, 1H), 5.39 (s, 1H), 3.99-3.60 (m, 10H), 3.57-3.27 (m, 3H), 3.08-2.82 (m, 3H), 2.41 (s, 3H).

Example 130: 2-(4,6-Dimethylpyrimidin-2-yl)-5-{[5-methyl-2-(2H-1,2,3-triazol-2-yl)phenyl]carbonyl}octahydropyrrolo[3,4-c]pyrrole

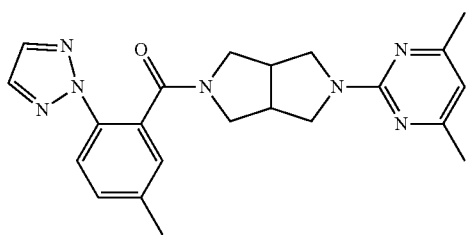 [SMILES: Cc1ccc(-n2nccn2)c(C(=O)N2CC3CN(c4nc(C)cc(C)n4)CC3C2)c1]

The title compound was prepared in a manner analogous to Example 15 utilizing Intermediate 19 and 2-chloro-4,6-dimethylpyrimidine. MS (ESI): mass calculated for $C_{22}H_{25}N_7O$, 403.49. m/z found 404.2 [M+H]$^+$. $^1$H NMR (400 MHz, CDCl$_3$): 7.84 (d, J=8.3, 1H), 7.72 (br s, 2H), 7.33-7.29 (m, 1H), 7.23-7.20 (m, 1H), 6.29 (s, 1H), 3.91-3.80 (m, 2H), 3.73-3.54 (m, 3H), 3.50-3.24 (m, 2H), 3.07-2.81 (m, 3H), 2.40 (s, 3H), 2.29 (s, 6H).

Example 131: 2-(4-Phenylpyrimidin-2-yl)-5-{[2-(2H-1,2,3-triazol-2-yl)phenyl]carbonyl}octahydro pyrrolo[3,4-c]pyrrole

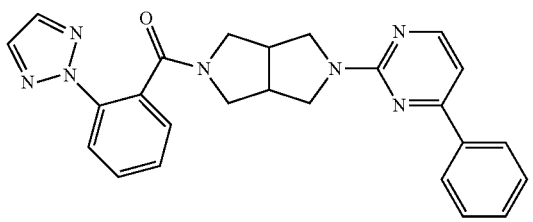 [SMILES: O=C(c1ccccc1-n1nccn1)N1CC2CN(c3nccc(-c4ccccc4)n3)CC2C1]

The title compound was prepared in a manner analogous to Example 15 utilizing Intermediate 26 and Intermediate 2. MS (ESI): mass calculated for $C_{25}H_{23}N_7O$, 437.50. m/z found 438.2 [M+H]$^+$. $^1$H NMR (400 MHz, CDCl$_3$): 8.46-8.31 (m, 1H), 8.21-7.91 (m, 3H), 7.82-7.59 (m, 2H), 7.58-7.39 (m, 6H), 7.01-6.97 (m, 1H), 4.04-3.31 (m, 7H), 3.17-2.86 (m, 3H).

Example 132: 2-(4,6-Dimethylpyrimidin-2-yl)-5-{[5-(2-fluorophenyl)-2-methyl-1,3-thiazol-4-yl]carbonyl}octahydropyrrolo[3,4-c]pyrrole

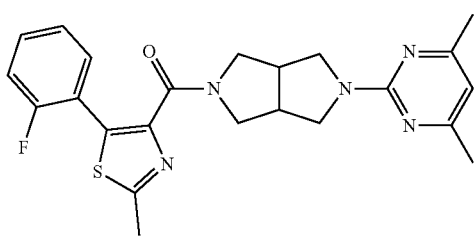 [SMILES: Cc1cc(C)nc(N2CC3CN(C(=O)c4nc(C)sc4-c4ccccc4F)CC3C2)n1]

The title compound was prepared in a manner analogous to Example 15 utilizing Intermediate 18 and 2-chloro-4,6-dimethylpyrimidine. MS (ESI): mass calculated for $C_{23}H_{24}FN_5OS$, 437.54. m/z found 438.2 [M+H]$^+$. $^1$H NMR (400 MHz, CDCl$_3$): 7.50-7.44 (m, 1H), 7.32-7.23 (m, 1H), 7.16-7.04 (m, 2H), 6.29 (s, 1H), 3.93-3.80 (m, 2H), 3.76-3.67 (m, 2H), 3.61-3.54 (m, 2H), 3.51-3.37 (m, 2H), 3.29-3.22 (m, 1H), 3.03-2.87 (m, 2H), 2.73 (s, 3H), 2.30 (s, 6H).

Example 133: 2-[(2-Thiophen-2-ylphenyl)carbonyl]-5-[6-(trifluoromethyl)pyridin-2-yl]octahydro pyrrolo[3,4-c]pyrrole

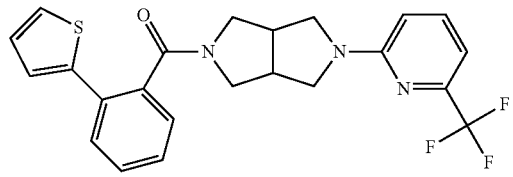 [SMILES: O=C(c1ccccc1-c1cccs1)N1CC2CN(c3cccc(C(F)(F)F)n3)CC2C1]

The title compound was prepared in a manner analogous to Example 15 utilizing Intermediate 37 and 2-chloro-6-trifluoromethyl-pyridine. MS (ESI): mass calculated for $C_{23}H_{20}F_3N_3OS$, 443.49. m/z found 444.1 [M+H]$^+$. $^1$H NMR (400 MHz, CDCl$_3$): 7.62-7.33 (m, 5H), 7.29-7.05 (m, 2H), 7.04-6.80 (m, 2H), 6.37 (s, 1H), 4.01-2.47 (m, 10H).

Example 134: 2-(6-Methylpyridin-2-yl)-5-[(2-thiophen-2-ylphenyl)carbonyl]octahydropyrrolo[3,4-c]pyrrole

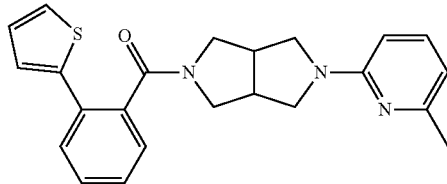 [SMILES: Cc1cccc(N2CC3CN(C(=O)c4ccccc4-c4cccs4)CC3C2)n1]

The title compound was prepared in a manner analogous to Example 15 utilizing Intermediate 37 and 2-chloro-6-methyl-pyridine. MS (ESI): mass calculated for $C_{23}H_{23}N_3OS$, 389.52. m/z found 390.2 [M+H]$^+$. $^1$H NMR (400 MHz, CDCl$_3$): 7.56-7.47 (m, 1H), 7.45-7.10 (m, 6H), 7.07-6.91 (m, 1H), 6.43 (d, J=7.2, 1H), 6.04 (s, 1H), 3.96-2.57 (m, 10H), 2.38 (s, 3H).

Example 135: 2-(4-Methylpyrimidin-2-yl)-5-{[2-(2H-1,2,3-triazol-2-yl)phenyl]carbonyl}octahydro pyrrolo[3,4-c]pyrrole

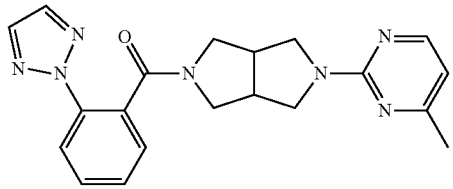 [SMILES: Cc1ccnc(N2CC3CN(C(=O)c4ccccc4-n4nccn4)CC3C2)n1]

The title compound was prepared in a manner analogous to Example 15 utilizing Intermediate 20 and 2-chloro-4-methyl-pyrimidine. MS (ESI): mass calculated for $C_{20}H_{21}N_7O$, 375.43. m/z found 376.2 [M+H]$^+$. $^1$H NMR (400 MHz, CDCl$_3$): 8.17 (d, J=5.0, 1H), 7.98 (d, J=8.1, 1H), 7.75 (s, 2H), 7.56-7.48 (m, 1H), 7.44-7.40 (m, 2H), 6.40 (d, J=5.0, 1H), 3.94-3.81 (m, 2H), 3.75-3.54 (m, 3H), 3.52-3.31 (m, 2H), 3.10-2.88 (m, 3H), 2.35 (s, 3H).

Example 136: 2-(4-Methylpyridin-2-yl)-5-[(2-thiophen-2-ylphenyl)carbonyl]octahydropyrrolo[3,4-c]pyrrole

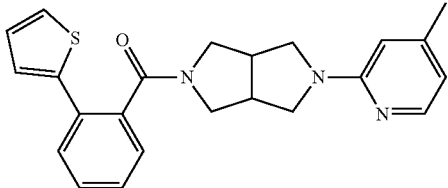 [SMILES: Cc1ccnc(N2CC3CN(C(=O)c4ccccc4-c4cccs4)CC3C2)c1]

The title compound was prepared in a manner analogous to Example 15 utilizing Intermediate 37 and 2-chloro-4-methyl-pyridine. MS (ESI): mass calculated for $C_{23}H_{23}N_3OS$, 389.52. m/z found 390.2 [M+H]$^+$. $^1$H NMR (400 MHz, CDCl$_3$): 8.00 (d, J=5.2, 1H), 7.56-7.47 (m, 1H), 7.45-7.31 (m, 3H), 7.25-7.11 (m, 2H), 7.09-6.90 (m, 1H), 6.42 (d, J=5.2, 1H), 6.06 (br s, 1H), 3.98-2.59 (m, 10H), 2.27 (s, 3H).

Example 137: 2-(6-Methoxypyridin-2-yl)-5-[(2-thiophen-2-ylphenyl)carbonyl]octahydro pyrrolo[3,4-c]pyrrole

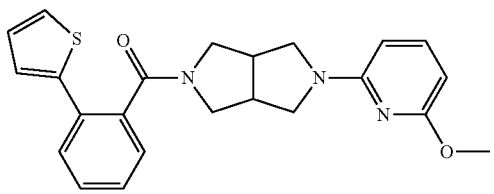 [SMILES: COc1cccc(N2CC3CN(C(=O)c4ccccc4-c4cccs4)CC3C2)n1]

The title compound was prepared in a manner analogous to Example 15 utilizing Intermediate 37 and 2-chloro-6-methoxy-pyridine. MS (ESI): mass calculated for $C_{23}H_{23}N_3O_2S$, 405.52. m/z found 406.2 [M+H]$^+$. $^1$H NMR (400 MHz, CDCl$_3$): 7.56-7.47 (m, 1H), 7.46-7.30 (m, 4H), 7.25-7.12 (m, 2H), 7.09-6.90 (m, 1H), 6.01 (d, J=7.6, 1H), 5.77 (br s, 1H), 3.85 (s, 3H), 3.71-2.59 (m, 10H).

Example 138: 2-(4,6-Dimethoxypyrimidin-2-yl)-5-[(2-thiophen-2-ylphenyl)carbonyl]octahydro pyrrolo[3,4-c]pyrrole

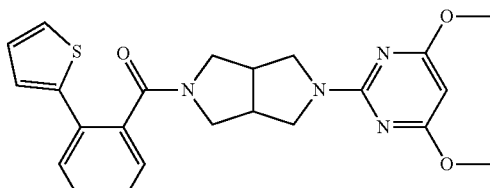

The title compound was prepared in a manner analogous to Example 15 utilizing Intermediate 37 and 2-chloro-4,6-dimethoxy-pyridine. MS (ESI): mass calculated for $C_{23}H_{24}N_4O_3S$, 436.54. m/z found 437.2 [M+H]$^+$. $^1$H NMR (400 MHz, CDCl$_3$): 7.52 (d, J=7.5, 1H), 7.45-7.33 (m, 3H), 7.30-7.15 (m, 2H), 7.00 (br s, 1H), 5.38 (s, 1H), 3.97-2.60 (m, 16H).

Example 139: 2-{5-[(2-Thiophen-2-ylphenyl)carbonyl]hexahydropyrrolo[3,4-c]pyrrol-2(1H)-yl}-1,3-benzoxazole

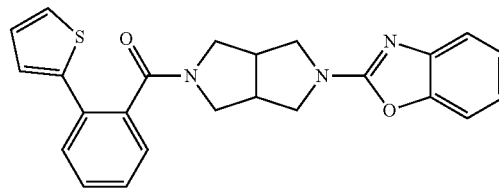

The title compound was prepared in a manner analogous to Example 15 utilizing Intermediate 37 and 2-chlorobenzooxazole. MS (ESI): mass calculated for $C_{24}H_{21}N_3O_2S$, 415.52. m/z found 416.1 [M+H]$^+$. $^1$H NMR (400 MHz, CDCl$_3$): 7.83-6.68 (m, 11H), 4.20-2.47 (m, 10H).

Example 140: 2-[(2-Thiophen-2-ylphenyl)carbonyl]-5-[3-(trifluoromethyl)pyridin-2-yl]octahydro pyrrolo[3,4-c]pyrrole

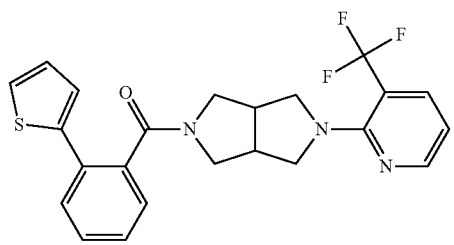 [SMILES: O=C(c1ccccc1-c1cccs1)N1CC2CN(c3ncccc3C(F)(F)F)CC2C1]

The title compound was prepared in a manner analogous to Example 15 utilizing Intermediate 37 and 2-chloro-3-trifluoromethyl-pyridine. MS (ESI): mass calculated for $C_{23}H_{20}F_3N_3OS$, 443.49. m/z found 444.1 [M+H]$^+$. $^1$H NMR (400 MHz, CDCl$_3$): 8.28 (dd, J=4.7, 1.4, 1H), 7.79 (dd, J=7.8, 1.8, 1H), 7.55-7.49 (m, 1H), 7.46-7.33 (m, 3H), 7.30-7.19 (m, 2H), 7.01 (br s, 1H), 6.71 (dd, J=7.7, 4.7, 1H), 3.98-2.54 (m, 10H).

Example 141: [5-(4-Phenyl-pyrimidin-2-yl)-hexahydro-pyrrolo[3,4-c]pyrrol-2-yl]-[2-(4H-[1,2,4]triazol-3-yl)-phenyl]-methanone

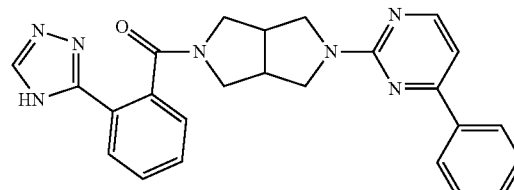

The title compound was prepared in a manner analogous to Example 15 utilizing Intermediate 26 and 2-(4H-[1,2,4]triazol-3-yl)-benzoic acid. MS (ESI): mass calculated for $C_{25}H_{23}N_7O$, 437.50. m/z found 438.2 [M+H]$^+$. $^1$H NMR (400 MHz, CDCl$_3$): 12.43 (br s, 1H), 8.36 (d, J=5.2 Hz, 1H), 8.14 (d, J=7.5 Hz, 1H), 8.08-7.91 (m, 3H), 7.60-7.42 (m, 5H), 7.39-7.31 (m, 1H), 6.98 (t, J=6.1 Hz, 1H), 4.01-3.87 (m, 2H), 3.85-3.65 (m, 3H), 3.61-3.40 (m, 2H), 3.28-2.89 (m, 3H).

Example 142: 2-(4,6-Dimethoxypyrimidin-2-yl)-5-{[5-(2-fluorophenyl)-2-methyl-1,3-thiazol-4-yl]carbonyl}octahydropyrrolo[3,4-c]pyrrole

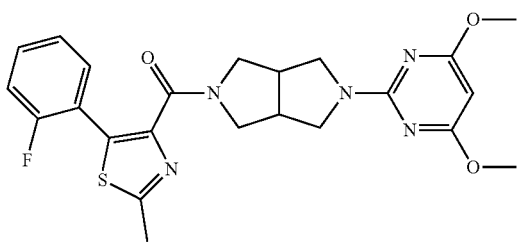 [SMILES: COc1cc(OC)nc(N2CC3CN(C(=O)c4nc(C)sc4-c4ccccc4F)CC3C2)n1]

The title compound was prepared in a manner analogous to Example 15 utilizing Intermediate 18 and 2-chloro-4,6-dimethoxypyrimidine. MS (ESI): mass calculated for C₂₃H₂₄FN₅O₃S, 469.54. m/z found 470.0 [M+H]⁺. ¹H NMR (400 MHz, CDCl₃): 7.47 (td, J=7.6, 1.7, 1H), 7.32-7.24 (m, 1H), 7.17-7.11 (m, 1H), 7.10-7.03 (m, 1H), 5.39 (s, 1H), 3.94-3.78 (m, 8H), 3.75-3.65 (m, 2H), 3.61 (dd, J=12.8, 4.3, 1H), 3.45-3.35 (m, 2H), 3.24 (dd, J=11.4, 5.4, 1H), 3.02-2.85 (m, 2H), 2.72 (s, 3H).

Example 143: 2-(4-Thiophen-2-ylpyrimidin-2-yl)-5-{[2-(2H-1,2,3-triazol-2-yl)phenyl]carbonyl} octahydropyrrolo[3,4-c]pyrrole

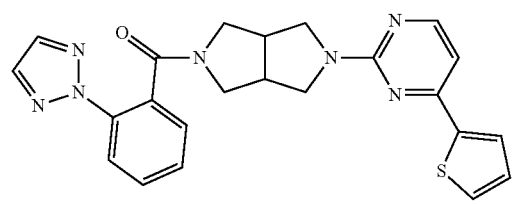 [SMILES: O=C(c1ccccc1-n1nccn1)N1CC2CN(c3nccc(-c4cccs4)n3)CC2C1]

The title compound was prepared in a manner analogous to Example 15 utilizing Intermediate 20 and 2-chloro-4-thiophen-2-yl-pyrimidine. MS (ESI): mass calculated for C₂₃H₂₁N₇OS, 443.53. m/z found 444.1 [M+H]⁺. ¹H NMR (400 MHz, CDCl₃): 8.35-8.25 (m, 1H), 7.98 (d, J=8.1, 1H), 7.80-7.63 (m, 3H), 7.56-7.38 (m, 4H), 7.18-7.09 (m, 1H), 6.85 (d, J=5.2, 1H), 4.00-3.35 (m, 7H), 3.13-2.89 (m, 3H).

Example 144: 2-[5-{[2-(2H-1,2,3-Triazol-2-yl)phenyl]carbonyl}hexahydropyrrolo[3,4-c]pyrrol-2(1H)-yl]-1,3-benzoxazole

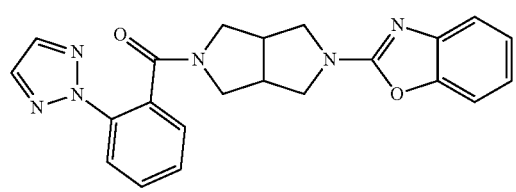 [SMILES: O=C(c1ccccc1-n1nccn1)N1CC2CN(c3nc4ccccc4o3)CC2C1]

The title compound was prepared in a manner analogous to Example 15 utilizing Intermediate 20 and 2-chlorobenzooxazole. MS (ESI): mass calculated for C₂₂H₂₀N₆O₂, 400.44. m/z found 401.2 [M+H]⁺. ¹H NMR (400 MHz, CDCl₃): 7.99 (d, J=8.1, 1H), 7.74 (s, 2H), 7.57-7.49 (m, 1H), 7.46-7.40 (m, 2H), 7.40-7.36 (m, 1H), 7.30-7.25 (m, 1H), 7.21-7.15 (m, 1H), 7.06-7.01 (m, 1H), 4.00-3.85 (m, 2H), 3.83-3.72 (m, 2H), 3.68-3.61 (m, 1H), 3.59-3.41 (m, 2H), 3.19-2.97 (m, 3H).

Example 145: 2-{5-[(2-Ethoxynaphthalen-1-yl)carbonyl]hexahydropyrrolo[3,4-c]pyrrol-2(1H)-yl}quinoxaline

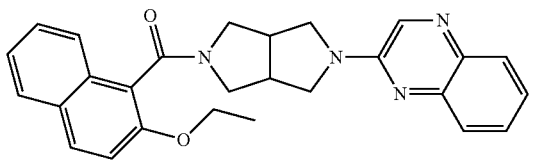 [SMILES: CCOc1ccc2ccccc2c1C(=O)N1CC2CN(c3cnc4ccccc4n3)CC2C1]

The title compound was prepared in a manner analogous to Example 15 utilizing 2-(hexahydro-pyrrolo[3,4-c]pyrrol-2-yl)-quinoxaline (Intermediate 35) and 2-ethoxy-naphthalene-1-carboxylic acid. MS (ESI): mass calculated for C₂₇H₂₆N₄O₂, 438.53. m/z found 439.2 [M+H]⁺. ¹H NMR (400 MHz, CDCl₃): 8.32 (d, J=16.4, 1H), 7.95-7.55 (m, 6H), 7.52-7.17 (m, 4H), 4.34-2.94 (m, 12H), 1.49-1.19 (m, 3H).

Example 146: 2-{5-[(5-Fluoro-2-pyrimidin-2-ylphenyl)carbonyl]hexahydropyrrolo[3,4-c]pyrrol-2(1H)-yl}quinoxaline

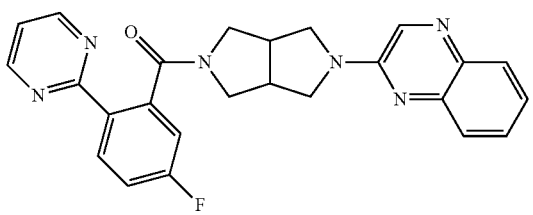 [SMILES: O=C(c1cc(F)ccc1-c1ncccn1)N1CC2CN(c3cnc4ccccc4n3)CC2C1]

The title compound was prepared in a manner analogous to Example 15 utilizing Intermediate 35 and Intermediate 13. MS (ESI): mass calculated for C₂₅H₂₁FN₆O, 440.48. m/z found 441.2 [M+H]⁺. ¹H NMR (400 MHz, CDCl₃): 8.71 (d, J=4.9, 2H), 8.37-8.30 (m, 2H), 7.92-7.88 (m, 1H), 7.72-7.69 (m, 1H), 7.63-7.57 (m, 1H), 7.43-7.37 (m, 1H), 7.23-7.17 (m, 1H), 7.11-7.05 (m, 2H), 4.03-3.93 (m, 2H), 3.87-3.70 (m, 3H), 3.67-3.56 (m, 2H), 3.26-3.03 (m, 3H).

Example 147: 2-(6-Ethoxypyridin-2-yl)-5-{[2-(2H-1,2,3-triazol-2-yl)phenyl]carbonyl}octahydro pyrrolo[3,4-c]pyrrole

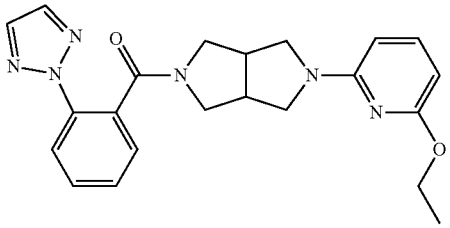 [SMILES: CCOc1cccc(N2CC3CN(C(=O)c4ccccc4-n4nccn4)CC3C2)n1]

The title compound was prepared in a manner analogous to Example 15 utilizing Intermediate 20 and 2-chloro-6-ethoxypyridine. MS (ESI): mass calculated for $C_{22}H_{24}N_6O_2$, 404.47. m/z found 405.2 [M+H]$^+$. $^1$H NMR (400 MHz, CDCl$_3$): 7.98 (d, J=8.1, 1H), 7.72 (s, 2H), 7.56-7.49 (m, 1H), 7.46-7.33 (m, 3H), 6.00 (d, J=7.7, 1H), 5.83 (d, J=7.9, 1H), 4.33-4.23 (m, 2H), 3.93-3.82 (m, 1H), 3.79-3.67 (m, 2H), 3.59-3.49 (m, 1H), 3.47-3.33 (m, 2H), 3.32-3.25 (m, 1H), 3.11-2.86 (m, 3H), 1.38 (t, J=7.1, 3H).

Example 148: 2-[(5-Fluoro-2-pyrimidin-2-ylphenyl)carbonyl]-5-[4-(trifluoromethyl)pyrimidin-2-yl]octahydropyrrolo[3,4-c]pyrrole

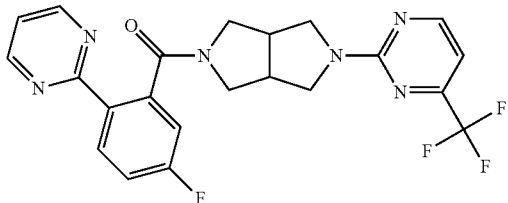 [SMILES: O=C(c1cc(F)ccc1-c1ncccn1)N1CC2CN(c3nccc(C(F)(F)F)n3)CC2C1]

The title compound was prepared in a manner analogous to Example 15 utilizing Intermediate 33 and Intermediate 13. MS (ESI): mass calculated for $C_{22}H_{18}F_4N_6O$, 459.42. m/z found 459.1 [M+H]$^+$. $^1$H NMR (400 MHz, CDCl$_3$): 8.74 (d, J=4.9, 2H), 8.60-8.28 (m, 2H), 7.23-7.04 (m, 3H), 6.84-6.75 (m, 1H), 4.03-2.97 (m, 10H).

Example 149: 2-[5-{[2-(2H-1,2,3-Triazol-2-yl)phenyl]carbonyl}hexahydropyrrolo[3,4-c]pyrrol-2(1H)-yl]quinoxaline

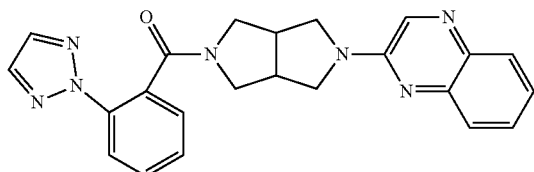

The title compound was prepared in a manner analogous to Example 15 utilizing Intermediate 20 and 2-chloroquinoxaline. MS (ESI): mass calculated for $C_{23}H_{21}N_7O$, 411.47. m/z found 412.2 [M+H]$^+$. $^1$H NMR (400 MHz, CDCl$_3$): 8.31 (s, 1H), 8.01-7.95 (m, 1H), 7.92-7.88 (m, 1H), 7.79-7.65 (m, 3H), 7.62-7.32 (m, 5H), 4.01-3.35 (m, 7H), 3.22-2.98 (m, 3H).

Example 150: 2-[(5-Fluoro-2-pyrimidin-2-ylphenyl)carbonyl]-5-(4-methoxypyrimidin-2-yl)octahydropyrrolo[3,4-c]pyrrole

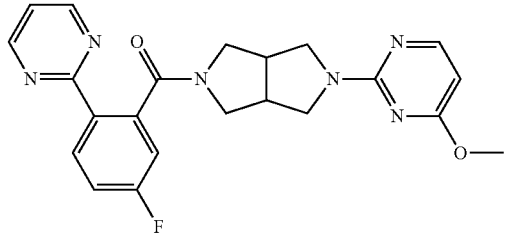 [SMILES: COc1ccnc(N2CC3CN(C(=O)c4cc(F)ccc4-c4ncccn4)CC3C2)n1]

The title compound was prepared in a manner analogous to Example 15 utilizing Intermediate 32 and Intermediate 13. MS (ESI): mass calculated for $C_{22}H_{21}FN_6O_2$, 420.45. m/z found 421.2 [M+H]$^+$. $^1$H NMR (400 MHz, CDCl$_3$): 8.73 (d, J=4.9, 2H), 8.35 (dd, J=8.8, 5.6, 1H), 8.06 (d, J=5.7, 1H), 7.23-7.02 (m, 3H), 6.01 (d, J=5.7, 1H), 4.01-3.43 (m, 10H), 3.23-2.90 (m, 3H).

Example 151: 2-(4-Furan-2-ylpyrimidin-2-yl)-5-{[2-(2H-1,2,3-triazol-2-yl)phenyl]carbonyl} octahydropyrrolo[3,4-c]pyrrole

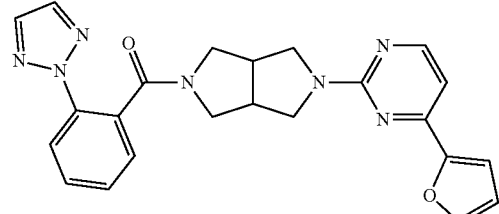

The title compound was prepared in a manner analogous to Example 15 utilizing Intermediate 20 and 2-chloro-4-furan-2-yl-pyrimidine. MS (ESI): mass calculated for $C_{23}H_{21}N_7OS$, 427.47. m/z found 428.2 [M+H]$^+$. $^1$H NMR (400 MHz, CDCl$_3$): 8.37-8.30 (m, 1H), 7.98 (d, J=8.1, 1H), 7.80-7.37 (m, 6H), 7.20-7.11 (m, 1H), 6.89 (d, J=5.1, 1H), 6.59-6.50 (m, 1H), 3.99-3.30 (m, 7H), 3.12-2.91 (m, 3H).

Example 152: 2-(5-Fluoropyridin-2-yl)-5-{[2-(2H-1,2,3-triazol-2-yl)phenyl]carbonyl}octahydro pyrrolo[3,4-c]pyrrole

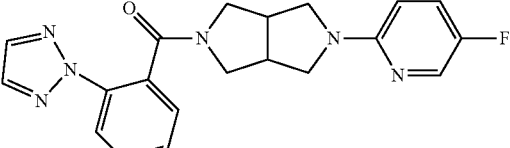

The title compound was prepared in a manner analogous to Example 15 utilizing Intermediate 20 and 2,5-difluoro-pyridine. MS (ESI): mass calculated for $C_{20}H_{19}FN_6O$, 378.41. m/z found 379.2 $[M+H]^+$. $^1H$ NMR (400 MHz, $CDCl_3$): 8.03 (d, J=3.0, 1H), 7.99 (d, J=8.1, 1H), 7.73 (br s, 2H), 7.58-7.37 (m, 3H), 7.30-7.18 (m, 1H), 6.26 (dd, J=9.1, 3.3, 1H), 3.95-3.84 (m, 1H), 3.77-3.24 (m, 6H), 3.13-2.89 (m, 3H).

Example 153: 2-{[2-(2H-1,2,3-Triazol-2-yl)phenyl]carbonyl}-5-[4-(trifluoromethyl)pyrimidin-2-yl]octahydropyrrolo[3,4-c]pyrrole

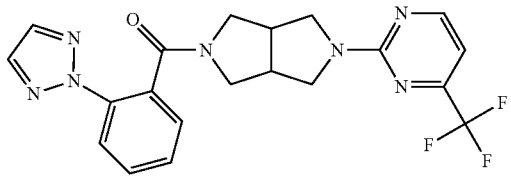 [SMILES: O=C(c1ccccc1-n1nccn1)N1CC2CN(c3nccc(C(F)(F)F)n3)CC2C1]

The title compound was prepared in a manner analogous to Example 15 utilizing Intermediate 20 and 2-chloro-4-trifluoromethyl-pyrimidine. MS (ESI): mass calculated for $C_{20}H_{18}F_3N_7O$, 429.40. m/z found 430.1 $[M+H]^+$. $^1H$ NMR (400 MHz, $CDCl_3$): 8.58-8.40 (m, 1H), 7.99 (d, J=8.1, 1H), 7.75 (br s, 2H), 7.56-7.48 (m, 1H), 7.45-7.39 (m, 2H), 6.80 (d, J=4.9, 1H), 3.99-3.29 (m, 7H), 3.19-2.91 (m, 3H).

Example 154: 2-(4-Methoxypyrimidin-2-yl)-5-{[2-(1H-1,2,4-triazol-5-yl)phenyl]carbonyl} octahydro-pyrrolo[3,4-c]pyrrole

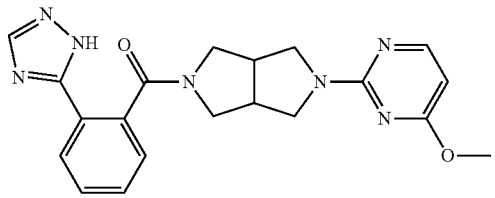 [SMILES: COc1ccnc(N2CC3CN(C(=O)c4ccccc4-c4ncn[nH]4)CC3C2)n1]

The title compound was prepared in a manner analogous to Example 15 utilizing Intermediate 32 and 2-(4H-[1,2,4]triazol-3-yl)-benzoic acid. MS (ESI): mass calculated for $C_{20}H_{21}N_7O$, 391.44. m/z found 392.2 $[M+H]^+$. $^1H$ NMR (400 MHz, $CDCl_3$): 8.16-7.92 (m, 3H), 7.55-7.44 (m, 2H), 7.39-7.34 (m, 1H), 6.00 (d, J=5.8, 1H), 4.02-3.33 (m, 10H), 3.20-2.83 (m, 4H).

Example 155: 2-(3,6-Dimethylpyrazin-2-yl)-5-{[2-(2H-1,2,3-triazol-2-yl)phenyl]carbonyl}octa hydro-pyrrolo[3,4-c]pyrrole

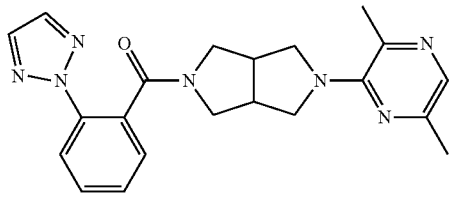 [SMILES: Cc1cnc(C)c(N2CC3CN(C(=O)c4ccccc4-n4nccn4)CC3C2)n1]

The title compound was prepared in a manner analogous to Example 15 utilizing Intermediate 20 and 3-chloro-2,5-dimethyl-pyrazine. MS (ESI): mass calculated for $C_{20}H_{21}N_7O_2$, 391.44. m/z found 390.2 $[M+H]^+$. $^1H$ NMR (400 MHz, $CDCl_3$): 8.00 (d, J=8.1, 1H), 7.88-7.67 (m, 3H), 7.62-7.39 (m, 3H), 3.90 (dd, J=12.6, 7.6, 1H), 3.77 (dd, J=10.7, 7.5, 1H), 3.72-3.60 (m, 2H), 3.52 (dd, J=10.8, 5.1, 1H), 3.43-3.28 (m, 2H), 3.10-2.97 (m, 2H), 2.95-2.85 (m, 1H), 2.51 (s, 3H), 2.36 (s, 3H).

Example 156: 2-(4-Methoxypyrimidin-2-yl)-5-{[2-(2H-1,2,3-triazol-2-yl)phenyl]carbonyl}octahydropyrrolo[3,4-c]pyrrole

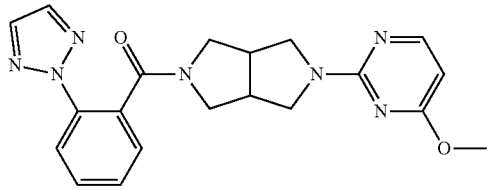 [SMILES: COc1ccnc(N2CC3CN(C(=O)c4ccccc4-n4nccn4)CC3C2)n1]

The title compound was prepared in a manner analogous to Example 15 utilizing Intermediate 20 and 2-chloro-4-methoxypyrimidine. MS (ESI): mass calculated for $C_{20}H_{21}N_7O_2$, 391.43. m/z found 392.2 $[M+H]^+$. $^1H$ NMR (400 MHz, $CDCl_3$): 8.08-8.03 (m, 1H), 7.99 (d, J=8.1, 1H), 7.75 (s, 2H), 7.57-7.48 (m, 1H), 7.44-7.41 (m, 2H), 6.00 (d, J=5.7, 1H), 3.97-3.79 (m, 5H), 3.77-3.63 (m, 2H), 3.61-3.53 (m, 1H), 3.50-3.30 (m, 2H), 3.09-2.89, (m, 3H).

Example 157: 2-{[5-Chloro-2-(2H-1,2,3-triazol-2-yl)phenyl]carbonyl}-5-(4,6-dimethylpyrimidin-2-yl)octahydropyrrolo[3,4-c]pyrrole

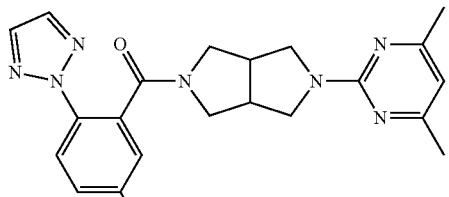

The title compound was prepared in a manner analogous to Example 15 utilizing Intermediate 23 and Intermediate 9. MS (ESI): mass calculated for $C_{21}H_{22}ClN_7O$, 423.91. m/z found 424.2 $[M+H]^+$. $^1H$ NMR (400 MHz, $CDCl_3$): 7.95 (d, J=8.7, 1H), 7.74 (s, 2H), 7.48 (dd, J=8.7, 2.3, 1H), 7.40 (d, J=2.3, 1H), 6.30 (s, 1H), 3.94-3.81 (m, 2H), 3.75-3.57 (m, 3H), 3.55-3.29 (m, 2H), 3.11-2.78 (m, 3H), 2.30 (s, 6H).

Example 158: 2-{[4-Fluoro-2-(2H-1,2,3-triazol-2-yl)phenyl]carbonyl}-5-(6-methylpyrazin-2-yl)octahydropyrrolo[3,4-c]pyrrole

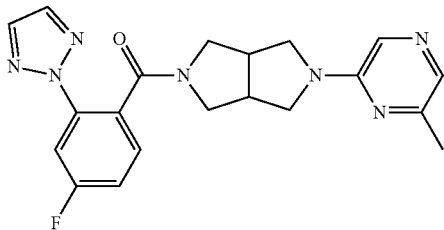 [SMILES: Cc1cncc(N2CC3CN(C(=O)c4ccc(F)cc4-n4nccn4)CC3C2)n1]

The title compound was prepared in a manner analogous to Example 15 utilizing Intermediate 22 and 2-chloro-6-methyl-pyrazine. MS (ESI): mass calculated for $C_{20}H_{20}FN_7O$, 393.43. m/z found 394.2 [M+H]$^+$. $^1$H NMR (400 MHz, CDCl$_3$): 7.82-7.69 (m, 4H), 7.64 (s, 1H), 7.40 (dd, J=8.5, 5.8, 1H), 7.17-7.10 (m, 1H), 3.97-3.83 (m, 1H), 3.81-3.68 (m, 2H), 3.65-3.55 (m, 1H), 3.53-3.29 (m, 3H), 3.18-2.88 (m, 3H), 2.38 (s, 3H).

Example 159: 2-{[4-Fluoro-2-(2H-1,2,3-triazol-2-yl)phenyl]carbonyl}-5-(4-methoxypyrimidin-2-yl)octahydropyrrolo[3,4-c]pyrrole

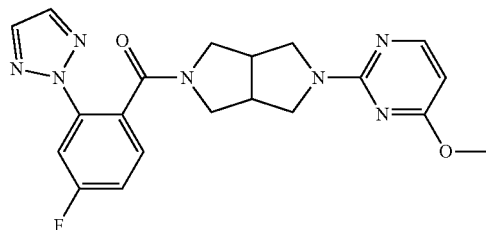 [SMILES: COc1ccnc(N2CC3CN(C(=O)c4ccc(F)cc4-n4nccn4)CC3C2)n1]

The title compound was prepared in a manner analogous to Example 15 utilizing Intermediate 22 and 2-chloro-4-methoxypyrimidine. MS (ESI): mass calculated for $C_{20}H_{20}FN_7O_2$, 409.43. m/z found 388.3 [M+H]$^+$. $^1$H NMR (400 MHz, CDCl$_3$): 8.06 (d, J=5.7, 1H), 7.88-7.62 (m, 3H), 7.45-7.37 (m, 1H), 7.18-7.10 (m, 1H), 6.01 (d, J=5.7, 1H), 4.00-3.81 (m, 5H), 3.70 (dd, J=20.4, 8.4, 2H), 3.62-3.53 (m, 1H), 3.51-3.28 (m, 2H), 3.13-2.84 (m, 3H).

Example 160: 2-(4,6-Dimethoxypyrimidin-2-yl)-5-{[4-fluoro-2-(2H-1,2,3-triazol-2-yl)phenyl]carbonyl}octahydropyrrolo[3,4-c]pyrrole

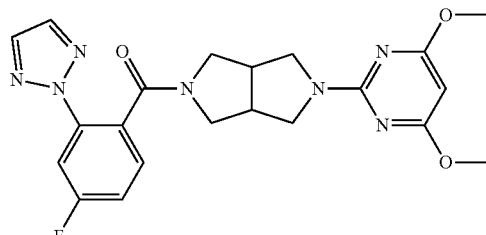

The title compound was prepared in a manner analogous to Example 15 utilizing Intermediate 22 and 2-chloro-4,6-dimethoxypyrimidine. MS (ESI): mass calculated for $C_{21}H_{22}FN_7O_3$, 439.45. m/z found 440.2 [M+H]$^+$. $^1$H NMR (400 MHz, CDCl$_3$): 7.86-7.66 (m, 3H), 7.47-7.34 (m, 1H), 7.17-7.06 (m, 1H), 5.40 (s, 1H), 3.98-3.77 (m, 8H), 3.76-3.61 (m, 2H), 3.60-3.52 (m, 1H), 3.50-3.29 (m, 2H), 3.09-2.84 (m, 3H).

Example 161: [5-(4,6-Dimethyl-pyrimidin-2-yl)-hexahydro-pyrrolo[3,4-c]pyrrol-2-yl]-(5-methoxy-2-[1,2,3]triazol-2-yl-phenyl)-methanone

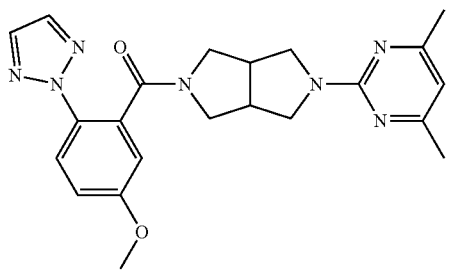 [SMILES: COc1ccc(-n2nccn2)c(C(=O)N2CC3CN(c4nc(C)cc(C)n4)CC3C2)c1]

The title compound was prepared in a manner analogous to Example 15 utilizing Intermediate 23 and Intermediate 10. MS (ESI): mass calculated for $C_{22}H_{25}N_7O_2$, 419.49. m/z found 420.3 [M+H]$^+$. $^1$H NMR (400 MHz, CDCl$_3$): 7.85 (d, 1H), 7.74-7.64 (m, 2H), 7.07-6.99 (m, 1H), 6.94-6.88 (m, 1H), 6.27 (s, J=20.0, 1H), 3.94-3.75 (m, 5H), 3.73-3.25 (m, 5H), 3.08-2.81 (m, 3H), 2.32-2.27 (m, 6H).

Example 162: (2-Fluoro-6-[1,2,3]triazol-2-yl-phenyl)-[5-(4-methoxy-pyrimidin-2-yl)-hexahydro-pyrrolo[3,4-c]pyrrol-2-yl]-methanone

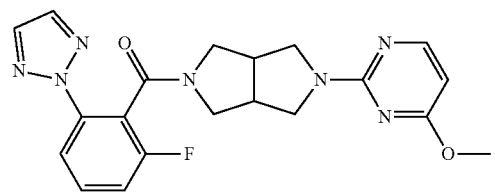 [SMILES: COc1ccnc(N2CC3CN(C(=O)c4c(F)cccc4-n4nccn4)CC3C2)n1]

The title compound was prepared in a manner analogous to Example 15 utilizing Intermediate 12 and 2-chloro-4-methoxypyrimidine. MS (ESI): mass calculated for $C_{20}H_{20}FN_7O_2$, 409.42. m/z found 410.2 [M+H]$^+$. $^1$H NMR (400 MHz, CDCl$_3$): 8.10-8.01 (m, 1H), 7.92-7.78 (m, 2H), 7.73 (s, 1H), 7.53-7.41 (m, 1H), 7.19-7.06 (m, 1H), 6.03-5.97 (m, 1H), 4.02-3.46 (m, 10H), 3.33-3.20 (m, 1H), 3.16-2.88 (m, 2H).

Example 163: 6-Chloro-2-{5-[(2,4-dimethoxyphenyl)carbonyl]hexahydropyrrolo[3,4-c]pyrrol-2(1H)-yl}-1,3-benzothiazole

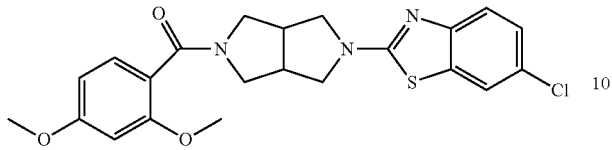

The title compound was prepared in a manner analogous to Example 15 utilizing Intermediate 40 and 2,4-dimethoxybenzoic acid. MS (ESI): mass calculated for $C_{22}H_{22}ClN_3O_3S$, 443.96. m/z found 444.2 [M+H]$^+$.

Example 164: 2-(Biphenyl-2-ylcarbonyl)-5-(4-phenylpyrimidin-2-yl)octahydropyrrolo[3,4-c]pyrrole

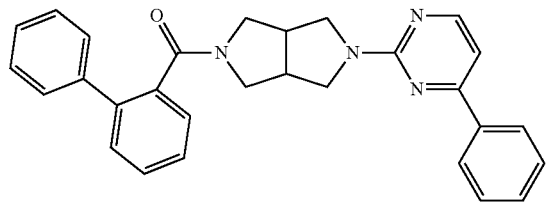 [SMILES: O=C(c1ccccc1-c1ccccc1)N1CC2CN(c3nccc(-c4ccccc4)n3)CC2C1]

The title compound was prepared in a manner analogous to Example 15 utilizing Intermediate 26 and biphenyl-2-carboxylic acid. MS (ESI) mass calcd. for $C_{29}H_{26}N_4O$, 446.56. m/z found, 447.3 [M+H]$^+$.

Example 165: 2-{5-[(2,6-Dimethoxyphenyl)carbonyl]hexahydropyrrolo[3,4-c]pyrrol-2(1H)-yl}quinoxaline

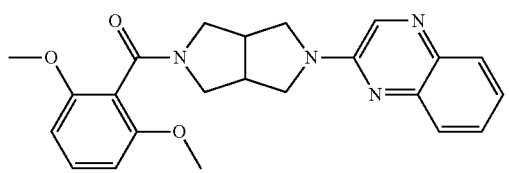 [SMILES: COc1cccc(OC)c1C(=O)N1CC2CN(c3cnc4ccccc4n3)CC2C1]

The title compound was prepared in a manner analogous to Example 15 utilizing Intermediate 35 and 2,6-dimethoxybenzoic acid. MS (ESI) mass calcd. for $C_{23}H_{24}N_4O_3$, 404.47. m/z found, 405.3 [M+H]$^+$.

Example 166: 2-[(2,6-Dimethoxyphenyl)carbonyl]-5-(4-phenylpyrimidin-2-yl)octahydropyrrolo [3,4-c]pyrrole

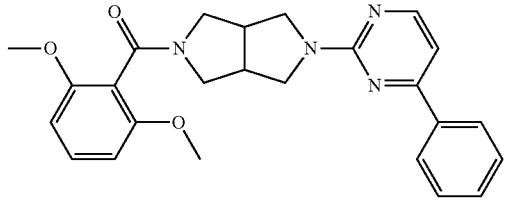 [SMILES: COc1cccc(OC)c1C(=O)N1CC2CN(c3nccc(-c4ccccc4)n3)CC2C1]

The title compound was prepared in a manner analogous to Example 15 utilizing Intermediate 26 and 2,6-dimethoxybenzoic acid. MS (ESI) mass calcd. for $C_{25}H_{26}N_4O_3$, 430.51. m/z found, 431.2 [M+H]$^+$.

Example 167: 2-[(2,4-Dimethoxyphenyl)carbonyl]-5-(4-phenylpyrimidin-2-yl)octahydropyrrolo[3,4-c]pyrrole

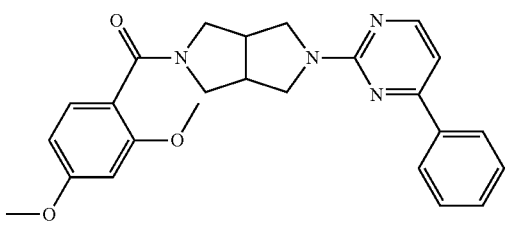 [SMILES: COc1ccc(C(=O)N2CC3CN(c4nccc(-c5ccccc5)n4)CC3C2)c(OC)c1]

The title compound was prepared in a manner analogous to Example 15 utilizing Intermediate 26 and 2,4-dimethoxybenzoic acid. MS (ESI) mass calcd. for $C_{25}H_{26}N_4O_3$, 430.51. m/z found, 431.2 [M+H]$^+$.

Example 168: 2-[5-(Biphenyl-2-ylcarbonyl)hexahydropyrrolo[3,4-c]pyrrol-2(1H)-yl]quinoxaline

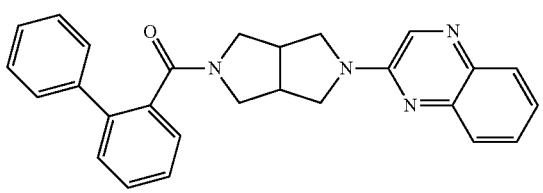 [SMILES: O=C(c1ccccc1-c1ccccc1)N1CC2CN(c3cnc4ccccc4n3)CC2C1]

The title compound was prepared in a manner analogous to Example 15 utilizing Intermediate 35 and biphenyl-2-carboxylic acid. MS (ESI) mass calcd. for $C_{27}H_{24}N_4O$, 420.52. m/z found, 421.3 [M+H]$^+$.

Example 169: 2-[5-(Biphenyl-2-ylcarbonyl)hexahydropyrrolo[3,4-c]pyrrol-2(1H)-yl]-1,3-benzothiazole

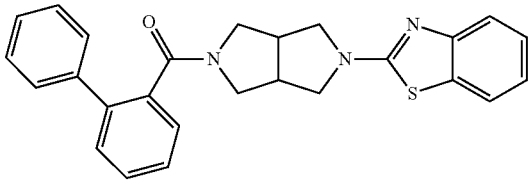 [SMILES: O=C(c1ccccc1-c1ccccc1)N1CC2CN(c3nc4ccccc4s3)CC2C1]

The title compound was prepared in a manner analogous to Example 15 utilizing Intermediate 17 and 2-chlorobenzothiazole. MS (ESI) mass calcd. for $C_{26}H_{23}N_3OS$, 425.56. m/z found, 426.2 [M+H]$^+$.

Example 170: 2-{5-[(2,4-Dimethoxyphenyl)carbonyl]hexahydropyrrolo[3,4-c]pyrrol-2(1H)-yl}-4-methylquinoline

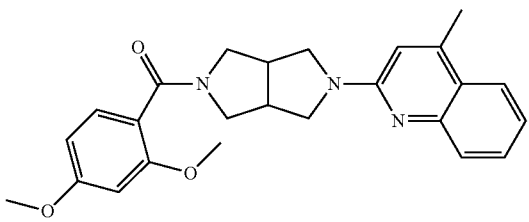 [SMILES: COc1ccc(C(=O)N2CC3CN(c4cc(C)c5ccccc5n4)CC3C2)c(OC)c1]

The title compound was prepared in a manner analogous to Example 15 utilizing Intermediate 38 and 2-chloro-4-methyl-quinoline. MS (ESI) mass calcd. for $C_{25}H_{27}N_3O_3$, 417.51. m/z found, 418.3 [M+H]$^+$.

Example 171: 2-{5-[(2,4-Dimethoxyphenyl)carbonyl]hexahydropyrrolo[3,4-c]pyrrol-2(1H)-yl}-6-methoxy-1,3-benzothiazole

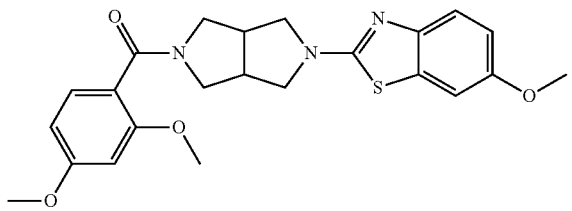

The title compound was prepared in a manner analogous to Example 15 utilizing Intermediate 38 and 2-chloro-6-methoxy-benzothiazole. MS (ESI) mass calcd. for $C_{23}H_{25}N_3O_4S$, 439.54. m/z found, 440.2 [M+H]$^+$.

Example 172: 2-{5-[(2,4-Dimethoxyphenyl)carbonyl]hexahydropyrrolo[3,4-c]pyrrol-2(1H)-yl}-6-methyl-1,3-benzothiazole

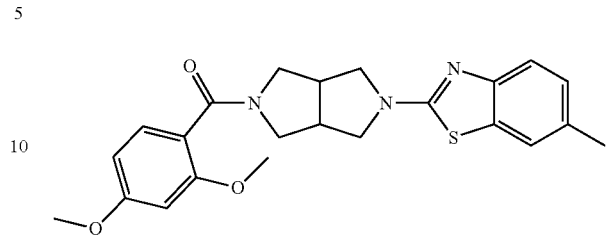

The title compound was prepared in a manner analogous to Example 15 utilizing Intermediate 38 and 2-chloro-6-methyl-benzothiazole. MS (ESI) mass calcd. for $C_{23}H_{25}N_3O_3S$, 423.54. m/z found, 424.2 [M+H]$^+$.

Example 173: 2-(Biphenyl-2-ylcarbonyl)-5-(6-methylpyridin-2-yl)octahydropyrrolo[3,4-c]pyrrole

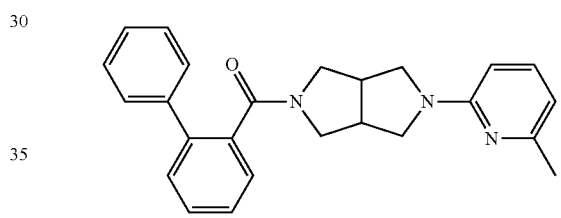

The title compound was prepared in a manner analogous to Example 15 utilizing Intermediate 17 and 2-chloro-6-methyl-pyridine. MS (ESI) mass calcd. for $C_{25}H_{25}N_4 _3O$, 383.5. m/z found, 384.3 [M+H]$^+$.

Example 174: 2-(Biphenyl-2-ylcarbonyl)-5-(4-methylpyrimidin-2-yl)octahydropyrrolo[3,4-c]pyrrole

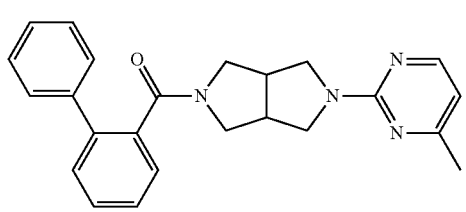 [SMILES: Cc1ccnc(N2CC3CN(C(=O)c4ccccc4-c4ccccc4)CC3C2)n1]

The title compound was prepared in a manner analogous to Example 15 utilizing Intermediate 17 and 2-chloro-4-methyl-pyrimidine. MS (ESI) mass calcd. for $C_{24}H_{24}N_4O$, 384.49. m/z found, 385.2 [M+H]$^+$.

Example 175: 2-[5-(Biphenyl-2-ylcarbonyl)hexahydropyrrolo[3,4-c]pyrrol-2(1H)-yl]quinoline

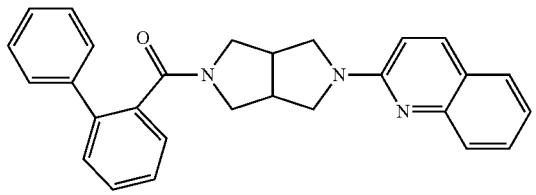 [SMILES: O=C(c1ccccc1-c1ccccc1)N1CC2CN(c3ccc4ccccc4n3)CC2C1]

The title compound was prepared in a manner analogous to Example 15 utilizing Intermediate 17 and 2-chloro-quinoline. MS (ESI) mass calcd. for $C_{28}H_{25}N_3O$, 419.53. m/z found, 420.3 $[M+H]^+$.

Example 176: 2-[5-(Biphenyl-2-ylcarbonyl)hexahydropyrrolo[3,4-c]pyrrol-2(1H)-yl]-6-fluoro-1,3-benzothiazole

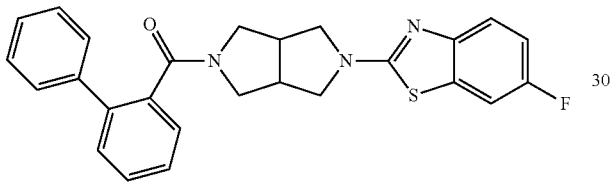

The title compound was prepared in a manner analogous to Example 15 utilizing Intermediate 17 and 2-chloro-6-fluoro-benzothiazole. MS (ESI) mass calcd. for $C_{26}H_{22}FN_3OS$, 443.55. m/z found, 444.2 $[M+H]^+$.

Example 177: 2-(Biphenyl-2-ylcarbonyl)-5-(4-methoxypyrimidin-2-yl)octahydropyrrolo[3,4-c]pyrrole

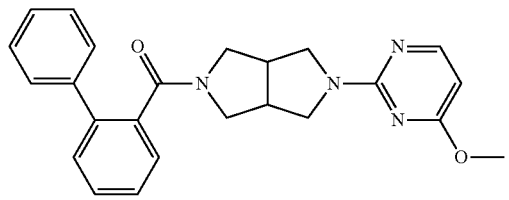 [SMILES: COc1ccnc(N2CC3CN(C(=O)c4ccccc4-c4ccccc4)CC3C2)n1]

The title compound was prepared in a manner analogous to Example 15 utilizing Intermediate 17 and 2-chloro-4-methoxypyrimidine. MS (ESI) mass calcd. for $C_{24}H_{24}N_4O_2$, 400.48. m/z found, 401.2 $[M+H]^+$.

Example 178: 2-[5-(Biphenyl-2-ylcarbonyl)hexahydropyrrolo[3,4-c]pyrrol-2(1H)-yl]-4-methylquinoline

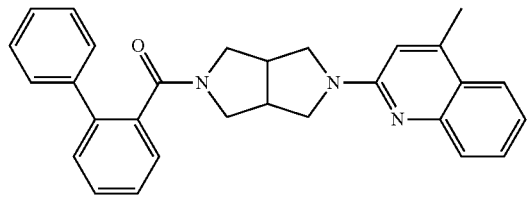 [SMILES: Cc1cc(N2CC3CN(C(=O)c4ccccc4-c4ccccc4)CC3C2)nc2ccccc12]

The title compound was prepared in a manner analogous to Example 15 utilizing Intermediate 17 and 2-chloro-4-methyl-quinoline. MS (ESI) mass calcd. for $C_{29}H_{27}N_3O$, 433.56. m/z found, 434.3 $[M+H]^+$.

Example 179: (2,4-Dimethoxy-phenyl)-[5-(4-methoxy-pyrimidin-2-yl)-hexahydro-pyrrolo[3,4-c]pyrrol-2-yl]-methanone

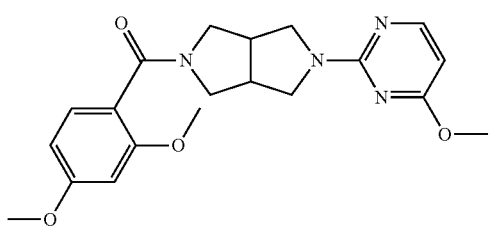

The title compound was prepared in a manner analogous to Example 15 utilizing Intermediate 38 and 2-chloro-4-methoxypyrimidine. MS (ESI): mass calculated for $C_{20}H_{24}N_4O_4$, 384.43. m/z found 385.2 $[M+H]^+$.

Example 180: (5-Benzooxazol-2-yl-hexahydro-pyrrolo[3,4-c]pyrrol-2-yl)-(2-methoxy-phenyl)-methanone

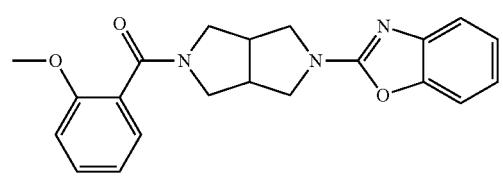 [SMILES: COc1ccccc1C(=O)N1CC2CN(c3nc4ccccc4o3)CC2C1]

The title compound was prepared in a manner analogous to Example 15 utilizing Intermediate 28 and 2-methoxybenzoic acid. MS (ESI): mass calculated for $C_{21}H_{21}N_3O_3$, 363.42. m/z found 364.2 $[M+H]^+$.

Example 181: (2-Pyridin-3-yl-phenyl)-(5-quinoxalin-2-yl-hexahydro-pyrrolo[3,4-c]pyrrol-2-yl)-methanone

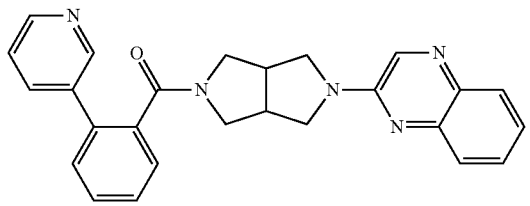 [SMILES: O=C(c1ccccc1-c1cccnc1)N1CC2CN(c3cnc4ccccc4n3)CC2C1]

The title compound was prepared in a manner analogous to Example 15 utilizing Intermediate 35 and 2-pyridin-3-yl-benzoic acid. MS (ESI): mass calculated for $C_{26}H_{23}N_5O$, 421.51. m/z found 422.3 [M+H]$^+$.

Example 182: [5-(4,6-Dimethyl-pyrimidin-2-yl)-hexahydro-pyrrolo[3,4-c]pyrrol-2-yl]-[2-(1H-imidazol-2-yl)-phenyl]-methanone

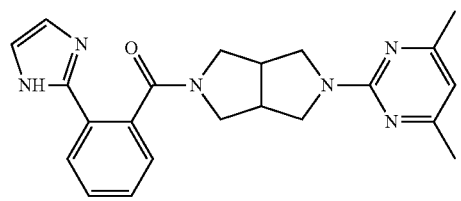 [SMILES: Cc1cc(C)nc(N2CC3CN(C(=O)c4ccccc4-c4ncc[nH]4)CC3C2)n1]

The title compound was prepared in a manner analogous to Example 15 utilizing Intermediate 23 and 2-(1H-imidazol-2-yl)-benzoic acid. MS (ESI) mass calcd. for $C_{22}H_{24}N_6O$, 388.47. m/z found, 398.2 [M+H]$^+$.

Example 183: (5-Benzooxazol-2-yl-hexahydro-pyrrolo[3,4-c]pyrrol-2-yl)-(2,4-dimethoxy-phenyl)-methanone

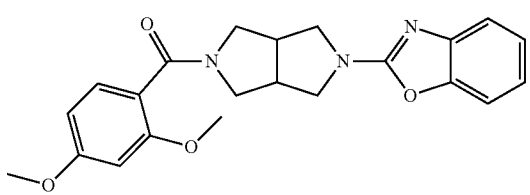 [SMILES: COc1ccc(C(=O)N2CC3CN(c4nc5ccccc5o4)CC3C2)c(OC)c1]

The title compound was prepared in a manner analogous to Example 15 utilizing Intermediate 28 and 2,4-dimethoxy-benzoic acid. MS (ESI): mass calculated for $C_{22}H_{23}N_3O_4$, 393.45. m/z found 394.2 [M+H]$^+$.

Example 184: (5-Benzooxazol-2-yl-hexahydro-pyrrolo[3,4-c]pyrrol-2-yl)-biphenyl-2-yl-methanone

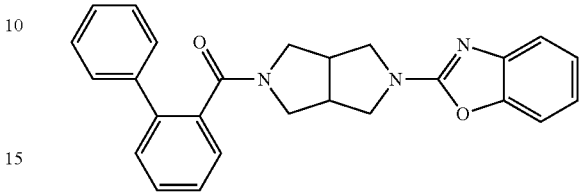

The title compound was prepared in a manner analogous to Example 15 utilizing Intermediate 17 and 2-chloro-benzooxazole. MS (ESI): mass calculated for $C_{26}H_{23}N_3O_2$, 409.49. m/z found 410.2 [M+H]$^+$.

Example 185: (2,4-Dimethoxy-phenyl)-[5-(6-methyl-pyridin-2-yl)-hexahydro-pyrrolo[3,4-c]pyrrol-2-yl]-methanone

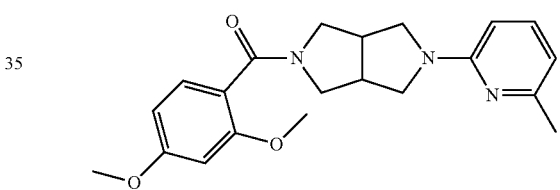

The title compound was prepared in a manner analogous to Example 15 utilizing Intermediate 38 and 2-chloro-6-methyl-pyridine. MS (ESI): mass calculated for $C_{21}H_{25}N_3O_3$, 367.45. m/z found 368.3 [M+H]$^+$.

Example 186: (2,4-Dimethoxy-phenyl)-[5-(4-methyl-pyrimidin-2-yl)-hexahydro-pyrrolo[3,4-c]pyrrol-2-yl]-methanone

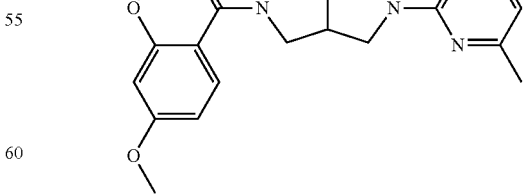

The title compound was prepared in a manner analogous to Example 15 utilizing Intermediate 38 and 2-chloro-4-methylpyrimidine. MS (ESI): mass calculated for $C_{20}H_{24}FN_4O_3$, 368.43. m/z found 369.3 [M+H]$^+$.

Example 187: Biphenyl-2-yl-[5-(6-methoxy-benzothiazol-2-yl)-hexahydro-pyrrolo[3,4-c]pyrrol-2-yl]-methanone

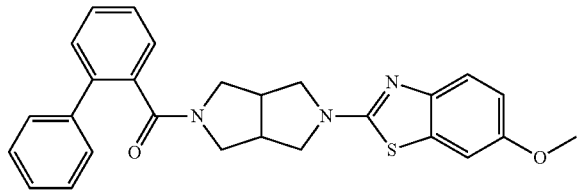 [SMILES: COc1ccc2nc(N3CC4CN(C(=O)c5ccccc5-c5ccccc5)CC4C3)sc2c1]

The title compound was prepared in a manner analogous to Example 15 utilizing Intermediate 17 and 2-chloro-6-methoxy-benzothiazole. MS (ESI): mass calculated for $C_{27}H_{25}N_3O_2S$, 455.57. m/z found 456.2 $[M+H]^+$.

Example 188: Biphenyl-2-yl-[5-(6-methyl-benzothiazol-2-yl)-hexahydro-pyrrolo[3,4-c]pyrrol-2-yl]-methanone

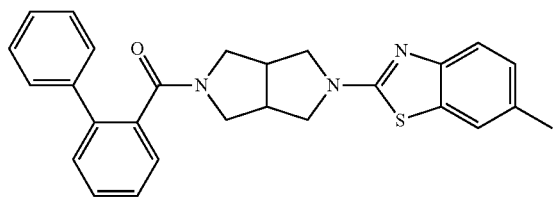 [SMILES: Cc1ccc2nc(N3CC4CN(C(=O)c5ccccc5-c5ccccc5)CC4C3)sc2c1]

The title compound was prepared in a manner analogous to Example 15 utilizing Intermediate 17 and 2-chloro-6-methyl-benzothiazole. MS (ESI): mass calculated for $C_{27}H_{25}N_3OS$, 439.57. m/z found 440.2 $[M+H]^+$.

Example 189: [5-(6-Chloro-benzothiazol-2-yl)-hexahydro-pyrrolo[3,4-c]pyrrol-2-yl]-(2,6-dimethoxy-phenyl)-methanone

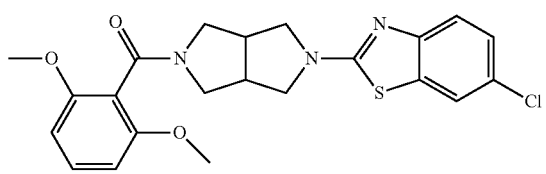 [SMILES: COc1cccc(OC)c1C(=O)N1CC2CN(c3nc4ccc(Cl)cc4s3)CC2C1]

The title compound was prepared in a manner analogous to Example 15 utilizing Intermediate 40 and 2,6-dimethoxy-benzoic acid. MS (ESI): mass calculated for $C_{22}H_{22}ClN_3O_3S$, 443.96. m/z found 444.2 $[M+H]^+$.

Example 190: Biphenyl-2-yl-[5-(6-chloro-benzothiazol-2-yl)-hexahydro-pyrrolo[3,4-c]pyrrol-2-yl]-methanone

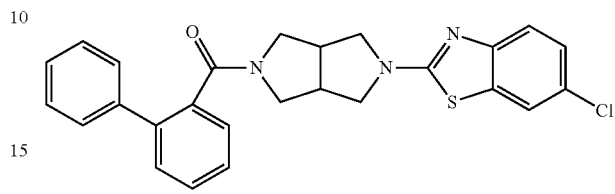

The title compound was prepared in a manner analogous to Example 15 utilizing Intermediate 40 and biphenyl-2-carboxylic acid. MS (ESI): mass calculated for $C_{26}H_{22}ClN_3O_3S$, 459.99. m/z found 460.2 $[M+H]^+$.

Example 191: (2,4-Dimethoxy-phenyl)-(5-quinoxalin-2-yl-hexahydro-pyrrolo[3,4-c]pyrrol-2-yl)-methanone

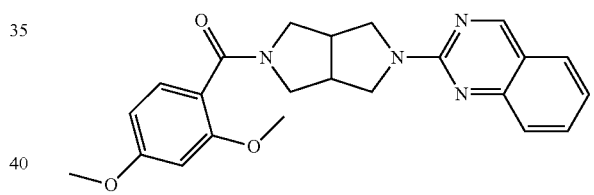

The title compound was prepared in a manner analogous to Example 15 utilizing Intermediate 35 and 2,4-dimethoxy-benzoic acid. MS (ESI): mass calculated for $C_{23}H_{24}N_4O_3$, 404.47. m/z found 405.3 $[M+H]^+$.

Example 192: (5-Benzooxazol-2-yl-hexahydro-pyrrolo[3,4-c]pyrrol-2-yl)-(2,6-dimethoxy-phenyl)-methanone

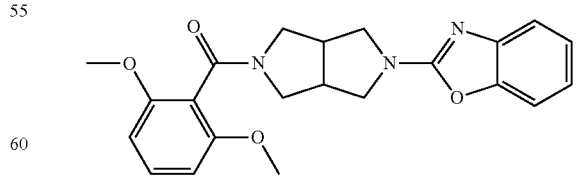

The title compound was prepared in a manner analogous to Example 15 utilizing Intermediate 41 and 2-chloro-benzooxazole. MS (ESI): mass calculated for $C_{22}H_{23}N_3O_4$, 393.45. m/z found 394.2 $[M+H]^+$.

Example 193: (4'-Methyl-biphenyl-2-yl)-(5-quinoxalin-2-yl-hexahydro-pyrrolo[3,4-c]pyrrol-2-yl)-methanone

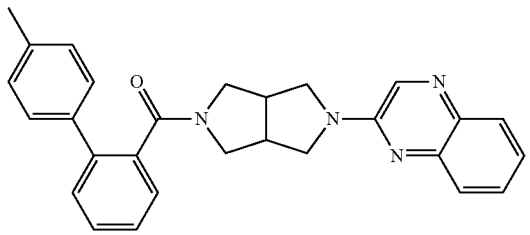 [SMILES: Cc1ccc(-c2ccccc2C(=O)N2CC3CN(c4cnc5ccccc5n4)CC3C2)cc1]

The title compound was prepared in a manner analogous to Example 15 utilizing Intermediate 35 and 4'-methyl-biphenyl-2-carboxylic acid. MS (ESI): mass calculated for $C_{28}H_{26}N_4O$, 434.55. m/z found 435.3 [M+H]$^+$.

Example 194: (5-Quinoxalin-2-yl-hexahydro-pyrrolo[3,4-c]pyrrol-2-yl)-(4'-trifluoromethyl-biphenyl-2-yl)-methanone

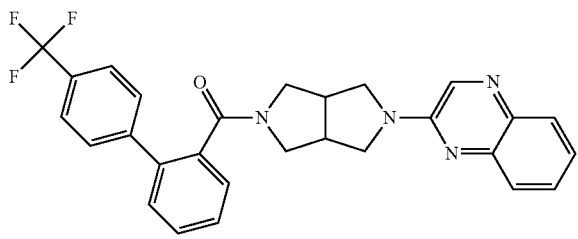 [SMILES: O=C(c1ccccc1-c1ccc(C(F)(F)F)cc1)N1CC2CN(c3cnc4ccccc4n3)CC2C1]

The title compound was prepared in a manner analogous to Example 15 utilizing Intermediate 35 and 4'-trifluoromethyl-biphenyl-2-carboxylic acid. MS (ESI): mass calculated for $C_{28}H_{23}F_3N_4O$, 488.50. m/z found 489.2 [M+H]$^+$.

Example 195: (4'-Methyl-biphenyl-2-yl)-[5-(4-phenyl-pyrimidin-2-yl)-hexahydro-pyrrolo[3,4-c]pyrrol-2-yl]-methanone

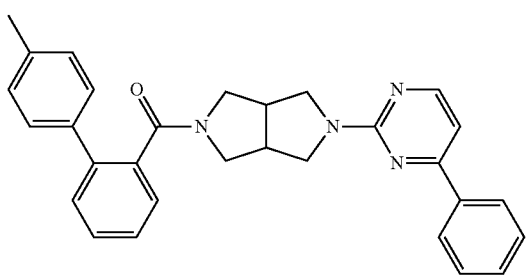 [SMILES: Cc1ccc(-c2ccccc2C(=O)N2CC3CN(c4nccc(-c5ccccc5)n4)CC3C2)cc1]

The title compound was prepared in a manner analogous to Example 15 utilizing Intermediate 26 and 4'-methyl-biphenyl-2-carboxylic acid. MS (ESI): mass calculated for $C_{30}H_{28}N_4O$, 460.58. m/z found 461.3 [M+H]$^+$.

Example 196: [5-(4-Phenyl-pyrimidin-2-yl)-hexahydro-pyrrolo[3,4-c]pyrrol-2-yl]-(4'-trifluoromethyl-biphenyl-2-yl)-methanone

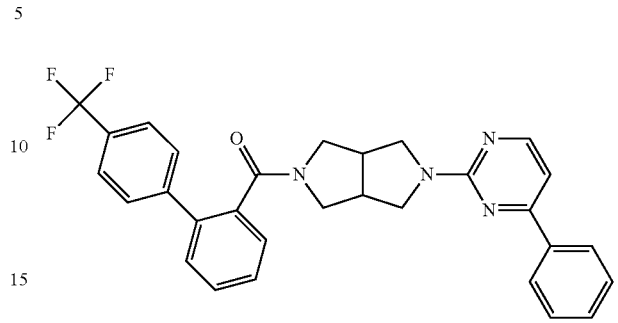

The title compound was prepared in a manner analogous to Example 15 utilizing Intermediate 26 and 4'-trifluoromethyl-biphenyl-2-carboxylic acid. MS (ESI): mass calculated for $C_{30}H_{53}F_3N_4O$, 514.56. m/z found 515.3 [M+H]$^+$.

Example 197: (4-Methoxy-2-methyl-phenyl)-(5-quinoxalin-2-yl-hexahydro-pyrrolo[3,4-c]pyrrol-2-yl)-methanone

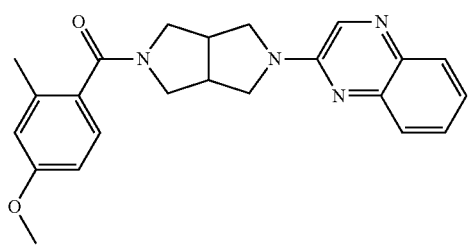 [SMILES: COc1ccc(C(=O)N2CC3CN(c4cnc5ccccc5n4)CC3C2)c(C)c1]

The title compound was prepared in a manner analogous to Example 15 utilizing Intermediate 35 and 4-methoxy-2-methyl-benzoic acid. MS (ESI): mass calculated for $C_{23}H_{24}N_4O_2$, 388.47. m/z found 389.2 [M+H]$^+$.

Example 198: (3'-Chloro-biphenyl-2-yl)-[5-(4-phenyl-pyrimidin-2-yl)-hexahydro-pyrrolo[3,4-c]pyrrol-2-yl]-methanone

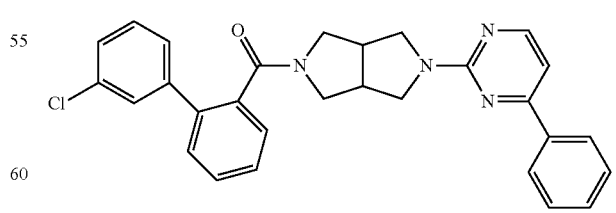

The title compound was prepared in a manner analogous to Example 15 utilizing Intermediate 26 and 3'-chloro-biphenyl-2-carboxylic acid. MS (ESI): mass calculated for $C_{29}H_{25}ClN_4O$, 480.99. m/z found 481.2 [M+H]$^+$.

Example 199: (2-Methoxy-phenyl)-[5-(4-methoxy-pyrimidin-2-yl)-hexahydro-pyrrolo[3,4-c]pyrrol-2-yl]-methanone

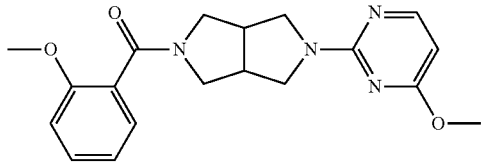

The title compound was prepared in a manner analogous to Example 15 utilizing Intermediate 32 and 2-methoxybenzoic acid. MS (ESI): mass calculated for $C_{19}H_{22}N_4O_3$, 354.41. m/z found 355.2 [M+H]$^+$.

Example 200: (2-Methoxy-phenyl)-[5-(4-methyl-pyrimidin-2-yl)-hexahydro-pyrrolo[3,4-c]pyrrol-2-yl]-methanone

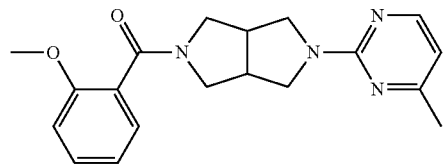

The title compound was prepared in a manner analogous to Example 15 utilizing Intermediate 27 and 2-methoxybenzoic acid. MS (ESI): mass calculated for $C_{19}H_{22}N_4O_2$, 338.41. m/z found 339.3 [M+H]$^+$.

Example 201: [5-(4,6-Dimethyl-pyrimidin-2-yl)-hexahydro-pyrrolo[3,4-c]pyrrol-2-yl]-(2-methoxy-phenyl)-methanone

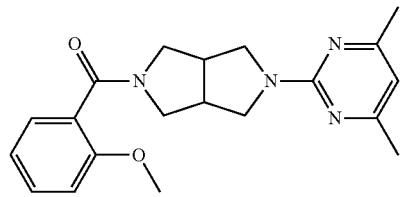 [SMILES: COc1ccccc1C(=O)N1CC2CN(c3nc(C)cc(C)n3)CC2C1]

The title compound was prepared in a manner analogous to Example 15 utilizing Intermediate 23 and 2-methoxybenzoic acid. MS (ESI): mass calculated for $C_{20}H_{24}N_4O_2$, 352.44. m/z found 353.3 [M+H]$^+$.

Example 202: 2-[5-(4,6-Dimethyl-pyrimidin-2-yl)-hexahydro-pyrrolo[3,4-c]pyrrole-2-carbonyl]-benzonitrile

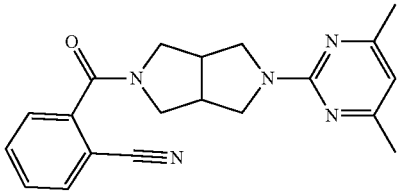 [SMILES: Cc1cc(C)nc(N2CC3CN(C(=O)c4ccccc4C#N)CC3C2)n1]

The title compound was prepared in a manner analogous to Example 15 utilizing Intermediate 23 and 2-cyanobenzoic acid. MS (ESI): mass calculated for $C_{20}H_{21}N_5O$, 347.42. m/z found 348.2 [M+H]$^+$. $^1$H NMR (400 MHz, CDCl$_3$): 8.51-8.39 (m, 2H), 7.37-7.32 (m, 1H), 7.25-7.06 (m, 3H), 6.76 (t, J=13.7 Hz, 1H), 4.18-3.96 (m, 3H), 3.48-3.33 (m, 1H), 3.05 (dd, J=12.9, 6.4 Hz, 1H), 2.69-2.27 (m, 10H), 1.68-1.50 (m, 5H), 1.50-1.37 (m, 3H).

Example 203: Cinnolin-4-yl-[5-(4,6-dimethyl-pyrimidin-2-yl)-hexahydro-pyrrolo[3,4-c]pyrrol-2-yl]-methanone

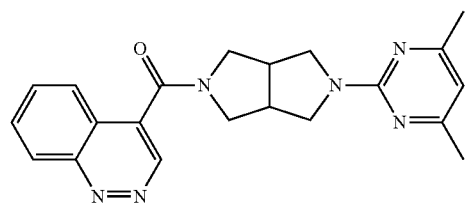 [SMILES: Cc1cc(C)nc(N2CC3CN(C(=O)c4cnnc5ccccc45)CC3C2)n1]

The title compound was prepared in a manner analogous to Example 15 utilizing Intermediate 23 and cinnoline-4-carboxylic acid. MS (ESI): mass calculated for $C_{21}H_{22}N_6O$, 374.45. m/z found 375.2 [M+H]$^+$. $^1$H NMR (400 MHz, CDCl$_3$): 9.26 (s, 1H), 8.61 (dd, J=8.4, 1.1 Hz, 1H), 7.96-7.85 (m, 2H), 7.83-7.74 (m, 1H), 6.33 (s, 1H), 4.13-4.07 (m, 1H), 3.92 (dd, J=11.7, 7.5 Hz, 1H), 3.84 (dd, J=13.0, 4.9 Hz, 1H), 3.78-3.68 (m, 2H), 3.54-3.42 (m, 2H), 3.20-3.09 (m, 2H), 3.04-2.98 (m, 1H), 2.29 (s, 6H).

Example 204: (5-Fluoro-2-pyrimidin-2-yl-phenyl)-[5-(6-methyl-2-trifluoromethyl-pyrimidin-4-yl)-hexahydro-pyrrolo[3,4-c]pyrrol-2-yl]-methanone

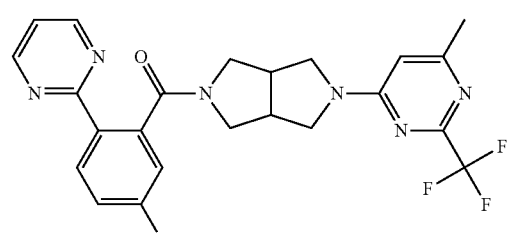

The title compound was prepared in a manner analogous to Example 15 utilizing Intermediate 13 and Intermediate 31. MS (ESI): mass calculated for $C_{23}H_{20}F_4N_6O$, 472.45. m/z found 473.2 $[M+H]^+$.

Example 205: [5-(4,6-Dimethyl-pyrimidin-2-yl)-hexahydro-pyrrolo[3,4-c]pyrrol-2-yl]-(2-[1,2,3]triazol-1-yl-phenyl)-methanone

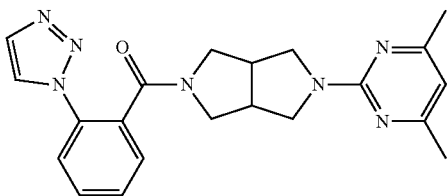 [SMILES: Cc1cc(C)nc(N2CC3CN(C(=O)c4ccccc4-n4ccnn4)CC3C2)n1]

The title compound was prepared in a manner analogous to Example 15 utilizing Intermediate 3 and Intermediate 15 as starting materials. In this case Intermediate C was coupled to Intermediate 15 first then the t-butylcarboxylate was removed prior to the addition of 2-chloro-4,6-methylpyrimidine. (ESI): mass calculated for $C_{21}H_{23}N_7O$, 389.46. m/z found 390.2 $[M+H]^+$. $^1$H NMR (400 MHz, CDCl$_3$): 7.99 (d, J=1.0 Hz, 1H), 7.79 (d, J=0.9 Hz, 1H), 7.67-7.62 (m, 1H), 7.62-7.52 (m, 2H), 7.49-7.45 (m, 1H), 7.27 (s, 1H), 3.87-3.65 (m, 3H), 3.54-3.44 (m, 2H), 3.38-3.25 (m, 2H), 3.04-2.78 (m, 3H), 2.29 (s, 6H).

Example 206: [5-(4,6-Dimethyl-pyrimidin-2-yl)-hexahydro-pyrrolo[3,4-c]pyrrol-2-yl]-(2-[1,2,4]triazol-1-yl-phenyl)-methanone

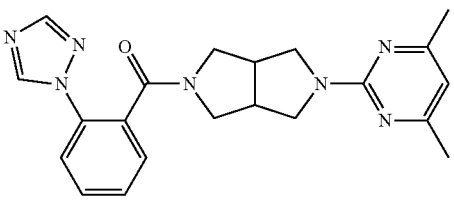 [SMILES: Cc1cc(C)nc(N2CC3CN(C(=O)c4ccccc4-n4cncn4)CC3C2)n1]

The title compound was prepared in a manner analogous to Example 15 utilizing Intermediate 23 and 2-(4H-[1,2,4]triazol-3-yl)-benzoic acid. MS (ESI) mass calcd. for $C_{21}H_{23}N_7O$, 389.46. m/z found, 390.2 $[M+H]^+$.

Example 207: [5-(4,6-Dimethoxy-pyrimidin-2-yl)-hexahydro-pyrrolo[3,4-c]pyrrol-2-yl]-(3-phenyl-pyridin-2-yl)-methanone

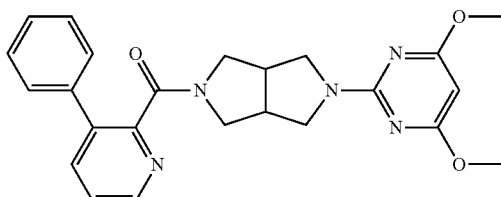

The title compound was prepared in a manner analogous to Example 15 utilizing Intermediate 39 and 3-phenyl-pyridine-2-carboxylic acid. MS (ESI): mass calculated for $C_{24}H_{25}N_5O_3$, 431.50. m/z found 432.3 $[M+H]^+$.

Example 208: [5-(4,6-Dimethyl-pyrimidin-2-yl)-hexahydro-pyrrolo[3,4-c]pyrrol-2-yl]-(3-phenyl-pyridin-2-yl)-methanone

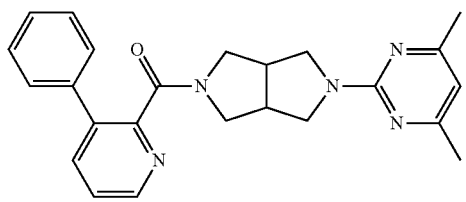 [SMILES: Cc1cc(C)nc(N2CC3CN(C(=O)c4ncccc4-c4ccccc4)CC3C2)n1]

The title compound was prepared in a manner analogous to Example 15 utilizing Intermediate 23 and 3-phenyl-pyridine-2-carboxylic acid. MS (ESI): mass calculated for $C_{24}H_{25}N_5O$, 399.5. m/z found 400.3 $[M+H]^+$.

Example 209: [5-(6-Methyl-2-propyl-pyrimidin-4-yl)-hexahydro-pyrrolo[3,4-c]pyrrol-2-yl]-(2-[1,2,3]triazol-2-yl-phenyl)-methanone

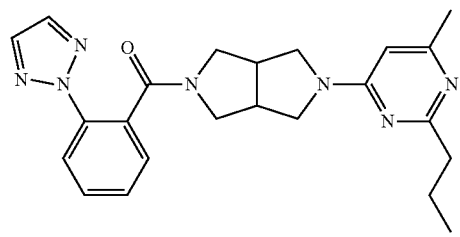 [SMILES: CCCc1nc(C)cc(N2CC3CN(C(=O)c4ccccc4-n4nccn4)CC3C2)n1]

The title compound was prepared in a manner analogous to Example 15 utilizing Intermediate 20 and 4-chloro-6-methyl-2-propyl-pyrimidine. MS (ESI): mass calculated for $C_{23}H_{27}N_7O$, 417.51. m/z found 418.2 $[M+H]^+$.

Example 210: [5-(2-Methyl-pyrimidin-4-yl)-hexahydro-pyrrolo[3,4-c]pyrrol-2-yl]-(2-[1,2,3]triazol-2-yl-phenyl)-methanone

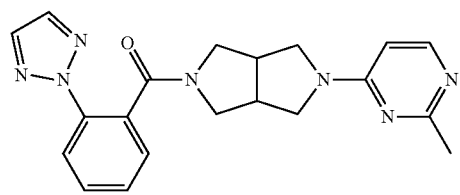 [SMILES: Cc1nccc(N2CC3CN(C(=O)c4ccccc4-n4nccn4)CC3C2)n1]

The title compound was prepared in a manner analogous to Example 15 utilizing Intermediate 20 and 4-chloro-2-methyl-pyrimidine. MS (ESI): mass calculated for $C_{20}H_{21}N_7O$, 375.43. m/z found 376.2 $[M+H]^+$.

Example 211: [5-(6-Methyl-pyrazin-2-yl)-hexahydro-pyrrolo[3,4-c]pyrrol-2-yl]-(2-[1,2,3]triazol-2-yl-phenyl)-methanone

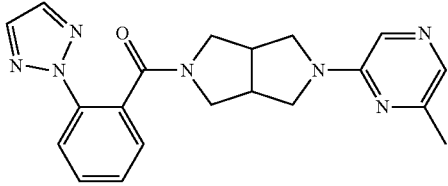 [SMILES: Cc1cncc(N2CC3CN(C(=O)c4ccccc4-n4nccn4)CC3C2)n1]

The title compound was prepared in a manner analogous to Example 15 utilizing Intermediate 20 and 2-chloro-6-methyl-pyrazine. MS (ESI): mass calculated for $C_{20}H_{21}N_7O$, 375.43. m/z found 376.2 $[M+H]^+$.

Example 212: [5-(3,6-Dimethyl-pyrazin-2-yl)-hexahydro-pyrrolo[3,4-c]pyrrol-2-yl]-(5-fluoro-2-pyrimidin-2-yl-phenyl)-methanone

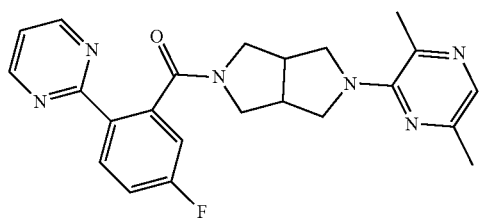 [SMILES: Cc1cnc(C)c(N2CC3CN(C(=O)c4cc(F)ccc4-c4ncccn4)CC3C2)n1]

The title compound was prepared in a manner analogous to Example 15 utilizing Intermediate 34 and Intermediate 13. MS (ESI): mass calculated for $C_{23}H_{23}FN_6O$, 418.47. m/z found 419.2 $[M+H]^+$.

Example 213: [5-(3,6-Dimethyl-pyrazin-2-yl)-hexahydro-pyrrolo[3,4-c]pyrrol-2-yl]-[2-(2H-[1,2,4]triazol-3-yl)-phenyl]-methanone

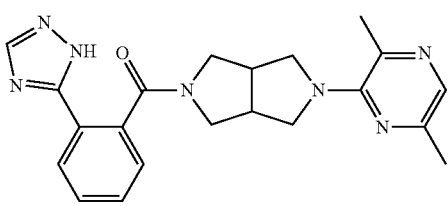 [SMILES: Cc1cnc(C)c(N2CC3CN(C(=O)c4ccccc4-c4ncn[nH]4)CC3C2)n1]

The title compound was prepared in a manner analogous to Example 15 utilizing Intermediate 34 and 2-(4H-[1,2,4]triazol-3-yl)-benzoic acid. MS (ESI): mass calculated for $C_{21}H_{23}N_7O$, 389.46. m/z found 390.2 $[M+H]^+$.

Example 214: [5-(2-Pyrrolidin-1-yl-6-trifluoromethyl-pyrimidin-4-yl)-hexahydro-pyrrolo[3,4-c]pyrrol-2-yl]-(2-[1,2,3]triazol-2-yl-phenyl)-methanone

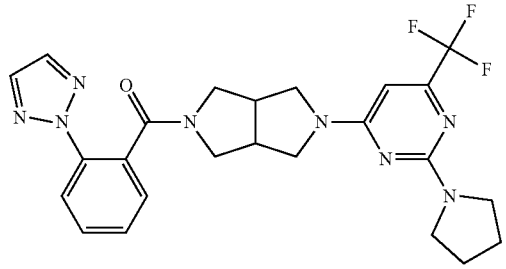 [SMILES: O=C(c1ccccc1-n1nccn1)N1CC2CN(c3cc(C(F)(F)F)nc(N4CCCC4)n3)CC2C1]

The title compound was prepared in a manner analogous to Example 15 utilizing Intermediate 20 and 4-chloro-2-pyrrolidin-1-yl-6-trifluoromethyl-pyrimidine acid. MS (ESI): mass calculated for $C_{24}H_{25}F_3N_5O$, 498.51. m/z found 499.2 $[M+H]^+$.

Example 215: 2-(2,6-Dimethylpyrimidin-4-yl)-5-{[5-fluoro-2-(2H-1,2,3-triazol-2-yl)phenyl]carbonyl}octahydropyrrolo[3,4-c]pyrrole

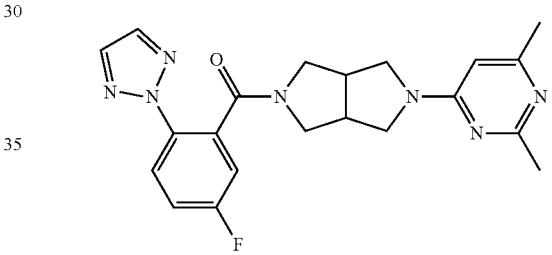

The title compound was prepared in a manner analogous to Intermediate 23, substituting (5-fluoro-2-(2H-1,2,3-triazol-2-yl)phenyl)(hexahydropyrrolo[3,4-c]pyrrol-2(1H)-yl)methanone (Intermediate 21) for hexahydro-pyrrolo[3,4-c]pyrrole-2-carboxylic acid tert-butyl ester and 4-chloro-2,6-dimethylpyrimidine for 2-chloro-4,6-dimethyl-pyrimidine in Step A. MS (ESI) mass calcd for $C_{21}H_{22}FN_7O$, 407.19. m/z found, 408.2 $[M+H]^+$.

Prophetic Examples 216-218 may be synthesized using the general schemes provided above.

Example 216: [5-(4,6-Dimethyl-pyrimidin-2-yl)-hexahydro-pyrrolo[3,4-c]pyrrol-2-yl]-(2-nitro-6-[1,2,3]triazol-2-yl-phenyl)-methanone

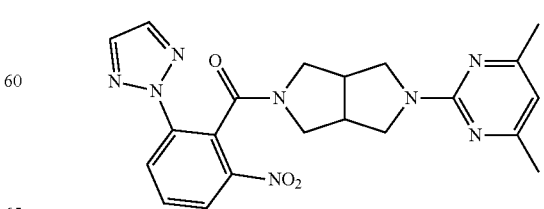

MS (ESI) mass calcd. for $C_{21}H_{22}N_8O_3$, 434.45.

Example 217: [5-(4,6-Dimethyl-pyrimidin-2-yl)-hexahydro-pyrrolo[3,4-c]pyrrol-2-yl]-(2-furan-2-yl-phenyl)-methanone

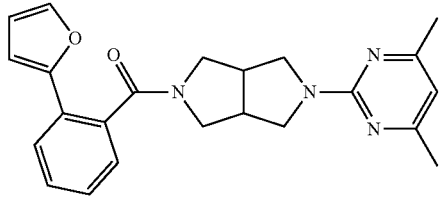 [SMILES: Cc1cc(C)nc(N2CC3CN(C(=O)c4ccccc4-c4ccco4)CC3C2)n1]

MS (ESI) mass calcd. for $C_{23}H_{24}N_4O_3$, 388.46.

Example 218: [5-(4,6-Dimethyl-pyrimidin-2-yl)-hexahydro-pyrrolo[3,4-c]pyrrol-2-yl]-(2-methyl-5-phenyl-thiazol-4-yl)-methanone

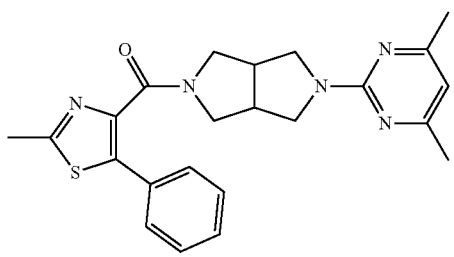

MS (ESI) mass calcd. for $C_{23}H_{25}N_5OS$, 419.54.

Example 219: 2-[(2,3-Dimethylphenyl)carbonyl]-5-(4,6-dimethylpyrimidin-2-yl)octahydropyrrolo[3,4-c]pyrrole

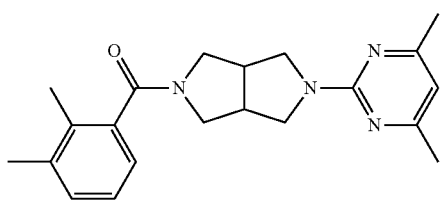

The title compound was prepared in a manner analogous to Example 15 utilizing Intermediate 23 and 2,3-dimethylbenzoic acid. MS (ESI): mass calculated for $C_{21}H_{26}N_4O$, 350.47. m/z found 351.3 [M+H]$^+$. $^1$H NMR (400 MHz, CDCl$_3$): 7.16-7.05 (m, 2H), 7.02 (d, J=7.1 Hz, 1H), 6.30 (s, 1H), 4.00-3.86 (m, 2H), 3.78 (dd, J=11.6, 7.4 Hz, 1H), 3.70-3.58 (m, 2H), 3.49-3.38 (m, 2H), 3.17-3.02 (m, 2H), 2.99-2.92 (m, 1H), 2.35-2.28 (s, 6H), 2.27 (s, 3H), 2.19 (s, 3H).

Example 220: 2-(4,6-Dimethylpyrimidin-2-yl)-5-[(3-fluoro-2-methylphenyl)carbonyl]octahydropyrrolo[3,4-c]pyrrole

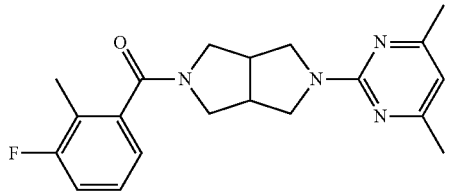 [SMILES: Cc1cc(C)nc(N2CC3CN(C(=O)c4cccc(F)c4C)CC3C2)n1]

The title compound was prepared in a manner analogous to Example 15 utilizing Intermediate 23 and 3-fluoro-2-methylbenzoic acid. MS (ESI): mass calculated for $C_{20}H_{23}FN_4O$, 354.4. m/z found 355.3 [M+H]$^+$. $^1$H NMR (400 MHz, CDCl$_3$): 7.22-7.14 (m, 1H), 7.06-6.95 (m, 2H), 6.30 (s, 1H), 4.00-3.86 (m, 2H), 3.78 (dd, J=11.6, 7.3 Hz, 1H), 3.70-3.58 (m, 2H), 3.52-3.39 (m, 2H), 3.19-3.02 (m, 2H), 3.02-2.92 (m, 1H), 2.30 (s, 6H), 2.21 (d, J=2.0 Hz, 3H).

Example 221: 2-(4,6-Dimethylpyrimidin-2-yl)-5-{[5-fluoro-2-(trifluoromethyl)phenyl]carbonyl}octahydropyrrolo[3,4-c]pyrrole

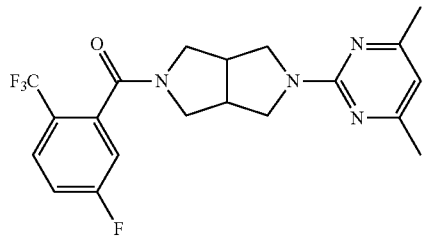 [SMILES: Cc1cc(C)nc(N2CC3CN(C(=O)c4cc(F)ccc4C(F)(F)F)CC3C2)n1]

The title compound was prepared in a manner analogous to Example 15 utilizing Intermediate 23 and 5-fluoro-2-(trifluoromethyl)benzoic acid. MS (ESI): mass calculated for $C_{20}H_{20}F_4N_4O$, 408.4. m/z found 409.2 [M+H]$^+$. $^1$H NMR (400 MHz, CDCl$_3$): 7.71 (dd, J=8.8, 5.0 Hz, 1H), 7.22-7.14 (m, 1H), 7.06 (dd, J=8.1, 2.3 Hz, 1H), 6.31 (s, 1H), 4.01-3.87 (m, 2H), 3.79 (dd, J=11.7, 7.3 Hz, 1H), 3.69-3.56 (m, 2H), 3.53-3.41 (m, 2H), 3.19-3.04 (m, 2H), 3.05-2.97 (m, 1H), 2.30 (s, 6H).

Example 222: 2-[(4-Chloro-2-methoxyphenyl)carbonyl]-5-(4,6-dimethylpyrimidin-2-yl)octahydropyrrolo[3,4-c]pyrrole

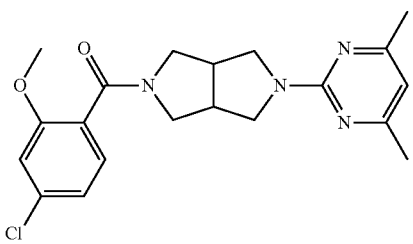 [SMILES: COc1cc(Cl)ccc1C(=O)N1CC2CN(c3nc(C)cc(C)n3)CC2C1]

The title compound was prepared in a manner analogous to Example 15 utilizing Intermediate 23 and 4-chloro-2-methoxybenzoic acid. MS (ESI): mass calculated for $C_{20}H_{23}ClN_4O_2$, 386.9. m/z found 389.2 [M+H]$^+$. $^1$H NMR (400 MHz, CDCl$_3$): 7.18 (d, J=8.0 Hz, 1H), 6.97 (dd, J=8.0, 1.8 Hz, 1H), 6.89 (d, J=1.7 Hz, 1H), 6.29 (s, 1H), 3.98-3.82 (m, 2H), 3.80 (s, 3H), 3.78-3.73 (m, 1H), 3.68-3.59 (m, 2H), 3.55-3.44 (m, 2H), 3.19 (dd, J=11.1, 5.0 Hz, 1H), 3.13-2.90 (m, 2H), 2.29 (s, 6H).

Example 223: 2-[(5-Chloro-2-methylphenyl)carbonyl]-5-(4,6-dimethylpyrimidin-2-yl)octahydropyrrolo[3,4-c]pyrrole

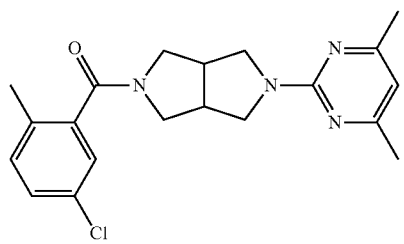 [SMILES: Cc1cc(C)nc(N2CC3CN(C(=O)c4cc(Cl)ccc4C)CC3C2)n1]

The title compound was prepared in a manner analogous to Example 15 utilizing Intermediate 23 and 5-chloro-2-methylbenzoic acid. MS (ESI): mass calculated for $C_{20}H_{23}ClN_4O$, 370.9. m/z found 371.2 [M+H]$^+$. $^1$H NMR (400 MHz, CDCl$_3$): 7.26-7.21 (m, 1H), 7.18-7.13 (m, 2H), 6.31 (s, 1H), 4.00-3.86 (m, 2H), 3.79 (dd, J=11.6, 7.3 Hz, 1H), 3.68-3.57 (m, 2H), 3.51-3.42 (m, 2H), 3.17-2.94 (m, 3H), 2.30 (s, 6H), 2.26 (s, 3H).

Example 224: 2-[(2,5-Dimethylphenyl)carbonyl]-5-(4,6-dimethylpyrimidin-2-yl)octahydropyrrolo[3,4-c]pyrrole

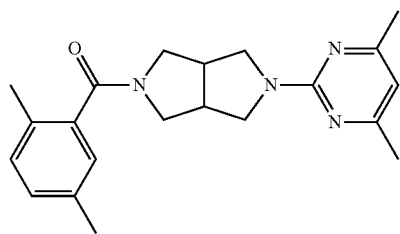 [SMILES: Cc1ccc(C)c(C(=O)N2CC3CN(c4nc(C)cc(C)n4)CC3C2)c1]

The title compound was prepared in a manner analogous to Example 15 utilizing Intermediate 23 and 2,5-dimethylbenzoic acid. MS (ESI): mass calculated for $C_{21}H_{26}N_4O$, 350.5. m/z found 351.3 [M+H]$^+$. $^1$H NMR (400 MHz, CDCl$_3$): 7.11-7.03 (m, 2H), 6.99 (s, 1H), 6.30 (s, 1H), 4.00-3.87 (m, 2H), 3.78 (dd, J=11.5, 7.4 Hz, 1H), 3.70-3.58 (m, 2H), 3.50-3.42 (m, 2H), 3.15-2.90 (m, 3H), 2.32 (s, 3H), 2.32 (s, 3H), 2.24 (s, 3H).

Example 225: 2-[(2,6-Dimethylphenyl)carbonyl]-5-(4,6-dimethylpyrimidin-2-yl)octahydropyrrolo[3,4-c]pyrrole

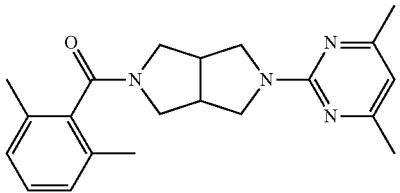 [SMILES: Cc1cc(C)nc(N2CC3CN(C(=O)c4c(C)cccc4C)CC3C2)n1]

The title compound was prepared in a manner analogous to Example 15 utilizing Intermediate 23 and 2,6-dimethylbenzoic acid. MS (ESI): mass calculated for $C_{21}H_{26}N_4O$, 350.5. m/z found 351.3 [M+H]$^+$. $^1$H NMR (400 MHz, CDCl$_3$): 7.13 (t, J=7.6 Hz, 1H), 7.51-7.00 (m, 2H), 6.30 (s, 1H), 4.15-3.87 (m, 2H), 3.85-3.75 (m, 1H), 3.73-3.67 (m, 1H), 3.63-3.55 (m, 1H), 3.50-3.44 (m, 1H), 3.40-3.33 (m, 1H), 3.08-2.90 (m, 3H), 2.28 (s, 6H), 2.21 (s, 3H), 1.80 (s, 3H).

Example 226: 2-(4,6-Dimethylpyrimidin-2-yl)-5-[(5-fluoro-2-methylphenyl)carbonyl]octahydropyrrolo[3,4-c]pyrrole

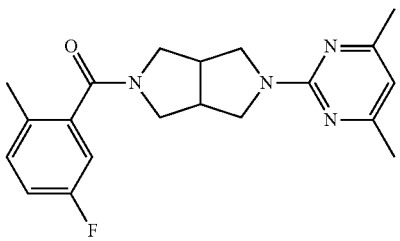

The title compound was prepared in a manner analogous to Example 15 utilizing Intermediate 23 and 5-fluoro-2-methylbenzoic acid. MS (ESI): mass calculated for $C_{20}H_{23}FN_4O$, 354.4. m/z found 355.3 [M+H]$^+$. $^1$H NMR (400 MHz, CDCl$_3$): 7.16 (dd, J=8.5, 5.4 Hz, 1H), 6.98-6.92 (m, 1H), 6.90 (dd, J=8.5, 2.7 Hz, 1H), 6.30 (s, 1H), 3.98-3.87 (m 2H), 3.79 (dd, J=11.6, 7.3 Hz, 1H), 3.68-3.57 (m, 2H), 3.50-3.43 (m, 2H), 3.16-2.94 (m, 3H), 2.30 (s, 6H), 2.26 (d, J=8.6 Hz, 3H).

Example 227: 2-[(2,4-Dimethylphenyl)carbonyl]-5-(4,6-dimethylpyrimidin-2-yl)octahydropyrrolo[3,4-c]pyrrole

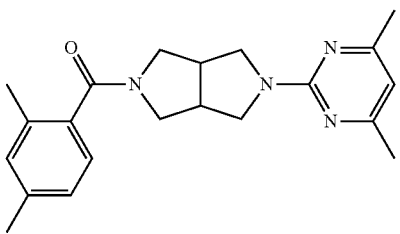 [SMILES: Cc1ccc(C(=O)N2CC3CN(c4nc(C)cc(C)n4)CC3C2)c(C)c1]

The title compound was prepared in a manner analogous to Example 15 utilizing Intermediate 23 and 2,4-dimethylbenzoic acid. MS (ESI): mass calculated for C₂₁H₂₆N₄O, 350.5. m/z found 351.3 [M+H]⁺. ¹H NMR (400 MHz, CDCl₃): 7.02 (s, 2H), 6.29 (s, 0H), 3.92 (ddd, J=19.2, 12.2, 7.7 Hz, 2H), 3.77 (dd, J=11.6, 7.4 Hz, 0H), 3.63 (ddd, J=18.1, 12.2, 4.9 Hz, 1H), 3.52-3.39 (m, 1H), 3.06 (ddd, J=50.9, 27.4, 6.2 Hz, 0H), 2.30 (d, J=6.6 Hz, 3H), 2.28-2.24 (m, 3H).

Example 228: 2-[(2,5-Diethoxyphenyl)carbonyl]-5-(4,6-dimethylpyrimidin-2-yl)octahydropyrrolo[3,4-c]pyrrole

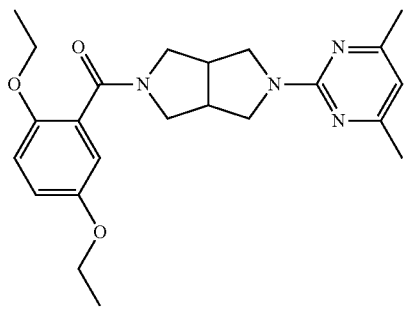 [SMILES: CCOc1ccc(OCC)c(C(=O)N2CC3CN(c4nc(C)cc(C)n4)CC3C2)c1]

The title compound was prepared in a manner analogous to Example 15 utilizing Intermediate 23 and 2,5-diethoxybenzoic acid. MS (ESI): mass calculated for C₂₃H₃₀N₄O₃, 410.5. m/z found 411.3 [M+H]⁺. ¹H NMR (400 MHz, CDCl₃): 6.89-6.77 (m, 3H), 6.28 (s, 1H), 4.04-3.83 (m, 6H), 3.80-3.74 (m, 1H), 3.70-3.44 (m, 4H), 3.27 (s, 1H), 3.13-2.90 (m, 2H), 2.26 (s, 6H), 1.44-1.23 (m, 6H).

Example 229: 2-[(2,6-Diethoxyphenyl)carbonyl]-5-(4,6-dimethylpyrimidin-2-yl)octahydropyrrolo[3,4-c]pyrrole

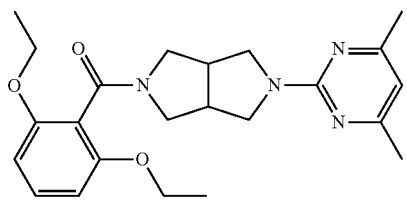 [SMILES: CCOc1cccc(OCC)c1C(=O)N1CC2CN(c3nc(C)cc(C)n3)CC2C1]

The title compound was prepared in a manner analogous to Example 15 utilizing Intermediate 23 and 2,6-diethoxybenzoic acid. MS (ESI): mass calculated for C₂₃H₃₀N₄O₃, 410.5. m/z found 411.3 [M+H]⁺. ¹H NMR (400 MHz, CDCl₃): 7.19 (t, J=8.4 Hz, 1H), 6.55-6.46 (m, 2H), 6.27 (s, 1H), 4.06 (q, J=7.0 Hz, 2H), 3.98 (q, J=7.0 Hz, 2H), 3.94-3.82 (m, 2H), 3.79-3.65 (m, 2H), 3.61 (dd, J=11.6, 5.0 Hz, 1H), 3.57-3.42 (m, 2H), 3.17 (dd, J=11.0, 5.0 Hz, 1H), 3.11-2.87 (m, 2H), 2.31-2.27 (m, 6H), 1.44-1.25 (m, 6H).

Example 230: 2-[(2-Chloro-6-methylphenyl)carbonyl]-5-(4,6-dimethylpyrimidin-2-yl)octahydropyrrolo[3,4-c]pyrrole

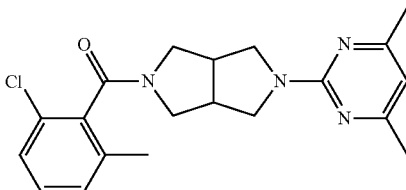

The title compound was prepared in a manner analogous to Example 15 utilizing Intermediate 23 and 2-chloro-6-methylbenzoic acid. MS (ESI): mass calculated for C₂₀H₂₃ClN₄O, 370.9. m/z found 371.2 [M+H]⁺. ¹H NMR (400 MHz, CDCl₃): (rotamers observed) 7.24-7.14 (m, 2H), 7.15-7.07 (m, 1H), 6.31-6.28 (m, 1H), 4.06-3.85 (m, 2H), 3.85-3.75 (m, 1H), 3.74-3.36 (m, 1H), 3.65-3.52 (m, 2H), 3.45-3.51 (m, 1H), 3.37-3.30 (m, 1H), 3.25-3.14 (m, 1H), 3.14-2.94 (m, 2H), 2.37-2.23 (m, 9H).

Example 231: (5-(4,6-Dimethylpyrimidin-2-yl)hexahydropyrrolo[3,4-c]pyrrol-2(1H)-yl)(4-fluoro-2-(pyrimidin-2-yl)phenyl)methanone

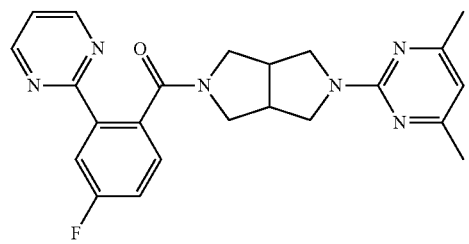 [SMILES: Cc1cc(C)nc(N2CC3CN(C(=O)c4ccc(F)cc4-c4ncccn4)CC3C2)n1]

The title compound was prepared in a manner analogous to Example 15, substituting Intermediate 87 for 3-fluoro-2-[1,2,3]triazol-2-yl-benzoic acid. MS (ESI) mass calcd. for C₂₃H₂₃FN₆O, 418.47. m/z found, 419.2 [M+H]⁺.

Example 232: (5-(4,6-Dimethylpyrimidin-2-yl)hexahydropyrrolo[3,4-c]pyrrol-2(1H)-yl)(3-fluoro-2-iodophenyl)methanone

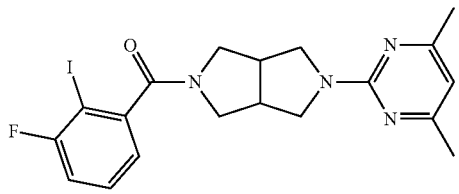 [SMILES: Cc1cc(C)nc(N2CC3CN(C(=O)c4cccc(F)c4I)CC3C2)n1]

The title compound was prepared in a manner analogous to Example 15 substituting 2-iodo-3-fluorobenzoic acid for 3-fluoro-2-[1,2,3]triazol-2-yl-benzoic acid. MS (ESI) mass calcd. for C₁₉H₂₀FIN₄O, 466.3. m/z found, 467.2 [M+H]⁺. ¹H NMR (400 MHz, CDCl₃): 7.36 (ddd, J=8.2, 7.5, 5.2 Hz, 1H), 7.04 (ddd, J=8.5, 7.7, 1.3 Hz, 2H), 6.30 (s, 1H), 3.94

(ddd, J=20.9, 12.2, 7.6 Hz, 2H), 3.79 (dd, J=11.7, 7.2 Hz, 1H), 3.69 (dd, J=12.8, 4.6 Hz, 1H), 3.64 (dd, J=11.7, 5.1 Hz, 1H), 3.58-3.51 (m, 1H), 3.47 (dd, J=10.8, 7.4 Hz, 1H), 3.16-2.98 (m, 3H), 2.29 (s, 6H).

Example 233: 2-(4,6-Dimethylpyrimidin-2-yl)-5-{[2-(trifluoromethyl)pyridin-3-yl]carbonyl}octahydropyrrolo[3,4-c]pyrrole

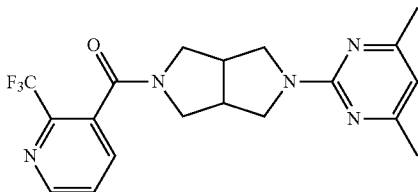 [SMILES: Cc1cc(C)nc(N2CC3CN(C(=O)c4cccnc4C(F)(F)F)CC3C2)n1]

The title compound was prepared in a manner analogous to Example 15 utilizing Intermediate 23 and 2-(trifluoromethyl)nicotinic acid. MS (ESI): mass calculated for $C_{19}H_{20}F_3N_5O$, 391.4. m/z found 392.9 [M+H]$^+$. $^1$H NMR (400 MHz, CDCl$_3$): 8.77 (dd, J=4.7, 1.0 Hz, 1H), 7.74 (d, J=6.9 Hz, 1H), 7.55 (dd, J=12.4, 6.2 Hz, 1H), 6.31 (s, 1H), 3.99 (dd, J=12.8, 7.7 Hz, 1H), 3.90 (dd, J=11.7, 7.6 Hz, 1H), 3.80 (dd, J=11.6, 7.3 Hz, 1H), 3.71-3.57 (m, 2H), 3.50-3.41 (m, 2H), 3.16-3.06 (m, 2H), 3.06-2.97 (m, 1H), 2.34 (s, 5H).

Example 234: 2-Bromopyridin-3-yl)(5-(4,6-dimethylpyrimidin-2-yl)hexahydropyrrolo[3,4-c]pyrrol-2(1H)-yl)methanone

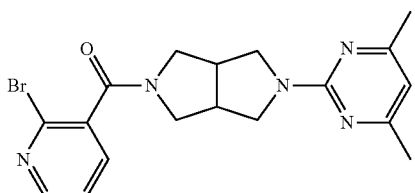

The title compound was prepared in a manner analogous to Example 1 utilizing Intermediate 23 and 2-bromopyridine-3-carboxylic acid. MS (ESI): mass calculated for $C_{18}H_{20}BrN_5O$, 401.09. m/z found 402.9 [M+H]$^+$. $^1$H NMR (600 MHz, CDCl$_3$): 8.41 (dd, J=4.7, 1.8, 1H), 7.66-7.54 (m, 1H), 7.34 (dd, J=7.4, 4.8, 1H), 6.38-6.24 (m, 1H), 3.94 (dd, J=12.1, 7.6, 2H), 3.80 (dd, J=11.5, 7.3, 1H), 3.74-3.46 (m, 4H), 3.31-3.01 (m, 3H), 2.40-2.23 (m, 6H).

Example 235: (5-(4,6-Dimethylpyrimidin-2-yl)hexahydropyrrolo[3,4-c]pyrrol-2(1H)-yl)(2-(pyrimidin-2-yl)pyridin-3-yl)methanone

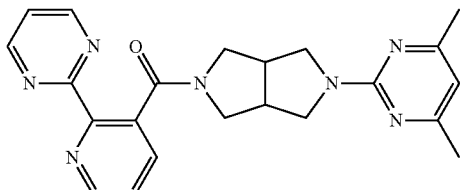

To a solution of 2-bromopyridin-3-yl)(5-(4,6-dimethylpyrimidin-2-yl)hexahydropyrrolo[3,4-c]pyrrol-2(1H)-yl)methanone (Example 234) (50 mg, 0.14 mmol), 2-tributylstannylpyrimidine (50 mg, 0.14 mmol), and copper iodide (2.6 mg, 0.014 mmol) in 1,4 dioxane (1 mL) was added Pd(PPh$_3$)$_4$ (16 mg, 0.014 mmol). The reaction was irradiated in a microwave reactor at 160° C. for one hour. The resulting solution was filtered through Celite®, washed with DCM, and concentrated. Purification (FCC) (MeOH (NH$_3$)/DCM) gave the title compound (35 mg, 64%). MS (ESI): mass calculated for $C_{22}H_{23}N_7O$, 401.20. m/z found 402.2 [M+H]$^+$. $^1$H NMR (500 MHz, CDCl$_3$): 8.85 (s, 3H), 7.70 (d, J=6.7, 1H), 7.48-7.42 (m, 1H), 7.21 (d, J=4.4, 1H), 6.32-6.24 (m, 1H), 3.93-3.79 (m, 2H), 3.75-3.61 (m, 3H), 3.52 (s, 1H), 3.52-3.42 (m, 1H), 3.17 (dd, J=10.8, 5.0, 1H), 3.09-2.88 (m, 2H), 2.37-2.22 (m, 6H).

Example 236: (5-(4,6-Dimethylpyrimidin-2-yl)hexahydropyrrolo[3,4-c]pyrrol-2(1H)-yl)(2-(1-(tetrahydro-2H-pyran-2-yl)-1H-pyrazol-5-yl)pyridin-3-yl)methanone

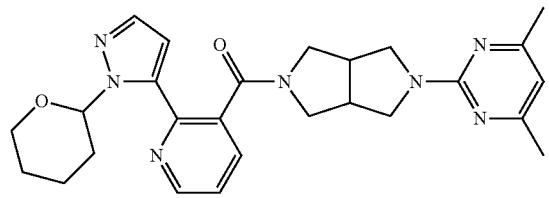 [SMILES: Cc1cc(C)nc(N2CC3CN(C(=O)c4cccnc4-c4ccnn4C4CCCCO4)CC3C2)n1]

To a solution of 2-bromopyridin-3-yl)(5-(4,6-dimethylpyrimidin-2-yl)hexahydropyrrolo[3,4-c]pyrrol-2(1H)-yl)methanone (Example 234) (50 mg, 0.12 mmol), 4-(tetrahydropyran-2H-yl)-1H pyrazole-5 boronic acid pinacol ester (35 mg, 0.12 mmol), TBAB (4.0 mg, 0.012 mmol), and PdCl$_2$(dppf) (10 mg, 0.012 mmol) in toluene (0.6 mL) was added 2N aq. Na$_2$CO$_3$ (0.12 ml, 0.25 mmol). The reaction was irradiated in a microwave reactor at 110° C. for one hour. The resulting solution was filtered through Celite®, washed with DCM, and concentrated. Purification (FCC) (MeOH (NH$_3$)/DCM) gave the title compound (52 mg, 88%). MS (ESI): mass calculated for $C_{26}H_{31}N_7O_2$, 473.25. m/z found 474.2 [M+H]$^+$. $^1$H NMR (500 MHz, CDCl$_3$): 8.72 (dd, J=4.7, 1.8, 1H), 7.76 (dd, J=8.0, 1.7, 1H), 7.62-7.45 (m, 1H), 7.34 (ddd, J=7.7, 4.8, 1.5, 1H), 6.56 (dd, J=18.2, 9.1, 1H), 6.33-6.23 (m, 1H), 3.91-3.71 (m, 2H), 3.72-3.53 (m, 3H), 3.53-3.36 (m, 2H), 3.36-3.06 (m, 3H), 2.98-2.70 (m, 3H), 2.65 (d, J=6.4, 1H), 2.51 (d, J=10.0, 1H), 2.28 (d, J=9.8, 6H), 2.18-2.01 (m, 2H), 1.94 (s, 3H).

Example 237: (2-(1H-Pyrazol-5-yl)pyridin-3-yl)(5-(4,6-dimethylpyrimidin-2-yl)hexahydropyrrolo[3,4-c]pyrrol-2(1H)-yl)methanone

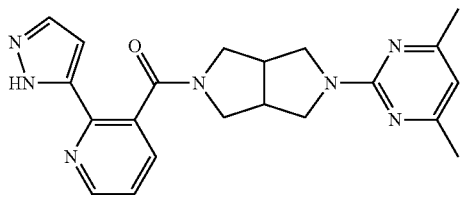 [SMILES: Cc1cc(C)nc(N2CC3CN(C(=O)c4cccnc4-c4ccn[nH]4)CC3C2)n1]

To a solution of (5-(4,6-dimethylpyrimidin-2-yl)hexahydropyrrolo[3,4-c]pyrrol-2(1H)-yl)(2-(1-(tetrahydro-2H-pyran-2-yl)-1H-pyrazol-5-yl)pyridin-3-yl)methanone (Example 236) (210 mg, 0.43 mmol) in THF (10 mL) and H$_2$O (1 mL) was added 4 N aq. HCl (1 mL). The reaction was let stir for 2 hours, neutralized with 3 N aq. NaOH, and extracted with DCM (3×20 mL). The organics were combined, dried with Na$_2$SO$_4$, and concentrated. Purification (FCC) (MeOH (NH$_3$)/DCM) gave the title compound (128 mg, 73%) (MS (ESI): mass calculated for C$_{21}$H$_{23}$N$_7$O, 389.20. m/z found 390.2 [M+H]$^+$. $^1$H NMR (500 MHz, CDCl$_3$): 8.68-8.59 (m, 1H), 7.63 (d, J=9.1, 2H), 7.32-7.20 (m, 1H), 6.80 (d, J=2.2, 1H), 6.33-6.19 (m, 1H), 3.92-3.55 (m, 5H), 3.54-2.78 (m, 5H), 2.37-2.24 (m, 6H).

Example 238: (2-(2H-1,2,3-Triazol-2-yl)pyridin-3-yl)(5-(4,6-dimethylpyrimidin-2-yl)hexahydropyrrolo[3,4-c]pyrrol-2(1H)-yl)methanone

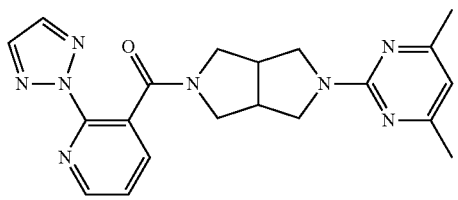 [SMILES: Cc1cc(C)nc(N2CC3CN(C(=O)c4cccnc4-n4nccn4)CC3C2)n1]

To a solution of 2-bromopyridin-3-yl)(5-(4,6-dimethylpyrimidin-2-yl)hexahydropyrrolo[3,4-c]pyrrol-2(1H)-yl)methanone (Example 234) (150 mg, 0.37 mmol), 1H-1,2,3 triazole (43 µL, 0.75 mmol), CsCO$_3$ (247 mg, 0.75 mmol), in H$_2$O (2 µL) and 1,4 dioxane (2 mL) was added (R,R)—(−)—N,N'-dimethyl-1,2-cyclohexyldiamine (12 µL, 0.75 mmol) and CuI (3.5 mg, 0.86 mmol). The reaction mixture was irradiated in a microwave reactor at 160° C. for 2 h. The resulting solution was filtered through Celite®, washed with DCM, and concentrated. Purification (FCC) (MeOH (NH$_3$)/DCM) gave the title compound (8 mg, 6%). MS (ESI): mass calculated for C$_{20}$H$_{22}$N$_8$O, 390.19; m/z found 391.2 [M+H]$^+$. $^1$H NMR (400 MHz, CDCl$_3$): 8.65 (dd, J=4.8, 1.8, 1H), 7.83 (dt, J=13.3, 6.6, 2H), 7.43 (dt, J=7.6, 4.5, 1H), 6.38-6.23 (m, 2H), 4.02-3.28 (m, 6H), 3.10-3.06 (m, 4H), 2.42-2.22 (m, 6H).

Example 239: (3-Fluoro-2-(pyrimidin-2-yl)phenyl)(5-(4,5,6-trimethylpyrimidin-2-yl)hexahydropyrrolo[3,4-c]pyrrol-2(1H)-yl)methanone

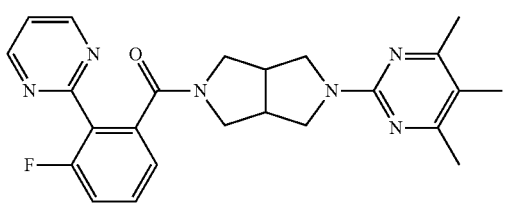 [SMILES: Cc1nc(N2CC3CN(C(=O)c4cccc(F)c4-c4ncccn4)CC3C2)nc(C)c1C]

The title compound was prepared in a manner analogous to Example 15, utilizing Intermediate 42 and 3-fluoro-2-(pyrimidin-2-yl)benzoic acid. MS (ESI): mass calculated for C$_{24}$H$_{25}$FN$_6$O, 432.21. m/z found 433.3 [M+H]$^+$. $^1$H NMR (600 MHz, CDCl$_3$): 8.41 (dd, J=4.7, 1.8, 2H), 7.66-7.54 (m, 2H), 7.34 (dd, J=7.4, 4.8, 2H), 3.94 (dd, J=12.1, 7.6, 2H), 3.80 (dd, J=11.5, 7.3, 1H), 3.74-3.46 (m, 4H), 3.31-3.01 (m, 3H), 2.40-2.13 (m, 9H).

Example 240: (3-Fluoro-2-(2H-1,2,3-triazol-2-yl)phenyl)(5-(4,5,6-trimethylpyrimidin-2-yl)hexahydropyrrolo[3,4-c]pyrrol-2(1H)-yl)methanone

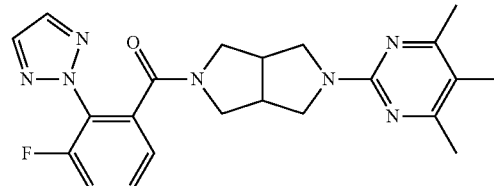

The title compound was prepared in a manner analogous to Example 15, utilizing Intermediate 42 and 3-fluoro-2-(2H-1,2,3-triazol-2-yl)benzoic acid. MS (ESI): mass calculated for C$_{22}$H$_{24}$FN$_7$O, 421.20. m/z found 422.2 [M+H]$^+$. $^1$H NMR (500 MHz, CDCl$_3$): 7.82-7.77 (m, 2H), 7.51-7.44 (m, 1H), 7.31 (ddd, J=9.8, 8.4, 1.3, 1H), 7.25-7.20 (m, 1H), 3.86-3.60 (m, 3H), 3.59-3.42 (m, 4H), 3.14 (dd, J=10.9, 5.3, 1H), 2.94 (dd, J=10.9, 7.1, 2H), 2.38-2.27 (m, 6H), 2.07 (d, J=7.2, 3H).

Example 241: (5-Methoxy-2-(2H-1,2,3-triazol-2-yl)phenyl)(5-(4,5,6-trimethylpyrimidin-2-yl)hexahydropyrrolo[3,4-c]pyrrol-2(1H)-yl)methanone

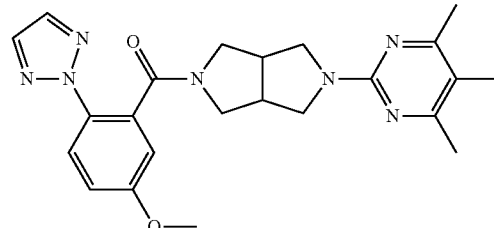

The title compound was prepared in a manner analogous to Example 15, utilizing Intermediate 42 and 5-methoxy-2-(2H-1,2,3-triazol-2-yl)benzoic acid. MS (ESI): mass calculated for C$_{23}$H$_{27}$N$_7$O$_2$, 433.22. m/z found 434.2 [M+H]$^+$. $^1$H NMR (500 MHz, CDCl$_3$): 7.84 (d, J=9.0, 1H), 7.69 (s, 2H), 7.01 (dd, J=9.0, 2.8, 1H), 6.91 (d, J=2.8, 1H), 3.91-3.74 (m, 5H), 3.70-3.58 (m, 2H), 3.55 (dd, J=11.4, 5.2, 1H), 3.47-3.28 (m, 2H), 3.04-2.82 (m, 3H), 2.41-2.25 (m, 5H), 2.13-2.01 (m, 4H).

Example 242: (3-Fluoro-2-(2H-1,2,3-triazol-2-yl)phenyl)(5-(6-fluoroquinazolin-2-yl)hexahydropyrrolo[3,4-c]pyrrol-2(1H)-yl)methanone

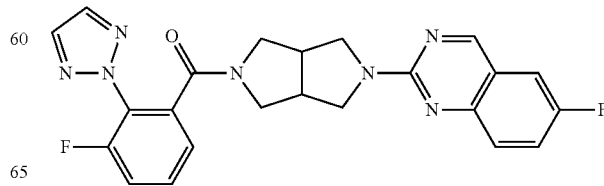

The title compound was prepared in a manner analogous to Example 15, utilizing Intermediate 43 and 3-fluoro-2-(2H-1,2,3-triazol-2-yl)benzoic acid. MS (ESI): mass calculated for $C_{23}H_{19}F_2N_7O$, 447.16. m/z found 448.1 [M+H]$^+$. $^1$H NMR (500 MHz, CDCl$_3$): 8.99 (s, 1H), 7.77 (d, J=15.8, 2H), 7.61 (dd, J=11.0, 5.5, 1H), 7.53-7.43 (m, 2H), 7.37-7.29 (m, 2H), 7.24 (s, 1H), 3.93 (d, J=9.9, 1H), 3.79 (dd, J=12.3, 7.4, 2H), 3.71-3.62 (m, 1H), 3.62 (s, 3H), 3.20 (dd, J=11.0, 5.3, 1H), 3.12-2.98 (m, 2H).

Example 243: (3-Fluoro-2-(pyrimidin-2-yl)phenyl) (5-(6-fluoroquinazolin-2-yl)hexahydropyrrolo[3,4-c] pyrrol-2(1H)-yl)methanone

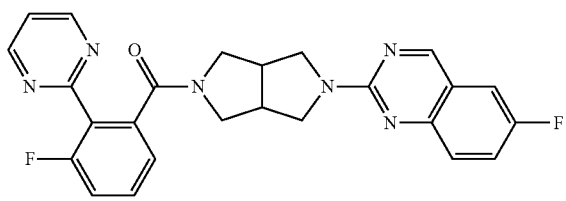 [SMILES: O=C(c1cccc(F)c1-c1ncccn1)N1CC2CN(c3ncc4cc(F)ccc4n3)CC2C1]

The title compound was prepared in a manner analogous to Example 15, utilizing Intermediate 43 and 3-fluoro-2-(pyrimidin-2-yl)benzoic acid. MS (ESI): mass calculated for $C_{25}H_{20}F_2N_6O$, 458.17. m/z found 459.1 [M+H]$^+$. $^1$H NMR (500 MHz, CDCl$_3$): 8.98 (d, J=8.1, 1H), 8.82-8.74 (m, 2H), 7.61 (dt, J=12.7, 6.4, 1H), 7.53-7.41 (m, 2H), 7.31 (td, J=8.0, 2.7, 1H), 7.25-7.18 (m, 2H), 7.15 (t, J=4.9, 1H), 4.00-3.88 (m, 1H), 3.89-3.69 (m, 3H), 3.68-3.52 (m, 3H), 3.36 (dd, J=10.9, 4.6, 1H), 3.14-2.97 (m, 2H).

Example 244: (5-(6,7-Difluoroquinoxalin-2-yl)hexahydropyrrolo[3,4-c]pyrrol-2(1H)-yl)(3-fluoro-2-(2H-1,2,3-triazol-2-yl)phenyl)methanone

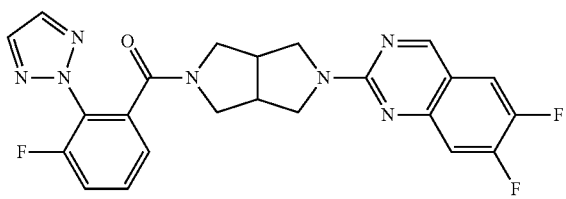 [SMILES: O=C(c1cccc(F)c1-n1nccn1)N1CC2CN(c3ncc4cc(F)c(F)cc4n3)CC2C1]

The title compound was prepared in a manner analogous to Example 15, utilizing Intermediate 44 and 3-fluoro-2-(2H-1,2,3-triazol-2-yl)benzoic acid. MS (ESI): mass calculated for $C_{23}H_{18}F_3N_7O$, 465.15. m/z found 466.1 [M+H]$^+$. $^1$H NMR (500 MHz, CDCl$_3$): 8.28 (s, 1H), 7.75 (d, J=20.8, 2H), 7.65 (dd, J=10.6, 8.4, 1H), 7.50 (tt, J=9.6, 4.8, 1H), 7.43 (dd, J=11.4, 8.0, 1H), 7.39-7.31 (m, 1H), 7.25 (dd, J=12.5, 4.9, 1H), 4.00-3.86 (m, 1H), 3.81 (dd, J=10.0, 5.6, 2H), 3.66-3.49 (m, 4H), 3.32-3.16 (m, 3H).

Example 245: (5-(6,7-Difluoroquinoxalin-2-yl)hexahydropyrrolo[3,4-c]pyrrol-2(1H)-yl)(5-methoxy-2-(2H-1,2,3-triazol-2-yl)phenyl)methanone

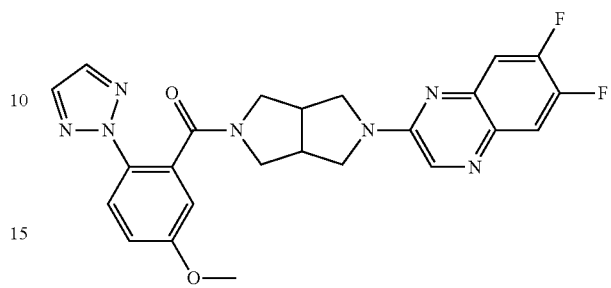

The title compound was prepared in a manner analogous to Example 15, utilizing Intermediate 44 and 5-methoxy-2-(2H-1,2,3-triazol-2-yl)benzoic acid. MS (ESI): mass calculated for $C_{24}H_{21}F_2N_7O_2$, 477.2. m/z found 478.1 [M+H]$^+$. $^1$H NMR (500 MHz, CDCl$_3$): 8.25 (s, 1H), 7.84 (t, J=7.6, 1H), 7.64 (dt, J=19.7, 10.8, 3H), 7.42 (dd, J=11.4, 8.0, 1H), 7.03 (dd, J=9.0, 2.8, 1H), 6.92 (d, J=2.8, 1H), 3.97-3.84 (m, 5H), 3.64 (dd, J=18.2, 14.6, 5H), 3.12 (dd, J=19.8, 8.6, 3H).

Example 246: (5-(6,7-Difluoroquinoxalin-2-yl)hexahydropyrrolo[3,4-c]pyrrol-2(1H)-yl)(2-fluoro-6-(2H-1,2,3-triazol-2-yl)phenyl)methanone

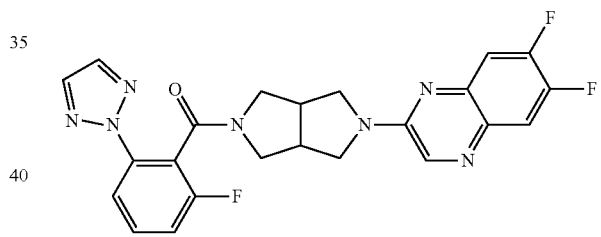

The title compound was prepared in a manner analogous to Example 15, utilizing Intermediate 44 and 2-fluoro-6-(2H-1,2,3-triazol-2-yl)benzoic acid. MS (ESI): mass calculated for $C_{23}H_{18}F_3N_7O$, 465.2. m/z found 466.1 [M+H]$^+$. $^1$H NMR (500 MHz, CDCl$_3$): 8.32-8.24 (m, 1H), 7.90-7.79 (m, 2H), 7.68 (s, 1H), 7.65 (ddd, J=10.7, 8.5, 4.2, 1H), 7.55-7.38 (m, 2H), 7.22-7.10 (m, 1H), 4.13-3.48 (m, 7H), 3.40-3.05 (m, 3H).

Example 247: (2-Bromo-3-fluorophenyl)(5-(6-fluoroquinazolin-2-yl)hexahydropyrrolo[3,4-c]pyrrol-2 (1H)-yl)methanone

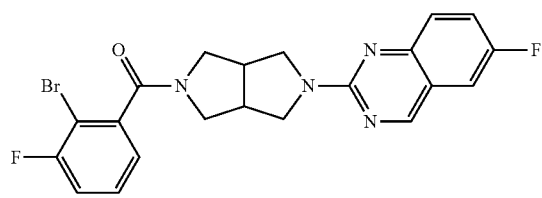 [SMILES: O=C(c1cccc(F)c1Br)N1CC2CN(c3ncc4cc(F)ccc4n3)CC2C1]

The title compound was prepared in a manner analogous to Example 15, utilizing Intermediate 43 and 2-bromo-3-fluorobenzoic acid. MS (ESI): mass calculated for $C_{21}H_{17}BrF_2N_4O$, 458.1. m/z found 459.0 [M+H]+. 1H NMR (400 MHz, CDCl3): 8.95 (d, J=19.8, 1H), 8.01 (s, 1H), 7.59 (dt, J=13.3, 6.7, 1H), 7.52-7.40 (m, 1H), 7.40-7.28 (m, 1H), 7.18-7.05 (m, 2H), 4.01 (dt, J=12.8, 8.4, 2H), 3.95-3.85 (m, 1H), 3.80-3.48 (m, 4H), 3.27-3.04 (m, 3H).

Example 248: (5-(4,6-dimethylpyrimidin-2-yl)hexahydropyrrolo[3,4-c]pyrrol-2(1H)-yl)(4-fluoro-2-(5-methylpyridin-2-yl)phenyl)methanone

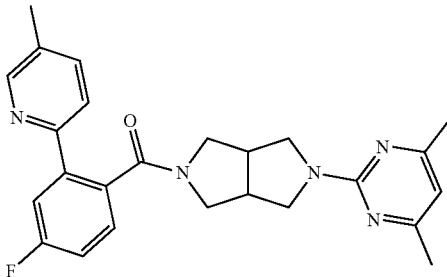 [SMILES: Cc1ccc(-c2cc(F)ccc2C(=O)N2CC3CN(c4nc(C)cc(C)n4)CC3C2)nc1]

(5-(4,6-Dimethylpyrimidin-2-yl)hexahydropyrrolo[3,4-c]pyrrol-2(1H)-yl)(4-fluoro-2-(5-methylpyridin-2-yl)phenyl)methanone. The title compound was prepared in a manner analogous to Intermediate 50, Step A, substituting (5-(4,6-dimethylpyrimidin-2-yl)hexahydropyrrolo[3,4-c]pyrrol-2(1H)-yl)(4-fluoro-2-iodophenyl)methanone for 2-iodo-3-fluorobenzonitrile, 5-methyl-2-(tributylstannyl)pyridine for 2-tributylstannane pyrimidine, dioxane for DME and heating to 130° C. for 60 minutes. The reactions were filtered through celite, rinsed with EtOAc and then concentrated and purified on RP agilent HPLC and fractions lyophilized. MS (ESI) mass calcd. for $C_{25}H_{26}FN_5O$, 431.21; found 432.2 [M+H]+.

Example 249: (2-Bromopyridin-3-yl)(5-(4,5,6-trimethylpyrimidin-2-yl)hexahydropyrrolo[3,4-c]pyrrol-2(1H)-yl)methanone

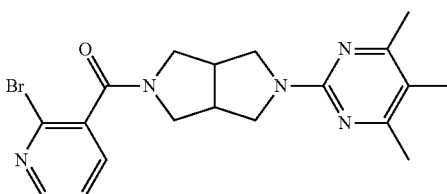

The title compound was prepared in a manner analogous to Example 1 utilizing Intermediate 42 and 2-bromopyridine-3-carboxylic acid. MS (ESI): mass calculated for $C_{18}H_{22}BrN_5O$, 415.10. m/z found 416.1 [M+H]+. 1H NMR (600 MHz, CDCl3): 8.44 (dd, J=4.7, 1.6, 1H), 7.33 (dd, J=7.6, 4.7, 1H), 6.38-6.24 (m, 1H), 3.94-3.90 (m, 2H), 3.88-3.84 (m, 1H), 3.74-3.50 (m, 4H), 3.31-3.01 (m, 3H), 2.40-2.23 (m, 6H), 2.12-2.06 (m, 3H).

Example 250: (2-(1-(Tetrahydro-2H-pyran-2-yl)-1H-pyrazol-5-yl)pyridin-3-yl)(5-(4,5,6-trimethylpyrimidin-2-yl)hexahydropyrrolo[3,4-c]pyrrol-2(1H)-yl)methanone

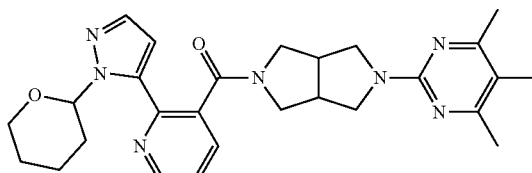

The title compound was prepared in a manner similar to Example 236, utilizing Example 249 and 4-(terahydropyran-2H-yl)-1H pyrazole-5 boronic acid pinacol ester. MS (ESI): mass calculated for $C_{27}H_{33}N_7O_2$, 487.27. m/z found 488.2 [M+H]+. 1H NMR (500 MHz, CDCl3): 8.78-8.72 (m, 1H), 7.80-7.75 (m, 1H), 7.62-7.45 (m, 1H), 7.34 (dd, J=4.8, 1.5, 1H), 6.33-6.23 (m, 1H), 3.91-3.78 (m, 2H), 3.72-3.53 (m, 3H), 3.53-3.36 (m, 2H), 3.36-3.15 (m, 3H), 2.98-2.70 (m, 3H), 2.65 (d, J=6.8, 1H), 2.38-2.27 (m, 6H), 2.10-2.06 (m, 3H), 2.18-2.01 (m, 2H), 1.94 (s, 3H).

Example 251: (2-(1H-Pyrazol-5-yl)pyridin-3-yl)(5-(4,5,6-trimethylpyrimidin-2-yl)hexahydropyrrolo[3,4-c]pyrrol-2(1H)-yl)methanone

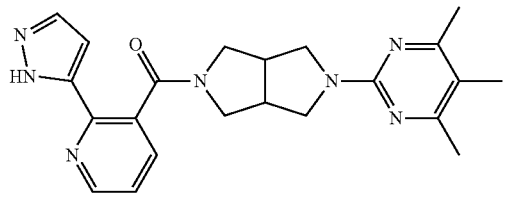 [SMILES: Cc1nc(N2CC3CN(C(=O)c4cccnc4-c4ccn[nH]4)CC3C2)nc(C)c1C]

The title compound was prepared in a manner similar to Example 237, utilizing (2-(1-(tetrahydro-2H-pyran-2-yl)-1H-pyrazol-5-yl)pyridin-3-yl)(5-(4,5,6-trimethylpyrimidin-2-yl)hexahydropyrrolo[3,4-c]pyrrol-2(1H)-yl)methanone (Example 250). MS (ESI): mass calculated for $C_{23}H_{18}F_3N_7O$, 403.21. m/z found 404.2 [M+H]+. 1H NMR (500 MHz, CDCl3): 11.90 (s, 1H), 8.65 (dd, J=4.7, 1.5, 1H), 7.65 (dd, J=7.7, 1.6, 1H), 7.50 (d, J=7.0, 1H), 7.34-7.21 (m, 1H), 6.81 (s, 1H), 3.66-3.60 (m, 6H), 3.26 (s, 4H), 2.39-2.25 (m, 6H), 2.09 (d, J=40.1, 3H).

Example 252: 6-[5-{[2-Fluoro-6-(2H-1,2,3-triazol-2-yl)phenyl]carbonyl}hexahydropyrrolo[3,4-c]pyrrol-2(1H)-yl]-2-methylpyrimidin-4(3H)-one

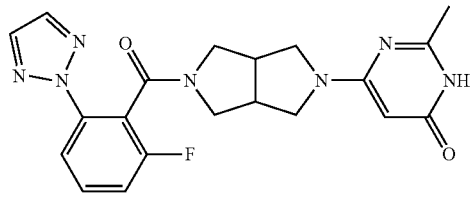 [SMILES: Cc1nc(N2CC3CN(C(=O)c4c(F)cccc4-n4nccn4)CC3C2)cc(=O)[nH]1]

To a solution of Intermediate 16 (35.3 mg, 0.117 mmol) in n-butanol (0.5 mL) was added triethylamine (0.065 mL, 0.47 mmol) and 6-chloro-2-methylpyrimidin-4-ol (33.9 mg, 0.234 mmol). The mixture was heated to 150° C. in the microwave for 18 minutes. The reaction was concentrated and purified by reverse phase HPLC to give the title compound (21.4 mg, 45%). MS (ESI): mass calculated for $C_{20}H_{20}FN_7O_2$, 409.4. m/z found [M+H]$^+$410.2. $^1$H NMR (400 MHz, CDCl$_3$): 7.91-7.76 (m, 3H), 7.54-7.42 (m, 1H), 7.15 (t, J=8.5 Hz, 1H), 4.07-2.94 (m, 11H), 2.37 (d, J=8.8 Hz, 3H).

Example 253: 2-(2,6-Dimethylpyrimidin-4-yl)-5-{[5-(4-fluorophenyl)-2-methyl-1,3-thiazol-4-yl]carbonyl}octahydropyrrolo[3,4-c]pyrrole

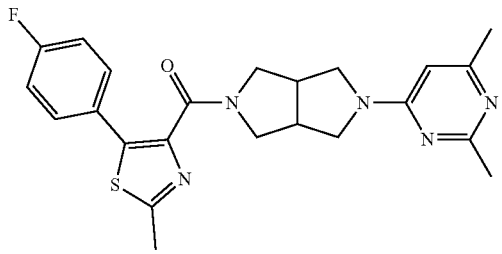 [SMILES: Cc1cc(N2CC3CN(C(=O)c4nc(C)sc4-c4ccc(F)cc4)CC3C2)nc(C)n1]

To a solution of Intermediate 48 (15.8 mg, 0.048 mmol) was added DMF (0.4 mL), 4-chloro-2,6-dimethylpyrimidine (8.2 mg, 0.057 mmol) and cesium carbonate (38.8 mg, 0.119 mmol). The mixture was heated to 100° C. for 18 hours, diluted with water and extracted with ethyl acetate. The organic layer was dried over Na$_2$SO$_4$ and concentrated. The residue was purified by reverse phase HPLC to give the title compound (12.9 mg, 62%). MS (ESI): mass calculated for $C_{23}H_{24}FN_5OS$, 437.5; m/z found [M+H]$^+$438.2. $^1$H NMR (400 MHz, CDCl$_3$): 7.51-7.41 (m, 2H), 7.06-6.95 (m, 2H), 6.29 (s, 1H), 3.892-3.76 (m, 2H), 3.73-3.51 (m, 3H), 3.44 (dd, J=11.6, 5.0 Hz, 1H), 3.32 (dd, J=11.6, 4.5 Hz, 1H), 3.10 (dd, J=11.3, 5.3 Hz, 1H), 3.02-2.80 (m, 2H), 2.70 (s, 3H), 2.31 (d, J=20.0 Hz, 6H).

Example 254: 2-(4,6-Dimethylpyrimidin-2-yl)-5-{[5-(4-fluorophenyl)-2-methyl-1,3-thiazol-4-yl]carbonyl}octahydropyrrolo[3,4-c]pyrrole

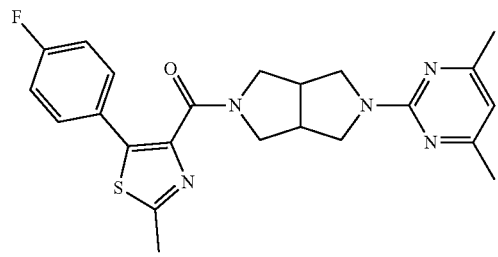 [SMILES: Cc1cc(C)nc(N2CC3CN(C(=O)c4nc(C)sc4-c4ccc(F)cc4)CC3C2)n1]

The title compound was prepared in a manner analogous to Example 253 substituting 2-chloro-4,6-dimethylpyrimidine for 4-chloro-2,6-dimethylpyrimidine. MS (ESI): mass calculated for $C_{23}H_{24}FN_5OS$, 437.5. m/z found [M+H]$^+$ 438.2. $^1$H NMR (400 MHz, CDCl$_3$): 7.53-7.41 (m, 2H), 7.06-6.97 (m, 2H), 6.29 (s, 1H), 3.90-3.76 (m, 2H), 3.69-3.49 (m, 3H), 3.44 (dd, J=11.6, 5.0 Hz, 1H), 3.32 (dd, J=11.6, 4.5 Hz, 1H), 3.10 (dd, J=11.3, 5.3 Hz, 1H), 3.02-2.82 (m, 2H), 2.70 (s, 3H), 2.29 (s, 6H).

Example 255: 6-[5-{[5-(4-Fluorophenyl)-2-methyl-1,3-thiazol-4-yl]carbonyl}hexahydropyrrolo[3,4-c]pyrrol-2(1H)-yl]-2-methylpyrimidin-4(3H)-one

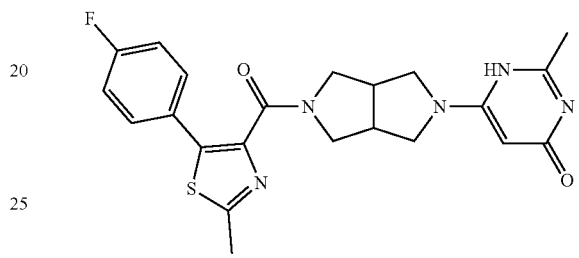

The title compound was prepared in a manner analogous to Example 252 substituting Intermediate 48 for Intermediate 16. MS (ESI): mass calculated for $C_{22}H_{22}FN_5O_2S$, 439.5. m/z found 440.1 [M+H]$^+$. $^1$H NMR (400 MHz, CDCl$_3$): 12.77 (s, 1H), 7.50-7.43 (m, 2H), 7.09-7.02 (m, 2H), 3.90-3.82 (m, 2H), 3.66-3.49 (m, 4H), 3.29-2.82 (m, 5H), 2.71 (s, 3H), 2.36 (s, 3H).

Example 256: 6-{5-[(5-Fluoro-2-pyrimidin-2-ylphenyl)carbonyl]hexahydropyrrolo[3,4-c]pyrrol-2(1H)-yl}-2-methylpyrimidin-4(3H)-one

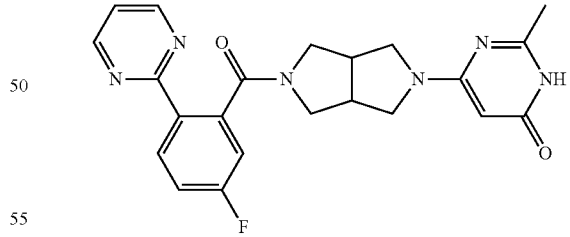

The title compound was prepared in a manner analogous to Example 252, substituting (5-fluoro-2-(pyrimidin-2-yl)phenyl)(hexahydropyrrolo[3,4-c]pyrrol-2(1H)-yl)methanone for Intermediate 16. MS (ESI): mass calculated for $C_{22}H_{21}FN_6O_2$, 420.5; m/z found 421.2 [M+H]$^+$. $^1$H NMR (400 MHz, CDCl$_3$): 12.85 (s, 1H), 8.73 (d, J=4.9 Hz, 2H), 8.35 (dd, J=8.8, 5.6 Hz, 1H), 7.24-7.13 (m, 2H), 7.07 (dd, J=8.4, 2.6 Hz, 1H), 3.90 (dd, J=12.6, 7.7 Hz, 1H), 3.76-3.65 (m, 3H), 3.55-3.48 (m, 2H), 3.24-2.90 (m, 4H), 2.36 (d, J=8.7 Hz, 3H).

Example 257: (5-(4,6-Dimethylpyrimidin-2-yl)hexahydropyrrolo[3,4-c]pyrrol-2(1H)-yl)(4-fluoro-2-(2H-1,2,3-triazol-2-yl)phenyl)methanone

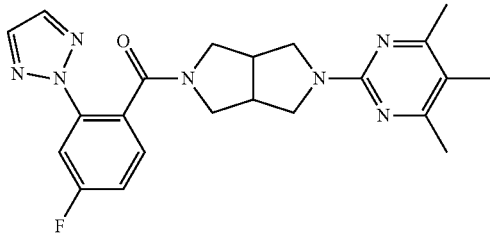 [SMILES: Cc1nc(N2CC3CN(C(=O)c4ccc(F)cc4-n4nccn4)CC3C2)nc(C)c1C]

The title compound was prepared in a manner analogous to Example 15, utilizing Intermediate 23 and Intermediate 4. MS (ESI): mass calculated for $C_{23}H_{24}FN_5O$, 407.19. m/z found 408.2 [M+H]$^+$. $^1$H NMR (400 MHz, CDCl$_3$): 7.80-7.68 (m, 3H), 7.39 (dd, J=8.4, 5.8, 1H), 7.17-7.09 (m, 1H), 6.40 (s, 1H), 6.17 (s, 2H), 3.89 (dd, J=12.7, 7.6, 2H), 3.69 (dd, J=12.8, 4.3, 2H), 3.61-3.48 (m, 2H), 3.45-3.32 (m, 2H), 3.25 (dd, J=9.5, 5.0, 2H), 1.25 (s, 6H).

Example 258: (5-(4,6-Dimethoxypyrimidin-2-yl)hexahydropyrrolo[3,4-c]pyrrol-2(1H)-yl)(2-fluoro-6-(2H-1,2,3-triazol-2-yl)phenyl)methanone

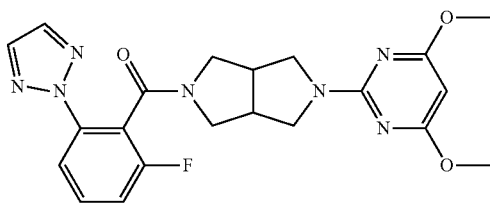 [SMILES: COc1cc(OC)nc(N2CC3CN(C(=O)c4c(F)cccc4-n4nccn4)CC3C2)n1]

The title compound was prepared in a manner analogous to Example 15, utilizing Intermediate 45 and Intermediate 12. MS (ESI): mass calculated for $C_{21}H_{22}FN_7O_3$, 439.18. m/z found 440.2 [M+H]$^+$. $^1$H NMR (400 MHz, CDCl$_3$): 7.89-7.80 (m, 2H), 7.73 (s, 1H), 7.53-7.43 (m, 1H), 7.15 (tdd, J=8.4, 3.7, 0.9, 1H), 5.39 (d, J=2.4, 1H), 4.02-3.48 (m, 13H), 3.31-2.89 (m, 3H).

Example 259: (5-(4,6-Dimethylpyrimidin-2-yl)hexahydropyrrolo[3,4-c]pyrrol-2(1H)-yl)(2-methyl-6-(2H-1,2,3-triazol-2-yl)phenyl)methanone

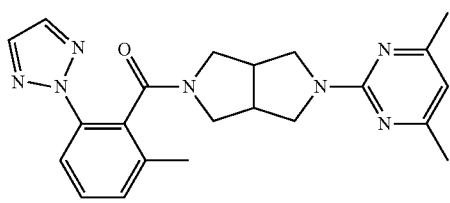 [SMILES: Cc1cc(C)nc(N2CC3CN(C(=O)c4c(C)cccc4-n4nccn4)CC3C2)n1]

The title compound was prepared in a manner analogous to Example 15, utilizing Intermediate 23 and Intermediate 11. MS (ESI): mass calculated for $C_{22}H_{25}N_7O$, 403.21. m/z found 404.2 [M+H]$^+$. $^1$H NMR (400 MHz, CDCl$_3$): 7.84-7.75 (m, 2H), 7.69 (s, 1H), 7.38 (td, J=7.9, 2.4, 1H), 7.25-7.22 (m, 1H), 6.29 (d, J=3.8, 1H), 3.98-3.30 (m, 8H), 3.01 (dd, J=11.5, 6.6, 2H), 2.30 (d, J=3.6, 3H), 1.57 (s, 6H).

Example 260: (5-(4,6-Dimethylpyrimidin-2-yl)hexahydropyrrolo[3,4-c]pyrrol-2(1H)-yl)(3-methyl-2-(2H-1,2,3-triazol-2-yl)phenyl)methanone

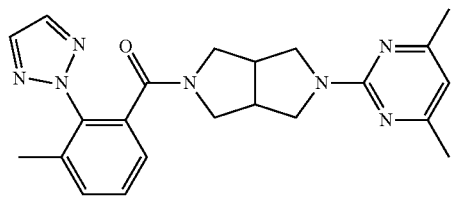 [SMILES: Cc1cc(C)nc(N2CC3CN(C(=O)c4cccc(C)c4-n4nccn4)CC3C2)n1]

The title compound was prepared in a manner analogous to Example 15, utilizing Intermediate 23 and 3-methyl-2-(2H-1,2,3-triazol-2-yl)benzoic acid (Intermediate 82). MS (ESI): mass calculated for $C_{22}H_{25}N_7O$, 403.21. m/z found 404.2 [M+H]$^+$. $^1$H NMR (400 MHz, CDCl$_3$): 7.76 (s, 1H), 7.44-7.34 (m, 2H), 7.25 (s, 1H), 7.24 (d, J=1.9, 1H), 6.30 (s, 1H), 3.88-3.40 (m, 8H), 3.23 (dd, J=11.0, 4.9, 1H), 3.00-2.83 (m, 1H), 2.36-2.26 (m, 3H), 2.24 (d, J=16.1, 3H), 1.63 (s, 3H).

Example 261: (2-Fluoro-6-(2H-1,2,3-triazol-2-yl)phenyl)(5-(5-nitropyrimidin-2-yl)hexahydropyrrolo[3,4-c]pyrrol-2(1H)-yl)methanone

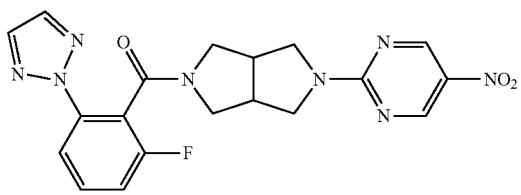 [SMILES: O=C(c1c(F)cccc1-n1nccn1)N1CC2CN(c3ncc([N+](=O)[O-])cn3)CC2C1]

The title compound was prepared in a manner analogous to Example 15, utilizing Intermediate 46 and Intermediate 12. MS (ESI): mass calculated for $C_{19}H_{17}FN_8O_3$, 424.14. m/z found 425.2 [M+H]$^+$. $^1$H NMR (400 MHz, CDCl$_3$): 9.10 (ddd, J=9.9, 5.7, 3.3, 2H), 7.90-7.79 (m, 2H), 7.74 (d, J=6.6, 1H), 7.55-7.44 (m, 1H), 7.22-7.10 (m, 1H), 4.13-3.60 (m, 7H), 3.40-3.07 (m, 3H).

Example 262: Methyl 2-(5-(2-fluoro-6-(2H-1,2,3-triazol-2-yl)benzoyl)hexahydropyrrolo[3,4-c]pyrrol-2(1H)-yl)-4-(trifluoromethyl)pyrimidine-5-carboxylate

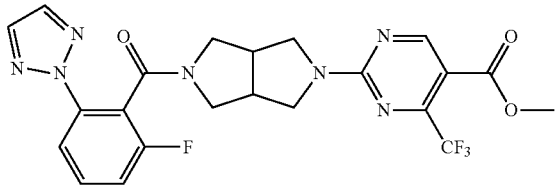 [SMILES: COC(=O)c1cnc(N2CC3CN(C(=O)c4c(F)cccc4-n4nccn4)CC3C2)nc1C(F)(F)F]

A mixture of Intermediate 16 (30 mg, 0.9 mmol), methyl 2-chloro-4-(trifluoromethyl)pyrimidine-5-carboxylate (22 mg, 0.09 mmol), Cs$_2$CO$_3$ (92.4 mg, 0.28 mmol), in DMA (1 mL) was heated to 100° C. for 72 hours. The mixture was cooled to rt diluted with H$_2$O and extracted with EtOAc. The organics were combined, dried and concentrated under reduced pressure. Purification (FCC) (10% MeOH, 0.1% NH$_4$OH in DCM/DCM) afforded the title compound (19 mg, 37%) MS (ESI): mass calculated for C$_{22}$H$_{19}$F$_4$N$_7$O$_3$, 505.15. m/z found 506.2 [M+H]$^+$. $^1$H NMR (400 MHz, CDCl$_3$): 8.98-8.85 (m, 1H), 7.92-7.78 (m, 2H), 7.73 (d, J=2.8, 1H), 7.54-7.42 (m, 1H), 7.15 (td, J=8.4, 4.9, 1H), 4.15-3.45 (m, 11H), 3.41-2.95 (m, 3H). The aqueous layer was acidified with 1 N HCl and extracted with EtOAc. The organics were combined, dried and concentrated under reduced pressure. Purification (FCC) (0-100% soln of 5% MeOH, 0.5% HOAc in DCM/DCM) to afford 2-(5-(2-fluoro-6-(2H-1,2,3-triazol-2-yl)benzoyl)hexahydropyrrolo[3,4-c]pyrrol-2(1H)-yl)-4-(trifluoromethyl)pyrimidine-5-carboxylic acid (22 mg, 44%).

Example 263: 2-(5-(2-Fluoro-6-(2H-1,2,3-triazol-2-yl)benzoyl)hexahydropyrrolo[3,4-c]pyrrol-2(1H)-yl)-4-(trifluoromethyl)pyrimidine-5-carboxylic Acid

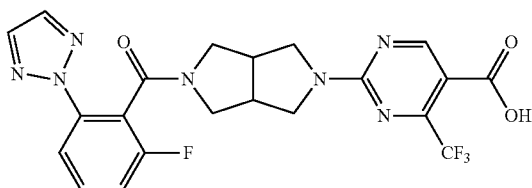

The title compound was isolated from the synthesis of Example 262. MS (ESI): mass calculated for C$_{21}$H$_{17}$F$_4$N$_7$O$_3$, 491.13. m/z found 492.1 [M+H]$^+$. $^1$H NMR (400 MHz, CD$_3$OD): 8.90 (t, J=11.7, 1H), 7.97 (s, 1H), 7.94-7.79 (m, 2H), 7.69-7.58 (m, 1H), 7.29 (dt, J=25.1, 12.6, 1H), 4.05-3.50 (m, 7H), 3.18 (tdd, J=19.6, 13.8, 6.8, 3H).

Example 264: (2-(4H-1,2,4-Triazol-4-yl)phenyl)(5-(4,6-dimethylpyrimidin-2-yl)hexahydropyrrolo[3,4-c]pyrrol-2(1H)-yl)methanone

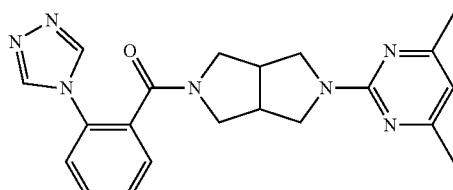

The title compound was prepared in a manner analogous to Example 15, utilizing Intermediate 23 and 2-(4H-1,2,4-triazol-4-yl)benzoic acid. MS (ESI): mass calculated for C$_{22}$H$_{19}$F$_4$N$_7$O$_3$, 505.15. m/z found 506.2 [M+H]$^+$. $^1$H NMR (400 MHz, CDCl$_3$): 8.49 (s, 2H), 7.54 (dd, J=7.6, 1.9, 3H), 7.45-7.37 (m, 1H), 6.31 (d, J=11.3, 1H), 3.88-3.65 (m, 4H), 3.50 (dd, J=12.0, 4.4, 2H), 3.33 (dt, J=11.2, 5.6, 1H), 3.08-2.80 (m, 3H), 2.28-2.26 (m, 6H).

Example 265: 2-(5-(2-Fluoro-6-(2H-1,2,3-triazol-2-yl)benzoyl)hexahydropyrrolo[3,4-c]pyrrol-2(1H)-yl)-6-methylpyrimidine-4-carboxylic Acid

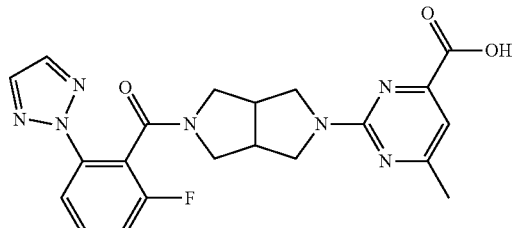

The title compound was prepared in a manner analogous to Example 262, substituting methyl 2-chloro-6-methylpyrimidine-4-carboxylate for methyl 2-chloro-4-(trifluoromethyl)pyrimidine-5-carboxylate. MS (ESI): mass calculated for C$_{21}$H$_{20}$FN$_7$O$_3$, 437.16. m/z found 438.2 [M+H]$^+$. $^1$H NMR (400 MHz, CD$_3$OD): 7.96 (d, J=6.2, 1H), 7.92-7.79 (m, 2H), 7.67-7.57 (m, 1H), 7.29 (d, J=8.4, 1H), 7.09 (s, 1H), 4.01-3.53 (m, 7H), 3.28-2.99 (m, 3H), 2.40-2.36 (m, 3H).

Example 266: (4,5-Difluoro-2-(4H-1,2,4-triazol-4-yl)phenyl)(5-(4,6-dimethylpyrimidin-2-yl)hexahydropyrrolo[3,4-c]pyrrol-2(1H)-yl)methanone

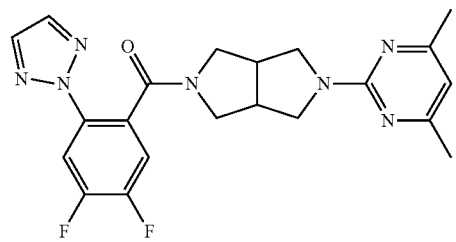 [SMILES: Cc1cc(C)nc(N2CC3CN(C(=O)c4cc(F)c(F)cc4-n4nccn4)CC3C2)n1]

The title compound was prepared in a manner analogous to Example 15, utilizing Intermediate 23 and 4,5-difluoro-2-(2H-1,2,3-triazol-2-yl)benzoic acid. MS (ESI): mass calculated for C$_{21}$H$_{21}$F$_2$N$_7$O, 425.18. m/z found 425.2 [M+H]$^+$. $^1$H NMR (400 MHz, CDCl$_3$): 7.86 (dd, J=10.8, 7.0, 1H), 7.74 (s, 2H), 7.26-7.19 (m, 1H), 6.30 (s, 1H), 3.86 (dd, J=11.8, 7.6, 2H), 3.66-3.50 (m, 5H), 3.10-2.86 (m, 3H), 2.36-2.23 (m, 6H).

Example 267: (5-(4,6-Dimethylpyrimidin-2-yl)hexahydropyrrolo[3,4-c]pyrrol-2(1H)-yl)(3-methyl-2-(1H-1,2,3-triazol-1-yl)phenyl)methanone

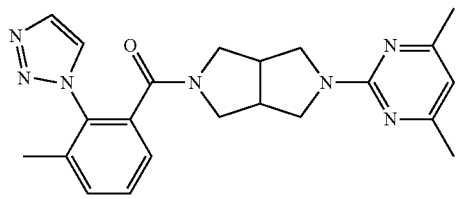 [SMILES: Cc1cc(C)nc(N2CC3CN(C(=O)c4cccc(C)c4-n4ccnn4)CC3C2)n1]

The title compound was prepared in a manner analogous to Example 15, utilizing Intermediate 23 and 3-methyl-2-

(1H-1,2,3-triazol-1-yl)benzoic acid. MS (ESI): mass calculated for $C_{22}H_{25}N_7O$, 403.21. m/z found 404.2 [M+H]⁺. ¹H NMR (400 MHz, CDCl₃): 7.87-7.77 (m, 1H), 7.52-7.38 (m, 2H), 7.25 (d, J=4.7, 2H), 6.28 (s, 1H), 3.76 (dd, J=11.6, 7.2, 2H), 3.65-3.29 (m, 6H), 3.12 (dd, J=11.1, 4.9, 1H), 2.96-2.83 (m, 1H), 2.29 (s, 6H), 2.15 (d, J=18.1, 3H).

Example 268: 2-(5-(2-Fluoro-6-(2H-1,2,3-triazol-2-yl)benzoyl)hexahydropyrrolo[3,4-c]pyrrol-2(1H)-yl)-N,N,6-trimethylpyrimidine-4-carboxamide

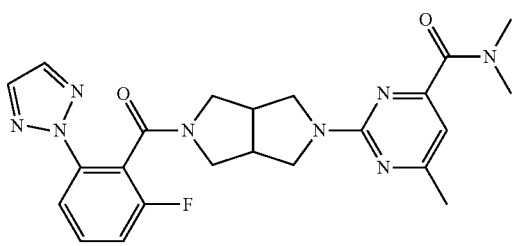 [SMILES: Cc1cc(C(=O)N(C)C)nc(N2CC3CN(C(=O)c4c(F)cccc4-n4nccn4)CC3C2)n1]

The title compound was prepared using Example 265 in a manner analogous to Example 15 substituting dimethylamine for 2-(4,6-dimethyl-pyrimidin-2-yl)-octahydro-pyrrolo[3,4-c]pyrrole and EDCl for HATU in the last step. MS (ESI): mass calculated for $C_{23}H_{25}FN_8O_2$, 464.21. m/z found 464.4[M+H]⁺. ¹H NMR (400 MHz, CDCl₃): 7.90-7.79 (m, 2H), 7.73 (s, 1H), 7.53-7.41 (m, 1H), 7.18-7.09 (m, 1H), 6.57 (d, J=9.8, 1H), 4.05-3.48 (m, 8H), 3.31-2.91 (m, 10H), 2.38 (s, 4H), 1.60 (s, 3H).

Example 269: 2-(5-(2-Fluoro-6-(2H-1,2,3-triazol-2-yl)benzoyl)hexahydropyrrolo[3,4-c]pyrrol-2(1H)-yl)-N,N-dimethyl-4-(trifluoromethyl) pyrimidine-5-carboxamide

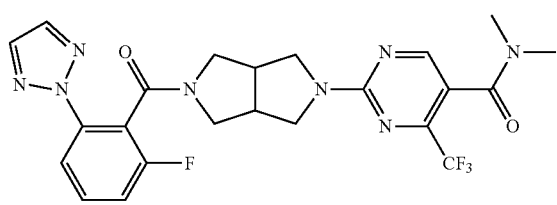 [SMILES: CN(C)C(=O)c1cnc(N2CC3CN(C(=O)c4c(F)cccc4-n4nccn4)CC3C2)nc1C(F)(F)F]

The title compound was prepared using Example 263 in a manner analogous to Example 15 substituting dimethylamine for 2-(4,6-dimethyl-pyrimidin-2-yl)-octahydro-pyrrolo[3,4-c]pyrrole and EDCl for HATU in the last step. MS (ESI): mass calculated for $C_{23}H_{22}F_4NO_2$, 518.18. m/z found 518.2 [M+H]⁺.

Example 270: (5-(4,6-Dimethylpyrimidin-2-yl)hexahydropyrrolo[3,4-c]pyrrol-2(1H)-yl)(mesityl)methanone

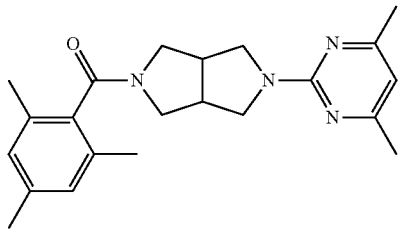 [SMILES: Cc1cc(C)c(C(=O)N2CC3CN(c4nc(C)cc(C)n4)CC3C2)c(C)c1]

The title compound was prepared in a manner analogous to Example 15, utilizing Intermediate 23 and 2,4,6-trimethylbenzoic acid. MS (ESI): mass calculated for $C_{22}H_{28}N_4O$, 364.23. m/z found 365.2 [M+H]⁺. ¹H NMR (400 MHz, CDCl₃): 6.82 (d, J=8.5, 2H), 6.29 (s, 1H), 4.03-3.29 (m, 8H), 3.11-2.89 (m, 2H), 2.35-2.11 (m, 15H).

Example 271: (2,3-Difluorophenyl)(5-(4,6-dimethylpyrimidin-2-yl)hexahydropyrrolo[3,4-c]pyrrol-2(1H)-yl)methanone

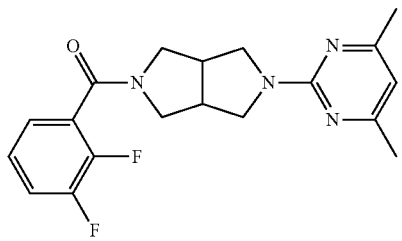 [SMILES: Cc1cc(C)nc(N2CC3CN(C(=O)c4cccc(F)c4F)CC3C2)n1]

The title compound was prepared in a manner analogous to Example 15, utilizing Intermediate 23 and 2,3-difluorobenzoic acid. MS (ESI): mass calculated for $C_{19}H_{20}F_2N_4O$, 358.16. m/z found 358.2 [M+H]⁺. ¹H NMR (400 MHz, CDCl₃): 7.26-7.08 (m, 3H), 6.30 (s, 1H), 4.03-3.73 (m, 3H), 3.71-3.57 (m, 3H), 3.39 (dd, J=11.3, 5.0, 2H), 3.16-2.95 (m, 2H), 2.36-2.19 (m, 6H).

Example 272: (5-(4,6-Dimethylpyrimidin-2-yl)hexahydropyrrolo[3,4-c]pyrrol-2(1H)-yl)(4-methoxy-2-(pyrimidin-2-yl)phenyl)methanone

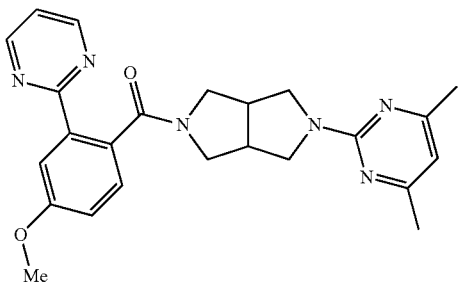 [SMILES: COc1ccc(C(=O)N2CC3CN(c4nc(C)cc(C)n4)CC3C2)c(-c2ncccn2)c1]

The title compound was prepared in a manner analogous to Example 15 substituting Intermediate 88 for 3-fluoro-2-

[1,2,3]triazol-2-yl-benzoic acid. MS (ESI) mass calcd. for $C_{24}H_{26}N_6O_2$, 430.5. m/z found, 431.3 [M+H]$^+$. $^1$H NMR (400 MHz, CDCl3): 8.78 (t, J=4.6 Hz, 2H), 7.80 (d, J=2.6 Hz, 1H), 7.33-7.27 (m, 1H), 7.16 (q, J=4.7 Hz, 1H), 7.05 (dd, J=8.4, 2.7 Hz, 1H), 6.30 (s, 1H), 3.91 (d, J=3.6 Hz, 3H), 3.85 (ddd, J=11.7, 7.8, 3.4 Hz, 2H), 3.72-3.60 (m, 3H), 3.54 (dd, J=11.6, 4.8 Hz, 1H), 3.47 (dd, J=11.0, 7.3 Hz, 1H), 3.16 (dd, J=11.1, 4.9 Hz, 1H), 3.00-2.87 (m, 2H), 2.30 (s, 6H).

Example 273: (2,3-Dimethoxyphenyl)(5-(4,6-dimethylpyrimidin-2-yl)hexahydropyrrolo[3,4-c]pyrrol-2(1H)-yl)methanone

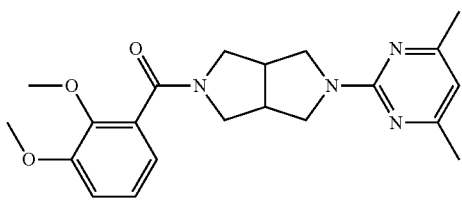

The title compound was prepared in a manner analogous to Example 15, utilizing Intermediate 23 and 2,3-dimethoxybenzoic acid. MS (ESI): mass calculated for $C_{21}H_{26}N_4O_3$, 382.20. m/z found 383.4 [M+H]$^+$. $^1$H NMR (400 MHz, CDCl$_3$): 7.09 (dd, J=17.8, 9.7, 1H), 6.89 (dd, J=7.9, 1.4, 2H), 6.33-6.19 (m, 1H), 4.02-3.43 (m, 13H), 3.32-2.83 (m, 3H), 2.39-2.21 (m, 6H).

Example 274: (5-(4,6-Dimethylpyrimidin-2-yl)hexahydropyrrolo[3,4-c]pyrrol-2(1H)-yl)(2-(trifluoromethoxy)phenyl)methanone

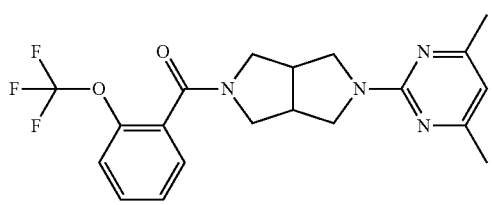 [SMILES: Cc1cc(C)nc(N2CC3CN(C(=O)c4ccccc4OC(F)(F)F)CC3C2)n1]

The title compound was prepared in a manner analogous to Example 15, utilizing Intermediate 23 and 2-(trifluoromethoxy)benzoic acid. MS (ESI): mass calculated for $C_{20}H_{21}F_3N_4O_2$, 406.16. m/z found 407.2 [M+H]$^+$. $^1$H NMR (400 MHz, CDCl$_3$): 7.49-7.27 (m, 4H), 6.30 (s, 1H), 4.08-3.36 (m, 8H), 3.28-2.80 (m, 3H), 2.40-2.19 (m, 6H).

Example 275: [5-(4,6-Dimethyl-pyrimidin-2-yl)-hexahydro-pyrrolo[3,4-c]pyrrol-2-yl]-(6-methyl-2-[1,2,3]triazol-2-yl-pyridin-3-yl)-methanone

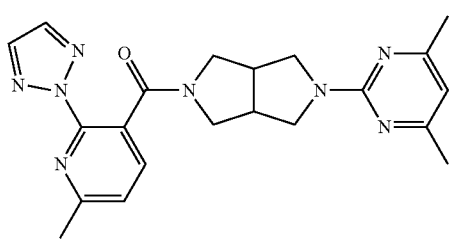 [SMILES: Cc1cc(C)nc(N2CC3CN(C(=O)c4ccc(C)nc4-n4nccn4)CC3C2)n1]

To a pale yellow solution of 2-(4,6-dimethylpyrimidin-2-yl)octahydropyrrolo[3,4-c]pyrrole (Intermediate 23) (50 mg, 0.23 mmol) in 2 mL of DMF was added 6-methyl-2-[1,2,3]triazol-2-yl-nicotinic acid (Intermediate 70) (51 mg, 0.25 mmol) followed by HATU (131 mg, 0.34 mmol) and DIPEA (0.118 mL, 0.69 mmol). The resulting solution was allowed to stir at room temp for 1 h and turned progressively more intense yellow as the reaction continued. The reaction was monitored via LCMS and quenched with H$_2$O once starting materials we no longer observed. The resulting biphasic mixture was extracted with EtOAc three times. The combined organic layers were washed with brine, dried with Na$_2$SO$_4$ and conc. into a pale yellow oil under reduced pressure. The yellow residue was purified via FCC using 5-50% 2M NH$_3$/MeOH in DCM. Minor impurities remained so the material was further purified via HPLC 0-99% CH$_3$N to give the desired product. MS (ESI) mass calcd. for $C_{21}H_{24}N_5O$, 404.47; m/z found 405.3 [M+H]$^+$. $^1$H NMR (400 MHz, CDCl$_3$) 7.80 (s, 2H), 7.72 (d, J=7.7 Hz, 1H), 7.29-7.24 (m, 1H), 6.30 (s, 1H), 3.90-3.80 (m, 2H), 3.73-3.63 (m, 2H), 3.59 (dd, J=11.6, 5.3 Hz, 1H), 3.47 (dd, J=11.6, 3.7 Hz, 1H), 3.33 (s, 1H), 3.00 (ddd, J=38.4, 21.7, 7.2 Hz, 3H), 2.68 (s, 3H), 2.30 (s, 6H).

Example 276: (5-(4,6-Dimethylpyrimidin-2-yl)hexahydropyrrolo[3,4-c]pyrrol-2(1H)-yl)(2-methoxy-4-methylphenyl)methanone

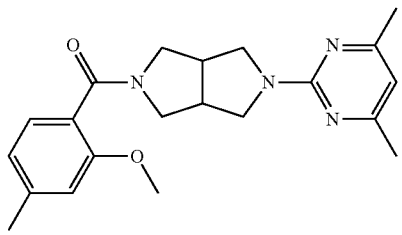 [SMILES: COc1cc(C)ccc1C(=O)N1CC2CN(c3nc(C)cc(C)n3)CC2C1]

The title compound was prepared in a manner analogous to Example 15, utilizing Intermediate 23 and 2-methoxy-4-methylbenzoic acid. MS (ESI): mass calculated for $C_{21}H_{26}N_4O_2$, 366.21. m/z found 367.3 [M+H]$^+$. $^1$H NMR (400 MHz, CDCl$_3$): 7.13 (d, J=7.6, 1H), 6.77 (d, J=7.6, 1H), 6.70 (s, 1H), 6.28 (s, 1H), 4.00-3.40 (m, 11H), 3.27-2.85 (m, 3H), 2.41-2.19 (m, 9H).

Example 277: (5-(4,6-Dimethylpyrimidin-2-yl)hexahydropyrrolo[3,4-c]pyrrol-2(1H)-yl)(4-methoxy-2-methylphenyl)methanone

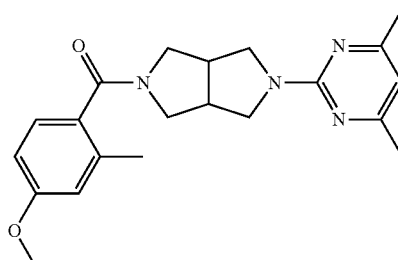

The title compound was prepared in a manner analogous to Example 15, utilizing Intermediate 23 and 4-methoxy-2-methylbenzoic acid. MS (ESI): mass calculated for $C_{21}H_{26}N_4O_2$, 366.21. m/z found 367.3 [M+H]$^+$. $^1$H NMR (400 MHz, CDCl$_3$): 7.11 (d, J=7.9, 1H), 6.77-6.67 (m, 2H), 6.29 (s, 1H), 4.01-3.83 (m, 2H), 3.83-3.72 (m, 4H), 3.72-3.55 (m, 2H), 3.46 (dt, J=11.9, 6.0, 2H), 3.21-2.89 (m, 3H), 2.37-2.25 (m, 9H).

Example 278: (2,6-Difluorophenyl)(5-(4,6-dimethylpyrimidin-2-yl)hexahydropyrrolo[3,4-c]pyrrol-2(1H)-ylmethanone

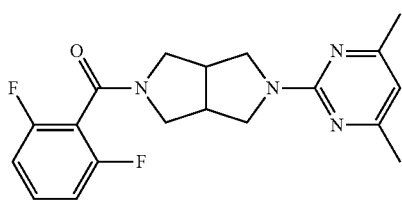 [SMILES: Cc1cc(C)nc(N2CC3CN(C(=O)c4c(F)cccc4F)CC3C2)n1]

The title compound was prepared in a manner analogous to Example 15, utilizing Intermediate 23 and 2,6-difluorobenzoic acid. MS (ESI): mass calculated for $C_{19}H_{20}F_2N_4O$, 358.16. m/z found 359.2 [M+H]$^+$. $^1$H NMR (400 MHz, CDCl$_3$): 7.34 (tt, J=8.4, 6.4, 1H), 6.93 (s, 2H), 6.30 (s, 1H), 4.12-3.76 (m, 3H), 3.75-3.45 (m, 4H), 3.36-2.88 (m, 3H), 2.30 (s, 6H).

Example 279: 2-[5-{[2-Fluoro-6-(2H-1,2,3-triazol-2-yl)phenyl]carbonyl}hexahydropyrrolo[3,4-c]pyrrol-2(1H)-yl]-6-methylpyrimidine-4-carbonitrile

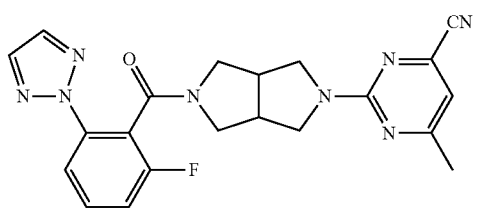

The title compound was prepared in a manner analogous to Example 15, utilizing Intermediate 12 and Intermediate 49. MS (ESI): mass calculated for $C_{21}H_{19}F_2N_5O$, 418.44. m/z found 419.2 [M+H]$^+$. $^1$H NMR (400 MHz, CDCl$_3$): 7.91-7.80 (m, 2H), 7.75 (s, 1H), 7.55-7.42 (m, 1H), 7.15 (ddd, J=8.4, 6.6, 4.0 Hz, 1H), 6.69 (d, J=5.5 Hz, 1H), 4.07-3.46 (m, 7H), 3.35-3.20 (m, 1H), 3.19-2.94 (m, 2H), 2.40 (s, 3H).

Example 280: 2-[4,6-Bis(trifluoromethyl)pyrimidin-2-yl]-5-{[2-fluoro-6-(2H-1,2,3-triazol-2-yl)phenyl]carbonyl}octahydropyrrolo[3,4-c]pyrrole

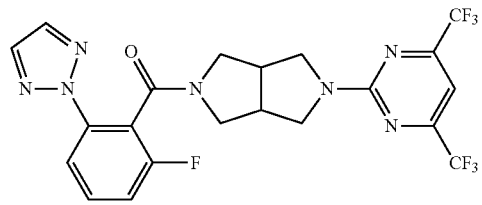 [SMILES: O=C(c1c(F)cccc1-n1nccn1)N1CC2CN(c3nc(C(F)(F)F)cc(C(F)(F)F)n3)CC2C1]

Step A: Intermediate 16 (100 mg, 0.332 mmol) was diluted with DCM (10 mL) and was treated with 1,3-di-boc-2-(trifluoromethylsulfonyl)guanidine (118.2 mg, 0.302 mmol) and triethyl amine (0.046 mL, 0.332 mmol). The reaction was stirred at room temperature overnight, then was diluted with DCM and water, extracted and concentrated to provide crude tert-butyl (((tert-butoxycarbonyl)imino)(5-(2-fluoro-6-(2H-1,2,3-triazol-2-yl)benzoyl)hexahydropyrrolo[3,4-c]pyrrol-2(1H)-yl)methyl)carbamate (165 mg) which was used as is in Step B. MS (ESI): mass calculated for $C_{26}H_{34}FN_7O_5$, 543.60. m/z found 544.3 [M+H]$^+$.

Step B: Crude tert-butyl (((tert-butoxycarbonyl)imino)(5-(2-fluoro-6-(2H-1,2,3-triazol-2-yl)benzoyl)hexahydropyrrolo[3,4-c]pyrrol-2(1H)-yl)methyl)carbamate was dissolved in dioxin (8 mL) and TFA (3 mL) was added and the reaction was stirred at room temperature overnight to form crude 5-(2-fluoro-6-(2H-1,2,3-triazol-2-yl)benzoyl)hexahydropyrrolo[3,4-c]pyrrole-2(1H)-carboximidamide (214 mg) as a TFA salt which was used directly in Step C.

Step C: Crude 5-(2-fluoro-6-(2H-1,2,3-triazol-2-yl)benzoyl)hexahydro-pyrrolo[3,4-c]pyrrole-2(1H)-carboximidamide—TFA salt (66 mg) was diluted with n-butanol (4 mL) and treated with sodium methoxide (51.9 mg, 0.961 mmol). The reaction is heated to reflux for 1 hour, then cooled and 1,1,1,5,5,5-hexafluoropentane-2,4-dione (400 mg, 1.92 mmol) is added prior to re-heating the reaction to reflux for 19 hours. The mixture was then cooled and concentrated, then diluted with DCM and saturated sodium bicarbonate. Extract with DCM and concentrate. Reverse phase HPLC gave the title compound (4.6 mg). MS (ESI): mass calculated for $C_{21}H_{16}F_7N_7O$, 515.39; m/z found 416.2 [M+H]$^+$. Rotamers observed in $^1$H NMR.

Example 281: 2-[5-{[2-Fluoro-6-(2H-1,2,3-triazol-2-yl)phenyl]carbonyl}hexahydropyrrolo[3,4-c]pyrrol-2(1H)-yl]-6-methyl pyrimidin-4-ol

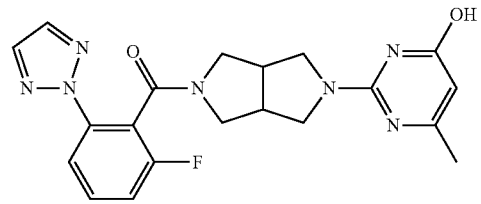 [SMILES: Cc1cc(O)nc(N2CC3CN(C(=O)c4c(F)cccc4-n4nccn4)CC3C2)n1]

The title compound was prepared in a manner analogous to Example 280, substituting methyl acetoacetate for 1,1,1,5,5,5-hexafluoropentane-2,4-dione in Step C. MS (ESI):

mass calculated for $C_{20}H_{20}FN_7O_2$, 409.42. m/z found 410.2 [M+H]$^+$. Rotamers observed in $^1$H NMR.

Example 282: (2-Fluoro-6-(2H-1,2,3-triazol-2-yl)phenyl)(5-(4-(furan-2-yl)-6-methylpyrimidin-2-yl)hexahydropyrrolo[3,4-c]pyrrol-2(1H)-yl)methanone

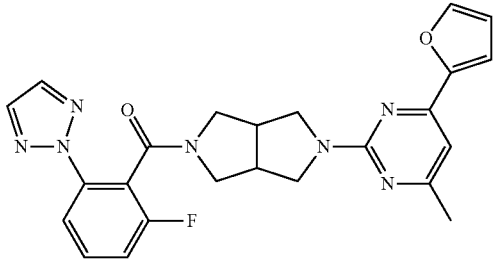 [SMILES: Cc1cc(-c2ccco2)nc(N2CC3CN(C(=O)c4c(F)cccc4-n4nccn4)CC3C2)n1]

The title compound was prepared in a manner analogous to Example 280, substituting 1-(furan-2-yl)butane-1,3-dione for 1,1,1,5,5,5-hexafluoropentane-2,4-dione in the Step C. MS (ESI): mass calculated for $C_{24}H_{22}FN_7O_2$, 459.49. m/z found 460.2 [M+H]$^+$. $^1$H NMR very broad peaks due to rotamers.

Example 283: 2-(4,6-Dimethylpyrimidin-2-yl)-5-[(3-fluoro-2-pyrimidin-2-ylphenyl)carbonyl]octahydropyrrolo[3,4-c]pyrrole

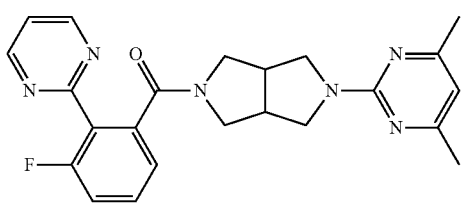 [SMILES: Cc1cc(C)nc(N2CC3CN(C(=O)c4cccc(F)c4-c4ncccn4)CC3C2)n1]

To a mixture of 2-(4,6-dimethyl-pyrimidin-2-yl)-octahydro-pyrrolo[3,4-c]pyrrole (1.4 g, 6.5 mmol), 3-fluoro-2-(pyrimidin-2-yl)benzoic acid (1.4 g, 6.5 mmol), and TEA (1.3 mL, 9.7 mmol) in DMF (32.0 mL) was added HATU (2.7 g, 7.1 mmol).

After 1 h, the reaction mixture was diluted with EtOAc and washed with water. The aqueous layer was then extracted with EtOAc (1×). The combined organic phases were dried (Na$_2$SO$_4$), filtered and concentrated to dryness. The crude product was purified using silica gel chromatography (0-5% MeOH in EtOAc) to yield pure title compound (1.2 g, 44%). MS (ESI) mass calcd. For $C_{23}H_{23}FN_6O$, 418.48. m/z found 419.2 [M+H]$^+$. $^1$H NMR (CDCl$_3$): 8.91-8.56 (m, 2H), 7.47-7.42 (m, 1H), 7.24-7.14 (m, 3H), 6.30 (s, 1H), 3.81 (dd, J=11.6, 7.2 Hz, 1H), 3.72 (ddd, J=9.0, 7.2, 2.2 Hz, 2H), 3.68-3.47 (m, 4H), 3.31 (dd, J=11.0, 4.8 Hz, 1H), 3.05-2.89 (m, 2H), 2.31 (s, 6H).

Example 284: 2-(4,6-Dimethylpyrimidin-2-yl)-5-{[3-fluoro-2-(1H-pyrazol-5-yl)phenyl]carbonyl}octahydropyrrolo[3,4-c]pyrrole

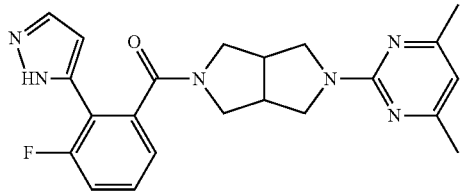 [SMILES: Cc1cc(C)nc(N2CC3CN(C(=O)c4cccc(F)c4-c4ccn[nH]4)CC3C2)n1]

The title compound was prepared in a manner analogous to Example 283, substituting Intermediate 86 for 3-fluoro-2-(pyrimidin-2-yl)benzoic acid. MS (ESI) mass calcd. $C_{22}H_{23}FN_6O$, 406.47. m/z found 407.2 [M+H]$^+$. $^1$H NMR (CDCl$_3$): 11.33 (s, 1H), 7.50 (m, 1H), 7.35-7.31 (m, 1H), 7.21-7.08 (m, 2H), 6.64 (s, 1H), 6.28 (s, 1H), 3.82-2.71 (m, 10H), 2.30 (s, 6H).

Example 285: 2-(4,6-Dimethylpyrimidin-2-yl)-5-{[3-methoxy-2-(2H-1,2,3-triazol-2-yl)phenyl]carbonyl}octahydropyrrolo[3,4-c]pyrrole

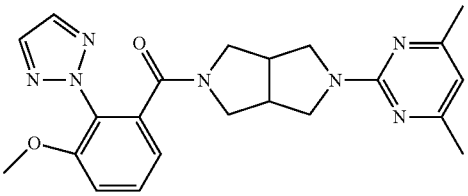

The title compound was prepared in a manner analogous to Example 283, substituting 3-methoxy-2-(2H-1,2,3-triazol-2-yl)benzoic acid for 3-fluoro-2-(pyrimidin-2-yl)benzoic acid. MS (ESI) mass calcd. $C_{22}H_{25}N_7O_2$, 419.49. m/z found 420.2 [M+H]$^+$. $^1$H NMR (CDCl$_3$): 7.74 (d, J=6.6 Hz, 2H), 7.51-7.45 (m, 1H), 7.09 (dd, J=8.4, 1.0 Hz, 1H), 7.00 (dd, J=7.6, 1.1 Hz, 1H), 6.29 (s, 1H), 3.87-3.76 (m, 4H), 3.66 (ddd, J=19.8, 12.1, 7.0 Hz, 2H), 3.58-3.50 (m, 2H), 3.47-3.37 (m, 2H), 3.22 (dd, J=11.0, 5.1 Hz, 1H), 2.97-2.86 (m, 2H), 2.28 (s, J=20.1 Hz, 6H).

Example 286: 2-(4,6-Dimethylpyrimidin-2-yl)-5-{[3-methoxy-2-(1H-1,2,3-triazol-1-yl)phenyl]carbonyl}octahydropyrrolo[3,4-c]pyrrole

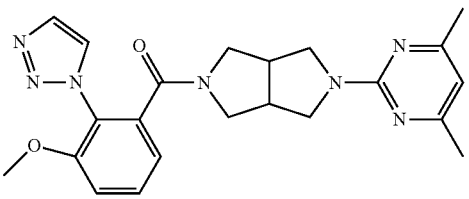

Step A: To 3-fluoro-2-(1H-1,2,3-triazol-1-yl)benzonitrile (2.1 g, 11.2 mmol) in MeOH (30 mL) was added 2 M aq. NaOH (10 mL). The reaction was heated at reflux until determined complete by HPLC then cooled to room temperature, acidified with 1 N aq. HCl to pH=1 and extracted with DCM (2×). The combined organics were washed with brine and dried (Na₂SO₄) resulting in a mixture of two products, 3-methoxy-2-(1H-1,2,3-triazol-1-yl)benzoic acid and 3-fluoro-2-(1H-1,2,3-triazol-1-yl)benzoic acid, which were used without further purification in the next step.

Step B: 2-(4,6-Dimethylpyrimidin-2-yl)-5-{[3-methoxy-2-(1H-1,2,3-triazol-1-yl)phenyl]carbonyl}octahydropyrrolo[3,4-c]pyrrole. Example 286 was prepared in a manner analogous to Example 283, utilizing a mixture of 3-methoxy-2-(1H-1,2,3-triazol-2-yl)benzoic acid and 3-fluoro-2-(1H-1,2,3-triazol-2-yl)benzoic acid in place of 3-fluoro-2-(pyrimidin-2-yl)benzoic acid which gave 2 products, Example 286 and Example 287. For Example 286: MS (ESI) mass calcd. $C_{22}H_{23}N_7O_2$, 419.49. m/z found 420.2 [M+H]⁺. ¹H NMR (CDCl₃): 7.87 (d, J=1.0 Hz, 1H), 7.77 (d, J=1.0 Hz, 1H), 7.52-7.45 (m, 1H), 7.09 (dd, J=8.5, 1.0 Hz, 1H), 7.00 (dd, J=7.7, 1.1 Hz, 1H), 6.29 (s, J=5.2 Hz, 1H), 3.89-3.81 (m, 4H), 3.79-3.65 (m, 3H), 3.54-3.46 (m, 2H), 3.43-3.36 (m, 1H), 3.24 (dt, J=12.4, 6.1 Hz, 1H), 3.02-2.91 (m, 2H), 2.29 (s, 6H).

Example 287: 2-(4,6-Dimethylpyrimidin-2-yl)-5-{[3-fluoro-2-(1H-1,2,3-triazol-1-yl)phenyl]carbonyl}octahydropyrrolo[3,4-c]pyrrole

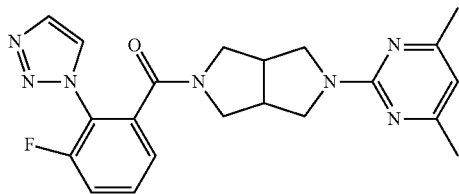 [SMILES: Cc1cc(C)nc(N2CC3CN(C(=O)c4cccc(F)c4-n4ccnn4)CC3C2)n1]

The title compound was isolated from Step B in Example 286. MS (ESI) mass calcd. $C_{21}H_{22}FN_7O$, 407.45. m/z found 408.2 [M+H]⁺. ¹H NMR (CDCl₃): 7.96-7.91 (m, 1H), 7.84-7.80 (m, 1H), 7.58-7.49 (m, 1H), 7.37-7.30 (m, 1H), 7.26-7.23 (m, 1H), 6.29 (s, 1H), 3.88-3.85 (m, 1H), 3.80-3.71 (m, 2H), 3.71-3.64 (m, 1H), 3.57-3.42 (m, 3H), 3.23 (dd, J=11.0, 5.0 Hz, 1H), 3.04-2.94 (m, 2H), 2.29 (s, 6H).

Example 288: 2-(4,6-Dimethylpyrimidin-2-yl)-5-{[4-methoxy-2-(2H-1,2,3-triazol-2-yl)phenyl]carbonyl}octahydropyrrolo[3,4-c]pyrrole

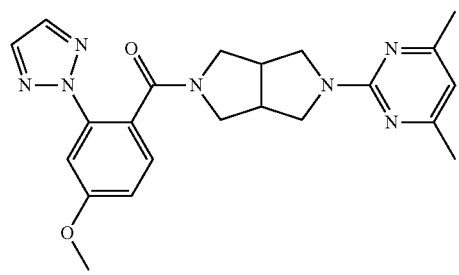 [SMILES: COc1ccc(C(=O)N2CC3CN(c4nc(C)cc(C)n4)CC3C2)c(-n2nccn2)c1]

Step A: (5-Benzylhexahydropyrrolo[3,4-c]pyrrol-2(1H)-yl)(4-methoxy-2-(2H-1,2,3-triazol-2-yl)phenyl)methanone. To a mixture of 2-benzyloctahydropyrrolo[3,4-c]pyrrole (282 mg, 1.4 mmol), 4-methoxy-2-(2H-1,2,3-triazol-2-yl)benzoic acid (306 mg, 1.4 mmol), and TEA (0.21 mL, 1.5 mmol) in DMF (7.5 mL) was added HATU (583 mg, 1.5 mmol). After 1 h, the reaction mixture was diluted with EtOAc and washed with water. The aqueous layer was then extracted with EtOAc (1×). The combined organics were dried (Na₂SO₄) and concentrated to give a residue. Purification via Agilent prep system (Basic) gave 327 mg (58%) of the title compound as a clear oil. ¹H NMR (CDCl₃): 7.79 (s, J=6.5 Hz, 2H), 7.50 (d, J=5.0 Hz, 1H), 7.36 (d, J=8.5 Hz, 1H), 7.34-7.21 (m, 5H), 6.95 (dd, J=8.5, 2.5 Hz, 1H), 3.93 (s, 3H), 3.86-3.72 (m, 1H), 3.65-3.46 (m, 3H), 3.13 (s, 1H), 2.90-2.74 (m, 2H), 2.74-2.59 (m, 2H), 2.57-2.39 (m, 2H), 2.16 (dd, J=9.2, 4.2 Hz, 1H).

Step B: (Hexahydropyrrolo[3,4-c]pyrrol-2(1H)-yl)(4-methoxy-2-(2H-1,2,3-triazol-2-yl)phenyl)methanone. (5-Benzylhexahydropyrrolo[3,4-c]pyrrol-2(1H)-yl)(4-methoxy-2-(2H-1,2,3-triazol-2-yl)phenyl)methanone in EtOH (20 mL) and AcOH (1 mL) was continuously flowed through a 20 wt % Pd(OH)₂/C cartridge at a rate of 1 mL/min for 2 h at 50° C. and 50 bar using a H-cube apparatus. Then the reaction was concentrated and neutralized with 5% Na₂CO₃ (aq), and extracted with CH₂Cl₂ (3×). Combined organics and dried (Na₂SO₄) to give (hexahydropyrrolo[3,4-c]pyrrol-2(1H)-yl)(4-methoxy-2-(2H-1,2,3-triazol-2-yl)phenyl)methanone as a clear oil that was used without further purification. ¹H NMR (CDCl₃): 7.83-7.80 (m, 2H), 7.50 (d, J=2.5 Hz, 1H), 7.32 (d, J=8.5 Hz, 1H), 6.96 (dd, J=8.5, 2.5 Hz, 1H), 3.89 (s, 3H), 3.75-3.63 (m, 2H), 3.27 (s, 1H), 3.08 (dd, J=11.9, 8.1 Hz, 1H), 2.94 (dt, J=11.4, 5.7 Hz, 2H), 2.88-2.75 (m, 2H), 2.69 (dd, J=17.8, 14.3 Hz, 1H), 2.56 (dd, J=11.4, 3.9 Hz, 1H).

Step C: 2-(4,6-Dimethylpyrimidin-2-yl)-5-{[4-methoxy-2-(2H-1,2,3-triazol-2-yl)phenyl]carbonyl}octahydropyrrolo[3,4-c]pyrrole. To (hexahydropyrrolo[3,4-c]pyrrol-2(1H)-yl)(4-methoxy-2-(2H-1,2,3-triazol-2-yl)phenyl)methanone (185 mg, 0.4 mmol) in DMF (2.2 mL) was added 2-chloro-4,6-dimethylpyrimidine (61 mg, 0.4 mmol). The flask was heated to 120° C. for 18 h. The flask was allowed to cool to rt, diluted with EtOAc and washed with H₂O. The aq was back-extracted with EtOAc (1×). The combined organics were washed with brine and dried (Na₂SO₄) to give an oil. Purification via silica gel (15-75% EtOAc in hexanes) gave 175 mg (97%) of the title compound. MS (ESI) mass calcd. $C_{22}H_{25}N_7O_2$, 419.49. m/z found 420.2 [M+H]⁺. ¹H NMR (CDCl₃): 7.73 (s, 2H), 7.49 (d, J=7.8 Hz, 1H), 7.33 (d, J=8.5 Hz, 1H), 6.95 (dd, J=8.5, 2.5 Hz, 1H), 6.29 (s, 1H), 3.93-3.80 (m, 5H), 3.72-3.63 (m, 2H), 3.58 (dd, J=11.6, 5.2 Hz, 1H), 3.46 (dd, J=11.6, 4.3 Hz, 1H), 3.39-3.28 (m, 1H), 3.05-2.84 (m, 3H), 2.33 (s, 6H).

Example 289: 2-(4,6-Dimethylpyrimidin-2-yl)-5-{[4-methoxy-2-(1H-1,2,3-triazol-2-yl)phenyl]carbonyl}octahydropyrrolo[3,4-c]pyrrole

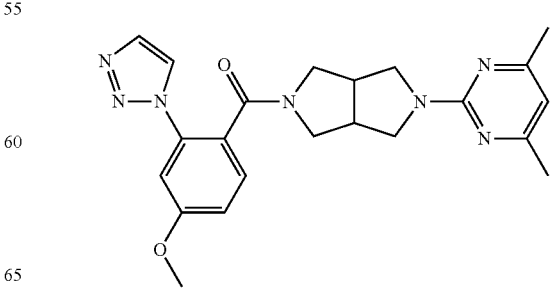

The title compound was prepared in a manner analogous to Example 283, utilizing a mixture of 4-methoxy-2-(1H-1,2,3-triazol-1-yl)benzoic acid and 4-methoxy-2-(2H-1,2,3-triazol-1-yl)benzoic acid obtained from the synthesis of Intermediate 54. Purification of the final compounds gave the title compound as an oil. MS (ESI) mass calcd. $C_{22}H_{25}N_7O_2$, 419.49. m/z found 420.2 [M+H]$^+$. $^1$H NMR (CDCl$_3$: 7.98 (s, J=2.9 Hz, 1H), 7.77 (s, J=4.1 Hz, 1H), 7.42-7.36 (m, 1H), 7.18 (d, J=2.5 Hz, 1H), 7.06 (dd, J=8.5, 2.5 Hz, 1H), 6.29 (s, 1H), 3.90 (s, J=7.6 Hz, 3H), 3.83-3.66 (m, 3H), 3.50-3.42 (m, 2H), 3.30 (dd, J=11.6, 4.7 Hz, 1H), 3.22 (dd, J=11.1, 7.3 Hz, 1H), 2.99-2.76 (m, 3H), 2.28 (d, J=16.2 Hz, 6H).

Example 290: 2-(5-Fluoro-4-methylpyrimidin-2-yl)-5-{[2-(2H-1,2,3-triazol-2-yl)phenyl]carbonyl}octahydropyrrolo[3,4-c]pyrrole

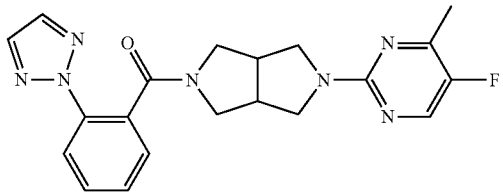 [SMILES: Cc1nc(N2CC3CN(C(=O)c4ccccc4-n4nccn4)CC3C2)ncc1F]

A mixture of Intermediate 20 (86 mg, 0.30 mmol), Intermediate 55 (44 mg, 0.3 mmol) and DIPEA (0.16 mL, 0.91 mmol) in ACN (1 mL) was heated in the microwave at 200° C. for 2 h. The mixture was concentrated in vacuo and chromatography (Hex to 100% EtOAc/Hex) afforded the title compound (82 mg, 69%). MS (ESI): mass calculated for $C_{20}H_{20}FN_7O$, 393.17, m/z found 394.2 [M+1]$^+$. $^1$H NMR (400 MHz, CDCl$_3$): 8.06 (d, J=1.7 Hz, 1H), 7.98 (d, J=8.1 Hz, 1H), 7.75 (s, 2H), 7.57-7.48 (m, 1H), 7.43 (d, J=6.2 Hz, 2H), 3.93-3.77 (m, 2H), 3.74-3.60 (m, 2H), 3.59-3.51 (m, 1H), 3.46-3.33 (m, 2H), 3.09-2.88 (m, 3H), 2.37 (d, J=2.5 Hz, 3H).

Example 291: 2-(2-Chloro-5-fluoropyrimidin-4-yl)-5-{[2-(2H-1,2,3-triazol-2-yl)phenyl]carbonyl}octahydropyrrolo[3,4-c]pyrrole

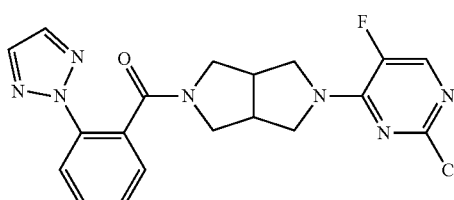

The title compound was prepared in a manner analogous to Example 290 utilizing Intermediate 20 and substituting 2,4-dichloro-5-fluoropyrimidine for Intermediate 55. MS (ESI) mass calculated for $C_{19}H_{17}ClFN_7O$, 413.85. m/z found, 414.2 [M+H]$^+$. $^1$H NMR (400 MHz, CDCl$_3$): 8.01 (d, J=8.3 Hz, 1H), 7.90 (d, J=5.0 Hz, 1H), 7.79 (s, 2H), 7.58-7.51 (m, 1H), 7.48-7.39 (m, 2H), 4.04-3.93 (m, 1H), 3.92-3.70 (m, 4H), 3.68-3.59 (m, 1H), 3.46 (br s, 1H), 3.13-2.88 (m, 3H).

Example 292: 2-(5-Fluoropyrimidin-2-yl)-5-{[2-fluoro-6-(2H-1,2,3-triazol-2-yl)phenyl]carbonyl}octahydropyrrolo[3,4-c]pyrrole

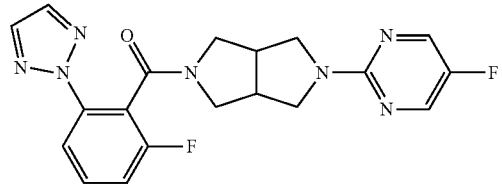 [SMILES: O=C(c1c(F)cccc1-n1nccn1)N1CC2CN(c3ncc(F)cn3)CC2C1]

The title compound was prepared in a manner analogous to Example 290 substituting Intermediate 16 for Intermediate 20 and 2-chloro-5-fluoropyrimidine for Intermediate 55. MS (ESI) mass calculated for $C_{19}H_{17}F_2N_7O$, 397.39. m/z found, 398.2. $^1$H NMR (400 MHz, CDCl$_3$): 8.26-8.17 (m, 2H), 7.89-7.78 (m, 2H), 7.73 (s, 1H), 7.53-7.44 (m, 1H), 7.19-7.10 (m, 1H), 4.02-3.45 (m, 7H), 3.30-3.23 (m, 1H), 3.17-2.97 (m, 2H).

Example 293: 2-(5-Fluoro-4-methylpyrimidin-2-yl)-5-{[2-fluoro-6-(2H-1,2,3-triazol-2-yl)phenyl]carbonyl}octahydropyrrolo[3,4-c]pyrrole

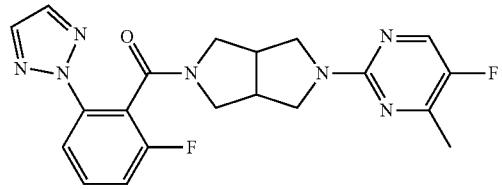 [SMILES: Cc1nc(N2CC3CN(C(=O)c4c(F)cccc4-n4nccn4)CC3C2)ncc1F]

The title compound was prepared in a manner analogous to Example 290 substituting Intermediate 16 for Intermediate 20. MS (ESI) mass calculated for $C_{20}H_{19}F_2N_7O$, 411.42. m/z found, 412.2. $^1$H NMR (400 MHz, CDCl$_3$): 8.09-8.03 (m, 1H), 7.88-7.79 (m, 2H), 7.72 (s, 1H), 7.51-7.43 (m, 1H), 7.18-7.10 (m, 1H), 4.01-3.45 (m, 7H), 3.30-3.21 (m, 1H), 3.15-2.95 (m, 2H), 2.37 (d, J=2.4 Hz, 3H).

Example 294: 2-{[2-Fluoro-6-(2H-1,2,3-triazol-2-yl)phenyl]carbonyl}-5-(4,5,6-trimethylpyrimidin-2-yl)octahydropyrrolo[3,4-c]pyrrole

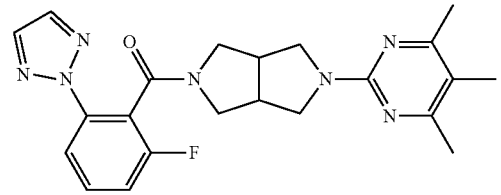 [SMILES: Cc1nc(N2CC3CN(C(=O)c4c(F)cccc4-n4nccn4)CC3C2)nc(C)c1C]

The title compound was prepared in a manner analogous to Example 290 substituting Intermediate 16 for Intermediate 20 and Intermediate 56 for Intermediate 55. MS (ESI) mass calculated for $C_{22}H_{24}FN_7O$, 421.48. m/z found, 422.2. $^1$H NMR (500 MHz, CDCl$_3$): 7.88-7.79 (m, 2H), 7.72 (s, 1H), 7.50-7.43 (m, 1H), 7.17-7.10 (m, 1H), 3.93-3.47 (m, 7H), 3.28-3.21 (m, 1H), 3.11-2.93 (m, 2H), 2.33 (s, 6H), 2.07 (s, 3H).

Example 295: 2-(4,5-Dimethylpyrimidin-2-yl)-5-{[2-fluoro-6-(2H-1,2,3-triazol-2-yl)phenyl]carbonyl}octahydropyrrolo[3,4-c]pyrrole

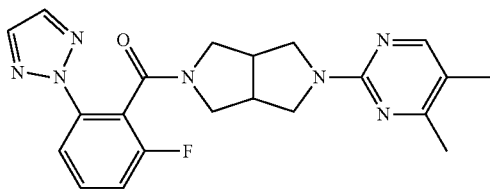 [SMILES: Cc1cnc(N2CC3CN(C(=O)c4c(F)cccc4-n4nccn4)CC3C2)nc1C]

The title compound was prepared in a manner analogous to Example 290 substituting Intermediate 16 for Intermediate 20 and Intermediate 57 for Intermediate 55. MS (ESI) mass calculated for $C_{21}H_{22}FN_7O$, 407.45. m/z found, 408.2. $^1$H NMR (400 MHz, CDCl$_3$): 7.99 (s, 1H), 7.89-7.78 (m, 2H), 7.72 (s, 1H), 7.53-7.42 (m, 1H), 7.19-7.08 (m, 1H), 4.02-3.46 (m, 7H), 3.31-3.21 (m, 1H), 3.15-2.95 (m, 2H), 2.32 (s, 3H), 2.09 (s, 3H).

Example 296: 2-{[2-Fluoro-6-(2H-1,2,3-triazol-2-yl)phenyl]carbonyl}-5-(4-methoxy-6-methylpyrimidin-2-yl)octahydropyrrolo[3,4-c]pyrrole

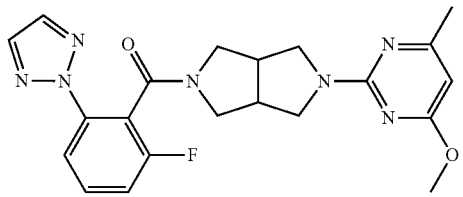 [SMILES: COc1cc(C)nc(N2CC3CN(C(=O)c4c(F)cccc4-n4nccn4)CC3C2)n1]

The title compound was isolated from the synthesis of Intermediate 58. MS (ESI) mass calculated for $C_{21}H_{22}FN_7O_2$, 423.45. m/z found, 424.0. $^1$H NMR (500 MHz, CDCl$_3$): 7.88-7.80 (m, 2H), 7.72 (s, 1H), 7.52-7.44 (m, 1H), 7.18-7.11 (m, 1H), 5.87 (d, J=4.3 Hz, 1H), 4.00-3.50 (m, 10H), 3.30-3.22 (m, 1H), 3.13-2.93 (m, 2H), 2.28 (s, 3H).

Example 297: 2-(4-Ethyl-6-methylpyrimidin-2-yl)-5-{[2-fluoro-6-(2H-1,2,3-triazol-2-yl)phenyl]carbonyl}octahydropyrrolo[3,4-c]pyrrole

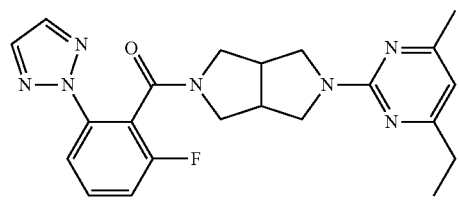 [SMILES: CCc1cc(C)nc(N2CC3CN(C(=O)c4c(F)cccc4-n4nccn4)CC3C2)n1]

The title compound was prepared in a manner analogous to Intermediate 55 substituting Intermediate 58 for 2,4-dichloro-5-fluoropyrimidine and 1.0 M EtMgBr in THF for 3.0 M MeMgBr in Et$_2$O. MS (ESI) mass calculated for $C_{22}H_{24}FN_7O$, 421.48. m/z found, 422.0. $^1$H NMR (500 MHz, CDCl$_3$): 7.88-7.79 (m, 2H), 7.71 (s, 1H), 7.51-7.43 (m, 1H), 7.18-7.11 (m, 1H), 6.29 (d, J=7.2 Hz, 1H), 4.01-3.50 (m, 7H), 3.31-3.22 (m, 1H), 3.13-2.94 (m, 2H), 2.56 (q, J=7.6 Hz, 2H), 2.31 (d, J=1.6 Hz, 3H), 1.27-1.21 (m, 3H).

Example 298: 2-{[2-Fluoro-6-(2H-1,2,3-triazol-2-yl)phenyl]carbonyl}-5-[4-methyl-6-(1-methylethyl)pyrimidin-2-yl]octahydropyrrolo[3,4-c]pyrrole

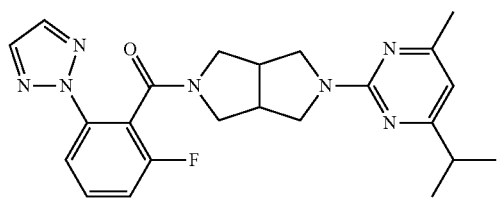 [SMILES: Cc1cc(C(C)C)nc(N2CC3CN(C(=O)c4c(F)cccc4-n4nccn4)CC3C2)n1]

The title compound was prepared in a manner analogous to Intermediate 55 substituting Intermediate 58 for 2,4-dichloro-5-fluoropyrimidine and 2.0 M iPrMgBr in THF for 3.0 M MeMgBr in Et$_2$O. Three products were formed in this reaction, 2-{[2-fluoro-6-(2H-1,2,3-triazol-2-yl)phenyl]carbonyl}-5-[4-methyl-6-(1-methylethyl)pyrimidin-2-yl]octahydropyrrolo[3,4-c]pyrrole, 2-[4-methyl-6-(1-methylethyl)pyrimidin-2-yl]-5-{[2-(2H-1,2,3-triazol-2-yl)phenyl]carbonyl}octahydropyrrolo[3,4-c]pyrrole and 2-{[5-(1-Methylethyl)-2-(2H-1,2,3-triazol-2-yl)phenyl]carbonyl}-5-[4-methyl-6-(1-methylethyl)pyrimidin-2-yl]octahydropyrrolo[3,4-c]pyrrole. MS (ESI) mass calculated for $C_{23}H_{26}FN_7O$, 435.51; m/z found, 436.2. $^1$H NMR (400 MHz, CDCl$_3$): 7.89-7.79 (m, 2H), 7.72 (s, 1H), 7.52-7.43 (m, 1H), 7.18-7.10 (m, 1H), 6.32-6.25 (m, 1H), 4.01-3.49 (m, 7H), 3.31-3.21 (m, 1H), 3.13-2.93 (m, 2H), 2.82-2.70 (m, 1H), 2.32 (d, J=2.1 Hz, 3H), 1.27-1.20 (m, 6H).

Example 299: 2-[4-Methyl-6-(1-methylethyl)pyrimidin-2-yl]-5-{[2-(2H-1,2,3-triazol-2-yl)phenyl]carbonyl}octahydroyrrolo[3,4-c]pyrrole

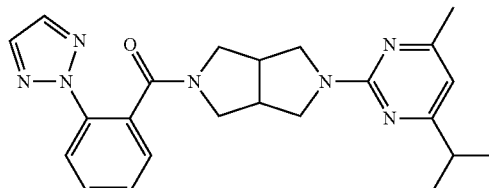

The title compound was isolated from the synthesis of Example 298. MS (ESI) mass calculated for $C_{23}H_{27}N_7O$, 417.52. m/z found, 418.2. $^1$H NMR (500 MHz, CDCl$_3$): 7.98 (d, J=8.1 Hz, 1H), 7.73 (s, 2H), 7.55-7.48 (m, 1H), 7.45-7.39 (m, 2H), 6.29 (s, 1H), 3.91-3.83 (m, 2H), 3.74-3.64 (m, 2H), 3.63-3.57 (m, 1H), 3.50-3.44 (m, 1H), 3.42-3.27 (m, 1H), 3.07-2.88 (m, 3H), 2.81-2.59 (m, 1H), 2.31 (s, 3H), 1.25-1.21 (m, 6H).

Example 300: 2-{[5-(1-Methylethyl)-2-(2H-1,2,3-triazol-2-yl)phenyl]carbonyl}-5-[4-methyl-6-(1-methylethyl)pyrimidin-2-yl]octahydropyrrolo[3,4-c]pyrrol

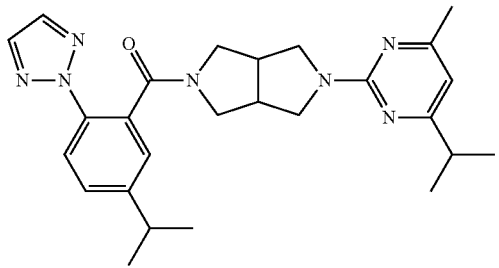 [SMILES: Cc1cc(C(C)C)nc(N2CC3CN(C(=O)c4cc(C(C)C)ccc4-n4nccn4)CC3C2)n1]

The title compound was isolated from the synthesis of Example 298. MS (ESI) mass calculated for $C_{26}H_{33}N_7O$, 459.6. m/z found, 460.3. $^1$H NMR (400 MHz, CDCl$_3$): 7.84-7.72 (m, 2H), 7.67 (s, 1H), 7.51-7.32 (m, 2H), 6.32-6.25 (m, 1H), 3.92-3.31 (m, 7H), 3.16-2.70 (m, 5H), 2.31 (d, J=4.7 Hz, 3H), 1.28-1.14 (m, 12H).

Example 301: 2-(4-tert-Butyl-6-methylpyrimidin-2-yl)-5-{[2-fluoro-6-(2H-1,2,3-triazol-2-yl)phenyl]carbonyl}octahydropyrrolo[3,4-c]pyrrole

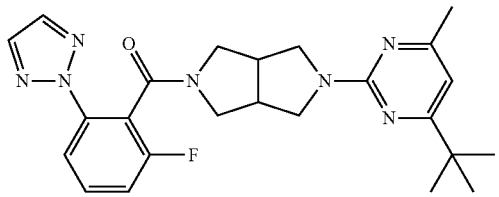 [SMILES: Cc1cc(C(C)(C)C)nc(N2CC3CN(C(=O)c4c(F)cccc4-n4nccn4)CC3C2)n1]

The title compound was prepared in a manner analogous to Intermediate 55 substituting Intermediate 58 for 2,4-dichloro-5-fluoropyrimidine and 1.0 M tBuMgBr in THF for 3.0 M MeMgBr in Et$_2$O. MS (ESI) mass calculated for $C_{24}H_{28}FN_7O$, 449.54. m/z found, 450.3. $^1$H NMR (500 MHz, CDCl$_3$): 7.93-7.72 (m, 3H), 7.54-7.45 (m, 1H), 7.20-7.11 (m, 1H), 6.66-6.59 (m, 1H), 4.23-3.60 (m, 7H), 3.38-3.06 (m, 3H), 2.67-2.43 (m, 3H), 1.29 (s, 9H).

Example 302: 2-(4-Cyclopropyl-6-methylpyrimidin-2-yl)-5-{[2-fluoro-6-(2H-1,2,3-triazol-2-yl)phenyl]carbonyl}octahydropyrrolo[3,4-c]pyrrole

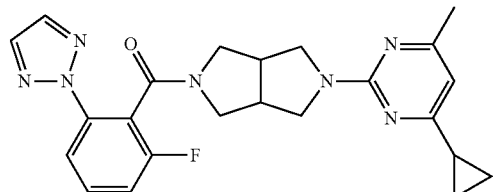

The title compound was prepared in a manner analogous to Intermediate 55 substituting Intermediate 58 for 2,4-dichloro-5-fluoropyrimidine and 0.5 M cyclopropylmagnesium bromide in THF for 3.0 M MeMgBr in Et$_2$O. MS (ESI) mass calculated for $C_{23}H_{24}FNO$, 433.49. m/z found, 434.2. $^1$H NMR (500 MHz, CDCl$_3$): 7.87-7.80 (m, 2H), 7.71 (s, 1H), 7.51-7.43 (m, 1H), 7.18-7.11 (m, 1H), 6.31-6.26 (m, 1H), 3.99-3.79 (m, 2H), 3.79-3.72 (m, 1H), 3.69-3.45 (m, 4H), 3.27-3.20 (m, 1H), 3.10-2.91 (m, 2H), 2.29 (s, 3H), 1.82-1.74 (m, 1H), 1.10-1.00 (m, 2H), 0.95-0.88 (m, 2H).

Example 303: 2-{[2-Fluoro-6-(2H-1,2,3-triazol-2-yl)phenyl]carbonyl}-5-(4-methyl-1,3,5-triazin-2-yl)octahydropyrrolo[3,4-c]pyrrole

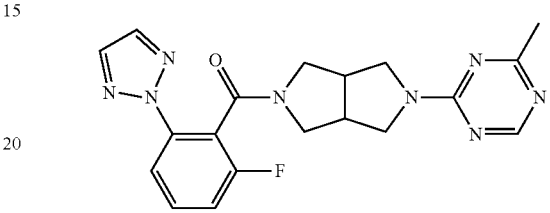

Step A: tert-Butyl 5-(4-chloro-1,3,5-triazin-2-yl)hexahydropyrrolo[3,4-c]pyrrole-2(1H)-carboxylate. To a solution of 2,4-dichloro-1,3,5-triazine (150 mg, 0.953 mmol) in ACN (5 mL) was added a solution of Intermediate 15 (202 mg, 0.953 mmol) and DIPEA (0.33 mL, 1.91 mmol) in ACN (5 mL) at 0° C. dropwise. After 10 min the mixture was diluted with saturated aqueous NH$_4$Cl solution. The aqueous layer was then extracted with DCM and the combined organic extracts were dried over Na$_2$SO$_4$, filtered and concentrated in vacuo. Chromatography (Hexanes to 80% EtOAc/Hexanes) afforded the desired product as a white solid (137 mg, 44%). MS (ESI) mass calculated for $C_{14}H_{20}ClN_5O_2$, 325.13. m/z found, 326.1.

Step B: tert-Butyl 5-(4-methyl-1,3,5-triazin-2-yl)hexahydropyrrolo[3,4-c]pyrrole-2(1H)-carboxylate. tert-Butyl 5-(4-methyl-1,3,5-triazin-2-yl)hexahydropyrrolo[3,4-c]pyrrole-2(1H)-carboxylate was prepared in a manner analogous to Intermediate 55 substituting the product of Step A for 2,4-dichloro-5-fluoropyrimidine. MS (ESI) mass calculated for $C_{15}H_{23}N_5O_2$, 305.18. m/z found, 306.0.

Step C: 2-(4-Methyl-1,3,5-triazin-2-yl)octahydropyrrolo[3,4-c]pyrrole. tert-Butyl 5-(4-methyl-1,3,5-triazin-2-yl)hexahydropyrrolo[3,4-c]pyrrole-2(1H)-carboxylate (43 mg, 0.142 mmol), DCM (1.4 mL) and TFA (0.71 mL) were stirred at room temperature for 2 h. The mixture was concentrated in vacuo and taken on to the next step without further purification.

Step D: 2-{[2-Fluoro-6-(2H-1,2,3-triazol-2-yl)phenyl]carbonyl}-5-(4-methyl-1,3,5-triazin-2-yl)octahydropyrrolo[3,4-c]pyrrole. Example 303 was prepared in a manner analogous to Intermediate 59 substituting the product of Step C for Intermediate 15 and Intermediate 12 for 2-(4H-[1,2,4]triazol-3-yl)-benzoic acid. MS (ESI) mass calculated for $C_{19}H_{19}FN_8O$, 394.41. m/z found, 395.0. $^1$H NMR (500 MHz, CDCl$_3$): 8.51-8.42 (m, 1H), 7.89-7.81 (m, 2H), 7.75 (d, J=3.5 Hz, 1H), 7.54-7.45 (m, 1H), 7.20-7.11 (m, 1H), 4.02-3.51 (m, 8H), 3.32-3.23 (m, 1H), 3.17-3.00 (m, 2H), 2.50-2.40 (m, 3H).

Example 304: 2-{[2-Fluoro-6-(2H-1,2,3-triazol-2-yl)phenyl]carbonyl}-5-(4-methyl-6-morpholin-4-ylpyrimidin-2-yl)octahydropyrrolo[3,4-c]pyrrole

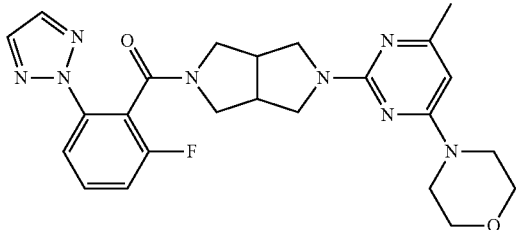 [SMILES: Cc1cc(N2CCOCC2)nc(N2CC3CN(C(=O)c4c(F)cccc4-n4nccn4)CC3C2)n1]

A mixture of Intermediate 58 (137 mg, 0.254 mmol) and morpholine (1.3 mL) was stirred 14 h at room temperature. The mixture was concentrated in vacuo. Chromatography (DCM to 8% 2 M $NH_3$ in MeOH/DCM) afforded the desired product as a pale yellow foam (95 mg, 78%). MS (ESI) mass calculated for $C_{24}H_{27}FN_8O_2$, 478.53; m/z found, 479.3. $^1$H NMR (500 MHz, $CDCl_3$): 7.86-7.78 (m, 2H), 7.72 (s, 1H), 7.51-7.44 (m, 1H), 7.18-7.10 (m, 1H), 5.77-5.72 (m, 1H), 3.99-3.47 (m, 13H), 3.28-3.21 (m, 1H), 3.09-2.91 (m, 2H), 2.90-2.86 (m, 2H), 2.25 (s, 3H).

Example 305: 2-{[2-(4H-1,2,4-Triazol-3-yl)phenyl]carbonyl}-5-(4,5,6-trimethylpyrimidin-2-yl)octahydropyrrolo[3,4-c]pyrrole

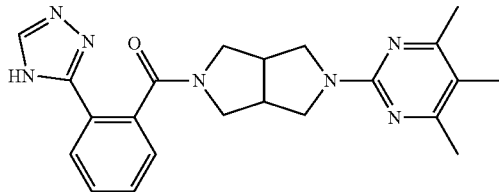 [SMILES: Cc1nc(N2CC3CN(C(=O)c4ccccc4-c4nnc[nH]4)CC3C2)nc(C)c1C]

Step A: (2-(4H-1,2,4-Triazol-3-yl)phenyl)(hexahydropyrrolo[3,4-c]pyrrol-2(1H)-yl)methanone. (2-(4H-1,2,4-Triazol-3-yl)phenyl)(hexahydropyrrolo[3,4-c]pyrrol-2(1H)-yl)methanone was prepared in a manner analogous to Example 303, substituting Intermediate 59 for the product of Example 303 in Step C. MS (ESI) mass calculated for $C_{15}H_{17}NO$, 283.14. m/z found, 284.2.

Step B: 2-{[2-(4H-1,2,4-Triazol-3-yl)phenyl]carbonyl}-5-(4,5,6-trimethylpyrimidin-2-yl)octahydropyrrolo[3,4-c]pyrrole. The product of Step A (167 mg, 0.421 mmol), Intermediate 56 (66 mg, 0.421 mmol) and DIPEA (0.29 mL, 1.68 mmol) were heated for 2 h at 200° C. in ACN (1.4 mL) in the microwave. The mixture was concentrated in vacuo. The crude product was purified using Agilent HPLC (basic system) to yield impure material. This material was subsequently purified using normal phase chromatography (DCM to 8% 2M $NH_3$ in MeOH/DCM) to afford the title compound (49 mg, 29%). MS (ESI) mass calculated for $C_{22}H_{25}N_7O$, 403.49. m/z found, 404.2. $^1$H NMR (500 MHz, $CDCl_3$): 8.16 (d, J=7.8 Hz, 1H), 8.06 (s, 1H), 7.54-7.49 (m, 1H), 7.48-7.44 (m, 1H), 7.35 (d, J=7.5 Hz, 1H), 3.96-3.89 (m, 1H), 3.85-3.77 (m, 1H), 3.74-3.68 (m, 1H), 3.68-3.55 (m, 2H), 3.42 (br s, 2H), 3.16 (br s, 1H), 3.04-2.96 (m, 1H), 2.89 (br s, 1H), 2.32 (s, 6H), 2.05 (s, 3H).

Example 306: 2-(4,6-Dimethylpyrimidin-2-yl)-5-{[2-(3-methyl-1,2,4-oxadiazol-5-yl)phenyl]carbonyl}octahydropyrrolo[3,4-c]pyrrole

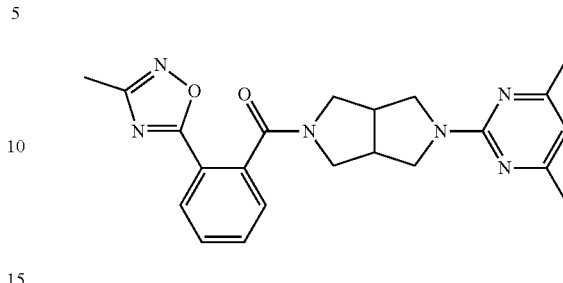

The title compound was prepared in a manner analogous to Intermediate 59 substituting Intermediate 23 for Intermediate 15 and 2-(3-methyl-1,2,4-oxadiazol-5-yl)benzoic acid for 2-(4H-[1,2,4]triazol-3-yl)-benzoic acid. MS (ESI) mass calculated for $C_{22}H_{24}N_6O_2$, 404.48. m/z found, 405.2. $^1$H NMR (500 MHz, $CDCl_3$): 8.10 (dd, J=7.9 Hz, 0.9 Hz, 1H), 7.62 (td, J=7.6 Hz, 1.2 Hz, 1H), 7.53 (td, J=7.7 Hz, 1.3 Hz, 1H), 7.42 (dd, J=7.6 Hz, 1.0 Hz, 1H), 6.28 (s, 1H), 3.99-3.88 (m, 2H), 3.80-3.75 (m, 1H), 3.74-3.65 (m, 2H), 3.53-3.48 (m, 1H), 3.46-3.40 (m, 1H), 3.12-3.04 (m, 2H), 3.01-2.93 (m, 1H), 2.42 (s, 3H), 2.28 (s, 6H).

Example 307: 2-(4,6-Dimethylpyrimidin-2-yl)-5-{[2-(1-methyl-1H-1,2,4-triazol-5-yl)phenyl]carbonyl}octahydropyrrolo[3,4-c]pyrrole

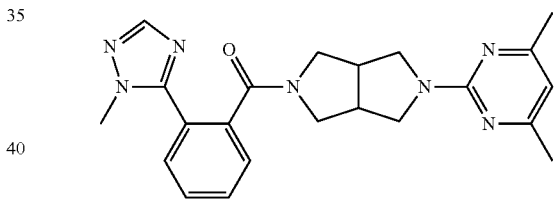

Step A: (Hexahydropyrrolo[3,4-c]pyrrol-2(1H)-yl)(2-(1-methyl-1H-1,2,4-triazol-5-yl)phenyl)methanone. Intermediate 60 (100 mg, 0.252 mmol), DCM (2.5 mL), TFA (0.5 mL) were stirred at room temperature for 2 h and then concentrated in vacuo. The residue was dissolved in DCM and treated with Dowex 550 A resin. After stirring for 2 h the resin was removed by filtration and the filtrate was concentrated in vacuo to a colorless oil which was taken on to the next step without further purification. MS (ESI) mass calculated for $C_{16}H_{19}N_5O$, 297.16. m/z found, 298.0.

Step B: 2-(4,6-Dimethylpyrimidin-2-yl)-5-{[2-(1-methyl-1H-1,2,4-triazol-5-yl)phenyl]carbonyl}octahydropyrrolo[3,4-c]pyrrole. Example 307 was prepared in a manner analogous to Example 290 substituting the product of Step A for Intermediate 20 and 2-chloro-4,6-dimethylpyrimidine for Intermediate 55. MS (ESI) mass calculated for $C_{22}H_{25}N_7O$, 403.21. m/z found, 404.2. $^1$H NMR (500 MHz, $CDCl_3$): 7.83 (s, 1H), 7.58-7.49 (m, 2H), 7.47-7.42 (m, 2H), 6.28 (s, 1H), 3.85-3.80 (m, 4H), 3.75-3.69 (m, 2H), 3.55-3.45 (m, 4H), 3.24-3.19 (m, 1H), 2.99-2.88 (m, 2H), 2.29 (s, 6H).

Example 308: 2-(4,6-Dimethylpyrimidin-2-yl)-5-{[2-(1-methyl-1H-1,2,4-triazol-3-yl)phenyl]carbonyl}octahydropyrrolo[3,4-c]pyrrole

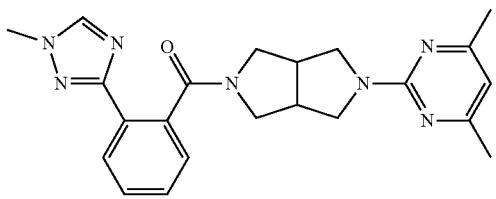

The title compound was prepared in a manner analogous to Example 307 substituting Intermediate 61 for Intermediate 60 in Step A. MS (ESI) mass calculated for $C_{22}H_{25}N_7O$, 403.21. m/z found, 404.2. $^1$H NMR (500 MHz, CDCl$_3$): 8.12-8.06 (m, 1H), 7.93 (s, 1H), 7.49-7.38 (m, 2H), 7.37-7.29 (m, 1H), 6.27 (s, 1H), 3.95-3.83 (m, 5H), 3.78-3.60 (m, 3H), 3.47-3.38 (m, 2H), 3.08-2.98 (m, 2H), 2.95-2.86 (m, 1H), 2.29 (s, 6H).

Example 309: 2-{[2-(3-Methyl-1,2,4-oxadiazol-5-yl)phenyl]carbonyl}-5-(4,5,6-trimethylpyrimidin-2-yl)octahydropyrrolo[3,4-c]pyrrole

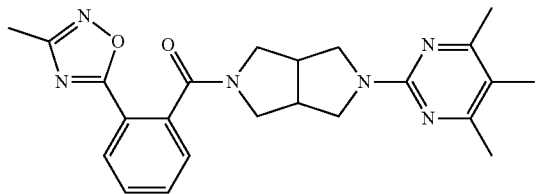

The title compound was prepared in a manner analogous to Example 307 substituting Intermediate 62 for Intermediate 60 in Step A, and Intermediate 56 for 2-chloro-4,6-dimethylpyrimidine in Step B. MS (ESI) mass calculated for $C_{23}H_{26}N_6O_2$, 418.21. m/z found, 419.3. $^1$H NMR (500 MHz, CDCl$_3$): 8.09 (dd, J=7.9 Hz, 0.9 Hz, 1H), 7.60 (td, J=7.6 Hz, 1.2 Hz, 1H), 7.52 (td, J=7.7 Hz, 1.3 Hz, 1H), 7.41 (dd, J=7.6 Hz, 1.0 Hz, 1H), 3.98-3.93 (m, 1H), 3.90-3.84 (m, 1H), 3.79-3.73 (m, 1H), 3.70-3.61 (m, 2H), 3.50-3.44 (m, 1H), 3.44-3.38 (m, 1H), 3.10-3.02 (m, 2H), 2.98-2.91 (m, 1H), 2.42 (s, 3H), 2.30 (s, 6H), 2.06 (s, 3H).

Example 310: 2-(5-Fluoro-4-methylpyrimidin-2-yl)-5-{[2-(3-methyl-1,2,4-oxadiazol-5-yl)phenyl]carbonyl}octahydropyrrolo[3,4-c]pyrrole

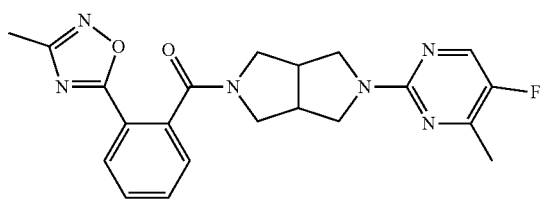 [SMILES: Cc1noc(-c2ccccc2C(=O)N2CC3CN(c4ncc(F)c(C)n4)CC3C2)n1]

The title compound was prepared in a manner analogous to Example 307 substituting Intermediate 62 for Intermediate 60 in Step A, and Intermediate 55 for 2-chloro-4,6-dimethylpyrimidine in Step B. MS (ESI) mass calculated for $C_{21}H_{21}FN_6O_2$, 408.17. m/z found, 409.2. $^1$H NMR (500 MHz, CDCl$_3$): 8.10 (dd, J=7.9 Hz, 0.9 Hz, 1H), 8.04 (d, J=1.8 Hz, 1H), 7.61 (td, J=7.6 Hz, 1.3 Hz, 1H), 7.53 (td, J=7.7 Hz, 1.3 Hz, 1H), 7.42 (dd, J=7.6 Hz, 1.0 Hz, 1H), 4.00-3.94 (m, 1H), 3.90-3.83 (m, 1H), 3.79-3.74 (m, 1H), 3.71-3.60 (m, 2H), 3.47-3.41 (m, 2H), 3.13-3.06 (m, 2H), 3.02-2.94 (m, 1H), 2.41 (s, 3H), 2.35 (d, J=2.5 Hz, 3H).

Example 311: 2-{[2-(1-Methyl-1H-1,2,4-triazol-3-yl)phenyl]carbonyl}-5-(4,5,6-trimethylpyrimidin-2-yl)octahydropyrrolo[3,4-c]pyrrole

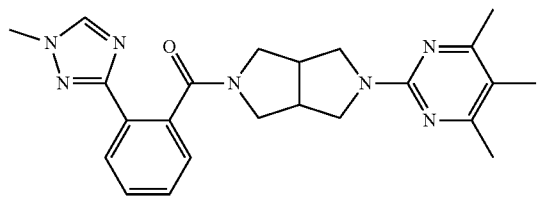

The title compound was prepared in a manner analogous to Example 307 substituting Intermediate 61 for Intermediate 60 in Step A, and Intermediate 56 for 2-chloro-4,6-dimethylpyrimidine in Step B. MS (ESI) mass calculated for $C_{23}H_{27}N_7O$, 417.23. m/z found, 418.2. $^1$H NMR (500 MHz, CDCl$_3$): 8.11-8.04 (m, 1H), 7.93 (s, 1H), 7.47-7.38 (m, 2H), 7.34-7.30 (m, 1H), 3.94-3.79 (m, 5H), 3.75-3.69 (m, 1H), 3.66-3.56 (m, 2H), 3.43-3.36 (m, 2H), 3.07-2.97 (m, 2H), 2.92-2.85 (m, 1H), 2.32 (s, 6H), 2.06 (s, 3H).

Example 312: 2-(5-Fluoro-4-methylpyrimidin-2-yl)-5-{[2-(1-methyl-1H-1,2,4-triazol-3-yl)phenyl]carbonyl}octahydropyrrolo[3,4-c]pyrrole

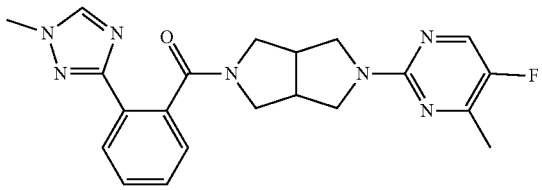 [SMILES: Cc1nc(N2CC3CN(C(=O)c4ccccc4-c4ncn(C)n4)CC3C2)ncc1F]

The title compound was prepared in a manner analogous to Example 307 substituting Intermediate 61 for Intermediate 60 in Step A, and Intermediate 55 for 2-chloro-4,6-dimethylpyrimidine in Step B. MS (ESI) mass calculated for $C_{21}H_{22}FN_7O$, 407.19. m/z found, 408.2. $^1$H NMR (500 MHz, CDCl$_3$): 8.09 (dd, J=7.5 Hz, 1.5 Hz, 1H), 8.04 (d, J=1.7 Hz, 1H), 7.94 (s, 1H), 7.47-7.39 (m, 2H), 7.34-7.30 (m, 1H), 3.97-3.85 (m, 4H), 3.85-3.78 (m, 1H), 3.76-3.70 (m, 1H), 3.66-3.55 (m, 2H), 3.45-3.36 (m, 2H), 3.09-3.00 (m, 2H), 2.97-2.88 (m, 1H), 2.35 (d, J=2.5 Hz, 3H).

Example 313: 2-[5-{[2-Fluoro-6-(2H-1,2,3-triazol-2-yl)phenyl]carbonyl}hexahydropyrrolo[3,4-c]pyrrol-2(1H)-yl]-4-methyl-6,7-dihydro-5H-cyclopenta[d]pyrimidine

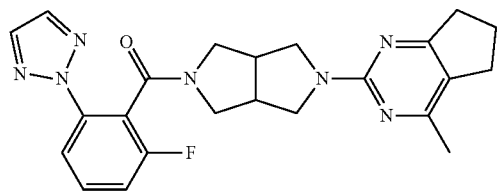 [SMILES: Cc1nc(N2CC3CN(C(=O)c4c(F)cccc4-n4nccn4)CC3C2)nc2c1CCC2]

The title compound was prepared in a manner analogous to Example 290 substituting Intermediate 16 for Intermediate 20 and 2-chloro-4-methyl-6,7-dihydro-5H-cyclopenta[d]pyrimidine for Intermediate 55. MS (ESI) mass calculated for $C_{23}H_{24}FN_7O$, 433.20. m/z found, 434.2. 1H NMR (500 MHz, CDCl$_3$): 7.87-7.78 (m, 2H), 7.72 (s, 1H), 7.49-7.42 (m, 1H), 7.17-7.09 (m, 1H), 4.01-3.84 (m, 2H), 3.82-3.49 (m, 5H), 3.29-3.22 (m, 1H), 3.13-2.93 (m, 2H), 2.86-2.79 (m, 2H), 2.78-2.72 (m, 2H), 2.28 (s, 3H), 2.09-2.00 (m, 2H).

Example 314: 2-(4,6-Dimethylpyrimidin-2-yl)-5-{[3-fluoro-2-(3-methyl-1,2,4-oxadiazol-5-yl)phenyl]carbonyl}octahydropyrrolo[3,4-c]pyrrole

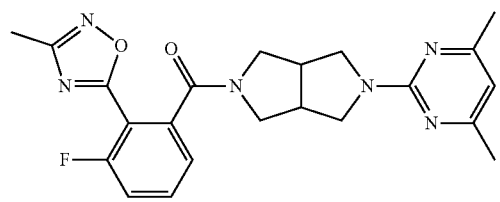

The title compound was prepared in a manner analogous to Intermediate 59 substituting Intermediate 23 for Intermediate 15 and Intermediate 63 for 2-(4H-[1,2,4]triazol-3-yl)benzoic acid. MS (ESI) mass calculated for $C_{22}H_{23}FN_6O_2$, 422.19. m/z found, 423.2. $^1$H NMR (500 MHz, CDCl$_3$): 7.62-7.56 (m, 1H), 7.31-7.26 (m, 1H), 7.24-7.20 (m, 1H), 6.29 (s, 1H), 3.93-3.86 (m, 2H), 3.77-3.62 (m, 3H), 3.57-3.47 (m, 2H), 3.21-3.16 (m, 1H), 3.10-2.96 (m, 2H), 2.43 (s, 3H), 2.28 (s, 6H).

Example 315: 2-(4,6-Dimethylpyrimidin-2-yl)-5-{[2-fluoro-6-(3-methyl-1,2,4-oxadiazol-5-yl)phenyl]carbonyl}octahydropyrrolo[3,4-c]pyrrole

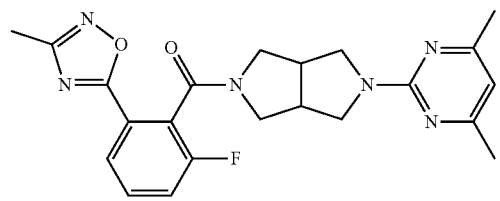

The title compound was prepared in a manner analogous to Intermediate 59 substituting Intermediate 23 for Intermediate 15 and Intermediate 64 for 2-(4H-[1,2,4]triazol-3-yl)benzoic acid. MS (ESI) mass calculated for $C_{22}H_{23}FN_6O_2$, 422.19. m/z found, 423.2. $^1$H NMR (500 MHz, CDCl$_3$): 7.96-7.86 (m, 1H), 7.55-7.47 (m, 1H), 7.38-7.29 (m, 1H), 6.32-6.23 (m, 1H), 3.99-3.46 (m, 7H), 3.27-2.95 (m, 3H), 2.49-2.37 (m, 3H), 2.36-2.21 (m, 6H).

Example 316: 2-(5-Chloro-4-methylpyrimidin-2-yl)-5-{[2-fluoro-6-(2H-1,2,3-triazol-2-yl)phenyl]carbonyl}octahydropyrrolo[3,4-c]pyrrole

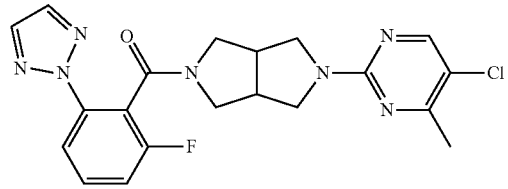 [SMILES: Cc1nc(N2CC3CN(C(=O)c4c(F)cccc4-n4nccn4)CC3C2)ncc1Cl]

The title compound was prepared in a manner analogous to Example 290 substituting Intermediate 16 for Intermediate 20 and Intermediate 65 for Intermediate 55. MS (ESI) mass calculated for $C_{20}H_{19}ClFN_7O$, 427.13. m/z found, 428.1. 1H NMR (500 MHz, CDCl$_3$): 8.13 (d, J=1.3 Hz, 1H), 7.87-7.79 (m, 2H), 7.71 (s, 1H), 7.51-7.43 (m, 1H), 7.17-7.11 (m, 1H), 4.00-3.54 (m, 7H), 3.28-3.23 (m, 1H), 3.14-2.97 (m, 2H), 2.43 (s, 3H).

Example 317: 2-(5-Chloro-4,6-dimethylpyrimidin-2-yl)-5-{[2-fluoro-6-(2H-1,2,3-triazol-2-yl)phenyl]carbonyl}octahydropyrrolo[3,4-c]pyrrole

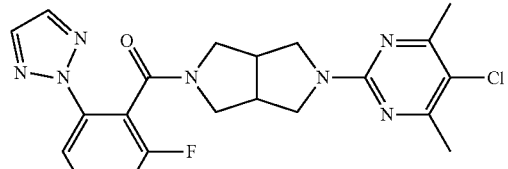

The title compound was prepared in a manner analogous to Example 290 substituting Intermediate 16 for Intermediate 20 and Intermediate 66 for Intermediate 55. MS (ESI) mass calculated for $C_{21}H_{21}ClFN_7O$, 441.15. m/z found, 442.1. 1H NMR (500 MHz, CDCl$_3$): 7.87-7.79 (m, 2H), 7.71 (s, 1H), 7.50-7.44 (m, 1H), 7.17-7.11 (m, 1H), 4.00-3.73 (m, 3H), 3.70-3.46 (m, 4H), 3.27-3.22 (m, 1H), 3.12-2.94 (m, 2H), 2.42 (s, 6H).

Example 318: 2-(5-Chloro-4,6-dimethylpyrimidin-2-yl)-5-{[2-(3-methyl-1,2,4-oxadiazol-5-yl)phenyl]carbonyl}octahydropyrrolo[3,4-c]pyrrole

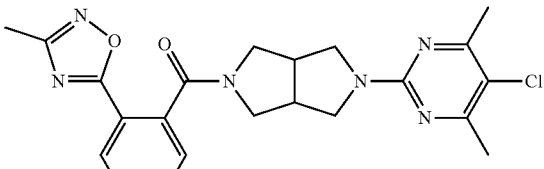

The title compound was prepared in a manner analogous to Example 307 substituting Intermediate 62 for Intermediate 60 in Step A, and Intermediate 66 for 2-chloro-4,6-dimethylpyrimidine in Step B. MS (ESI) mass calculated for $C_{22}H_{23}ClN_6O_2$, 438.16. m/z found, 439.2. 1H NMR (500 MHz, CDCl$_3$): 8.11 (dd, J=7.6 Hz, 1.2 Hz, 1H), 7.62 (td, J=7.6 Hz, 1.2 Hz, 1H), 7.54 (td, J=7.6 Hz, 1.2 Hz, 1H), 7.42 (dd, J=7.6 Hz, 1.2 Hz, 1H), 3.99-3.92 (m, 1H), 3.90-3.84 (m, 1H), 3.80-3.74 (m, 1H), 3.70-3.61 (m, 2H), 3.50-3.41 (m, 2H), 3.12-3.04 (m, 2H), 3.02-2.94 (m, 1H), 2.46-2.36 (m, 9H).

Example 319: 4-Methyl-2-[5-{[2-(3-methyl-1,2,4-oxadiazol-5-yl)phenyl]carbonyl}hexahydropyrrolo[3,4-c]pyrrol-2(1H)-yl]-6,7-dihydro-5H-cyclopenta[d]pyrimidine

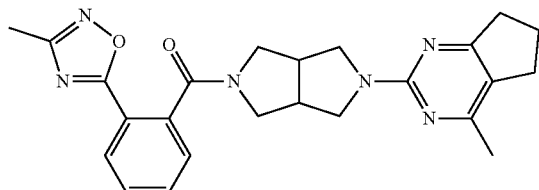 [SMILES: Cc1noc(-c2ccccc2C(=O)N2CC3CN(c4nc(C)c5c(n4)CCC5)CC3C2)n1]

The title compound was prepared in a manner analogous to Example 307 substituting Intermediate 62 for Intermediate 60 in Step A, and 2-chloro-4-methyl-6,7-dihydro-5H-cyclopenta[d]pyrimidine for 2-chloro-4,6-dimethylpyrimidine in Step B. MS (ESI) mass calculated for $C_{24}H_{26}N_6O_2$, 430.21. m/z found, 431.2. $^1$H NMR (500 MHz, CDCl$_3$): 8.10 (dd, J=7.9 Hz, 0.9 Hz, 1H), 7.61 (td, J=7.6 Hz, 1.3 Hz, 1H), 7.53 (td, J=7.6 Hz, 1.3 Hz, 1H), 7.42 (dd, J=7.6 Hz, 1.0 Hz, 1H), 3.99-3.87 (m, 2H), 3.80-3.74 (m, 1H), 3.73-3.65 (m, 2H), 3.52-3.47 (m, 1H), 3.45-3.39 (m, 1H), 3.11-3.05 (m, 2H), 3.01-2.93 (m, 1H), 2.83-2.72 (m, 4H), 2.43 (s, 3H), 2.26 (s, 3H), 2.08-2.00 (m, 2H).

Example 320: 2-(5-Chloro-4,6-dimethylpyrimidin-2-yl)-5-{[2-(1-methyl-1H-1,2,4-triazol-3-yl)phenyl]carbonyl}octahydropyrrolo[3,4-c]pyrrole

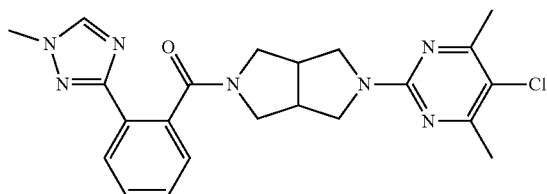 [SMILES: Cc1nc(N2CC3CN(C(=O)c4ccccc4-c4ncn(C)n4)CC3C2)nc(C)c1Cl]

The title compound was prepared in a manner analogous to Example 307 substituting Intermediate 61 for Intermediate 60 in Step A, and Intermediate 66 for 2-chloro-4,6-dimethylpyrimidine in Step B. MS (ESI) mass calculated for $C_{22}H_{24}ClN_7O$, 437.17. m/z found, 438.2. $^1$H NMR (500 MHz, CDCl$_3$): 8.12-8.06 (m, 1H), 7.95 (s, 1H), 7.47-7.40 (m, 2H), 7.34-7.31 (m, 1H), 3.96-3.85 (m, 4H), 3.85-3.78 (m, 1H), 3.77-3.70 (m, 1H), 3.65-3.57 (m, 2H), 3.45-3.38 (m, 2H), 3.08-3.00 (m, 2H), 2.95-2.87 (m, 1H), 2.41 (s, 6H).

Example 321: 2-(5-Chloro-4-methylpyrimidin-2-yl)-5-{[2-(1-methyl-1H-1,2,4-triazol-3-yl)phenyl]carbonyl}octahydropyrrolo[3,4-c]pyrrole

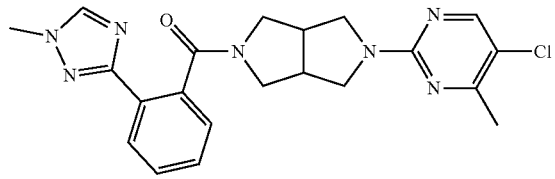 [SMILES: Cc1nc(N2CC3CN(C(=O)c4ccccc4-c4ncn(C)n4)CC3C2)ncc1Cl]

The title compound was prepared in a manner analogous to Example 307 substituting Intermediate 61 for Intermediate 60 in Step A, and Intermediate 65 for 2-chloro-4,6-dimethylpyrimidine in Step B. MS (ESI) mass calculated for $C_{21}H_{22}ClN_7O$, 423.16. m/z found, 424.2. $^1$H NMR (500 MHz, CDCl$_3$): 8.15-8.06 (m, 2H), 7.96 (s, 1H), 7.48-7.40 (m, 2H), 7.36-7.30 (m, 1H), 3.96-3.80 (m, 5H), 3.79-3.70 (m, 1H), 3.67-3.55 (m, 2H), 3.47-3.37 (m, 2H), 3.10-3.01 (m, 2H), 2.99-2.90 (m, 1H), 2.41 (s, 3H).

Example 322: 2-(5-Ethyl-4,6-dimethylpyrimidin-2-yl)-5-{[2-(1-methyl-1H-1,2,4-triazol-3-yl)phenyl]carbonyl}octahydropyrrolo[3,4-c]pyrrole

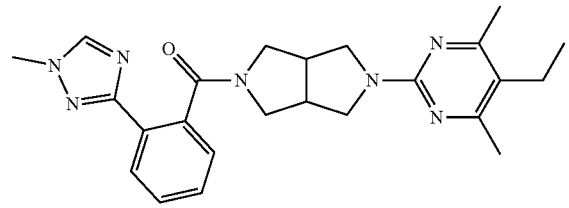 [SMILES: CCc1c(C)nc(N2CC3CN(C(=O)c4ccccc4-c4ncn(C)n4)CC3C2)nc1C]

The title compound was prepared in a manner analogous to Example 307 substituting Intermediate 61 for Intermediate 60 in Step A, and Intermediate 67 for 2-chloro-4,6-dimethylpyrimidine in Step B. MS (ESI) mass calculated for $C_{24}H_{29}N_7O$, 431.24. m/z found, 432.2. $^1$H NMR (500 MHz, CDCl$_3$): 8.11-8.05 (m, 1H), 7.95 (s, 1H), 7.48-7.39 (m, 2H), 7.35-7.30 (m, 1H), 3.96-3.79 (m, 5H), 3.77-3.70 (m, 1H), 3.66-3.55 (m, 2H), 3.43-3.35 (m, 2H), 3.08-2.97 (m, 2H), 2.94-2.86 (m, 1H), 2.52 (q, J=7.5 Hz, 2H), 2.34 (s, 6H), 1.08 (t, J=7.5 Hz, 3H).

Example 323: 2-{[3-(2H-1,2,3-Triazol-2-yl)pyridin-2-yl]carbonyl}-5-(4,5,6-trimethylpyrimidin-2-yl)octahydropyrrolo[3,4-c]pyrrole

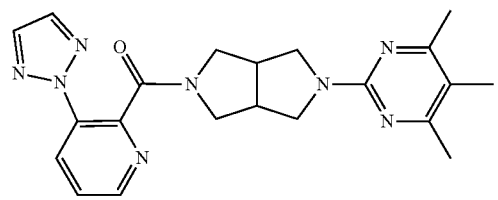 [SMILES: Cc1nc(N2CC3CN(C(=O)c4ncccc4-n4nccn4)CC3C2)nc(C)c1C]

The title compound was prepared in a manner analogous to Example 290 substituting Intermediate 68 for Intermediate 20 and Intermediate 56 for Intermediate 55. MS (ESI) mass calculated for $C_{21}H_{24}N_5O$, 404.21. m/z found, 405.2. $^1H$ NMR (500 MHz, CDCl$_3$): 8.62 (dd, J=4.7 Hz, 1.4 Hz, 1H), 8.33 (dd, J=8.3 Hz, 1.4 Hz, 1H), 7.79 (s, 2H), 7.48 (dd, J=8.3 Hz, 4.7 Hz, 1H), 3.96-3.84 (m, 2H), 3.78-3.63 (m, 4H), 3.60-3.54 (m, 1H), 3.29-3.23 (m, 1H), 3.12-2.98 (m, 2H), 2.33 (s, 6H), 2.07 (s, 3H).

Example 324: 2-(5-Chloro-4,6-dimethylpyrimidin-2-yl)-5-{[3-(2H-1,2,3-triazol-2-yl)pyridin-2-yl]carbonyl}octahydropyrrolo[3,4-c]pyrrole

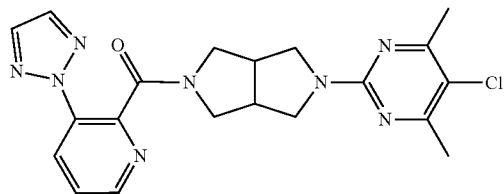 [SMILES: Cc1nc(N2CC3CN(C(=O)c4ncccc4-n4nccn4)CC3C2)nc(C)c1Cl]

The title compound was prepared in a manner analogous to Example 290 substituting Intermediate 68 for Intermediate 20 and Intermediate 66 for Intermediate 55. MS (ESI) mass calculated for $C_{20}H_{21}ClN_8O$, 424.15. m/z found, 425.1. $^1H$ NMR (500 MHz, CDCl$_3$): 8.62 (dd, J=4.7 Hz, 1.4 Hz, 1H), 8.33 (dd, J=8.3 Hz, 1.4 Hz, 1H), 7.81 (s, 2H), 7.48 (dd, J=8.3 Hz, 4.7 Hz, 1H), 3.95-3.89 (m, 1H), 3.89-3.83 (m, 1H), 3.79-3.74 (m, 1H), 3.73-3.64 (m, 3H), 3.60-3.53 (m, 1H), 3.28-3.23 (m, 1H), 3.13-2.98 (m, 2H), 2.42 (s, 6H).

Example 325: 2-(5-Fluoro-4,6-dimethylpyrimidin-2-yl)-5-{[3-(2H-1,2,3-triazol-2-yl)pyridin-2-yl]carbonyl}octahydropyrrolo[3,4-c]pyrrole

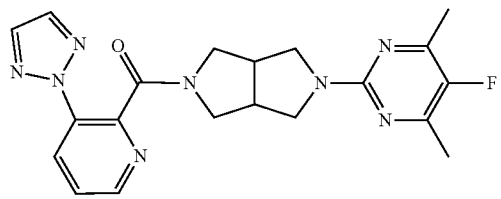 [SMILES: Cc1nc(N2CC3CN(C(=O)c4ncccc4-n4nccn4)CC3C2)nc(C)c1F]

The title compound was prepared in a manner analogous to Example 290 substituting Intermediate 68 for Intermediate 20 and Intermediate 69 for Intermediate 55. MS (ESI) mass calculated for $C_{20}H_{21}FN_8O$, 408.18. m/z found, 409.1. $^1H$ NMR (500 MHz, CDCl$_3$): 8.62 (dd, J=4.7 Hz, 1.4 Hz, 1H), 8.34 (dd, J=8.3 Hz, 1.4 Hz, 1H), 7.79 (s, 2H), 7.48 (dd, J=8.3 Hz, 4.7 Hz, 1H), 3.97-3.89 (m, 1H), 3.88-3.82 (m, 1H), 3.78-3.73 (m, 1H), 3.72-3.62 (m, 3H), 3.57-3.51 (m, 1H), 3.29-3.23 (m, 1H), 3.12-2.99 (m, 2H), 2.33 (d, J=2.6 Hz, 6H).

Example 326: 2-(4,6-Dimethylpyrimidin-2-yl)-5-(9H-fluoren-4-ylcarbonyl)octahydropyrrolo[3,4-c]pyrrole

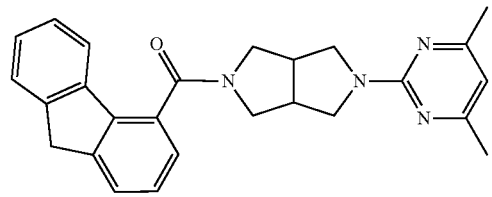 [SMILES: Cc1cc(C)nc(N2CC3CN(C(=O)c4cccc5c4-c4ccccc4C5)CC3C2)n1]

The title compound was prepared in a manner analogous to Example 15 substituting 9H-fluorene-4-carboxylic acid for 3-fluoro-2-[1,2,3]triazol-2-yl-benzoic acid. MS (ESI) mass calculated for $C_{20}H_{21}FN_8O$, 410.52. m/z found, 411.2. $^1H$ NMR (400 MHz, CDCl$_3$): 7.68-7.61 (m, 1H), 7.58-7.51 (m, 2H), 7.35-7.23 (m, 4H), 6.28 (s, 1H), 4.13 (dd, J=12.8, 7.9 Hz, 1H), 3.94-3.87 (m, 3H), 3.80 (dd, J=12.8, 5.0 Hz, 1H), 3.73-3.64 (m, 2H), 3.46 (s, 2H), 3.11 (dtd, J=12.5, 7.5, 4.9 Hz, 2H), 2.97-2.86 (m, 1H), 2.28 (s, 6H).

Example 327: [5-(4,6-Dimethyl-pyrimidin-2-yl)-hexahydro-pyrrolo[3,4-c]pyrrol-2-yl]-(5-[1,2,3]triazol-2-yl-benzo[1,3]dioxol-4-yl)-methanone

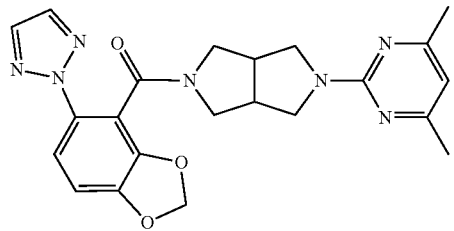 [SMILES: Cc1cc(C)nc(N2CC3CN(C(=O)c4c(-n5nccn5)ccc5c4OCO5)CC3C2)n1]

The title compound was prepared in a manner analogous to Example 275 substituting 5-[1,2,3]triazol-2-yl-benzo[1,3]dioxole-4-carboxylic acid (Intermediate 76) for 6-methyl-2-[1,2,3]triazol-2-yl-nicotinic acid. MS (ESI) mass calcd. for $C_{22}H_{23}N_7O_3$, 433.47. m/z found 434.3 [M+H]$^+$. $^1H$ NMR (400 MHz, CDCl$_3$): 7.75 (s, 1H), 7.64 (s, 1H), 7.42 (t, J=8.7 Hz, 1H), 6.89 (d, J=8.5 Hz, 1H), 6.29 (d, J=3.4 Hz, 1H), 6.13-5.99 (m, 2H), 3.95-3.75 (m, 3H), 3.74-3.50 (m, 5H), 3.26 (ddd, J=43.0, 10.7, 5.1 Hz, 1H), 3.09-2.92 (m, 2H), 2.30 (s, 6H).

Example 328: [5-(4,6-Dimethyl-pyrimidin-2-yl)-hexahydro-pyrrolo[3,4-c]pyrrol-2-yl]-(8-[1,2,3]triazol-2-yl-naphthalen-1-yl)-methanone

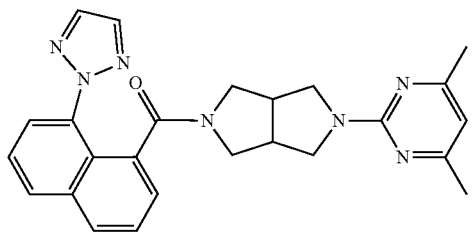 [SMILES: Cc1cc(C)nc(N2CC3CN(C(=O)c4cccc5cccc(-n6nccn6)c45)CC3C2)n1]

The title compound was prepared in a manner analogous to Example 275 substituting 8-[1,2,3]triazol-2-yl-naphthalene-1-carboxylic acid (Intermediate 75) for 6-methyl-2-[1,2,3]triazol-2-yl-nicotinic acid. MS (ESI) mass calcd. for C₂H₂₅N₇O, 439.41; m/z found 440.3 [M+H]⁺. ¹H NMR (400 MHz, CDCl₃) 8.00 (m, J=11.0, 7.1, 2.7 Hz, 2H), 7.80 (m, J=51.6 Hz, 2H), 7.69-7.49 (m, 4H), 6.31 (m, J=12.7 Hz, 1H), 3.91 (m, J=11.6, 7.7 Hz, 1H), 3.85-3.62 (m, 4H), 3.57-3.47 (m, 2H), 3.38-3.28 (m, 1H), 3.18 (m, J=10.9, 5.9 Hz, 1H), 3.06-2.93 (m, 2H), 2.30 (m, J=8.3 Hz, 6H).

Example 329: [5-(4,6-Dimethyl-pyrimidin-2-yl)-hexahydro-pyrrolo[3,4-c]pyrrol-2-yl]-(4-[1,2,3]triazol-1-yl-pyridin-3-yl)-methanone

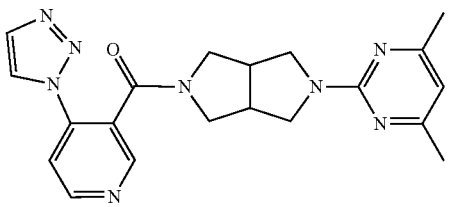 [SMILES: Cc1cc(C)nc(N2CC3CN(C(=O)c4cnccc4-n4ccnn4)CC3C2)n1]

The title compound was prepared in a manner analogous to Example 275 substituting 4-(1H-1,2,3-triazol-1-yl)nicotinic acid (Intermediate 81) for 6-methyl-2-[1,2,3]triazol-2-yl-nicotinic acid. MS (ESI) mass calcd. for C₂₀H₂₂N₈O, 390.40. m/z found 391.4 [M+H]⁺. ¹H NMR (400 MHz, CDCl₃): 8.83 (d, J=5.4 Hz, 1H), 8.75 (s, 1H), 8.10 (d, J=1.0 Hz, 1H), 7.82 (d, J=0.9 Hz, 1H), 7.69 (d, J=5.4 Hz, 1H), 6.31 (s, 1H), 3.86 (ddd, J=16.6, 12.3, 7.7 Hz, 2H), 3.75-3.67 (m, 1H), 3.56 (ddd, J=16.5, 12.3, 4.8 Hz, 2H), 3.35 (dt, J=14.9, 7.7 Hz, 2H), 3.04-2.86 (m, 3H), 2.30 (s, 6H).

Example 330: (5-tert-Butyl-2-methoxy-phenyl)-[5-(4,6-dimethyl-pyrimidin-2-yl)-hexahydro-pyrrolo[3,4-c]pyrrol-2-yl]-methanone

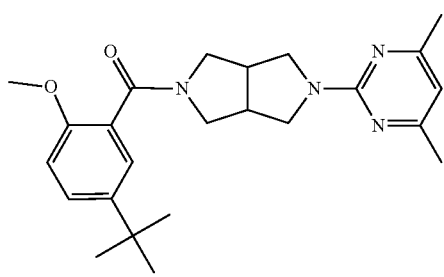

The title compound was prepared in a manner analogous to Example 275 substituting 5-tert-butyl-2-methoxybenzoic acid for 6-methyl-2-[1,2,3]triazol-2-yl-nicotinic acid. MS (ESI) mass calcd. for C₂₄H₃₂N₄O₂, 408.54. m/z found 409.3 [M+H]⁺. ¹H NMR (400 MHz, CDCl₃): 7.34 (dd, J=8.7, 2.5 Hz, 1H), 7.27-7.24 (m, 1H), 6.82 (d, J=8.7 Hz, 1H), 6.29 (s, 1H), 3.96 (dd, J=12.7, 7.9 Hz, 1H), 3.87 (dd, J=11.6, 7.4 Hz, 1H), 3.80-3.73 (m, 4H), 3.67-3.60 (m, 2H), 3.57-3.45 (m, 2H), 3.21 (dd, J=11.0, 4.7 Hz, 1H), 3.09-3.00 (m, 1H), 2.99-2.91 (m, 1H), 2.29 (s, 6H), 1.28 (s, 9H).

Example 331: [5-(4,6-Dimethyl-pyrimidin-2-yl)-hexahydro-pyrrolo[3,4-c]pyrrol-2-yl]-(1-[1,2,3]triazol-2-yl-naphthalen-2-yl)-methanone

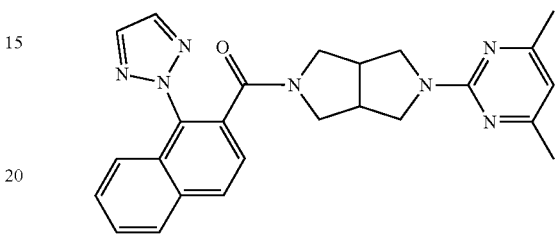

The title compound was prepared in a manner analogous to Example 275 substituting 1-[1,2,3]triazol-2-yl-naphthalene-2-carboxylic acid (Intermediate 73) for 6-methyl-2-[1,2,3]triazol-2-yl-nicotinic acid. MS (ESI) mass calcd. for C₂₅H₂₅N₇O, 439.52. m/z found 440.3 [M+H]⁺. ¹H NMR (400 MHz, CDCl₃): 8.02 (d, J=8.4 Hz, 1H), 7.95-7.91 (m, 1H), 7.88 (s, 2H), 7.72 (d, J=8.3 Hz, 1H), 7.56 (dddd, J=14.9, 8.2, 6.9, 1.3 Hz, 2H), 7.52-7.48 (m, 1H), 6.30 (s, 1H), 3.83 (dd, J=11.6, 7.5 Hz, 1H), 3.72 (ddd, J=14.6, 12.2, 7.1 Hz, 2H), 3.56-3.45 (m, 4H), 3.19 (dd, J=11.0, 5.4 Hz, 1H), 3.00-2.87 (m, 3H), 2.31 (s, 6H).

Example 332: [5-(4,6-Dimethyl-pyrimidin-2-yl)-hexahydro-pyrrolo[3,4-c]pyrrol-2-yl]-(3-[1,2,3]triazol-2-yl-pyridin-2-yl)-methanone

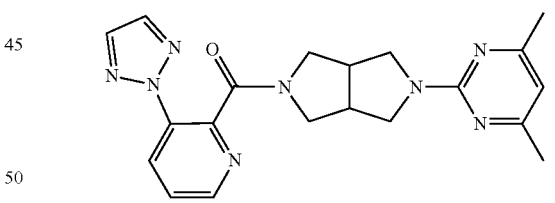

The title compound was prepared in a manner analogous to Example 275 substituting 3-[1,2,3]triazol-2-yl-pyridine-2-carboxylic acid (Intermediate 72) for 6-methyl-2-[1,2,3]triazol-2-yl-nicotinic acid. Excess amounts of acetic acid from the purification of the acid (in previous steps) still remained and allowed the acetamide to be formed in significant quantities as a byproduct, which was isolated in addition to the title compound. MS (ESI) mass calcd. for C₂₀H₂₂N₅O, 390.44. m/z found 391.3 [M+H]⁺. ¹H NMR (400 MHz, CDCl₃): 8.62 (dd, J=4.7, 1.3 Hz, 1H), 8.33 (dd, J=8.3, 1.3 Hz, 1H), 7.79 (s, 2H), 7.48 (dd, J=8.3, 4.7 Hz, 1H), 6.28 (s, 1H), 3.92 (td, J=12.5, 7.4 Hz, 2H), 3.80-3.57 (m, 5H), 3.26 (dd, J=10.8, 5.3 Hz, 1H), 3.12-2.98 (m, 2H), 2.30 (s, 6H).

Example 333: (2-Bromo-4,5-dimethoxy-phenyl)-[5-(4,6-dimethyl-pyrimidin-2-yl)-hexahydro-pyrrolo[3,4-c]pyrrol-2-yl]-methanone

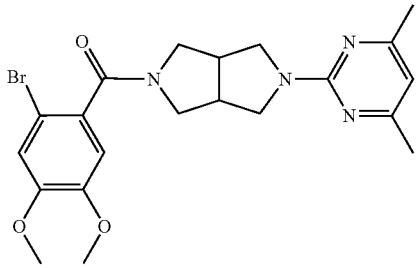 [SMILES: COc1cc(Br)c(C(=O)N2CC3CN(c4nc(C)cc(C)n4)CC3C2)cc1OC]

The title compound was prepared in a manner analogous to Example 275 substituting 5-acetamido-2-bromobenzoic acid for 6-methyl-2-[1,2,3]triazol-2-yl-nicotinic acid. MS (ESI) mass calcd. for $C_{21}H_{25}BrN_4O_3$, 461.35. m/z found 463.3 [M+H]$^+$. $^1$H NMR (400 MHz, CDCl$_3$): 6.98 (s, 1H), 6.77 (s, 1H), 6.30 (s, 1H), 3.98-3.89 (m, 2H), 3.86 (d, J=9.2 Hz, 6H), 3.79 (dd, J=11.6, 7.2 Hz, 1H), 3.67-3.59 (m, 2H), 3.53 (dd, J=11.5, 4.4 Hz, 2H), 3.22 (s, 1H), 3.12-2.96 (m, 2H), 2.29 (s, 6H).

Example 334: (3,4-Dihydro-2H-benzo[b][1,4]dioxepin-6-yl)-[5-(4,6-dimethyl-pyrimidin-2-yl)-hexahydro-pyrrolo[3,4-c]pyrrol-2-yl]-methanone

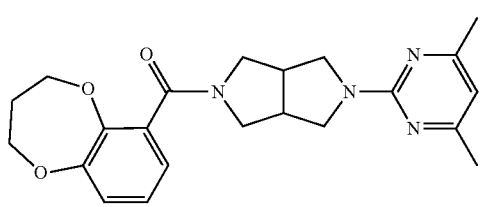 [SMILES: Cc1cc(C)nc(N2CC3CN(C(=O)c4cccc5c4OCCCO5)CC3C2)n1]

The title compound was prepared in a manner analogous to Example 275 substituting 3,4-dihydro-2H-1,5-benzodioxepine-6-carboxylic acid for 6-methyl-2-[1,2,3]triazol-2-yl-nicotinic acid. MS (ESI) mass calcd. for $C_{22}H_{26}N_4O_3$, 394.47; m/z found 395.3 [M+H]$^+$. $^1$H NMR (400 MHz, CDCl$_3$): 6.99 (dd, J=7.9, 1.9 Hz, 1H), 6.93 (t, J=7.6 Hz, 1H), 6.88 (dd, J=7.4, 1.9 Hz, 1H), 6.29 (s, 1H), 4.20 (s, 2H), 3.90 (ddd, J=19.1, 12.1, 7.6 Hz, 2H), 3.81-3.73 (m, 1H), 3.68-3.58 (m, 2H), 3.57-3.45 (m, 2H), 3.23 (dd, J=10.9, 4.7 Hz, 1H), 3.09-2.90 (m, 2H), 2.29 (s, 6H), 2.14 (d, J=5.9 Hz, 2H).

Example 335: (5-(4,6-dimethylpyrimidin-2-yl)hexahydropyrrolo[3,4-c]pyrrol-2(1H)-yl)(4-fluoro-2-(6-methylpyridin-2-yl)phenyl)methanone

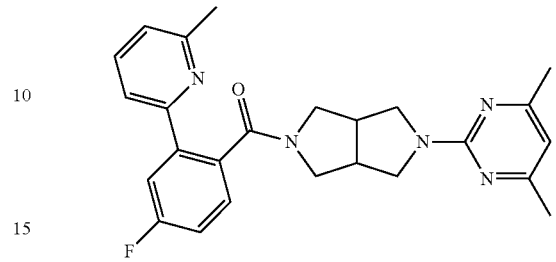

The title compound was prepared in a manner analogous to Example 248, substituting 6-methyl-2-(tributylstannyl)pyridine for 5-methyl-2-(tributylstannyl)pyridine. MS (ESI) mass calcd. for $C_{25}H_{26}FN_5O$, 431.21; found 432.2 [M+H]$^+$.

Example 336: [5-(4,6-Dimethyl-pyrimidin-2-yl)-hexahydro-pyrrolo[3,4-c]pyrrol-2-yl]-(6-methyl-2-[1,2,3]triazol-1-yl-pyridin-3-yl)-methanone

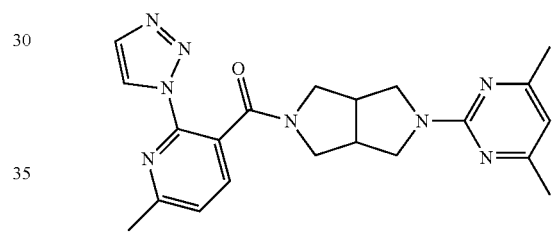

The title compound was prepared in a manner analogous to Example 275 substituting 6-methyl-2-[1,2,3]triazol-1-yl-nicotinic acid (Intermediate 71) for 6-methyl-2-[1,2,3]triazol-2-yl-nicotinic acid. MS (ESI) mass calcd. for $C_{21}H_{24}N_8O$, 404.47; m/z found 405.3 [M+H]$^+$. $^1$H NMR (400 MHz, CDCl$_3$): 8.45 (d, J=0.7 Hz, 1H), 7.78 (s, 1H), 7.71 (d, J=7.7 Hz, 1H), 7.26 (t, J=3.9 Hz, 1H), 6.29 (s, 1H), 4.01 (dd, J=12.6, 7.7 Hz, 1H), 3.91 (dd, J=11.6, 7.7 Hz, 1H), 3.76 (dd, J=11.6, 7.2 Hz, 1H), 3.65-3.58 (m, 2H), 3.51 (ddd, J=16.0, 11.1, 5.9 Hz, 2H), 3.15 (dt, J=10.1, 5.1 Hz, 1H), 3.12-2.95 (m, 2H), 2.61 (s, 3H), 2.30 (s, 6H).

Example 337: (1-Bromo-naphthalen-2-yl)-[5-(4,6-dimethyl-pyrimidin-2-yl)-hexahydro-pyrrolo[3,4-c]pyrrol-2-yl]-methanone

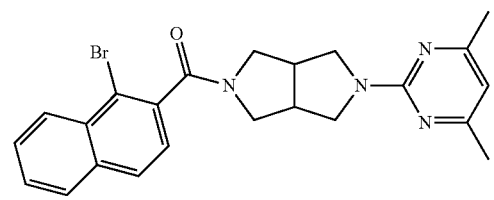 [SMILES: Cc1cc(C)nc(N2CC3CN(C(=O)c4ccc5ccccc5c4Br)CC3C2)n1]

The title compound was prepared in a manner analogous to Example 275 substituting 5-acetamido-2-bromobenzoic acid for 6-methyl-2-[1,2,3]triazol-2-yl-nicotinic acid. MS (ESI) mass calcd. for C₂₃H₂₃BrN₄O, 451.36. m/z found 451.3 [M+H]⁺. ¹H NMR (400 MHz, CDCl₃): 8.29 (d, J=7.1 Hz, 1H), 7.85 (t, J=7.5 Hz, 2H), 7.64 (t, J=7.4 Hz, 1H), 7.60-7.54 (m, 1H), 7.33 (s, 1H), 6.30 (s, 1H), 4.03 (s, 1H), 3.91 (s, 1H), 3.77 (dt, J=14.9, 7.4 Hz, 2H), 3.66 (dd, J=11.6, 5.0 Hz, 1H), 3.51 (d, J=52.5 Hz, 2H), 3.18 (d, J=65.6 Hz, 2H), 2.98 (d, J=21.2 Hz, 1H), 2.30 (s, 6H).

Example 338: [5-(4,6-Dimethyl-pyrimidin-2-yl)-hexahydro-pyrrolo[3,4-c]pyrrol-2-yl]-(3-methoxy-naphthalen-2-yl)-methanone

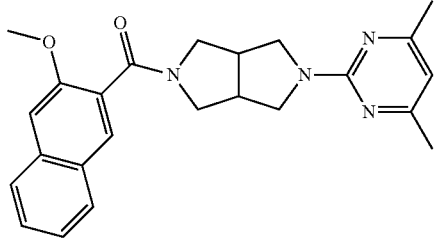

The title compound was prepared in a manner analogous to Example 275 substituting 3-methoxy-2-naphthoic acid for 6-methyl-2-[1,2,3]triazol-2-yl-nicotinic acid. MS (ESI) mass calcd. for C₂₄H₂₆N₄O₂, 402.49. m/z found 403.3 [M+H]⁺. ¹H NMR (400 MHz, CDCl₃): 7.78-7.70 (m, 3H), 7.49-7.43 (m, 1H), 7.39-7.32 (m, 1H), 7.15 (s, 1H), 6.29 (s, 1H), 3.99 (d, J=12.7, 7.9 Hz, 1H), 3.93-3.85 (m, 4H), 3.79-3.62 (m, 3H), 3.56-3.45 (m, 2H), 3.21 (dd, J=11.1, 4.9 Hz, 1H), 3.11-3.02 (m, 1H), 2.99-2.90 (m, 1H), 2.30 (s, 6H).

Example 339: [5-(4,6-Dimethyl-pyrimidin-2-yl)-hexahydro-pyrrolo[3,4-c]pyrrol-2-yl]-(8-[1,2,3]triazol-2-yl-naphthalen-1-yl)-methanone

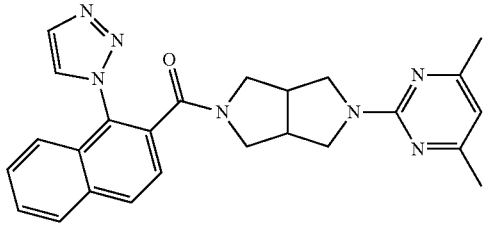 [SMILES: Cc1cc(C)nc(N2CC3CN(C(=O)c4ccc5ccccc5c4-n4ccnn4)CC3C2)n1]

The title compound was prepared in a manner analogous to Example 275 substituting 1-[1,2,3]triazol-1-yl-naphthalene-2-carboxylic acid (Intermediate 74) for 6-methyl-2-[1,2,3]triazol-2-yl-nicotinic acid. MS (ESI) mass calcd. for C₂₅H₂₅N₇O, 439.52. m/z found 440.3 [M+H]⁺. ¹H NMR (400 MHz, CDCl₃): 8.08 (d, J=8.4 Hz, 1H), 8.01 (d, J=0.8 Hz, 1H), 7.97 (d, J=8.0 Hz, 1H), 7.92 (d, J=0.8 Hz, 1H), 7.65-7.59 (m, 1H), 7.56 (ddd, J=8.1, 7.0, 1.2 Hz, 1H), 7.51-7.47 (m, 1H), 7.36 (d, J=8.4 Hz, 1H), 6.29 (s, 1H), 3.82 (dd, J=11.6, 7.3 Hz, 1H), 3.76-3.63 (m, 2H), 3.56 (dd, J=11.2, 7.1 Hz, 1H), 3.49 (dd, J=11.5, 3.8 Hz, 1H), 3.45-3.36 (m, 2H), 3.14 (dd, J=11.2, 4.9 Hz, 1H), 2.96-2.84 (m, 2H), 2.29 (s, 6H).

Example 340: [5-(4,6-Dimethyl-pyrimidin-2-yl)-hexahydro-pyrrolo[3,4-c]pyrrol-2-yl]-(1-methoxy-naphthalen-2-yl)-methanone

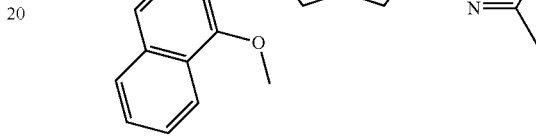

The title compound was prepared in a manner analogous to Example 275 substituting 1-methoxy-2-naphthoic acid for 6-methyl-2-[1,2,3]triazol-2-yl-nicotinic acid. MS (ESI) mass calcd. for C₂₄H₂₆N₄O₂, 402.49. m/z found 403.3 [M+H]⁺. ¹H NMR (400 MHz, CDCl₃): 8.19-8.12 (m, 1H), 7.84 (dt, J=6.2, 2.6 Hz, 1H), 7.62 (d, J=8.4 Hz, 1H), 7.56-7.49 (m, 2H), 7.36 (d, J=8.4 Hz, 1H), 6.30 (s, 1H), 4.07-3.97 (m, 4H), 3.91 (dd, J=11.5, 7.5 Hz, 1H), 3.80-3.55 (m, 4H), 3.48 (dd, J=11.5, 4.6 Hz, 1H), 3.33 (s, 1H), 3.13-3.04 (m, 1H), 3.01-2.92 (m, 1H), 2.30 (s, 6H).

Example 341: (4,5-Dimethoxy-2-[1,2,3]triazol-1-yl-phenyl)-[5-(4,6-dimethyl-pyrimidin-2-yl)-hexahydro-pyrrolo[3,4-c]pyrrol-2-yl]-methanone

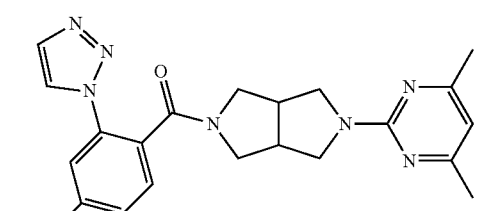

The title compound was prepared in a manner analogous to Example 275 substituting 2,3-dimethoxy-6-[1,2,3]triazol-1-yl-benzoic acid (Intermediate 78) for 6-methyl-2-[1,2,3]triazol-2-yl-nicotinic acid. MS (ESI) mass calcd. for C₂₃H₂₇N₇O₃, 449.51. m/z found 450.3 [M+H]⁺. ¹H NMR (400 MHz, CDCl₃): 7.93 (s, 1H), 7.77 (s, 1H), 7.17 (s, 1H), 6.92 (s, 1H), 6.29 (s, 1H), 3.95 (d, J=1.6 Hz, 6H), 3.74 (ddd, J=29.3, 15.1, 7.9 Hz, 3H), 3.46 (d, J=8.6 Hz, 2H), 3.28 (d, J=7.5 Hz, 1H), 3.14 (d, J=7.4 Hz, 1H), 2.89 (s, 2H), 2.77 (d, J=6.0 Hz, 1H), 2.29 (s, 6H).

Example 342: (4,5-Dimethoxy-2-[1,2,3]triazol-2-yl-phenyl)-[5-(4,6-dimethyl-pyrimidin-2-yl)-hexahydro-pyrrolo[3,4-c]pyrrol-2-yl]-methanone

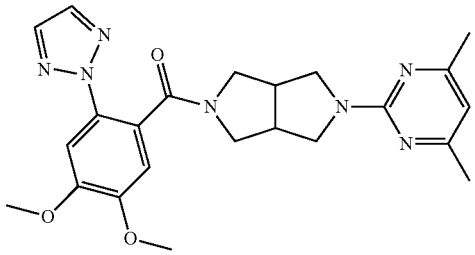

The title compound was prepared in a manner analogous to Example 275 substituting 2,3-dimethoxy-6-[1,2,3]triazol-2-yl-benzoic acid (Intermediate 77) for 6-methyl-2-[1,2,3]triazol-2-yl-nicotinic acid. MS (ESI) mass calcd. for $C_{23}H_{27}N_7O_3$, 449.51; m/z found 450.3 [M+H]$^+$. $^1$H NMR (400 MHz, CDCl$_3$): 7.70 (s, 2H), 7.45 (s, 1H), 6.89 (s, 1H), 6.29 (s, 1H), 3.97 (s, 3H), 3.93 (s, 3H), 3.84 (dt, J=11.6, 7.6 Hz, 2H), 3.65 (dd, J=12.5, 4.1 Hz, 2H), 3.55 (dd, J=11.5, 5.2 Hz, 1H), 3.44 (dd, J=11.6, 3.8 Hz, 1H), 3.27 (s, 1H), 3.03-2.93 (m, 1H), 2.85 (d, J=24.5 Hz, 2H), 2.30 (s, 6H).

Example 343: (5-(4,6-Dimethylpyrimidin-2-yl)hexahydropyrrolo[3,4-c]pyrrol-2(1H)-yl)(4-fluoro-2-(4-methylpyridin-2-yl)phenyl)methanone

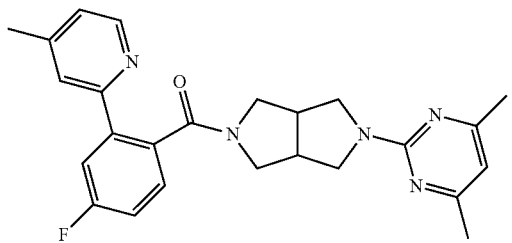

The title compound was prepared in a manner analogous to Example 248 substituting 4-methyl-2-(tributylstannyl)pyridine for 5-methyl-2-(tributylstannyl)pyridine. MS (ESI) mass calcd. for $C_{25}H_{26}FN_5O$, 431.21. m/z found 432.2 [M+H]$^+$.

Example 344: (5-(4,6-dimethylpyrimidin-2-yl)hexahydropyrrolo[3,4-c]pyrrol-2(1H)-yl)(3-propoxypyridin-2-yl)methanone

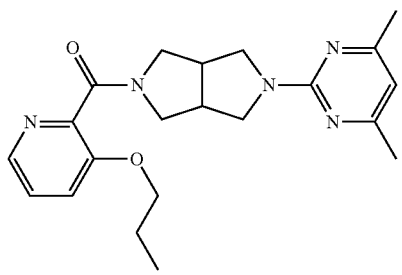 [SMILES: CCCOc1cccnc1C(=O)N1CC2CN(c3nc(C)cc(C)n3)CC2C1]

The title compound was prepared in a manner analogous to Example 15, utilizing Intermediate 23 and 2-propoxynicotinic acid. MS (ESI) mass calcd. $C_{21}H_{27}N_5O_2$, 381.48. m/z found 382.0 [M+H]$^+$. $^1$H NMR (CD$_3$OD): 8.47 (d, J=5.5 Hz, 1H), 8.37 (d, J=8.9 Hz, 1H), 8.06 (dd, J=8.9, 5.5 Hz, 1H), 6.83 (s, 1H), 4.36-4.24 (m, 2H), 4.10-3.97 (m, 3H), 3.81-3.67 (m, 4H), 3.50-3.44 (m, 1H), 3.39-3.33 (m, 1H), 3.30-3.22 (m, 1H), 2.54 (s, 6H), 1.92-1.80 (m, 2H), 1.03 (t, J=7.4 Hz, 3H).

The following prophetic example may be prepared using the procedures described in the previous examples.

Example 345: (3-Propoxypyridin-2-yl)(5-(5-(trifluoromethyl)pyrimidin-2-yl)hexahydropyrrolo[3,4-c]pyrrol-2(1H)-yl)methanone

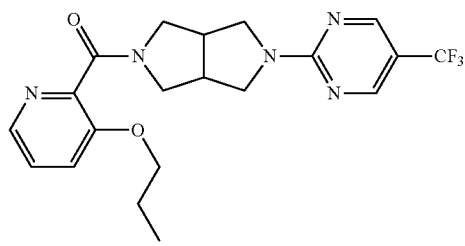 [SMILES: CCCOc1cccnc1C(=O)N1CC2CN(c3ncc(C(F)(F)F)cn3)CC2C1]

MS (ESI) mass calcd. For $C_{20}H_{23}F_3N_5O_2$, 421.17.

Example 346: (5-(4,6-Dimethylpyrimidin-2-yl)hexahydropyrrolo[3,4-c]pyrrol-2(1H)-yl)(4-fluoro-2-(3-fluoropyridin-2-yl)phenyl)methanone

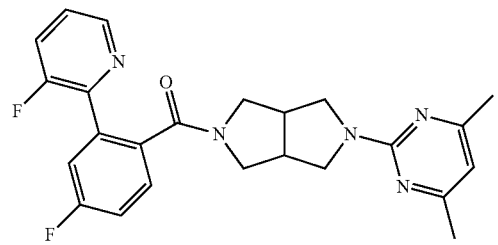 [SMILES: Cc1cc(C)nc(N2CC3CN(C(=O)c4ccc(F)cc4-c4ncccc4F)CC3C2)n1]

The title compound was prepared in a manner analogous to Example 248, substituting 3-fluoro-2-(tributylstannyl)pyridine for 5-methyl-2-(tributylstannyl)pyridine. MS (ESI) mass calcd. for $C_{24}H_{23}F_2N_5O$, 435.19; found 436.2 [M+H]$^+$.

Prophetic examples 347-348 may be prepared using the procedures described in the previous examples.

Example 347: (3-Propoxypyridin-2-yl)(5-(quinoxa-lin-2-yl)hexahydropyrrolo[3,4-c]pyrrol-2(1H)-yl)methanone

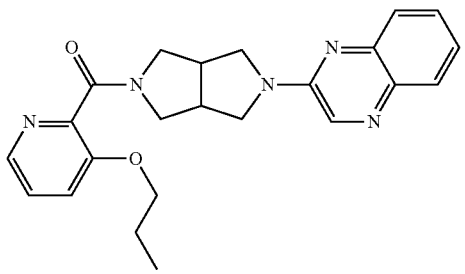 [SMILES: CCCOc1cccnc1C(=O)N1CC2CN(c3cnc4ccccc4n3)CC2C1]

MS (ESI) mass calcd. For $C_{23}H_{25}N_5O_2$, 403.20.

Example 348: 2-(5-([1,1'-biphenyl]-2-ylsulfonyl)hexahydropyrrolo[3,4-c]pyrrol-2(1H)-yl)quinoxaline

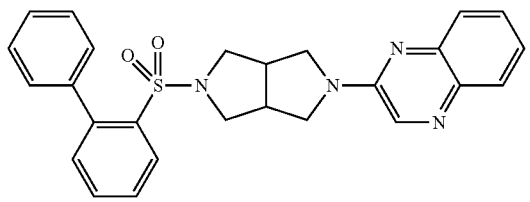 [SMILES: O=S(=O)(c1ccccc1-c1ccccc1)N1CC2CN(c3cnc4ccccc4n3)CC2C1]

The title prophetic compound may be synthesized using biphenylsulfonylchloride and Intermediate 35. MS (ESI) mass calcd. for $C_{26}H_{24}N_4O_2S$, 456.16.

Example 349: 2-[(2,6-Dimethoxyphenyl)carbonyl]-5-[5-(trifluoromethyl)pyridin-2-yl]octahydropyrrolo[3,4-c]pyrrole

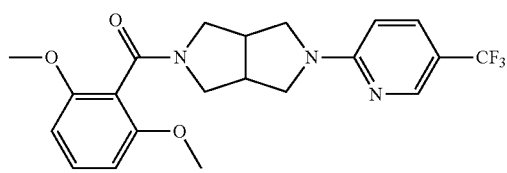 [SMILES: COc1cccc(OC)c1C(=O)N1CC2CN(c3ncc(C(F)(F)F)cn3)CC2C1]

The title compound was prepared in a manner analogous to Example 15, utilizing 5-(trifluoromethyl)pyridin-2-yl]octahydropyrrolo[3,4-c]pyrrole and 2,6-dimethoxybenzoic acid. MS (ESI) mass calcd. $C_{21}H_{22}F_3N_3O_3$, 421.42. m/z found 422.0 [M+H]+. 1H NMR (CD3OD): 8.12 (d, J=8.9 Hz, 1H), 7.34 (t, J=8.4 Hz, 1H), 7.27 (d, J=9.2 Hz, 1H), 6.72-6.66 (m, 2H), 4.03-3.48 (m, 14H), 3.28-3.22 (m, 2H).

Example 350: (2,6-Dimethoxyphenyl)(5-(5-(trifluoromethyl)pyrimidin-2-yl)hexahydropyrrolo[3,4-c]pyrrol-2(1H)-yl)methanone

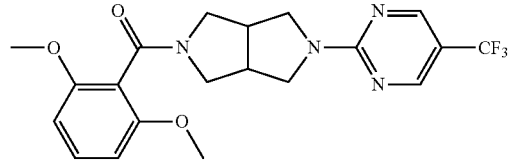

The title prophetic compound may be synthesized in a manner analogous to Example 15 utilizing 5-(trifluoromethyl)pyrimidin-2-yl)hexahydropyrrolo[3,4-c]pyrrole and 2,6-dimethoxybenzoic acid. MS (ESI) mass calcd. For $C_{20}H_{21}F_3N_4O_3$, 422.16.

Example 351: (2,6-Dimethoxyphenyl)(5-(4,6-dimethylpyrimidin-2-yl)hexahydropyrrolo[3,4-c]pyrrol-2(1H)-yl)methanone

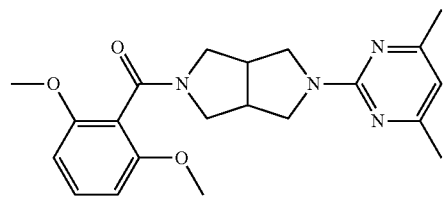

The title compound was prepared in a manner analogous to Example 15 utilizing in a manner analogous to Example 15, utilizing Intermediate 23 and 2,6-dimethoxybenzoic acid. MS (ESI) mass calcd. $C_{21}H_{26}N_4O_3$, 382.47. m/z found 383.1 [M+H]+. 1H NMR (CD3OD): 7.38 (t, J=8.4 Hz, 1H), 6.81 (s, 1H), 6.81-6.70 (m, 2H), 4.04-3.89 (m, 3H), 3.84 (s, 3H), 3.79 (s, 3H), 3.76-3.55 (m, 4H), 3.27-3.13 (m, 3H), 2.53 (s, 6H).

Example 352: (5-(4,6-Dimethylpyrimidin-2-yl)hexahydropyrrolo[3,4-c]pyrrol-2(1H)-yl)(3-methylfuran-2-yl)methanone

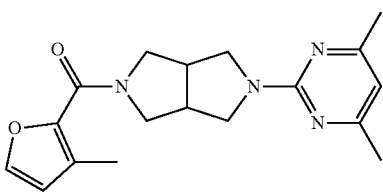 [SMILES: Cc1cc(C)nc(N2CC3CN(C(=O)c4occc4C)CC3C2)n1]

The title compound was prepared in a manner analogous to Example 15, substituting 3-methylfuran-2-carboxylic acid for 3-fluoro-2-[1,2,3]triazol-2-yl-benzoic acid. MS (ESI) mass calcd. For $C_{18}H_{22}N_4O_2$, 326.17. m/z found 327.2 [M+H]+.

Example 353: 2-[(3-Methylfuran-2-yl)carbonyl]-5-[5-(trifluoromethyl)pyridin-2-yl]octahydropyrrolo[3,4-c]pyrrole

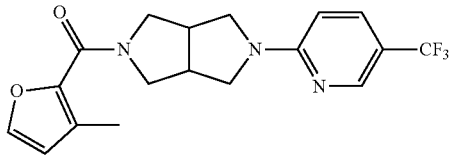 [SMILES: Cc1ccoc1C(=O)N1CC2CN(c3ncc(C(F)(F)F)cn3)CC2C1]

The title compound was prepared in a manner analogous to Example 15, utilizing 2-(5-(trifluoromethyl)pyridin-2-yl)octahydropyrrolo[3,4-c]pyrrole and 3-methylfuran-2-carboxylic acid. MS (ESI) mass calcd. $C_{18}H_{18}F_3N_3O_2$, 365.36. m/z found 366.0 [M+H]$^+$. $^1$H NMR (CDCl$_3$): 8.39 (s, 1H), 7.62 (d, J=9.1 Hz, 1H), 7.32 (d, J=1.4 Hz, 1H), 6.39 (d, J=8.8 Hz, 1H), 6.32 (d, J=1.4 Hz, 1H), 4.17 (brs, 1H), 3.94 (brs, 1H), 3.81 (brs, 3H), 3.71-3.67 (m, 1H), 3.50 (br s, 2H), 3.11 (brs, 2H), 2.37 (s, 3H).

Example 354: (3-Methylfuran-2-yl)(5-(5-(trifluoromethyl)pyrimidin-2-yl)hexahydropyrrolo[3,4-c]pyrrol-2(1H)-yl)methanone

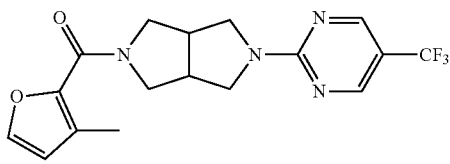

The title prophetic compound may be prepared analogous to Example 15, utilizing 5-(trifluoromethyl)pyrimidin-2-yl)hexahydropyrrolo[3,4-c]pyrrole and 3-methylfuran-2-carboxylic acid. MS (ESI) mass calcd. For $C_{17}H_{17}F_3N_4O_2$, 366.13.

Example 355: (3-Methylfuran-2-yl)(5-(quinoxalin-2-yl)hexahydropyrrolo[3,4-c]pyrrol-2(1H)-ylmethanone

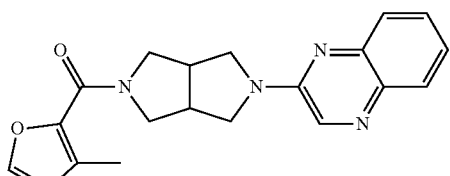

The title compound was prepared in a manner analogous to Example 15 utilizing Intermediate 35 and 3-methylfuran-2-carboxylic acid. MS (ESI) mass calcd. For $C_{20}H_{20}N_4O_2$, 348.16. m/z found 349.0 [M+H]$^+$.

Example 356: 2-([1,1'-Biphenyl]-2-ylsulfonyl)-5-(5-(trifluoromethyl)pyridin-2-yl)octahydropyrrolo[3,4-c]pyrrole

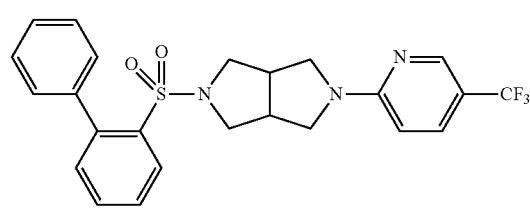 [SMILES: O=S(=O)(c1ccccc1-c1ccccc1)N1CC2CN(c3ccc(C(F)(F)F)cn3)CC2C1]

The title compound may be prepared using biphenylsulfonylchloride and 5-(trifluoromethyl)pyridin-2-yl)octahydropyrrolo[3,4-c]pyrrole. MS (ESI) mass calcd. For $C_{24}H_{22}F_3N_3O_2S$, 473.14. m/z found 474.1 [M+H]$^+$.

Example 357: 2-([1,1'-Biphenyl]-2-ylsulfonyl)-5-(5-(trifluoromethyl)pyrimidin-2-yl)octahydropyrrolo[3,4-c]pyrrole

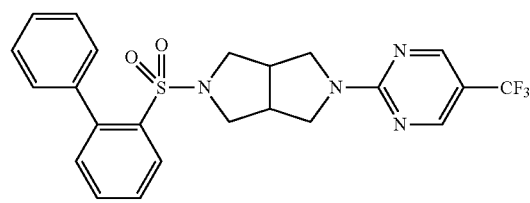 [SMILES: O=S(=O)(c1ccccc1-c1ccccc1)N1CC2CN(c3ncc(C(F)(F)F)cn3)CC2C1]

The title prophetic compound may be prepared using biphenylsulfonylchloride and 5-(trifluoromethyl)pyrimidin-2-yl)octahydropyrrolo[3,4-c]pyrrole MS (ESI) mass calcd. For $C_{23}H_{21}F_3N_4O_2S$, 474.13.

Example 358: 2-([1,1'-Biphenyl]-2-ylsulfonyl)-5-(4,6-dimethylpyrimidin-2-yl)octahydropyrrolo[3,4-c]pyrrole

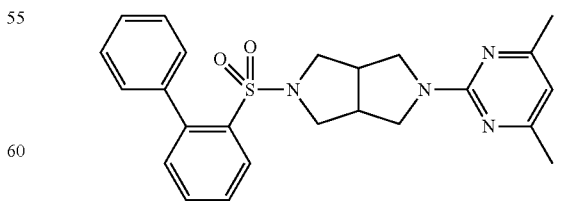

The title compound was prepared using biphenylsulfonylchloride and 4,6-dimethylpyrimidin-2-yl)octahydropyrrolo[3,4-c]pyrrole. MS (ESI) mass calcd. For $C_{24}H_{26}N_4O_2S$, 434.18. m/z found 435.2 [M+H]$^+$.

Example 359: 2-(4,6-Dimethylpyrimidin-2-yl)-5-((2-methoxyphenyl)sulfonyl)octahydropyrrolo[3,4-c]pyrrole

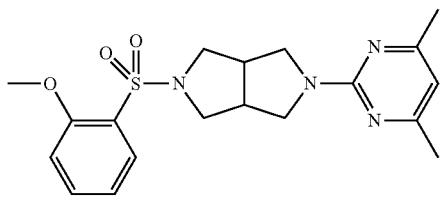

The title compound was prepared using 2-methoxyphenyl)sulfonylchloride and Intermediate 23. MS (ESI) mass calcd. For $C_{19}H_{24}N_4O_3S$, 388.16. m/z found 389.2 $[M+H]^+$.

Example 360: 2-((2-Methoxyphenyl)sulfonyl)-5-(5-(trifluoromethyl)pyrimidin-2-yl)octahydropyrrolo[3,4-c]pyrrole

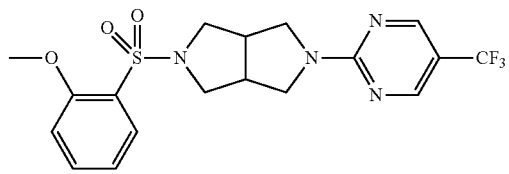 [SMILES: COc1ccccc1S(=O)(=O)N1CC2CN(c3ncc(C(F)(F)F)cn3)CC2C1]

The title prophetic compound may be prepared using 2-methoxyphenyl)sulfonylchloride and 5-(trifluoromethyl) pyrimidin-2-yl)octahydropyrrolo[3,4-c]pyrrole. MS (ESI) mass calcd. For $C_{18}H_{19}F_3N_4O_3S$, 428.11.

Example 361: 2-((2-Methoxyphenyl)sulfonyl)-5-(5-(trifluoromethyl)pyridin-2-yl)octahydropyrrolo[3,4-c]pyrrole

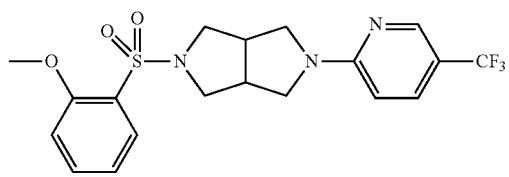 [SMILES: COc1ccccc1S(=O)(=O)N1CC2CN(c3ccc(C(F)(F)F)cn3)CC2C1]

The title compound was prepared using 2-methoxyphenyl)sulfonylchloride and 5-(trifluoromethyl)pyridin-2-yl) octahydropyrrolo[3,4-c]pyrrole. MS (ESI) mass calcd. For $C_{19}H_{20}F_3N_3O_3S$, 427.12. m/z found 428.2 $[M+H]^+$.

Example 362: 2-(5-((2-Methoxyphenyl)sulfonyl)hexahydropyrrolo[3,4-c]pyrrol-2(1H)-yl)quinoxaline

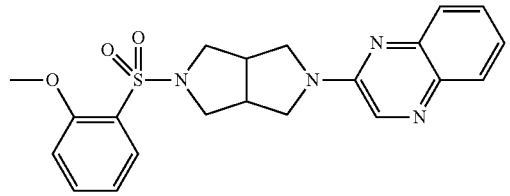 [SMILES: COc1ccccc1S(=O)(=O)N1CC2CN(c3cnc4ccccc4n3)CC2C1]

The title compound was prepared using 2-methoxyphenyl)sulfonylchloride and Intermediate 35. MS (ESI) mass calcd. For $C_{21}H_{22}N_4O_3S$, 410.14. m/z found 411.1 $[M+H]^+$.

Prophetic Examples 363-365 may be prepared as previously described.

Example 363: (3,6'-Dimethyl-[2,3'-bipyridin]-2'-yl)(5-(quinoxalin-2-yl)hexahydropyrrolo[3,4-c]pyrrol-2(1H)-yl)methanone

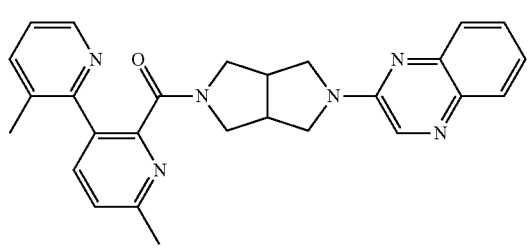 [SMILES: Cc1ccc(-c2ncccc2C)c(C(=O)N2CC3CN(c4cnc5ccccc5n4)CC3C2)n1]

MS (ESI) mass calcd. For $C_{27}H_{26}N_6O$, 450.22.

Example 364: (3,6'-Dimethyl-[2,3'-bipyridin]-2'-yl)(5-(5-(trifluoromethyl)pyrimidin-2-yl)hexahydropyrrolo[3,4-c]pyrrol-2(1H)-yl)methanone

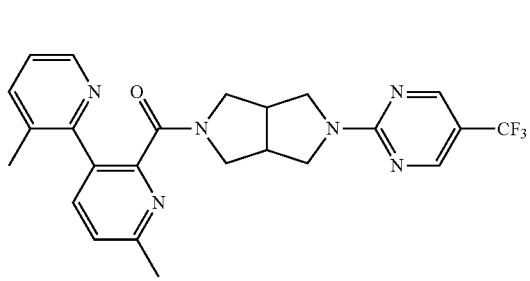 [SMILES: Cc1ccc(-c2ncccc2C)c(C(=O)N2CC3CN(c4ncc(C(F)(F)F)cn4)CC3C2)n1]

MS (ESI) mass calcd. For $C_{27}H_{23}F_3N_6O$, 468.19.

Example 365: (3,6'-Dimethyl-[2,3'-bipyridin]-2'-yl)(5-(5-(trifluoromethyl)pyridin-2-yl)hexahydropyrrolo[3,4-c]pyrrol-2(1H)-yl)methanone

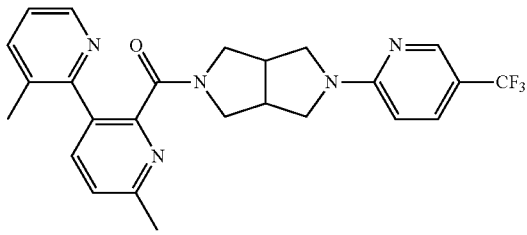 [SMILES: Cc1ccc(-c2ncccc2C)c(C(=O)N2CC3CN(c4ccc(C(F)(F)F)cn4)CC3C2)n1]

MS (ESI) mass calcd. For $C_{25}H_{24}F_3N_5O$, 467.19.

Example 366: (5-(4,6-Dimethylpyrimidin-2-yl)hexahydropyrrolo[3,4-c]pyrrol-2(1H)-yl)(4-fluoro-2-(pyridin-2-yl)phenyl)methanone

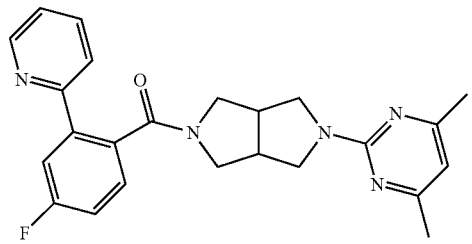 [SMILES: Cc1cc(C)nc(N2CC3CN(C(=O)c4ccc(F)cc4-c4ccccn4)CC3C2)n1]

The title compound was prepared in a manner analogous to Example 367 substituting (5-(4,6-dimethylpyrimidin-2-yl)hexahydropyrrolo[3,4-c]pyrrol-2(1H)-yl)(4-fluoro-2-iodophenyl)methanone for (5-(4,6-dimethylpyrimidin-2-yl)hexahydropyrrolo[3,4-c]pyrrol-2(1H)-yl)(3-fluoro-2-iodophenyl)methanone, with the addition of catalytic CuI, substituting dioxane for DME, heating 130° C. in microwave for 60 min. The reaction was filtered through celite, rinsed with EtOAc and then concentrated and purified on RP agilent HPLC and fractions lyophilized. MS (ESI) mass calcd. for $C_{24}H_{24}FN_5O$, 417.20. m/z found, 418.2 [M+H]$^+$.

Example 367: (5-(4,6-Dimethylpyrimidin-2-yl)hexahydropyrrolo[3,4-c]pyrrol-2(1H)-yl)(3-fluoro-2-(pyridin-2-yl)phenyl)methanone

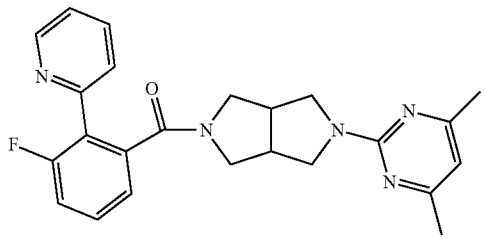 [SMILES: Cc1cc(C)nc(N2CC3CN(C(=O)c4cccc(F)c4-c4ccccn4)CC3C2)n1]

(5-(4,6-Dimethylpyrimidin-2-yl)hexahydropyrrolo[3,4-c]pyrrol-2(1H)-yl)(3-fluoro-2-(pyridin-2-yl)phenyl)methanone. (5-(4,6-Dimethylpyrimidin-2-yl)hexahydropyrrolo[3,4-c]pyrrol-2(1H)-yl)(3-fluoro-2-iodophenyl)methanone (51 mg, 0.11 mmol) and 2-tributylstannane pyridine (57 mg, 0.13 mmol) were combined and dissolved in degassed DME then purged with bubbling N$_2$ for 5 minutes. The reaction was treated with Pd(PPh$_3$)$_4$ and then purged with bubbling for 5 minutes in a sealed vessel and then heated to 160° C. in microwave for 90 min. Reaction was filtered through celite, concentrated and purified on 16 g SiO$_2$ with 0-3.5% NH$_3$ MeOH/CH$_2$Cl$_2$. MS (ESI) mass calcd. for $C_{24}H_{24}FN_5O$, 417.49. m/z found, 418.2 [M+H]$^+$. $^1$H NMR (500 MHz, CDCl$_3$): 7.71-7.64 (m, 1H), 7.57-7.52 (m, 1H), 7.46 (dddd, J=8.2, 5.6, 2.8, 1.2 Hz, 1H), 7.37 (td, J=7.9, 5.5 Hz, 1H), 7.30-7.24 (m, 2H), 7.20 (ddd, J=9.0, 2.5, 1.5 Hz, 1H), 7.11 (tdd, J=8.4, 2.6, 1.0 Hz, 1H), 6.31 (s, 1H), 3.97 (dd, J=12.7, 7.8 Hz, 1H), 3.89 (dd, J=11.5, 7.7 Hz, 1H), 3.82-3.70 (m, 2H), 3.70-3.60 (m, 2H), 3.50 (dd, J=11.5, 4.6 Hz, 1H), 3.40 (dd, J=10.9, 5.4 Hz, 1H), 3.07 (d, J=7.2 Hz, 1H), 3.03-2.94 (m, 1H), 2.30 (s, 6H).

Example 368: [2,3'-bipyridin]-2'-yl(5-(4,6-dimethylpyrimidin-2-yl)hexahydropyrrolo[3,4-c]pyrrol-2(1H)-yl)methanone

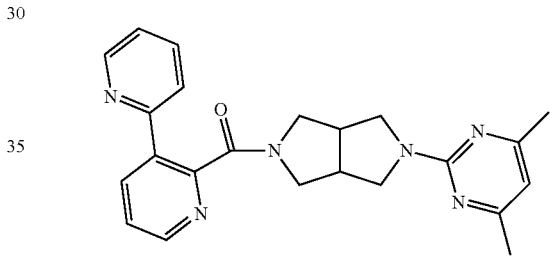

The title prophetic example may be synthesized according to a procedure as previously described. MS (ESI) mass calcd. for $C_{23}H_{24}N_6O$, 400.48

Example 369: (5-(4,6-Dimethylpyrimidin-2-yl)hexahydropyrrolo[3,4-c]pyrrol-2(1H)-yl)(4-fluoro-2-(oxazol-2-yl)phenyl)methanone

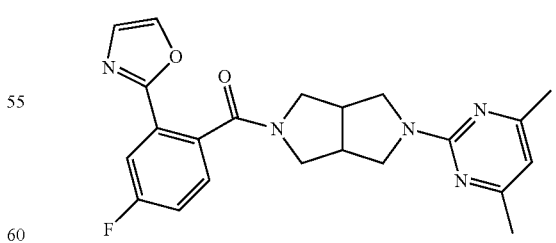

The title compound was prepared in a manner analogous to Example 248, substituting 2-(tri-N-butylstannyl)oxazole for 2-tributylstannane pyridine. MS (ESI) mass calcd. for $C_{22}H_{22}FN_5O_2$, 407.18; found 408.2 [M+H]$^+$.

Example 370: (5-(4,6-Dimethylpyrimidin-2-yl)hexahydropyrrolo[3,4-c]pyrrol-2(1H)-yl)(3-fluoro-2-(6-methylpyridin-2-yl)phenyl)methanone

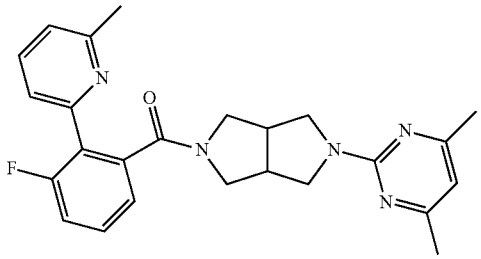 [SMILES: Cc1cccc(-c2c(F)cccc2C(=O)N2CC3CN(c4nc(C)cc(C)n4)CC3C2)n1]

The title compound was prepared in a manner analogous to Example 367, substituting 6-methyl-2-(tributylstannyl)pyridine for 2-tributylstannane pyridine. MS (ESI) mass calcd. for $C_{25}H_{26}FN_5O$, 431.51. m/z found, 432.2 [M+H]$^+$. $^1$H NMR (500 MHz, CDCl$_3$): 7.60 (t, J=7.7 Hz, 1H), 7.43-7.35 (m, 2H), 7.21-7.15 (m, J=13.8, 4.5 Hz, 2H), 7.05 (d, J=7.7 Hz, 1H), 6.30 (s, 1H), 3.84-3.73 (m, J=20.1, 12.0, 7.6 Hz, 2H), 3.67 (dd, J=11.5, 7.0 Hz, 1H), 3.63-3.53 (m, 1H), 3.40 (t, J=13.3 Hz, 2H), 3.30-3.20 (m, 1H), 3.10 (dd, J=10.8, 5.7 Hz, 1H), 2.98-2.84 (m, 2H), 2.43 (s, 3H), 2.30 (s, 6H).

Example 372: (2-(3-Chloropyridin-2-yl)-3-fluorophenyl)(5-(4,6-dimethylpyrimidin-2-yl)hexahydropyrrolo[3,4-c]pyrrol-2(1H)-yl)methanone

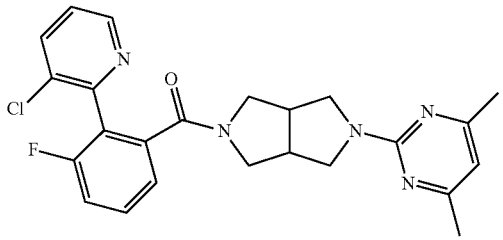

The title compound was prepared in a manner analogous to Example 367. MS (ESI) mass calcd. for $C_{24}H_{23}ClFN_5O$, 451.93. m/z found, 452.1 [M+H]$^+$. $^1$H NMR (400 MHz, CDCl$_3$): 8.51 (d, J=3.7 Hz, 1H), 7.71 (dd, J=28.1, 8.0 Hz, 1H), 7.45 (td, J=7.9, 5.3 Hz, 1H), 7.25-7.14 (m, J=10.6, 7.7 Hz, 3H), 6.30 (s, 1H), 3.77 (s, 2H), 3.72-3.59 (m, J=23.3, 9.8 Hz, 2H), 3.59-3.53 (m, 1H), 3.45 (dd, J=33.2, 12.0 Hz, 2H), 3.37-3.11 (m, J=59.6 Hz, 1H), 3.02-2.88 (m, 2H), 2.31 (s, 6H).

Example 371: (5-(4,6-Dimethylpyrimidin-2-yl)hexahydropyrrolo[3,4-c]pyrrol-2(1H)-yl)(3-fluoro-2-(3-methylpyridin-2-yl)phenyl)methanone

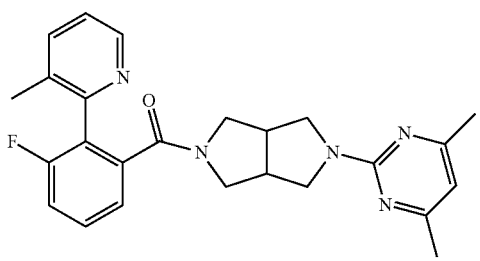 [SMILES: Cc1cc(C)nc(N2CC3CN(C(=O)c4cccc(F)c4-c4ncccc4C)CC3C2)n1]

The title compound was prepared in a manner analogous to Example 367. MS (ESI) mass calcd. for $C_{25}H_{26}FN_5O$, 431.51. m/z found, 432.2 [M+H]$^+$. $^1$H NMR (500 MHz, CDCl$_3$): 8.37 (d, J=40.0 Hz, 1H), 7.56-7.49 (m, 1H), 7.41 (td, J=7.9, 5.3 Hz, 1H), 7.23-7.04 (m, J=19.5, 9.7 Hz, 3H), 6.30 (s, 1H), 3.96-3.45 (m, 6H), 3.46-3.19 (m, J=11.6, 7.6 Hz, 2H), 3.01-2.85 (m, 2H), 2.31 (s, 6H), 2.23 (s, 3H).

Example 373: (5-(4,6-Dimethylpyrimidin-2-yl)hexahydropyrrolo[3,4-c]pyrrol-2(1H)-yl)(3-fluoro-2-(4-methylpyridin-2-yl)phenyl)methanone

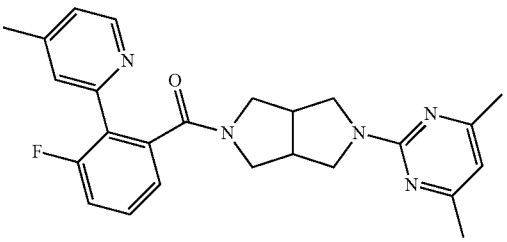

The title compound was prepared in a manner analogous to Example 367. MS (ESI) mass calcd. for $C_{25}H_{26}FN_5O$, 431.51. m/z found, 432.2 [M+H]$^+$. $^1$H NMR (400 MHz, CDCl$_3$): 8.44 (d, J=5.0 Hz, 1H), 7.43-7.40 (m, 1H), 7.40-7.34 (m, 1H), 7.21-7.14 (m, J=2.7, 1.1 Hz, 2H), 6.99 (d, J=4.5 Hz, 1H), 6.29 (s, 1H), 3.79 (dd, J=11.5, 7.3 Hz, 1H), 3.69 (ddd, J=8.7, 7.1, 2.1 Hz, 2H), 3.58-3.50 (m, 2H), 3.46 (dd, J=12.6, 4.3 Hz, 1H), 3.40 (dd, J=10.9, 4.2 Hz, 1H), 3.25 (dd, J=11.0, 5.1 Hz, 1H), 2.99-2.85 (m, 2H), 2.34 (s, 3H), 2.31 (s, 6H).

Example 374: (5-(4,6-Dimethylpyrimidin-2-yl)hexahydropyrrolo[3,4-c]pyrrol-2(1H)-yl)(3-fluoro-2-(5-methylpyridin-2-yl)phenyl)methanone

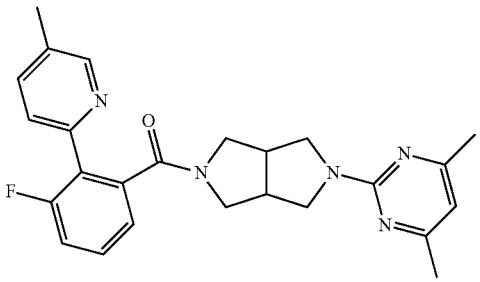 [SMILES: Cc1ccc(-c2c(F)cccc2C(=O)N2CC3CN(c4nc(C)cc(C)n4)CC3C2)nc1]

The title compound was prepared in a manner analogous to Example 367. MS (ESI) mass calcd. for $C_{25}H_{26}FN_5O$, 431.51. m/z found, 432.2 [M+H]$^+$. $^1$H NMR (400 MHz, CDCl$_3$): 8.42 (s, 1H), 7.53-7.48 (m, 2H), 7.42-7.33 (m, 1H), 7.21-7.12 (m, 2H), 6.29 (s, 1H), 3.81 (dd, J=11.5, 7.3 Hz, 1H), 3.76-3.67 (m, J=11.3, 7.2, 4.3 Hz, 2H), 3.58-3.39 (m, 4H), 3.28 (dd, J=10.9, 4.8 Hz, 1H), 3.01-2.86 (m, 2H), 2.31 (s, 9H).

Example 375: (5-(4,6-Dimethylpyrimidin-2-yl)hexahydropyrrolo[3,4-c]pyrrol-2(1H)-yl)(3-fluoro-2-(3-fluoropyridin-2-yl)phenyl)methanone

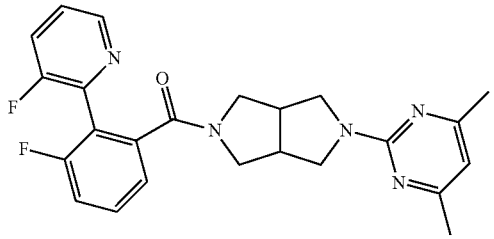 [SMILES: Cc1cc(C)nc(N2CC3CN(C(=O)c4cccc(F)c4-c4ncccc4F)CC3C2)n1]

The title compound was prepared in a manner analogous to Example 367 substituting 3-fluoro-2-(tributylstannyl)pyridine for 2-tributylstannane pyridine. MS (ESI) mass calcd. for $C_{24}H_{23}F_2N_5O$, 435.48. m/z found, 436.2 [M+H]$^+$. $^1$H NMR (400 MHz, CDCl$_3$): 8.45 (dt, J=4.6, 1.5 Hz, 1H), 7.49-7.39 (m, 2H), 7.29-7.16 (m, 3H), 6.30 (s, 1H), 3.85-3.60 (m, 5H), 3.53-3.42 (m, 2H), 3.38 (dd, J=10.9, 4.4 Hz, 1H), 3.03-2.91 (m, 2H), 2.31 (s, 6H).

Example 376: (5-(4,6-Dimethylpyrimidin-2-yl)hexahydropyrrolo[3,4-c]pyrrol-2(1H)-yl)(3-fluoro-2-(oxazol-2-yl)phenyl)methanone

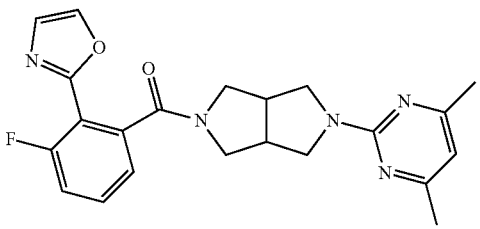 [SMILES: Cc1cc(C)nc(N2CC3CN(C(=O)c4cccc(F)c4-c4ncco4)CC3C2)n1]

The title compound was prepared in a manner analogous to Example 367 substituting 2-(tri-N-butylstannyl)oxazole for 2-tributylstannane pyridine. MS (ESI) mass calcd. for $C_{22}H_{22}FN_5O_2$, 407.45. m/z found, 408.2 [M+H]$^+$. $^1$H NMR (500 MHz, CDCl$_3$): 7.73 (d, J=0.6 Hz, 1H), 7.51-7.44 (m, 1H), 7.25-7.20 (m, 2H), 7.18 (dd, J=7.6, 0.9 Hz, 1H), 6.29 (s, 1H), 3.90-3.83 (m, 2H), 3.74-3.60 (m, 3H), 3.52 (dd, J=11.6, 4.4 Hz, 1H), 3.45 (dd, J=10.9, 7.5 Hz, 1H), 3.11 (dd, J=10.9, 5.4 Hz, 1H), 3.08-3.00 (m, 1H), 3.00-2.93 (m, 1H), 2.30 (s, 6H).

Example 377: 2-(5-Fluoro-4-methylpyrimidin-2-yl)-5-{[4-methoxy-2-(2H-1,2,3-triazol-2-yl)phenyl]carbonyl}octahydropyrrolo[3,4-c]pyrrole

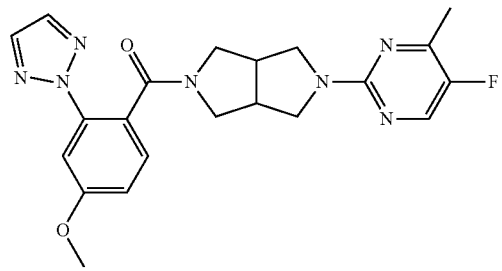 [SMILES: COc1ccc(C(=O)N2CC3CN(c4ncc(F)c(C)n4)CC3C2)c(-n2nccn2)c1]

(Hexahydropyrrolo[3,4-c]pyrrol-2(1H)-yl)(4-methoxy-2-(2H-1,2,3-triazol-2-yl)phenyl)methanone (Example 288—step B, 33 mg, 0.10 mmol), 2-chloro-5-fluoro-4-methylpyrimidine (Intermediate 55, 15 mg, 0.10 mmol) and DIPEA (54 µL, 0.3 mmol) in ACN (1 mL) were heated in a microwave reactor for 2 h at 200° C. Then the reaction mixture was concentrated and purified via prep HPLC (Agilent, basic) gave the title compound as a clear oil. MS (ESI) mass calcd. $C_{21}H_{22}FN_7O_2$, 423.45. m/z found 424.2 [M+H]$^+$. $^1$H NMR (CDCl$_3$): 8.06 (d, J=1.8 Hz, 1H), 7.74 (s, 2H), 7.50 (d, J=5.8 Hz, 1H), 7.33 (d, J=8.5 Hz, 1H), 6.95 (dd, J=8.5, 2.5 Hz, 1H), 3.93-3.76 (m, 5H), 3.71-3.59 (m, 2H), 3.53 (dd, J=11.4, 5.2 Hz, 1H), 3.44-3.30 (m, 2H), 3.07-2.87 (m, 3H), 2.37 (t, J=4.9 Hz, 3H).

Example 378: 2-(5-Chloro-4-methylpyrimidin-2-yl)-5-{[4-methoxy-2-(2H-1,2,3-triazol-2-yl)phenyl]carbonyl}octahydropyrrolo[3,4-c]pyrrole

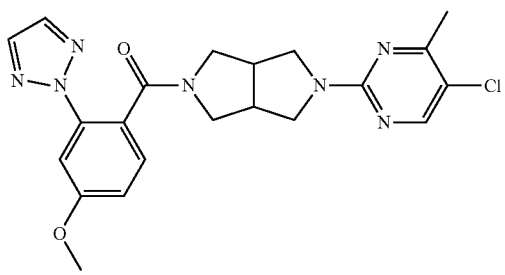 [SMILES: COc1ccc(C(=O)N2CC3CN(c4ncc(Cl)c(C)n4)CC3C2)c(-n2nccn2)c1]

The title compound was prepared in a manner analogous to Example 377, utilizing 2,5-dichloro-4-methylpyrimidine (Intermediate 65) in place of 2-chloro-5-fluoro-4-methylpyrimidine. MS (ESI) mass calcd. $C_{21}H_{22}ClN_7O_2$, 439.91. m/z found 440.2 [M+H]$^+$. $^1$H NMR (CDCl$_3$): 8.13 (s, 1H), 7.74 (s, 2H), 7.51 (d, J=10.9 Hz, 1H), 7.32 (d, J=6.8 Hz, 1H), 6.94

(dd, J=20.6, 10.3 Hz, 1H), 3.93-3.78 (m, 5H), 3.73-3.60 (m, 2H), 3.59-3.50 (m, 1H), 3.47-3.30 (m, 2H), 3.08-2.87 (m, 3H), 2.44 (s, J=11.6 Hz, 3H).

Example 379: 2-(5-Fluoro-4,6-dimethylpyrimidin-2-yl)-5-{[4-methoxy-2-(2H-1,2,3-triazol-2-yl)phenyl]carbonyl}octahydropyrrolo[3,4-c]pyrrole

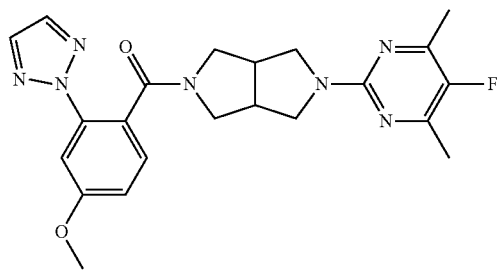 [SMILES: COc1ccc(C(=O)N2CC3CN(c4nc(C)c(F)c(C)n4)CC3C2)c(-n2nccn2)c1]

The title compound was prepared in a manner analogous to Example 377, utilizing 2-chloro-5-fluoro-4,6-dimethylpyrimidine (Intermediate 69) in place of 2-chloro-5-fluoro-4-methylpyrimidine. MS (ESI) mass calcd. $C_{22}H_{24}FN_7O_2$, 437.48; m/z found 438.2 [M+H]$^+$. $^1$H NMR (CDCl$_3$): 7.74 (s, 2H), 7.50 (d, J=2.5 Hz, 1H), 7.35-7.30 (m, 1H), 6.95 (dd, J=8.5, 2.5 Hz, 1H), 3.92-3.75 (m, 5H), 3.70-3.58 (m, 2H), 3.53 (dd, J=11.5, 5.2 Hz, 1H), 3.43-3.29 (m, 2H), 3.04-2.84 (m, 3H), 2.32 (d, J=6.7 Hz, 6H).

Example 380: 2-(4,5-Dimethylpyrimidin-2-yl)-5-{[4-methoxy-2-(2H-1,2,3-triazol-2-yl)phenyl]carbonyl}octahydropyrrolo[3,4-c]pyrrole

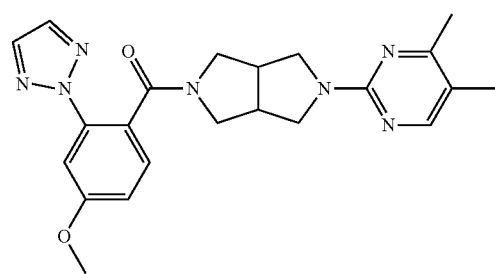 [SMILES: COc1ccc(C(=O)N2CC3CN(c4ncc(C)c(C)n4)CC3C2)c(-n2nccn2)c1]

The title compound was prepared in a manner analogous to Example 377, utilizing 2-chloro-4,5-dimethylpyrimidine (Intermediate 57) in place of 2-chloro-5-fluoro-4-methylpyrimidine. MS (ESI) mass calcd. $C_{22}H_{25}N_7O_2$, 419.49. m/z found 420.1 [M+H]$^+$. $^1$H NMR (CDCl$_3$): 7.99 (s, 1H), 7.74 (s, 2H), 7.49 (d, J=7.3 Hz, 1H), 7.32 (d, J=8.2 Hz, 1H), 6.94 (dd, J=8.5, 2.5 Hz, 1H), 3.92-3.78 (m, 5H), 3.72-3.61 (m, 2H), 3.54 (dd, J=11.4, 5.2 Hz, 1H), 3.42 (dd, J=11.4, 4.2 Hz, 1H), 3.34 (s, 1H), 3.07-2.85 (m, 3H), 2.32 (s, 3H), 2.09 (s, 3H).

Example 381: 2-[(3-Propoxypyridin-2-yl)carbonyl]-5-[5-(trifluoromethyl)pyridin-2-yl]octahydropyrrolo[3,4-c]pyrrole

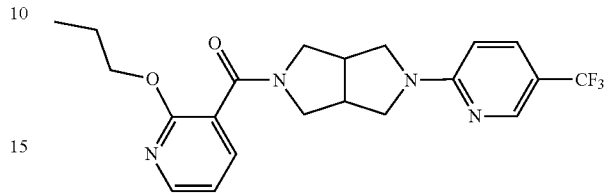

The title compound was prepared in a manner analogous to Example 15, utilizing 5-(trifluoromethyl)pyridin-2-yl]octahydropyrrolo[3,4-c]pyrrole and 2-propoxynicotinic acid. MS (ESI) mass calcd. $C_{21}H_{23}F_3N_4O_2$, 420.40. m/z found 421.1 [M+H]$^+$. $^1$H NMR (CD$_3$OD): 8.31 (s, 2H), 8.19 (dd, J=9.6, 2.3 Hz, 1H), 8.02 (s, 1H), 7.80 (s, 1H), 7.26 (d, J=9.4 Hz, 1H), 4.22-4.17 (m, 2H), 4.07-3.93 (m, 3H), 3.79-3.60 (m, 4H), 3.44-3.35 (m, 3H), 1.88-1.77 (m, 2H), 1.02 (t, J=7.4 Hz, 3H).

Example 382: 2-{4,6-Bis[($^2$H$_3$)methyl]($^2$H)pyrimidin-2-yl}-5-{[2-fluoro-6-(2H-1,2,3-triazol-2-yl)phenyl]carbonyl}octahydropyrrolo[3,4-c]pyrrole

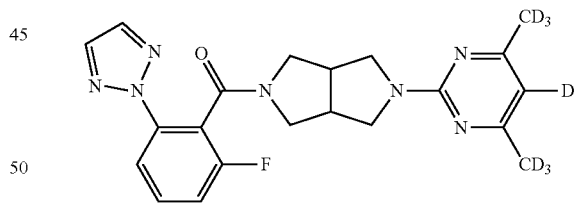

To a solution of Intermediate 91 (150 mg, 0.26 mmol) in DCM (2.6 mL) was added Intermediate 12 (55 mg, 0.26 mmol) followed by EDCl (76 mg, 0.4 mmol), HOBt (54 mg, 0.4 mmol) and TEA (0.15 mL, 1.06 mmol). The mixture was stirred for 14 h at room temperature and an additional amount of EDCl (76 mg, 0.4 mmol) and TEA (0.15 mL, 1.06 mmol) were added. After an additional 24 h at room temperature the mixture was concentrated in vacuo and chromatography (Hex to 100% EtOAc/Hex) afforded the desired product as a colorless foam (63 mg, 58%). MS (ESI): mass calculated for $C_{21}H_{15}D_7FN_7O$, 414.23. m/z found 415.2 [M+1]$^+$. 1 H NMR (500 MHz, CDCl$_3$): 7.87-7.80 (m, 2H), 7.71 (s, 1H), 7.51-7.44 (m, 1H), 7.18-7.10 (m, 1H), 4.01-3.50 (m, 7H), 3.32-3.21 (m, 1H), 3.12-2.94 (m, 2H).

Example 383: 2-{4,6-Bis[($^2$H$_3$)methyl]($^2$H)pyrimidin-2-yl}-5-{[3-fluoro-2-(3-methyl-1,2,4-oxadiazol-5-yl)phenyl]carbonyl}octahydropyrrolo[3,4-c]pyrrole

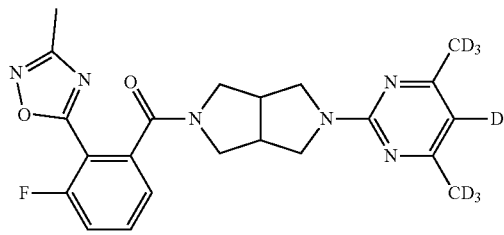 [SMILES: [2H]c1c(C([2H])([2H])[2H])nc(N2CC3CN(C(=O)c4cccc(F)c4-c4nc(C)no4)CC3C2)nc1C([2H])([2H])[2H]]

The title compound was prepared in a manner analogous to Example 382 substituting Intermediate 63 for Intermediate 12. MS (ESI): mass calculated for C$_{22}$H$_{16}$D$_7$FN$_6$O$_2$, 429.23. m/z found 430.2 [M+1]$^+$. 1 H NMR (500 MHz, CDCl$_3$): 7.63-7.57 (m, 1H), 7.31-7.27 (m, 1H), 7.24-7.21 (m, 1H), 3.94-3.87 (m, 2H), 3.78-3.62 (m, 3H), 3.58-3.48 (m, 2H), 3.22-3.15 (m, 1H), 3.12-2.96 (m, 2H), 2.43 (s, 3H).

Example 384: 2-{4,6-Bis[($^2$H$_3$)methyl]($^2$H)pyrimidin-2-yl}-5-{[4-methoxy-2-(2H-1,2,3-triazol-2-yl)phenyl]carbonyl}octahydropyrrolo[3,4-c]pyrrole

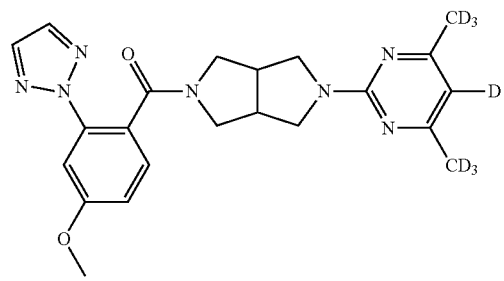 [SMILES: [2H]c1c(C([2H])([2H])[2H])nc(N2CC3CN(C(=O)c4ccc(OC)cc4-n4nccn4)CC3C2)nc1C([2H])([2H])[2H]]

The title compound was prepared in a manner analogous to Example 382 substituting Intermediate 54 for Intermediate 12. MS (ESI): mass calculated for C$_{22}$H$_{18}$D$_7$N$_7$O$_2$, 426.25. m/z found 427.3 [M+1]$^+$. $^1$H NMR (500 MHz, CDCl$_3$): 7.73 (s, 2H), 7.50 (d, J=2.5 Hz, 1H), 7.33 (d, J=8.5 Hz, 1H), 6.95 (dd, J=8.5 Hz, 2.5 Hz, 1H), 3.94-3.80 (m, 5H), 3.71-3.63 (m, 2H), 3.61-3.55 (m, 1H), 3.49-3.43 (m, 1H), 3.38-3.29 (m, 1H), 3.05-2.86 (m, 3H).

Example 385: 2-(5-Ethyl-4,6-dimethylpyrimidin-2-yl)-5-{[3-(2H-1,2,3-triazol-2-yl)pyridin-2-yl]carbonyl}octahydropyrrolo[3,4-c]pyrrole

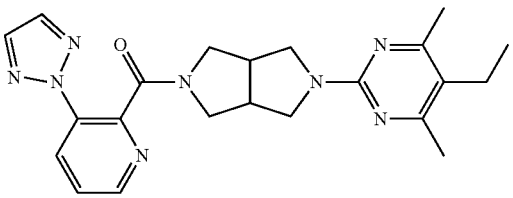 [SMILES: CCc1c(C)nc(N2CC3CN(C(=O)c4ncccc4-n4nccn4)CC3C2)nc1C]

The title compound was prepared in a manner analogous to Example 290 substituting Intermediate 68 for Intermediate 20 and Intermediate 67 for Intermediate 55. MS (ESI) mass calculated for C$_{22}$H$_{26}$N$_5$O, 418.22. m/z found, 419.2. 1H NMR (500 MHz, CDCl$_3$): 8.62 (dd, J=4.7 Hz, 1.3 Hz, 1H), 8.33 (dd, J=8.3 Hz, 1.4 Hz, 1H), 7.79 (s, 2H), 7.48 (dd, J=8.3 Hz, 4.7 Hz, 1H), 3.97-3.84 (m, 2H), 3.78-3.63 (m, 4H), 3.59-3.55 (m, 1H), 3.29-3.23 (m, 1H), 3.13-2.98 (m, 2H), 2.52 (q, J=7.5 Hz, 2H), 2.38 (s, 6H), 1.08 (t, J=7.5 Hz, 3H).

Example 386: 2-(4,6-Dimethylpyrimidin-2-yl)-5-{[3-(3-methyl-1,2,4-oxadiazol-5-yl)pyridin-2-yl]carbonyl}octahydropyrrolo[3,4-c]pyrrole

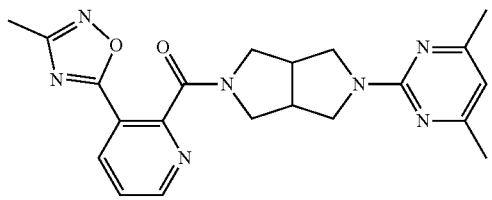

Step A: 2-(Methoxycarbonyl)nicotinic acid. 2,3-Pyridinecarboxylic anhydride (2.32 g, 15.55 mmol) was dissolved in MeOH (11 mL) and heated to reflux for 14 h. The mixture was concentrated in vacuo to a white solid that was a mixture of 2-(methoxycarbonyl)nicotinic acid and 3-(methoxycarbonyl)picolinic acid. This mixture was used as is. MS (ESI) mass calculated for C$_8$H$_7$NO$_4$, 181.04. m/z found, 181.9.

Step B: (E)-Methyl 3-((((1-aminoethylidene)amino)oxy)carbonyl) picolinate. To the product of Step A (250 mg, 1.38 mmol) in THF (7 mL) at 0° C. was added ethyl chloroformate (0.17 mL, 1.38 mmol) followed by TEA (0.29 mL, 2.07 mmol). After 10 min the ice bath was removed and after 2 h N-hydroxyacetamidine (102 mg, 1.38 mmol) was added in one portion. After 14 h at room temperature the mixture was concentrated in vacuo and chromatography (Hex to 100% EtOAc/Hex) afforded the desired (E)-methyl 3-((((1-aminoethylidene)amino)oxy)carbonyl)picolinate (200 mg, 70%) and (E)-methyl 2-((((1-aminoethylidene)amino)oxy)carbonyl)nicotinate (60 mg, 18%). MS (ESI) mass calculated for C$_{10}$H$_{11}$N$_3$O$_4$, 237.08. m/z found, 238.1. 1H NMR (500 MHz, CDCl$_3$): 8.79 (dd, J=4.8 Hz, 1.6 Hz, 1H), 8.28 (dd, J=7.9 Hz, 1.6 Hz, 1H), 7.58-7.51 (m, 1H), 3.99 (s, 3H), 2.04 (s, 3H).

Step C: 3-(3-Methyl-1,2,4-oxadiazol-5-yl)picolinic acid. To the product of Step B (180 mg, 0.76 mmol) was added t-BuOH (4 mL) followed by NaOAc (94 mg, 1.14 mmol) and the mixture was heated at 100° C. for 14 h. The mixture was allowed to cool to room temperature and filtered to afford 3-(3-methyl-1,2,4-oxadiazol-5-yl)picolinic acid (60 mg, 39%) as a white solid.

Step D: 2-(4,6-Dimethylpyrimidin-2-yl)-5-{[3-(3-methyl-1,2,4-oxadiazol-5-yl)pyridin-2-yl]carbonyl}octahydropyrrolo[3,4-c]pyrrole. To a solution of the product of Step C (60 mg, 0.30 mmol) in DCM (3 mL) was added Intermediate 23 (65 mg, 0.30 mmol) followed by EDCI (85 mg, 0.44 mmol), HOBt (60 mg, 0.44 mmol) and TEA (0.08 mL, 0.59 mmol). The mixture was stirred at room temperature for 14 h and then concentrated in vacuo. Chromatography (DCM to 8% 2 M NH$_3$ in MeOH/DCM) afforded the desired compound as a colorless foam (49 mg, 41%). MS (ESI) mass calculated for $C_{21}H_{23}N_7O_2$, 405.19. m/z found, 406.2. 1H NMR (500 MHz, CDCl$_3$): 8.82-8.75 (m, 1H), 8.42-8.36 (m, 1H), 7.52-7.47 (m, 1H), 6.31-6.26 (m, 1H), 4.02-3.90 (m, 2H), 3.86-3.79 (m, 1H), 3.76-3.69 (m, 2H), 3.66-3.54 (m, 2H), 3.24-3.18 (m, 1H), 3.14-2.99 (m, 2H), 2.48-2.42 (m, 3H), 2.33-2.24 (m, 6H).

Example 387: (5-(6,7-Difluoroquinoxalin-2-yl)hexahydropyrrolo[3,4-c]pyrrol-2(1H)-yl)(3-fluoro-2-(pyrimidin-2-yl)phenyl)methanone

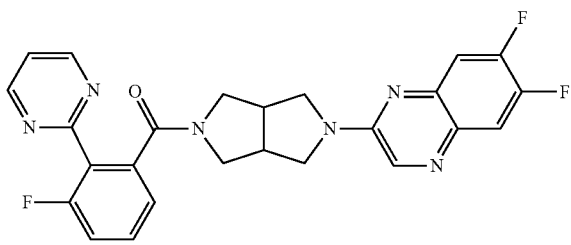 [SMILES: O=C(c1cccc(F)c1-c1ncccn1)N1CC2CN(c3cnc4cc(F)c(F)cc4n3)CC2C1]

The title compound was prepared in a manner analogous to Example 15, utilizing Intermediate 44 and Intermediate 50 in the last step MS (ESI): mass calculated for $C_{25}H_{19}F_3N_6O$, 476.16. m/z found 477.2 [M+H]$^+$. $^1$H NMR (500 MHz, CDCl$_3$) 8.74 (t, J=12.5, 2H), 8.25 (d, J=20.5, 1H), 7.65 (dd, J=10.5, 8.4, 1H), 7.52-7.40 (m, 2H), 7.26-7.12 (m, 3H), 3.97-3.74 (m, 3H), 3.73-3.52 (m, 4H), 3.38 (dd, J=11.1, 4.6, 1H), 3.22-3.02 (m, 2H).

Example 388: (5-(6,7-Difluoroquinoxalin-2-yl)hexahydropyrrolo[3,4-c]pyrrol-2(1H)-yl)(3-fluoro-2-(pyrimidin-2-yl)phenyl)methanone

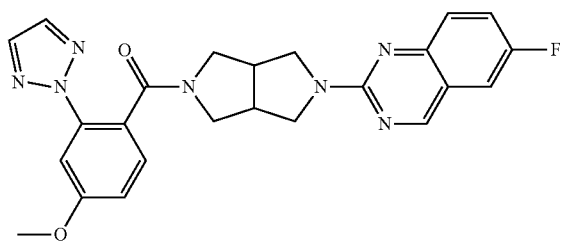 [SMILES: COc1ccc(C(=O)N2CC3CN(c4ncc5cc(F)ccc5n4)CC3C2)c(-n2nccn2)c1]

The title compound was prepared in a manner analogous to Example 15, utilizing Intermediate 43 and Intermediate 54 in the last step MS (ESI): mass calculated for $C_{24}H_{22}FN_7O_2$, 459.18. m/z found 460.2 [M+H]$^+$. $^1$H NMR (500 MHz, CDCl$_3$) 8.97 (s, 1H), 7.71 (s, 2H), 7.59 (dd, J=9.0, 4.7, 1H), 7.47 (ddd, J=17.7, 9.5, 2.6, 2H), 7.37-7.28 (m, 2H), 6.95 (dd, J=8.5, 2.5, 1H), 4.01-3.85 (m, 5H), 3.74 (ddt, J=17.0, 11.6, 8.8, 3H), 3.64-3.33 (m, 2H), 3.12-2.93 (m, 3H).

Example 389: (5-(6,7-Difluoroquinoxalin-2-yl)hexahydropyrrolo[3,4-c]pyrrol-2(1H)-yl)(4-methoxy-2-(2H-1,2,3-triazol-2-yl)phenyl)methanone

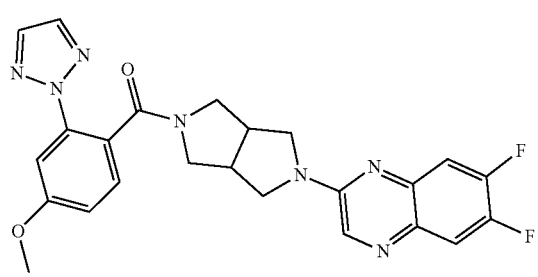 [SMILES: COc1ccc(C(=O)N2CC3CN(c4cnc5cc(F)c(F)cc5n4)CC3C2)c(-n2nccn2)c1]

The title compound was prepared in a manner analogous to Example 15, utilizing Intermediate 44 and Intermediate 54 in the last step MS (ESI): mass calculated for $C_{24}H_{21}F_2N_7O_2$, 477.17. m/z found 478.1 [M+H]$^+$. $^1$H NMR (500 MHz, CDCl$_3$) 8.26 (d, J=14.7, 1H), 7.71 (s, 2H), 7.63 (dd, J=10.6, 8.5, 1H), 7.49 (t, J=7.1, 1H), 7.41 (dd, J=11.4, 8.0, 1H), 7.33 (t, J=6.7, 1H), 6.95 (dt, J=8.4, 4.2, 1H), 3.99-3.85 (m, 5H), 3.83-3.69 (m, 2H), 3.70-3.57 (m, 1H), 3.52 (dd, J=11.0, 3.5, 1H), 3.44 (s, 1H), 3.19-3.09 (m, 1H), 3.09-2.97 (m, 2H).

Example 390: (5-(6-(Dimethylamino)pyrimidin-4-yl)hexahydropyrrolo[3,4-c]pyrrol-2(1H)-yl)(4-methoxy-2-(2H-1,2,3-triazol-2-yl)phenyl)methanone

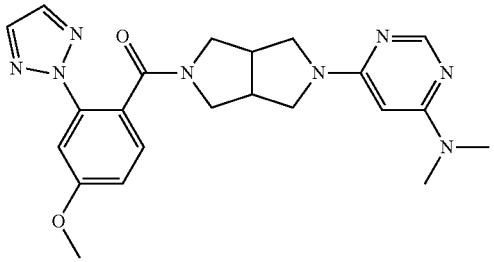 [SMILES: COc1ccc(C(=O)N2CC3CN(c4cc(N(C)C)ncn4)CC3C2)c(-n2nccn2)c1]

The title compound was prepared utilizing (hexahydropyrrolo[3,4-c]pyrrol-2(1H)-yl)(4-methoxy-2-(2H-1,2,3-triazol-2-yl)phenyl)methanone (Example 288, product from Step B) and 6-chloro-N,N-dimethylpyrimidin-4-amine. MS (ESI) mass calcd. $C_{22}H_{26}NO_2$, 434.49. m/z found 435.2 [M+H]$^+$.

Example 391: (5-(6-(Dimethylamino)-2-methylpyrimidin-4-yl)hexahydropyrrolo[3,4-c]pyrrol-2(1H)-yl)(4-methoxy-2-(2H-1,2,3-triazol-2-yl)phenyl)methanone

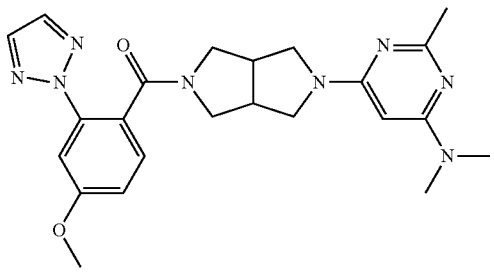 [SMILES: COc1ccc(C(=O)N2CC3CN(c4cc(N(C)C)nc(C)n4)CC3C2)c(-n2nccn2)c1]

The title compound was prepared utilizing (hexahydropyrrolo[3,4-c]pyrrol-2(1H)-yl)(4-methoxy-2-(2H-1,2,3-triazol-2-yl)phenyl)methanone (Example 288, product from Step B) and 6-chloro-N,N,2-trimethylpyrimidin-4-amine. MS (ESI) mass calcd. $C_{23}H_{26}N_8O_2$, 448.52. m/z found 449.2 [M+H]$^+$.

Prophetic examples 392-398 may be made using the procedures described previously.

Example 392: (5-(6-(Dimethylamino)-2-methylpyrimidin-4-yl)hexahydropyrrolo[3,4-c]pyrrol-2(1H)-yl)(3-fluoro-2-(pyrimidin-2-yl)phenyl)methanone

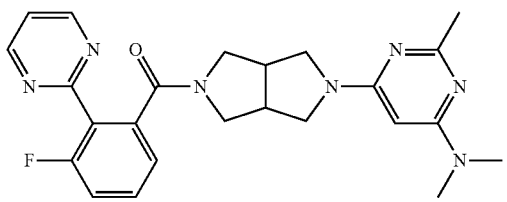

The title prophetic compound may be synthesized utilizing 6-chloro-N,N,2-trimethylpyrimidin-4-amine and MS (ESI) mass calcd. $C_{24}H_{26}FN_7O$, 447.51

Example 393: (5-(6-(Dimethylamino)pyrimidin-4-yl)hexahydropyrrolo[3,4-c]pyrrol-2(1H)-yl)(3-fluoro-2-(pyrimidin-2-yl)phenyl)methanone

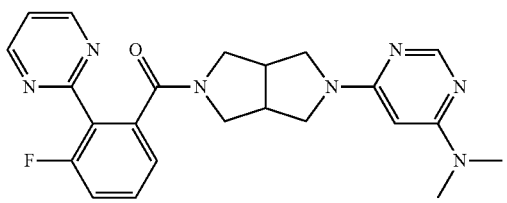 [SMILES: CN(C)c1cc(N2CC3CN(C(=O)c4cccc(F)c4-c4ncccn4)CC3C2)ncn1]

The title prophetic compound may be synthesized utilizing 3-fluoro-2-(pyrimidin-2-yl)benzoic acid and 6-chloro-N,N-dimethylpyrimidin-4-amine. MS (ESI) mass calcd. $C_{23}H_{24}FN_7O$, 433.48

Example 394: (3-Fluoro-2-(pyrimidin-2-yl)phenyl)(5-(5-fluoro-4,6-dimethylpyrimidin-2-yl)hexahydropyrrolo[3,4-c]pyrrol-2(1H)-yl)methanone

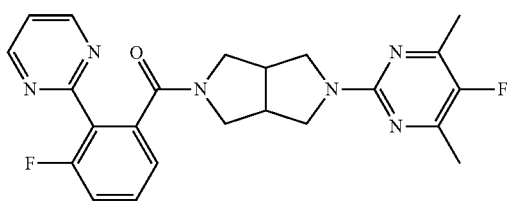 [SMILES: Cc1nc(N2CC3CN(C(=O)c4cccc(F)c4-c4ncccn4)CC3C2)nc(C)c1F]

The title prophetic compound may be synthesized utilizing 3-fluoro-2-(pyrimidin-2-yl)benzoic acid and 2-chloro-5-fluoro-4,6-dimethylpyrimidine. MS (ESI) mass calcd. $C_{23}H_{22}F_2N_6O$, 436.46

Example 395: (5-(5-Chloro-4,6-dimethylpyrimidin-2-yl)hexahydropyrrolo[3,4-c]pyrrol-2(1H)-yl)(3-fluoro-2-(pyrimidin-2-yl)phenyl) methanone

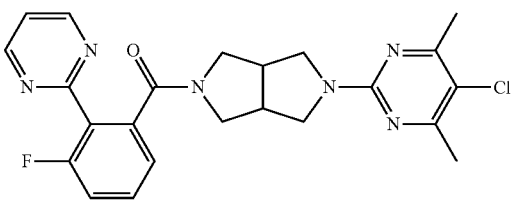 [SMILES: Cc1nc(N2CC3CN(C(=O)c4cccc(F)c4-c4ncccn4)CC3C2)nc(C)c1Cl]

The title prophetic compound may be synthesized utilizing 3-fluoro-2-(pyrimidin-2-yl)benzoic acid and 2,5-dichloro-4,6-dimethylpyrimidine. MS (ESI) mass calcd. $C_{23}H_{22}ClFN_6O_2$, 452.91

Example 396: (5-(5-Chloro-4-methylpyrimidin-2-yl)hexahydropyrrolo[3,4-c]pyrrol-2(1H)-yl)(3-fluoro-2-(pyrimidin-2-yl)phenyl)methanone

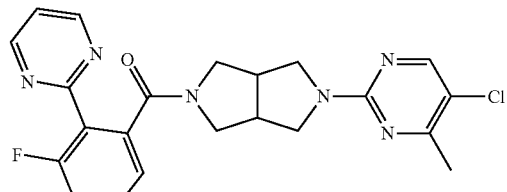

The title prophetic compound may be synthesized utilizing 3-fluoro-2-(pyrimidin-2-yl)benzoic acid and 2,5-dichloro-4-methylpyrimidine. MS (ESI) mass calcd. $C_{22}H_{20}ClFN_6O$, 438.89.

Example 397: (3-Fluoro-2-(pyrimidin-2-yl)phenyl)
(5-(5-fluoro-4-methylpyrimidin-2-yl)hexahydropyr-
rolo[3,4-c]pyrrol-2(1H)-yl)methanone

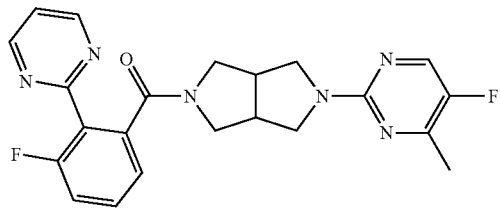 [SMILES: Cc1nc(N2CC3CN(C(=O)c4cccc(F)c4-c4ncccn4)CC3C2)ncc1F]

The title prophetic compound may be synthesized utilizing 3-fluoro-2-(pyrimidin-2-yl)benzoic acid and 2-chloro-5-fluoro-4-methylpyrimidine. MS (ESI) mass calcd. $C_{22}H_{20}F_2N_6O$, 434.49.

Example 398: (5-(4,5-Dimethylpyrimidin-2-yl)hexa-
hydropyrrolo[3,4-c]pyrrol-2(1H)-yl)(3-fluoro-2-
(pyrimidin-2-yl)phenyl)methanone

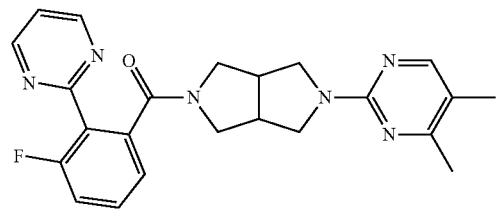 [SMILES: Cc1cnc(N2CC3CN(C(=O)c4cccc(F)c4-c4ncccn4)CC3C2)nc1C]

MS (ESI) mass calcd. $C_{23}H_{23}FN_6O$, 418.47

Example 399: (5-(4,6-Dimethylpyrimidin-2-yl)hexa-
hydropyrrolo[3,4-c]pyrrol-2(1H)-yl)(5-fluoro-2-(6-
methylpyridin-2-yl)phenyl)methanone

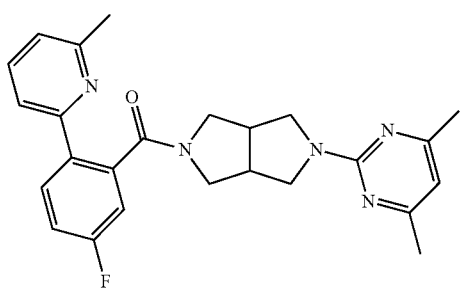 [SMILES: Cc1cccc(-c2ccc(F)cc2C(=O)N2CC3CN(c4nc(C)cc(C)n4)CC3C2)n1]

The title compound was prepared in a manner analogous to Example 248, substituting (5-(4,6-dimethylpyrimidin-2-yl)hexahydropyrrolo[3,4-c]pyrrol-2(1H)-yl)(5-fluoro-2-iodophenyl)methanone for (5-(4,6-dimethylpyrimidin-2-yl)hexahydropyrrolo[3,4-c]pyrrol-2(1H)-yl)(4-fluoro-2-iodophenyl)methanone and 6-methyl-2-(tributylstannyl)pyridine for 2-tributylstannane pyrimidine, with the addition of CuI. MS (ESI) mass calcd. for $C_{25}H_{26}FN_5O$, 431.21. m/z found 432.2 [M+1]$^+$.

Example 400: (5-(4,6-Dimethylpyrimidin-2-yl)hexa-
hydropyrrolo[3,4-c]pyrrol-2(1H)-yl)(5-fluoro-2-(4-
methylpyridin-2-yl)phenyl)methanone

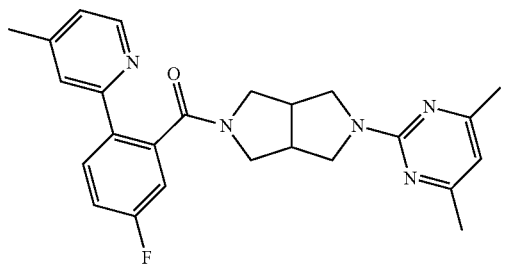

The title compound was prepared in a manner analogous to Example 399, substituting 4-methyl-2-(tributylstannyl)pyridine for 6-methyl-2-(tributylstannyl)pyridine. MS (ESI) mass calcd. for $C_{25}H_{26}FN_5O$, 431.21. m/z found 432.2 [M+1]$^+$.

Example 401: (5-(4,6-Dimethylpyrimidin-2-yl)hexa-
hydropyrrolo[3,4-c]pyrrol-2(1H)-yl)(5-fluoro-2-(5-
methylpyridin-2-yl)phenyl)methanone

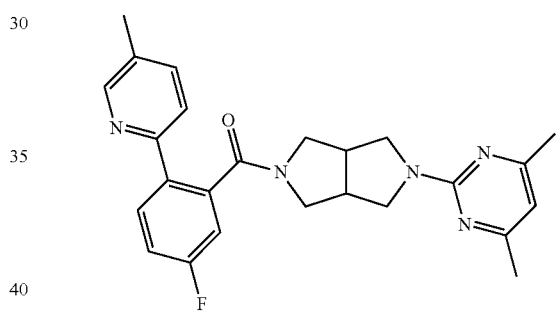

The title compound was prepared in a manner analogous to Example 399, substituting 5-methyl-2-(tributylstannyl)pyridine for 6-methyl-2-(tributylstannyl)pyridine. MS (ESI) mass calcd. for $C_{25}H_{26}FN_5O$, 431.21. m/z found 432.2 [M+1]$^+$.

Example 402: (5-(4,6-Dimethylpyrimidin-2-yl)hexa-
hydropyrrolo[3,4-c]pyrrol-2(1H)-yl)(5-fluoro-2-(3-
fluoropyridin-2-yl)phenyl)methanone

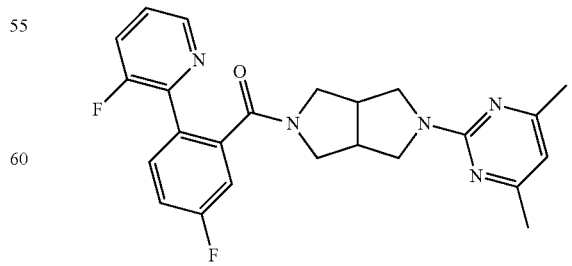

The title compound was prepared in a manner analogous to Example 399, substituting 3-fluoro-2-(tributylstannyl)

pyridine for 6-methyl-2-(tributylstannyl)pyridine. MS (ESI) mass calcd. for $C_{24}H_{23}F_2N_5O$, 435.19. m/z found 436.2 [M+1]$^+$.

Example 403: (5-(4,6-Dimethylpyrimidin-2-yl)hexahydropyrrolo[3,4-c]pyrrol-2(1H)-yl)(5-fluoro-2-(pyridin-2-yl)phenyl)methanone

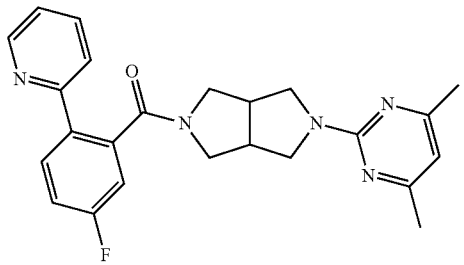 [SMILES: Cc1cc(C)nc(N2CC3CN(C(=O)c4cc(F)ccc4-c4ccccn4)CC3C2)n1]

The title compound was prepared in a manner analogous to Example 399, substituting 2-tri-N-butylstannylpyridine for 6-methyl-2-(tributylstannyl)pyridine. MS (ESI) mass calcd. for $C_{24}H_{24}FN_5O$, 417.20. m/z found 418.2 [M+1]$^+$.

Example 404: (5-(4,6-Dimethylpyrimidin-2-yl)hexahydropyrrolo[3,4-c]pyrrol-2(1H)-yl)(5-fluoro-2-(oxazol-2-yl)phenyl)methanone

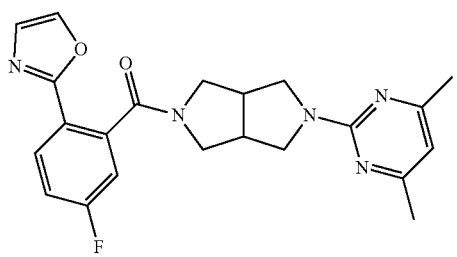 [SMILES: Cc1cc(C)nc(N2CC3CN(C(=O)c4cc(F)ccc4-c4ncco4)CC3C2)n1]

The title compound was prepared in a manner analogous to Example 399, substituting 2-(tri-N-butylstannyl)oxazole for 6-methyl-2-(tributylstannyl)pyridine. MS (ESI) mass calcd. for $C_{22}H_{22}FN_5O_2$, 407.18; $^1$H NMR (400 MHz, CDCl$_3$): 8.04 (dd, J=8.8, 5.3 Hz, 1H), 7.65 (s, 1H), 7.20-7.13 (m, 2H), 7.07 (dd, J=8.3, 2.6 Hz, 1H), 6.29 (s, 1H), 3.95 (dd, J=12.6, 7.6 Hz, 1H), 3.88 (dd, J=11.6, 7.6 Hz, 1H), 3.78-3.63 (m, 3H), 3.51-3.45 (m, 1H), 3.41 (dd, J=10.8, 7.5 Hz, 1H), 3.11-3.02 (m, 2H), 3.00-2.90 (m, 1H), 2.29 (s, 6H).

Prophetic examples 405-410 may be made using the procedures described previously.

Example 405: (5-(4,6-Dimethylpyrimidin-2-yl)hexahydropyrrolo[3,4-c]pyrrol-2(1H)-yl)(6-fluoro-2-(6-methylpyridin-2-yl)phenyl)methanone

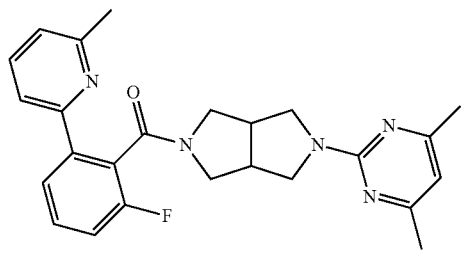 [SMILES: Cc1cccc(-c2cccc(F)c2C(=O)N2CC3CN(c4nc(C)cc(C)n4)CC3C2)n1]

MS (ESI) mass calcd. for $C_{25}H_{26}FN_5O$, 431.21;

Example 406: (5-(4,6-Dimethylpyrimidin-2-yl)hexahydropyrrolo[3,4-c]pyrrol-2(1H)-yl)(6-fluoro-2-(4-methylpyridin-2-yl)phenyl)methanone

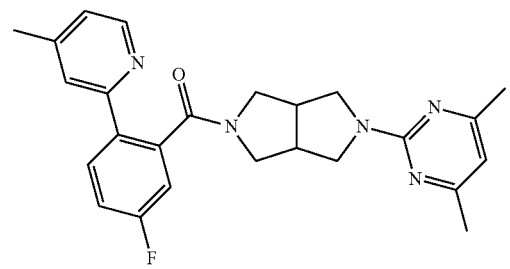

MS (ESI) mass calcd. for $C_{25}H_{26}FN_5O$, 431.21;

Example 407: (5-(4,6-Dimethylpyrimidin-2-yl)hexahydropyrrolo[3,4-c]pyrrol-2(1H)-yl)(6-fluoro-2-(5-methylpyridin-2-yl)phenyl)methanone

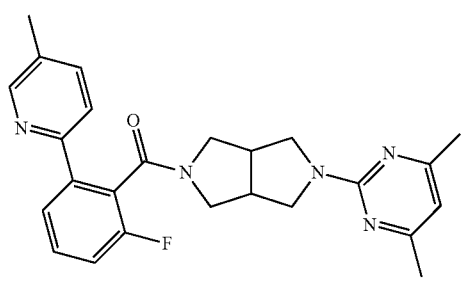 [SMILES: Cc1ccc(-c2cccc(F)c2C(=O)N2CC3CN(c4nc(C)cc(C)n4)CC3C2)nc1]

MS (ESI) mass calcd. for $C_{25}H_{26}FN_5O$, 431.21;

Example 408: (5-(4,6-Dimethylpyrimidin-2-yl)hexahydropyrrolo[3,4-c]pyrrol-2(1H)-yl)(6-fluoro-2-(3-fluoropyridin-2-yl)phenyl)methanone

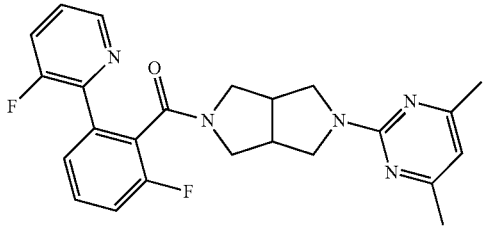 [SMILES: Cc1cc(C)nc(N2CC3CN(C(=O)c4c(F)cccc4-c4ncccc4F)CC3C2)n1]

MS (ESI) mass calcd. for $C_{24}H_{23}F_2N_5O$, 435.19;

Example 409: (5-(4,6-Dimethylpyrimidin-2-yl)hexahydropyrrolo[3,4-c]pyrrol-2(1H)-yl)(6-fluoro-2-(pyridin-2-yl)phenyl)methanone

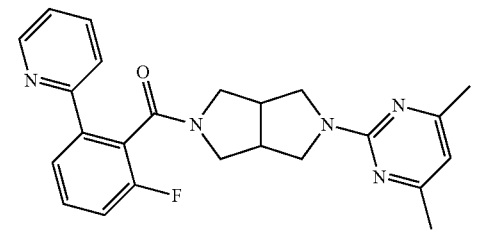 [SMILES: Cc1cc(C)nc(N2CC3CN(C(=O)c4c(F)cccc4-c4ccccn4)CC3C2)n1]

MS (ESI) mass calcd. for $C_{24}H_{24}FN_5O$, 417.20;

Example 410: (5-(4,6-Dimethylpyrimidin-2-yl)hexahydropyrrolo[3,4-c]pyrrol-2(1H)-yl)(6-fluoro-2-(oxazol-2-yl)phenyl)methanone

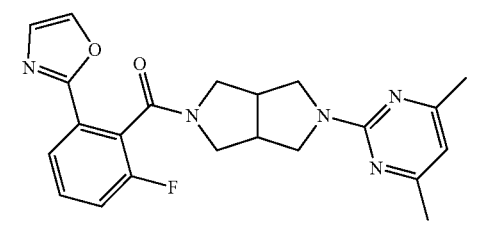 [SMILES: Cc1cc(C)nc(N2CC3CN(C(=O)c4c(F)cccc4-c4ncco4)CC3C2)n1]

MS (ESI) mass calcd. for $C_{22}H_{22}FN_5O_2$, 407.18;

Example 411: (3,6'-Dimethyl-[2,3'-bipyridin]-2'-yl)(5-(quinoxalin-2-yl)hexahydropyrrolo[3,4-c]pyrrol-2(1H)-yl)methanone

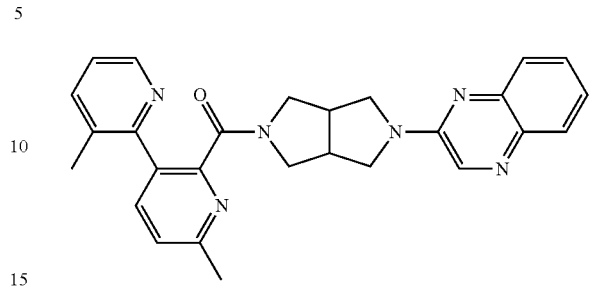

MS (ESI) mass calcd. For $C_{27}H_{26}N_6O$, 450.22.

Example 412: [5-(4,6-Dimethyl-pyrimidin-2-yl)-hexahydro-pyrrolo[3,4-c]pyrrol-2-yl]-(2-fluoro-6-[1,2,3]triazol-2-yl-phenyl)-methanone·HCl·1.65H$_2$O

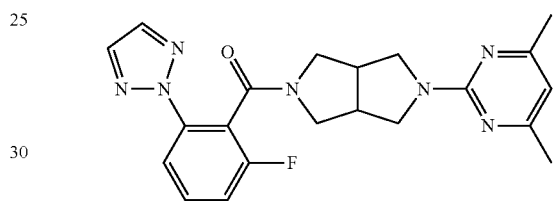

To a mixture of [5-(4,6-dimethyl-pyrimidin-2-yl)-hexahydro-pyrrolo[3,4-c]pyrrol-2-yl]-(2-fluoro-6-[1,2,3]triazol-2-yl-phenyl)-methanone (200 mg, 0.47 mmol) and IPA (1.5 mL) at room temperature was added 6 M HCl$_{(aq)}$ (83 µL, 0.5 mmol). The mixture was warmed to 75° C. and then slowly cooled to 35° C. The mixture was then seeded with solids formed previously [The seeds were formed as follows: To a mixture of [5-(4,6-dimethyl-pyrimidin-2-yl)-hexahydro-pyrrolo[3,4-c]pyrrol-2-yl]-(2-fluoro-6-[1,2,3]triazol-2-yl-phenyl)-methanone (200 mg, 0.47 mmol) and IPA (2 mL) at room temperature was added 5 M HCl in IPA (100 µL, 0.5 mmol). The mixture became homogeneous and was stirred at room temperature for 3 weeks. Solids formed when the solvent was allowed to evaporate under an ambient atmosphere.]. Once seeded, the mixture was cooled to room temperature and stirred for 3 days. The resulting solids were filtered and washed with IPA (0.5 mL). The solids were then dried in a vacuum oven for 2 h at 45° C. to give the title compound as a white solid (201.9 mg, 91%). $^1$H NMR (600 MHz, DMSO-d$_6$): 8.16 (s, 0.8H), 8.05 (s, 1.2H), 7.83 (d, J=8.2, 0.4H), 7.79 (d, J=8.2, 0.6H), 7.70-7.64 (m, 1H), 7.48-7.41 (m, 1H), 6.71 (bs, 1H), 4.0-3.4 (m, 7H), 3.25-2.96 (m, 3H), 2.48-2.33 (m, 6H). Anal. Calcd. For $C_{21}H_{22}FN_7O·HCl·1.65H_2O$ C, 53.25; H, 5.60; N, 20.70; Cl, 7.49. found C, 53.54; H, 5.64; N, 21.04; Cl, 7.10. Water calculated, 6.28%. found by Karl-Fisher titration, 6.32%.

Biological Assays

The in vitro affinity of the compounds for the human orexin-1 and orexin-2 receptors was determined by competitive radioligand binding using [$^3$H]SB SB674042 (1-(5-(2-fluoro-phenyl)-2-methyl-thiazol-4-yl)-1-((S)-2-(5-phenyl-(1,3,4)oxadiazol-2-ylmethyl)-pyrrolidin-1-yl)-methanone) (Langmead et al., *British Journal of Pharmacology* 2004, 141:340-346.) and [$^3$H]EMPA (N-ethyl-2[(6-methoxy-pyridin-3-yl)-(toluene-2-sulfonyl)-amino]-N-pyridin-3-ylmethyl acetamide) (Malherbe et al., *British Journal of Pharmacology*, 2009, 156(8), 1326-1341), respectively.

The in vitro functional antagonism of the compounds on the human orexin-1 and orexin-2 receptors was determined using fluorometric imaging plate reader (FLIPR) based calcium assays.

Human Orexin 1 Receptor Radioligand Binding Studies

Chinese ovary cells (CHO) stably expressing human orexin 1 receptor (Genebank accession number NM_001526) were grown to confluency in DMEM/F12 (Gibco, Cat #11039), 10% FBS, 1× Pen/Strep, 600 µg/mL G418 media on 150 cm² tissue culture plates, washed with 5 mM EDTA in PBS (HyClone Dulbecco's Phosphate Buffered Saline 1× with Calcium and Magnesium, Cat #SH30264.01, hereafter referred to simply as PBS) and scraped into 50 ml tubes. After centrifugation (2K×G, 10 min at 4° C.), the supernatant was aspirated and the pellets frozen and stored at −80° C. Cells were resuspended in PBS in the presence of 1 tablet of protease inhibitor cocktail (Roche, Cat. #11836145001) per 50 mL. Each cell pellet from a 15 cm plate was resuspended in 10 mL, stored on ice, and vortexed for 45 sec just prior to addition to the reactions. Competition binding experiments in 96 well polypropylene plates were performed using [³H]-SB674042 (Moravek Corporation, specific activity=35.3 Ci/mmol), diluted to a 10 nM concentration in PBS (4 nM final). Compounds were solubilized in 100% DMSO (Acros Organics, Cat. #61042-1000) and tested over a range of 7 concentrations (from 0.1 nM to 10 µM). The final concentration of DMSO in the reactions is equal to or less than 0.1%. Total and nonspecific binding was determined in the absence and presence of 10 µM (1-(6,8-difluoro-2-methylquinolin-4-yl)-3-[4-(dimethylamino)phenyl]urea, CAS Registry #288150-92-5). The total volume of each reaction is 200 µL (20 µL of diluted compounds, 80 µL of [³H]-SB674042 diluted in PBS and 100 µL of the cell suspension). Reactions were run for 60 min at room temperature and terminated by filtration through GF/C filter plates (PerkinElmer, Cat. #6005174) presoaked in 0.3% polyethylenimine using the cell harvester (PerkinElmer Filtermate). The plates were washed 3 times by aspirating 30 ml PBS through the plates. Plates were dried in 55° C. oven for 60 min, scintillation fluid was added, and the radioactivity was counted on a Topcount (Packard).

$IC_{50}$ values (i.e. concentration of unlabelled compound required to compete for 50% of specific binding to the radioligand) were calculated using the GraphPad Prism software (GraphPad Prism Software Inc., San Diego, Calif.) with a fit to a sigmoidal dose-response curve. Apparent $K_i$ values were calculated as $K_i=IC_{50}/(1+C/K_d)$, where C is concentration of radioligand and $K_d$=4 nM.

Human Orexin 2 Receptor Radioligand Binding Studies

HEK293 stably expressing human orexin-2 receptor (Genebank accession number NM_001526) were grown to confluency in DMEM/F12 (Gibco, Cat #11039), in DMEM, 10% FBS, 1× Pen/Strep, 1× NaPyruvate, 1×HEPES, 600 ug/ml G418 media on 150 cm² tissue culture plates, washed with 5 mM EDTA in PBS (HyClone Dulbecco's Phosphate Buffered Saline 1× with Calcium and Magnesium, Cat #SH30264.01, hereafter referred to simply as PBS) and scraped into 50 ml tubes. After centrifugation (2K×G, 10 min at 4° C.), the supernatant was aspirated and the pellets frozen and stored at −80° C. Cells were resuspended in PBS in the presence of 1 tablet of protease inhibitor cocktail (Roche, Cat. #11836145001) per 50 mL. Each cell pellet from a 15 cm plate was resuspended in 10 mL, stored on ice, and vortexed for 45 sec just prior to addition to the reactions. Competition binding experiments in 96 well polypropylene plates were performed using [³H]-EMPA (Moravek Corporation, specific activity=27 Ci/mmol), diluted to a 20 nM concentration in PBS (5 nM final concentration). Compounds were solubilized in 100% DMSO (Acros Organics, Cat. #61042-1000) and tested over a range of 7 concentrations (from 0.1 nM to 10 µM). The final concentration of DMSO in the reactions is equal to or less than 0.1%. Total and nonspecific binding was determined in the absence and presence of 10 µM (N-[2-(3,4-dimethoxyphenyl)ethyl]-N-methylnaphthalene-1-carboxamide, CAS Registry #1089563-88-1). The total volume of each reaction is 200 µL (20 µL of diluted compounds, 80 µL of [³H]-EMPA diluted in PBS and 100 µL of the cell suspension). Reactions were run for 60 min at room temperature and terminated by filtration through GF/C filter plates (PerkinElmer, Cat. #6005174) presoaked in 0.3% polyethylenimine using the cell harvester (PerkinElmer Filtermate). The plates were washed 3 times by aspirating 30 ml PBS through the plates. Plates were dried in 55° C. oven for 60 min, scintillation fluid was added, and the radioactivity was counted on a Topcount (Packard). $IC_{50}$ values (i.e. concentration of unlabelled compound required to compete for 50% of specific binding to the radioligand) were calculated using the GraphPad Prism software (GraphPad Prism Software Inc., San Diego, Calif.) with a fit to a sigmoidal dose-response curve. Apparent $K_i$ values were calculated as $K_i=IC_{50}/(1+C/K_d)$, where C is concentration of radioligand and $K_d$=2 nM.

Human Orexin 1 Receptor $Ca^{2+}$ Mobilization Assay

CHO cells stably transfected with the human orexin-1 receptor (Genebank accession number NM_001526) were grown to confluency in DMEM/F12, 10% FBS, 1× Na Pyruvate, 1× pen-strep, 400 µg/ml G418. Cells were seeded on to 96-well Packard viewplates at a density of 50,000 cells/well and incubated overnight at 37° C., 5% $CO_2$. The cells were dye-loaded with 4 µM $Ca^{2+}$ dye Fluo-3AM in serum-free DMEM/F-12 with 2.5 mM probenecid and incubated at 37° C., 5% $CO_2$ for one hour. Cells were pre-incubated with compounds (diluted in DMEM/F-12) for 30 minutes before agonist (orexin A, 10 nM) stimulation. Ligand-induced $Ca^{2+}$ release was measured using a Fluorometric Imaging Plate Reader (FLIPR, Molecular Devices, Sunnyvale, Calif.). Functional responses were measured as peak fluorescence intensity minus basal. The concentration of agonist that produced a half-maximal response is represented by the $EC_{50}$ value. Antagonistic potency values were converted to apparent $pK_B$ values using a modified Cheng-Prusoff correction. Apparent $pK_B$=−log $IC_{50}/1+$[conc agonist/$EC_{50}$]. Data are expressed as mean±S.E.M.

Human Orexin 2 Receptor $Ca^{2+}$ Mobilization Assay

PFSK cells endogenously expressing the human orexin 2 receptor were grown to confluency in RPMI1640, 10% FBS, 1× pen-strep. Cells were seeded on to 96-well Packard viewplates at a density of 50,000 cells/well and incubated overnight at 37° C., 5% $CO_2$. The cells were dye-loaded with 4 µM $Ca^{2+}$ dye Fluo-3AM in serum-free DMEM/F-12 with 2.5 mM probenecid and incubated at 37° C., 5% $CO_2$ for one hour. Cells were pre-incubated with compounds (diluted in DMEM/F-12) for 30 minutes before agonist (orexin B, 100 nM) stimulation. Ligand-induced $Ca^{2+}$ release was measured using a Fluorometric Imaging Plate Reader (FLIPR, Molecular Devices, Sunnyvale, Calif.). Functional responses were measured as peak fluorescence intensity minus basal. The concentration of agonist that produced a half-maximal response is represented by the EC$_{50}$ value. Antagonistic potency values were converted to apparent pK$_B$ values using a modified Cheng-Prusoff correction. Apparent pK$_B$=−log IC$_{50}$/1+[conc agonist/EC$_{50}$]. Data are expressed as mean S.E.M, the designation of NT means not tested.

| Ex # | OR 2 Ki (nM) | OR 2 Kb | OR 1 Ki (nM) |
|---|---|---|---|
| 1 | 37 | 10 | 100 |
| 2 | 33 | 16 | 189 |
| 3 | 42 | 14 | 127 |
| 4 | 65 | 32 | 447 |
| 5 | 14 | 5 | 63 |
| 6 | 67 | 25 | 154 |
| 7 | 42 | 13 | 139 |
| 8 | 542 | NT | 10000 |
| 9 | 101 | 56 | 691 |
| 10 | 170 | NT | 6708 |
| 11 | 1438 | NT | 10000 |
| 12 | 46 | 32 | 4378 |
| 13 | 89 | 79 | 10000 |
| 14 | 28 | 9 | 2780 |
| 15 | 13 | 2 | 1824 |
| 16 | 300 | NT | 10000 |
| 17 | 730 | NT | NT |
| 18 | 519 | NT | 1264 |
| 19 | 24 | 31 | 77 |
| 20 | 92 | 129 | 263 |
| 21 | 352 | NT | 1091 |
| 22 | 70 | 158 | 303 |
| 23 | 364 | NT | 677 |
| 24 | 415 | NT | 1544 |
| 25 | 110 | 99 | 162 |
| 26 | 8999 | NT | NT |
| 27 | 740 | NT | NT |
| 28 | 575 | NT | 1787 |
| 29 | 135 | NT | 1009 |
| 30 | 790 | NT | NT |
| 31 | 425 | NT | 651 |
| 32 | 47 | 32 | 8999 |
| 33 | 250 | NT | 488 |
| 34 | 79 | NT | 143 |
| 35 | 722 | NT | 4370 |
| 36 | 449 | NT | 1459 |
| 37 | 181 | NT | 137 |
| 38 | 515 | NT | 887 |
| 39 | 8999 | NT | 10000 |
| 40 | 559 | NT | 1433 |
| 41 | 356 | NT | 2512 |
| 42 | 616 | NT | 5000 |
| 43 | 7 | 10 | 422 |
| 44 | 142 | 63 | 10000 |
| 45 | 36 | 10 | 723 |
| 46 | 132 | NT | 294 |
| 47 | 38 | 32 | 1124 |
| 48 | 716 | NT | 10000 |
| 49 | 78 | 32 | 1692 |
| 50 | 215 | NT | 10000 |
| 51 | 644 | NT | 10000 |
| 52 | 65 | 50 | 8999 |
| 53 | 5000 | NT | 10000 |
| 54 | 769 | NT | 5000 |
| 55 | 744 | NT | 8999 |
| 56 | 80 | 40 | 800 |
| 57 | 167 | NT | 2323 |
| 58 | 227 | NT | 5000 |
| 59 | 778 | NT | 8999 |
| 60 | 173 | NT | 2644 |
| 61 | 224 | NT | 2272 |
| 62 | 42 | 40 | 689 |
| 63 | 44 | 20 | 2171 |
| 64 | 579 | NT | 10000 |
| 65 | 228 | NT | 207 |
| 66 | 449 | NT | 415 |
| 67 | 119 | NT | 10000 |
| 68 | 13 | 16 | 225 |
| 69 | 17 | 8 | 3082 |
| 70 | 52 | 40 | 2630 |
| 71 | 1000 | NT | 10000 |
| 72 | 318 | NT | 8999 |
| 73 | 7 | 5 | 69 |
| 74 | 14 | 10 | 4275 |
| 75 | 119 | 32 | 9226 |
| 76 | 237 | NT | 10000 |
| 77 | 25 | 16 | 547 |
| 78 | 550 | NT | 10000 |
| 79 | 480 | NT | 8999 |
| 80 | 314 | NT | 8999 |
| 81 | 1223 | NT | 6708 |
| 82 | 379 | NT | 10000 |
| 83 | 12 | 4 | 1766 |
| 84 | 53 | 25 | 1322 |
| 85 | 98 | 63 | 1162 |
| 86 | 256 | NT | 2603 |
| 87 | 509 | NT | 10000 |
| 88 | 75 | 25 | 8999 |
| 89 | 452 | NT | 10000 |
| 90 | 38 | 25 | 1734 |
| 91 | 541 | NT | 10000 |
| 92 | 766 | NT | 8999 |
| 93 | 64 | 40 | 5000 |
| 94 | 551 | NT | 847 |
| 95 | 215 | NT | 774 |
| 96 | 68 | 50 | 2429 |
| 97 | 25 | 16 | 354 |
| 98 | 28 | 10 | 275 |
| 99 | 15 | 16 | 180 |
| 100 | 238 | NT | 10000 |
| 101 | 48 | 25 | 4234 |
| 102 | 17 | 6 | 463 |
| 103 | 38 | 32 | 2280 |
| 104 | 42 | 25 | 3604 |
| 105 | 20 | 20 | 2451 |
| 106 | 26 | 20 | 212 |
| 107 | 9 | 2 | 868 |
| 108 | 57 | 25 | 80 |
| 109 | 46 | 25 | 65 |
| 110 | 52 | 32 | 350 |
| 111 | 28 | 16 | 153 |
| 112 | 95 | 20 | 122 |
| 113 | 50 | 63 | 90 |
| 114 | 224 | NT | 3061 |
| 115 | 5000 | NT | 10000 |
| 116 | 22 | 13 | 61 |
| 117 | 24 | 8 | 42 |
| 118 | 19 | 5 | 1843 |
| 119 | 51 | 13 | 3568 |
| 120 | 71 | 13 | 2867 |
| 121 | 15 | 13 | 42 |
| 122 | 865 | NT | 10000 |
| 123 | 44 | 79 | 10000 |
| 124 | 422 | NT | 10000 |
| 125 | 901 | NT | 8999 |
| 126 | 95 | 100 | 75 |
| 127 | 55 | 20 | 40 |
| 128 | 18 | 4 | 1250 |
| 129 | 111 | 100 | 1538 |
| 130 | 32 | 16 | 3438 |
| 131 | 75 | 79 | 131 |
| 132 | 125 | 79 | 7071 |
| 133 | 291 | NT | 390 |
| 134 | 102 | 12 | 2722 |
| 135 | 90 | 40 | 10000 |
| 136 | 104 | 50 | 8999 |
| 137 | 50 | 25 | 891 |
| 138 | 30 | 40 | 231 |
| 139 | 63 | 63 | 83 |
| 140 | 119 | NT | 1538 |
| 141 | 1034 | NT | 415 |
| 142 | 315 | NT | 2318 |
| 143 | 81 | 79 | 150 |
| 144 | 87 | 63 | 537 |
| 145 | 45 | 32 | 70 |
| 146 | 27 | 16 | 137 |
| 147 | 85 | 63 | 2946 |

| Ex # | OR 2 Ki (nM) | OR 2 Kb | OR 1 Ki (nM) |
|---|---|---|---|
| 148 | 129 | NT | 947 |
| 149 | 173 | NT | 142 |
| 150 | 92 | 40 | 5000 |
| 151 | 184 | NT | 504 |
| 152 | 125 | NT | 10000 |
| 153 | 75 | 40 | 2645 |
| 154 | 241 | NT | 9654 |
| 155 | 33 | 16 | 8999 |
| 156 | 39 | 16 | 5000 |
| 157 | 69 | 16 | 5000 |
| 158 | 55 | 8 | 5000 |
| 159 | 45 | 8 | 2447 |
| 160 | 58 | 20 | 659 |
| 161 | 46 | 7 | 5317 |
| 162 | 43 | 5 | 5000 |
| 163 | 380 | 501 | NT |
| 164 | 289 | 200 | 722 |
| 165 | 852 | NT | 4637 |
| 166 | 465 | NT | 752 |
| 167 | 411 | 631 | 2803 |
| 168 | 66 | 126 | 851 |
| 169 | 595 | NT | 1784 |
| 170 | 945 | NT | NT |
| 171 | 780 | NT | NT |
| 172 | 450 | NT | NT |
| 173 | 950 | NT | NT |
| 174 | 729 | NT | NT |
| 175 | 669 | NT | 1391 |
| 176 | 236 | 158 | 923 |
| 177 | 339 | NT | NT |
| 178 | 123 | 126 | 762 |
| 179 | 8999 | NT | NT |
| 180 | 2300 | NT | NT |
| 181 | 3564 | NT | 8999 |
| 182 | 2198 | NT | 10000 |
| 183 | 5000 | NT | NT |
| 184 | 1037 | NT | 879 |
| 185 | 8999 | NT | NT |
| 186 | 10000 | NT | NT |
| 187 | 2283 | NT | NT |
| 188 | 2608 | NT | NT |
| 189 | 1600 | NT | NT |
| 190 | 1300 | NT | 5000 |
| 191 | 2658 | NT | NT |
| 192 | 1015 | NT | NT |
| 193 | 1156 | NT | 814 |
| 194 | 10000 | NT | NT |
| 195 | 1099 | NT | 646 |
| 196 | 10000 | NT | NT |
| 197 | 1163 | NT | NT |
| 198 | 1312 | NT | 2012 |
| 199 | 3777 | NT | NT |
| 200 | 10000 | NT | 10000 |
| 201 | 1372 | NT | 10000 |
| 202 | 5000 | NT | 10000 |
| 203 | 5000 | NT | 10000 |
| 204 | 50 | 20 | 169 |
| 205 | 3189 | NT | 10000 |
| 206 | 1266 | NT | 10000 |
| 207 | 8999 | NT | 10000 |
| 208 | 2100 | NT | 10000 |
| 209 | 8999 | NT | 10000 |
| 210 | 3000 | NT | 10000 |
| 211 | 44 | 25 | 10000 |
| 212 | 33 | 32 | 5000 |
| 213 | 56 | 50 | 10000 |
| 214 | 1227 | NT | 1077 |
| 215 | 5000 | NT | 10000 |
| 219 | 404 | NT | 10000 |
| 220 | 500 | NT | 10000 |
| 221 | 2211 | NT | 10000 |
| 222 | 3621 | NT | 10000 |
| 223 | 340 | NT | 10000 |
| 224 | 635 | NT | 10000 |
| 225 | 423 | NT | 10000 |
| 226 | 836 | NT | 10000 |
| 227 | 1472 | NT | 10000 |
| 228 | 184 | NT | 10000 |
| 229 | 319 | NT | 10000 |
| 230 | 254 | NT | 10000 |
| 231 | 68 | 7 | 1613 |
| 232 | 52 | 7 | 2078 |
| 233 | 2100 | NT | 10000 |
| 234 | 10000 | NT | 10000 |
| 235 | 560 | NT | 10000 |
| 236 | 10000 | NT | 10000 |
| 237 | 69 | 18 | 8247 |
| 238 | 243 | NT | 10000 |
| 239 | 7 | 4 | 173 |
| 240 | 7 | 3 | 460 |
| 241 | 17 | 7 | 978 |
| 242 | 39 | 13 | 633 |
| 243 | 16 | 6 | 358 |
| 244 | 18 | 5 | 660 |
| 245 | 58 | 15 | 369 |
| 246 | 11 | 11 | 208 |
| 247 | 650 | NT | 4399 |
| 248 | 170 | NT | 1400 |
| 249 | NT | NT | NT |
| 250 | NT | NT | NT |
| 251 | 25 | 2 | 1470 |
| 252 | 10000 | NT | 10000 |
| 253 | 5000 | NT | 10000 |
| 254 | 2200 | NT | 10000 |
| 255 | 10000 | NT | 10000 |
| 256 | 10000 | NT | 10000 |
| 257 | 19 | 5 | 1843 |
| 258 | 46 | 25 | 927 |
| 259 | 8 | 3 | 335 |
| 260 | 90 | 16 | 8999 |
| 261 | 477 | NT | 10000 |
| 262 | 500 | NT | 10000 |
| 263 | 10000 | NT | 10000 |
| 264 | 10000 | NT | 10000 |
| 265 | 8999 | NT | 10000 |
| 266 | 127 | NT | 8999 |
| 267 | 10000 | NT | 10000 |
| 268 | 265 | NT | 10000 |
| 269 | 10000 | NT | 10000 |
| 270 | 1033 | NT | 10000 |
| 271 | 5000 | NT | 10000 |
| 272 | 33 | 7 | 598 |
| 273 | 5000 | NT | 10000 |
| 274 | 61 | 16 | 8999 |
| 275 | 487 | NT | 10000 |
| 276 | 2947 | NT | 10000 |
| 277 | 680 | NT | 10000 |
| 278 | 2274 | NT | 10000 |
| 279 | 23 | 10 | 1603 |
| 280 | 41 | 63 | 71 |
| 281 | 8999 | NT | 10000 |
| 282 | 858 | NT | 1436 |
| 283 | 10 | 2 | 978 |
| 284 | 8 | 2 | 587 |
| 285 | 1500 | NT | 10000 |
| 286 | 10000 | NT | 10000 |
| 287 | 1400 | NT | 10000 |
| 288 | 11 | 3 | 1606 |
| 289 | 1800 | NT | 10000 |
| 290 | 19 | 7 | 2150 |
| 291 | 266 | NT | 10000 |
| 292 | 428 | NT | 10000 |
| 293 | 19 | 79 | 2186 |
| 294 | 4 | 3 | 125 |
| 295 | 24 | 10 | 1100 |
| 296 | 9 | 3 | 235 |
| 297 | 6 | NT | 261 |
| 298 | 9 | NT | 160 |
| 299 | 15 | NT | 389 |
| 300 | 290 | NT | 2800 |
| 301 | 36 | 20 | 114 |
| 302 | 17 | 8 | 173 |

| Ex # | OR 2 Ki (nM) | OR 2 Kb | OR 1 Ki (nM) |
|---|---|---|---|
| 303 | 1700 | NT | 10000 |
| 304 | 3100 | NT | 10000 |
| 305 | 7 | NT | 775 |
| 306 | 39 | 13 | 2300 |
| 307 | 10000 | NT | 10000 |
| 308 | 26 | 5 | 1743 |
| 309 | 7 | 6 | 414 |
| 310 | 64 | 15 | 4996 |
| 311 | 7 | 3 | 312 |
| 312 | 79 | 11 | 3472 |
| 313 | 7 | 3 | 128 |
| 314 | 13 | 4 | 958 |
| 315 | 38 | 10 | 2837 |
| 316 | 10 | 8 | 306 |
| 317 | 3 | 3 | 34 |
| 318 | 5 | 3 | 89 |
| 319 | 18 | 7 | 537 |
| 320 | 4 | 2 | 54 |
| 321 | 29 | 10 | 816 |
| 322 | 10 | 5 | 378 |
| 323 | 25 | 4 | 2474 |
| 324 | 16 | 4 | 388 |
| 325 | 16 | 2 | 1662 |
| 326 | 8 | 4 | 151 |
| 327 | 103 | 50 | 5500 |
| 328 | 112 | 40 | 6345 |
| 329 | 10000 | NT | 10000 |
| 330 | 10000 | NT | 10000 |
| 331 | 81 | 32 | 3791 |
| 332 | 114 | 63 | 10000 |
| 333 | 10000 | NT | 10000 |
| 334 | 277 | NT | 10000 |
| 335 | 59 | NT | 3200 |
| 336 | 288 | NT | 10000 |
| 337 | 513 | NT | 10000 |
| 338 | 1604 | NT | 10000 |
| 339 | 8999 | NT | 10000 |
| 340 | 1521 | NT | 10000 |
| 341 | 10000 | NT | 10000 |
| 342 | 9486 | NT | 10000 |
| 343 | 36 | NT | 2900 |
| 344 | 1500 | NT | 10000 |
| 346 | 25 | NT | 1800 |
| 347 | 3100 | NT | 10000 |
| 349 | 10000 | NT | 10000 |
| 351 | 1200 | NT | 10000 |
| 352 | 10000 | NT | 3111 |
| 353 | 10000 | NT | 10000 |
| 355 | 10000 | NT | 10000 |
| 356 | 10000 | NT | 10000 |
| 358 | 230 | NT | 10000 |
| 359 | 180 | NT | 10000 |
| 361 | 4399 | NT | 10000 |
| 362 | 1800 | NT | 2700 |
| 366 | 23 | NT | 1900 |
| 367 | 15 | 3 | 839 |
| 369 | 19 | NT | 1200 |
| 370 | 84 | 7 | 7874 |
| 371 | 3400 | NT | 10000 |
| 372 | 109 | NT | 8000 |
| 373 | 42 | 5 | 10000 |
| 374 | 73 | 12 | 1049 |
| 375 | 21 | 4 | 3186 |
| 376 | 17 | NT | 1591 |
| 377 | 17 | 2 | 2186 |
| 378 | 10 | 2 | 508 |
| 379 | 9 | 5 | 202 |
| 380 | 15 | 5 | 2039 |
| 381 | 10000 | NT | 10000 |
| 382 | 14 | 3 | 854 |
| 383 | 13 | 4 | 920 |
| 384 | 10 | 5 | 1385 |
| 385 | 42 | 8 | 3688 |
| 386 | 940 | NT | 10000 |
| 387 | 16 | 9 | 437 |
| 388 | 30 | NT | 694 |
| 389 | 22 | 14 | 492 |
| 390 | 190 | NT | 10000 |
| 391 | 28 | NT | 1200 |
| 399 | 570 | NT | 10000 |
| 400 | 510 | NT | 10000 |
| 401 | 830 | NT | 10000 |
| 402 | 120 | NT | 10000 |
| 403 | 180 | NT | 10000 |
| 404 | 19 | NT | 1200 |

Powder X-Ray Diffraction

[5-(4,6-Dimethyl-pyrimidin-2-yl)-hexahydro-pyrrolo[3,4-c]pyrrol-2-yl]-(2-fluoro-6-[1,2,3]triazol-2-yl-phenyl)-methanone Powder X-Ray Diffraction of the reference compound was performed on a Philips X'PERT PRO with X'Celerator Cu detector equipped with a real time multiple strips X-ray detection technology to obtain the X-ray powder patterns in FIG. 1. The samples were scanned from 4° to 40° 2θ, at a step size 0.0167° 2θ and a time per step of 29.8450 seconds. The tube voltage and current were 45 kV and 40 mA, respectively. The samples were placed onto zero background holders and analyzed on a spinning stage.

What is claimed is:

1. A process for preparing a compound of Formula (I):

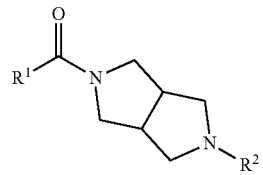

wherein:
$R^1$ is selected from the group consisting of:
A) phenyl substituted or unsubstituted with one or two $R^a$ members, and substituted in the ortho position with $R^b$, wherein:
$R^a$ is independently selected from the group consisting of —H, halo, —$C_{1-4}$alkyl, —$C_{1-4}$alkoxy, and —$NO_2$, wherein two adjacent $R^a$ members may come together to form a six membered aromatic ring;
$R^b$ is a member selected from the group consisting of:
a) halo, —$C_{1-4}$alkoxy, —$C_{1-4}$alkyl, —$CF_3$, —$OCF_3$, or —CN;
b) 5-membered heteroaryl ring containing one oxygen or one sulfur members;
c) 5-6 membered heteroaryl ring containing one, two or three nitrogen members, optionally containing one oxygen member, substituted or unsubstituted with halo or —$C_{1-4}$alkyl; and
d) phenyl substituted or unsubstituted with halo, —$CH_3$, or —$CF_3$;
B) pyridine substituted or unsubstituted with one or two $R^c$ members and substituted with $R^d$, wherein $R^d$ is positioned adjacent to the point of attachment by $R^1$;
$R^c$ is $C_{1-4}$alkyl;

$R^d$ is a member selected from the group consisting of:
a) 5-6 membered heteroaryl ring selected from the group consisting of 1H-1,2,3-triazol-1-yl, 2H-1,2,3-triazol-2-yl, 1H-pyrazol-5-yl, 3-methyl-1,2,4-oxadiazol-5-yl, pyridinyl, 3-methyl-pyridin-2-yl, 1-(tetrahydro-2H-pyran-2-yl)-1H-pyrazol-5-yl), and pyrimidin-2-yl;
b) —$CF_3$, —Br, and —$C_{1-4}$alkoxy;
C) 5-membered heteroaryl ring selected from the group consisting of 2-methyl-1,3-thiazol-yl, 1H-pyrazol-5-yl, oxazole, isoxazolyl, thiophen-2-yl, and furan-2-yl, each substituted with phenyl substituted or unsubstituted with —F; and
D) 5-13 membered aryl or heteroaryl ring selected from the group consisting of 3-methylfuran-2-yl, 9H-fluorene, quinoline, cinnoline, 3-(1H-pyrrol-1-yl)thiophen-2-yl, 8-[1,2,3]-triazol-2-yl-naphthalen-1-yl, 2,3-dihydro-1,4-benzodioxin-5-yl, 1H-indol-7-yl, 4-fluoronaphthalen-1-yl, and naphthalen-1-yl;

$R^2$ is selected from the group consisting of:
A) 6-membered heteroaryl ring containing two nitrogen members substituted with one or more members independently selected from the group consisting of halo, —$C_{1-4}$alkyl, —$CD_3$, -D, —$C_{1-4}$alkoxy, cyclopropyl, morpholin-2-yl, —$CO_2C_{1-4}$alkyl, —$CO_2H$, —$CH_2OH$, —$C(O)N(C_{1-4}alkyl)_2$, —$CF_3$, —CN, —OH, —$NO_2$, —$N(C_{1-4}alkyl)_2$, phenyl, furan-2-yl, thiophen-2-yl, 1H-pyrazol-4-yl, and pyrrolidin-1-yl;
B) pyridine substituted with one or two members independently selected from the group consisting of halo, —$C_{1-4}$alkyl, —$C_{1-4}$alkoxy, and —$CF_3$;
C) 9-membered heteroaryl ring selected from the group consisting of benzooxazol-2-yl, 6-fluoro-1,3-benzothiazole, 1,3-benzothiazole, 6-methoxy-1,3-benzothiazole, 6-methyl-1,3-benzothiazole, 6-chloro-benzothiazol-2-yl, and 4-methyl-6,7-dihydro-5H-cyclopenta[d]pyrimidine;
D) 10-membered heteroaryl ring selected from the group consisting of quinoxalin-2-yl, 3-methylquinoxalin-2-yl, 6,7-difluoroquinoxalin-2-yl, 3-(trifluoromethyl)quinoxaline, quinoline, 4-methylquinoline, and 6-fluoroquinazolin-2-yl; and
E) 4-methyl-1,3,5-triazin-2-yl or 2-methylpyrimidin-4(3H)-one, the process comprising reacting a compound of Formula (I-a):

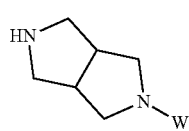

(I-a)

wherein, W is benzyl or BOC, with $R^1CO_2H$ or $R^1COCl$ to form a compound of Formula (I-b):

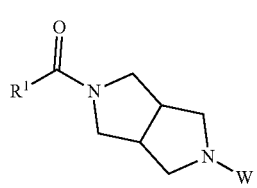

(I-b)

deprotecting the compound of Formula (I-b) to form a compound of formula (I-c):

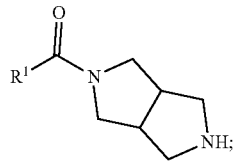

(I-c)

and
reacting the compound of Formula (I-c) with $R^2Cl$ to form the compound of Formula (I).

2. The process of claim 1, wherein the compound of Formula (I-a) is reacted with $R^1CO_2H$ under amide formation conditions.

3. The process of claim 2, wherein the amide formation conditions comprise a dehydrating agent and base.

4. The process of claim 3, wherein the dehydrating agent is HOBt/EDAC, CDI, HATU, or HOAT.

5. The process of claim 3, wherein the base is DIPEA or TEA.

6. The process of claim 3, wherein the dehydrating agent is HATU and the base is DIPEA.

7. The process of claim 1, further comprising converting $R^1CO_2H$ to $R^1COCl$.

8. The process of claim 7, comprising reacting $R^1CO_2H$ with thionyl chloride.

9. The process of claim 1, wherein the deprotecting is performed using HCl, TFA, or p-toluenesulfonic acid.

10. The process of claim 1, further comprising reacting a compound of Formula (I-d), wherein W is Boc, with hydrogen gas in the presence of a catalyst to form the compound of Formula (I-b):

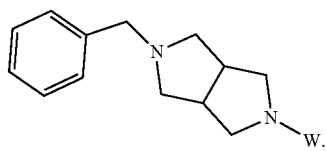

(I-d)

11. The process of claim 10, wherein the catalyst is palladium on carbon.

12. The process of claim 10, further comprising reacting 2-benzyl-octahydro-pyrrolo[3,4-c]pyrrole with di-tert-butyl-dicarbonate.

13. The process of claim 1, wherein the reaction with $R^2Cl$ is performed in the presence of a tertiary organic or inorganic base.

14. The process of claim 13, wherein the base is $Cs_2CO_3$, $Na_2CO_3$, or TEA.

15. A process for preparing a compound of Formula (I):

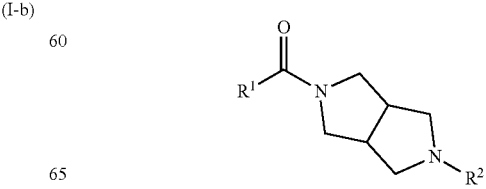

(I)

wherein:
R¹ is selected from the group consisting of:
A) phenyl substituted or unsubstituted with one or two $R^a$ members, and substituted in the ortho position with $R^b$, wherein:
  $R^a$ is independently selected from the group consisting of —H, halo, —C$_{1-4}$alkyl, —C$_{1-4}$alkoxy, and —NO$_2$, wherein two adjacent $R^a$ members may come together to form a six membered aromatic ring;
  $R^b$ is a member selected from the group consisting of:
    a) halo, —C$_{1-4}$alkoxy, —C$_{1-4}$alkyl, —CF$_3$, —OCF$_3$, or —CN;
    b) 5-membered heteroaryl ring containing one oxygen or one sulfur members;
    c) 5-6 membered heteroaryl ring containing one, two or three nitrogen members, optionally containing one oxygen member, substituted or unsubstituted with halo or —C$_{1-4}$alkyl; and
    d) phenyl substituted or unsubstituted with halo, —CH$_3$, or —CF$_3$;
B) pyridine substituted or unsubstituted with one or two $R^c$ members and substituted with $R^d$, wherein $R^d$ is positioned adjacent to the point of attachment by R¹;
  $R^c$ is C$_{1-4}$alkyl;
  $R^d$ is a member selected from the group consisting of:
    a) 5-6 membered heteroaryl ring selected from the group consisting of 1H-1,2,3-triazol-1-yl, 2H-1,2,3-triazol-2-yl, 1H-pyrazol-5-yl, 3-methyl-1,2,4-oxadiazol-5-yl, pyridinyl, 3-methyl-pyridin-2-yl, 1-(tetrahydro-2H-pyran-2-yl)-1H-pyrazol-5-yl), and pyrimidin-2-yl; and
    b) —CF$_3$, —Br, and —C$_{1-4}$alkoxy;
C) 5-membered heteroaryl ring selected from the group consisting of 2-methyl-1,3-thiazol-yl, 1H-pyrazol-5-yl, oxazole, isoxazolyl, thiophen-2-yl, and furan-2-yl, each substituted with phenyl substituted or unsubstituted with —F; and
D) 5-13 membered aryl or heteroaryl ring selected from the group consisting of 3-methylfuran-2-yl, 9H-fluorene, quinoline, cinnoline, 3-(1H-pyrrol-1-yl)thiophen-2-yl, 8-[1,2,3]-triazol-2-yl-naphthalen-1-yl, 2,3-dihydro-1,4-benzodioxin-5-yl, 1H-indol-7-yl, 4-fluoronaphthalen-1-yl, and naphthalen-1-yl;
R² is selected from the group consisting of:
A) 6-membered heteroaryl ring containing two nitrogen members substituted with one or more members independently selected from the group consisting of halo, —C$_{1-4}$alkyl, —CD$_3$, -D, —C$_{1-4}$alkoxy, cyclopropyl, morpholin-2-yl, —CO$_2$C$_{1-4}$alkyl, —CO$_2$H, —CH$_2$OH, —C(O)N(C$_{1-4}$alkyl)$_2$, —CF$_3$, —CN, —OH, —NO$_2$, —N(C$_{1-4}$alkyl)$_2$, phenyl, furan-2-yl, thiophen-2-yl, 1H-pyrazol-4-yl, and pyrrolidin-1-yl;
B) pyridine substituted with one or two members independently selected from the group consisting of halo, —C$_{1-4}$alkyl, —C$_{1-4}$alkoxy, and —CF$_3$;
C) 9-membered heteroaryl ring selected from the group consisting of benzooxazol-2-yl, 6-fluoro-1,3-benzothiazole, 1,3-benzothiazole, 6-methoxy-1,3-benzothiazole, 6-methyl-1,3-benzothiazole, 6-chloro-benzothiazol-2-yl, and 4-methyl-6,7-dihydro-5H-cyclopenta[d]pyrimidine;
D) 10-membered heteroaryl ring selected from the group consisting of quinoxalin-2-yl, 3-methylquinoxalin-2-yl, 6,7-difluoroquinoxalin-2-yl, 3-(trifluoromethyl)quinoxaline, quinoline, 4-methylquinoline, and 6-fluoroquinazolin-2-yl; and
E) 4-methyl-1,3,5-triazin-2-yl or 2-methylpyrimidin-4(3H)-one,
  the process comprising reacting a compound of Formula (I-a):

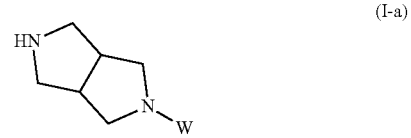

(I-a)

wherein W is benzyl or BOC, with R²Cl to form a compound of Formula (I-e):

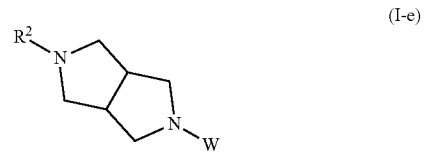

(I-e)

deprotecting the compound of Formula (I-e) to form a compound of Formula (I-f):

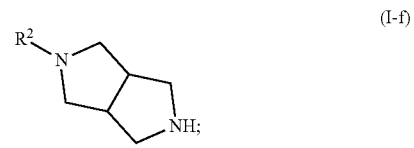

(I-f)

and
reacting the compound of Formula (I-f) with R¹CO$_2$H or R¹COCl to form the compound of Formula (I).

16. The process of claim 15, wherein the reaction with R²Cl is performed in the presence of a tertiary organic or inorganic base.

17. The process of claim 16, wherein the tertiary organic or inorganic base is Cs$_2$CO$_3$, Na$_2$CO$_3$, or TEA.

18. The process of claim 15, further comprising converting R¹CO$_2$H to R¹COCl.

19. The process of claim 18, comprising reacting R¹CO$_2$H with thionyl chloride.

20. The process of claim 15, wherein when W is BOC, the deprotecting is performed using HCl, TFA, or p-toluenesulfonic acid.

21. The process of claim 15, wherein when W is benzyl, the deprotecting is performed using hydrogen gas in the presence of a catalyst.

22. The process of claim 21, wherein the catalyst is palladium on carbon.

23. A process for preparing a compound of Formula (I):

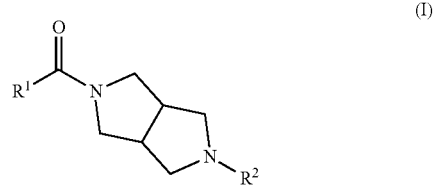

(I)

wherein:
R¹ is selected from the group consisting of:
A) phenyl substituted or unsubstituted with one or two R$^a$ members, and substituted in the ortho position with R$^b$, wherein:
R$^a$ is independently selected from the group consisting of —H, halo, —C$_{1-4}$alkyl, —C$_{1-4}$alkoxy, and —NO$_2$, wherein two adjacent R$^a$ members may come together to form a six membered aromatic ring;
R$^b$ is a member selected from the group consisting of:
a) halo, —C$_{1-4}$alkoxy, —C$_{1-4}$alkyl, —CF$_3$, —OCF$_3$, or —CN;
b) 5-membered heteroaryl ring containing one oxygen or one sulfur members;
c) 5-6 membered heteroaryl ring containing one, two or three nitrogen members, optionally containing one oxygen member, substituted or unsubstituted with halo or —C$_{1-4}$alkyl; and
d) phenyl substituted or unsubstituted with halo, —CH$_3$, or —CF$_3$;
B) pyridine substituted or unsubstituted with one or two R$^c$ members and substituted with R$^d$, wherein R$^d$ is positioned adjacent to the point of attachment by R¹;
R$^c$ is C$_{1-4}$alkyl;
R$^d$ is a member selected from the group consisting of:
a) 5-6 membered heteroaryl ring selected from the group consisting of 1H-1,2,3-triazol-1-yl, 2H-1,2,3-triazol-2-yl, 1H-pyrazol-5-yl, 3-methyl-1,2,4-oxadiazol-5-yl, pyridinyl, 3-methyl-pyridin-2-yl, 1-(tetrahydro-2H-pyran-2-yl)-1H-pyrazol-5-yl), and pyrimidin-2-yl; and
b) —CF$_3$, —Br, and —C$_{1-4}$alkoxy;
C) 5-membered heteroaryl ring selected from the group consisting of 2-methyl-1,3-thiazol-yl, 1H-pyrazol-5-yl, oxazole, isoxazolyl, thiophen-2-yl, and furan-2-yl, each substituted with phenyl substituted or unsubstituted with —F; and
D) 5-13 membered aryl or heteroaryl ring selected from the group consisting of 3-methylfuran-2-yl, 9H-fluorene, quinoline, cinnoline, 3-(1H-pyrrol-1-yl)thiophen-2-yl, 8-[1,2,3]-triazol-2-yl-naphthalen-1-yl, 2,3-dihydro-1,4-benzodioxin-5-yl, 1H-indol-7-yl, 4-fluoronaphthalen-1-yl, and naphthalen-1-yl;
R² is selected from the group consisting of:
A) 6-membered heteroaryl ring containing two nitrogen members substituted with one or more members independently selected from the group consisting of halo, —C$_{1-4}$alkyl, —CD$_3$, -D, —C$_{1-4}$alkoxy, cyclopropyl, morpholin-2-yl, —CO$_2$C$_{1-4}$alkyl, —CO$_2$H, —CH$_2$OH, —C(O)N(C$_{1-4}$alkyl)$_2$, —CF$_3$, —CN, —OH, —NO$_2$, —N(C$_{1-4}$alkyl)$_2$, phenyl, furan-2-yl, thiophen-2-yl, 1H-pyrazol-4-yl, and pyrrolidin-1-yl;
B) pyridine substituted with one or two members independently selected from the group consisting of halo, —C$_{1-4}$alkyl, —C$_{1-4}$alkoxy, and —CF$_3$;
C) 9-membered heteroaryl ring selected from the group consisting of benzooxazol-2-yl, 6-fluoro-1,3-benzothiazole, 1,3-benzothiazole, 6-methoxy-1,3-benzothiazole, 6-methyl-1,3-benzothiazole, 6-chloro-benzothiazol-2-yl, and 4-methyl-6,7-dihydro-5H-cyclopenta[d]pyrimidine;
D) 10-membered heteroaryl ring selected from the group consisting of quinoxalin-2-yl, 3-methylquinoxalin-2-yl, 6,7-difluoroquinoxalin-2-yl, 3-(trifluoromethyl)quinoxaline, quinoline, 4-methylquinoline, and 6-fluoroquinazolin-2-yl; and
E) 4-methyl-1,3,5-triazin-2-yl or 2-methylpyrimidin-4(3H)-one,
the process comprising reacting a compound of Formula (I-f) with R¹CO$_2$H or R¹COCl to form the compound of Formula (I):

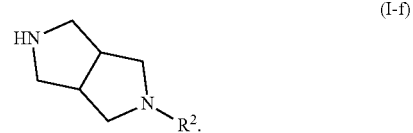

(I-f)

24. The process of claim 23, wherein the compound of Formula (I-f) is reacted with R¹CO$_2$H under amide formation conditions.

25. The process of claim 24, wherein the amide formation conditions comprise a dehydrating agent and base.

26. The process of claim 25, wherein the dehydrating agent is HOBt/EDAC, CDI, HATU, or HOAT.

27. The process of claim 25, wherein the base is DIPEA or TEA.

28. The process of claim 25, wherein the dehydrating agent is HATU and the base is DIPEA.

29. The process of claim 23, further comprising converting R¹CO$_2$H to R¹COCl.

30. The process of claim 29, comprising reacting R¹CO$_2$H with thionyl chloride.

31. A process for preparing a compound of Formula (II):

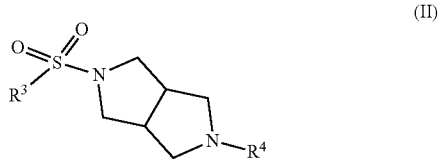

(II)

wherein:
R³ is phenyl substituted or unsubstituted with a member independently selected from the group consisting of —C$_{1-4}$alkoxy and phenyl; and
R⁴ is a member selected from the group consisting of (5-trifluoromethyl)-pyridin-2-yl, (5-trifluoromethyl)-pyrimidin-2-yl, 4,6-dimethylpyrimidin-2-yl, and quinoxalin-2-yl;
the process comprising reacting a compound of Formula (I-a):

(I-a)

wherein, W is benzyl or BOC, with $R^3SO_2Cl$ to form a compound of Formula (II-b);
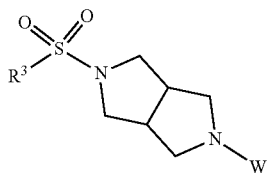
(II-b)
deprotecting the compound of Formula (II-b); and reacting the deprotected compound of Formula (II-b) with $R^4Cl$ to form the compound of Formula (II).
* * * * *